(12) United States Patent
Wei et al.

(10) Patent No.: US 12,091,387 B2
(45) Date of Patent: *Sep. 17, 2024

(54) QUINOLINE cGAS ANTAGONIST COMPOUNDS

(71) Applicants: IMMUNESENSOR THERAPEUTICS, INC., Dallas, TX (US); THE BOARD OF REGENTS OF THE UNIVERSITY OF TEXAS SYSTEM, Austin, TX (US)

(72) Inventors: Qi Wei, Dallas, TX (US); Heping Shi, Coppell, TX (US); Matt Tschantz, Plano, TX (US); Jian Qiu, Dallas, TX (US); Youtong Wu, Dallas, TX (US); Huiling Tan, Dallas, TX (US); Lijun Sun, Dallas, TX (US); Chuo Chen, Dallas, TX (US); Zhijian Chen, Dallas, TX (US)

(73) Assignees: IMMUNESENSOR THERAPEUTICS, INC., Dallas, TX (US); THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/353,718

(22) Filed: Jul. 17, 2023

(65) Prior Publication Data
US 2023/0357158 A1 Nov. 9, 2023

Related U.S. Application Data

(63) Continuation of application No. 18/177,732, filed on Mar. 2, 2023.

(60) Provisional application No. 63/478,467, filed on Jan. 4, 2023, provisional application No. 63/315,968, filed on Mar. 2, 2022.

(51) Int. Cl.
| | | |
|---|---|---|
| *C07D 215/12* | (2006.01) |
| *C07D 401/04* | (2006.01) |
| *C07D 401/14* | (2006.01) |
| *C07D 405/14* | (2006.01) |
| *C07D 409/14* | (2006.01) |
| *C07D 413/14* | (2006.01) |
| *C07D 417/14* | (2006.01) |

(52) U.S. Cl.
CPC ......... *C07D 215/12* (2013.01); *C07D 401/04* (2013.01); *C07D 401/14* (2013.01); *C07D 405/14* (2013.01); *C07D 409/14* (2013.01); *C07D 413/14* (2013.01); *C07D 417/14* (2013.01)

(58) Field of Classification Search
CPC .. C07D 215/12; C07D 401/04; C07D 401/14; C07D 405/14; C07D 409/14; C07D 413/14; C07D 417/14

USPC ...................................................... 514/217.07
See application file for complete search history.

(56) References Cited

U.S. PATENT DOCUMENTS

| | | |
|---|---|---|
| 3,542,785 A | 11/1970 | Carney |
| 3,668,207 A | 6/1972 | Carney |
| 11,873,291 B2 | 1/2024 | Qiu et al. |
| 2021/0161898 A1 | 6/2021 | Leleti et al. |
| 2021/0369747 A1 | 12/2021 | Li et al. |
| 2022/0073470 A1 | 3/2022 | Lowery et al. |
| 2023/0081291 A1 | 3/2023 | Qiu et al. |
| 2023/0103498 A1 | 4/2023 | Li et al. |
| 2023/0183179 A1 | 6/2023 | Koyuncu et al. |
| 2024/0002346 A1 | 1/2024 | Wei et al. |
| 2024/0092760 A1 | 3/2024 | Qiu et al. |

FOREIGN PATENT DOCUMENTS

| | | | |
|---|---|---|---|
| CN | 109111426 A | 1/2019 | |
| WO | WO 2004/002960 A1 | 1/2004 | |
| WO | WO-2009040290 A1 * | 4/2009 | ........... C07D 215/38 |
| WO | WO 2017/102677 A1 | 6/2017 | |
| WO | WO 2019/051269 A1 | 3/2019 | |
| WO | WO 2019/241787 A1 | 12/2019 | |
| WO | WO 2020/023846 A1 | 1/2020 | |
| WO | WO 2020/048694 A1 | 3/2020 | |
| WO | WO 2020/142735 A1 | 7/2020 | |
| WO | WO 2021/150645 A1 | 7/2021 | |
| WO | WO 2022/010948 A1 | 1/2022 | |
| WO | WO 2022/051634 A1 | 3/2022 | |
| WO | WO 2023/168367 A1 | 9/2023 | |

OTHER PUBLICATIONS

Kaoud et al. European Journal of Medicinal Chemistry (2020), 186, 111885 pp. 1-19.*
Ishak et al. International Journal of Pharmaceutical and Phytopharmacological Research (2013), 2(6), 431-435.*
Bering, Luis et al. "Regioselective Metal-Free Cross-Coupling of Quinoline N-Oxides with Boronic Acids," Org Lett (2015), 17(12): 3134-3137. XP055862048.
Decout, A., et al., "The cGAS-STING pathway as a therapeutic target in inflammatory diseases," *Nature Reviews Immunology*, 2021, vol. 21, pp. 548-569.
Eiden, F., et al., English abstract "Acetamidacetal-Cyclisierung, 2. Mitt. 2-Aminochinoline und Pyrrolo[2,3-b]chinoline", Archiv Der Pharmazie, Wiley Verlag, Weinheim, vol. 319, No. 4, Jan. 1, 1986, pp. 338-347, XP002483905, ISSN: 0365-6233, DOI: 10.1002/ARDP. 19863190409.
El-Feky, Said A. et al. "Synthesis, molecular modeling and anti-inflammatory screening of novel fluorinated quinoline incorporated benzimidazole derivatives using the Pfitzinger reaction," J Fluorine Chem (2014), 161: 87-94. XP055862414.

(Continued)

*Primary Examiner* — Kahsay Habte
(74) *Attorney, Agent, or Firm* — Hugo Garrido; Carl A. Morales; Fenwick & West LLP

(57) ABSTRACT

The present disclosure provides compounds that are cGAS antagonists, methods of preparation of the compounds, pharmaceutical compositions comprising the compounds, and their use in medical therapy.

29 Claims, No Drawings

(56) References Cited

OTHER PUBLICATIONS

Faldu, V.J. et al. "Synthesis, Characterization and Biological Evaluation of some Newer 5-[6-Chloro/Fluoro/Nitro-2-(p-Chloro/Fluoro/Methyl Phenyl)-Quinolin-4-yl]-1,3,4-Oxadiazole-2-Thiols," Int'l Lett Chemistry, Physics and Astronomy (2014), 25: 26-32. XP055862416.
International Preliminary Report on Patentability, Chapter I, Patent Cooperation Treaty Application No. PCT/US2021/049084, mailing date Mar. 16, 2023, 9 pages.
International Search Report and Written Opinion, Patent Cooperation Treaty Application No. PCT/US2021/049084 (WO/2022/051634 A1), mailed Nov. 26, 2021, 13 pages.
International Search Report and Written Opinion, Patent Cooperation Treaty Application No. PCT/US2023/063623, mailing date Jun. 5, 2023, 13 pages.
Ishiwaka, T., et al., "Reaction of 2-Aminobenzophenones with Aliphatic Acids in the Presence of Polyphosphoric Acid", Bulletin of the Chemical Society of Japan, vol. 43, Issue 6, Jun. 1970, pp. 1839-1843, XP00905724 7, ISSN: 0009-2673.
Jensen, J.A., et al., "New one-step synthesis of 2,4-bis(dialkylamino)quinolines and 4,6-bis(dialkylamino)thieno[2,3-b]pyridines", Chemica Scripta, Kungliga Vetenskapsakademien, Se, vol. 28, No. 4, Jan. 1, 1988 (Jan. 1, 1988), pp. 435-437, XP009544590, ISSN: 0004-2056.
Jiang, M., et al., "cGAS-STING, an important pathway in cancer immunotherapy," *Journal of Hematology & Oncology*, vol. 13, Article No. 81, 2020, pp. 1-11.
Kaoud, T.S., et al., "No. releasing STAT3 inhibitors suppress BRAF-mutant melanoma growth," *European Journal of Medicinal Chemistry*, vol. 186, Jan. 15, 2020, 111885, pp. 1-19.
Kobayashi, K., et al., "A convenient synthesis of quinolines by reactions of o-isocyano-β-methoxystyrenes with nucleophiles", Tetrahedron, Elsevier Sience Publishers, Amsterdam, NL, vol. 60, No. 50, Dec. 6, 2004 (Dec. 6, 2004), pp. 11639-11645, XP004628626,ISSN: 0040-4020, DOI:10.1016/J.TET.2004.09.069.
Lakhani et al. "ChemInform Abstract: Studies on Imidazolines and Benzimidazoles. Preparation and Antimicrobial Activity of 2-(2'-Aryl-6'/7'-substituted-quinolin-4'-yl)-4,5-dihydroimidazoles/benzimidazoles and Their Mannich Bases", J Indian Chem Soc (1988), 65(3): 197-199. XP055862106.
Osama, Lamiaa et al. "Synthesis and molecular modeling of new quinoline derivatives as antitumor agents," Der Pharma Chemica (2016), 8(14): 100-110. XP55106829.
Pirrung, Michael C. et al. "High-Throughput Catch-and-Release Synthesis of Oxazoline Hydroxamates. Structure-Activity Relationships in Novel Inhibitors of *Escherichia coli* LpxC: In Vitro Enzyme Inhibition and Antibacterial Properties," J American Chem Soc (2003), 125(6): 1575-1586. XP055106829.
Rane, Rajesh A. et al. "Synthesis and evaluation of novel 4-nitropyrrole-based 1,3,4-oxadiazole derivatives as antimicrobial and antitubercular agents," European J Medicinal Chem (2013),70: 49-58. XP028794132.
Suresh, Ranjendran, et al., "$SnCl_2$-Catalyzed Selective Atom Economic Imino Diels-Alder Reaction: Synthesis of 2-(1H-Pyrrolo[2,3-b]pyridin-3-yl)quinolines," J ORG CHEM (2012), 77(3): 1468-1476. XP055607680.
Verbanac, Donatella et al. "Synthesis and evaluation of antibacterial and antioxidant activity of novel 2-phenyl-quinoline analogs derivatized at position 4 with aromatically substituted 4H-1,2,4-triazoles," J Enzyme Inhibition and Medicinal Chem (2016), 31(sup2): 104-110. XP055862418.
Yu, X.Y., et al. "A series of Quinoline Analogues as Potent Inhibitors of *C. albicans* Prolyl tRNA Synthetase," Bioorg Med Chem Lett (2001), 11(4): 541-544. XP004230054.
Zhao, J., et al., "Small molecules targeting cGAS-STING pathway for autoimmune disease," *European Journal of Medicinal Chemistry*, vol. 238, Aug. 5, 2022, 114480, pp. 1-9.
Song, J., et al., "The discovery of quinoline derivatives, as NF-κB inducing kinase (NIK) inhibitors with anti-inflammatory effects in vitro, low toxicities against T cell growth," Bioorganic & Medicinal Chemistry, vol. 29, Jan. 1, 2021, 115856, pp. 1-13.

\* cited by examiner

QUINOLINE cGAS ANTAGONIST COMPOUNDS

1. BACKGROUND

Cyclic GMP-AMP synthase (cGAS) (UniProtKB—Q8N884) is an enzyme that acts as a DNA sensor to elicit an immune response to pathogens via activation of the stimulator of interferon genes (STING) receptor. Aberrant activation of cGAS by self-DNA is shown to underlie debilitating and sometimes fatal autoimmune diseases. Knockout studies in animal models have indicated that inhibiting cGAS is a promising approach for therapeutic intervention. Additionally, recent studies have shown that the cGAS-STING pathway plays a key role in the innate immune response to tumors, and stimulation of the pathway is a promising strategy being tested clinically for cancer immunotherapy.

An ongoing need exists in the art for effective treatments of human autoimmune and auto-inflammatory diseases, such as systemic lupus erythematosus (SLE), scleroderma, psoriasis, Aicardi Goutières syndrome (AGS), Sjogren's syndrome, rheumatoid arthritis, inflammatory bowel diseases, multiple sclerosis, diabetes, cardiovascular, and neurodegenerative diseases. Accordingly, there remains a need to find potent and selective small molecule inhibitors of cGAS useful for the treatment of these and other debilitating human diseases associated with the aberrant activation of cGAS.

2. SUMMARY

The present disclosure relates to small molecule cGAS antagonist compounds, methods of preparation of the compounds, pharmaceutical compositions comprising the compounds, and their use in medical therapy. In particular, the present disclosure provides quinoline cGAS antagonist compounds, which find utility as inhibitors of cGAS. An advantage of the compounds provided herein is that a broad range of pharmacological activities is possible, consistent with the inhibition of cGAS. In addition, the disclosure provides methods of using the compounds described herein for the treatment of inflammatory, allergic, autoimmune, and infectious diseases. The compounds can also be used for the treatment of senescence- or age-related diseases, such as neurodegenerative diseases, cardiovascular diseases, liver and renal diseases, cancer, and premature aging.

It has now been found that compounds of the disclosure, and pharmaceutically acceptable compositions thereof, are effective for the inhibition of cGAS. Such compounds of the disclosure have the general formula I.

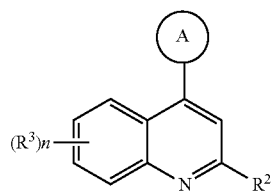

I or a pharmaceutically acceptable salt thereof, wherein each variable is as defined and described herein.

Compounds of the present disclosure, and pharmaceutically acceptable compositions thereof, are useful for treating a variety of diseases, disorders, or conditions, associated with aberrant activation of cGAS. Such diseases, disorders, or conditions include those described herein.

Compounds provided by the present disclosure are also useful for the study of cGAS enzymes in biological and pathological phenomena and the comparative evaluation of new cGAS antagonists or other regulators of cGAS, signaling pathways, and cytokine levels in vitro or in vivo.

3. DETAILED DESCRIPTION

In the following disclosure, certain specific details are set forth in order to provide a thorough understanding of various embodiments. However, one skilled in the art will understand that the methods and uses described herein may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

3.1. Definitions

Compounds of the present disclosure include those described generally herein, and are further illustrated by the classes, subclasses, and species disclosed herein. As used herein, the following definitions shall apply unless otherwise indicated. For purposes of this disclosure, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1 to 6 aliphatic carbon atoms. In some embodiments, aliphatic groups contain 1 to 5 aliphatic carbon atoms. In other embodiments, aliphatic groups contain 1 to 4 aliphatic carbon atoms. In still other embodiments, aliphatic groups contain 1 to 3 aliphatic carbon atoms, and in yet other embodiments, aliphatic groups contain 1 to 2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7 to 12 ring members and 0 to 4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

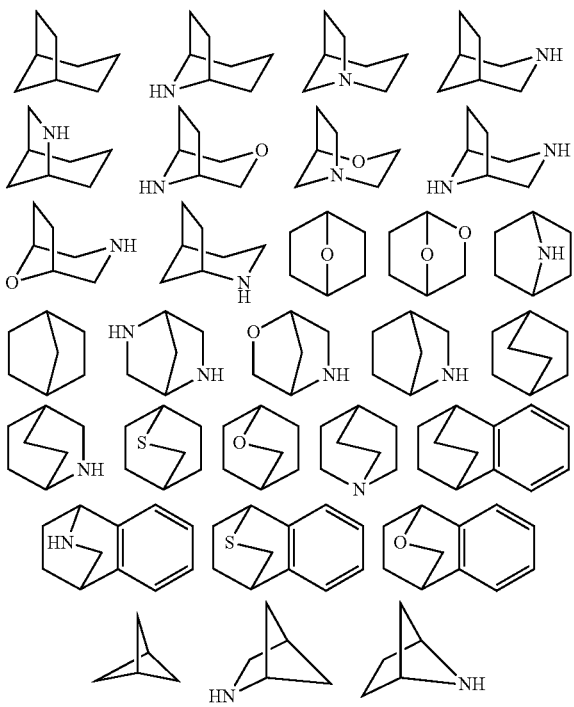

In some embodiments, bicyclo[1.1.1.]pentane is a phenyl isostere.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon); the quaternized form of any basic nitrogen; or an oxygen, sulfur, nitrogen, phosphorus, or silicon atom in a heterocyclic ring.

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

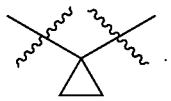 [SMILES: *C1(*)CC1]

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of 4 to 14 ring members, wherein at least one ring in the system is aromatic and wherein each ring in the system contains 3 to 7 ring members. The term "aryl" may be used interchangeably with the term "aryl ring." In certain embodiments of the present disclosure, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from 1 to 5 heteroatoms. The term "heteroatom" in the context of "heteroaryl" particularly includes, but is not limited to, nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic or bicyclic. A heteroaryl ring may include one or more oxo (=O) or thioxo (=S) substituent. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7- to 10-membered bicyclic heterocyclic moiety that is either saturated or partially unsaturated, and having, in addition to carbon atoms, one or more, preferably 1 to 4, heteroatoms, as defined above. When used in reference to a ring atom of a heterocycle, the term "nitrogen" includes a substituted nitrogen. As an example, in a saturated or partially unsaturated ring may have 0 to 3 heteroatoms selected from oxygen, sulfur or nitrogen.

A heterocyclic ring can be attached to a provided compound at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be monocyclic, bicyclic, bridged bicyclic, or spirocyclic. A heterocyclic ring may include one or more oxo (=O) or thioxo (=S) substituent. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation but is not intended to include aryl or heteroaryl moieties, as herein defined.

As described herein, compounds of the disclosure may contain "substituted" moieties. In general, the term "substituted" means that one or more hydrogens of the designated moiety are replaced with a suitable substituent. Unless otherwise indicated, an "optionally substituted" group may have a suitable substituent at one or more substitutable position of the group, and when more than one position in any given structure is substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-6}R^\circ$; $-(CH_2)_{0-6}OR^\circ$; $-O(CH_2)_{0-6}R^\circ$; $-O-(CH_2)_{0-6}C(O)OR^\circ$; $-(CH_2)_{0-6}CH(OR^\circ)_2$; $-(CH_2)_{0-6}SR^\circ$; $-(CH_2)_{0-6}Ph$, which Ph may be substituted with $R^\circ$; $-(CH_2)_{0-6}O(CH_2)_{0-1}Ph$ which Ph may be substituted with $R^\circ$; $-CH=CHPh$, which Ph may be substituted with $R^\circ$; $-(CH_2)_{0-6}O(CH_2)_{0-1}$-pyridyl which pyridyl may be substituted with $R^\circ$; $-NO_2$; $-CN$; $-N_3$; $-(CH_2)_{0-6}N(R^\circ)_2$; $-(CH_2)_{0-6}N(R^\circ)C(O)R^\circ$; $-N(R^\circ)C(S)R^\circ$; $-(CH_2)_{0-6}N(R^\circ)C(O)NR^\circ_2$; $-N(R^\circ)C(S)NR^\circ_2$; $-(CH_2)_{0-6}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-6}C(O)R^\circ$; $-C(S)R^\circ$; $-(CH_2)_{0-6}C(O)OR^\circ$; $-(CH_2)_{0-6}C(O)SR^\circ$; $-(CH_2)_{0-6}C(O)OSiR^\circ_3$; $-(CH_2)_{0-6}OC(O)R^\circ$; $-OC(O)(CH_2)_{0-6}SR^\circ$, $-(CH_2)_{0-6}SC(O)R^\circ$; $-(CH_2)_{0-6}C(O)NR^\circ_2$; $-C(S)NR^\circ_2$; $-C(S)SR^\circ$; $-SC(S)SR^\circ$, $-(CH_2)_{0-6}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-6}SSR^\circ$; $-(CH_2)_{0-6}S(O)_2R^\circ$; $-(CH_2)_{0-6}S(O)_2OR^\circ$; $-(CH_2)_{0-6}OS(O)_2R^\circ$; $-S(O)_2NR^\circ_2$; $-(CH_2)_{0-6}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-P(O)(OR^\circ)_2$; $-OP(O)(R^\circ)OR^\circ$; $-OP(O)R^\circ_2$; $-OP(O)(OR^\circ)_2$; $SiR^\circ_3$; $-(C_{1-4}$ straight or branched alkylene)$O-N(R^\circ)_2$; or $-(C_{1-4}$ straight or branched alkylene)$C(O)O-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5- to 6-membered heteroaryl ring), or a 5- to 6-membered saturated, partially unsaturated, or aryl ring having 0 to 4 heteroatoms independently selected from nitrogen, oxygen, or sulfur, or, notwithstanding the definition above, two independent occurrences of $R^\circ$, taken together with their intervening atom(s), form a 3- to 12-membered saturated, partially unsaturated, or aryl mono- or bicyclic ring having 0 to 4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$, $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5- to 6-membered saturated, partially unsaturated, or aryl ring having 0 to 4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5- to 6-membered saturated, partially unsaturated, or aryl ring having 0 to 4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5- to 6-membered saturated, partially unsaturated, or aryl ring having 0 to 4 heteroatoms independently selected from nitrogen, oxygen, or sulfur.

Suitable substituents on the aliphatic group of R* include halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5- to 6-membered saturated, partially unsaturated, or aryl ring having 0 to 4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5- to 6-membered saturated, partially unsaturated, or aryl ring having 0 to 4 heteroatoms independently selected from nitrogen, oxygen, or sulfur, or, notwithstanding the definition above, two independent occurrences of R†, taken together with their intervening atom(s) form an unsubstituted 3- to 12-membered saturated, partially unsaturated, or aryl monocyclic or bicyclic ring having 0 to 4 heteroatoms independently selected from nitrogen, oxygen, or sulfur.

Suitable substituents on the aliphatic group of R† are independently halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5- to 6-membered saturated, partially unsaturated, or aryl ring having 0 to 4 heteroatoms independently selected from nitrogen, oxygen, or sulfur.

As used herein, the term "provided compound" refers to any genus, subgenus, and/or species set forth herein.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, which is incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, trifluoro acetic acid (TFA), oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. In certain embodiments, some of the compounds disclosed herein are prepared as TFA salts.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the disclosure. Unless otherwise stated, all tautomeric forms of the compounds of the disclosure are within the scope of the disclosure. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this disclosure. Such compounds are useful, for example, as analytical tools, as probes in biological assays, or as therapeutic agents in accordance with the present disclosure.

As used herein, the term "antagonist" is defined as a compound that binds to and/or inhibits cGAS with measurable affinity. In certain embodiments, a cGAS antagonist has an IC$_{50}$ and/or binding constant of less than about 30 µM or less than about 2 µM.

3.2. Compounds of the Present Disclosure

Compounds of the present disclosure, and compositions thereof, are useful as cGAS antagonists. In some embodiments, a provided compound inhibits cGAS.

The present disclosure provides a compound, wherein the compound is of formula I:

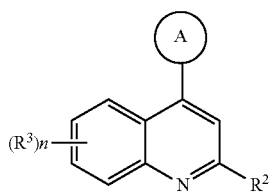

I or is a pharmaceutically acceptable salt thereof, wherein:
Ring A is an optionally substituted group selected from phenyl, HetAr, and HetCy;
HetAr is a 5- to 6-membered heteroaryl ring having 1 to 4 heteroatoms independently selected from nitrogen, oxygen, and sulfur; wherein the 5- to 6-membered heteroaryl ring is not imidazole or pyrazole;
HetCy is a 4- to 7-membered saturated or partially unsaturated heterocyclic ring having 1 to 3 heteroatoms independently selected from nitrogen, oxygen, and sulfur;
$R^2$ is halogen, —OR, —$NR_2$, —$NRNR_2$, —NRC(O)OR, —NRC(O)R, —NRC(O)$NR_2$, —$NRSO_2R$, —SR, —$SO_2R$, —$SO_2NR_2$, —S(O)R, or $R^B$, particularly —$NR_2$ or $R^B$;
each $R^3$ is independently halogen, —OR, —$NR_2$, —SR, or $R^C$, particularly halogen, such as chloro;
$R^B$ and $R^C$, independently, are an optionally substituted group selected from $C_{1-6}$ aliphatic; phenyl; a 4- to 10-membered saturated or partially unsaturated monocyclic or bicyclic carbocyclic or heterocyclic ring having 1 to 3 heteroatoms independently selected from nitrogen, oxygen, phosphorus, and sulfur; and a 5- to 6-membered heteroaryl ring having 1 to 4 heteroatoms independently selected from nitrogen, oxygen, phosphorus, and sulfur;
each R is independently hydrogen or an optionally substituted group selected from $C_{1-6}$ aliphatic; benzyl; phenyl; a 4- to 10-membered saturated or partially unsaturated monocyclic or bicyclic carbocyclic or heterocyclic ring having 1 to 3 heteroatoms independently selected from nitrogen, oxygen, phosphorus, and sulfur; and a 5- to 6-membered heteroaryl ring having 1 to 4 heteroatoms independently selected from nitrogen, oxygen, phosphorus, and sulfur, or:
  two R groups on the same nitrogen are optionally taken together with their intervening atoms to form an optionally substituted 4- to 7-membered saturated, partially unsaturated, or heteroaryl ring having 0 to 3 heteroatoms, in addition to the nitrogen, independently selected from nitrogen, oxygen, phosphorus, and sulfur; and
n is 1, 2, 3, or 4;
provided that the compound is preferably not:

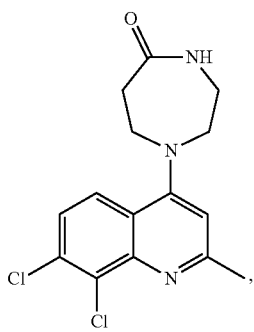

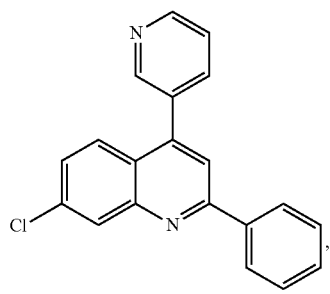

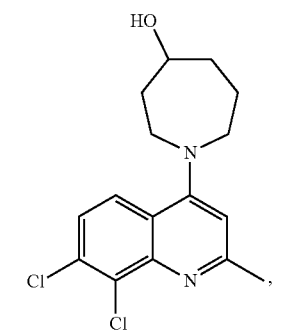

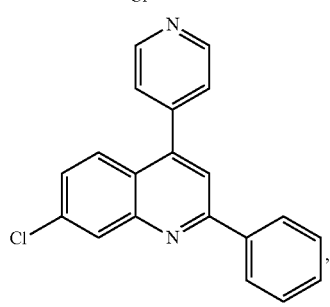

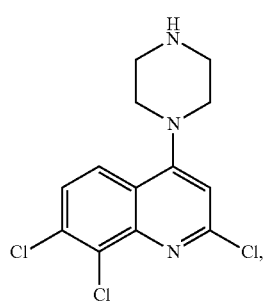

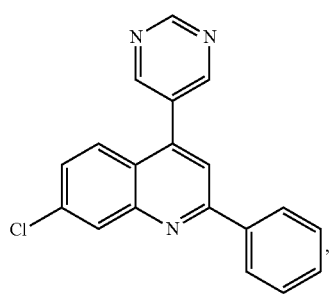

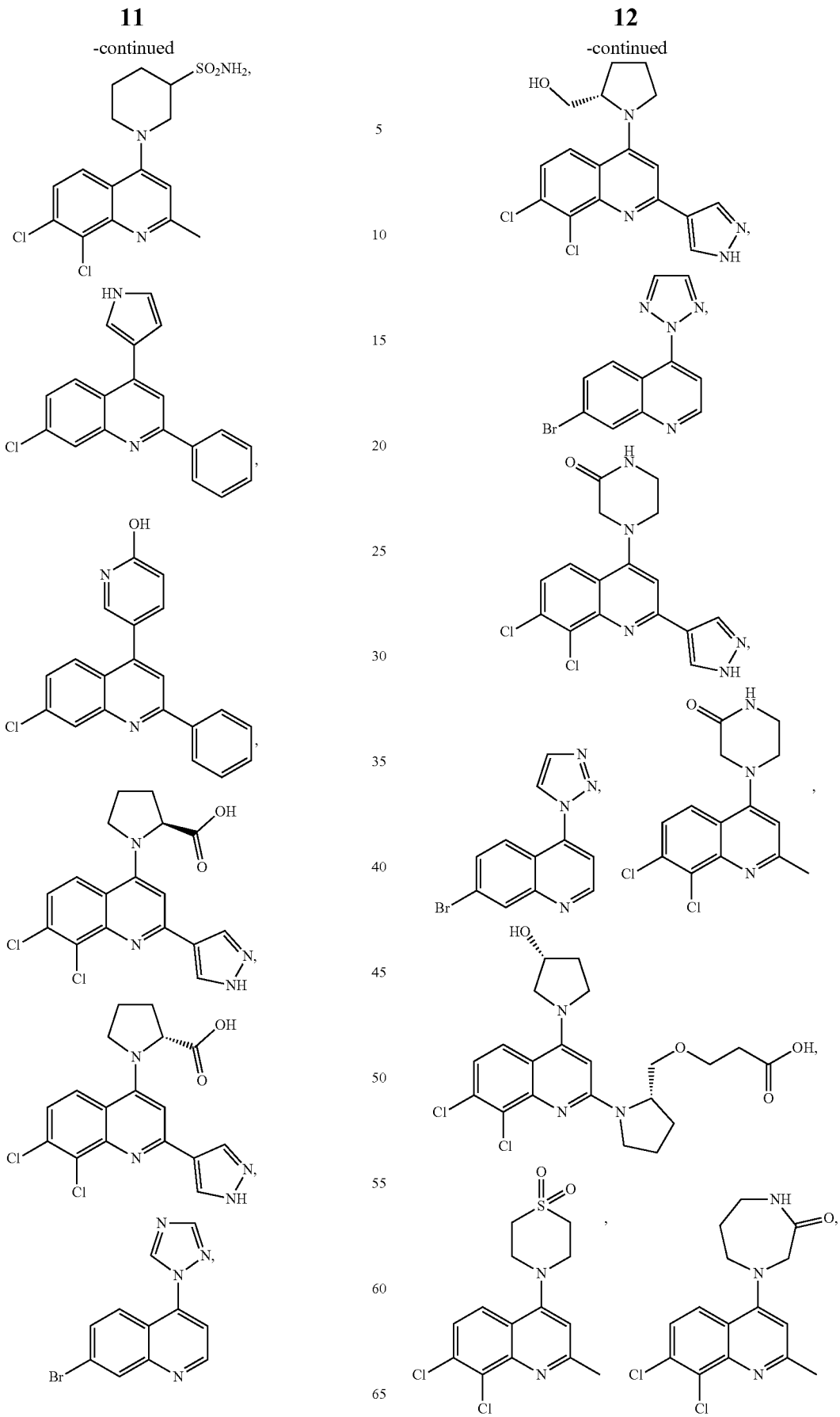

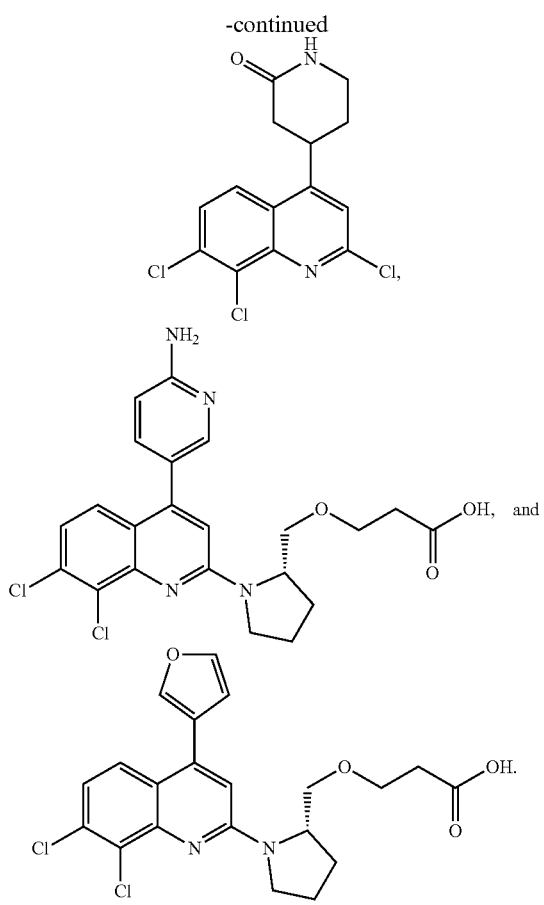

In some embodiments, the above defined compound (i.e., the compound of formula I or a pharmaceutically acceptable salt thereof) is not a compound that is specifically disclosed in international application no. PCT/US2021/49084.

In certain embodiments, the present disclosure provides a compound, wherein the compound is of formula I, wherein Ring A is an optionally substituted phenyl, preferably substituted phenyl.

In certain embodiments, the present disclosure provides a compound of formula I, wherein Ring A is optionally substituted HetAr. For example, in certain embodiments, Ring A is optionally substituted HetAr, and HetAr is selected from optionally substituted thienyl, furanyl, pyrrolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, and phenoxazinyl. In further such embodiments, Ring A is optionally substituted HetAr, and HetAr is selected from optionally substituted thienyl, triazolyl, oxazolyl, isoxazolyl, thiazolyl, isothiazolyl, pyridyl, pyridazinyl, and pyrimidinyl. In preferred embodiments, Ring A is optionally substituted HetAr, and HetAr is selected from optionally substituted triazolyl, oxazolyl, isoxazolyl, thiazolyl, and isothiazolyl.

In certain embodiments, the present disclosure provides a compound of formula I, wherein Ring A is an optionally substituted HetCy. For example, in certain embodiments, Ring A is optionally substituted HetCy, and HetCy is selected from optionally substituted tetrahydrofuranyl, tetrahydrothiophenyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, quinuclidinyl, indolinyl, 3H-indolyl, chromanyl, phenanthridinyl, tetrahydroquinolinyl, 4H-quinolizinyl, tetrahydroquinolinyl, tetrahydroisoquinolinyl, and pyrido[2,3-b]-1,4-oxazin-3(4H)-one. In further such embodiments, Ring A is optionally substituted HetCy, and HetCy is selected from optionally substituted morpholinyl, piperazinyl, 2,5-dihydro-1H-pyrrole and 2,3-dihydro-1H-pyrrole.

In certain embodiments, the present disclosure provides a compound, wherein the compound is of formula I, wherein:
Ring A is an optionally substituted group selected from phenyl, HetAr, and HetCy;
$R^2$ is $R^B$, wherein $R^B$ is a substituted 4- to 7-membered saturated heterocyclic ring (e.g., monocyclic or bicyclic) having 1 to 3 heteroatoms independently selected from nitrogen, oxygen, phosphorus, and sulfur (particularly pyrrolidine, piperidine, morpholine, and piperazine, preferably pyrrolidine), e.g., substituted with one or two groups selected from halogen, $=O$, $=CH_2$, $C_{1-4}$alkyl, $C_{1-4}$haloalkyl, $C_{3-6}$cycloalkyl, —OH, —(CH$_2$)$_{1-2}$—OH, —OC$_{1-4}$alkyl, —(CH$_2$)$_{0-2}$CO$_2$H, —(CH$_2$)$_{0-2}$O(CH$_2$)$_{1-5}$CO$_2$H, —(CH$_2$)$_{0-2}$O(CH$_2$)$_{1-5}$CO$_2$C$_{1-4}$alkyl, —(CH$_2$)$_{0-2}$CO$_2$C$_{1-4}$alkyl, —NH$_2$, —(CH$_2$)$_{0-2}$CONH$_2$, —(CH$_2$)$_{0-2}$CONR$^a$ —(CH$_2$)$_{1-2}$CO$_2$H, —(CH$_2$)$_{0-2}$SO$_3$H, —(CH$_2$)$_{0-2}$SO$_2$NH$_2$, —(CH$_2$)$_{0-2}$SO$_2$NHC$_{1-4}$alkyl, or —(CH$_2$)$_{0-2}$NR$^a$SO$_2$C$_{1-4}$alkyl, wherein $R^a$, independently for each occurrence, is H or C$_{1-4}$alkyl; and
each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In other embodiments, the present disclosure provides a compound of formula I, wherein:
Ring A is an optionally substituted group selected from phenyl, HetAr, and HetCy;
$R^2$ is —NR$_2$, wherein one R is H or lower alkyl (particularly methyl), and the other R is substituted $C_{1-6}$ aliphatic, including optionally substituted —C$_{1-5}$alkylene-X; wherein X is selected from —OH, —OC$_{1-4}$alkyl, —O—C$_{1-4}$alkylene-CO$_2$H, —O—C$_{1-4}$alkylene-CO$_2$C$_{1-4}$alkyl, —CO$_2$H, —CO$_2$C$_{1-4}$alkyl, —NH$_2$, —CONH$_2$, —CONHC$_{1-4}$alkyl, —CONR$^a$—(CH$_2$)$_{1-2}$—OH, —CONR$^a$—(CH$_2$)$_{1-2}$—COOH, —CONR$^a$—(CH$_2$)$_{1-2}$—CONH$_2$, —SO$_3$H, —SO$_2$NH$_2$, —SO$_2$NHC$_{1-4}$alkyl, —NR$^a$SO$_2$C$_{1-4}$alkyl, —P(O)(OH)$_2$, and —OP(O)(H)(OH), wherein $R^a$, independently for each occurrence, is H or C$_{1-4}$alkyl; and
each $R^3$ is independently halogen, such as chloro, including dichloro, including wherein n is 2 and $R^3$ is chloro at the 7- and 8-positions with respect to the quinoline ring.

In some embodiments, the present disclosure provides a compound of formula I, wherein:
Ring A is an optionally substituted group selected from phenyl, HetAr, and HetCy;
$R^2$ is $R^B$, wherein $R^B$ is an optionally substituted 5- to 6-membered heteroaryl ring having 1 to 4 heteroatoms independently selected from nitrogen, oxygen, phosphorus, and sulfur (particularly imidazole or pyrazole, including 1-imidazole or 4-pyrazole); and each $R^3$ is independently halogen, such as chloro, including dichloro, including wherein n is 2 and $R^3$ is chloro at the 7- and 8-positions with respect to the quinoline ring.

In other embodiments, the present disclosure provides a compound of formula I, wherein:
Ring A is an optionally substituted group selected from phenyl, HetAr, and HetCy; $R^2$ is substituted phenyl (particularly substituted with one or two groups selected from halogen, $C_{1-4}$alkyl, —OH, —O$C_{1-4}$alkyl, —$CO_2$H, —$CO_2C_{1-4}$alkyl, —$(CH_2)_{0-2}$O$(CH_2)_{1-5}CO_2$H, —$(CH_2)_{0-2}$O$(CH_2)_{1-5}CO_2C_{1-4}$alkyl, —$NH_2$, and —$CONH_2$); and
each $R^3$ is independently halogen, such as chloro, including dichloro, including wherein n is 2 and $R^3$ is chloro at the 7- and 8-positions with respect to the quinoline ring.

In other embodiments, the present disclosure provides a compound of formula I, wherein:
Ring A is an optionally substituted group selected from phenyl, HetAr, and HetCy;
$R^2$ is $R^B$, wherein $R^B$ is an optionally substituted $C_{1-6}$ aliphatic, preferably a substituted $C_{1-6}$ aliphatic (particularly —$(CR_2)_{1-4}NR(CR_2)_{0-6}CO_2R$); and
each $R^3$ is independently halogen, such as chloro, including dichloro, including wherein n is 2 and $R^3$ is chloro at the 7- and 8-positions with respect to the quinoline ring.

In certain embodiments, the disclosure provides a compound, wherein the compound is of formula I, wherein:
Ring A is an optionally substituted group selected from phenyl, HetAr, and HetCy;
$R^2$ is —$NR^aR^5$,

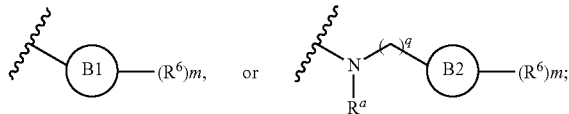

each $R^3$ is independently halogen, —OR, —$NR_2$, —SR, or $R^C$;
Ring B1 is phenyl, preferably substituted phenyl; a 4- to 10-membered saturated or partially unsaturated monocyclic or bicyclic carbocyclic or heterocyclic ring having 1 to 3 heteroatoms independently selected from nitrogen, oxygen, and sulfur; or a 5- to 6-membered heteroaryl ring having 1 to 4 heteroatoms independently selected from nitrogen, oxygen, and sulfur;
Ring B2 is phenyl; a 4- to 7-membered saturated or partially unsaturated carbocyclic or heterocyclic ring having 1 to 3 heteroatoms independently selected from nitrogen, oxygen, and sulfur; or a 5- to 6-membered heteroaryl ring having 1 to 4 heteroatoms independently selected from nitrogen, oxygen, and sulfur;
each R is independently hydrogen or an optionally substituted group selected from $C_{1-6}$ aliphatic; benzyl; phenyl; a 4- to 7-membered saturated or partially unsaturated carbocyclic or heterocyclic ring having 1 to 3 heteroatoms independently selected from nitrogen, oxygen, and sulfur; and a 5- to 6-membered heteroaryl ring having 1 to 4 heteroatoms independently selected from nitrogen, oxygen, and sulfur,
$R^5$ is —$(CR_2)_{0-4}$OR, —$(CR_2)_{0-5}CO_2R$, —$(CR_2)_{0-5}CONR_2$, —$(CR_2)_{0-4}C(O)NR(CR_2)_{0-4}CO_2R$, —$(CR_2)_{0-4}C(O)NR(CR_2)_{0-4}CONR_2$, —$(CR_2)_{0-4}NRC(O)R$, —$(CR_2)_{0-4}SO_3R$, —$(CR_2)_{0-4}SO_2NR_2$, —$(CR_2)_{0-4}OSO_2NR_2$, —$(CR_2)_{0-4}NRSO_2R$, —$(CR_2)_{0-4}NRSO_2OR$, —$(CR_2)_{0-4}OP(OR)_2$, —$(CR_2)_{0-4}OP(O)(OR)_2$, —$(CR_2)_{0-4}P(O)(OR)_2$, —$(CR_2)_{0-4}OP(O)(H)OR$, or $R^B$;

each $R^6$ is independently halogen, =O, =$CH_2$, $C_{1-4}$alkyl, $C_{1-4}$haloalkyl, $C_{3-6}$cycloalkyl, —COR, —$(CR_2)_{0-4}CO_2R$ (e.g., —$(CH_2)_{0-2}CO_2H$ or —$(CH_2)_{0-2}CO_2C_{1-4}$alkyl), —$(CH_2)_{0-2}O(CH_2)_{1-5}CO_2H$, —$(CH_2)_{0-2}O(CH_2)_{1-5}CO_2C_{1-4}$alkyl, —$(CH_2)_{0-2}CONR^a$—$(CH_2)_{1-2}CO_2H$; —$(CR_2)_{0-4}CONR_2$ (e.g., —$(CH_2)_{0-2}CONH_2$), —OR (e.g., —OH or —O$C_{1-4}$alkyl), —$(CR_2)_{1-4}OR$ (e.g., —$(CH_2)_{1-2}$—OH), —$NR_2$ (e.g., —$NH_2$), —$(CR_2)_{1-4}NR_2$, —NRC(O)OR, —NRC(O)R, —NRC(O)$NR_2$, —SR, —$SO_2R$, —S(O)R, —$(CR_2)_{0-4}SO_3R$ (e.g., —$(CH_2)_{0-2}SO_3H$), —$(CR_2)_{0-4}SO_2NR_2$ (e.g., —$(CH_2)_{0-2}SO_2NH_2$ or —$(CH_2)_{0-2}SO_2NHC_{1-4}$alkyl), —$(CR_2)_{0-4}OSO_2NR_2$, —$(CR_2)_{0-4}NRSO_2R$ (e.g., —$(CH_2)_{0-2}NR^aSO_2C_{1-4}$alkyl), —$(CR_2)_{0-4}NRSO_2OR$, —$(CR_2)_{0-4}OP(OR)_2$, —$(CR_2)_{0-4}OP(O)(OR)_2$, —$(CR_2)_{0-4}P(O)(OR)_2$, —$(CR_2)_{0-4}OP(O)(H)OR$, —$B(OR)_2$, or $R^B$ wherein $R^a$, independently for each occurrence, is H or $C_{1-4}$alkyl;
$R^B$ and $R^C$, independently, are an optionally substituted group selected from $C_{1-6}$ aliphatic; phenyl; a 4- to 10-membered saturated or partially unsaturated monocyclic or bicyclic carbocyclic or heterocyclic ring having 1 to 3 heteroatoms independently selected from nitrogen, oxygen, and sulfur; and a 5- to 6-membered heteroaryl ring having 1 to 4 heteroatoms independently selected from nitrogen, oxygen, and sulfur;
each $R^a$ is independently H or $C_{1-6}$alkyl;
each m is 0, 1, 2, 3, or 4;
n is 1, 2, 3, or 4;
q is 0, 1, or 2.

In some embodiments, Ring A is unsubstituted phenyl. In preferred embodiments, Ring A is substituted phenyl. In some embodiments, Ring A is

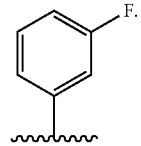 [SMILES: *c1cccc(F)c1]

In some embodiments, Ring A is

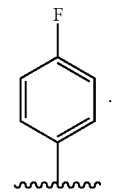

In some embodiments, Ring A is

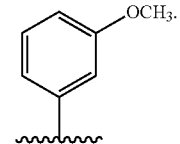 [SMILES: *c1cccc(OC)c1]

In some embodiments, Ring A is

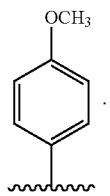

In some embodiments, Ring A is

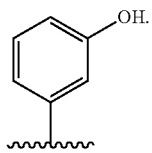 [SMILES: *c1cccc(O)c1]

In some embodiments, Ring A is

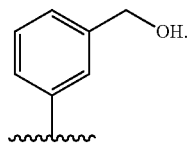 [SMILES: *c1cccc(CO)c1]

In some embodiments, Ring A is an optionally substituted HetCy, wherein HetCy is a 4- to 7-membered saturated or partially unsaturated heterocyclic ring having 1 to 3 heteroatoms independently selected from nitrogen, oxygen, and sulfur. In certain embodiments, Ring A is unsubstituted HetCy. In other embodiments, Ring A is substituted HetCy.

In some embodiments, Ring A is an optionally substituted HetCy, wherein HetCy is a 4- to 7-membered saturated heterocyclic ring having 1 to 3 heteroatoms independently selected from nitrogen, oxygen, and sulfur. In some embodiments, Ring A is an optionally substituted

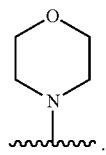 [SMILES: *N1CCOCC1]

In some embodiments, Ring A is an optionally substituted

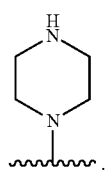 [SMILES: *N1CCNCC1]

In some embodiments, Ring A is an optionally substituted

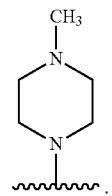

In other embodiments, Ring A is an optionally substituted HetCy, wherein HetCy is a 4- to 7-membered partially unsaturated heterocyclic ring having 1 to 3 heteroatoms independently selected from nitrogen, oxygen, and sulfur. In some embodiments, Ring A is an optionally substituted

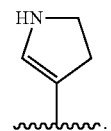

In some embodiments, Ring A is an optionally substituted

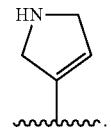

In some embodiments, Ring A is an optionally substituted HetAr, wherein HetAr is a 5- to 6-membered heteroaryl ring having 1 to 4 heteroatoms independently selected from nitrogen, oxygen, and sulfur; wherein the 5- to 6-membered heteroaryl ring is not imidazole or pyrazole. In certain embodiments, Ring A is unsubstituted HetAr. In other embodiments, Ring A is substituted HetAr. In some embodiments, Ring A is an optionally substituted

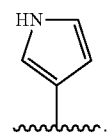

In some embodiments, Ring A is an optionally substituted

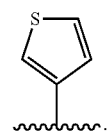 [SMILES: *c1ccsc1]

In some embodiments, Ring A is an optionally substituted

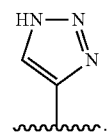

In some embodiments, Ring A is an optionally substituted

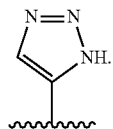

In some embodiments, Ring A is an optionally substituted

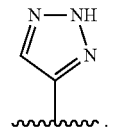

In some embodiments, Ring A is an optionally substituted

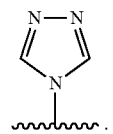

In some embodiments, Ring A is an optionally substituted

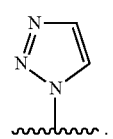

In some embodiments, Ring A is an optionally substituted

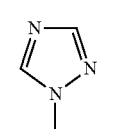

In some embodiments, Ring A is an optionally substituted

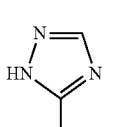

In some embodiments, Ring A is an optionally substituted

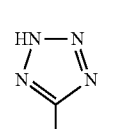

In some embodiments, Ring A is an optionally substituted

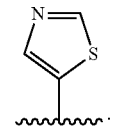 [SMILES: *c1cncs1]

In some embodiments, Ring A is an optionally substituted

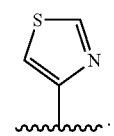

In some embodiments, Ring A is an optionally substituted

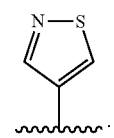

In some embodiments, Ring A is an optionally substituted

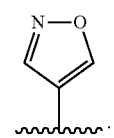 [SMILES: *c1cnoc1]

In some embodiments, Ring A is an optionally substituted

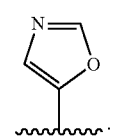 [SMILES: *c1cnco1]

In some embodiments, Ring A is an optionally substituted

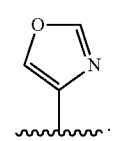

In some embodiments, Ring A is an optionally substituted

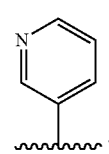

In some embodiments, Ring A is an optionally substituted

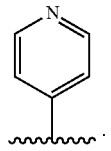

In some embodiments, Ring A is an optionally substituted

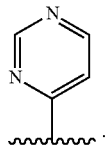

In some embodiments, Ring A is an optionally substituted

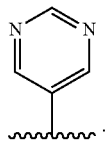

In some embodiments, Ring A is an optionally substituted

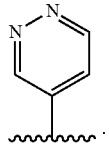

In some embodiments, Ring A is selected from those groups depicted in Table 1.

In some embodiments, Ring A is selected from those groups depicted in Table 2.

In some embodiments, at least one occurrence of $R^3$ is halogen, such as chloro or bromo. In some embodiments, at least one occurrence of $R^3$ is chloro. In some embodiments, at least one occurrence of $R^3$ is bromo, such at the 7-position with respect to the quinoline ring. In some embodiments, n is 2 and both $R^3$ are halo, such as both $R^3$ are chloro. In some embodiments, n is 2 and $R^3$ is chloro at the 7- and 8-positions with respect to the quinoline ring. In some embodiments, n is 2 and one occurrence of $R^3$ is chloro, and the other occurrence of $R^3$ is bromo, such as bromo at the 7-position and chloro at the 8-position with respect to the quinoline ring. In some embodiments, n is 3 and all occurrences of $R^3$ are halo, such as bromo at the 6-position and chloro at the 7- and 8-positions with respect to the quinoline ring.

In certain embodiments, at least one occurrence of $R^3$ is optionally substituted $C_{1-6}$ aliphatic, such as methyl. In some embodiments, n is 2 and one occurrence of $R^3$ is halo, such as bromo, and the other occurrence of $R^3$ is optionally substituted $C_{1-6}$ aliphatic, such as methyl. In some embodiments, n is 2 and one occurrence of $R^3$ is bromo at the 7-position with respect to the quinoline ring, and the other occurrence of $R^3$ is methyl at the 8-position with respect to the quinoline ring.

In some embodiments, $R^2$ is $-NR^aR^5$.

In some embodiments, $R^5$ is $-(CR_2)_{2-4}OR$, $-(CR_2)_{0-5}CO_2R$, $-(CR_2)_{0-5}CONR_2$, $-(CR_2)_{0-4}C(O)NR(CR_2)_{0-4}CO_2R$, $-(CR_2)_{0-4}C(O)NR(CR_2)_{0-4}CONR_2$, $-(CR_2)_{0-4}NRC(O)R$, $-(CR_2)_{0-4}SO_3R$, $-(CR_2)_{0-4}SO_2NR_2$, $-(CR_2)_{0-4}OSO_2NR_2$, $-(CR_2)_{0-4}NRSO_2R$, $-(CR_2)_{0-4}NRSO_2OR$, $-(CR_2)_{0-4}OP(OR)_2$, $-(CR_2)_{0-4}OP(O)(OR)_2$, $-(CR_2)_{0-4}P(O)(OR)_2$, or $-(CR_2)_{0-4}OP(O)(H)OR$.

In some embodiments, $R^5$ is $-(CR_2)_{2-4}OR$, $-(CR_2)_{1-5}CO_2R$, $-(CR_2)_{1-5}CONR_2$, $-(CR_2)_{0-4}C(O)NR(CR_2)_{0-4}CO_2R$, $-(CR_2)_{0-4}C(O)NR(CR_2)_{0-4}CONR_2$, $-(CR_2)_{0-4}NRC(O)R$, $-(CR_2)_{0-4}SO_3R$, $-(CR_2)_{0-4}SO_2NR_2$, $-(CR_2)_{0-4}OSO_2NR_2$, $-(CR_2)_{0-4}NRSO_2R$, $-(CR_2)_{0-4}NRSO_2OR$, $-(CR_2)_{0-4}OP(OR)_2$, $-(CR_2)_{0-4}OP(O)(OR)_2$, $-(CR_2)_{0-4}P(O)(OR)_2$, or $-(CR_2)_{0-4}OP(O)(H)OR$.

In some embodiments, $R^5$ is $-(CH_2)_{2-4}OH$, $-(CH_2)_{2-4}O(CH_2)_{1-5}CO_2H$, $-(CH_2)_{2-4}O(CH_2)_{1-5}CO_2C_{1-4}alkyl$, $-(CH_2)_{0-3}CH(CH_2OH)_2$, $-(CH_2)_{2-4}OC_{1-4}alkyl$, $-(CH_2)_{1-5}CO_2H$, $-(CH_2)_{1-5}CO_2C_{1-4}alkyl$, $-(CH_2)_{1-4}CONH_2$, $-(CH_2)_{1-4}CONHC_{1-4}alkyl$, $-(CH_2)_{1-4}CON(C_{1-4}alkyl)_2$, $-(CH_2)_{1-4}C(O)NR^a(CH_2)_{1-4}CO_2H$, $-(CH_2)_{1-4}C(O)NR^a(CH_2)_{1-4}CONH_2$, $-(CH_2)_{1-4}C(O)NR^a(CH_2)_{1-4}CONHC_{1-4}alkyl$, $-(CH_2)_{1-4}C(O)NR^a(CH_2)_{1-4}CON(C_{1-4}alkyl)_2$, $-(CH_2)_{0-4}NR^aC(O)(CH_2)_{1-5}CO_2H$, $-(CH_2)_{0-4}NR^aC(O)(CH_2)_{1-5}CO_2C_{1-4}alkyl$, $-(CH_2)_{2-4}SO_3H$, $-(CH_2)_{2-4}SO_3C_{1-4}alkyl$, $-(CH_2)_{2-4}SO_2NH_2$, $-(CH_2)_{2-4}SO_2NHC_{1-4}alkyl$, $-(CH_2)_{2-4}SO_2N(C_{1-4}alkyl)_2$, $-(CH_2)_{2-4}OSO_2NH_2$, $-(CH_2)_{2-4}NR^aSO_2C_{1-4}alkyl$, $-(CH_2)_{2-4}NR^aSO_3H$, $-(CH_2)_{1-4}OP(OH)_2$, $-(CH_2)_{1-4}P(O)(OH)_2$, $-(CH_2)_{1-4}P(O)(OH)(OC_{1-4}alkyl)$, or $-(CH_2)_{2-4}OP(O)(H)OH$, wherein $R^a$, independently for each occurrence, is H or $C_{1-6}alkyl$.

In some embodiments, $R^5$ is $-(CH_2)_{2-4}OH$, $-(CH_2)_{2-4}O(CH_2)_{1-5}CO_2H$, $-(CH_2)_{2-4}O(CH_2)_{1-5}CO_2C_{1-4}alkyl$, $-(CH_2)_{0-3}CH(CH_2OH)_2$, $-(CH_2)_{1-5}CO_2H$, $-(CH_2)_{1-5}CONH_2$, $-(CH_2)_{1-4}C(O)NR^a(CH_2)_{1-4}CO_2H$, $-(CH_2)_{1-4}C(O)NR^a(CH_2)_{1-4}CONH_2$, $-(CH_2)_{0-4}NR^aC(O)(CH_2)_{1-5}CO_2H$, $-(CH_2)_{0-4}NR^aC(O)(CH_2)_{1-5}CO_2C_{1-4}alkyl$, $-(CH_2)_{2-4}SO_3H$, $-(CH_2)_{2-4}SO_2NH_2$, $-(CH_2)_{2-4}SO_2NR^aC_{1-4}alkyl$, $-(CH_2)_{2-4}NR^aSO_2C_{1-4}alkyl$, $-(CH_2)_{1-4}P(O)(OH)_2$, or $-(CH_2)_{2-4}OP(O)(H)OH$, wherein $R^a$, independently for each occurrence, is H or $C_{1-4}alkyl$.

In some embodiments, $R^2$ is

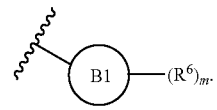

In some embodiments, m is 1, 2, 3, or 4.

In some embodiments, Ring B1 is substituted phenyl. In some embodiments, the phenyl is substituted with one or more carboxyl groups.

In some embodiments, Ring B1 is a 3-carboxyphenyl group that is optionally substituted with one or more $R^6$ groups.

In some embodiments, Ring B1 is a 3,5-dicarboxyphenyl group that is optionally substituted with one or more $R^6$ groups.

In some embodiments, Ring B1 is a 4- to 10-membered saturated or partially unsaturated monocyclic or bicyclic carbocyclic or heterocyclic ring having 1 to 3 heteroatoms independently selected from nitrogen, oxygen, and sulfur.

In some embodiments, Ring B1 is a 5- to 6-membered heteroaryl ring having 1 to 4 heteroatoms independently selected from nitrogen, oxygen, and sulfur.

In some embodiments, $R^2$ is

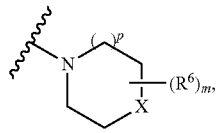

wherein X is absent (i.e., a bond in the ring), —CR$_2$—, —NR—, —O—, —S—, or —SO$_2$—; and p is 0, 1, or 2. In some embodiments, X is —CR$_2$—, —NR—, or —O—. In some embodiments, p is 1. In some embodiments, m is 1, 2, 3, or 4.

In some embodiments, each $R^6$ is independently halogen, —C$_{1-4}$alkyl, —C$_{1-4}$haloalkyl, C$_{3-6}$cycloalkyl, —(CH$_2$)$_{0-4}$CO$_2$H, —(CH$_2$)$_{0-4}$CO$_2$C$_{1-4}$alkyl, —(CH$_2$)$_{0-4}$CO$_2$C$_{1-4}$haloalkyl, —(CH$_2$)$_{0-4}$CONH$_2$, —(CH$_2$)$_{0-4}$CONHC$_{1-4}$alkyl, —(CH$_2$)$_{0-4}$CON(C$_{1-4}$alkyl)$_2$, —(CH$_2$)$_{0-4}$CO(N-proline), —(CH$_2$)$_{0-4}$C(O)NR$^a$(CH$_2$)$_{1-4}$CO$_2$H, —(CH$_2$)$_{0-4}$C(O)NR$^a$(CH$_2$)$_{1-4}$CONH$_2$, —(CH$_2$)$_{0-4}$C(O)NR$^a$(CH$_2$)$_{1-4}$CONHC$_{1-4}$alkyl, —(CH$_2$)$_{0-4}$C(O)NR$^a$(CH$_2$)$_{1-4}$CON(C$_{1-4}$alkyl)$_2$, —OH, —(CH$_2$)$_{1-4}$OH, —(CH$_2$)$_{0-4}$OC$_{1-4}$alkyl, —(CH$_2$)$_{0-4}$O(CH$_2$)$_{1-5}$CO$_2$H, —(CH$_2$)$_{0-4}$O(CH$_2$)$_{1-5}$CO$_2$C$_{1-4}$alkyl, —(CH$_2$)$_{0-4}$OC(O)C$_{1-4}$alkyl, —NH$_2$, —(CH$_2$)$_{1-4}$NH$_2$, —(CH$_2$)$_{0-4}$NHC$_{1-4}$alkyl, —(CH$_2$)$_{0-4}$N(C$_{1-4}$alkyl)$_2$, —(CH$_2$)$_{0-4}$SO$_3$H, —(CH$_2$)$_{0-4}$SO$_2$NH$_2$, —(CH$_2$)$_{0-4}$SO$_2$NHC$_{1-4}$alkyl, —(CH$_2$)$_{0-4}$NR$^a$SO$_2$C$_{1-4}$alkyl, —(CH$_2$)$_{0-4}$OP(OH)$_2$, —(CH$_2$)$_{0-4}$OP(OH)(OC$_{1-4}$alkyl), or —(CR$_2$)$_{0-4}$OP(O)(H)OH, wherein $R^a$, independently for each occurrence, is H or C$_{1-4}$alkyl.

In some embodiments, each $R^6$ is independently halogen, —C$_{1-4}$alkyl, —C$_{1-4}$haloalkyl, C$_{3-6}$cycloalkyl, —(CH$_2$)$_{0-4}$CO$_2$H, —(CH$_2$)$_{0-4}$CO$_2$C$_{1-4}$alkyl, —(CH$_2$)$_{0-4}$CO(N-proline), —(CH$_2$)$_{0-4}$C(O)NR$^a$(CH$_2$)$_{1-4}$CO$_2$H, —OH, —(CH$_2$)$_{1-4}$OH, —(CH$_2$)$_{0-4}$OC$_{1-4}$alkyl, —(CH$_2$)$_{0-4}$O(CH$_2$)$_{1-5}$CO$_2$H, —(CH$_2$)$_{0-4}$O(CH$_2$)$_{1-5}$CO$_2$C$_{1-4}$alkyl, —(CH$_2$)$_{0-4}$OC(O)C$_{1-4}$alkyl, —(CH$_2$)$_{0-4}$SO$_3$H, —(CH$_2$)$_{0-4}$SO$_2$NH$_2$, —(CH$_2$)$_{0-4}$NR$^a$SO$_2$C$_{1-4}$alkyl, —(CH$_2$)$_{0-4}$OP(OH)$_2$, or —(CR$_2$)$_{0-4}$OP(O)(H)OH.

In some embodiments, $R^6$ is independently halogen, —C$_{1-4}$alkyl, —C$_{1-4}$haloalkyl, C$_{3-6}$cycloalkyl, —(CH$_2$)$_{0-2}$CO$_2$H, —(CH$_2$)$_{0-2}$CO$_2$C$_{1-4}$alkyl, —(CH$_2$)$_{1-4}$CO(N-proline), —(CH$_2$)$_{0-2}$C(O)NR$^a$(CH$_2$)$_{1-4}$CO$_2$H, —OH, —(CH$_2$)$_{1-2}$OH, —(CH$_2$)$_{0-2}$OC$_{1-4}$alkyl, —(CH$_2$)$_{0-4}$O(CH$_2$)$_{1-5}$CO$_2$H, —(CH$_2$)$_{0-4}$O(CH$_2$)$_{1-5}$CO$_2$C$_{1-4}$alkyl, —(CH$_2$)$_{0-2}$OC(O)C$_{1-4}$alkyl, —(CH$_2$)$_{0-2}$SO$_3$H, —(CH$_2$)$_{0-2}$SO$_2$NH$_2$, —(CH$_2$)$_{0-2}$NR$^a$SO$_2$C$_{0-2}$alkyl, —(CH$_2$)$_{0-2}$OP(OH)$_2$, or —(CR$_2$)$_{0-2}$OP(O)(H)OH, wherein $R^a$, independently for each occurrence, is H or C$_{1-4}$alkyl.

In some embodiments, each $R^6$ is independently halogen, —C$_{1-4}$alkyl, —C$_{1-4}$haloalkyl, C$_{3-6}$cycloalkyl, —(CH$_2$)$_{1-4}$CO$_2$H, —(CH$_2$)$_{1-4}$CO(N-proline), —(CH$_2$)$_{1-4}$C(O)NR$^a$(CH$_2$)$_{1-4}$CO$_2$H, —OH, —(CH$_2$)$_{1-4}$OH, —(CH$_2$)$_{0-4}$O(CH$_2$)$_{1-5}$CO$_2$H, —(CH$_2$)$_{0-4}$O(CH$_2$)$_{1-5}$CO$_2$C$_{1-4}$alkyl, —(CH$_2$)$_{1-4}$SO$_3$H, —(CH$_2$)$_{1-4}$SO$_2$NH$_2$, —(CH$_2$)$_{1-4}$NR$^a$SO$_2$C$_{1-4}$alkyl, —(CH$_2$)$_{1-4}$OP(OH)$_2$, or —(CR$_2$)$_{1-4}$OP(O)(H)OH.

In some embodiments, each $R^6$ is independently halogen, —C$_{1-4}$alkyl, —C$_{1-4}$haloalkyl, —CO$_2$H, —CO$_2$C$_{1-4}$alkyl, —CO(N-proline), —CH$_2$CO$_2$H, —OH, —OC$_{1-4}$alkyl, —(CH$_2$)$_{0-4}$O(CH$_2$)$_{1-5}$CO$_2$H, —(CH$_2$)$_{0-4}$O(CH$_2$)$_{1-5}$CO$_2$C$_{1-4}$alkyl, —OC(O)C$_{1-4}$alkyl, —SO$_3$H, —SO$_2$NH$_2$, —NR$^a$SO$_2$C$_{1-4}$alkyl, —OP(OH)$_2$, or —OP(O)(H)OH.

In some embodiments, $R^2$ is

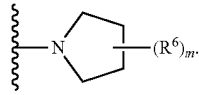

In some embodiments, m is 1, 2, 3, or 4. In some embodiments, m is 1 or 2.

In some embodiments, $R^2$ is

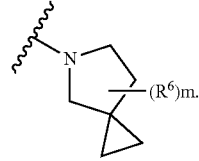

In some embodiments, m is 1, 2, 3, or 4. In some embodiments, m is 1 or 2.

In some embodiments, each $R^6$ is independently halogen, =CH$_2$, =O, —C$_{1-4}$alkyl, —C$_{1-4}$haloalkyl, C$_{3-6}$cycloalkyl, —(CH$_2$)$_{0-4}$CO$_2$H, —(CH$_2$)$_{0-4}$CO$_2$C$_{1-4}$alkyl, —(CH$_2$)$_{0-4}$CO$_2$C$_{1-4}$haloalkyl, —(CH$_2$)$_{0-4}$CONH$_2$, —(CH$_2$)$_{0-4}$CONHC$_{1-4}$alkyl, —(CH$_2$)$_{0-4}$CON(C$_{1-4}$alkyl)$_2$, —(CH$_2$)$_{0-4}$CO(N-proline), —(CH$_2$)$_{0-4}$CO(N-pyrrolidine-3-carboxylic acid), —(CH$_2$)$_{0-4}$C(O)NR$^a$(CH$_2$)$_{1-4}$CO$_2$H, —(CH$_2$)$_{0-4}$C(O)NR$^a$—CH(C$_{1-4}$alkyl)-CO$_2$H, —(CH$_2$)$_{0-4}$C(O)NR$^a$(CH$_2$)$_{1-4}$CONH$_2$, —(CH$_2$)$_{0-4}$C(O)NR$^a$(CH$_2$)$_{1-4}$CONHC$_{1-4}$alkyl, —(CH$_2$)$_{0-4}$C(O)NR$^a$(CH$_2$)$_{1-4}$CON(C$_{1-4}$alkyl)$_2$, —OH, —(CH$_2$)$_{1-4}$OH, —(CH$_2$)$_{0-4}$OC$_{1-4}$alkyl, —(CH$_2$)$_{0-4}$O(CH$_2$)$_{1-5}$CO$_2$H, —(CH$_2$)$_{0-4}$O(CH$_2$)$_{1-5}$CO$_2$C$_{1-4}$alkyl, —(CH$_2$)$_{0-4}$OC(O)C$_{1-4}$alkyl, —NH$_2$, —(CH$_2$)$_{1-4}$NH$_2$, —(CH$_2$)$_{0-4}$NHC$_{1-4}$alkyl, —(CH$_2$)$_{0-4}$NR$^a$C(O)C$_{1-4}$alkyl, —(CH$_2$)$_{0-4}$NR$^a$C(O)Ph, —(CH$_2$)$_{0-4}$NR$^a$CO(CH$_2$)$_{1-4}$OH, —(CH$_2$)$_{0-4}$N(C$_{1-4}$alkyl)$_2$, —(CH$_2$)$_{0-4}$SO$_3$H, —(CH$_2$)$_{0-4}$SO$_2$NH$_2$, —(CH$_2$)$_{0-4}$SO$_2$NR$^a$C$_{1-4}$alkyl, —(CH$_2$)$_{0-4}$NR$^a$SO$_2$C$_{1-4}$alkyl, —(CH$_2$)$_{0-4}$NR$^a$SO$_2$Ph, —(CH$_2$)$_{0-4}$NR$^a$SO$_2$(CH$_2$)$_{1-4}$CO$_2$H, —(CH$_2$)$_{0-4}$OP(OH)$_2$, —(CH$_2$)$_{0-4}$OP(OH)(OC$_{1-4}$alkyl), or —(CR$_2$)$_{0-4}$OP(O)(H)OH, wherein $R^a$, independently for each occurrence, is H or C$_{1-6}$alkyl.

In some embodiments, each $R^6$ is independently halogen, =CH$_2$, =O, —C$_{1-4}$alkyl, —C$_{1-4}$haloalkyl, C$_{3-6}$cycloalkyl, —(CH$_2$)$_{0-4}$CO$_2$H, —(CH$_2$)$_{0-4}$CO$_2$C$_{1-4}$alkyl, —(CH$_2$)$_{0-4}$CO$_2$C$_{1-4}$haloalkyl, —(CH$_2$)$_{0-4}$CO(N-proline), —(CH$_2$)$_{0-4}$CO(N-pyrrolidine-3-carboxylic acid), —(CH$_2$)$_{0-4}$C(O)NR$^a$(CH$_2$)$_{1-4}$CO$_2$H, —(CH$_2$)$_{0-4}$C(O)NR$^a$—CH(C$_{1-4}$alkyl)-CO$_2$H, —OH, —(CH$_2$)$_{1-4}$OH, —OC$_{1-4}$alkyl, —(CH$_2$)$_{0-4}$O(CH$_2$)$_{1-5}$CO$_2$H, —(CH$_2$)$_{0-4}$O(CH$_2$)$_{1-5}$CO$_2$C$_{1-4}$alkyl, —(CH$_2$)$_{0-4}$NR$^a$C(O)C$_{1-4}$alkyl, —(CH$_2$)$_{0-4}$NR$^a$C(O)Ph, —(CH$_2$)$_{0-4}$NR$^a$CO(CH$_2$)$_{1-4}$OH, —(CH$_2$)$_{0-4}$SO$_3$H, —(CH$_2$)$_{0-4}$SO$_2$NH$_2$, —(CH$_2$)$_{0-4}$NR$^a$SO$_2$C$_{1-4}$alkyl, —(CH$_2$)$_{0-4}$NR$^a$SO$_2$Ph, —(CH$_2$)$_{0-4}$NR$^a$SO$_2$(CH$_2$)$_{1-4}$CO$_2$H, —(CH$_2$)$_{0-4}$OP(OH)$_2$, or —(CR$_2$)$_{0-4}$OP(O)(H)OH, wherein $R^a$, independently for each occurrence, is H or C$_{1-4}$alkyl.

In some embodiments, each $R^6$ is independently halogen, =CH$_2$, =O, —C$_{1-4}$alkyl, —C$_{1-4}$haloalkyl, —CO$_2$H, —CO$_2$C$_{1-4}$alkyl, —CO$_2$C$_{1-4}$haloalkyl, —CO(N-proline), —CO(N-pyrrolidine-3-carboxylic acid), —C(O)NR$^a$(CH$_2$)$_{1-4}$CO$_2$H, —C(O)NR$^a$—CH(C$_{1-4}$alkyl)-CO$_2$H, —OH, —OC$_{1-4}$alkyl, —(CH$_2$)$_{0-4}$O(CH$_2$)$_{1-5}$CO$_2$H, —(CH$_2$)$_{0-4}$O(CH$_2$)$_{1-5}$CO$_2$C$_{1-4}$alkyl, —NR$^a$C(O)C$_{1-4}$alkyl, —NR$^a$C(O)Ph, —NR$^a$CO(CH$_2$)$_{1-4}$OH, —SO$_3$H, —SO$_2$NH$_2$, —NR$^a$SO$_2$C$_{1-4}$alkyl, —NR$^a$SO$_2$Ph, —NR$^a$SO$_2$(CH$_2$)$_{1-4}$CO$_2$H, —OP(OH)$_2$, or —OP(O)(H)OH, wherein $R^a$, independently for each occurrence, is H or C$_{1-4}$alkyl.

In some embodiments, each $R^6$ is independently fluoro, =O, =CH$_2$, methyl, cyclohexyl, morpholinyl, phenyl, —CF$_3$, —OMe, —OtBu, —CO$_2$H, —CO$_2$C$_{1-4}$alkyl, —CO$_2$C$_{1-4}$haloalkyl, —(CH$_2$)$_{1-4}$O(CH$_2$)$_{1-5}$CO$_2$H, —(CH$_2$)$_{1-4}$O(CH$_2$)$_{1-5}$CO$_2$C$_{1-4}$alkyl, or —OH.

In some embodiments, Ring B1 is a 5- to 6-membered heteroaryl ring having 1 to 4 heteroatoms independently selected from nitrogen, oxygen and sulfur, wherein a carbon atom of the 5- to 6-membered heteroaryl ring is directly bonded to the carbon at the 2-position of the quinolone ring.

In some embodiments, Ring B1 is imidazole or pyrazole. In some embodiments, the imidazole or pyrazole are unsubstituted.

In some embodiments, $R^2$ is

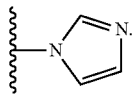

In some embodiments, $R^2$ is

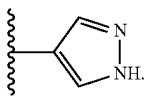

In some embodiments, $R^2$ is

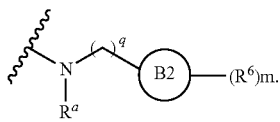

In some embodiments, m is 1, 2, 3, or 4.

In some embodiments, Ring B2 is phenyl.

In some embodiments, Ring B2 is a 4- to 7-membered saturated or partially unsaturated carbocyclic or heterocyclic ring having 1 to 3 heteroatoms independently selected from nitrogen, oxygen, and sulfur.

In some embodiments, Ring B2 is a 5- to 6-membered heteroaryl ring having 1 to 4 heteroatoms independently selected from nitrogen, oxygen, and sulfur.

In some embodiments, $R^2$ is

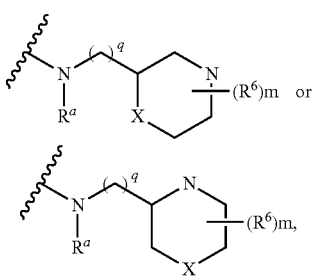

wherein X is absent (i.e., a bond in the ring), —CR$_2$—, —NR—, —O—, —S—, or —SO$_2$—; and m is 1, 2, 3, or 4. In some embodiments, $R^2$ is

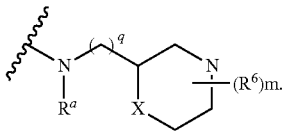

In some embodiments, $R^2$ is

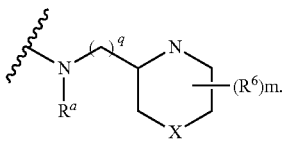

In some embodiments, X is —CR$_2$—, —NR—, or —O—. In some embodiments, q is 1 or 2. In some embodiments, q is 1. In some embodiments, m is 1 or 2.

In some embodiments, each $R^6$ is independently halogen, —(CH$_2$)$_{0-4}$CO$_2$H, —(CH$_2$)$_{0-4}$CO$_2$C$_{1-4}$alkyl, —(CH$_2$)$_{0-4}$CONH$_2$, —(CH$_2$)$_{0-4}$CONHC$_{1-4}$alkyl, —(CH$_2$)$_{0-4}$CON(C$_{1-4}$alkyl)$_2$, —(CH$_2$)$_{0-4}$CO(N-proline), —(CH$_2$)$_{0-4}$C(O)NR$^a$(CH$_2$)$_{1-4}$CO$_2$H, —(CH$_2$)$_{0-4}$C(O)NR$^a$(CH$_2$)$_{1-4}$CONH$_2$, —(CH$_2$)$_{0-4}$C(O)NR$^a$(CH$_2$)$_{1-4}$CONHC$_{1-4}$alkyl, —(CH$_2$)$_{0-4}$C(O)NR$^a$(CH$_2$)$_{1-4}$CON(C$_{1-4}$alkyl)$_2$, —OH, —(CH$_2$)$_{1-4}$OH, —(CH$_2$)$_{0-4}$OC$_{1-4}$alkyl, —NH$_2$, —(CH$_2$)$_{1-4}$NH$_2$, —(CH$_2$)$_{0-4}$NHC$_{1-4}$alkyl, —(CH$_2$)$_{0-4}$N(C$_{1-4}$alkyl)$_2$, —(CH$_2$)$_{0-4}$SO$_3$H, —(CH$_2$)$_{0-4}$SO$_2$NH$_2$, —(CH$_2$)$_{0-4}$SO$_2$NHC$_{1-4}$alkyl, —(CH$_2$)$_{0-4}$NR$^a$SO$_2$C$_{1-4}$alkyl, —(CH$_2$)$_{0-4}$OP(OH)$_2$, —(CH$_2$)$_{0-4}$OP(OH)(OC$_{1-4}$alkyl), or —(CR$_2$)$_{0-4}$OP(O)(H)OH, wherein $R^a$, independently for each occurrence, is H or C$_{1-4}$alkyl.

In some embodiments, each $R^6$ is independently halogen, —(CH$_2$)$_{0-4}$CO$_2$H, —(CH$_2$)$_{0-4}$CO(N-proline), —(CH$_2$)$_{0-4}$C(O)NR$^a$(CH$_2$)$_{1-4}$CO$_2$H, —OH, —(CH$_2$)$_{1-4}$OH, —(CH$_2$)$_{0-4}$SO$_3$H, —(CH$_2$)$_{0-4}$SO$_2$NH$_2$, —(CH$_2$)$_{0-4}$NR$^a$SO$_2$C$_{1-4}$alkyl, —(CH$_2$)$_{0-4}$OP(OH)$_2$, or —(CR$_2$)$_{0-4}$OP(O)(H)OH, wherein $R^a$, independently for each occurrence, is H or C$_{1-4}$alkyl.

In some embodiments, each $R^6$ is independently halogen, —CO$_2$H, —CO(N-proline), —C(O)NR$^a$(CH$_2$)$_{1-4}$CO$_2$H, —OH, —SO$_3$H, —SO$_2$NH$_2$, —NR$^a$SO$_2$C$_{1-4}$alkyl, —OP(OH)$_2$, or —OP(O)(H)OH, wherein $R^a$, independently for each occurrence, is H or C$_{1-4}$alkyl.

In some embodiments, $R^6$ is not $R^B$.

In some embodiments, m is at least 1, and at least one $R^6$ includes a terminal —CO$_2$H or —CO$_2$C$_{1-4}$alkyl group.

In some embodiments, at least one $R^6$ is —(CH$_2$)$_{0-4}$O(CH$_2$)$_{1-5}$CO$_2$H, —(CH$_2$)$_{0-4}$O(CH$_2$)$_{1-5}$CO$_2$C$_{1-4}$alkyl, —(CH$_2$)$_{0-4}$CO$_2$H or —(CH$_2$)$_{0-4}$CO$_2$C$_{1-4}$alkyl.

In some embodiments, the present disclosure provides a pharmaceutical composition comprising a compound of formula I or a pharmaceutically acceptable salt thereof.

In some embodiments, the present disclosure provides a method of antagonizing cyclic GMP-AMP synthase (cGAS) in a patient in need thereof, comprising administering an effective amount of a compound of formula I or a pharmaceutically acceptable salt thereof, or a pharmaceutical composition thereof.

In some embodiments, the present disclosure provides a method of treating an inflammatory, allergic, or autoimmune disease in a patient in need thereof, comprising administering an effective amount of a compound of formula I or a pharmaceutically acceptable salt thereof, or a pharmaceutical composition thereof.

In some embodiments, the present disclosure provides a compound of formula I, wherein $R^2$ is $-NR_2$ thereby forming a compound of formula I-a-1:

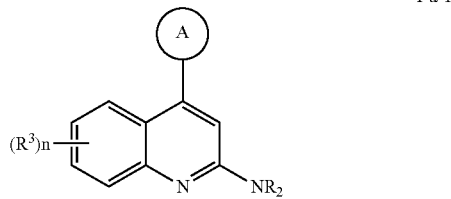

I-a-1 or a pharmaceutically acceptable salt thereof, wherein each of Ring A, R, $R^3$, and n is as defined above and described in embodiments herein, both singly and in combination.

In certain embodiments, the present disclosure provides a compound of formula I-a-1, wherein $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In certain embodiments, the present disclosure provides a compound of formula I-a-1, wherein Ring A is an optionally substituted phenyl, preferably substituted phenyl. In certain embodiments, the present disclosure provides a compound of formula I-a-1, wherein Ring A is optionally substituted HetCy. In certain embodiments, the present disclosure provides a compound of formula I-a-1, wherein Ring A is an optionally substituted HetAr.

In some embodiments, the present disclosure provides a compound of formula I, wherein $R^2$ is $-NRR^5$ thereby forming a compound of formula I-a-2:

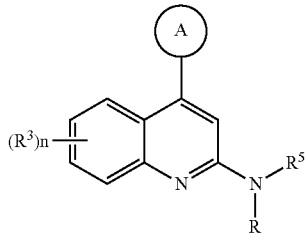

I-a-2 or a pharmaceutically acceptable salt thereof, wherein:
$R^5$ is $-(CR_2)_{2-4}OR$, $-(CR_2)_{0-6}CO_2R$, $-(CR_2)_{0-6}CONR_2$, $-(CR_2)_{0-6}C(O)NR(CR_2)_{0-6}CO_2R$, $-(CR_2)_{0-6}C(O)NR(CR_2)_{0-6}CONR_2$, $-(CR_2)_{0-4}NRC(O)R$, $-(CR_2)_{0-6}SO_3R$, $-(CR_2)_{0-6}SO_2NR_2$, $-(CR_2)_{0-6}OSO_2NR_2$, $-(CR_2)_{0-6}NRSO_2R$, $-(CR_2)_{0-6}NRSO_2OR$, $-(CR_2)_{0-6}OP(OR)_2$, $-(CR_2)_{0-6}OP(O)(OR)_2$, $-(CR_2)_{0-6}P(O)(OR)_2$, $-(CR_2)_{0-6}OP(O)(H)OR$, or $R^B$; and each of Ring A, R, $R^3$, $R^B$, and n is as defined above and described in embodiments herein, both singly and in combination.

In certain embodiments, the present disclosure provides a compound of formula I-a-2, wherein Ring A is an optionally substituted phenyl, preferably substituted phenyl. In certain embodiments, the present disclosure provides a compound of formula I-a-2, wherein Ring A is optionally substituted HetCy. In certain embodiments, the present disclosure provides a compound of formula I-a-2, wherein Ring A is an optionally substituted HetAr.

In certain embodiments, the present disclosure provides a compound of formula I-a-2, wherein $R^5$ is $-(CR_2)_{2-4}OR$, $-(CR_2)_{1-4}CO_2R$, $-(CR_2)_{1-4}CONR_2$, $-(CR_2)_{0-6}C(O)NR(CR_2)_{0-6}CO_2R$, $-(CR_2)_{0-6}C(O)NR(CR_2)_{0-6}CONR_2$, $-(CR_2)_{0-4}NRC(O)R$, $-(CR_2)_{0-6}SO_3R$, $-(CR_2)_{0-6}SO_2NR_2$, $-(CR_2)_{0-6}OSO_2NR_2$, $-(CR_2)_{0-6}NRSO_2R$, $-(CR_2)_{0-6}NRSO_2OR$, $-(CR_2)_{0-6}OP(OR)_2$, $-(CR_2)_{0-6}OP(O)(OR)_2$, $-(CR_2)_{0-6}P(O)(OR)_2$, $-(CR_2)_{0-6}OP(O)(H)OR$, or $R^B$.

In some embodiments, the present disclosure provides a compound of formula I-a-2, wherein $R^5$ is not $R^B$.

In some embodiments, the present disclosure provides a compound of formula I-a-2, wherein R in $-NRR^5$ is $R^a$, which is H or $C_{1-6}$alkyl.

In certain embodiments, the present disclosure provides a compound of formula I-a-1, wherein $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In certain embodiments, the present disclosure provides a compound of formula I-a-2, wherein:
R in $-NRR^5$ is H or lower alkyl, particularly methyl;
$R^5$ is $-(CR_2)_{0-6}OR$, $-(CR_2)_{0-6}CO_2R$, $-(CR_2)_{0-6}CONR_2$, $-(CR_2)_{0-6}C(O)NR(CR_2)_{0-6}CO_2R$, $-(CR_2)_{0-6}C(O)NR(CR_2)_{0-6}CONR_2$, $-(CR_2)_{0-4}NRC(O)R$, $-(CR_2)_{0-6}SO_3R$, $-(CR_2)_{0-6}SO_2NR_2$, $-(CR_2)_{0-6}OSO_2NR_2$, $-(CR_2)_{0-6}NRSO_2R$, $-(CR_2)_{0-6}NRSO_2OR$, $-(CR_2)_{0-6}OP(OR)_2$, $-(CR_2)_{0-6}OP(O)(OR)_2$, $-(CR_2)_{0-6}P(O)(OR)_2$, or $-(CR_2)_{0-6}OP(O)(H)OR$; and
each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In particular embodiments, the present disclosure provides a compound of formula I-a-2, wherein:
R in $-NRR^5$ is H or lower alkyl, particularly methyl;
$R^5$ is $-(CH_2)_{2-4}OH$, $-(CH_2)_{2-4}O(CH_2)_{1-5}CO_2H$, $-(CH_2)_{2-4}O(CH_2)_{1-5}CO_2C_{1-4}alkyl$, $-(CH_2)_{0-3}CH(CH_2OH)_2$, $-(CH_2)_{2-4}OC_{1-4}alkyl$, $-(CH_2)_{1-4}CO_2H$, $-(CH_2)_{1-4}CO_2C_{1-4}alkyl$, $-(CH_2)_{1-4}CONH_2$, $-(CH_2)_{1-4}CONHC_{1-4}alkyl$, $-(CH_2)_{1-4}CON(C_{1-4}alkyl)_2$, $-(CH_2)_{1-4}C(O)NR^a(CH_2)_{1-4}CO_2H$, $-(CH_2)_{1-4}C(O)NR^a(CH_2)_{1-4}CONH_2$, $-(CH_2)_{1-4}C(O)NR^a(CH_2)_{1-4}CONHC_{1-4}alkyl$, $-(CH_2)_{1-4}C(O)NR^a(CH_2)_{1-4}CON(C_{1-4}alkyl)_2$, $-(CH_2)_{0-4}NR^aC(O)(CH_2)_{1-5}CO_2H$, $-(CH_2)_{0-4}NR^aC(O)(CH_2)_{1-5}CO_2C_{1-4}alkyl$, $-(CH_2)_{2-4}SO_3H$, $-(CH_2)_{2-4}SO_3C_{1-4}alkyl$, $-(CH_2)_{2-4}SO_2NH_2$, $-(CH_2)_{2-4}SO_2NHC_{1-4}alkyl$, $-(CH_2)_{2-4}SO_2N(C_{1-4}alkyl)_2$, $-(CH_2)_{2-4}OSO_2NH_2$, $-(CH_2)_{2-4}NR^aSO_2C_{1-4}alkyl$, $-(CH_2)_{2-4}NR^aSO_3H$, $-(CH_2)_{1-4}OP(OH)_2$, $-(CH_2)_{1-4}P(O)(OH)_2$, $-(CH_2)_{1-4}P(O)(OH)(OC_{1-4}alkyl)$, or $-(CH_2)_{2-4}OP(O)(H)OH$, wherein $R^a$, independently for each occurrence, is H or $C_{1-4}alkyl$; and
each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In particular embodiments, the present disclosure provides a compound of formula I-a-2, wherein:

R in —NRR$^5$ is H or lower alkyl, particularly methyl;
R$^5$ is —(CH$_2$)$_{2-4}$OH, —(CH$_2$)$_{0-3}$CH(CH$_2$OH)$_2$, —(CH$_2$)$_{2-4}$OC$_{1-4}$alkyl, —(CH$_2$)$_{1-4}$CO$_2$H, —(CH$_2$)$_{1-4}$CO$_2$C$_{1-4}$alkyl, —(CH$_2$)$_{1-4}$CONH$_2$, —(CH$_2$)$_{1-4}$CONHC$_{1-4}$alkyl, —(CH$_2$)$_{1-4}$CON(C$_{1-4}$alkyl)$_2$, —(CH$_2$)$_{1-4}$C(O)NR$^a$(CH$_2$)$_{1-4}$CO$_2$H, —(CH$_2$)$_{1-4}$C(O)NR$^a$(CH$_2$)$_{1-4}$CONH$_2$, —(CH$_2$)$_{1-4}$C(O)NR$^a$(CH$_2$)$_{1-4}$CONHC$_{1-4}$alkyl, —(CH$_2$)$_{1-4}$C(O)NR$^a$(CH$_2$)$_{1-4}$CON(C$_{1-4}$alkyl)$_2$, —(CH$_2$)$_{2-4}$SO$_3$H, —(CH$_2$)$_{2-4}$SO$_3$C$_{1-4}$alkyl, —(CH$_2$)$_{2-4}$SO$_2$NH$_2$, —(CH$_2$)$_{2-4}$SO$_2$NHC$_{1-4}$alkyl, —(CH$_2$)$_{2-4}$SO$_2$N(C$_{1-4}$alkyl)$_2$, —(CH$_2$)$_{2-4}$OSO$_2$NH$_2$, —(CH$_2$)$_{2-4}$NR$^a$SO$_2$C$_{1-4}$alkyl, —(CH$_2$)$_{2-4}$NR$^a$SO$_3$H, —(CH$_2$)$_{1-4}$OP(OH)$_2$, —(CH$_2$)$_{1-4}$P(O)(OH)$_2$, —(CH$_2$)$_{1-4}$P(O)(OH)(OC$_{1-4}$alkyl), or —(CH$_2$)$_{2-4}$OP(O)(H)OH, wherein R$^a$, independently for each occurrence, is H or C$_{1-4}$alkyl; and each R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In further particular embodiments, the present disclosure provides a compound of formula I-a-2, wherein:
R in —NRR$^5$ is H or lower alkyl, particularly methyl;
R$^5$ is —(CH$_2$)$_{2-4}$OH, —(CH$_2$)$_{2-4}$O(CH$_2$)$_{1-5}$CO$_2$H, —(CH$_2$)$_{2-4}$O(CH$_2$)$_{1-5}$CO$_2$C$_{1-4}$alkyl, —(CH$_2$)$_{0-3}$CH(CH$_2$OH)$_2$, —(CH$_2$)$_{1-4}$CO$_2$H, —(CH$_2$)$_{1-4}$CONH$_2$, —(CH$_2$)$_{1-4}$C(O)NR$^a$(CH$_2$)$_{1-4}$CO$_2$H, —(CH$_2$)$_{1-4}$C(O)NR$^a$(CH$_2$)$_{1-4}$CONH$_2$, —(CH$_2$)$_{0-4}$NR$^a$C(O)(CH$_2$)$_{1-5}$CO$_2$H, —(CH$_2$)$_{0-4}$NR$^a$C(O)(CH$_2$)$_{1-5}$CO$_2$C$_{1-4}$alkyl, —(CH$_2$)$_{2-4}$SO$_3$H, —(CH$_2$)$_{2-4}$SO$_2$NH$_2$, —(CH$_2$)$_{2-4}$SO$_2$NR$^a$C$_{1-4}$alkyl, —(CH$_2$)$_{2-4}$NR$^a$SO$_2$C$_{1-4}$alkyl, —(CH$_2$)$_{1-4}$P(O)(OH)$_2$, or —(CH$_2$)$_{2-4}$OP(O)(H)OH, wherein R$^a$, independently for each occurrence, is H or C$_{1-4}$alkyl; and each R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In further particular embodiments, the present disclosure provides a compound of formula I-a-2, wherein:
R in —NRR$^5$ is H or lower alkyl, particularly methyl;
R$^5$ is —(CH$_2$)$_{2-4}$OH, —(CH$_2$)$_{0-3}$CH(CH$_2$OH)$_2$, —(CH$_2$)$_{1-4}$CO$_2$H, —(CH$_2$)$_{1-4}$CONH$_2$, —(CH$_2$)$_{1-4}$C(O)NR$^a$(CH$_2$)$_{1-4}$CO$_2$H, —(CH$_2$)$_{1-4}$C(O)NR$^a$(CH$_2$)$_{1-4}$CONH$_2$, —(CH$_2$)$_{2-4}$SO$_3$H, —(CH$_2$)$_{2-4}$SO$_2$NH$_2$, —(CH$_2$)$_{2-4}$SO$_2$NR$^a$C$_{1-4}$alkyl, —(CH$_2$)$_{2-4}$NR$^a$SO$_2$C$_{1-4}$alkyl, —(CH$_2$)$_{1-4}$P(O)(OH)$_2$, or —(CH$_2$)$_{2-4}$OP(O)(H)OH, wherein R$^a$, independently for each occurrence, is H or C$_{1-4}$alkyl; and each R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In certain embodiments, for the above disclosed compounds of formula I-a-2, R$^5$ includes a terminal —CO$_2$H group. For example, in certain instances, R$^5$ includes a terminal —(CH$_2$)$_{0-4}$CO$_2$H group.

In some embodiments, the present disclosure provides a compound of formula I, wherein R$^2$ is

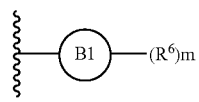

thereby forming a compound of formula I-a-3:

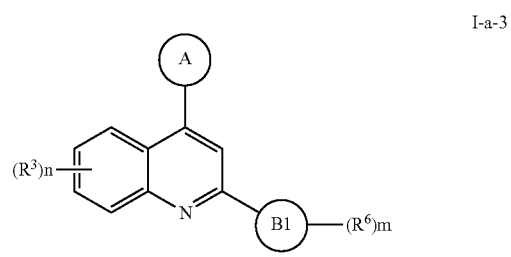

I-a-3 or a pharmaceutically acceptable salt thereof, wherein:
Ring B1 is phenyl, preferably substituted phenyl; a 4- to 10-membered saturated or partially unsaturated monocyclic or bicyclic carbocyclic or heterocyclic ring having 1 to 3 heteroatoms independently selected from nitrogen, oxygen, phosphorus, and sulfur; or a 5- to 6-membered heteroaryl ring having 1 to 4 heteroatoms independently selected from nitrogen, oxygen, phosphorus, and sulfur;

each R$^6$ is independently halogen, —COR, —(CR$_2$)$_{0-6}$CO$_2$R, —(CR$_2$)$_{0-6}$CONR$_2$, —OR, —(CR$_2$)$_{1-4}$OR, —NR$_2$, —(CR$_2$)$_{1-4}$NR$_2$, —NRC(O)OR, —NRC(O)R, —NRC(O)NR$_2$, —SR, —SO$_2$R, —S(O)R, —(CR$_2$)$_{0-6}$SO$_3$R, —(CR$_2$)$_{0-6}$SO$_2$NR$_2$, —(CR$_2$)$_{0-6}$OSO$_2$NR$_2$, —(CR$_2$)$_{0-6}$NRSO$_2$R, —(CR$_2$)$_{0-6}$NRSO$_2$OR, —(CR$_2$)$_{0-6}$OP(OR)$_2$, —(CR$_2$)$_{0-6}$OP(O)(OR)$_2$, —(CR$_2$)$_{0-6}$P(O)(OR)$_2$, —(CR$_2$)$_{0-6}$OP(O)(H)OR, —B(OR)$_2$, or R$^B$;

m is 0, 1, 2, 3, or 4, particularly 1, 2, 3, or 4; and
each of Ring A, R, R$^3$, R$^B$, and n is as defined above and described in embodiments herein, both singly and in combination.

In certain embodiments, the present disclosure provides a compound of formula I-a-3, wherein Ring A is an optionally substituted phenyl, preferably substituted phenyl. In certain embodiments, the present disclosure provides a compound of formula I-a-3, wherein Ring A is optionally substituted HetCy. In certain embodiments, the present disclosure provides a compound of formula I-a-3, wherein Ring A is an optionally substituted HetAr.

In certain embodiments, the present disclosure provides a compound of formula I-a-3, wherein Ring B1 is phenyl, particularly substituted phenyl. In other embodiments, Ring B1 is not phenyl. For example, Ring B1 may be a 4- to 10-membered saturated or partially unsaturated monocyclic or bicyclic carbocyclic or heterocyclic ring having 1 to 3 heteroatoms independently selected from nitrogen, oxygen, phosphorus, and sulfur. In some embodiments, Ring B1 is a 5- to 6-membered heteroaryl ring having 1 to 4 heteroatoms independently selected from nitrogen, oxygen, phosphorus, and sulfur.

In some embodiments, the present disclosure provides a compound of formula I-a-3, wherein R$^6$ is not R$^B$.

In certain embodiments, the present disclosure provides a compound of formula I-a-3, wherein R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In certain embodiments, for the above disclosed compounds of formula I-a-3, m is 1 or 2, and at least one R$^6$ includes a terminal —CO$_2$H group. For example, in certain instances, at least one R$^6$ is —(CH$_2$)$_{0-4}$CO$_2$H or —(CH$_2$)$_{0-4}$O(CH$_2$)$_{1-5}$CO$_2$H.

In some embodiments, the present disclosure provides a compound of formula I, wherein $R^2$ is

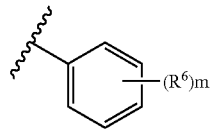

thereby forming a compound of formula I-a-4:

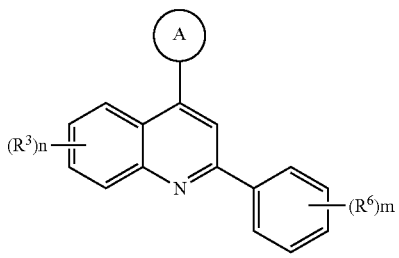

I-a-4 or a pharmaceutically acceptable salt thereof, wherein:
each $R^6$ is independently halogen, —COR, —(CR$_2$)$_{0-6}$CO$_2$R, —(CR$_2$)$_{0-6}$CONR$_2$, —OR, —(CR$_2$)$_{1-4}$OR, —NR$_2$, —(CR$_2$)$_{1-4}$NR$_2$, —NRC(O)OR, —NRC(O)R, —NRC(O)NR$_2$, —SR, —SO$_2$R, —S(O)R, —(CR$_2$)$_{0-6}$SO$_3$R, —(CR$_2$)$_{0-6}$SO$_2$NR$_2$, —(CR$_2$)$_{0-6}$OSO$_2$NR$_2$, —(CR$_2$)$_{0-6}$NRSO$_2$R, —(CR$_2$)$_{0-6}$NRSO$_2$OR, —(CR$_2$)$_{0-6}$OP(OR)$_2$, —(CR$_2$)$_{0-6}$OP(O)(OR)$_2$, —(CR$_2$)$_{0-6}$P(O)(OR)$_2$, —(CR$_2$)$_{0-6}$OP(O)(H)OR, —B(OR)$_2$, or $R^B$;

m is 0, 1, 2, 3, or 4, particularly 1, 2, 3, or 4; and each of Ring A, R, $R^3$, $R^B$, and n is as defined above and described in embodiments herein, both singly and in combination.

In certain embodiments, the present disclosure provides a compound of formula I-a-4, wherein Ring A is an optionally substituted phenyl, preferably substituted phenyl. In certain embodiments, the present disclosure provides a compound of formula I-a-4, wherein Ring A is optionally substituted HetCy. In certain embodiments, the present disclosure provides a compound of formula I-a-4, wherein Ring A is an optionally substituted HetAr.

In some embodiments, the present disclosure provides a compound of formula I-a-4, wherein $R^6$ is not $R^B$.

In certain embodiments, the present disclosure provides a compound of formula I-a-4, wherein $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In certain embodiments, for the above disclosed compounds of formula I-a-4, m is 1 or 2, and at least one $R^6$ includes a terminal —CO$_2$H group. For example, in certain instances, at least one $R^6$ is —(CH$_2$)$_{0-4}$CO$_2$H or —(CH$_2$)$_{0-4}$O(CH$_2$)$_{1-5}$CO$_2$H.

In some embodiments, the present disclosure provides a compound of formula I, wherein $R^2$ is

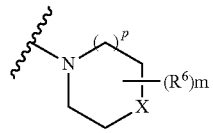

thereby forming a compound of formula I-a-5:

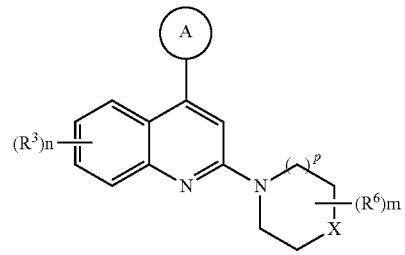

I-a-5 or a pharmaceutically acceptable salt thereof, wherein:
each $R^6$ is independently halogen, =O, —COR, —(CR$_2$)$_{0-6}$CO$_2$R, —(CR$_2$)$_{0-6}$CONR$_2$, —OR, —(CR$_2$)$_{1-4}$OR, —NR$_2$, —(CR$_2$)$_{1-4}$NR$_2$, —NRC(O)OR, —NRC(O)R, —NRC(O)NR$_2$, —SR, —SO$_2$R, —S(O)R, —(CR$_2$)$_{0-6}$SO$_3$R, —(CR$_2$)$_{0-6}$SO$_2$NR$_2$, —(CR$_2$)$_{0-6}$OSO$_2$NR$_2$, —(CR$_2$)$_{0-6}$NRSO$_2$R, —(CR$_2$)$_{0-6}$NRSO$_2$OR, —(CR$_2$)$_{0-6}$OP(OR)$_2$, —(CR$_2$)$_{0-6}$OP(O)(OR)$_2$, —(CR$_2$)$_{0-6}$P(O)(OR)$_2$, —(CR$_2$)$_{0-6}$OP(O)(H)OR, —B(OR)$_2$, or $R^B$;

X is absent (i.e., a bond in the ring), —CR$_2$—, —NR—, —O—, —S—, or —SO$_2$—; particularly —CR$_2$—, —NR—, —O—, —S—, or —SO$_2$—; more particularly —CR$_2$—, —NR—, or —O—;

m is 0, 1, 2, 3, or 4, particularly 1, 2, 3, or 4;

p is 0, 1, or 2, particularly 1; and each of Ring A, R, $R^3$, $R^B$, and n is as defined above and described in embodiments herein, both singly and in combination.

In certain embodiments, the present disclosure provides a compound of formula I-a-5, wherein Ring A is an optionally substituted phenyl, preferably substituted phenyl. In certain embodiments, the present disclosure provides a compound of formula I-a-5, wherein Ring A is optionally substituted HetCy. In certain embodiments, the present disclosure provides a compound of formula I-a-5, wherein Ring A is an optionally substituted HetAr.

In some embodiments, the present disclosure provides a compound of formula I-a-5, wherein $R^6$ is not $R^B$.

In certain embodiments, the present disclosure provides a compound of formula I-a-5, wherein $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In certain embodiments, the present disclosure provides a compound of formula I-a-5, wherein:
each $R^6$ is independently halogen, —C$_{1-4}$alkyl, —C$_{1-4}$haloalkyl, =CR$_2$, =O, —COR, —(CR$_2$)$_{0-6}$CO$_2$R, —(CR$_2$)$_{0-6}$CONR$_2$, —OR, —(CR$_2$)$_{1-4}$OR, —NR$_2$, —(CR$_2$)$_{1-4}$NR$_2$, —NRC(O)OR, —NRC(O)R, —NRC(O)NR$_2$, —SR, —SO$_2$R, —S(O)R, —(CR$_2$)$_{0-6}$SO$_3$R, —(CR$_2$)$_{0-6}$SO$_2$NR$_2$, —(CR$_2$)$_{0-6}$OSO$_2$NR$_2$, —(CR$_2$)$_{0-6}$NRSO$_2$R, —(CR$_2$)$_{0-6}$NRSO$_2$OR, —(CR$_2$)$_{0-6}$ OP(OR)$_2$, —(CR$_2$)$_{0-6}$OP(O)(OR)$_2$, —(CR$_2$)$_{0-6}$P(O)(OR)$_2$, —(CR$_2$)$_{0-6}$OP(O)(H)OR, or —B(OR)$_2$;
m is 1, 2, 3, or 4, particularly 1 or 2;
p is 0 or 1, particularly 1; and
each R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In particular embodiments, the present disclosure provides a compound of formula I-a-5, wherein:
each R$^6$ is independently halogen, —C$_{1-4}$alkyl, —C$_{1-4}$haloalkyl, =CH$_2$, =O, —(CH$_2$)$_{0-4}$CO$_2$H, —(CH$_2$)$_{0-4}$CO$_2$C$_{1-4}$alkyl, —(CH$_2$)$_{0-4}$O(CH$_2$)$_{1-5}$CO$_2$H, —(CH$_2$)$_{0-4}$O(CH$_2$)$_{1-5}$CO$_2$C$_{1-4}$alkyl, —(CH$_2$)$_{1-4}$O(CH$_2$)$_{1-4}$CHFCO$_2$H, —(CH$_2$)$_{1-4}$O(CH$_2$)$_{1-4}$CHFCO$_2$C$_{1-4}$alkyl, —(CH$_2$)$_{1-4}$OCH(CH$_3$)(CH$_2$)$_{1-4}$CO$_2$H, —(CH$_2$)$_{1-4}$OCH(CH$_3$)(CH$_2$)$_{1-4}$CO$_2$C$_{1-4}$alkyl, —(CH$_2$)$_{1-4}$O(CH$_2$)$_{1-4}$CH(CH$_3$)CO$_2$H, —(CH$_2$)$_{1-4}$O(CH$_2$)$_{1-4}$CH(CH$_3$)CO$_2$C$_{1-4}$alkyl, —CHOH(CH$_2$)$_{1-4}$O(CH$_2$)$_{1-5}$CO$_2$H, —CHOH(CH$_2$)$_{1-4}$O(CH$_2$)$_{1-5}$CO$_2$C$_{1-4}$alkyl, —CHCF$_3$(CH$_2$)$_{1-4}$O(CH$_2$)$_{1-5}$CO$_2$H, —CHCF$_3$(CH$_2$)$_{1-4}$O—(CH$_2$)$_{1-5}$CO$_2$C$_{1-4}$alkyl, —(CH$_2$)$_{1-4}$O(CH$_2$)$_{1-5}$CONR$^a$$_2$, —(CH$_2$)$_{1-4}$O(CH$_2$)$_{1-5}$CONR$^a$OH, —(CH$_2$)$_{1-4}$O(CH$_2$)$_{1-5}$CONR$^a$CN, —(CH$_2$)$_{1-4}$O(CH$_2$)$_{1-5}$P(O)OH$_2$, —(CH$_2$)$_{0-4}$CONH$_2$, —(CH$_2$)$_{0-4}$CONHC$_{1-4}$alkyl, —(CH$_2$)$_{0-4}$CON(C$_{1-4}$alkyl)$_2$, —(CH$_2$)$_{0-4}$CO(N-proline), —(CH$_2$)$_{0-4}$(N-pyrazole)-(CH$_2$)$_{0-4}$CO$_2$H, —(CH$_2$)$_{0-4}$CO(N-pyrazole)-(CH$_2$)$_{0-4}$CO$_2$C$_{1-4}$alkyl, —(CH$_2$)$_{0-4}$(N-pyrrole)-(CH$_2$)$_{0-4}$CO$_2$H, —(CH$_2$)$_{0-4}$CO(N-pyrrole)-(CH$_2$)$_{0-4}$CO$_2$C$_{1-4}$alkyl, —(CH$_2$)$_{0-4}$—O(phenyl)-(CH$_2$)$_{0-4}$CO$_2$H, —(CH$_2$)$_{0-4}$—O(phenyl)-(CH$_2$)$_{0-4}$CO$_2$C$_{1-4}$alkyl, —(CH$_2$)$_{0-4}$—O(cycloalkane)-(CH$_2$)$_{0-4}$CO$_2$H, —(CH$_2$)$_{0-4}$—O(cycloalkane)-(CH$_2$)$_{0-4}$CO$_2$C$_{1-4}$alkyl, —(CH$_2$)$_{0-4}$C(O)NR$^a$(CH$_2$)$_{1-4}$CO$_2$H, —(CH$_2$)$_{0-4}$C(O)NR$^a$(CH$_2$)$_{1-4}$CONH$_2$, —(CH$_2$)$_{0-4}$C(O)NR$^a$(CH$_2$)$_{1-4}$CONHC$_{1-4}$alkyl, —(CH$_2$)$_{0-4}$C(O)NR$^a$(CH$_2$)$_{1-4}$CON(C$_{1-4}$alkyl)$_2$, —OH, —(CH$_2$)$_{1-4}$OH, —(CH$_2$)$_{0-4}$OC$_{1-4}$alkyl, —NH$_2$, —(CH$_2$)$_{0-4}$NR$^a$(CH$_2$)$_{1-4}$CO$_2$H, —(CH$_2$)$_{0-4}$NR$^a$(CH$_2$)$_{1-4}$CO$_2$C$_{1-4}$alkyl, —(CH$_2$)$_{0-4}$N[(CH$_2$)$_{1-4}$CO$_2$C$_{1-4}$alkyl]$_2$, —(CH$_2$)$_{1-4}$NH$_2$, —(CH$_2$)$_{0-4}$NHC$_{1-4}$alkyl, —(CH$_2$)$_{0-4}$N(C$_{1-4}$alkyl)$_2$, —(CH$_2$)$_{0-4}$SO$_3$H, —(CH$_2$)$_{0-4}$SO$_2$NH$_2$, —(CH$_2$)$_{0-4}$SO$_2$NHC$_{1-4}$alkyl, —(CH$_2$)$_{0-4}$NR$^a$SO$_2$C$_{1-4}$alkyl, —(CH$_2$)$_{0-4}$OP(OH)$_2$, —(CH$_2$)$_{0-4}$OP(OH)(OC$_{1-4}$alkyl), or —(CR$_2$)$_{0-4}$OP(O)(H)OH, wherein R$^a$, independently for each occurrence, is H or C$_{1-4}$alkyl;
X is —CH$_2$—, —NH—, or —O—;
m is 1, 2, 3, or 4, particularly 1 or 2;
p is 1; and
each R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In particular embodiments, the present disclosure provides a compound of formula I-a-5, wherein each R$^6$ is independently fluoro, -methyl, -methoxy, —(CH$_2$)$_{1-5}$CO$_2$H, —(CH$_2$)$_{1-5}$CO$_2$C$_{1-4}$alkyl, —(CH$_2$)$_{0-4}$O(CH$_2$)$_{1-5}$CO$_2$H, —(CH$_2$)$_{0-4}$O(CH$_2$)$_{1-5}$CO$_2$C$_{1-4}$alkyl, or —OH; and m is 1, 2, or 3, particularly 1 or 2.

In particular embodiments, the present disclosure provides a compound of formula I-a-5, wherein:
each R$^6$ is independently halogen, —C$_{1-4}$alkyl, —C$_{1-4}$haloalkyl, —C$_{3-6}$cycloalkyl, =CH$_2$, =O, —(CH$_2$)$_{0-4}$CO$_2$H, —(CH$_2$)$_{0-4}$CO$_2$C$_{1-4}$alkyl, —(CH$_2$)$_{0-4}$O(CH$_2$)$_{1-5}$CO$_2$H, —(CH$_2$)$_{0-4}$O(CH$_2$)$_{1-5}$CO$_2$C$_{1-4}$alkyl, —(CH$_2$)$_{0-4}$CONH$_2$, —(CH$_2$)$_{0-4}$CONHC$_{1-4}$alkyl, —(CH$_2$)$_{0-4}$CON(C$_{1-4}$alkyl)$_2$, —(CH$_2$)$_{0-4}$CO(N-proline), —(CH$_2$)$_{0-4}$C(O)NR$^a$(CH$_2$)$_{1-4}$CO$_2$H, —(CH$_2$)$_{0-4}$C(O)NR$^a$(CH$_2$)$_{1-4}$CONH$_2$, —(CH$_2$)$_{0-4}$C(O)NR$^a$(CH$_2$)$_{1-4}$CONHC$_{1-4}$alkyl, —(CH$_2$)$_{0-4}$C(O)NR$^a$(CH$_2$)$_{1-4}$CON(C$_{1-4}$alkyl)$_2$, —OH, —(CH$_2$)$_{1-4}$OH, —(CH$_2$)$_{0-4}$OC$_{1-4}$alkyl, —NH$_2$, —(CH$_2$)$_{1-4}$NH$_2$, —(CH$_2$)$_{0-4}$NHC$_{1-4}$alkyl, —(CH$_2$)$_{0-4}$N(C$_{1-4}$alkyl)$_2$, —(CH$_2$)$_{0-4}$SO$_3$H, —(CH$_2$)$_{0-4}$SO$_2$NH$_2$, —(CH$_2$)$_{0-4}$SO$_2$NHC$_{1-4}$alkyl, —(CH$_2$)$_{0-4}$NR$^a$SO$_2$C$_{1-4}$alkyl, —(CH$_2$)$_{0-4}$OP(OH)$_2$, —(CH$_2$)$_{0-4}$OP(OH)(OC$_{1-4}$alkyl), or —(CR$_2$)$_{0-4}$OP(O)(H)OH, wherein R$^a$, independently for each occurrence, is H or C$_{1-4}$alkyl;
X is —CH$_2$—, —NH—, or —O—;
m is 1, 2, 3, or 4, particularly 1 or 2;
p is 1; and
each R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In further particular embodiments, the present disclosure provides a compound of formula I-a-5, wherein:
each R$^6$ is independently halogen, —C$_{1-4}$alkyl, —C$_{1-4}$haloalkyl, —C$_{3-6}$cycloalkyl, =CH$_2$, —(CH$_2$)$_{0-4}$CO$_2$H, —(CH$_2$)$_{1-4}$O(CH$_2$)$_{1-5}$CO$_2$H, —(CH$_2$)$_{1-4}$O(CH$_2$)$_{1-5}$CO$_2$C$_{1-4}$alkyl, —(CH$_2$)$_{0-4}$CO(N-proline), —(CH$_2$)$_{0-4}$C(O)NR$^a$(CH$_2$)$_{1-4}$CO$_2$H, —OH, —(CH$_2$)$_{1-4}$OH, —(CH$_2$)$_{0-4}$SO$_3$H, —(CH$_2$)$_{0-4}$SO$_2$NH$_2$, —(CH$_2$)$_{0-4}$NR$^a$SO$_2$C$_{1-4}$alkyl, —(CH$_2$)$_{0-4}$OP(OH)$_2$, or —(CR$_2$)$_{0-4}$OP(O)(H)OH;
X is —CH$_2$—, —NH—, or —O—;
m is 1 or 2;
p is 1; and
each R$^3$ is independently halogen, such as chloro, including dichloro, including wherein n is 2 and R$^3$ is chloro at the 7- and 8-positions with respect to the quinoline ring.

In certain embodiments, for the above disclosed compounds of formula I-a-5, m is 1 or 2, and at least one R$^6$ includes a terminal —CO$_2$H group. For example, in certain instances, at least one R$^6$ is —(CH$_2$)$_{0-4}$CO$_2$H or —(CH$_2$)$_{0-4}$O(CH$_2$)$_{1-5}$CO$_2$H.

In particular embodiments, the present disclosure provides a compound of formula I-a-5, wherein:
each R$^6$ is independently halogen, —C$_{1-4}$alkyl, —C$_{1-4}$haloalkyl, =CH$_2$, =O, —(CH$_2$)$_{0-4}$CO$_2$H, —(CH$_2$)$_{0-4}$CO$_2$C$_{1-4}$alkyl, —(CH$_2$)$_{0-4}$CONH$_2$, —(CH$_2$)$_{0-4}$CONHC$_{1-4}$alkyl, —(CH$_2$)$_{0-4}$CON(C$_{1-4}$alkyl)$_2$, —(CH$_2$)$_{0-4}$CO(N-proline), —(CH$_2$)$_{0-4}$C(O)NR$^a$(CH$_2$)$_{1-4}$CO$_2$H, —(CH$_2$)$_{0-4}$C(O)NR$^a$(CH$_2$)$_{1-4}$CONH$_2$, —(CH$_2$)$_{0-4}$C(O)NR$^a$(CH$_2$)$_{1-4}$CONHC$_{1-4}$alkyl, —(CH$_2$)$_{0-4}$C(O)NR$^a$(CH$_2$)$_{1-4}$CON(C$_{1-4}$alkyl)$_2$, —OH, —(CH$_2$)$_{1-4}$OH, —(CH$_2$)$_{0-4}$OC$_{1-4}$alkyl, —(CH$_2$)$_{0-4}$O(CH$_2$)$_{1-5}$CO$_2$H, —(CH$_2$)$_{0-4}$O(CH$_2$)$_{1-5}$CO$_2$C$_{1-4}$alkyl, —NH$_2$, —(CH$_2$)$_{1-4}$NH$_2$, —(CH$_2$)$_{0-4}$NHC$_{1-4}$alkyl, —(CH$_2$)$_{0-4}$N(C$_{1-4}$alkyl)$_2$, —(CH$_2$)$_{0-4}$SO$_3$H, —(CH$_2$)$_{0-4}$SO$_2$NH$_2$, —(CH$_2$)$_{0-4}$SO$_2$NHC$_{1-4}$alkyl, —(CH$_2$)$_{0-4}$NR$^a$SO$_2$C$_{1-4}$alkyl, —(CH$_2$)$_{0-4}$OP(OH)$_2$, —(CH$_2$)$_{0-4}$OP(OH)(OC$_{1-4}$alkyl), or —(CR$_2$)$_{0-4}$OP(O)(H)OH, wherein R$^a$, independently for each occurrence, is H or C$_{1-4}$alkyl;
X is —CH$_2$—, —NH—, or —O—;
m is 1, 2, 3, or 4, particularly 1 or 2;
p is 1; and
each R$^3$ is independently optionally substituted C$_{1-6}$ aliphatic, such as methyl, or halogen, such as bromo and/or chloro, including dichloro, including wherein n is 2 and $R^3$ is chloro at the 7- and 8-positions with respect to the quinoline ring.

In further particular embodiments, the present disclosure provides a compound of formula I-a-5, wherein:

each $R^6$ is independently halogen, —$C_{1-4}$alkyl, —$C_{1-4}$haloalkyl, =$CH_2$, —$(CH_2)_{0-4}CO_2H$, —$(CH_2)_{0-4}CO(N$-proline), —$(CH_2)_{0-4}C(O)NR^a$ $(CH_2)_{1-4}CO_2H$, —OH, —$(CH_2)_{1-4}OH$, —$(CH_2)_{0-4}O$ $(CH_2)_{1-5}CO_2H$, —$(CH_2)_{0-4}O(CH_2)_{1-5}CO_2C_{1-4}$alkyl, —$(CH_2)_{0-4}SO_3H$, —$(CH_2)_{0-4}SO_2NH_2$, —$(CH_2)_{0-4}NR^aSO_2C_{1-4}$alkyl, —$(CH_2)_{0-4}OP(OH)_2$, or —$(CR_2)_{0-4}OP(O)(H)OH$;

X is —$CH_2$—, —NH—, or —O—;

m is 1 or 2;

p is 1; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In certain embodiments, for the above disclosed compounds of formula I-a-5, m is 1 or 2, and at least one $R^6$ includes a terminal —$CO_2H$ group. For example, in certain instances, at least one $R^6$ is —$(CH_2)_{0-4}CO_2H$ or —$(CH_2)_{0-4}O(CH_2)_{1-5}CO_2H$.

In particular embodiments, the present disclosure provides a compound of formula I-a-5, wherein:

each $R^6$ is independently halogen, =O, —$(CH_2)_{0-4}CO_2H$, —$(CH_2)_{0-4}CO_2C_{1-4}$alkyl, —$(CH_2)_{0-4}CONH_2$, —$(CH_2)_{0-4}CONHC_{1-4}$alkyl, —$(CH_2)_{0-4}CON(C_{1-4}$alkyl$)_2$, —$(CH_2)_{0-4}CO(N$-proline), —$(CH_2)_{0-4}C(O)NR^a$ $(CH_2)_{1-4}CO_2H$, —$(CH_2)_{0-4}C(O)NR^a(CH_2)_{1-4}CONH_2$, —$(CH_2)_{0-4}C(O)NR^a(CH_2)_{1-4}CONHC_{1-4}$alkyl, —$(CH_2)_{0-4}C(O)NR^a(CH_2)_{1-4}CON(C_{1-4}$alkyl$)_2$, —OH, —$(CH_2)_{1-4}OH$, —$(CH_2)_{0-4}OC_{1-4}$alkyl, —$NH_2$, —$(CH_2)_{1-4}NH_2$, —$(CH_2)_{0-4}NHC_{1-4}$alkyl, —$(CH_2)_{0-4}N(C_{1-4}$alkyl$)_2$, —$(CH_2)_{0-4}SO_3H$, —$(CH_2)_{0-4}SO_2NH_2$, —$(CH_2)_{0-4}SO_2NHC_{1-4}$alkyl, —$(CH_2)_{0-4}NR^aSO_2C_{1-4}$alkyl, —$(CH_2)_{0-4}OP(OH)_2$, —$(CH_2)_{0-4}OP(OH)(OC_{1-4}$alkyl), or —$(CR_2)_{0-4}OP(O)(H)OH$, wherein $R^a$, independently for each occurrence, is H or $C_{1-4}$alkyl;

X is —$CH_2$—, —NH—, or —O—;

m is 1, 2, 3, or 4, particularly 1 or 2;

p is 1; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In further particular embodiments, the present disclosure provides a compound of formula I-a-5, wherein:

each $R^6$ is independently halogen, —$(CH_2)_{0-4}CO_2H$, —$(CH_2)_{0-4}CO(N$-proline), —$(CH_2)_{0-4}C(O)NR^a$ $(CH_2)_{1-4}CO_2H$, —OH, —$(CH_2)_{1-4}OH$, —$(CH_2)_{0-4}SO_3H$, —$(CH_2)_{0-4}SO_2NH_2$, —$(CH_2)_{0-4}NR^aSO_2C_{1-4}$alkyl, —$(CH_2)_{0-4}OP(OH)_2$, or —$(CR_2)_{0-4}OP(O)(H)OH$;

X is —$CH_2$—, —NH—, or —O—;

m is 1 or 2;

p is 1; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In certain embodiments, for the above disclosed compounds of formula I-a-5, m is 1 or 2, and at least one $R^6$ includes a terminal —$CO_2H$ group. For example, in certain instances, at least one $R^6$ is —$(CH_2)_{0-4}CO_2H$ or —$(CH_2)_{0-4}O(CH_2)_{1-5}CO_2H$.

In some embodiments, the present disclosure provides a compound of formula I, wherein $R^2$ is

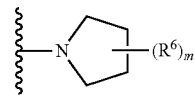

thereby forming a compound of formula I-a-6:

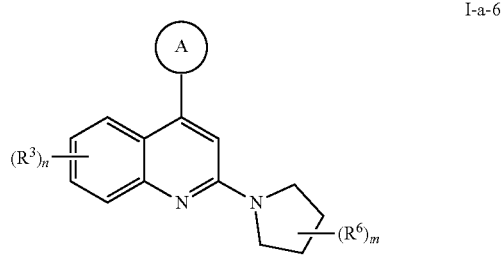

I-a-6 or a pharmaceutically acceptable salt thereof, wherein:

each $R^6$ is independently halogen, =O, =$CR_2$, —COR, —$(CR_2)_{0-6}CO_2R$, —$(CR_2)_{0-6}CONR_2$, —OR, —$(CR_2)_{1-4}OR$, —$NR_2$, —$(CR_2)_{1-4}NR_2$, —NRC(O) OR, —NRC(O)R, —NRC(O)$NR_2$, —SR, —$SO_2R$, —S(O)R, —$(CR_2)_{0-6}SO_3R$, —$(CR_2)_{0-6}SO_2NR_2$, —$(CR_2)_{0-6}OSO_2NR_2$, —$(CR_2)_{0-6}NRSO_2R$, —$(CR_2)_{0-6}NRSO_2OR$, —$(CR_2)_{0-6}OP(OR)_2$, —$(CR_2)_{0-6}OP(O)(OR)_2$, —$(CR_2)_{0-6}P(O)(OR)_2$, —$(CR_2)_{0-6}OP(O)(H)OR$, —$B(OR)_2$, or $R^B$;

m is 0, 1, 2, 3, or 4, particularly 1, 2, 3, or 4; and each of Ring A, R, $R^3$, $R^B$, and n is as defined above and described in embodiments herein, both singly and in combination.

In certain embodiments, the present disclosure provides a compound of formula I-a-6, wherein Ring A is an optionally substituted phenyl, preferably substituted phenyl. In certain embodiments, the present disclosure provides a compound of formula I-a-6, wherein Ring A is optionally substituted HetCy. In certain embodiments, the present disclosure provides a compound of formula I-a-6, wherein Ring A is an optionally substituted HetAr.

In some embodiments, the present disclosure provides a compound of formula I-a-6, wherein $R^6$ is not $R^B$.

In certain embodiments, the present disclosure provides a compound of formula I-a-6, wherein $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In certain embodiments, the present disclosure provides a compound of formula I-a-6, wherein:

each $R^6$ is independently halogen, —$C_{1-4}$alkyl, —$C_{1-4}$haloalkyl, =$CR_2$, =O, —COR, —$(CR_2)_{0-6}CO_2R$, —$(CR_2)_{0-6}CONR_2$, —OR, —$(CR_2)_{1-4}OR$, —$NR_2$, —$(CR_2)_{1-4}NR_2$, —NRC(O) OR, —NRC(O)R, —NRC(O)$NR_2$, —SR, —$SO_2R$, —S(O)R, —$(CR_2)_{0-6}SO_3R$, —$(CR_2)_{0-6}SO_2NR_2$, —(CR$_2$)$_{0-6}$OSO$_2$NR$_2$, —(CR$_2$)$_{0-6}$NRSO$_2$R, —(CR$_2$)$_{0-6}$NRSO$_2$OR, —(CR$_2$)$_{0-6}$OP(OR)$_2$, —(CR$_2$)$_{0-6}$OP(O)(OR)$_2$, —(CR$_2$)$_{0-6}$P(O)(OR)$_2$, —(CR$_2$)$_{0-6}$OP(O)(H)OR, or —B(OR)$_2$;

m is 1, 2, 3, or 4, particularly 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In particular embodiments, the present disclosure provides a compound of formula I-a-6, wherein:

each $R^6$ is independently halogen, —C$_{1-4}$alkyl, —C$_{1-4}$haloalkyl, =CH$_2$, =O, —(CH$_2$)$_{0-4}$CO$_2$H, —(CH$_2$)$_{0-4}$CO$_2$C$_{1-4}$alkyl, —(CH$_2$)$_{0-4}$CO$_2$C$_{1-4}$haloalkyl, —(CH$_2$)$_{0-4}$CONH$_2$, —(CH$_2$)$_{0-4}$CONHC$_{1-4}$alkyl, —(CH$_2$)$_{0-4}$CON(C$_{1-4}$alkyl)$_2$, —(CH$_2$)$_{0-4}$CO(N-proline), —(CH$_2$)$_{0-4}$CO(N-pyrrolidine-3-carboxylic acid), —(CH$_2$)$_{0-4}$(N-pyrazole)-(CH$_2$)$_{0-4}$CO$_2$H, —(CH$_2$)$_{0-4}$CO(N-pyrazole)-(CH$_2$)$_{0-4}$CO$_2$C$_{1-4}$alkyl, —(CH$_2$)$_{0-4}$(N-pyrrole)-(CH$_2$)$_{0-4}$CO$_2$H, —(CH$_2$)$_{0-4}$CO(N-pyrrole)-(CH$_2$)$_{0-4}$CO$_2$C$_{1-4}$alkyl, —(CH$_2$)$_{0-4}$—O(phenyl)-(CH$_2$)$_{0-4}$CO$_2$H, —(CH$_2$)$_{0-4}$—O(phenyl)-(CH$_2$)$_{0-4}$CO$_2$C$_{1-4}$alkyl, —(CH$_2$)$_{0-4}$—O(cycloalkane)-(CH$_2$)$_{0-4}$CO$_2$H, —(CH$_2$)$_{0-4}$—O(cycloalkane)-(CH$_2$)$_{0-4}$CO$_2$C$_{1-4}$alkyl, —(CH$_2$)$_{0-4}$C(O)NR$^a$(CH$_2$)$_{1-4}$CO$_2$H, —(CH$_2$)$_{0-4}$C(O)NR$^a$—CH(C$_{1-4}$alkyl)-CO$_2$H, —(CH$_2$)$_{0-4}$C(O)NR$^a$(CH$_2$)$_{1-4}$CONH$_2$, —(CH$_2$)$_{0-4}$C(O)NR$^a$(CH$_2$)$_{1-4}$CONHC$_{1-4}$alkyl, —(CH$_2$)$_{0-4}$C(O)NR$^a$(CH$_2$)$_{1-4}$CON(C$_{1-4}$alkyl)$_2$, —OH, —(CH$_2$)$_{1-4}$OH, —(CH$_2$)$_{0-4}$OC$_{1-4}$alkyl, —(CH$_2$)$_{0-4}$O(CH$_2$)$_{1-5}$CO$_2$H, —(CH$_2$)$_{0-4}$O(CH$_2$)$_{1-5}$CO$_2$C$_{1-4}$alkyl, —(CH$_2$)$_{1-4}$O(CH$_2$)$_{1-4}$CHFCO$_2$H, —(CH$_2$)$_{1-4}$O(CH$_2$)$_{1-4}$CHFCO$_2$C$_{1-4}$alkyl, —(CH$_2$)$_{1-4}$OCH(CH$_3$)(CH$_2$)$_{1-4}$CO$_2$H, —(CH$_2$)$_{1-4}$OCH(CH$_3$)(CH$_2$)$_{1-4}$CO$_2$C$_{1-4}$alkyl, —(CH$_2$)$_{1-4}$O(CH$_2$)$_{1-4}$CH(CH$_3$)CO$_2$H, —(CH$_2$)$_{1-4}$O(CH$_2$)$_{1-4}$CH(CH$_3$)CO$_2$C$_{1-4}$alkyl, —CHOH(CH$_2$)$_{1-4}$O(CH$_2$)$_{1-5}$CO$_2$H, —CHOH(CH$_2$)$_{1-4}$O(CH$_2$)$_{1-5}$CO$_2$C$_{1-4}$alkyl, —CHCF$_3$(CH$_2$)$_{1-4}$O(CH$_2$)$_{1-5}$CO$_2$H, —CHCF$_3$(CH$_2$)$_{1-4}$O—(CH$_2$)$_{1-5}$CO$_2$C$_{1-4}$alkyl, —(CH$_2$)$_{1-4}$O(CH$_2$)$_{1-5}$CONR$^a$$_2$, —(CH$_2$)$_{1-4}$O(CH$_2$)$_{1-5}$CONR$^a$OH, —(CH$_2$)$_{1-4}$O(CH$_2$)$_{1-5}$CONR$^a$CN, —(CH$_2$)$_{1-4}$O(CH$_2$)$_{1-5}$P(O)OH$_2$, —NH$_2$, —(CH$_2$)$_{0-4}$NR$^a$(CH$_2$)$_{1-4}$CO$_2$H, —(CH$_2$)$_{0-4}$NR$^a$(CH$_2$)$_{1-4}$CO$_2$C$_{1-4}$alkyl, —(CH$_2$)$_{1-4}$NH$_2$, —(CH$_2$)$_{0-4}$NHC$_{1-4}$alkyl, —(CH$_2$)$_{0-4}$NR$^a$C(O)C$_{1-4}$alkyl, —(CH$_2$)$_{0-4}$NR$^a$C(O)Ph, —(CH$_2$)$_{0-4}$NR$^a$CO(CH$_2$)$_{1-4}$OH, —(CH$_2$)$_{0-4}$N(C$_{1-4}$alkyl)$_2$, —(CH$_2$)$_{0-4}$SO$_3$H, —(CH$_2$)$_{0-4}$SO$_2$NH$_2$, —(CH$_2$)$_{0-4}$SO$_2$NR$^a$C$_{1-4}$alkyl, —(CH$_2$)$_{0-4}$NR$^a$SO$_2$C$_{1-4}$alkyl, —(CH$_2$)$_{0-4}$NR$^a$SO$_2$Ph, —(CH$_2$)$_{0-4}$NR$^a$SO$_2$(CH$_2$)$_{1-4}$CO$_2$H, —(CH$_2$)$_{0-4}$OP(OH)$_2$, —(CH$_2$)$_{0-4}$OP(OH)(OC$_{1-4}$alkyl), or —(CR$_2$)$_{0-4}$OP(O)(H)OH, wherein R$^a$, independently for each occurrence, is H or C$_{1-4}$alkyl;

m is 1, 2, 3, or 4, particularly 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In further particular embodiments, the present disclosure provides a compound of formula I-a-6, wherein:

each $R^6$ is independently halogen, —C$_{1-4}$alkyl, —C$_{1-4}$haloalkyl, =CH$_2$, —(CH$_2$)$_{0-4}$CO$_2$H, —(CH$_2$)$_{0-4}$CO$_2$C$_{1-4}$alkyl, —(CH$_2$)$_{0-4}$CO$_2$C$_{1-4}$haloalkyl, —(CH$_2$)$_{0-4}$CO(N-proline), —(CH$_2$)$_{0-4}$CO(N-pyrrolidine-3-carboxylic acid), —(CH$_2$)$_{0-4}$C(O)NR$^a$(CH$_2$)$_{1-4}$CO$_2$H, —(CH$_2$)$_{0-4}$C(O)NR$^a$—CH(C$_{1-4}$alkyl)-CO$_2$H, —OH, —(CH$_2$)$_{1-4}$OH, —(CH$_2$)$_{0-4}$OC$_{1-4}$alkyl, —(CH$_2$)$_{0-4}$O(CH$_2$)$_{1-5}$CO$_2$H, —(CH$_2$)$_{0-4}$O(CH$_2$)$_{1-5}$CO$_2$C$_{1-4}$alkyl, —(CH$_2$)$_{0-4}$NR$^a$C(O)C$_{1-4}$alkyl, —(CH$_2$)$_{0-4}$NR$^a$C(O)Ph, —(CH$_2$)$_{0-4}$NR$^a$CO(CH$_2$)$_{1-4}$OH, —(CH$_2$)$_{0-4}$SO$_3$H, —(CH$_2$)$_{0-4}$SO$_2$NH$_2$, —(CH$_2$)$_{0-4}$NR$^a$SO$_2$C$_{1-4}$alkyl, —(CH$_2$)$_{0-4}$NR$^a$SO$_2$Ph, —(CH$_2$)$_{0-4}$NR$^a$SO$_2$(CH$_2$)$_{1-4}$CO$_2$H, —(CH$_2$)$_{0-4}$OP(OH)$_2$, or —(CR$_2$)$_{0-4}$OP(O)(H)OH, wherein R$^a$, independently for each occurrence, is H or C$_{1-4}$alkyl;

m is 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In particular embodiments, the present disclosure provides a compound of formula I-a-6, wherein:

each $R^6$ is independently halogen, —C$_{1-4}$alkyl, —C$_{1-4}$haloalkyl, —C$_{3-6}$cycloalkyl, =CH$_2$, =O, —(CH$_2$)$_{0-4}$CO$_2$H, —(CH$_2$)$_{0-4}$CO$_2$C$_{1-4}$alkyl, —(CH$_2$)$_{0-4}$CO$_2$C$_{1-4}$haloalkyl, —(CH$_2$)$_{0-4}$O(CH$_2$)$_{1-5}$CO$_2$H, —(CH$_2$)$_{0-4}$O(CH$_2$)$_{1-5}$CO$_2$C$_{1-4}$alkyl, —(CH$_2$)$_{1-4}$O(CH$_2$)$_{1-4}$CHFCO$_2$H, —(CH$_2$)$_{1-4}$O(CH$_2$)$_{1-4}$CHFCO$_2$C$_{1-4}$alkyl, —(CH$_2$)$_{1-4}$OCH(CH$_3$)(CH$_2$)$_{1-4}$CO$_2$H, —(CH$_2$)$_{1-4}$OCH(CH$_3$)(CH$_2$)$_{1-4}$CO$_2$C$_{1-4}$alkyl, —(CH$_2$)$_{1-4}$O(CH$_2$)$_{1-4}$CH(CH$_3$)CO$_2$H, —(CH$_2$)$_{1-4}$O(CH$_2$)$_{1-4}$CH(CH$_3$)CO$_2$C$_{1-4}$alkyl, —CHOH(CH$_2$)$_{1-4}$O(CH$_2$)$_{1-5}$CO$_2$H, —CHOH(CH$_2$)$_{1-4}$O(CH$_2$)$_{1-5}$CO$_2$C$_{1-4}$alkyl, —CHCF$_3$(CH$_2$)$_{1-4}$O(CH$_2$)$_{1-5}$CO$_2$H, —CHCF$_3$(CH$_2$)$_{1-4}$O—(CH$_2$)$_{1-5}$CO$_2$C$_{1-4}$alkyl, —(CH$_2$)$_{1-4}$O(CH$_2$)$_{1-5}$CONR$^a$$_2$, —(CH$_2$)$_{1-4}$O(CH$_2$)$_{1-5}$CONR$^a$OH, —(CH$_2$)$_{1-4}$O(CH$_2$)$_{1-5}$CONR$^a$CN, —(CH$_2$)$_{1-4}$O(CH$_2$)$_{1-5}$P(O)OH$_2$, —(CH$_2$)$_{0-4}$CONH$_2$, —(CH$_2$)$_{0-4}$CONHC$_{1-4}$alkyl, —(CH$_2$)$_{0-4}$CON(C$_{1-4}$alkyl)$_2$, —(CH$_2$)$_{0-4}$CO(N-proline), —(CH$_2$)$_{0-4}$CO(N-pyrrolidine-3-carboxylic acid), —(CH$_2$)$_{0-4}$(N-pyrazole)-(CH$_2$)$_{0-4}$CO$_2$H, —(CH$_2$)$_{0-4}$CO(N-pyrazole)-(CH$_2$)$_{0-4}$CO$_2$C$_{1-4}$alkyl, —(CH$_2$)$_{0-4}$(N-pyrrole)-(CH$_2$)$_{0-4}$CO$_2$H, —(CH$_2$)$_{0-4}$CO(N-pyrrole)-(CH$_2$)$_{0-4}$CO$_2$C$_{1-4}$alkyl, —(CH$_2$)$_{0-4}$—O(phenyl)-(CH$_2$)$_{0-4}$CO$_2$H, —(CH$_2$)$_{0-4}$—O(phenyl)-(CH$_2$)$_{0-4}$CO$_2$C$_{1-4}$alkyl, —(CH$_2$)$_{0-4}$—O(cycloalkane)-(CH$_2$)$_{0-4}$CO$_2$H, —(CH$_2$)$_{0-4}$—O(cycloalkane)-(CH$_2$)$_{0-4}$CO$_2$C$_{1-4}$alkyl, —(CH$_2$)$_{0-4}$C(O)NR$^a$(CH$_2$)$_{1-4}$CO$_2$H, —(CH$_2$)$_{0-4}$C(O)NR$^a$—CH(C$_{1-4}$alkyl)-CO$_2$H, —(CH$_2$)$_{0-4}$C(O)NR$^a$(CH$_2$)$_{1-4}$CONH$_2$, —(CH$_2$)$_{0-4}$C(O)NR$^a$(CH$_2$)$_{1-4}$CONHC$_{1-4}$alkyl, —(CH$_2$)$_{0-4}$C(O)NR$^a$(CH$_2$)$_{1-4}$CON(C$_{1-4}$alkyl)$_2$, —OH, —(CH$_2$)$_{1-4}$OH, —(CH$_2$)$_{0-4}$OC$_{1-4}$alkyl, —(CH$_2$)$_{0-4}$OC(O)C$_{1-4}$alkyl, —NH$_2$, —(CH$_2$)$_{0-4}$NR$^a$(CH$_2$)$_{1-4}$CO$_2$H, —(CH$_2$)$_{0-4}$NR$^a$(CH$_2$)$_{1-4}$CO$_2$C$_{1-4}$alkyl, —(CH$_2$)$_{1-4}$NH$_2$, —(CH$_2$)$_{0-4}$NHC$_{1-4}$alkyl, —(CH$_2$)$_{0-4}$NR$^a$C(O)C$_{1-4}$alkyl, —(CH$_2$)$_{0-4}$NR$^a$C(O)Ph, —(CH$_2$)$_{0-4}$NR$^a$CO(CH$_2$)$_{1-4}$OH, —(CH$_2$)$_{0-4}$N(C$_{1-4}$alkyl)$_2$, —(CH$_2$)$_{0-4}$SO$_3$H, —(CH$_2$)$_{0-4}$SO$_2$NH$_2$, —(CH$_2$)$_{0-4}$SO$_2$NR$^a$C$_{1-4}$alkyl, —(CH$_2$)$_{0-4}$NR$^a$SO$_2$C$_{1-4}$alkyl, —(CH$_2$)$_{0-4}$NR$^a$SO$_2$Ph, —(CH$_2$)$_{0-4}$NR$^a$SO$_2$(CH$_2$)$_{1-4}$CO$_2$H, —(CH$_2$)$_{0-4}$OP(OH)$_2$, —(CH$_2$)$_{0-4}$OP(OH)(OC$_{1-4}$alkyl), or —(CR$_2$)$_{0-4}$OP(O)(H)OH, wherein R$^a$, independently for each occurrence, is H or C$_{1-4}$alkyl;

m is 1, 2, 3, or 4, particularly 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In further particular embodiments, the present disclosure provides a compound of formula I-a-6, wherein:

each $R^6$ is independently halogen, —$C_{1-4}$alkyl, —$C_{1-4}$haloalkyl, —$C_{3-6}$cycloalkyl, =$CH_2$, —$(CH_2)_{0-4}CO_2H$, —$(CH_2)_{0-4}O(CH_2)_{1-5}CO_2H$, —$(CH_2)_{0-4}O(CH_2)_{1-5}CO_2C_{1-4}$alkyl, —$(CH_2)_{0-4}CO(N$-proline), —$(CH_2)_{0-4}CO(N$-pyrrolidine-3-carboxylic acid), —$(CH_2)_{0-4}C(O)NR^a(CH_2)_{1-4}CO_2H$, —$(CH_2)_{0-4}C(O)NR^a$—$CH(C_{1-4}$alkyl$)$-$CO_2H$, —OH, —$(CH_2)_{1-4}OH$, —$(CH_2)_{0-4}OC_{1-4}$alkyl, —$(CH_2)_{0-4}OC(O)C_{1-4}$alkyl, —$(CH_2)_{0-4}NR^aC(O)C_{1-4}$alkyl, —$(CH_2)_{0-4}NR^aC(O)Ph$, —$(CH_2)_{0-4}NR^aCO(CH_2)_{1-4}OH$, —$(CH_2)_{0-4}SO_3H$, —$(CH_2)_{0-4}SO_2NH_2$, —$(CH_2)_{0-4}NR^aSO_2C_{1-4}$alkyl, —$(CH_2)_{0-4}NR^aSO_2Ph$, —$(CH_2)_{0-4}NR^aSO_2(CH_2)_{1-4}CO_2H$, —$(CH_2)_{0-4}OP(OH)_2$, or —$(CR_2)_{0-4}OP(O)(H)OH$, wherein $R^a$, independently for each occurrence, is H or $C_{1-4}$alkyl;

m is 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In further particular embodiments, the present disclosure provides a compound of formula I-a-6, wherein each $R^6$ is independently fluoro, -methyl, cyclohexyl, -methoxy, —OtBu, —$CF_3$, —$(CH_2)_{1-5}CO_2H$, —$(CH_2)_{1-5}CO_2C_{1-4}$alkyl, —$(CH_2)_{0-4}O(CH_2)_{1-5}CO_2H$, —$(CH_2)_{0-4}O(CH_2)_{1-5}CO_2C_{1-4}$alkyl, or —OH; and m is 1, 2, or 3, particularly 1 or 2.

In particular embodiments, the present disclosure provides a compound of formula I-a-6, wherein:

each $R^6$ is independently halogen, —$C_{1-4}$alkyl, —$C_{1-4}$haloalkyl, —$C_{3-6}$cycloalkyl, =$CH_2$, =O, —$(CH_2)_{0-4}CO_2H$, —$(CH_2)_{0-4}CO_2C_{1-4}$alkyl, —$(CH_2)_{0-4}O(CH_2)_{1-5}CO_2H$, —$(CH_2)_{0-4}O(CH_2)_{1-5}CO_2C_{1-4}$alkyl, —$(CH_2)_{0-4}CONH_2$, —$(CH_2)_{0-4}CONHC_{1-4}$alkyl, —$(CH_2)_{0-4}CON(C_{1-4}$alkyl$)_2$, —$(CH_2)_{0-4}CO(N$-proline), —$(CH_2)_{0-4}CO(N$-pyrrolidine-3-carboxylic acid), —$(CH_2)_{0-4}C(O)NR^a(CH_2)_{1-4}CO_2H$, —$(CH_2)_{0-4}C(O)NR^a$—$CH(C_{1-4}$alkyl$)$-$CO_2H$, —$(CH_2)_{0-4}C(O)NR^a(CH_2)_{1-4}CONH_2$, —$(CH_2)_{0-4}C(O)NR^a(CH_2)_{1-4}CONHC_{1-4}$alkyl, —$(CH_2)_{0-4}C(O)NR^a(CH_2)_{1-4}CON(C_{1-4}$alkyl$)_2$, —OH, —$(CH_2)_{1-4}OH$, —$(CH_2)_{0-4}OC_{1-4}$alkyl, —$NH_2$, —$(CH_2)_{1-4}NH_2$, —$(CH_2)_{0-4}NHC_{1-4}$alkyl, —$(CH_2)_{0-4}NR^aC(O)C_{1-4}$alkyl, —$(CH_2)_{0-4}NR^aC(O)Ph$, —$(CH_2)_{0-4}NR^aCO(CH_2)_{1-4}OH$, —$(CH_2)_{0-4}N(C_{1-4}$alkyl$)_2$, —$(CH_2)_{0-4}SO_3H$, —$(CH_2)_{0-4}SO_2NH_2$, —$(CH_2)_{0-4}SO_2NR^aC_{1-4}$alkyl, —$(CH_2)_{0-4}NR^aSO_2C_{1-4}$alkyl, —$(CH_2)_{0-4}NR^aSO_2Ph$, —$(CH_2)_{0-4}NR^aSO_2(CH_2)_{1-4}CO_2H$, —$(CH_2)_{0-4}OP(OH)_2$, —$(CH_2)_{0-4}OP(OH)(OC_{1-4}$alkyl), or —$(CR_2)_{0-4}OP(O)(H)OH$, wherein $R^a$, independently for each occurrence, is H or $C_{1-4}$alkyl;

m is 1, 2, 3, or 4, particularly 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In further particular embodiments, the present disclosure provides a compound of formula I-a-6, wherein:

each $R^6$ is independently halogen, —$C_{1-4}$alkyl, —$C_{1-4}$haloalkyl, —$C_{3-6}$cycloalkyl, =$CH_2$, —$(CH_2)_{0-4}CO_2H$, —$(CH_2)_{1-4}O(CH_2)_{1-5}CO_2H$, —$(CH_2)_{1-4}O(CH_2)_{1-5}CO_2C_{1-4}$alkyl, —$(CH_2)_{0-4}CO(N$-proline), —$(CH_2)_{0-4}CO(N$-pyrrolidine-3-carboxylic acid), —$(CH_2)_{0-4}C(O)NR^a(CH_2)_{1-4}CO_2H$, —$(CH_2)_{0-4}C(O)NR^a$—$CH(C_{1-4}$alkyl$)$-$CO_2H$, —OH, —$(CH_2)_{1-4}OH$, —$(CH_2)_{0-4}OC_{1-4}$alkyl, —$(CH_2)_{0-4}NR^aC(O)C_{1-4}$alkyl, —$(CH_2)_{0-4}NR^aC(O)Ph$, —$(CH_2)_{0-4}NR^aCO(CH_2)_{1-4}OH$, —$(CH_2)_{0-4}SO_3H$, —$(CH_2)_{0-4}SO_2NH_2$, —$(CH_2)_{0-4}NR^aSO_2C_{1-4}$alkyl, —$(CH_2)_{0-4}NR^aSO_2Ph$, —$(CH_2)_{0-4}NR^aSO_2(CH_2)_{1-4}CO_2H$, —$(CH_2)_{0-4}OP(OH)_2$, or —$(CR_2)_{0-4}OP(O)(H)OH$, wherein $R^a$, independently for each occurrence, is H or $C_{1-4}$alkyl;

m is 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In certain embodiments, the present disclosure provides a compound of formula I-a-6, wherein:

each $R^6$ is independently halogen, =O, —COR, —$(CR_2)_{0-6}CO_2R$, —$(CR_2)_{0-6}CONR_2$, —OR, —$(CR_2)_{1-4}OR$, —$NR_2$, —$(CR_2)_{1-4}NR_2$, —NRC(O)OR, —NRC(O)R, —NRC(O)NR_2, —SR, —$SO_2R$, —S(O)R, —$(CR_2)_{0-6}SO_3R$, —$(CR_2)_{0-6}SO_2NR_2$, —$(CR_2)_{0-6}OSO_2NR_2$, —$(CR_2)_{0-6}NRSO_2R$, —$(CR_2)_{0-6}NRSO_2OR$, —$(CR_2)_{0-6}OP(OR)_2$, —$(CR_2)_{0-6}OP(O)(OR)_2$, —$(CR_2)_{0-6}P(O)(OR)_2$, —$(CR_2)_{0-6}OP(O)(H)OR$, or —$B(OR)_2$;

m is 1, 2, 3, or 4, particularly 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In particular embodiments, the present disclosure provides a compound of formula I-a-6, wherein:

each $R^6$ is independently halogen, =O, —$(CH_2)_{0-4}CO_2H$, —$(CH_2)_{0-4}CO_2C_{1-4}$alkyl, —$(CH_2)_{0-4}CONH_2$, —$(CH_2)_{0-4}CONHC_{1-4}$alkyl, —$(CH_2)_{0-4}CON(C_{1-4}$alkyl$)_2$, —$(CH_2)_{0-4}CO(N$-proline), —$(CH_2)_{0-4}CO(N$-pyrrolidine-3-carboxylic acid), —$(CH_2)_{0-4}C(O)NR^a(CH_2)_{1-4}CO_2H$, —$(CH_2)_{0-4}C(O)NR^a$—$CH(C_{1-4}$alkyl$)$-$CO_2H$, —$(CH_2)_{0-4}C(O)NR^a(CH_2)_{1-4}CONH_2$, —$(CH_2)_{0-4}C(O)NR^a(CH_2)_{1-4}CONHC_{1-4}$alkyl, —$(CH_2)_{0-4}C(O)NR^a(CH_2)_{1-4}CON(C_{1-4}$alkyl$)_2$, —OH, —$(CH_2)_{1-4}OH$, —$(CH_2)_{0-4}OC_{1-4}$alkyl, —$NH_2$, —$(CH_2)_{1-4}NH_2$, —$(CH_2)_{0-4}NHC_{1-4}$alkyl, —$(CH_2)_{0-4}NR^aC(O)C_{1-4}$alkyl, —$(CH_2)_{0-4}NR^aC(O)Ph$, —$(CH_2)_{0-4}NR^aCO(CH_2)_{1-4}OH$, —$(CH_2)_{0-4}N(C_{1-4}$alkyl$)_2$, —$(CH_2)_{0-4}SO_3H$, —$(CH_2)_{0-4}SO_2NH_2$, —$(CH_2)_{0-4}SO_2NR^aC_{1-4}$alkyl, —$(CH_2)_{0-4}NR^aSO_2C_{1-4}$alkyl, —$(CH_2)_{0-4}NR^aSO_2Ph$, —$(CH_2)_{0-4}NR^aSO_2(CH_2)_{1-4}CO_2H$, —$(CH_2)_{0-4}OP(OH)_2$, —$(CH_2)_{0-4}OP(OH)(OC_{1-4}$alkyl), or —$(CR_2)_{0-4}OP(O)(H)OH$, wherein $R^a$, independently for each occurrence, is H or $C_{1-4}$alkyl;

m is 1, 2, 3, or 4, particularly 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In further particular embodiments, the present disclosure provides a compound of formula I-a-6, wherein:

each $R^6$ is independently halogen, $-(CH_2)_{0-4}CO_2H$, $-(CH_2)_{0-4}CO(N\text{-proline})$, $-(CH_2)_{0-4}CO(N\text{-pyrrolidine-3-carboxylic acid})$, $-(CH_2)_{0-4}C(O)NR^a(CH_2)_{1-4}CO_2H$, $-(CH_2)_{0-4}C(O)NR^a-CH(C_{1-4}\text{alkyl})\text{-}CO_2H$, $-OH$, $-(CH_2)_{1-4}OH$, $-(CH_2)_{0-4}NR^aC(O)C_{1-4}\text{alkyl}$, $-(CH_2)_{0-4}NR^aC(O)Ph$, $-(CH_2)_{0-4}NR^aCO(CH_2)_{1-4}OH$, $-(CH_2)_{0-4}SO_3H$, $-(CH_2)_{0-4}SO_2NH_2$, $-(CH_2)_{0-4}NR^aSO_2C_{1-4}\text{alkyl}$, $-(CH_2)_{0-4}NR^aSO_2Ph$, $-(CH_2)_{0-4}NR^aSO_2(CH_2)_{1-4}CO_2H$, $-(CH_2)_{0-4}OP(OH)_2$, or $-(CR_2)_{0-4}OP(O)(H)OH$, wherein $R^a$, independently for each occurrence, is H or $C_{1-4}$alkyl;

m is 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In particular embodiments, the present disclosure provides a compound of formula I-a-6, wherein, m is 1;

$R^6$ is $-(CH_2)_{0-4}O(CH_2)_{1-5}CO_2H$, such as $-(CH_2)_{1-2}O(CH_2)_{2-3}CO_2H$, including $-CH_2O(CH_2)_2CO_2H$; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In certain embodiments, for the above disclosed compounds of formula I-a-6, m is 1 or 2, and at least one $R^6$ includes a terminal $-CO_2H$ group. For example, in certain instances, at least one $R^6$ is $-(CH_2)_{0-4}CO_2H$ or $-(CH_2)_{0-4}O(CH_2)_{1-5}CO_2H$.

In particular embodiments, the present disclosure provides a compound of formula I-a-6, wherein n is 2, $R^3$ is chloro at the 7- and 8-positions with respect to the quinoline ring and one instance of $R^6$ is $-(CH_2)_{0-4}O(CH_2)_{1-5}CO_2H$. In certain of such embodiments, the compound of formula I-a-6 is a compound of formula I-a-6*:

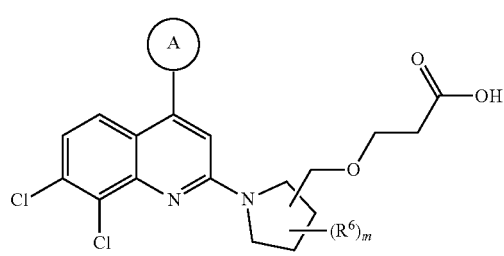

I-a-6* or a pharmaceutically acceptable salt thereof, wherein:
each of Ring A, $R^6$, and m is as defined above and described in embodiments herein, both singly and in combination. In particular embodiments, m is preferably zero.

In certain embodiments, the present disclosure provides a compound of formula I-a-6*, wherein Ring A is an optionally substituted phenyl, preferably substituted phenyl. In certain embodiments, the present disclosure provides a compound of formula I-a-6,* wherein Ring A is optionally substituted HetCy. In certain embodiments, the present disclosure provides a compound of formula I-a-6*, wherein Ring A is an optionally substituted HetAr.

In some embodiments, the present disclosure provides a compound of formula I, wherein $R^2$ is

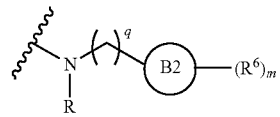

thereby forming a compound of formula I-a-7:

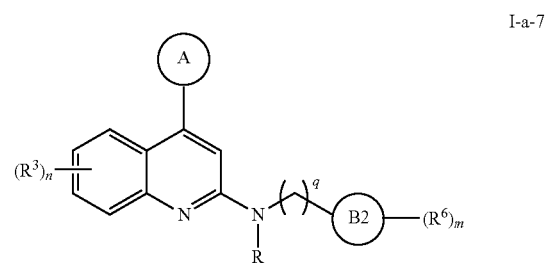

I-a-7 or a pharmaceutically acceptable salt thereof, wherein:
Ring B2 is phenyl; a 4- to 7-membered saturated or partially unsaturated carbocyclic or heterocyclic ring having 1 to 3 heteroatoms independently selected from nitrogen, oxygen, phosphorus, and sulfur; or a 5- to 6-membered heteroaryl ring having 1 to 4 heteroatoms independently selected from nitrogen, oxygen, phosphorus, and sulfur;

each $R^6$ is independently halogen, $-COR$, $-(CR_2)_{0-6}CO_2R$, $-(CR_2)_{0-6}CONR_2$, $-OR$, $-(CR_2)_{1-4}OR$, $-NR_2$, $-(CR_2)_{1-4}NR_2$, $-NRC(O)OR$, $-NRC(O)R$, $-NRC(O)NR_2$, $-SR$, $-SO_2R$, $-S(O)R$, $-(CR_2)_{0-6}SO_3R$, $-(CR_2)_{0-6}SO_2NR_2$, $-(CR_2)_{0-6}OSO_2NR_2$, $-(CR_2)_{0-6}NRSO_2R$, $-(CR_2)_{0-6}NRSO_2OR$, $-(CR_2)_{0-6}OP(OR)_2$, $-(CR_2)_{0-6}OP(O)(OR)_2$, $-(CR_2)_{0-6}P(O)(OR)_2$, $-(CR_2)_{0-6}OP(O)(H)OR$, $-B(OR)_2$, or $R^B$;

m is 0, 1, 2, 3, or 4, particularly 1, 2, 3, or 4;

q is 0, 1, or 2; and each of Ring A, R, $R^3$, $R^B$, and n is as defined above and described in embodiments herein, both singly and in combination.

In certain embodiments, the present disclosure provides a compound of formula I-a-7, wherein Ring A is an optionally substituted phenyl, preferably substituted phenyl. In certain embodiments, the present disclosure provides a compound of formula I-a-7, wherein Ring A is optionally substituted HetCy. In certain embodiments, the present disclosure provides a compound of formula I-a-7, wherein Ring A is an optionally substituted HetAr.

In certain embodiments, the present disclosure provides a compound of formula I-a-7, wherein Ring B2 is phenyl, particularly substituted phenyl. In other embodiments, Ring B2 is not phenyl. For example, Ring B2 may be a 4- to 10-membered saturated or partially unsaturated monocyclic or bicyclic carbocyclic or heterocyclic ring having 1 to 3 heteroatoms independently selected from nitrogen, oxygen, phosphorus, and sulfur. In some embodiments, Ring B2 is a 5- to 6-membered heteroaryl ring having 1 to 4 heteroatoms independently selected from nitrogen, oxygen, phosphorus, and sulfur.

In some embodiments, the present disclosure provides a compound of formula I-a-7, wherein $R^6$ is not $R^B$.

In some embodiments, the present disclosure provides a compound of formula I-a-7, wherein R in

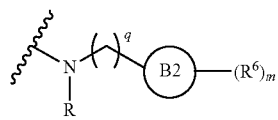

is $R^a$, which is H or $C_{1-6}$alkyl.

In certain embodiments, the present disclosure provides a compound of formula I-a-7, wherein $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In certain embodiments, for the above disclosed compounds of formula I-a-7, m is 1 or 2, and at least one $R^6$ includes a terminal —$CO_2H$ group. For example, in certain instances, at least one $R^6$ is —$(CH_2)_{0-4}CO_2H$ or —$(CH_2)_{0-4}O(CH_2)_{1-5}CO_2H$.

In some embodiments, the present disclosure provides a compound of formula I, wherein $R^2$ is

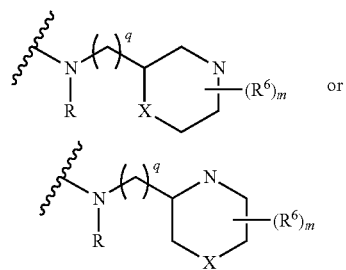

or thereby forming a compound of formula I-a-8 or formula I-a-8*, respectively:

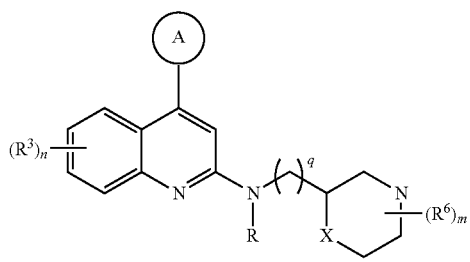

I-a-8

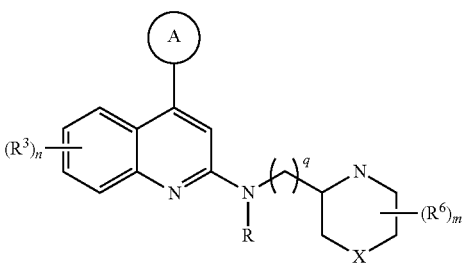

I-a-8* or a pharmaceutically acceptable salt thereof, wherein: each $R^6$ is independently hydrogen (only on N), halogen (not on N), —COR, —$(CR_2)_{0-6}CO_2R$, —$(CR_2)_{0-6}CONR_2$, —OR, —$(CR_2)_{1-4}OR$, —$NR_2$, —$(CR_2)_{1-4}NR_2$, —NRC(O)OR, —NRC(O)R, —NRC(O)$NR_2$, —SR, —$SO_2R$, —S(O)R, —$(CR_2)_{0-6}SO_3R$, —$(CR_2)_{0-6}SO_2NR_2$, —$(CR_2)_{0-6}OSO_2NR_2$, —$(CR_2)_{0-6}NRSO_2R$, —$(CR_2)_{0-6}NRSO_2OR$, —$(CR_2)_{0-6}OP(OR)_2$, —$(CR_2)_{0-6}OP(O)(OR)_2$, —$(CR_2)_{0-6}P(O)(OR)_2$, —$(CR_2)_{0-6}OP(O)(H)OR$, —$B(OR)_2$, or $R^B$;

X is absent (i.e., a bond in the ring), —$CR_2$—, —NR—, —O—, —S—, or —$SO_2$—, particularly —$CR_2$—, —NR—, or —O;

m is 1, 2, 3, or 4;

q is 0, 1, or 2; and each of Ring A, R, $R^3$, $R^B$, and n is as defined above and described in embodiments herein, both singly and in combination.

In certain embodiments, the present disclosure provides a compound of formula I-a-8 or formula I-a-8*, wherein Ring A is an optionally substituted phenyl, preferably substituted phenyl. In certain embodiments, the present disclosure provides a compound of formula I-a-8 or formula I-a-8*, wherein Ring A is optionally substituted HetCy. In certain embodiments, the present disclosure provides a compound of formula I-a-8 or formula I-a-8*, wherein Ring A is an optionally substituted HetAr.

In some embodiments, the present disclosure provides a compound of formula I-a-8 or formula I-a-8*, wherein $R^6$ is not $R^B$.

In some embodiments, the present disclosure provides a compound of formula I-a-8 or formula I-a-8*, wherein R in

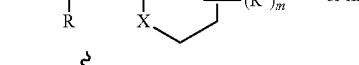

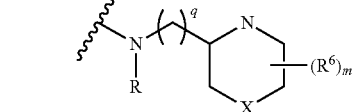

is $R^a$, which is H or $C_{1-6}$alkyl.

In certain embodiments, the present disclosure provides a compound of formula I-a-8 or formula I-a-8*, wherein $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In certain embodiments, the present disclosure provides a compound of formula I-a-8 or formula I-a-8*, wherein:

each $R^6$ is independently halogen, =O, —COR, —$(CR_2)_{0-6}CO_2R$, —$(CR_2)_{0-6}CONR_2$, —OR, —$(CR_2)_{1-4}OR$, —$NR_2$, —$(CR_2)_{1-4}NR_2$, —NRC(O)OR, —NRC(O)R, —NRC(O)$NR_2$, —SR, —$SO_2R$, —S(O)R, —$(CR_2)_{0-6}SO_3R$, —$(CR_2)_{0-6}SO_2NR_2$, —$(CR_2)_{0-6}OSO_2NR_2$, —$(CR_2)_{0-6}NRSO_2R$, —$(CR_2)_{0-6}NRSO_2OR$, —$(CR_2)_{0-6}OP(OR)_2$, —$(CR_2)_{0-6}OP(O)(OR)_2$, —$(CR_2)_{0-6}P(O)(OR)_2$, —$(CR_2)_{0-6}OP(O)(H)OR$, or —$B(OR)_2$;

m is 1, 2, 3, or 4, particularly 1 or 2;

q is 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In particular embodiments, the present disclosure provides a compound of formula I-a-8 or formula I-a-8*, wherein:

each R⁶ is independently halogen, =O, —(CH₂)₀₋₄CO₂H, —(CH₂)₀₋₄CO₂C₁₋₄alkyl, —(CH₂)₀₋₄CONH₂, —(CH₂)₀₋₄CONHC₁₋₄alkyl, —(CH₂)₀₋₄CON(C₁₋₄alkyl)₂, —(CH₂)₀₋₄CO(N-proline), —(CH₂)₀₋₄C(O)NRᵃ(CH₂)₁₋₄CO₂H, —(CH₂)₀₋₄C(O)NRᵃ(CH₂)₁₋₄CONH₂, —(CH₂)₀₋₄C(O)NRᵃ(CH₂)₁₋₄CONHC₁₋₄alkyl, —(CH₂)₀₋₄C(O)NRᵃ(CH₂)₁₋₄CON(C₁₋₄alkyl)₂, —OH, —(CH₂)₁₋₄OH, —(CH₂)₀₋₄OC₁₋₄alkyl, —NH₂, —(CH₂)₁₋₄NH₂, —(CH₂)₀₋₄NHC₁₋₄alkyl, —(CH₂)₀₋₄N(C₁₋₄alkyl)₂, —(CH₂)₀₋₄SO₃H, —(CH₂)₀₋₄SO₂NH₂, —(CH₂)₀₋₄SO₂NHC₁₋₄alkyl, —(CH₂)₀₋₄NRᵃSO₂C₁₋₄alkyl, —(CH₂)₀₋₄OP(OH)₂, —(CH₂)₀₋₄OP(OH)(OC₁₋₄alkyl), or —(CR₂)₀₋₄OP(O)(H)OH, wherein Rᵃ, independently for each occurrence, is H or C₁₋₄alkyl;

m is 1, 2, 3, or 4, particularly 1 or 2;

q is 1; and each R³ is independently optionally substituted C₁₋₆ aliphatic, such as methyl, or halogen, such as bromo and/or chloro, including dichloro, including wherein n is 2 and R³ is chloro at the 7- and 8-positions with respect to the quinoline ring.

In further particular embodiments, the present disclosure provides a compound of formula I-a-8 or formula I-a-8*, wherein:

each R⁶ is independently halogen, —(CH₂)₀₋₄CO₂H, —(CH₂)₀₋₄CO(N-proline), —(CH₂)₀₋₄C(O)NRᵃ(CH₂)₁₋₄CO₂H, —OH, —(CH₂)₁₋₄OH, —(CH₂)₀₋₄SO₃H, —(CH₂)₀₋₄SO₂NH₂, —(CH₂)₀₋₄NRᵃSO₂C₁₋₄alkyl, —(CH₂)₀₋₄OP(OH)₂, or —(CR₂)₀₋₄OP(O)(H)OH, wherein Rᵃ, independently for each occurrence, is H or C₁₋₄alkyl;

m is 1 or 2;

q is 1; and each R³ is independently optionally substituted C₁₋₆ aliphatic, such as methyl, or halogen, such as bromo and/or chloro, including dichloro, including wherein n is 2 and R³ is chloro at the 7- and 8-positions with respect to the quinoline ring.

In certain embodiments, for the above disclosed compounds of formula I-a-8 or I-a-8*, m is 1 or 2, and at least one R⁶ includes a terminal —CO₂H group. For example, in certain instances, at least one R⁶ is —(CH₂)₀₋₄CO₂H or —(CH₂)₀₋₄O(CH₂)₁₋₅CO₂H.

In some embodiments, the present disclosure provides a compound of formula I, wherein R² is

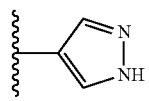 [SMILES: *c1cn[nH]c1]

thereby forming a compound of formula I-a-9:

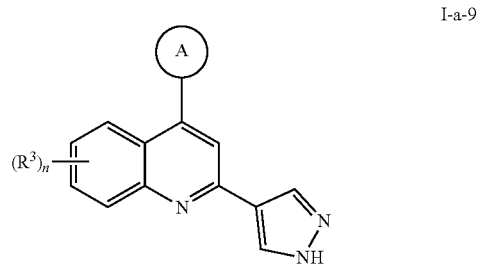

I-a-9 or a pharmaceutically acceptable salt thereof, wherein each of Ring A, R³, and n is as defined above and described in embodiments herein, both singly and in combination.

In certain embodiments, the present disclosure provides a compound of formula I-a-9, wherein Ring A is an optionally substituted phenyl, preferably substituted phenyl. In certain embodiments, the present disclosure provides a compound of formula I-a-9, wherein Ring A is optionally substituted HetCy. In certain embodiments, the present disclosure provides a compound of formula I-a-9, wherein Ring A is an optionally substituted HetAr.

In certain embodiments, the present disclosure provides a compound of formula I-a-9, wherein R³ is independently optionally substituted C₁₋₆ aliphatic, such as methyl, or halogen, such as bromo and/or chloro, including dichloro, including wherein n is 2 and R³ is chloro at the 7- and 8-positions with respect to the quinoline ring.

In some embodiments, the present disclosure provides a compound of formula I, wherein R² is

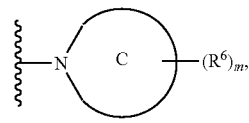

thereby forming a compound of formula I-a-10:

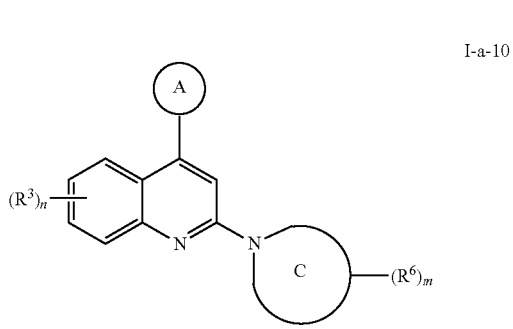

I-a-10 or a pharmaceutically acceptable salt thereof, wherein:
Ring C is pyrrolyl or a 4- to 10-membered saturated or partially unsaturated monocyclic, bicyclic, bridged bicyclic, or spirocyclic heterocyclic ring having 0 to 3 heteroatoms (in addition to the nitrogen already depicted in Ring C) independently selected from nitrogen, oxygen, and sulfur;
each R⁶ is independently halogen, =O, —COR, —(CR₂)₀₋₆CO₂R, —(CR₂)₀₋₆CONR₂, —OR, —(CR$_2$)$_{1-4}$OR, —NR$_2$, —(CR$_2$)$_{1-4}$NR$_2$, —NRC(O) OR, —NRC(O)R, —NRC(O)NR$_2$, —SR, —SO$_2$R, —S(O)R, —(CR$_2$)$_{0-6}$SO$_3$R, —(CR$_2$)$_{0-6}$SO$_2$NR$_2$, —(CR$_2$)$_{0-6}$OSO$_2$NR$_2$, —(CR$_2$)$_{0-6}$NRSO$_2$R, —(CR$_2$)$_{0-6}$NRSO$_2$OR, —(CR$_2$)$_{0-6}$OP(OR)$_2$, —(CR$_2$)$_{0-6}$OP(O)(OR)$_2$, —(CR$_2$)$_{0-6}$P(O)(OR)$_2$, —(CR$_2$)$_{0-6}$OP(O)(H)OR, —B(OR)$_2$, or R$^B$;

m is 1, 2, 3, or 4; and each of Ring A, R, R$^B$, R$^3$, and n is as defined above and described in embodiments herein, both singly and in combination.

In certain embodiments, the present disclosure provides a compound of formula I-a-10, wherein Ring A is an optionally substituted phenyl, preferably substituted phenyl. In certain embodiments, the present disclosure provides a compound of formula I-a-10, wherein Ring A is optionally substituted HetCy. In certain embodiments, the present disclosure provides a compound of formula I-a-10, wherein Ring A is an optionally substituted HetAr.

In some embodiments, the present disclosure provides a compound of formula I-a-10, wherein Ring C is azetidinyl, pyrrolyl, 2,3-dihydro-1H-pyrrolyl, pyrrolidinyl, piperidinyl, morpholinyl, thiazolidinyl, indolinyl, isoindolinyl, octahydroindolyl, azepanyl, an oxazepane, an azabicyclohexane, an azabicycloheptane, an azabicyclooctane, an azabicyclononane, an azaspiroheptane, or an octahydrocyclicpentapyrrole.

In particular embodiments, the present disclosure provides a compound of formula I-a-10, wherein Ring C is pyrrolyl, 2-azabicyclo[3.1.0]hexanyl, 3-azabicyclo[3.1.0] hexane, 5-azaspiro[2.4]heptanyl, or octahydrocyclopenta[b]pyrrolyl.

In particular embodiments, the present disclosure provides a compound of formula I-a-10, wherein Ring C is 3-hydroxyproline, C$_{1-6}$alkyl 3-hydroxyproline ester, or C$_{1-6}$haloalkyl 3-hydroxyproline ester.

In some embodiments, the present disclosure provides a compound of formula I-a-10, wherein:

each R$^6$ is independently fluoro, —CN, methyl, —C$_{3-6}$cycloalkyl, —CF$_3$, —CO$_2$H, —NH$_2$, —OH, —OC$_{1-4}$alkyl, =CH$_2$, =O, tetrazolyl, imidazoyl, thiophenyl, 1,2,4-oxadiazol-3(2H)-onyl, morpholinyl, phenyl, —(CH$_2$)$_{1-4}$OC$_{1-4}$alkyl, —(CH$_2$)$_{1-4}$O(CH$_2$)$_{1-5}$CO$_2$H, —(CH$_2$)$_{1-4}$O(CH$_2$)$_{1-5}$CO$_2$C$_{1-4}$alkyl, —(CH$_2$)$_{1-4}$O(CH$_2$)$_{1-4}$CHFCO$_2$H, —(CH$_2$)$_{1-4}$O(CH$_2$)$_{1-4}$CHFCO$_2$C$_{1-4}$alkyl, —(CH$_2$)$_{1-4}$OCH(CH$_3$)(CH$_2$)$_{1-4}$CO$_2$H, —(CH$_2$)$_{1-4}$OCH(CH$_3$)(CH$_2$)$_{1-4}$CO$_2$C$_{1-4}$alkyl, —(CH$_2$)$_{1-4}$O(CH$_2$)$_{1-4}$CH(CH$_3$)CO$_2$H, —(CH$_2$)$_{1-4}$O(CH$_2$)$_{1-4}$CH(CH$_3$)CO$_2$C$_{1-4}$alkyl, —CHOH(CH$_2$)$_{1-4}$O(CH$_2$)$_{1-5}$CO$_2$H, —CHOH—(CH$_2$)$_{1-4}$O(CH$_2$)$_{1-5}$CO$_2$C$_{1-4}$alkyl, —CHCF$_3$(CH$_2$)$_{1-4}$O(CH$_2$)$_{1-5}$CO$_2$H, —CHCF$_3$(CH$_2$)$_{1-4}$O(CH$_2$)$_{1-5}$CO$_2$C$_{1-4}$alkyl, —(CH$_2$)$_{0-4}$O(CH$_2$)$_{1-5}$CONR$^a$$_2$, —(CH$_2$)$_{1-4}$O(CH$_2$)$_{1-5}$CONR$^a$OH, —(CH$_2$)$_{1-4}$O(CH$_2$)$_{1-5}$CONR$^a$CN, —(CH$_2$)$_{1-4}$O(CH$_2$)$_{1-5}$P(O)OH$_2$, —CH(OH)CF$_3$, —COH(CF$_3$)$_2$, —(CH$_2$)$_{1-5}$CO$_2$H, —(CH$_2$)$_{1-5}$CO$_2$C$_{1-4}$alkyl, —(CH$_2$)$_{0-4}$CHCHCO$_2$H, —(CH$_2$)$_{0-4}$CHCHCO$_2$C$_{1-4}$alkyl, —CO$_2$C$_{1-4}$alkyl, —CO$_2$C$_{1-4}$haloalkyl, —OCOC$_{1-4}$alkyl, —O(CH$_2$)$_{1-4}$CO$_2$H, —O(CH$_2$)$_{1-4}$CO$_2$C$_{1-4}$alkyl, —OCONR$^a$(CH$_2$)$_{0-4}$CO$_2$H, —OCONR$^a$(CH$_2$)$_{0-4}$CO$_2$C$_{1-4}$alkyl, —OCO—(N-morpholine), —CONH$_2$, —CONHOH, —CONHOC$_{1-4}$alkyl, —(CH$_2$)$_{0-4}$C(O)NR$^a$(CH$_2$)$_{1-4}$CO$_2$H, —(CH$_2$)$_{0-4}$C(O)NR$^a$(CH$_2$)$_{1-4}$CO$_2$C$_{1-4}$alkyl, —(CH$_2$)$_{0-4}$C(O)NR$^a$(CH$_2$)$_{1-4}$(pyrrolid-2-one), —(CH$_2$)$_{0-4}$C(O)NR$^a$(CH$_2$)$_{1-4}$(piperidin-2-one), —(CH$_2$)$_{0-4}$C(O)NR$^a$(CH$_2$)$_{1-4}$C(OH)(CF$_3$)$_2$, —(CH$_2$)$_{0-4}$C(O)NR$^a$(CH$_2$)$_{1-4}$CONH$_2$, —(CH$_2$)$_{0-4}$CONR$^a$SO$_2$C$_{1-4}$haloalkyl, —(CH$_2$)$_{0-4}$CO(N-pyrrolidine)-(CH$_2$)$_{0-4}$CO$_2$H, —(CH$_2$)$_{0-4}$CO(N-pyrrolidine)-(CH$_2$)$_{0-4}$CO$_2$C$_{1-4}$alkyl, —(CH$_2$)$_{0-4}$(N-pyrazole)-(CH$_2$)$_{0-4}$CO$_2$H, —(CH$_2$)$_{0-4}$CO(N-pyrazole)-(CH$_2$)$_{0-4}$CO$_2$C$_{1-4}$alkyl, —(CH$_2$)$_{0-4}$(N-pyrrole)-(CH$_2$)$_{0-4}$CO$_2$H, —(CH$_2$)$_{0-4}$CO(N-pyrrole)-(CH$_2$)$_{0-4}$CO$_2$C$_{1-4}$alkyl, —(CH$_2$)$_{0-4}$—O-(phenyl)-(CH$_2$)$_{0-4}$CO$_2$H, —(CH$_2$)$_{0-4}$—O-(phenyl)-(CH$_2$)$_{0-4}$CO$_2$C$_{1-4}$alkyl, —(CH$_2$)$_{0-4}$—O(cycloalkane)-(CH$_2$)$_{0-4}$CO$_2$H, —(CH$_2$)$_{0-4}$—O(cycloalkane)-(CH$_2$)$_{0-4}$CO$_2$C$_{1-4}$alkyl, —(CH$_2$)$_{0-4}$CO(N-pyrrolidine)-(CH$_2$)$_{0-4}$SO$_2$NH$_2$, —(CH$_2$)$_{0-4}$CO(N-pyrrolidine)-(tetrazole), —(CH$_2$)$_{0-4}$CO(N-piperidine)-(CH$_2$)$_{0-4}$CO$_2$H, —(CH$_2$)$_{0-4}$CO(N-piperidine)-(CH$_2$)$_{0-4}$CO$_2$C$_{1-4}$alkyl, —(CH$_2$)$_{0-4}$CO(N-morpholine)-(CH$_2$)$_{0-4}$CO$_2$H, —CONR$^a$(bicyclo[1.1.1]pentane)-(CH$_2$)$_{0-4}$CO$_2$H, —NH$_2$, —(CH$_2$)$_{0-4}$NR$^a$(CH$_2$)$_{1-4}$CO$_2$H, —(CH$_2$)$_{0-4}$NR$^a$(CH$_2$)$_{1-4}$CO$_2$C$_{1-4}$alkyl, —(CH$_2$)$_{0-4}$N[(CH$_2$)$_{1-4}$CO$_2$C$_{1-4}$alkyl]$_2$, —(CH$_2$)$_{0-4}$NR$^a$CO(isoxazole)-OH, —(CH$_2$)$_{0-4}$NR$^a$SO$_2$(benzene)-CO$_2$H, —(CH$_2$)$_{0-4}$NR$^a$SO$_2$(CH$_2$)$_{1-4}$CO$_2$H, —(CH$_2$)$_{0-4}$NR$^a$SO$_2$(CH$_2$)$_{1-4}$CO$_2$C$_{1-4}$alkyl, —(CH$_2$)$_{0-4}$NR$^a$SO$_2$(CH$_2$)$_{1-4}$(imidazolidine-2,4-dione), —(CH$_2$)$_{0-4}$OP(O)(H)OH, wherein R$^a$, independently for each occurrence, is H or C$_{1-4}$alkyl; and m is 1, 2, 3, or 4.

In particular embodiments, the present disclosure provides a compound of formula I-a-10, wherein each R$^6$ is independently fluoro, -methyl, cyclohexyl, —CF$_3$, —CO$_2$H, —CO$_2$C$_{1-4}$alkyl, —CO$_2$C$_{1-4}$haloalkyl, or —OH; and m is 1, 2, or 3, particularly 1 or 2.

In particular embodiments, the present disclosure provides a compound of formula I-a-10, wherein each R$^6$ is independently fluoro, -methyl, cyclohexyl, —CF$_3$, -methoxy, —(CH$_2$)$_{1-5}$CO$_2$H, —(CH$_2$)$_{1-5}$CO$_2$C$_{1-4}$alkyl, —(CH$_2$)$_{0-4}$O(CH$_2$)$_{1-5}$CO$_2$H, —(CH$_2$)$_{0-4}$O(CH$_2$)$_{1-5}$CO$_2$C$_{1-4}$alkyl, or —OH; and m is 1, 2, or 3, particularly 1 or 2.

In certain embodiments, the present disclosure provides a compound of formula I-a-10, wherein R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In some embodiments, the present disclosure provides a compound of formula I, wherein R$^2$ is

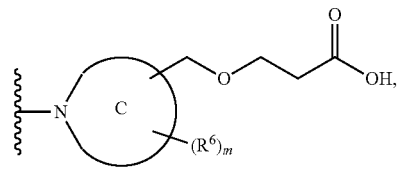

thereby forming a compound of formula I-a-11:

I-a-11

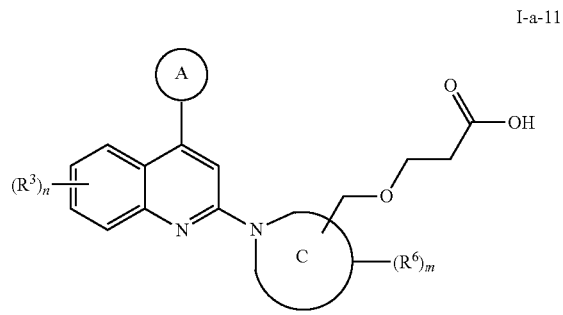

or a pharmaceutically acceptable salt thereof, wherein:

Ring C is pyrrolyl or a 4- to 10-membered saturated or partially unsaturated monocyclic, bicyclic, bridged bicyclic, or spirocyclic heterocyclic ring having 0 to 3 heteroatoms (in addition to the nitrogen already depicted in Ring C) independently selected from nitrogen, oxygen, and sulfur;

each $R^6$ is independently halogen, =O, —COR, —(CR$_2$)$_{0-6}$CO$_2$R, —(CR$_2$)$_{0-6}$CONR$_2$, —OR, —(CR$_2$)$_{1-4}$OR, —NR$_2$, —(CR$_2$)$_{1-4}$NR$_2$, —NRC(O)OR, —NRC(O)R, —NRC(O)NR$_2$, —SR, —SO$_2$R, —S(O)R, —(CR$_2$)$_{0-6}$SO$_3$R, —(CR$_2$)$_{0-6}$SO$_2$NR$_2$, —(CR$_2$)$_{0-6}$OSO$_2$NR$_2$, —(CR$_2$)$_{0-6}$NRSO$_2$R, —(CR$_2$)$_{0-6}$NRSO$_2$OR, —(CR$_2$)$_{0-6}$OP(OR)$_2$, —(CR$_2$)$_{0-6}$OP(O)(OR)$_2$, —(CR$_2$)$_{0-6}$P(O)(OR)$_2$, —(CR$_2$)$_{0-6}$OP(O)(H)OR, —B(OR)$_2$, or $R^B$;

m is 0, 1, 2, or 3; and each of Ring A, R, $R^B$, $R^3$, and n is as defined above and described in embodiments herein, both singly and in combination.

In certain embodiments, the present disclosure provides a compound of formula I-a-11, wherein Ring A is an optionally substituted phenyl, preferably substituted phenyl.

In certain embodiments, the present disclosure provides a compound of formula I-a-11, wherein Ring A is optionally substituted HetCy. For example, in certain embodiments, Ring A is optionally substituted HetCy, and HetCy is selected from optionally substituted tetrahydrofuranyl, tetrahydrothiophenyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, quinuclidinyl, indolinyl, 3H-indolyl, chromanyl, phenanthridinyl, tetrahydroquinolinyl, 4H-quinolizinyl, tetrahydroquinolinyl, tetrahydroisoquinolinyl, and pyrido[2,3-b]-1,4-oxazin-3 (4H)-one. In further such embodiments, Ring A is optionally substituted HetCy, and HetCy is selected from optionally substituted morpholinyl, piperazinyl, 2,5-dihydro-1H-pyrrole and 2,3-dihydro-1H-pyrrole.

In certain embodiments, the present disclosure provides a compound of formula I-a-11, wherein Ring A is an optionally substituted HetAr. For example, in certain embodiments, Ring A is optionally substituted HetAr, and HetAr is selected from optionally substituted thienyl, furanyl, pyrrolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, and phenoxazinyl. In further such embodiments, Ring A is optionally substituted HetAr, and HetAr is selected from optionally substituted thienyl, triazolyl, oxazolyl, isoxazolyl, thiazolyl, isothiazolyl, pyridyl, pyridazinyl, and pyrimidinyl. In preferred embodiments, Ring A is optionally substituted HetAr, and HetAr is selected from optionally substituted triazolyl, oxazolyl, isoxazolyl, thiazolyl, and isothiazolyl.

In some embodiments, the present disclosure provides a compound of formula I-a-11, wherein Ring C is azetidinyl, pyrrolyl, 2,3-dihydro-1H-pyrrolyl, pyrrolidinyl, piperidinyl, morpholinyl, thiazolidinyl, indolinyl, isoindolinyl, octahydroindolyl, azepanyl, an oxazepane, an azabicyclohexane, an azabicycloheptane, an azabicyclooctane, an azabicyclononane, an azaspiroheptane, or an octahydrocyclicpentapyrrole.

In particular embodiments, the present disclosure provides a compound of formula I-a-11, wherein each $R^6$ is independently fluoro, -methyl, =O, =CH$_2$, -cyclohexyl, phenyl, morpholinyl, —OMe, —OtBu, —CF$_3$, —CO$_2$H, —CO$_2$C$_{1-4}$alkyl, —CO$_2$C$_{1-4}$haloalkyl, or —OH; and m is 0 or 1, or 2, particularly 0 or 1.

In certain embodiments, the present disclosure provides a compound of formula I-a-11, wherein $R^3$ is independently optionally substituted C$_{1-6}$ aliphatic, such as methyl, or halogen, such as bromo and/or chloro, including dichloro, including wherein n is 2 and $R^3$ is chloro at the 7- and 8-positions with respect to the quinoline ring.

In some embodiments, the present disclosure provides a compound of formula I, wherein at least one $R^3$ is halogen, such as chloro at the 8-position, thereby forming a compound of formula I-b-1:

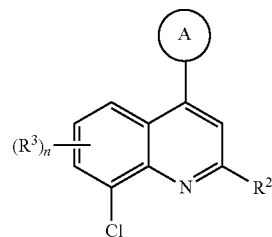

I-b-1 or a pharmaceutically acceptable salt thereof, wherein each of Ring A, $R^2$, and $R^3$ is as defined above and described in embodiments herein, and n is 0, 1, 2, or 3, both singly and in combination.

In certain embodiments, the present disclosure provides a compound of formula I-b-1, wherein Ring A is an optionally substituted phenyl, preferably substituted phenyl. In certain embodiments, the present disclosure provides a compound of formula I-b-1, wherein Ring A is optionally substituted HetCy. In certain embodiments, the present disclosure provides a compound of formula I-b-1, wherein Ring A is an optionally substituted HetAr.

In certain embodiments, the present disclosure provides a compound of formula I-b-1, wherein $R^2$ is $R^B$, wherein $R^B$ is an optionally substituted C$_{1-6}$ aliphatic, preferably a substituted C$_{1-6}$ aliphatic, such as —(CR$_2$)$_{1-4}$NR(CR$_2$)$_{0-6}$CO$_2$R, —(CR$_2$)$_{1-4}$O(CR$_2$)$_{0-4}$CO$_2$R, —(CR$_2$)$_{1-4}$CO$_2$R, —(CR$_2$)$_{1-4}$OH, —(CR$_2$)$_{1-4}$NH$_2$, —(CR$_2$)$_{1-4}$C(O)NH$_2$, —(CR$_2$)$_{1-4}$C(O)NHC$_{1-4}$alkyl, or —(CR$_2$)$_{1-4}$C(O)N(C$_{1-4}$alkyl)$_2$, particularly —(CR$_2$)$_{1-4}$NR(CR$_2$)$_{0-4}$CO$_2$R or —(CR$_2$)$_{1-4}$CO$_2$R. In some embodiments, $R^2$ is —(CH$_2$)$_{1-4}$NR$^a$(CH$_2$)$_{0-4}$CO$_2$R$^a$, such as —(CH$_2$)$_{1-4}$NR$^a$(CH$_2$)$_{0-4}$CO$_2$H, wherein R$^a$, independently for each occurrence, is H or C$_{1-4}$alkyl. In other embodiments, $R^2$ is —(CH$_2$)$_{1-4}$N(SO$_2$C$_{1-4}$alkyl)(CH$_2$)$_{0-4}$CO$_2$R$^a$, such as is —(CH$_2$)$_{1-4}$N(SO$_2$C$_{1-4}$alkyl)(CH$_2$)$_{0-4}$CO$_2$H, wherein R$^a$, independently for each occurrence, is H or C$_{1-4}$alkyl. In other embodiments, $R^2$ is —(CR$_2$)$_{1-4}$CO$_2$R, such as —(CR$_2$)$_{1-4}$CO$_2$H, including —(CH$_2$)$_{1-4}$CO$_2$H. In certain embodiments, $R^2$ includes a terminal —CO$_2$H group. For example, in certain instances, $R^2$ includes a terminal —(CH$_2$)$_{0-4}$CO$_2$H group.

In some embodiments, the present disclosure provides a compound of formula I, wherein n is 2 and $R^3$ is chloro at the 7- and 8-positions, thereby forming a compound of formula I-b-2:

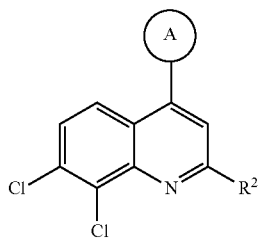

I-b-2 or a pharmaceutically acceptable salt thereof, wherein each of Ring A and $R^2$ is as defined above and described in embodiments herein, both singly and in combination.

In certain embodiments, the present disclosure provides a compound of formula I-b-2, wherein Ring A is an optionally substituted phenyl, preferably substituted phenyl. In certain embodiments, the present disclosure provides a compound of formula I-b-2, wherein Ring A is optionally substituted HetCy. In certain embodiments, the present disclosure provides a compound of formula I-b-2, wherein Ring A is an optionally substituted HetAr.

In certain embodiments, the present disclosure provides a compound of formula I-b-2, wherein $R^2$ is $R^B$, wherein $R^B$ is an optionally substituted $C_{1-6}$ aliphatic, preferably a substituted $C_{1-6}$ aliphatic, such as $-(CR_2)_{1-4}NR(CR_2)_{0-6}CO_2R$, $-(CR_2)_{1-4}O(CR_2)_{0-6}CO_2R$, $-(CR_2)_{1-4}CO_2R$, $-(CR_2)_{1-4}OH$, $-(CR_2)_{1-4}NH_2$, $-(CR_2)_{1-4}C(O)NH_2$, $-(CR_2)_{1-4}C(O)NHC_{1-4}alkyl$, or $-(CR_2)_{1-4}C(O)N(C_{1-4}alkyl)_2$, particularly $-(CR_2)_{1-4}NR(CR_2)_{0-6}CO_2R$ or $-(CR_2)_{1-4}CO_2R$. In some embodiments, $R^2$ is $-(CH_2)_{1-4}NR^a(CH_2)_{0-4}CO_2R^a$, such as $-(CH_2)_{1-4}NR^a(CH_2)_{0-4}CO_2H$, wherein $R^a$, independently for each occurrence, is H or $C_{1-4}alkyl$. In other embodiments, $R^2$ is $-(CH_2)_{1-4}N(SO_2C_{1-4}alkyl)(CH_2)_{0-4}CO_2R^a$, such as is $-(CH_2)_{1-4}N(SO_2C_{1-4}alkyl)(CH_2)_{0-4}CO_2H$, wherein $R^a$, independently for each occurrence, is H or $C_{1-4}alkyl$. In other embodiments, $R^2$ is $-(CR_2)_{1-4}CO_2R$, such as $-(CR_2)_{1-4}CO_2H$, including $-(CH_2)_{1-4}CO_2H$. In certain embodiments, $R^2$ includes a terminal $-CO_2H$ group. For example, in certain instances, $R^2$ includes a terminal $-(CH_2)_{0-4}CO_2H$ group.

In some embodiments, the present disclosure provides a compound of formula I, wherein $R^2$ is

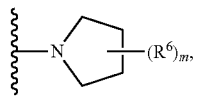

and $R^3$ is chloro at the 7- and 8-positions thereby forming a compound of formula I-c-1:

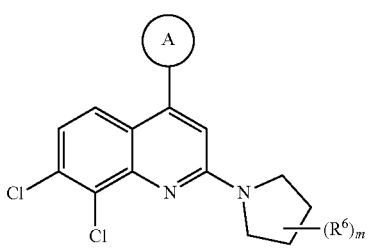

I-c-1 or a pharmaceutically acceptable salt thereof, wherein:
each $R^6$ is independently halogen, =O, $-COR$, $-(CR_2)_{0-6}CO_2R$, $-(CR_2)_{0-6}CONR_2$, $-OR$, $-(CR_2)_{1-4}OR$, $-NR_2$, $-(CR_2)_{1-4}NR_2$, $-NRC(O)OR$, $-NRC(O)R$, $-NRC(O)NR_2$, $-SR$, $-SO_2R$, $-S(O)R$, $-(CR_2)_{0-6}SO_3R$, $-(CR_2)_{0-6}SO_2NR_2$, $-(CR_2)o-OSO_2NR_2$, $-(CR_2)_{0-6}NRSO_2R$, $-(CR_2)_{0-6}NRSO_2OR$, $-(CR_2)_{0-6}OP(OR)_2$, $-(CR_2)_{0-6}OP(O)(OR)_2$, $-(CR_2)_{0-6}P(O)(OR)_2$, $-(CR_2)_{0-6}OP(O)(H)OR$, $-B(OR)_2$, or $R^B$;
m is 1, 2, 3, or 4; and
each of Ring A, R and $R^B$ is as defined above and described in embodiments herein, both singly and in combination.

In certain embodiments, the present disclosure provides a compound of formula I-c-1, wherein Ring A is an optionally substituted phenyl, preferably substituted phenyl.

In certain embodiments, the present disclosure provides a compound of formula I-c-1, wherein Ring A is optionally substituted HetCy. For example, in certain embodiments, Ring A is optionally substituted HetCy, and HetCy is selected from optionally substituted tetrahydrofuranyl, tetrahydrothiophenyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, quinuclidinyl, indolinyl, 3H-indolyl, chromanyl, phenanthridinyl, tetrahydroquinolinyl, 4H-quinolizinyl, tetrahydroquinolinyl, tetrahydroisoquinolinyl, and pyrido[2,3-b]-1,4-oxazin-3 (4H)-one. In further such embodiments, Ring A is optionally substituted HetCy, and HetCy is selected from optionally substituted morpholinyl, piperazinyl, 2,5-dihydro-1H-pyrrole and 2,3-dihydro-1H-pyrrole.

In certain embodiments, the present disclosure provides a compound of formula I-c-1, wherein Ring A is an optionally substituted HetAr. For example, in certain embodiments, Ring A is optionally substituted HetAr, and HetAr is selected from optionally substituted thienyl, furanyl, pyrrolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, and phenoxazinyl. In further such embodiments, Ring A is optionally substituted HetAr, and HetAr is selected from optionally substituted thienyl, triazolyl, oxazolyl, isoxazolyl, thiazolyl, isothiazolyl, pyridyl, pyridazinyl, and pyrimidinyl. In preferred embodiments, Ring A is optionally substituted HetAr, and HetAr is selected from optionally substituted triazolyl, oxazolyl, isoxazolyl, thiazolyl, and isothiazolyl.

In some embodiments, the present disclosure provides a compound of formula I-c-1, wherein:
each $R^6$ is independently fluoro, $-CN$, methyl, =O, =$CH_2$, $-C_{3-6}$cycloalkyl, $-CF_3$, $-CO_2H$, $-NH_2$, $-OH$, $-OC_{1-4}alkyl$, tetrazolyl, imidazoyl, thiophenyl, 1,2,4-oxadiazol-3(2H)-onyl, morpholinyl, phenyl, $-(CH_2)_{1-4}OC_{1-4}alkyl$, $-(CH_2)_{0-4}O(CH_2)_{1-5}CO_2H$, $-(CH_2)_{0-4}O(CH_2)_{1-5}CO_2C_{1-4}alkyl$, $-(CH_2)_{1-4}O(CH_2)_{1-4}CHFCO_2H$, $-(CH_2)_{1-4}O(CH_2)_{1-4}CHFCO_2C_{1-4}alkyl$, $-(CH_2)_{1-4}OCH(CH_3)(CH_2)_{1-4}CO_2H$, $-(CH_2)_{1-4}OCH(CH_3)(CH_2)_{1-4}CO_2C_{1-4}alkyl$, $-(CH_2)_{1-4}O(CH_2)_{1-4}CH(CH_3)CO_2H$, $-(CH_2)_{1-4}O(CH_2)_{1-4}CH(CH_3)CO_2C_{1-4}alkyl$, $-CHOH(CH_2)_{1-4}O(CH_2)_{1-5}CO_2H$, $-CHOH(CH_2)_{1-4}O(CH_2)_{1-5}CO_2$ $C_{1-4}$alkyl, —CHCF$_3$(CH$_2$)$_{1-4}$O(CH$_2$)$_{1-5}$CO$_2$H, —CHCF$_3$(CH$_2$)$_{1-4}$O—(CH$_2$)$_{1-5}$CO$_2$C$_{1-4}$alkyl, —(CH$_2$)$_{1-4}$O(CH$_2$)$_{1-5}$CONR$^a{}_2$, —(CH$_2$)$_{1-4}$O(CH$_2$)$_{1-5}$CONR$^a$OH, —(CH$_2$)$_{1-4}$O(CH$_2$)$_{1-5}$CONR$^a$CN, —(CH$_2$)$_{1-4}$O(CH$_2$)$_{1-5}$P(O)OH$_2$, —CH(OH)CF$_3$, —COH(CF$_3$)$_2$, —(CH$_2$)$_{1-5}$CO$_2$H, —(CH$_2$)$_{1-5}$CO$_2$C$_{1-4}$alkyl, —(CH$_2$)$_{0-4}$CHCHCO$_2$H, —(CH$_2$)$_{0-4}$CHCHCO$_2$C$_{1-4}$alkyl, —CO$_2$C$_{1-4}$alkyl, —CO$_2$C$_{1-4}$haloalkyl, —OCOC$_{1-4}$alkyl, —O(CH$_2$)$_{1-4}$CO$_2$H, —O(CH$_2$)$_{1-4}$CO$_2$C$_{1-4}$alkyl, —OCONR$^a$(CH$_2$)$_{0-4}$CO$_2$H, —OCONR$^a$(CH$_2$)$_{0-4}$CO$_2$C$_{1-4}$alkyl, —OCO—(N-morpholine), —CONH$_2$, —CONHOH, —CONHOC$_{1-4}$alkyl, —(CH$_2$)$_{0-4}$C(O)NR$^a$(CH$_2$)$_{1-4}$CO$_2$H, —(CH$_2$)$_{0-4}$C(O)NR$^a$(CH$_2$)$_{1-4}$CO$_2$C$_{1-4}$alkyl, —(CH$_2$)$_{0-4}$C(O)NR$^a$(CH$_2$)$_{1-4}$(pyrrolid-2-one), —(CH$_2$)$_{0-4}$C(O)NR$^a$(CH$_2$)$_{1-4}$(piperidin-2-one), —(CH$_2$)$_{0-4}$C(O)NR$^a$(CH$_2$)$_{1-4}$C(OH)(CF$_3$)$_2$, —(CH$_2$)$_{0-4}$C(O)NR$^a$(CH$_2$)$_{1-4}$CONH$_2$, —(CH$_2$)$_{0-4}$CONR$^a$SO$_2$C$_{1-4}$haloalkyl, —(CH$_2$)$_{0-4}$CO(N-pyrrolidine)-(CH$_2$)$_{0-4}$CO$_2$H, —(CH$_2$)$_{0-4}$CO(N-pyrrolidine)-(CH$_2$)$_{0-4}$CO$_2$C$_{1-4}$alkyl, —(CH$_2$)$_{0-4}$(N-pyrazole)-(CH$_2$)$_{0-4}$CO$_2$H, —(CH$_2$)$_{0-4}$CO(N-pyrazole)-(CH$_2$)$_{0-4}$CO$_2$C$_{1-4}$alkyl, —(CH$_2$)$_{0-4}$(N-pyrrole)-(CH$_2$)$_{0-4}$CO$_2$H, —(CH$_2$)$_{0-4}$CO(N-pyrrole)-(CH$_2$)$_{0-4}$CO$_2$C$_{1-4}$alkyl, —(CH$_2$)$_{0-4}$—O(phenyl)-(CH$_2$)$_{0-4}$CO$_2$H, —(CH$_2$)$_{0-4}$—O(phenyl)-(CH$_2$)$_{0-4}$CO$_2$C$_{1-4}$alkyl, —(CH$_2$)$_{0-4}$—O(cycloalkane)-(CH$_2$)$_{0-4}$CO$_2$H, —(CH$_2$)$_{0-4}$—O(cycloalkane)-(CH$_2$)$_{0-4}$CO$_2$C$_{1-4}$alkyl, —(CH$_2$)$_{0-4}$CO(N-pyrrolidine)-(CH$_2$)$_{0-4}$SO$_2$NH$_2$, —(CH$_2$)$_{0-4}$CO(N-pyrrolidine)-(tetrazole), —(CH$_2$)$_{0-4}$CO(N-piperidine)-(CH$_2$)$_{0-4}$CO$_2$H, —(CH$_2$)$_{0-4}$CO—(N-piperidine)-(CH$_2$)$_{0-4}$CO$_2$C$_{1-4}$alkyl, —(CH$_2$)$_{0-4}$CO(N-morpholine)-(CH$_2$)$_{0-4}$CO$_2$H, —CONR$^a$(bicyclo[1.1.1]pentane)-(CH$_2$)$_{0-4}$CO$_2$H, —NH$_2$, —(CH$_2$)$_{0-4}$NR$^a$(CH$_2$)$_{1-4}$CO$_2$H, —(CH$_2$)$_{0-4}$NR$^a$(CH$_2$)$_{1-4}$CO$_2$C$_{1-4}$alkyl, —(CH$_2$)$_{0-4}$N[(CH$_2$)$_{1-4}$CO$_2$C$_{1-4}$alkyl]$_2$, —(CH$_2$)$_{0-4}$NR$^a$CO(isoxazole)OH, —(CH$_2$)$_{0-4}$NR$^a$SO$_2$(phenyl)-CO$_2$H, —(CH$_2$)$_{0-4}$NR$^a$SO$_2$(CH$_2$)$_{1-4}$CO$_2$H, —(CH$_2$)$_{0-4}$NR$^a$SO$_2$(CH$_2$)$_{1-4}$CO$_2$C$_{1-4}$alkyl, —(CH$_2$)$_{0-4}$NR$^a$SO$_2$(CH$_2$)$_{1-4}$(imidazolidine-2,4-dione), —(CH$_2$)$_{0-4}$OP(O)(H)OH, wherein R$^a$, independently for each occurrence, is H or C$_{1-4}$alkyl; and m is 1, 2, 3, or 4.

In particular embodiments, the present disclosure provides a compound of formula I-c-1, wherein each R$^6$ is independently fluoro, =O, =CH$_2$, -methyl, cyclohexyl, —CF$_3$, —CO$_2$H, —CO$_2$C$_{1-4}$alkyl, —CO$_2$C$_{1-4}$haloalkyl, or —OH; m is 1, 2, or 3, particularly 1 or 2.

In particular embodiments, the present disclosure provides a compound of formula I-c-1, wherein each R$^6$ is independently fluoro, =O, =CH$_2$, -methyl, cyclohexyl, —CF$_3$, -methoxy, —OtBu, —(CH$_2$)$_{1-5}$CO$_2$H, —(CH$_2$)$_{1-5}$CO$_2$C$_{1-4}$alkyl, —(CH$_2$)$_{0-4}$O(CH$_2$)$_{1-5}$CO$_2$H, —(CH$_2$)$_{0-4}$O(CH$_2$)$_{1-5}$CO$_2$C$_{1-4}$alkyl, —(CH$_2$)$_{1-4}$O(CH$_2$)$_{1-5}$CONR$^a{}_2$, or —OH; and m is 1, 2, or 3, particularly 1 or 2.

In particular embodiments, the present disclosure provides a compound of formula I-c-1, wherein m is 1; and R$^6$ is —(CH$_2$)$_{0-4}$O(CH$_2$)$_{1-5}$CO$_2$H, such as —(CH$_2$)$_{1-2}$O(CH$_2$)$_{2-3}$CO$_2$H, including —CH$_2$O(CH$_2$)$_2$CO$_2$H.

In some embodiments, the present disclosure provides a compound of formula I, wherein R$^2$ is —NRR$^5$, and R$^3$ is chloro at the 7- and 8-positions thereby forming a compound of formula I-c-2:

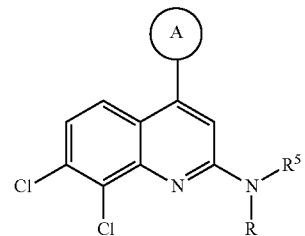

I-c-2 or a pharmaceutically acceptable salt thereof, wherein:
R$^5$ is —(CR$_2$)$_{2-4}$OR, —(CR$_2$)$_{0-6}$CO$_2$R, —(CR$_2$)$_{0-6}$CONR$_2$, —(CR$_2$)$_{0-6}$C(O)NR(CR$_2$)$_{0-6}$CO$_2$R, —(CR$_2$)$_{0-6}$C(O)NR(CR$_2$)$_{0-6}$CONR$_2$, —(CR$_2$)$_{0-6}$NRCOR, —(CR$_2$)$_{0-4}$NR$^a$C(O)R, —(CR$_2$)$_{0-6}$SO$_3$R, —(CR$_2$)$_{0-6}$SO$_2$NR$_2$, —(CR$_2$)$_{0-6}$OSO$_2$NR$_2$, —(CR$_2$)$_{0-6}$NRSO$_2$R, —(CR$_2$)$_{0-6}$NRSO$_2$OR, —(CR$_2$)$_{0-6}$OP(OR)$_2$, —(CR$_2$)$_{0-6}$OP(O)(OR)$_2$, —(CR$_2$)$_{0-6}$P(O)(OR)$_2$, —(CR$_2$)$_{0-6}$OP(O)(H)OR, or R$^B$; and each of Ring A, R and R$^B$ is as defined above and described in embodiments herein, both singly and in combination.

In certain embodiments, the present disclosure provides a compound of formula I-c-2, wherein Ring A is an optionally substituted phenyl, preferably substituted phenyl. In certain embodiments, the present disclosure provides a compound of formula I-c-2, wherein Ring A is optionally substituted HetCy. In certain embodiments, the present disclosure provides a compound of formula I-c-2, wherein Ring A is an optionally substituted HetAr.

In some embodiments, the present disclosure provides a compound of formula I-c-2, wherein R$^5$ is not R$^B$.

In particular embodiments, the present disclosure provides a compound of formula I-c-2, wherein R$^5$ is —(CH$_2$)$_{2-4}$OH, —(CH$_2$)$_{2-4}$O(CH$_2$)$_{1-5}$CO$_2$H, —(CH$_2$)$_{2-4}$O(CH$_2$)$_{1-5}$CO$_2$C$_{1-4}$alkyl, —(CH$_2$)$_{0-3}$CH(CH$_2$OH)$_2$, —(CH$_2$)$_{2-4}$OC$_{1-4}$alkyl, —(CH$_2$)$_{1-4}$CO$_2$H, —(CH$_2$)$_{1-4}$CO$_2$C$_{1-4}$alkyl, —(CH$_2$)$_{1-4}$CONH$_2$, —(CH$_2$)$_{1-4}$CONHC$_{1-4}$alkyl, —(CH$_2$)$_{1-4}$CON(C$_{1-4}$alkyl)$_2$, —(CH$_2$)$_{1-4}$C(O)NR$^a$(CH$_2$)$_{1-4}$CO$_2$H, —(CH$_2$)$_{1-4}$C(O)NR$^a$(CHMe)CO$_2$H, —(CH$_2$)$_{1-4}$C(O)NR$^a$(CH$_2$)$_{1-4}$CONH$_2$, —(CH$_2$)$_{1-4}$C(O)NR$^a$(CH$_2$)$_{1-4}$CONHC$_{1-4}$alkyl, —(CH$_2$)$_{1-4}$C(O)NR$^a$(CH$_2$)$_{1-4}$CON(C$_{1-4}$alkyl)$_2$, —(CH$_2$)$_{0-4}$NR$^a$C(O)(CH$_2$)$_{1-5}$CO$_2$H, —(CH$_2$)$_{0-4}$NR$^a$C(O)(CH$_2$)$_{1-5}$CO$_2$C$_{1-4}$alkyl, —(CH$_2$)$_{2-4}$SO$_3$H, —(CH$_2$)$_{2-4}$SO$_3$C$_{1-4}$alkyl, —(CH$_2$)$_{2-4}$SO$_2$NH$_2$, —(CH$_2$)$_{1-4}$C(O)NR$^a$(CH$_2$)$_{2-4}$SO$_2$NH$_2$, —(CH$_2$)$_{1-4}$CO(N-pyrrolidine)-SO$_2$NH$_2$, —(CH$_2$)$_{2-4}$SO$_2$NHC$_{1-4}$alkyl, —(CH$_2$)$_{2-4}$SO$_2$N(C$_{1-4}$alkyl)$_2$, —(CH$_2$)$_{2-4}$OSO$_2$NH$_2$, —(CH$_2$)$_{2-4}$NR$^a$(CH$_2$)$_{2-4}$CO$_2$H, —(CH$_2$)$_{2-4}$NR$^a$CO(CH$_2$)$_{2-4}$CO$_2$H, —(CH$_2$)$_{2-4}$NR$^a$CO(cyclopentane)-CO$_2$H, —(CH$_2$)$_{2-4}$NR$^a$CO(benzene)-OH, —(CH$_2$)$_{2-4}$NR$^a$CO(benzene)-CO$_2$H, —(CH$_2$)$_{2-4}$NR$^a$SO$_3$H, —(CH$_2$)$_{2-4}$NR$^a$SO$_2$C$_{1-4}$alkyl, —(CH$_2$)$_{2-4}$NR$^a$SO$_2$(CH$_2$)$_{2-4}$OH, —(CH$_2$)$_{2-4}$NR$^a$SO$_2$(CH$_2$)$_{2-4}$OC$_{1-4}$alkyl, —(CH$_2$)$_{2-4}$NR$^a$SO$_2$(CH$_2$)$_{2-4}$CO$_2$H, —(CH$_2$)$_{2-4}$NR$^a$SO$_2$(benzene)-CO$_2$H, —(CH$_2$)$_{2-4}$NR$^a$SO$_2$(benzene)-CO$_2$C$_{1-4}$alkyl, —(CH$_2$)$_{2-4}$SO$_2$NR$^a$(CH$_2$)$_{2-4}$OH, —(CH$_2$)$_{2-4}$(N-saccharin), —(CH$_2$)$_{2-4}$SO$_2$NR$^a$(CH$_2$)$_{2-4}$CO$_2$H, —(CH$_2$)$_{2-4}$SO$_2$NR$^a$(cyclopentane)-CO$_2$H, —(CH$_2$)$_{2-4}$NR$^a$(cyclohexane)-CO$_2$C$_{1-4}$alkyl, —(CH$_2$)$_{2-4}$SO$_2$(N-pyrrolidine)-CO$_2$H, —(CH$_2$)$_{2-4}$SO$_2$(N-piperidine)-CO$_2$H, —(CH$_2$)$_{1-4}$OP(OH)$_2$, —(CH$_2$)$_{1-4}$P(O)(OH)$_2$, —(CH$_2$)$_{1-4}$P(O)(OH)

(OC$_{1-4}$alkyl), or —(CH$_2$)$_{2-4}$OP(O)(H)OH, wherein R$^a$, independently for each occurrence, is H, C$_{1-4}$alkyl, or —SO$_2$C$_{1-4}$alkyl.

In some embodiments, the present disclosure provides a compound of formula I-c-2, wherein R in —NRR$^5$ is R$^a$, which is H or C$_{1-6}$alkyl, particularly methyl.

In some embodiments, the present disclosure provides a compound of formula I, wherein Ring A is

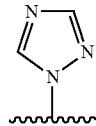

thereby forming a compound of formula I-d-1:

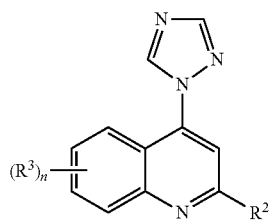

I-d-1 or a pharmaceutically acceptable salt thereof, wherein each of R$^2$, R$^3$, and n is as defined above and described in embodiments herein, both singly and in combination.

In certain embodiments, the present disclosure provides a compound of formula I-d-1, wherein R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In certain embodiments, the present disclosure provides a compound of formula I-d-1, wherein R$^2$ is R$^B$, wherein R$^B$ is an optionally substituted C$_{1-6}$ aliphatic, preferably a substituted C$_{1-6}$ aliphatic, such as —(CR$_2$)$_{1-4}$NR(CR$_2$)$_{0-6}$CO$_2$R, —(CR$_2$)$_{1-4}$O(CR$_2$)$_{0-6}$CO$_2$R, —(CR$_2$)$_{1-4}$CO$_2$R, —(CR$_2$)$_{1-4}$OH, —(CR$_2$)$_{1-4}$NH$_2$, —(CR$_2$)$_{1-4}$C(O)NH$_2$, —(CR$_2$)$_{1-4}$C(O)NHC$_{1-4}$alkyl, or —(CR$_2$)$_{1-4}$C(O)N(C$_{1-4}$alkyl)$_2$, particularly —(CR$_2$)$_{1-4}$NR(CR$_2$)$_{0-6}$CO$_2$R or —(CR$_2$)$_{1-4}$CO$_2$R. In some embodiments, R$^2$ is —(CH$_2$)$_{1-4}$NR$^a$(CH$_2$)$_{0-4}$CO$_2$R$^a$, such as —(CH$_2$)$_{1-4}$NR$^a$(CH$_2$)$_{0-4}$CO$_2$H, wherein R$^a$, independently for each occurrence, is H or C$_{1-4}$alkyl. In other embodiments, R$^2$ is —(CH$_2$)$_{1-4}$N(SO$_2$C$_{1-4}$alkyl)(CH$_2$)$_{0-4}$CO$_2$R$^a$, such as is —(CH$_2$)$_{1-4}$N(SO$_2$C$_{1-4}$alkyl)(CH$_2$)$_{0-4}$CO$_2$H, wherein R$^a$, independently for each occurrence, is H or C$_{1-4}$alkyl. In other embodiments, R$^2$ is —(CR$_2$)$_{1-4}$CO$_2$R, such as —(CR$_2$)$_{1-4}$CO$_2$H, including —(CH$_2$)$_{1-4}$CO$_2$H. In certain embodiments, R$^2$ includes a terminal —CO$_2$H group. For example, in certain instances, R$^2$ includes a terminal —(CH$_2$)$_{0-4}$CO$_2$H group.

In some embodiments, the present disclosure provides a compound of formula I, wherein Ring A is

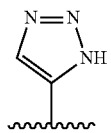

thereby forming a compound of formula I-d-2:

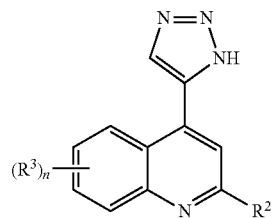

I-d-2 or a pharmaceutically acceptable salt thereof, wherein each of R$^2$, R$^3$, and n is as defined above and described in embodiments herein, both singly and in combination.

In certain embodiments, the present disclosure provides a compound of formula I-d-2, wherein R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In certain embodiments, the present disclosure provides a compound of formula I-d-2, wherein R$^2$ is R$^B$, wherein R$^B$ is an optionally substituted C$_{1-6}$ aliphatic, preferably a substituted C$_{1-6}$ aliphatic, such as —(CR$_2$)$_{1-4}$NR(CR$_2$)$_{0-6}$CO$_2$R, —(CR$_2$)$_{1-4}$O(CR$_2$)$_{0-6}$CO$_2$R, —(CR$_2$)$_{1-4}$CO$_2$R, —(CR$_2$)$_{1-4}$OH, —(CR$_2$)$_{1-4}$NH$_2$, —(CR$_2$)$_{1-4}$C(O)NH$_2$, —(CR$_2$)$_{1-4}$C(O)NHC$_{1-4}$alkyl, or —(CR$_2$)$_{1-4}$C(O)N(C$_{1-4}$alkyl)$_2$, particularly —(CR$_2$)$_{1-4}$NR(CR$_2$)$_{0-6}$CO$_2$R or —(CR$_2$)$_{1-4}$CO$_2$R. In some embodiments, R$^2$ is —(CH$_2$)$_{1-4}$NR$^a$(CH$_2$)$_{0-4}$CO$_2$R$^a$, such as —(CH$_2$)$_{1-4}$NR$^a$(CH$_2$)$_{0-4}$CO$_2$H, wherein R$^a$, independently for each occurrence, is H or C$_{1-4}$alkyl. In other embodiments, R$^2$ is —(CH$_2$)$_{1-4}$N(SO$_2$C$_{1-4}$alkyl)(CH$_2$)$_{0-4}$CO$_2$R$^a$, such as is —(CH$_2$)$_{1-4}$N(SO$_2$C$_{1-4}$alkyl)(CH$_2$)$_{0-4}$CO$_2$H, wherein R$^a$, independently for each occurrence, is H or C$_{1-4}$alkyl. In other embodiments, R$^2$ is —(CR$_2$)$_{1-4}$CO$_2$R, such as —(CR$_2$)$_{1-4}$CO$_2$H, including —(CH$_2$)$_{1-4}$CO$_2$H. In certain embodiments, R$^2$ includes a terminal —CO$_2$H group. For example, in certain instances, R$^2$ includes a terminal —(CH$_2$)$_{0-4}$CO$_2$H group.

In some embodiments, the present disclosure provides a compound of formula I, wherein Ring A is

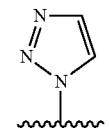

thereby forming a compound of formula I-d-3:

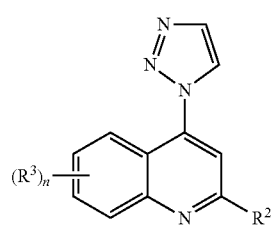

I-d-3 or a pharmaceutically acceptable salt thereof, wherein each of $R^2$, $R^3$, and n is as defined above and described in embodiments herein, both singly and in combination.

In certain embodiments, the present disclosure provides a compound of formula I-d-3, wherein $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In certain embodiments, the present disclosure provides a compound of formula I-d-3 wherein $R^2$ is $R^B$, wherein $R^B$ is an optionally substituted $C_{1-6}$ aliphatic, preferably a substituted $C_{1-6}$ aliphatic, such as —$(CR_2)_{1-4}NR(CR_2)_{0-6}CO_2R$, —$(CR_2)_{1-4}O(CR_2)_{0-6}CO_2R$, —$(CR_2)_{1-4}CO_2R$, —$(CR_2)_{1-4}OH$, —$(CR_2)_{1-4}NH_2$, —$(CR_2)_{1-4}C(O)NH_2$, —$(CR_2)_{1-4}C(O)NHC_{1-4}alkyl$, or —$(CR_2)_{1-4}C(O)N(C_{1-4}alkyl)_2$, particularly —$(CR_2)_{1-4}NR(CR_2)_{0-6}CO_2R$ or —$(CR_2)_{1-4}CO_2R$. In some embodiments, $R^2$ is —$(CH_2)_{1-4}NR^a(CH_2)_{0-4}CO_2R^a$, such as —$(CH_2)_{1-4}NR^a(CH_2)_{0-4}CO_2H$, wherein $R^a$, independently for each occurrence, is H or $C_{1-4}alkyl$. In other embodiments, $R^2$ is —$(CH_2)_{1-4}N(SO_2C_{1-4}alkyl)(CH_2)_{0-4}CO_2R^a$, such as is —$(CH_2)_{1-4}N(SO_2C_{1-4}alkyl)(CH_2)_{0-4}CO_2H$, wherein $R^a$, independently for each occurrence, is H or $C_{1-4}alkyl$. In other embodiments, $R^2$ is —$(CR_2)_{1-4}CO_2R$, such as —$(CR_2)_{1-4}CO_2H$, including —$(CH_2)_{1-4}CO_2H$. In certain embodiments, $R^2$ includes a terminal —$CO_2H$ group. For example, in certain instances, $R^2$ includes a terminal —$(CH_2)_{0-4}CO_2H$ group.

In some embodiments, the present disclosure provides a compound of formula I, wherein Ring A is

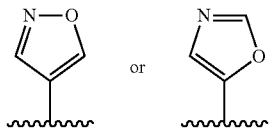 [SMILES: *c1cnoc1 ; *c1cnco1]

thereby forming a compound of formula I-d-4 or I-d-4*, respectively:

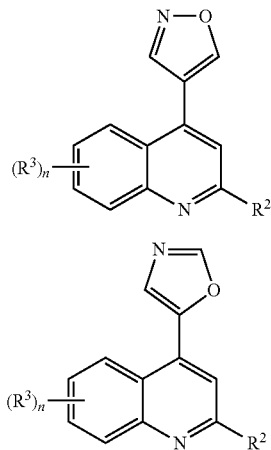

or a pharmaceutically acceptable salt thereof, wherein each of $R^2$, $R^3$, and n is as defined above and described in embodiments herein, both singly and in combination.

In certain embodiments, the present disclosure provides a compound of formula I-d-4 or formula I-d-4*, wherein $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In certain embodiments, the present disclosure provides a compound of formula I-d-4 or I-d-4* wherein $R^2$ is $R^B$, wherein $R^B$ is an optionally substituted $C_{1-6}$ aliphatic, preferably a substituted $C_{1-6}$ aliphatic, such as —$(CR_2)_{1-4}NR(CR_2)_{0-6}CO_2R$, —$(CR_2)_{1-4}O(CR_2)_{0-6}CO_2R$, —$(CR_2)_{1-4}CO_2R$, —$(CR_2)_{1-4}OH$, —$(CR_2)_{1-4}NH_2$, —$(CR_2)_{1-4}C(O)NH_2$, —$(CR_2)_{1-4}C(O)NHC_{1-4}alkyl$, or —$(CR_2)_{1-4}C(O)N(C_{1-4}alkyl)_2$, particularly —$(CR_2)_{1-4}NR(CR_2)_{0-6}CO_2R$ or —$(CR_2)_{1-4}CO_2R$. In some embodiments, $R^2$ is —$(CH_2)_{1-4}NR^a(CH_2)_{0-4}CO_2R^a$, such as —$(CH_2)_{1-4}NR^a(CH_2)_{0-4}CO_2H$, wherein $R^a$, independently for each occurrence, is H or $C_{1-4}alkyl$. In other embodiments, $R^2$ is —$(CH_2)_{1-4}N(SO_2C_{1-4}alkyl)(CH_2)_{0-4}CO_2R^a$, such as is —$(CH_2)_{1-4}N(SO_2C_{1-4}alkyl)(CH_2)_{0-4}CO_2H$, wherein $R^a$, independently for each occurrence, is H or $C_{1-4}alkyl$. In other embodiments, $R^2$ is —$(CR_2)_{1-4}CO_2R$, such as —$(CR_2)_{1-4}CO_2H$, including —$(CH_2)_{1-4}CO_2H$. In certain embodiments, $R^2$ includes a terminal —$CO_2H$ group. For example, in certain instances, $R^2$ includes a terminal —$(CH_2)_{0-4}CO_2H$ group.

In some embodiments, the present disclosure provides a compound of formula I, wherein Ring A is

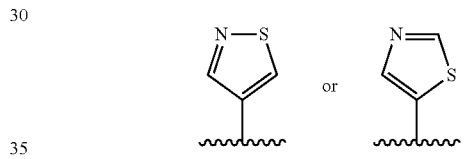

thereby forming a compound of formula I-d-5 or I-d-5*, respectively:

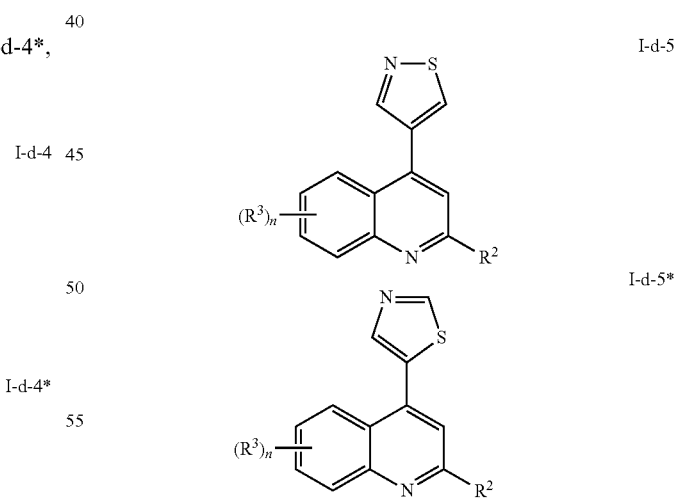

or a pharmaceutically acceptable salt thereof, wherein each of $R^2$, $R^3$, and n is as defined above and described in embodiments herein, both singly and in combination.

In certain embodiments, the present disclosure provides a compound of formula I-d-5 or formula I-d-5*, wherein $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In certain embodiments, the present disclosure provides a compound of formula I-d-5 or I-d-5*, wherein $R^2$ is $R^B$, wherein $R^B$ is an optionally substituted $C_{1-6}$ aliphatic, preferably a substituted $C_{1-6}$ aliphatic, such as $-(CR_2)_{1-4}NR(CR_2)_{0-6}CO_2R$, $-(CR_2)_{1-4}O(CR_2)_{0-6}CO_2R$, $-(CR_2)_{1-4}CO_2R$, $-(CR_2)_{1-4}OH$, $-(CR_2)_{1-4}NH_2$, $-(CR_2)_{1-4}C(O)NH_2$, $-(CR_2)_{1-4}C(O)NHC_{1-4}alkyl$, or $-(CR_2)_{1-4}C(O)N(C_{1-4}alkyl)_2$, particularly $-(CR_2)_{1-4}NR(CR_2)_{0-6}CO_2R$ or $-(CR_2)_{1-4}CO_2R$. In some embodiments, $R^2$ is $-(CH_2)_{1-4}NR^a(CH_2)_{0-4}CO_2R^a$, such as $-(CH_2)_{1-4}NR^a(CH_2)_{0-4}CO_2H$, wherein $R^a$, independently for each occurrence, is H or $C_{1-4}alkyl$. In other embodiments, $R^2$ is $-(CH_2)_{1-4}N(SO_2C_{1-4}alkyl)(CH_2)_{0-4}CO_2R^a$, such as is $-(CH_2)_{1-4}N(SO_2C_{1-4}alkyl)(CH_2)_{0-4}CO_2H$, wherein $R^a$, independently for each occurrence, is H or $C_{1-4}alkyl$. In other embodiments, $R^2$ is $-(CR_2)_{1-4}CO_2R$, such as $-(CR_2)_{1-4}CO_2H$, including $-(CH_2)_{1-4}CO_2H$. In certain embodiments, $R^2$ includes a terminal $-CO_2H$ group. For example, in certain instances, $R^2$ includes a terminal $-(CH_2)_{0-4}CO_2H$ group.

In some embodiments, the present disclosure provides a compound of formula I, wherein Ring A is

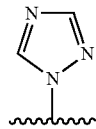

and $R^2$ is

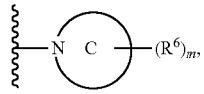

thereby forming a compound of formula I-e-1:

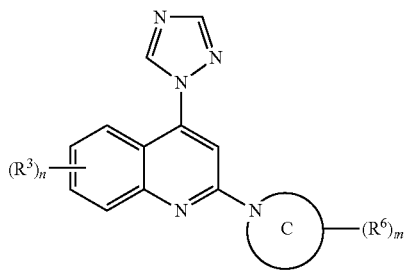

or a pharmaceutically acceptable salt thereof, wherein:
Ring C is pyrrolyl or a 4- to 10-membered saturated or partially unsaturated monocyclic, bicyclic, bridged bicyclic, or spirocyclic heterocyclic ring having 0 to 3 heteroatoms (in addition to the nitrogen already depicted in Ring C) independently selected from nitrogen, oxygen, and sulfur;
each $R^6$ is independently halogen, $=O$, $-COR$, $-(CR_2)_{0-6}CO_2R$, $-(CR_2)_{0-6}CONR_2$, $-OR$, $-(CR_2)_{1-4}OR$, $-NR_2$, $-(CR_2)_{1-4}NR_2$, $-NRC(O)OR$, $-NRC(O)R$, $-NRC(O)NR_2$, $-SR$, $-SO_2R$, $-S(O)R$, $-(CR_2)_{0-6}SO_3R$, $-(CR_2)_{0-6}SO_2NR_2$, $-(CR_2)_{0-6}OSO_2NR_2$, $-(CR_2)_{0-6}NRSO_2R$, $-(CR_2)_{0-6}NRSO_2OR$, $-(CR_2)_{0-6}OP(OR)_2$, $-(CR_2)_{0-6}OP(O)(OR)_2$, $-(CR_2)_{0-6}P(O)(OR)_2$, $-(CR_2)_{0-6}OP(O)(H)OR$, $-B(OR)_2$, or $R^B$;
m is 1, 2, 3, or 4; and
each of R, $R^B$, $R^3$, and n is as defined above and described in embodiments herein, both singly and in combination.

In some embodiments, the present disclosure provides a compound of formula I-e-1, wherein Ring C is azetidinyl, pyrrolyl, 2,3-dihydro-1H-pyrrolyl, pyrrolidinyl, piperidinyl, morpholinyl, thiazolidinyl, indolinyl, isoindolinyl, octahydroindolyl, azepanyl, an oxazepane, an azabicyclohexane, an azabicycloheptane, an azabicyclooctane, an azabicyclononane, an azaspiroheptane, or an octahydrocyclicpentapyrrole.

In particular embodiments, the present disclosure provides a compound of formula I-e-1, wherein Ring C is pyrrolyl, 2-azabicyclo[3.1.0]hexanyl, 3-azabicyclo[3.1.0]hexane, 5-azaspiro[2.4]heptanyl, or octahydrocyclopenta[b]pyrrolyl.

In particular embodiments, the present disclosure provides a compound of formula I-e-1, wherein Ring C is 3-hydroxyproline, $C_{1-6}alkyl$ 3-hydroxyproline ester, or $C_{1-6}haloalkyl$ 3-hydroxyproline ester.

In some embodiments, the present disclosure provides a compound of formula I-e-1, wherein:
each $R^6$ is independently fluoro, $-CN$, methyl, $-C_{3-6}cycloalkyl$, $-CF_3$, $-CO_2H$, $-NH_2$, $-OH$, $-OC_{1-4}alkyl$, $=CH_2$, $=O$, tetrazolyl, imidazoyl, thiophenyl, 1,2,4-oxadiazol-3(2H)-onyl, morpholinyl, phenyl, $-(CH_2)_{1-4}OC_{1-4}alkyl$, $-(CH_2)_{1-4}O(CH_2)_{1-5}CO_2H$, $-(CH_2)_{1-4}O(CH_2)_{1-5}CO_2C_{1-4}alkyl$, $-(CH_2)_{1-4}O(CH_2)_{1-4}CHFCO_2H$, $-(CH_2)_{1-4}O(CH_2)_{1-4}CHFCO_2C_{1-4}alkyl$, $-(CH_2)_{1-4}OCH(CH_3)(CH_2)_{1-4}CO_2H$, $-(CH_2)_{1-4}OCH(CH_3)(CH_2)_{1-4}CO_2C_{1-4}alkyl$, $-(CH_2)_{1-4}O(CH_2)_{1-4}CH(CH_3)CO_2H$, $-(CH_2)_{1-4}O(CH_2)_{1-4}CH(CH_3)CO_2C_{1-4}alkyl$, $-CHOH(CH_2)_{1-4}O(CH_2)_{1-5}CO_2H$, $-CHOH-(CH_2)_{1-4}O(CH_2)_{1-5}CO_2C_{1-4}alkyl$, $-CHCF_3(CH_2)_{1-4}O(CH_2)_{1-5}CO_2H$, $-CHCF_3(CH_2)_{1-4}O(CH_2)_{1-5}CO_2C_{1-4}alkyl$, $-(CH_2)_{0-4}O(CH_2)_{1-5}CONR^a_2$, $-(CH_2)_{1-4}O(CH_2)_{1-5}CONR^aOH$, $-(CH_2)_{1-4}O(CH_2)_{1-5}CONR^aCN$, $-(CH_2)_{1-4}O(CH_2)_{1-5}P(O)OH_2$, $-CH(OH)CF_3$, $-COH(CF_3)_2$, $-(CH_2)_{1-5}CO_2H$, $-(CH_2)_{1-5}CO_2C_{1-4}alkyl$, $-(CH_2)_{0-4}CHCHCO_2H$, $-(CH_2)_{0-4}CHCHCO_2C_{1-4}alkyl$, $-CO_2C_{1-4}alkyl$, $-CO_2C_{1-4}haloalkyl$, $-OCOC_{1-4}alkyl$, $-O(CH_2)_{1-4}CO_2H$, $-O(CH_2)_{1-4}CO_2C_{1-4}alkyl$, $-OCONR^a(CH_2)_{0-4}CO_2H$, $-OCONR^a(CH_2)_{0-4}CO_2C_{1-4}alkyl$, $-OCO-(N-morpholine)$, $-CONH_2$, $-CONHOH$, $-CONHOC_{1-4}alkyl$, $-(CH_2)_{0-4}C(O)NR^a(CH_2)_{1-4}CO_2H$, $-(CH_2)_{0-4}C(O)NR^a(CH_2)_{1-4}CO_2C_{1-4}alkyl$, $-(CH_2)_{0-4}C(O)NR^a(CH_2)_{1-4}(pyrrolid-2-one)$, $-(CH_2)_{0-4}C(O)NR^a(CH_2)_{1-4}(piperidin-2-one)$, $-(CH_2)_{0-4}C(O)NR^a(CH_2)_{1-4}C(OH)(CF_3)_2$, $-(CH_2)_{0-4}C(O)NR^a(CH_2)_{1-4}CONH_2$, $-(CH_2)_{0-4}CONR^aSO_2C_{1-4}haloalkyl$, $-(CH_2)_{0-4}CO(N-pyrrolidine)-(CH_2)_{0-4}CO_2H$, $-(CH_2)_{0-4}CO(N-pyrrolidine)-(CH_2)_{0-4}CO_2C_{1-4}alkyl$, $-(CH_2)_{0-4}(N-pyrazole)-(CH_2)_{0-4}CO_2H$, $-(CH_2)_{0-4}CO(N-pyrazole)-(CH_2)_{0-4}CO_2C_{1-4}alkyl$, $-(CH_2)_{0-4}(N-pyrrole)-(CH_2)_{0-4}CO_2H$, $-(CH_2)_{0-4}CO(N-pyrrole)-(CH_2)_{0-4}CO_2C_{1-4}alkyl$, $-(CH_2)_{0-4}-O-(phenyl)-(CH_2)_{0-4}CO_2H$, $-(CH_2)_{0-4}-O-(phenyl)-(CH_2)_{0-4}CO_2C_{1-4}alkyl$, $-(CH_2)_{0-4}-O(cycloalkane)-

—(CH$_2$)$_{0-4}$CO$_2$H, —(CH$_2$)$_{0-4}$—O(cycloalkane)-(CH$_2$)$_{0-4}$CO$_2$C$_{1-4}$alkyl, —(CH$_2$)$_{0-4}$CO(N-pyrrolidine)-(CH$_2$)$_{0-4}$SO$_2$NH$_2$, —(CH$_2$)$_{0-4}$CO(N-pyrrolidine)-(tetrazole), —(CH$_2$)$_{0-4}$CO(N-piperidine)-(CH$_2$)$_{0-4}$CO$_2$H, —(CH$_2$)$_{0-4}$CO(N-piperidine)-(CH$_2$)$_{0-4}$CO$_2$C$_{1-4}$alkyl, —(CH$_2$)$_{0-4}$CO(N-morpholine)-(CH$_2$)$_{0-4}$CO$_2$H, —CONR$^a$(bicyclo[1.1.1]pentane)-(CH$_2$)$_{0-4}$CO$_2$H, —NH$_2$, —(CH$_2$)$_{0-4}$NR$^a$(CH$_2$)$_{1-4}$CO$_2$H, —(CH$_2$)$_{0-4}$NR$^a$(CH$_2$)$_{1-4}$CO$_2$C$_{1-4}$alkyl, —(CH$_2$)$_{0-4}$N[(CH$_2$)$_{1-4}$CO$_2$C$_{1-4}$alkyl]$_2$, —(CH$_2$)$_{0-4}$NR$^a$CO(isoxazole)-OH, —(CH$_2$)$_{0-4}$NR$^a$SO$_2$(benzene)-CO$_2$H, —(CH$_2$)$_{0-4}$NR$^a$SO$_2$(CH$_2$)$_{1-4}$CO$_2$H, —(CH$_2$)$_{0-4}$NR$^a$SO$_2$(CH$_2$)$_{1-4}$CO$_2$C$_{1-4}$alkyl, —(CH$_2$)$_{0-4}$NR$^a$SO$_2$(CH$_2$)$_{1-4}$(imidazolidine-2,4-dione), —(CH$_2$)$_{0-4}$OP(O)(H)OH, wherein R$^a$, independently for each occurrence, is H or C$_{1-4}$alkyl; and m is 1, 2, 3, or 4.

In particular embodiments, the present disclosure provides a compound of formula I-e-1, wherein each R$^6$ is independently fluoro, -methyl, cyclohexyl, —CF$_3$, —CO$_2$H, —CO$_2$C$_{1-4}$alkyl, —CO$_2$C$_{1-4}$haloalkyl, or —OH; and m is 1, 2, or 3, particularly 1 or 2.

In particular embodiments, the present disclosure provides a compound of formula I-e-1, wherein each R$^6$ is independently fluoro, -methyl, cyclohexyl, —CF$_3$, -methoxy, —(CH$_2$)$_{1-5}$CO$_2$H, —(CH$_2$)$_{1-5}$CO$_2$C$_{1-4}$alkyl, —(CH$_2$)$_{0-4}$O(CH$_2$)$_{1-5}$CO$_2$H, —(CH$_2$)$_{0-4}$O(CH$_2$)$_{1-5}$CO$_2$C$_{1-4}$alkyl, or —OH; and m is 1, 2, or 3, particularly 1 or 2.

In certain embodiments, the present disclosure provides a compound of formula I-e-1, wherein R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In some embodiments, the present disclosure provides a compound of formula I, wherein Ring A is

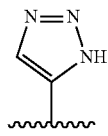

and R$^2$ is

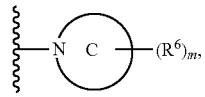

thereby forming a compound of formula I-e-2:

I-e-2

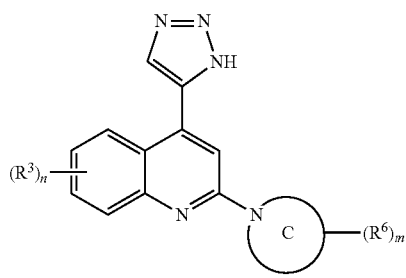

or a pharmaceutically acceptable salt thereof, wherein:

Ring C is pyrrolyl or a 4- to 10-membered saturated or partially unsaturated monocyclic, bicyclic, bridged bicyclic, or spirocyclic heterocyclic ring having 0 to 3 heteroatoms (in addition to the nitrogen already depicted in Ring C) independently selected from nitrogen, oxygen, and sulfur;

each R$^6$ is independently halogen, =O, —COR, —(CR$_2$)$_{0-6}$CO$_2$R, —(CR$_2$)$_{0-6}$CONR$_2$, —OR, —(CR$_2$)$_{1-4}$OR, —NR$_2$, —(CR$_2$)$_{1-4}$NR$_2$, —NRC(O)OR, —NRC(O)R, —NRC(O)NR$_2$, —SR, —SO$_2$R, —S(O)R, —(CR$_2$)$_{0-6}$SO$_3$R, —(CR$_2$)$_{0-6}$SO$_2$NR$_2$, —(CR$_2$)$_{0-6}$OSO$_2$NR$_2$, —(CR$_2$)$_{0-6}$NRSO$_2$R, —(CR$_2$)$_{0-6}$NRSO$_2$OR, —(CR$_2$)$_{0-6}$OP(OR)$_2$, —(CR$_2$)$_{0-6}$OP(O)(OR)$_2$, —(CR$_2$)$_{0-6}$P(O)(OR)$_2$, —(CR$_2$)$_{0-6}$OP(O)(H)OR, —B(OR)$_2$, or R$^B$;

m is 1, 2, 3, or 4; and each of R, R$^B$, R$^3$, and n is as defined above and described in embodiments herein, both singly and in combination.

In some embodiments, the present disclosure provides a compound of formula I-e-2, wherein Ring C is azetidinyl, pyrrolyl, 2,3-dihydro-1H-pyrrolyl, pyrrolidinyl, piperidinyl, morpholinyl, thiazolidinyl, indolinyl, isoindolinyl, octahydroindolyl, azepanyl, an oxazepane, an azabicyclohexane, an azabicycloheptane, an azabicyclooctane, an azabicyclononane, an azaspiroheptane, or an octahydrocyclicpentapyrrole.

In particular embodiments, the present disclosure provides a compound of formula I-e-2, wherein Ring C is pyrrolyl, 2-azabicyclo[3.1.0]hexanyl, 3-azabicyclo[3.1.0]hexane, 5-azaspiro[2.4]heptanyl, or octahydrocyclopenta[b]pyrrolyl.

In particular embodiments, the present disclosure provides a compound of formula I-e-2, wherein Ring C is 3-hydroxyproline, C$_{1-6}$alkyl 3-hydroxyproline ester, or C$_{1-6}$haloalkyl 3-hydroxyproline ester.

In some embodiments, the present disclosure provides a compound of formula I-e-2, wherein:

each R$^6$ is independently fluoro, —CN, methyl, —C$_{3-6}$cycloalkyl, —CF$_3$, —CO$_2$H, —NH$_2$, —OH, —OC$_{1-4}$alkyl, =CH$_2$, =O, tetrazolyl, imidazoyl, thiophenyl, 1,2,4-oxadiazol-3(2H)-onyl, morpholinyl, phenyl, —(CH$_2$)$_{1-4}$OC$_{1-4}$alkyl, —(CH$_2$)$_{1-4}$O(CH$_2$)$_{1-5}$CO$_2$H, —(CH$_2$)$_{1-4}$O(CH$_2$)$_{1-5}$CO$_2$C$_{1-4}$alkyl, —(CH$_2$)$_{1-4}$O(CH$_2$)$_{1-4}$CHFCO$_2$H, —(CH$_2$)$_{1-4}$O(CH$_2$)$_{1-4}$CHFCO$_2$C$_{1-4}$alkyl, —(CH$_2$)$_{1-4}$OCH(CH$_3$)(CH$_2$)$_{1-4}$CO$_2$H, —(CH$_2$)$_{1-4}$OCH(CH$_3$)(CH$_2$)$_{1-4}$CO$_2$C$_{1-4}$alkyl, —(CH$_2$)$_{1-4}$O(CH$_2$)$_{1-4}$CH(CH$_3$)CO$_2$H, —(CH$_2$)$_{1-4}$O(CH$_2$)$_{1-4}$CH(CH$_3$)CO$_2$C$_{1-4}$alkyl, —CHOH(CH$_2$)$_{1-4}$O(CH$_2$)$_{1-5}$CO$_2$H, —CHOH—(CH$_2$)$_{1-4}$O(CH$_2$)$_{1-5}$CO$_2$C$_{1-4}$alkyl, —CHCF$_3$(CH$_2$)$_{1-4}$O(CH$_2$)$_{1-5}$CO$_2$H, —CHCF$_3$(CH$_2$)$_{1-4}$O(CH$_2$)$_{1-5}$CO$_2$C$_{1-4}$alkyl, —(CH$_2$)$_{0-4}$O(CH$_2$)$_{1-5}$CONR$^a$$_2$, —(CH$_2$)$_{1-4}$O(CH$_2$)$_{1-5}$CONR$^a$OH, —(CH$_2$)$_{1-4}$O(CH$_2$)$_{1-5}$CONR$^a$CN, —(CH$_2$)$_{1-4}$O(CH$_2$)$_{1-5}$P(O)OH$_2$, —CH(OH)CF$_3$, —COH(CF$_3$)$_2$, —(CH$_2$)$_{1-5}$CO$_2$H, —(CH$_2$)$_{1-5}$CO$_2$C$_{1-4}$alkyl, —(CH$_2$)$_{0-4}$CHCHCO$_2$H, —(CH$_2$)$_{0-4}$CHCHCO$_2$C$_{1-4}$alkyl, —CO$_2$C$_{1-4}$alkyl, —CO$_2$C$_{1-4}$haloalkyl, —OCOC$_{1-4}$alkyl, —O(CH$_2$)$_{1-4}$CO$_2$H, —O(CH$_2$)$_{1-4}$CO$_2$C$_{1-4}$alkyl, —OCONR$^a$(CH$_2$)$_{0-4}$CO$_2$H, —OCONR$^a$(CH$_2$)$_{0-4}$CO$_2$C$_{1-4}$alkyl, —OCO—(N-morpholine), —CONH$_2$, —CONHOH, —CONHOC$_{1-4}$alkyl, —(CH$_2$)$_{0-4}$C(O)NR$^a$(CH$_2$)$_{1-4}$CO$_2$H, —(CH$_2$)$_{0-4}$C(O)NR$^a$(CH$_2$)$_{1-4}$CO$_2$C$_{1-4}$alkyl, —(CH$_2$)$_{0-4}$C(O)NR$^a$(CH$_2$)$_{1-4}$(pyrrolid-2-one), —(CH$_2$)$_{0-4}$C(O)NR$^a$(CH$_2$)$_{1-4}$(piperidin-2-one), —(CH$_2$)$_{0-4}$C(O)NR$^a$(CH$_2$)$_{1-4}$C(OH)(CF$_3$)$_2$, —(CH$_2$)$_{0-4}$C(O)NR$^a$(CH$_2$)$_{1-4}$CONH$_2$, —(CH$_2$)$_{0-4}$CONR$^a$SO$_2$C$_{1-4}$haloalkyl, —(CH$_2$)$_{0-4}$CO(N-pyrrolidine)-(CH$_2$)$_{0-4}$CO$_2$H, —(CH$_2$)$_{0-4}$CO(N-pyrrolidine)-(CH$_2$)$_{0-4}$CO$_2$C$_{1-4}$alkyl, —(CH$_2$)$_{0-4}$(N-pyrazole)-(CH$_2$)$_{0-4}$CO$_2$H, —(CH$_2$)$_{0-4}$CO(N-pyrazole)-(CH$_2$)$_{0-4}$CO$_2$C$_{1-4}$alkyl, —(CH$_2$)$_{0-4}$(N-pyrrole)-(CH$_2$)$_{0-4}$CO$_2$H, —(CH$_2$)$_{0-4}$CO(N-pyrrole)-(CH$_2$)$_{0-4}$CO$_2$C$_{1-4}$alkyl, —(CH$_2$)$_{0-4}$—O-(phenyl)-(CH$_2$)$_{0-4}$CO$_2$H, —(CH$_2$)$_{0-4}$—O-(phenyl)-(CH$_2$)$_{0-4}$CO$_2$C$_{1-4}$alkyl, —(CH$_2$)$_{0-4}$—O(cycloalkane)-(CH$_2$)$_{0-4}$CO$_2$H, —(CH$_2$)$_{0-4}$—O(cycloalkane)-(CH$_2$)$_{0-4}$CO$_2$C$_{1-4}$alkyl, —(CH$_2$)$_{0-4}$CO(N-pyrrolidine)-(CH$_2$)$_{0-4}$SO$_2$NH$_2$, —(CH$_2$)$_{0-4}$CO(N-pyrrolidine)-(tetrazole), —(CH$_2$)$_{0-4}$CO(N-piperidine)-(CH$_2$)$_{0-4}$CO$_2$H, —(CH$_2$)$_{0-4}$CO(N-piperidine)-(CH$_2$)$_{0-4}$CO$_2$C$_{1-4}$alkyl, —(CH$_2$)$_{0-4}$CO(N-morpholine)-(CH$_2$)$_{0-4}$CO$_2$H, —CONR$^a$(bicyclo[1.1.1]pentane)-(CH$_2$)$_{0-4}$CO$_2$H, —NH$_2$, —(CH$_2$)$_{0-4}$NR$^a$(CH$_2$)$_{1-4}$CO$_2$H, —(CH$_2$)$_{0-4}$NR$^a$(CH$_2$)$_{1-4}$CO$_2$C$_{1-4}$alkyl, —(CH$_2$)$_{0-4}$N[(CH$_2$)$_{1-4}$CO$_2$C$_{1-4}$alkyl]$_2$, —(CH$_2$)$_{0-4}$NR$^a$CO(isoxazole)-OH, —(CH$_2$)$_{0-4}$NR$^a$SO$_2$(benzene)-CO$_2$H, —(CH$_2$)$_{0-4}$NR$^a$SO$_2$(CH$_2$)$_{1-4}$CO$_2$H, —(CH$_2$)$_{0-4}$NR$^a$SO$_2$(CH$_2$)$_{1-4}$CO$_2$C$_{1-4}$alkyl, —(CH$_2$)$_{0-4}$NR$^a$SO$_2$(CH$_2$)$_{1-4}$(imidazolidine-2,4-dione), —(CH$_2$)$_{0-4}$OP(O)(H)OH, wherein R$^a$, independently for each occurrence, is H or C$_{1-4}$alkyl; and m is 1, 2, 3, or 4.

In particular embodiments, the present disclosure provides a compound of formula I-e-2, wherein each R$^6$ is independently fluoro, -methyl, cyclohexyl, —CF$_3$, —CO$_2$H, —CO$_2$C$_{1-4}$alkyl, —CO$_2$C$_{1-4}$haloalkyl, or —OH; and m is 1, 2, or 3, particularly 1 or 2.

In particular embodiments, the present disclosure provides a compound of formula I-e-2, wherein each R$^6$ is independently fluoro, -methyl, cyclohexyl, —CF$_3$, -methoxy, —(CH$_2$)$_{1-5}$CO$_2$H, —(CH$_2$)$_{1-5}$CO$_2$C$_{1-4}$alkyl, —(CH$_2$)$_{0-4}$O(CH$_2$)$_{1-5}$CO$_2$H, —(CH$_2$)$_{0-4}$O(CH$_2$)$_{1-5}$CO$_2$C$_{1-4}$alkyl, or —OH; and m is 1, 2, or 3, particularly 1 or 2.

In certain embodiments, the present disclosure provides a compound of I-e-2, wherein R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In some embodiments, the present disclosure provides a compound of formula I, wherein Ring A is

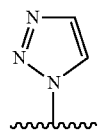

and R$^2$ is

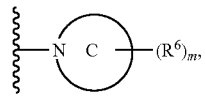

thereby forming a compound of formula I-e-3:

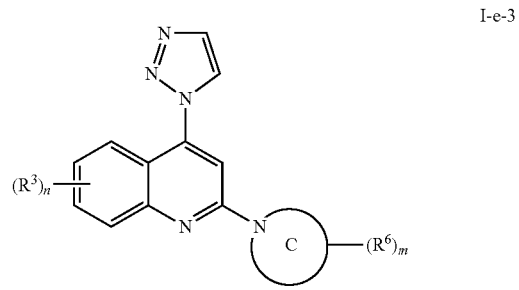

I-e-3 or a pharmaceutically acceptable salt thereof, wherein:
Ring C is pyrrolyl or a 4- to 10-membered saturated or partially unsaturated monocyclic, bicyclic, bridged bicyclic, or spirocyclic heterocyclic ring having 0 to 3 heteroatoms (in addition to the nitrogen already depicted in Ring C) independently selected from nitrogen, oxygen, and sulfur;

each R$^6$ is independently halogen, =O, —COR, —(CR$_2$)$_{0-6}$CO$_2$R, —(CR$_2$)$_{0-6}$CONR$_2$, —OR, —(CR$_2$)$_{1-4}$OR, —NR$_2$, —(CR$_2$)$_{1-4}$NR$_2$, —NRC(O)OR, —NRC(O)R, —NRC(O)NR$_2$, —SR, —SO$_2$R, —S(O)R, —(CR$_2$)$_{0-6}$SO$_3$R, —(CR$_2$)$_{0-6}$SO$_2$NR$_2$, —(CR$_2$)$_{0-6}$OSO$_2$NR$_2$, —(CR$_2$)$_{0-6}$NRSO$_2$R, —(CR$_2$)$_{0-6}$NRSO$_2$OR, —(CR$_2$)$_{0-6}$OP(OR)$_2$, —(CR$_2$)$_{0-6}$OP(O)(OR)$_2$, —(CR$_2$)$_{0-6}$P(O)(OR)$_2$, —(CR$_2$)$_{0-6}$OP(O)(H)OR, —B(OR)$_2$, or R$^B$;

m is 1, 2, 3, or 4; and
each of R, R$^B$, R$^3$, and n is as defined above and described in embodiments herein, both singly and in combination.

In some embodiments, the present disclosure provides a compound of formula I-e-3, wherein Ring C is azetidinyl, pyrrolyl, 2,3-dihydro-1H-pyrrolyl, pyrrolidinyl, piperidinyl, morpholinyl, thiazolidinyl, indolinyl, isoindolinyl, octahydroindolyl, azepanyl, an oxazepane, an azabicyclohexane, an azabicycloheptane, an azabicyclooctane, an azabicyclononane, an azaspiroheptane, or an octahydrocyclicpentapyrrole.

In particular embodiments, the present disclosure provides a compound of formula I-e-3, wherein Ring C is pyrrolyl, 2-azabicyclo[3.1.0]hexanyl, 3-azabicyclo[3.1.0]hexane, 5-azaspiro[2.4]heptanyl, or octahydrocyclopenta[b]pyrrolyl.

In particular embodiments, the present disclosure provides a compound of formula I-e-3, wherein Ring C is 3-hydroxyproline, C$_{1-6}$alkyl 3-hydroxyproline ester, or C$_{1-6}$haloalkyl 3-hydroxyproline ester.

In some embodiments, the present disclosure provides a compound of formula I-e-3, wherein:
each R$^6$ is independently fluoro, —CN, methyl, —C$_{3-6}$cycloalkyl, —CF$_3$, —CO$_2$H, —NH$_2$, —OH, —OC$_{1-4}$alkyl, =CH$_2$, =O, tetrazolyl, imidazoyl, thiophenyl, 1,2,4-oxadiazol-3(2H)-onyl, morpholinyl, phenyl, —(CH$_2$)$_{1-4}$OC$_{1-4}$alkyl, —(CH$_2$)$_{1-4}$O(CH$_2$)$_{1-5}$CO$_2$H, —(CH$_2$)$_{1-4}$O(CH$_2$)$_{1-5}$CO$_2$C$_{1-4}$alkyl, —(CH$_2$)$_{1-4}$O(CH$_2$)$_{1-4}$CHFCO$_2$H, —(CH$_2$)$_{1-4}$O(CH$_2$)$_{1-4}$CHFCO$_2$C$_{1-4}$alkyl, —(CH$_2$)$_{1-4}$OCH(CH$_3$)(CH$_2$)$_{1-4}$CO$_2$H, —(CH$_2$)$_{1-4}$OCH(CH$_3$)(CH$_2$)$_{1-4}$CO$_2$C$_{1-4}$alkyl, —(CH$_2$)$_{1-4}$O(CH$_2$)$_{1-4}$CH(CH$_3$)CO$_2$H, —(CH$_2$)$_{1-4}$O(CH$_2$)$_{1-4}$CH(CH$_3$)CO$_2$C$_{1-4}$alkyl, —CHOH(CH$_2$)$_{1-4}$O(CH$_2$)$_{1-5}$CO$_2$H, —CHOH—

—(CH$_2$)$_{1-4}$O(CH$_2$)$_{1-5}$CO$_2$C$_{1-4}$alkyl, —CHCF$_3$(CH$_2$)$_{1-4}$O(CH$_2$)$_{1-5}$CO$_2$H, —CHCF$_3$(CH$_2$)$_{1-4}$O(CH$_2$)$_{1-5}$CO$_2$C$_{1-4}$alkyl, —(CH$_2$)$_{0-4}$O(CH$_2$)$_{1-5}$CONR$^a$$_2$, —(CH$_2$)$_{1-4}$O(CH$_2$)$_{1-5}$CONR$^a$OH, —(CH$_2$)$_{1-4}$O(CH$_2$)$_{1-5}$CONR$^a$CN, —(CH$_2$)$_{1-4}$O(CH$_2$)$_{1-5}$P(O)OH$_2$, —CH(OH)CF$_3$, —COH(CF$_3$)$_2$, —(CH$_2$)$_{1-5}$CO$_2$H, —(CH$_2$)$_{1-5}$CO$_2$C$_{1-4}$alkyl, —(CH$_2$)$_{0-4}$CHCHCO$_2$H, —(CH$_2$)$_{0-4}$CHCHCO$_2$C$_{1-4}$alkyl, —CO$_2$C$_{1-4}$haloalkyl, —OCOC$_{1-4}$alkyl, —O(CH$_2$)$_{1-4}$CO$_2$H, —O(CH$_2$)$_{1-4}$CO$_2$C$_{1-4}$alkyl, —OCONR$^a$(CH$_2$)$_{0-4}$CO$_2$H, —OCONR$^a$(CH$_2$)$_{0-4}$CO$_2$C$_{1-4}$alkyl, —OCO—(N-morpholine), —CONH$_2$, —CONHOH, —CONHOC$_{1-4}$alkyl, —(CH$_2$)$_{0-4}$C(O)NR$^a$(CH$_2$)$_{1-4}$CO$_2$H, —(CH$_2$)$_{0-4}$C(O)NR$^a$(CH$_2$)$_{1-4}$CO$_2$C$_{1-4}$alkyl, —(CH$_2$)$_{0-4}$C(O)NR$^a$(CH$_2$)$_{1-4}$(pyrrolid-2-one), —(CH$_2$)$_{0-4}$C(O)NR$^a$(CH$_2$)$_{1-4}$(piperidin-2-one), —(CH$_2$)$_{0-4}$C(O)NR$^a$(CH$_2$)$_{1-4}$C(OH)(CF$_3$)$_2$, —(CH$_2$)$_{0-4}$C(O)NR$^a$(CH$_2$)$_{1-4}$CONH$_2$, —(CH$_2$)$_{0-4}$CONR$^a$SO$_2$C$_{1-4}$haloalkyl, —(CH$_2$)$_{0-4}$CO(N-pyrrolidine)-(CH$_2$)$_{0-4}$CO$_2$H, —(CH$_2$)$_{0-4}$CO(N-pyrrolidine)-(CH$_2$)$_{0-4}$CO$_2$C$_{1-4}$alkyl, —(CH$_2$)$_{0-4}$CO(N-pyrazole)-(CH$_2$)$_{0-4}$CO$_2$H, —(CH$_2$)$_{0-4}$CO(N-pyrazole)-(CH$_2$)$_{0-4}$CO$_2$C$_{1-4}$alkyl, —(CH$_2$)$_{0-4}$(N-pyrrole)-(CH$_2$)$_{0-4}$CO$_2$H, —(CH$_2$)$_{0-4}$CO(N-pyrrole)-(CH$_2$)$_{0-4}$CO$_2$C$_{1-4}$alkyl, —(CH$_2$)$_{0-4}$—O-(phenyl)-(CH$_2$)$_{0-4}$CO$_2$H, —(CH$_2$)$_{0-4}$—O-(phenyl)-(CH$_2$)$_{0-4}$CO$_2$C$_{1-4}$alkyl, —(CH$_2$)$_{0-4}$—O(cycloalkane)-(CH$_2$)$_{0-4}$CO$_2$H, —(CH$_2$)$_{0-4}$—O(cycloalkane)-(CH$_2$)$_{0-4}$CO$_2$C$_{1-4}$alkyl, —(CH$_2$)$_{0-4}$CO(N-pyrrolidine)-(CH$_2$)$_{0-4}$SO$_2$NH$_2$, —(CH$_2$)$_{0-4}$CO(N-pyrrolidine)-(tetrazole), —(CH$_2$)$_{0-4}$CO(N-piperidine)-(CH$_2$)$_{0-4}$CO$_2$H, —(CH$_2$)$_{0-4}$CO(N-piperidine)-(CH$_2$)$_{0-4}$CO$_2$C$_{1-4}$alkyl, —(CH$_2$)$_{0-4}$CO(N-morpholine)-(CH$_2$)$_{0-4}$CO$_2$H, —CONR$^a$(bicyclo[1.1.1]pentane)-(CH$_2$)$_{0-4}$CO$_2$H, —NH$_2$, —(CH$_2$)$_{0-4}$NR$^a$(CH$_2$)$_{1-4}$CO$_2$H, —(CH$_2$)$_{0-4}$NR$^a$(CH$_2$)$_{1-4}$CO$_2$C$_{1-4}$alkyl, —(CH$_2$)$_{0-4}$N[(CH$_2$)$_{1-4}$CO$_2$C$_{1-4}$alkyl]$_2$, —(CH$_2$)$_{0-4}$NR$^a$CO(isoxazole)-OH, —(CH$_2$)$_{0-4}$NR$^a$SO$_2$(benzene)-CO$_2$H, —(CH$_2$)$_{0-4}$NR$^a$SO$_2$(CH$_2$)$_{1-4}$CO$_2$H, —(CH$_2$)$_{0-4}$NR$^a$SO$_2$(CH$_2$)$_{1-4}$CO$_2$C$_{1-4}$alkyl, —(CH$_2$)$_{0-4}$NR$^a$SO$_2$(CH$_2$)$_{1-4}$(imidazolidine-2,4-dione), —(CH$_2$)$_{0-4}$OP(O)(H)OH, wherein R$^a$, independently for each occurrence, is H or C$_{1-4}$alkyl; and m is 1, 2, 3, or 4.

In particular embodiments, the present disclosure provides a compound of formula I-e-3, wherein each R$^6$ is independently fluoro, -methyl, cyclohexyl, —CF$_3$, —CO$_2$H, —CO$_2$C$_{1-4}$alkyl, —CO$_2$C$_{1-4}$haloalkyl, or —OH; and m is 1, 2, or 3, particularly 1 or 2.

In particular embodiments, the present disclosure provides a compound of formula I-e-3, wherein each R$^6$ is independently fluoro, -methyl, cyclohexyl, —CF$_3$, -methoxy, —(CH$_2$)$_{1-5}$CO$_2$H, —(CH$_2$)$_{1-5}$CO$_2$C$_{1-4}$alkyl, —(CH$_2$)$_{0-4}$O(CH$_2$)$_{1-5}$CO$_2$H, —(CH$_2$)$_{0-4}$O(CH$_2$)$_{1-5}$CO$_2$C$_{1-4}$alkyl, or —OH; and m is 1, 2, or 3, particularly 1 or 2.

In certain embodiments, the present disclosure provides a compound of formula I-e-3, wherein R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In some embodiments, the present disclosure provides a compound of formula I, wherein Ring A is

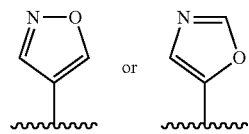 [SMILES: *c1cnoc1 ; *c1cnco1]

and R$^2$ is

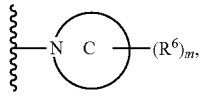

thereby forming a compound of formula I-e-4 or

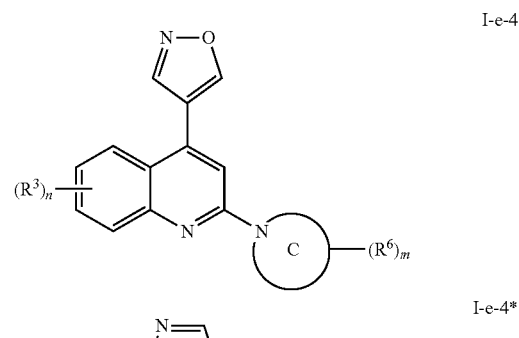

I-e-4

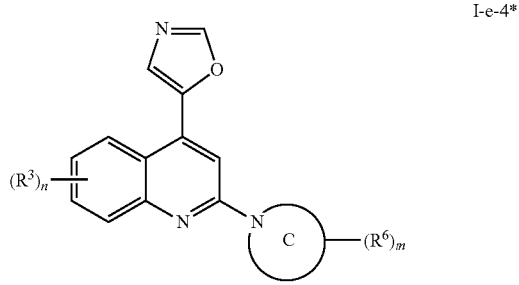

I-e-4* or a pharmaceutically acceptable salt thereof, wherein:

Ring C is pyrrolyl or a 4- to 10-membered saturated or partially unsaturated monocyclic, bicyclic, bridged bicyclic, or spirocyclic heterocyclic ring having 0 to 3 heteroatoms (in addition to the nitrogen already depicted in Ring C) independently selected from nitrogen, oxygen, and sulfur;

each R$^6$ is independently halogen, =O, —COR, —(CR$_2$)$_{0-6}$CO$_2$R, —(CR$_2$)$_{0-6}$CONR$_2$, —OR, —(CR$_2$)$_{1-4}$OR, —NR$_2$, —(CR$_2$)$_{1-4}$NR$_2$, —NRC(O)OR, —NRC(O)R, —NRC(O)NR$_2$, —SR, —SO$_2$R, —S(O)R, —(CR$_2$)$_{0-6}$SO$_3$R, —(CR$_2$)$_{0-6}$SO$_2$NR$_2$, —(CR$_2$)$_{0-6}$OSO$_2$NR$_2$, —(CR$_2$)$_{0-6}$NRSO$_2$R, —(CR$_2$)$_{0-6}$NRSO$_2$OR, —(CR$_2$)$_{0-6}$OP(OR)$_2$, —(CR$_2$)$_{0-6}$OP(O)(OR)$_2$, —(CR$_2$)$_{0-6}$P(O)(OR)$_2$, —(CR$_2$)$_{0-6}$OP(O)(H)OR, —B(OR)$_2$, or R$^B$;

m is 1, 2, 3, or 4; and each of R, R$^B$, R$^3$, and n is as defined above and described in embodiments herein, both singly and in combination.

In some embodiments, the present disclosure provides a compound of formula I-e-4 or formula I-e-4*, wherein Ring C is azetidinyl, pyrrolyl, 2,3-dihydro-1H-pyrrolyl, pyrrolidinyl, piperidinyl, morpholinyl, thiazolidinyl, indolinyl, isoindolinyl, octahydroindolyl, azepanyl, an oxazepane, an azabicyclohexane, an azabicycloheptane, an azabicyclooctane, an azabicyclononane, an azaspiroheptane, or an octahydrocyclicpentapyrrole.

In particular embodiments, the present disclosure provides a compound of formula I-e-4 or formula I-e-4*, wherein Ring C is pyrrolyl, 2-azabicyclo[3.1.0]hexanyl, 3-azabicyclo[3.1.0]hexane, 5-azaspiro[2.4]heptanyl, or octahydrocyclopenta[b]pyrrolyl.

In particular embodiments, the present disclosure provides a compound of formula I-e-4 or formula I-e-4*, wherein Ring C is 3-hydroxyproline, $C_{1-6}$alkyl 3-hydroxyproline ester, or $C_{1-6}$haloalkyl 3-hydroxyproline ester.

In some embodiments, the present disclosure provides a compound of formula I-e-4 or formula I-e-4*, wherein:
each $R^6$ is independently fluoro, —CN, methyl, —$C_{3-6}$cycloalkyl, —$CF_3$, —$CO_2H$, —$NH_2$, —OH, —$OC_{1-4}$alkyl, =$CH_2$, =O, tetrazolyl, imidazoyl, thiophenyl, 1,2,4-oxadiazol-3(2H)-onyl, morpholinyl, phenyl, —$(CH_2)_{1-4}OC_{1-4}$alkyl, —$(CH_2)_{1-4}O(CH_2)_{1-5}CO_2H$, —$(CH_2)_{1-4}O(CH_2)_{1-5}CO_2C_{1-4}$alkyl, —$(CH_2)_{1-4}O(CH_2)_{1-4}CHFCO_2H$, —$(CH_2)_{1-4}O(CH_2)_{1-4}CHFCO_2C_{1-4}$alkyl, —$(CH_2)_{1-4}OCH(CH_3)(CH_2)_{1-4}CO_2H$, —$(CH_2)_{1-4}OCH(CH_3)(CH_2)_{1-4}CO_2C_{1-4}$alkyl, —$(CH_2)_{1-4}O(CH_2)_{1-4}CH(CH_3)CO_2H$, —$(CH_2)_{1-4}O(CH_2)_{1-4}CH(CH_3)CO_2C_{1-4}$alkyl, —$CHOH(CH_2)_{1-4}O(CH_2)_{1-5}CO_2H$, —CHOH—$(CH_2)_{1-4}O(CH_2)_{1-5}CO_2C_{1-4}$alkyl, —$CHCF_3(CH_2)_{1-4}O(CH_2)_{1-5}CO_2H$, —$CHCF_3(CH_2)_{1-4}O(CH_2)_{1-5}CO_2C_{1-4}$alkyl, —$(CH_2)_{0-4}O(CH_2)_{1-5}CONR^a{}_2$, —$(CH_2)_{1-4}O(CH_2)_{1-5}CONR^aOH$, —$(CH_2)_{1-4}O(CH_2)_{1-5}CONR^aCN$, —$(CH_2)_{1-4}O(CH_2)_{1-5}P(O)OH_2$, —$CH(OH)CF_3$, —$COH(CF_3)_2$, —$(CH_2)_{1-5}CO_2H$, —$(CH_2)_{1-5}CO_2C_{1-4}$alkyl, —$(CH_2)_{0-4}CHCHCO_2H$, —$(CH_2)_{0-4}CHCHCO_2C_{1-4}$alkyl, —$CO_2C_{1-4}$alkyl, —$CO_2C_{1-4}$haloalkyl, —$OCOC_{1-4}$alkyl, —$O(CH_2)_{1-4}CO_2H$, —$O(CH_2)_{1-4}CO_2C_{1-4}$alkyl, —$OCONR^a(CH_2)_{0-4}CO_2H$, —$OCONR^a(CH_2)_{0-4}CO_2C_{1-4}$alkyl, —OCO—(N-morpholine), —$CONH_2$, —CONHOH, —$CONHOC_{1-4}$alkyl, —$(CH_2)_{0-4}C(O)NR^a(CH_2)_{1-4}CO_2H$, —$(CH_2)_{0-4}C(O)NR^a(CH_2)_{1-4}CO_2C_{1-4}$alkyl, —$(CH_2)_{0-4}C(O)NR^a(CH_2)_{1-4}$(pyrrolid-2-one), —$(CH_2)_{0-4}C(O)NR^a(CH_2)_{1-4}$(piperidin-2-one), —$(CH_2)_{0-4}C(O)NR^a(CH_2)_{1-4}C(OH)(CF_3)_2$, —$(CH_2)_{0-4}C(O)NR^a(CH_2)_{1-4}CONH_2$, —$(CH_2)_{0-4}CONR^aSO_2C_{1-4}$haloalkyl, —$(CH_2)_{0-4}CO(N$-pyrrolidine$)$-$(CH_2)_{0-4}CO_2H$, —$(CH_2)_{0-4}CO(N$-pyrrolidine$)$-$(CH_2)_{0-4}CO_2C_{1-4}$alkyl, —$(CH_2)_{0-4}(N$-pyrazole$)$-$(CH_2)_{0-4}CO_2H$, —$(CH_2)_{0-4}CO(N$-pyrazole$)$-$(CH_2)_{0-4}CO_2C_{1-4}$alkyl, —$(CH_2)_{0-4}(N$-pyrrole$)$-$(CH_2)_{0-4}CO_2H$, —$(CH_2)_{0-4}CO(N$-pyrrole$)$-$(CH_2)_{0-4}CO_2C_{1-4}$alkyl, —$(CH_2)_{0-4}$-O-(phenyl)-$(CH_2)_{0-4}CO_2H$, —$(CH_2)_{0-4}$-O-(phenyl)-$(CH_2)_{0-4}CO_2C_{1-4}$alkyl, —$(CH_2)_{0-4}$-O(cycloalkane)-$(CH_2)_{0-4}CO_2H$, —$(CH_2)_{0-4}$-O(cycloalkane)-$(CH_2)_{0-4}CO_2C_{1-4}$alkyl, —$(CH_2)_{0-4}CO(N$-pyrrolidine$)$-$(CH_2)_{0-4}SO_2NH_2$, —$(CH_2)_{0-4}CO(N$-pyrrolidine$)$-(tetrazole), —$(CH_2)_{0-4}CO(N$-piperidine$)$-$(CH_2)_{0-4}CO_2H$, —$(CH_2)_{0-4}CO(N$-piperidine$)$-$(CH_2)_{0-4}CO_2C_{1-4}$alkyl, —$(CH_2)_{0-4}CO(N$-morpholine$)$-$(CH_2)_{0-4}CO_2H$, —$CONR^a$(bicyclo[1.1.1]pentane)-$(CH_2)_{0-4}CO_2H$, —$NH_2$, —$(CH_2)_{0-4}NR^a(CH_2)_{1-4}CO_2H$, —$(CH_2)_{0-4}NR^a(CH_2)_{1-4}CO_2C_{1-4}$alkyl, —$(CH_2)_{0-4}N[(CH_2)_{1-4}CO_2C_{1-4}$alkyl$]_2$, —$(CH_2)_{0-4}NR^aCO$(isoxazole)-OH, —$(CH_2)_{0-4}NR^aSO_2$(benzene)-$CO_2H$, —$(CH_2)_{0-4}NR^aSO_2(CH_2)_{1-4}CO_2H$, —$(CH_2)_{0-4}NR^aSO_2(CH_2)_{1-4}CO_2C_{1-4}$alkyl, —$(CH_2)_{0-4}NR^aSO_2(CH_2)_{1-4}$(imidazolidine-2,4-dione), —$(CH_2)_{0-4}OP(O)(H)OH$, wherein $R^a$, independently for each occurrence, is H or $C_{1-4}$alkyl; and
m is 1, 2, 3, or 4.

In particular embodiments, the present disclosure provides a compound of formula I-e-4 or formula I-e-4*, wherein each $R^6$ is independently fluoro, -methyl, cyclohexyl, —$CF_3$, —$CO_2H$, —$CO_2C_{1-4}$alkyl, —$CO_2C_{1-4}$haloalkyl, or —OH; and m is 1, 2, or 3, particularly 1 or 2.

In particular embodiments, the present disclosure provides a compound of formula I-e-4 or formula I-e-4*, wherein each $R^6$ is independently fluoro, -methyl, cyclohexyl, —$CF_3$, -methoxy, —$(CH_2)_{1-5}CO_2H$, —$(CH_2)_{1-5}CO_2C_{1-4}$alkyl, —$(CH_2)_{0-4}O(CH_2)_{1-5}CO_2H$, —$(CH_2)_{0-4}O(CH_2)_{1-5}CO_2C_{1-4}$alkyl, or —OH; and m is 1, 2, or 3, particularly 1 or 2.

In certain embodiments, the present disclosure provides a compound of I-e-4 or formula I-e-4*, wherein $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In some embodiments, the present disclosure provides a compound of formula I, wherein Ring A is

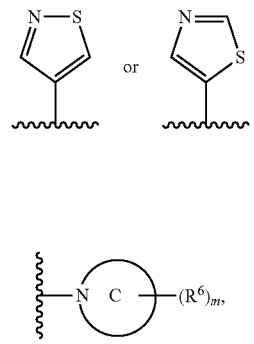

and $R^2$ is

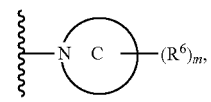

thereby forming a compound of formula I-e-5 or formula I-e-5*, respectively:

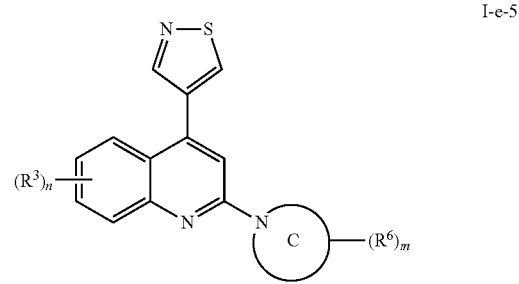

I-e-5

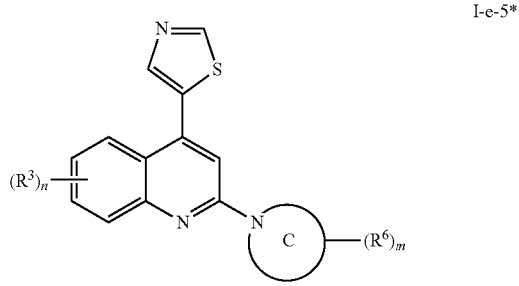

I-e-5* or a pharmaceutically acceptable salt thereof, wherein:
Ring C is pyrrolyl or a 4- to 10-membered saturated or partially unsaturated monocyclic, bicyclic, bridged bicyclic, or spirocyclic heterocyclic ring having 0 to 3 heteroatoms (in addition to the nitrogen already depicted in Ring C) independently selected from nitrogen, oxygen, and sulfur;
each $R^6$ is independently halogen, =O, —COR, —$(CR_2)_{0-6}CO_2R$, —$(CR_2)_{0-6}CONR_2$, —OR, —(CR$_2$)$_{1-4}$OR, —NR$_2$, —(CR$_2$)$_{1-4}$NR$_2$, —NRC(O)OR, —NRC(O)R, —NRC(O)NR$_2$, —SR, —SO$_2$R, —S(O)R, —(CR$_2$)$_{0-6}$SO$_3$R, —(CR$_2$)$_{0-6}$SO$_2$NR$_2$, —(CR$_2$)$_{0-6}$OSO$_2$NR$_2$, —(CR$_2$)$_{0-6}$NRSO$_2$R, —(CR$_2$)$_{0-6}$NRSO$_2$OR, —(CR$_2$)$_{0-6}$OP(OR)$_2$, —(CR$_2$)$_{0-6}$OP(O)(OR)$_2$, —(CR$_2$)$_{0-6}$P(O)(OR)$_2$, —(CR$_2$)$_{0-6}$OP(O)(H)OR, —B(OR)$_2$, or R$^B$;

m is 1, 2, 3, or 4; and each of R, R$^B$, R$^3$, and n is as defined above and described in embodiments herein, both singly and in combination.

In some embodiments, the present disclosure provides a compound of formula I-e-5 or formula I-e-5*, wherein Ring C is azetidinyl, pyrrolyl, 2,3-dihydro-1H-pyrrolyl, pyrrolidinyl, piperidinyl, morpholinyl, thiazolidinyl, indolinyl, isoindolinyl, octahydroindolyl, azepanyl, an oxazepane, an azabicyclohexane, an azabicycloheptane, an azabicyclooctane, an azabicyclononane, an azaspiroheptane, or an octahydrocyclicpentapyrrole.

In particular embodiments, the present disclosure provides a compound of formula I-e-5 or formula I-e-5*, wherein Ring C is pyrrolyl, 2-azabicyclo[3.1.0]hexanyl, 3-azabicyclo[3.1.0]hexane, 5-azaspiro[2.4]heptanyl, or octahydrocyclopenta[b]pyrrolyl.

In particular embodiments, the present disclosure provides a compound of formula I-e-5 or formula I-e-5*, wherein Ring C is 3-hydroxyproline, C$_{1-6}$alkyl 3-hydroxyproline ester, or C$_{1-6}$haloalkyl 3-hydroxyproline ester.

In some embodiments, the present disclosure provides a compound of formula I-e-5 or I-e-5*, wherein:

each R$^6$ is independently fluoro, —CN, methyl, —C$_{3-6}$cycloalkyl, —CF$_3$, —CO$_2$H, —NH$_2$, —OH, —OC$_{1-4}$alkyl, =CH$_2$, =O, tetrazolyl, imidazoyl, thiophenyl, 1,2,4-oxadiazol-3(2H)-onyl, morpholinyl, phenyl, —(CH$_2$)$_{1-4}$OC$_{1-4}$alkyl, —(CH$_2$)$_{1-4}$O(CH$_2$)$_{1-5}$CO$_2$H, —(CH$_2$)$_{1-4}$O(CH$_2$)$_{1-5}$CO$_2$C$_{1-4}$alkyl, —(CH$_2$)$_{1-4}$O(CH$_2$)$_{1-4}$CHFCO$_2$H, —(CH$_2$)$_{1-4}$O(CH$_2$)$_{1-4}$CHFCO$_2$C$_{1-4}$alkyl, —(CH$_2$)$_{1-4}$OCH(CH$_3$)(CH$_2$)$_{1-4}$CO$_2$H, —(CH$_2$)$_{1-4}$OCH(CH$_3$)(CH$_2$)$_{1-4}$CO$_2$C$_{1-4}$alkyl, —(CH$_2$)$_{1-4}$O(CH$_2$)$_{1-4}$CH(CH$_3$)CO$_2$H, —(CH$_2$)$_{1-4}$O(CH$_2$)$_{1-4}$CH(CH$_3$)CO$_2$C$_{1-4}$alkyl, —CHOH(CH$_2$)$_{1-4}$O(CH$_2$)$_{1-5}$CO$_2$H, —CHOH—(CH$_2$)$_{1-4}$O(CH$_2$)$_{1-5}$CO$_2$C$_{1-4}$alkyl, —CHCF$_3$(CH$_2$)$_{1-4}$O(CH$_2$)$_{1-5}$CO$_2$H, —CHCF$_3$(CH$_2$)$_{1-4}$O(CH$_2$)$_{1-5}$CO$_2$C$_{1-4}$alkyl, —(CH$_2$)$_{0-4}$O(CH$_2$)$_{1-5}$CONR$^a$$_2$, —(CH$_2$)$_{1-4}$O(CH$_2$)$_{1-5}$CONR$^a$OH, —(CH$_2$)$_{1-4}$O(CH$_2$)$_{1-5}$CONR$^a$CN, —(CH$_2$)$_{1-4}$O(CH$_2$)$_{1-5}$P(O)OH$_2$, —CH(OH)CF$_3$, —COH(CF$_3$)$_2$, —(CH$_2$)$_{1-5}$CO$_2$H, —(CH$_2$)$_{1-5}$CO$_2$C$_{1-4}$alkyl, —(CH$_2$)$_{0-4}$CHCHCO$_2$H, —(CH$_2$)$_{0-4}$CHCHCO$_2$C$_{1-4}$alkyl, —CO$_2$C$_{1-4}$alkyl, —CO$_2$C$_{1-4}$haloalkyl, —OCOC$_{1-4}$alkyl, —O(CH$_2$)$_{1-4}$CO$_2$H, —O(CH$_2$)$_{1-4}$CO$_2$C$_{1-4}$alkyl, —OCONR$^a$(CH$_2$)$_{0-4}$CO$_2$H, —OCONR$^a$(CH$_2$)$_{0-4}$CO$_2$C$_{1-4}$alkyl, —OCO—(N-morpholine), —CONH$_2$, —CONHOH, —CONHOC$_{1-4}$alkyl, —(CH$_2$)$_{0-4}$C(O)NR$^a$(CH$_2$)$_{1-4}$CO$_2$H, —(CH$_2$)$_{0-4}$C(O)NR$^a$(CH$_2$)$_{1-4}$CO$_2$C$_{1-4}$alkyl, —(CH$_2$)$_{0-4}$C(O)NR$^a$(CH$_2$)$_{1-4}$(pyrrolid-2-one), —(CH$_2$)$_{0-4}$C(O)NR$^a$(CH$_2$)$_{1-4}$(piperidin-2-one), —(CH$_2$)$_{0-4}$C(O)NR$^a$(CH$_2$)$_{1-4}$C(OH)(CF$_3$)$_2$, —(CH$_2$)$_{0-4}$C(O)NR$^a$(CH$_2$)$_{1-4}$CONH$_2$, —(CH$_2$)$_{0-4}$CONR$^a$SO$_2$C$_{1-4}$haloalkyl, —(CH$_2$)$_{0-4}$CO(N-pyrrolidine)-(CH$_2$)$_{0-4}$CO$_2$H, —(CH$_2$)$_{0-4}$CO(N-pyrrolidine)-(CH$_2$)$_{0-4}$CO$_2$C$_{1-4}$alkyl, —(CH$_2$)$_{0-4}$(N-pyrazole)-(CH$_2$)$_{0-4}$CO$_2$H, —(CH$_2$)$_{0-4}$CO(N-pyrazole)-(CH$_2$)$_{0-4}$CO$_2$C$_{1-4}$alkyl, —(CH$_2$)$_{0-4}$(N-pyrrole)-(CH$_2$)$_{0-4}$CO$_2$H, —(CH$_2$)$_{0-4}$CO(N-pyrrole)-(CH$_2$)$_{0-4}$CO$_2$C$_{1-4}$alkyl, —(CH$_2$)$_{0-4}$—O-(phenyl)-(CH$_2$)$_{0-4}$CO$_2$H, —(CH$_2$)$_{0-4}$—O-(phenyl)-(CH$_2$)$_{0-4}$CO$_2$C$_{1-4}$alkyl, —(CH$_2$)$_{0-4}$—O(cycloalkane)-(CH$_2$)$_{0-4}$CO$_2$H, —(CH$_2$)$_{0-4}$—O(cycloalkane)-(CH$_2$)$_{0-4}$CO$_2$C$_{1-4}$alkyl, —(CH$_2$)$_{0-4}$CO(N-pyrrolidine)-(CH$_2$)$_{0-4}$SO$_2$NH$_2$, —(CH$_2$)$_{0-4}$CO(N-pyrrolidine)-(tetrazole), —(CH$_2$)$_{0-4}$CO(N-piperidine)-(CH$_2$)$_{0-4}$CO$_2$H, —(CH$_2$)$_{0-4}$CO(N-piperidine)-(CH$_2$)$_{0-4}$CO$_2$C$_{1-4}$alkyl, —(CH$_2$)$_{0-4}$CO(N-morpholine)-(CH$_2$)$_{0-4}$CO$_2$H, —CONR$^a$(bicyclo[1.1.1]pentane)-(CH$_2$)$_{0-4}$CO$_2$H, —NH$_2$, —(CH$_2$)$_{0-4}$NR$^a$(CH$_2$)$_{1-4}$CO$_2$H, —(CH$_2$)$_{0-4}$NR$^a$(CH$_2$)$_{1-4}$CO$_2$C$_{1-4}$alkyl, —(CH$_2$)$_{0-4}$N[(CH$_2$)$_{1-4}$CO$_2$C$_{1-4}$alkyl]$_2$, —(CH$_2$)$_{0-4}$NR$^a$CO(isoxazole)-OH, —(CH$_2$)$_{0-4}$NR$^a$SO$_2$(benzene), —(CH$_2$)$_{0-4}$NR$^a$SO$_2$(CH$_2$)$_{1-4}$CO$_2$H, —(CH$_2$)$_{0-4}$NR$^a$SO$_2$(CH$_2$)$_{1-4}$CO$_2$C$_{1-4}$alkyl, —(CH$_2$)$_{0-4}$NR$^a$SO$_2$(CH$_2$)$_{1-4}$(imidazolidine-2,4-dione), —(CH$_2$)$_{0-4}$OP(O)(H)OH, wherein R$^a$, independently for each occurrence, is H or C$_{1-4}$alkyl; and m is 1, 2, 3, or 4.

In particular embodiments, the present disclosure provides a compound of formula I-e-5 or formula I-e-5*, wherein each R$^6$ is independently fluoro, -methyl, cyclohexyl, —CF$_3$, —CO$_2$H, —CO$_2$C$_{1-4}$alkyl, —CO$_2$C$_{1-4}$haloalkyl, or —OH; and m is 1, 2, or 3, particularly 1 or 2.

In particular embodiments, the present disclosure provides a compound of formula I-e-5 or formula I-e-5*, wherein each R$^6$ is independently fluoro, -methyl, cyclohexyl, —CF$_3$, -methoxy, —(CH$_2$)$_{1-5}$CO$_2$H, —(CH$_2$)$_{1-5}$CO$_2$C$_{1-4}$alkyl, —(CH$_2$)$_{0-4}$O(CH$_2$)$_{1-5}$CO$_2$H, —(CH$_2$)$_{0-4}$O(CH$_2$)$_{1-5}$CO$_2$C$_{1-4}$alkyl, or —OH; and m is 1, 2, or 3, particularly 1 or 2.

In certain embodiments, the present disclosure provides a compound of formula I-e-5 or formula I-e-5*, wherein R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In some embodiments, the present disclosure provides a compound of formula I, wherein Ring A is

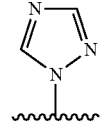

and R$^2$ is

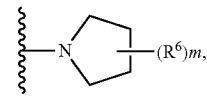

thereby forming a compound of formula I-f-1:

I-f-1

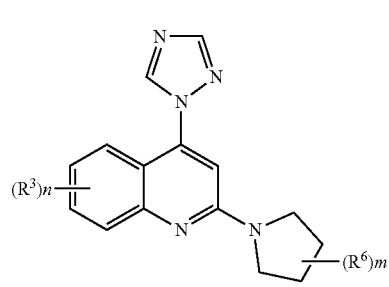

or a pharmaceutically acceptable salt thereof, wherein:

each $R^6$ is independently halogen, =O, —COR, —$(CR_2)_{0-6}CO_2R$, —$(CR_2)_{0-6}CONR_2$, —OR, —$(CR_2)_{1-4}OR$, —$NR_2$, —$(CR_2)_{1-4}NR_2$, —NRC(O)OR, —NRC(O)R, —NRC(O)$NR_2$, —SR, —$SO_2R$, —S(O)R, —$(CR_2)_{0-6}SO_3R$, —$(CR_2)_{0-6}SO_2NR_2$, —$(CR_2)_{0-6}OSO_2NR_2$, —$(CR_2)_{0-6}NRSO_2R$, —$(CR_2)_{0-6}NRSO_2OR$, —$(CR_2)_{0-6}OP(OR)_2$, —$(CR_2)_{0-6}OP(O)(OR)_2$, —$(CR_2)_{0-6}P(O)(OR)_2$, —$(CR_2)_{0-6}OP(O)(H)OR$, —$B(OR)_2$, or $R^B$;

m is 0, 1, 2, 3, or 4, particularly 1, 2, 3, or 4; and each of R, $R^3$, $R^B$, and n is as defined above and described in embodiments herein, both singly and in combination.

In some embodiments, the present disclosure provides a compound of formula I-f-1, wherein $R^6$ is not $R^B$.

In certain embodiments, the present disclosure provides a compound of formula I-f-1, wherein $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In certain embodiments, the present disclosure provides a compound of formula I-f-1, wherein:

each $R^6$ is independently halogen, —$C_{1-4}$alkyl, —$C_{1-4}$haloalkyl, =$CR_2$, =O, —COR, —$(CR_2)_{0-6}CO_2R$, —$(CR_2)_{0-6}CONR_2$, —OR, —$(CR_2)_{1-4}OR$, —$NR_2$, —$(CR_2)_{1-4}NR_2$, —NRC(O)OR, —NRC(O)R, —NRC(O)$NR_2$, —SR, —$SO_2R$, —S(O)R, —$(CR_2)_{0-6}SO_3R$, —$(CR_2)_{0-6}SO_2NR_2$, —$(CR_2)_{0-6}OSO_2NR_2$, —$(CR_2)_{0-6}NRSO_2R$, —$(CR_2)_{0-6}NRSO_2OR$, —$(CR_2)_{0-6}OP(OR)_2$, —$(CR_2)_{0-6}OP(O)(OR)_2$, —$(CR_2)_{0-6}P(O)(OR)_2$, —$(CR_2)_{0-6}OP(O)(H)OR$, or —$B(OR)_2$;

m is 1, 2, 3, or 4, particularly 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In particular embodiments, the present disclosure provides a compound of formula I-f-1, wherein:

each $R^6$ is independently halogen, —$C_{1-4}$alkyl, —$C_{1-4}$haloalkyl, =$CH_2$, =O, —$(CH_2)_{0-4}CO_2H$, —$(CH_2)_{0-4}CO_2C_{1-4}$alkyl, —$(CH_2)_{0-4}CO_2C_{1-4}$haloalkyl, —$(CH_2)_{0-4}CONH_2$, —$(CH_2)_{0-4}CONHC_{1-4}$alkyl, —$(CH_2)_{0-4}CON(C_{1-4}$alkyl$)_2$, —$(CH_2)_{0-4}CO(N$-proline), —$(CH_2)_{0-4}CO(N$-pyrrolidine-3-carboxylic acid), —$(CH_2)_{0-4}(N$-pyrazole)-$(CH_2)_{0-4}CO_2H$, —$(CH_2)_{0-4}CO(N$-pyrazole)-$(CH_2)_{0-4}CO_2C_{1-4}$alkyl, —$(CH_2)_{0-4}(N$-pyrrole)-$(CH_2)_{0-4}CO_2H$, —$(CH_2)_{0-4}CO(N$-pyrrole)-$(CH_2)_{0-4}CO_2C_{1-4}$alkyl, —$(CH_2)_{0-4}$—O(phenyl)-$(CH_2)_{0-4}CO_2H$, —$(CH_2)_{0-4}$—O(phenyl)-$(CH_2)_{0-4}CO_2C_{1-4}$alkyl, —$(CH_2)_{0-4}$—O(cycloalkane)-$(CH_2)_{0-4}CO_2H$, —$(CH_2)_{0-4}$—O(cycloalkane)-$(CH_2)_{0-4}CO_2C_{1-4}$alkyl, —$(CH_2)_{0-4}C(O)NR^a(CH_2)_{1-4}CO_2H$, —$(CH_2)_{0-4}C(O)NR^a$—CH$(C_{1-4}$alkyl)-$CO_2H$, —$(CH_2)_{0-4}C(O)NR^a(CH_2)_{1-4}CONH_2$, —$(CH_2)_{0-4}C(O)NR^a(CH_2)_{1-4}CONHC_{1-4}$alkyl, —$(CH_2)_{0-4}C(O)NR^a(CH_2)_{1-4}CON(C_{1-4}$alkyl$)_2$, —OH, —$(CH_2)_{1-4}OH$, —$(CH_2)_{0-4}OC_{1-4}$alkyl, —$(CH_2)_{0-4}O(CH_2)_{1-5}CO_2H$, —$(CH_2)_{0-4}O(CH_2)_{1-5}CO_2C_{1-4}$alkyl, —$(CH_2)_{1-4}O(CH_2)_{1-4}$CHFCO$_2$H, —$(CH_2)_{1-4}O(CH_2)_{1-4}$CHFCO$_2C_{1-4}$alkyl, —$(CH_2)_{1-4}OCH(CH_3)(CH_2)_{1-4}CO_2H$, —$(CH_2)_{1-4}OCH(CH_3)(CH_2)_{1-4}CO_2C_{1-4}$alkyl, —$(CH_2)_{1-4}O(CH_2)_{1-4}CH(CH_3)CO_2H$, —$(CH_2)_{1-4}O(CH_2)_{1-4}CH(CH_3)CO_2C_{1-4}$alkyl, —CHOH$(CH_2)_{1-4}O(CH_2)_{1-5}CO_2H$, —CHOH$(CH_2)_{1-4}O(CH_2)_{1-5}CO_2C_{1-4}$alkyl, —CHCF$_3(CH_2)_{1-4}O(CH_2)_{1-5}CO_2H$, —CHCF$_3(CH_2)_{1-4}O$—$(CH_2)_{1-5}CO_2C_{1-4}$alkyl, —$(CH_2)_{1-4}O(CH_2)_{1-5}CONR^a_2$, —$(CH_2)_{1-4}O(CH_2)_{1-5}CONR^aOH$, —$(CH_2)_{1-4}O(CH_2)_{1-5}CONR^aCN$, —$(CH_2)_{1-4}O(CH_2)_{1-5}P(O)OH_2$, —$NH_2$, —$(CH_2)_{0-4}NR^a(CH_2)_{1-4}CO_2H$, —$(CH_2)_{0-4}NR^a(CH_2)_{1-4}CO_2C_{1-4}$alkyl, —$(CH_2)_{1-4}NH_2$, —$(CH_2)_{0-4}NHC_{1-4}$alkyl, —$(CH_2)_{0-4}NR^aC(O)C_{1-4}$alkyl, —$(CH_2)_{0-4}NR^aC(O)Ph$, —$(CH_2)_{0-4}NR^aCO(CH_2)_{1-4}OH$, —$(CH_2)_{0-4}N(C_{1-4}$alkyl$)_2$, —$(CH_2)_{0-4}SO_3H$, —$(CH_2)_{0-4}SO_2NH_2$, —$(CH_2)_{0-4}SO_2NR^aC_{1-4}$alkyl, —$(CH_2)_{0-4}NR^aSO_2C_{1-4}$alkyl, —$(CH_2)_{0-4}NR^aSO_2Ph$, —$(CH_2)_{0-4}NR^aSO_2(CH_2)_{1-4}CO_2H$, —$(CH_2)_{0-4}OP(OH)_2$, —$(CH_2)_{0-4}OP(OH)(OC_{1-4}$alkyl), or —$(CR_2)_{0-4}OP(O)(H)OH$, wherein $R^a$, independently for each occurrence, is H or $C_{1-4}$alkyl;

m is 1, 2, 3, or 4, particularly 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In further particular embodiments, the present disclosure provides a compound of formula I-f-1, wherein:

each $R^6$ is independently halogen, —$C_{1-4}$alkyl, —$C_{1-4}$haloalkyl, =$CH_2$, —$(CH_2)_{0-4}CO_2H$, —$(CH_2)_{0-4}CO_2C_{1-4}$alkyl, —$(CH_2)_{0-4}CO_2C_{1-4}$haloalkyl, —$(CH_2)_{0-4}CO(N$-proline), —$(CH_2)_{0-4}CO(N$-pyrrolidine-3-carboxylic acid), —$(CH_2)_{0-4}C(O)NR^a(CH_2)_{1-4}CO_2H$, —$(CH_2)_{0-4}C(O)NR^a$—CH$(C_{1-4}$alkyl)-$CO_2H$, —OH, —$(CH_2)_{1-4}OH$, —$(CH_2)_{0-4}OC_{1-4}$alkyl, —$(CH_2)_{0-4}O(CH_2)_{1-5}CO_2H$, —$(CH_2)_{0-4}O(CH_2)_{1-5}CO_2C_{1-4}$alkyl, —$(CH_2)_{0-4}NR^aC(O)C_{1-4}$alkyl, —$(CH_2)_{0-4}NR^aC(O)Ph$, —$(CH_2)_{0-4}NR^aCO(CH_2)_{1-4}OH$, —$(CH_2)_{0-4}SO_3H$, —$(CH_2)_{0-4}SO_2NH_2$, —$(CH_2)_{0-4}NR^aSO_2C_{1-4}$alkyl, —$(CH_2)_{0-4}NR^aSO_2Ph$, —$(CH_2)_{0-4}NR^aSO_2(CH_2)_{1-4}CO_2H$, —$(CH_2)_{0-4}OP(OH)_2$, or —$(CR_2)_{0-4}OP(O)(H)OH$, wherein $R^a$, independently for each occurrence, is H or $C_{1-4}$alkyl;

m is 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In particular embodiments, the present disclosure provides a compound of formula I-f-1, wherein:

each $R^6$ is independently halogen, —$C_{1-4}$alkyl, —$C_{1-4}$haloalkyl, —$C_{3-6}$cycloalkyl, =$CH_2$, =O, —$(CH_2)_{0-4}CO_2H$, —$(CH_2)_{0-4}CO_2C_{1-4}$alkyl, —$(CH_2)_{0-4}CO_2C_{1-4}$haloalkyl, —$(CH_2)_{0-4}O(CH_2)_{1-5}CO_2H$, —$(CH_2)_{0-4}O(CH_2)_{1-5}CO_2C_{1-4}$alkyl, —$(CH_2)_{1-4}O(CH_2)_{1-4}$CHFCO$_2$H, —$(CH_2)_{1-4}O(CH_2)_{1-4}$CHFCO$_2C_{1-4}$alkyl, —$(CH_2)_{1-4}OCH(CH_3)(CH_2)_{1-4}CO_2H$, —$(CH_2)_{1-4}OCH(CH_3)(CH_2)_{1-4}CO_2C_{1-4}$alkyl, —$(CH_2)_{1-4}O(CH_2)_{1-4}CH(CH_3)CO_2H$, —$(CH_2)_{1-4}O(CH_2)_{1-4}CH(CH_3)CO_2C_{1-4}$alkyl, —CHOH$(CH_2)_{1-4}O(CH_2)_{1-5}CO_2H$, —CHOH$(CH_2)_{1-4}O(CH_2)_{1-5}CO_2C_{1-4}$alkyl, —CHCF$_3(CH_2)_{1-4}O(CH_2)_{1-5}CO_2H$, —CHCF$_3(CH_2)_{1-4}O$—$(CH_2)_{1-5}CO_2C_{1-4}$alkyl, —$(CH_2)_{1-4}O(CH_2)_{1-5}CONR^a_2$, —$(CH_2)_{1-4}O(CH_2)_{1-5}CONR^aOH$, —$(CH_2)_{1-4}O(CH_2)_{1-5}CONR^aCN$, —$(CH_2)_{1-4}O(CH_2)_{1-5}P(O)OH_2$, —$(CH_2)_{0-4}CONH_2$, —$(CH_2)_{0-4}CONHC_{1-4}$alkyl, —$(CH_2)_{0-4}CON(C_{1-4}$alkyl$)_2$, —$(CH_2)_{0-4}CO(N$-proline), —$(CH_2)_{0-4}CO(N$-pyrrolidine-3-carboxylic acid), —$(CH_2)_{0-4}$(N-pyrazole)-$(CH_2)_{0-4}CO_2H$, —$(CH_2)_{0-4}CO$(N-pyrazole)-$(CH_2)_{0-4}CO_2C_{1-4}$alkyl, —$(CH_2)_{0-4}$(N-pyrrole)-$(CH_2)_{0-4}CO_2H$, —$(CH_2)_{0-4}CO$(N-pyrrole)-$(CH_2)_{0-4}CO_2C_{1-4}$alkyl, —$(CH_2)_{0-4}$—O(phenyl)-$(CH_2)_{0-4}CO_2H$, —$(CH_2)_{0-4}$—O(phenyl)-$(CH_2)_{0-4}CO_2C_{1-4}$alkyl, —$(CH_2)_{0-4}$—O(cycloalkane)-$(CH_2)_{0-4}CO_2H$, —$(CH_2)_{0-4}$—O(cycloalkane)-$(CH_2)_{0-4}CO_2C_{1-4}$alkyl, —$(CH_2)_{0-4}C(O)NR^a(CH_2)_{1-4}CO_2H$, —$(CH_2)_{0-4}C(O)NR^a$—$CH(C_{1-4}$alkyl$)$-$CO_2H$, —$(CH_2)_{0-4}C(O)NR^a(CH_2)_{1-4}CONH_2$, —$(CH_2)_{0-4}C(O)NR^a(CH_2)_{1-4}CONHC_{1-4}$alkyl, —$(CH_2)_{0-4}C(O)NR^a(CH_2)_{1-4}CON(C_{1-4}$alkyl$)_2$, —OH, —$(CH_2)_{1-4}OH$, —$(CH_2)_{0-4}OC_{1-4}$alkyl, —$(CH_2)_{0-4}OC(O)C_{1-4}$alkyl, —$NH_2$, —$(CH_2)_{0-4}NR^a(CH_2)_{1-4}CO_2H$, —$(CH_2)_{0-4}NR^a(CH_2)_{1-4}CO_2C_{1-4}$alkyl, —$(CH_2)_{1-4}NH_2$, —$(CH_2)_{0-4}NHC_{1-4}$alkyl, —$(CH_2)_{0-4}NR^aC(O)C_{1-4}$alkyl, —$(CH_2)_{0-4}NR^aC(O)Ph$, —$(CH_2)_{0-4}NR^aCO(CH_2)_{1-4}OH$, —$(CH_2)_{0-4}N(C_{1-4}$alkyl$)_2$, —$(CH_2)_{0-4}SO_3H$, —$(CH_2)_{0-4}SO_2NH_2$, —$(CH_2)_{0-4}SO_2NR^aC_{1-4}$alkyl, —$(CH_2)_{0-4}NR^aSO_2C_{1-4}$alkyl, —$(CH_2)_{0-4}NR^aSO_2Ph$, —$(CH_2)_{0-4}NR^aSO_2(CH_2)_{1-4}CO_2H$, —$(CH_2)_{0-4}OP(OH)_2$, —$(CH_2)_{0-4}OP(OH)(OC_{1-4}$alkyl$)$, or —$(CR_2)_{0-4}OP(O)(H)OH$, wherein $R^a$, independently for each occurrence, is H or $C_{1-4}$alkyl;

m is 1, 2, 3, or 4, particularly 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In further particular embodiments, the present disclosure provides a compound of formula I-f-1, wherein:
each $R^6$ is independently halogen, —$C_{1-4}$alkyl, —$C_{1-4}$haloalkyl, —$C_{3-6}$cycloalkyl, =$CH_2$, —$(CH_2)_{0-4}CO_2H$, —$(CH_2)_{0-4}O(CH_2)_{1-5}CO_2H$, —$(CH_2)_{0-4}O(CH_2)_{1-5}CO_2C_{1-4}$alkyl, —$(CH_2)_{0-4}CO$(N-proline), —$(CH_2)_{0-4}CO$(N-pyrrolidine-3-carboxylic acid), —$(CH_2)_{0-4}C(O)NR^a(CH_2)_{1-4}CO_2H$, —$(CH_2)_{0-4}C(O)NR^a$—$CH(C_{1-4}$alkyl$)$-$CO_2H$, —OH, —$(CH_2)_{1-4}OH$, —$(CH_2)_{0-4}OC_{1-4}$alkyl, —$(CH_2)_{0-4}OC(O)C_{1-4}$alkyl, —$(CH_2)_{0-4}NR^aC(O)C_{1-4}$alkyl, —$(CH_2)_{0-4}NR^aC(O)Ph$, —$(CH_2)_{0-4}NR^aCO(CH_2)_{1-4}OH$, —$(CH_2)_{0-4}SO_3H$, —$(CH_2)_{0-4}SO_2NH_2$, —$(CH_2)_{0-4}NR^aSO_2C_{1-4}$alkyl, —$(CH_2)_{0-4}NR^aSO_2Ph$, —$(CH_2)_{0-4}NR^aSO_2(CH_2)_{1-4}CO_2H$, —$(CH_2)_{0-4}OP(OH)_2$, or —$(CR_2)_{0-4}OP(O)(H)OH$, wherein $R^a$, independently for each occurrence, is H or $C_{1-4}$alkyl;

m is 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In further particular embodiments, the present disclosure provides a compound of formula I-f-1, wherein each $R^6$ is independently fluoro, -methyl, cyclohexyl, -methoxy, —OtBu, —$CF_3$, —$(CH_2)_{1-5}CO_2H$, —$(CH_2)_{1-5}CO_2C_{1-4}$alkyl, —$(CH_2)_{0-4}O(CH_2)_{1-5}CO_2H$, —$(CH_2)_{0-4}O(CH_2)_{1-5}CO_2C_{1-4}$alkyl, or —OH; and m is 1, 2, or 3, particularly 1 or 2.

In particular embodiments, the present disclosure provides a compound of formula I-f-1, wherein:
each $R^6$ is independently halogen, —$C_{1-4}$alkyl, —$C_{1-4}$haloalkyl, —$C_{3-6}$cycloalkyl, =$CH_2$, =O, —$(CH_2)_{0-4}CO_2H$, —$(CH_2)_{0-4}CO_2C_{1-4}$alkyl, —$(CH_2)_{0-4}O(CH_2)_{1-5}CO_2H$, —$(CH_2)_{0-4}O(CH_2)_{1-5}CO_2C_{1-4}$alkyl, —$(CH_2)_{0-4}CONH_2$, —$(CH_2)_{0-4}CONHC_{1-4}$alkyl, —$(CH_2)_{0-4}CON(C_{1-4}$alkyl$)_2$, —$(CH_2)_{0-4}CO$(N-proline), —$(CH_2)_{0-4}CO$(N-pyrrolidine-3-carboxylic acid), —$(CH_2)_{0-4}C(O)NR^a(CH_2)_{1-4}CO_2H$, —$(CH_2)_{0-4}C(O)NR^a$—$CH(C_{1-4}$alkyl$)$-$CO_2H$, —$(CH_2)_{0-4}C(O)NR^a(CH_2)_{1-4}CONH_2$, —$(CH_2)_{0-4}C(O)NR^a(CH_2)_{1-4}CONHC_{1-4}$alkyl, —$(CH_2)_{0-4}C(O)NR^a(CH_2)_{1-4}CON(C_{1-4}$alkyl$)_2$, —OH, —$(CH_2)_{1-4}OH$, —$(CH_2)_{0-4}OC_{1-4}$alkyl, —$NH_2$, —$(CH_2)_{1-4}NH_2$, —$(CH_2)_{0-4}NHC_{1-4}$alkyl, —$(CH_2)_{0-4}NR^aC(O)C_{1-4}$alkyl, —$(CH_2)_{0-4}NR^aC(O)Ph$, —$(CH_2)_{0-4}NR^aCO(CH_2)_{1-4}OH$, —$(CH_2)_{0-4}N(C_{1-4}$alkyl$)_2$, —$(CH_2)_{0-4}SO_3H$, —$(CH_2)_{0-4}SO_2NH_2$, —$(CH_2)_{0-4}SO_2NR^aC_{1-4}$alkyl, —$(CH_2)_{0-4}NR^aSO_2C_{1-4}$alkyl, —$(CH_2)_{0-4}NR^aSO_2Ph$, —$(CH_2)_{0-4}NR^aSO_2(CH_2)_{1-4}CO_2H$, —$(CH_2)_{0-4}OP(OH)_2$, —$(CH_2)_{0-4}OP(OH)(OC_{1-4}$alkyl$)$, or —$(CR_2)_{0-4}OP(O)(H)OH$, wherein $R^a$, independently for each occurrence, is H or $C_{1-4}$alkyl;

m is 1, 2, 3, or 4, particularly 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In further particular embodiments, the present disclosure provides a compound of formula I-f-1, wherein:
each $R^6$ is independently halogen, —$C_{1-4}$alkyl, —$C_{1-4}$haloalkyl, —$C_{3-6}$cycloalkyl, =$CH_2$, —$(CH_2)_{0-4}CO_2H$, —$(CH_2)_{1-4}O(CH_2)_{1-5}CO_2H$, —$(CH_2)_{1-4}O(CH_2)_{1-5}CO_2C_{1-4}$alkyl, —$(CH_2)_{0-4}CO$(N-proline), —$(CH_2)_{0-4}CO$(N-pyrrolidine-3-carboxylic acid), —$(CH_2)_{0-4}C(O)NR^a(CH_2)_{1-4}CO_2H$, —$(CH_2)_{0-4}C(O)NR^a$—$CH(C_{1-4}$alkyl$)$-$CO_2H$, —OH, —$(CH_2)_{1-4}OH$, —$(CH_2)_{0-4}OC_{1-4}$alkyl, —$(CH_2)_{0-4}NR^aC(O)C_{1-4}$alkyl, —$(CH_2)_{0-4}NR^aC(O)Ph$, —$(CH_2)_{0-4}NR^aCO(CH_2)_{1-4}OH$, —$(CH_2)_{0-4}SO_3H$, —$(CH_2)_{0-4}SO_2NH_2$, —$(CH_2)_{0-4}NR^aSO_2C_{1-4}$alkyl, —$(CH_2)_{0-4}NR^aSO_2Ph$, —$(CH_2)_{0-4}NR^aSO_2(CH_2)_{1-4}CO_2H$, —$(CH_2)_{0-4}OP(OH)_2$, or —$(CR_2)_{0-4}OP(O)(H)OH$, wherein $R^a$, independently for each occurrence, is H or $C_{1-4}$alkyl;

m is 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In certain embodiments, the present disclosure provides a compound of formula I-f-1, wherein:
each $R^6$ is independently halogen, =O, —COR, —$(CR_2)_{0-6}CO_2R$, —$(CR_2)_{0-6}CONR_2$, —OR, —$(CR_2)_{1-4}OR$, —$NR_2$, —$(CR_2)_{1-4}NR_2$, —$NRC(O)OR$, —$NRC(O)R$, —$NRC(O)NR_2$, —SR, —$SO_2R$, —$S(O)R$, —$(CR_2)_{0-6}SO_3R$, —$(CR_2)_{0-6}SO_2NR_2$, —$(CR_2)_{0-6}OSO_2NR_2$, —$(CR_2)_{0-6}NRSO_2R$, —$(CR_2)_{0-6}NRSO_2OR$, —$(CR_2)_{0-6}OP(OR)_2$, —$(CR_2)_{0-6}OP(O)(OR)_2$, —$(CR_2)_{0-6}P(O)(OR)_2$, —$(CR_2)_{0-6}OP(O)(H)OR$, or —$B(OR)_2$;

m is 1, 2, 3, or 4, particularly 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In particular embodiments, the present disclosure provides a compound of formula I-f-1, wherein:

each $R^6$ is independently halogen, =O, —(CH$_2$)$_{0-4}$CO$_2$H, —(CH$_2$)$_{0-4}$CO$_2$C$_{1-4}$alkyl, —(CH$_2$)$_{0-4}$CONH$_2$, —(CH$_2$)$_{0-4}$CONHC$_{1-4}$alkyl, —(CH$_2$)$_{0-4}$CON(C$_{1-4}$alkyl)$_2$, —(CH$_2$)$_{0-4}$CO(N-proline), —(CH$_2$)$_{0-4}$CO(N-pyrrolidine-3-carboxylic acid), —(CH$_2$)$_{0-4}$C(O)NR$^a$(CH$_2$)$_{1-4}$CO$_2$H, —(CH$_2$)$_{0-4}$C(O)NR$^a$—CH(C$_{1-4}$alkyl)-CO$_2$H, —(CH$_2$)$_{0-4}$C(O)NR$^a$(CH$_2$)$_{1-4}$CONH$_2$, —(CH$_2$)$_{0-4}$C(O)NR$^a$(CH$_2$)$_{1-4}$CONHC$_{1-4}$alkyl, —(CH$_2$)$_{0-4}$C(O)NR$^a$(CH$_2$)$_{1-4}$CON(C$_{1-4}$alkyl)$_2$, —OH, —(CH$_2$)$_{1-4}$OH, —(CH$_2$)$_{0-4}$OC$_{1-4}$alkyl, —NH$_2$, —(CH$_2$)$_{1-4}$NH$_2$, —(CH$_2$)$_{0-4}$NHC$_{1-4}$alkyl, —(CH$_2$)$_{0-4}$NR$^a$C(O)C$_{1-4}$alkyl, —(CH$_2$)$_{0-4}$NR$^a$C(O)Ph, —(CH$_2$)$_{0-4}$NR$^a$CO(CH$_2$)$_{1-4}$OH, —(CH$_2$)$_{0-4}$N(C$_{1-4}$alkyl)$_2$, —(CH$_2$)$_{0-4}$SO$_3$H, —(CH$_2$)$_{0-4}$SO$_2$NH$_2$, —(CH$_2$)$_{0-4}$SO$_2$NR$^a$C$_{1-4}$alkyl, —(CH$_2$)$_{0-4}$NR$^a$SO$_2$C$_{1-4}$alkyl, —(CH$_2$)$_{0-4}$NR$^a$SO$_2$Ph, —(CH$_2$)$_{0-4}$NR$^a$SO$_2$(CH$_2$)$_{1-4}$CO$_2$H, —(CH$_2$)$_{0-4}$OP(OH)$_2$, —(CH$_2$)$_{0-4}$OP(OH)(OC$_{1-4}$alkyl), or —(CR$_2$)$_{0-4}$OP(O)(H)OH, wherein R$^a$, independently for each occurrence, is H or C$_{1-4}$alkyl;

m is 1, 2, 3, or 4, particularly 1 or 2; and each $R^3$ is independently optionally substituted C$_{1-6}$ aliphatic, such as methyl, or halogen, such as bromo and/or chloro, including dichloro, including wherein n is 2 and $R^3$ is chloro at the 7- and 8-positions with respect to the quinoline ring.

In further particular embodiments, the present disclosure provides a compound of formula I-f-1, wherein:

each $R^6$ is independently halogen, —(CH$_2$)$_{0-4}$CO$_2$H, —(CH$_2$)$_{0-4}$CO(N-proline), —(CH$_2$)$_{0-4}$CO(N-pyrrolidine-3-carboxylic acid), —(CH$_2$)$_{0-4}$C(O)NR$^a$(CH$_2$)$_{1-4}$CO$_2$H, —(CH$_2$)$_{0-4}$C(O)NR$^a$—CH(C$_{1-4}$alkyl)-CO$_2$H, —OH, —(CH$_2$)$_{1-4}$OH, —(CH$_2$)$_{0-4}$NR$^a$C(O)C$_{1-4}$alkyl, —(CH$_2$)$_{0-4}$NR$^a$C(O)Ph, —(CH$_2$)$_{0-4}$NR$^a$CO(CH$_2$)$_{1-4}$OH, —(CH$_2$)$_{0-4}$SO$_3$H, —(CH$_2$)$_{0-4}$SO$_2$NH$_2$, —(CH$_2$)$_{0-4}$NR$^a$SO$_2$C$_{1-4}$alkyl, —(CH$_2$)$_{0-4}$NR$^a$SO$_2$Ph, —(CH$_2$)$_{0-4}$NR$^a$SO$_2$(CH$_2$)$_{1-4}$CO$_2$H, —(CH$_2$)$_{0-4}$OP(OH)$_2$, or —(CR$_2$)$_{0-4}$OP(O)(H)OH, wherein R$^a$, independently for each occurrence, is H or C$_{1-4}$alkyl;

m is 1 or 2; and each $R^3$ is independently optionally substituted C$_{1-6}$ aliphatic, such as methyl, or halogen, such as bromo and/or chloro, including dichloro, including wherein n is 2 and $R^3$ is chloro at the 7- and 8-positions with respect to the quinoline ring.

In particular embodiments, the present disclosure provides a compound of formula I-f-1, wherein, m is 1;

$R^6$ is —(CH$_2$)$_{0-4}$O(CH$_2$)$_{1-5}$CO$_2$H, such as —(CH$_2$)$_{1-2}$O (CH$_2$)$_{2-3}$CO$_2$H, including —CH$_2$O(CH$_2$)$_2$CO$_2$H; and each $R^3$ is independently optionally substituted C$_{1-6}$ aliphatic, such as methyl, or halogen, such as bromo and/or chloro, including dichloro, including wherein n is 2 and $R^3$ is chloro at the 7- and 8-positions with respect to the quinoline ring.

In certain embodiments, for the above disclosed compounds of formula I-f-1, m is 1 or 2, and at least one $R^6$ includes a terminal —CO$_2$H group. For example, in certain instances, at least one $R^6$ is —(CH$_2$)$_{0-4}$CO$_2$H or —(CH$_2$)$_{0-4}$O(CH$_2$)$_{1-5}$CO$_2$H.

In some embodiments, the present disclosure provides a compound of formula I, wherein Ring A is

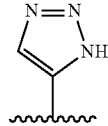

and $R^2$ is

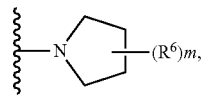

thereby forming a compound of formula I-f-2:

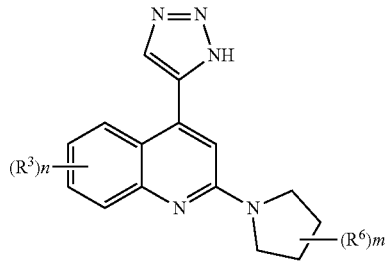

I-f-2 or a pharmaceutically acceptable salt thereof, wherein:

each $R^6$ is independently halogen, =O, —COR, —(CR$_2$)$_{0-6}$CO$_2$R, —(CR$_2$)$_{0-6}$CONR$_2$, —OR, —(CR$_2$)$_{1-4}$OR, —NR$_2$, —(CR$_2$)$_{1-4}$NR$_2$, —NRC(O)OR, —NRC(O)R, —NRC(O)NR$_2$, —SR, —SO$_2$R, —S(O)R, —(CR$_2$)$_{0-6}$SO$_3$R, —(CR$_2$)$_{0-6}$SO$_2$NR$_2$, —(CR$_2$)o-OSO$_2$NR$_2$, —(CR$_2$)$_{0-6}$NRSO$_2$R, —(CR$_2$)$_{0-6}$NRSO$_2$OR, —(CR$_2$)$_{0-6}$OP(OR)$_2$, —(CR$_2$)$_{0-6}$OP(O)(OR)$_2$, —(CR$_2$)$_{0-6}$P(O)(OR)$_2$, —(CR$_2$)$_{0-6}$OP(O)(H)OR, —B(OR)$_2$, or $R^B$;

m is 0, 1, 2, 3, or 4, particularly 1, 2, 3, or 4; and each of R, $R^3$, $R^B$, and n is as defined above and described in embodiments herein, both singly and in combination.

In some embodiments, the present disclosure provides a compound of formula I-f-2, wherein $R^6$ is not $R^B$.

In certain embodiments, the present disclosure provides a compound of formula I-f-2, wherein $R^3$ is independently optionally substituted C$_{1-6}$ aliphatic, such as methyl, or halogen, such as bromo and/or chloro, including dichloro, including wherein n is 2 and $R^3$ is chloro at the 7- and 8-positions with respect to the quinoline ring.

In certain embodiments, the present disclosure provides a compound of formula I-f-2, wherein:

each $R^6$ is independently halogen, —C$_{1-4}$alkyl, —C$_{1-4}$haloalkyl, =CR$_2$, =O, —COR, —(CR$_2$)$_{0-6}$CO$_2$R, —(CR$_2$)$_{0-6}$CONR$_2$, —OR, —(CR$_2$)$_{1-4}$OR, —NR$_2$, —(CR$_2$)$_{1-4}$NR$_2$, —NRC(O)OR, —NRC(O)R, —NRC(O)NR$_2$, —SR, —SO$_2$R, —S(O)R, —(CR$_2$)$_{0-6}$SO$_3$R, —(CR$_2$)$_{0-6}$SO$_2$NR$_2$, —(CR$_2$)$_{0-6}$OSO$_2$NR$_2$, —(CR$_2$)$_{0-6}$NRSO$_2$R, —(CR$_2$)$_{0-6}$NRSO$_2$OR, —(CR$_2$)$_{0-6}$OP(OR)$_2$, —(CR$_2$)$_{0-6}$OP(O)(OR)$_2$, —(CR$_2$)$_{0-6}$P(O)(OR)$_2$, —(CR$_2$)$_{0-6}$OP(O)(H)OR, or —B(OR)$_2$;

m is 1, 2, 3, or 4, particularly 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In particular embodiments, the present disclosure provides a compound of formula I-f-2, wherein:

each $R^6$ is independently halogen, —$C_{1-4}$alkyl, —$C_{1-4}$haloalkyl, =$CH_2$, =O, —$(CH_2)_{0-4}CO_2H$, —$(CH_2)_{0-4}CO_2C_{1-4}$alkyl, —$(CH_2)_{0-4}CO_2C_{1-4}$haloalkyl, —$(CH_2)_{0-4}CONH_2$, —$(CH_2)_{0-4}CONHC_{1-4}$alkyl, —$(CH_2)_{0-4}CON(C_{1-4}$alkyl$)_2$, —$(CH_2)_{0-4}CO(N$-proline$)$, —$(CH_2)_{0-4}CO(N$-pyrrolidine-3-carboxylic acid$)$, —$(CH_2)_{0-4}(N$-pyrazole$)$-$(CH_2)_{0-4}CO_2H$, —$(CH_2)_{0-4}CO(N$-pyrazole$)$-$(CH_2)_{0-4}CO_2C_{1-4}$alkyl, —$(CH_2)_{0-4}(N$-pyrrole$)$-$(CH_2)_{0-4}CO_2H$, —$(CH_2)_{0-4}CO(N$-pyrrole$)$-$(CH_2)_{0-4}CO_2C_{1-4}$alkyl, —$(CH_2)_{0-4}$—O(phenyl)-$(CH_2)_{0-4}CO_2H$, —$(CH_2)_{0-4}$—O(phenyl)-$(CH_2)_{0-4}CO_2C_{1-4}$alkyl, —$(CH_2)_{0-4}$—O(cycloalkane)-$(CH_2)_{0-4}CO_2H$, —$(CH_2)_{0-4}$—O(cycloalkane)-$(CH_2)_{0-4}CO_2C_{1-4}$alkyl, —$(CH_2)_{0-4}C(O)NR^a(CH_2)_{1-4}CO_2H$, —$(CH_2)_{0-4}C(O)NR^a$—$CH(C_{1-4}$alkyl$)$-$CO_2H$, —$(CH_2)_{0-4}C(O)NR^a(CH_2)_{1-4}CONH_2$, —$(CH_2)_{0-4}C(O)NR^a(CH_2)_{1-4}CONHC_{1-4}$alkyl, —$(CH_2)_{0-4}C(O)NR^a(CH_2)_{1-4}CON(C_{1-4}$alkyl$)_2$, —OH, —$(CH_2)_{1-4}OH$, —$(CH_2)_{0-4}OC_{1-4}$alkyl, —$(CH_2)_{0-4}O(CH_2)_{1-5}CO_2H$, —$(CH_2)_{0-4}O(CH_2)_{1-5}CO_2C_{1-4}$alkyl, —$(CH_2)_{1-4}O(CH_2)_{1-4}CHFCO_2H$, —$(CH_2)_{1-4}O(CH_2)_{1-4}CHFCO_2C_{1-4}$alkyl, —$(CH_2)_{1-4}OCH(CH_3)(CH_2)_{1-4}CO_2H$, —$(CH_2)_{1-4}OCH(CH_3)(CH_2)_{1-4}CO_2C_{1-4}$alkyl, —$(CH_2)_{1-4}O(CH_2)_{1-4}CH(CH_3)CO_2H$, —$(CH_2)_{1-4}O(CH_2)_{1-4}CH(CH_3)CO_2C_{1-4}$alkyl, —CHOH$(CH_2)_{1-4}O(CH_2)_{1-5}CO_2H$, —CHOH$(CH_2)_{1-4}O(CH_2)_{1-5}CO_2C_{1-4}$alkyl, —$CHCF_3(CH_2)_{1-4}O(CH_2)_{1-5}CO_2H$, —$CHCF_3(CH_2)_{1-4}O$—$(CH_2)_{1-5}CO_2C_{1-4}$alkyl, —$(CH_2)_{1-4}O(CH_2)_{1-5}CONR^a{}_2$, —$(CH_2)_{1-4}O(CH_2)_{1-5}CONR^aOH$, —$(CH_2)_{1-4}O(CH_2)_{1-5}CONR^aCN$, —$(CH_2)_{1-4}O(CH_2)_{1-5}P(O)OH_2$, —$NH_2$, —$(CH_2)_{0-4}NR^a(CH_2)_{1-4}CO_2H$, —$(CH_2)_{0-4}NR^a(CH_2)_{1-4}CO_2C_{1-4}$alkyl, —$(CH_2)_{1-4}NH_2$, —$(CH_2)_{0-4}NHC_{1-4}$alkyl, —$(CH_2)_{0-4}NR^aC(O)C_{1-4}$alkyl, —$(CH_2)_{0-4}NR^aC(O)Ph$, —$(CH_2)_{0-4}NR^aCO(CH_2)_{1-4}OH$, —$(CH_2)_{0-4}N(C_{1-4}$alkyl$)_2$, —$(CH_2)_{0-4}SO_3H$, —$(CH_2)_{0-4}SO_2NH_2$, —$(CH_2)_{0-4}SO_2NR^aC_{1-4}$alkyl, —$(CH_2)_{0-4}NR^aSO_2C_{1-4}$alkyl, —$(CH_2)_{0-4}NR^aSO_2Ph$, —$(CH_2)_{0-4}NR^aSO_2(CH_2)_{1-4}CO_2H$, —$(CH_2)_{0-4}OP(OH)_2$, —$(CH_2)_{0-4}OP(OH)(OC_{1-4}$alkyl$)$, or —$(CR_2)_{0-4}OP(O)(H)OH$, wherein $R^a$, independently for each occurrence, is H or $C_{1-4}$alkyl;

m is 1, 2, 3, or 4, particularly 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In further particular embodiments, the present disclosure provides a compound of formula I-f-2, wherein:

each $R^6$ is independently halogen, —$C_{1-4}$alkyl, —$C_{1-4}$haloalkyl, =$CH_2$, —$(CH_2)_{0-4}CO_2H$, —$(CH_2)_{0-4}CO_2C_{1-4}$alkyl, —$(CH_2)_{0-4}CO_2C_{1-4}$haloalkyl, —$(CH_2)_{0-4}CO(N$-proline$)$, —$(CH_2)_{0-4}CO(N$-pyrrolidine-3-carboxylic acid$)$, —$(CH_2)_{0-4}C(O)NR^a(CH_2)_{1-4}CO_2H$, —$(CH_2)_{0-4}C(O)NR^a$—$CH(C_{1-4}$alkyl$)$-$CO_2H$, —OH, —$(CH_2)_{1-4}OH$, —$(CH_2)_{0-4}OC_{1-4}$alkyl, —$(CH_2)_{0-4}O(CH_2)_{1-5}CO_2H$, —$(CH_2)_{0-4}O(CH_2)_{1-5}CO_2C_{1-4}$alkyl, —$(CH_2)_{0-4}NR^aC(O)C_{1-4}$alkyl, —$(CH_2)_{0-4}NR^aC(O)Ph$, —$(CH_2)_{0-4}NR^aCO(CH_2)_{1-4}OH$, —$(CH_2)_{0-4}SO_3H$, —$(CH_2)_{0-4}SO_2NH_2$, —$(CH_2)_{0-4}SO_2NH_2$, —$(CH_2)_{0-4}NR^aSO_2C_{1-4}$alkyl, —$(CH_2)_{0-4}NR^aSO_2Ph$, —$(CH_2)_{0-4}NR^aSO_2(CH_2)_{1-4}CO_2H$, —$(CH_2)_{0-4}OP(OH)_2$, or —$(CR_2)_{0-4}OP(O)(H)OH$, wherein $R^a$, independently for each occurrence, is H or $C_{1-4}$alkyl;

m is 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In particular embodiments, the present disclosure provides a compound of formula I-f-2, wherein:

each $R^6$ is independently halogen, —$C_{1-4}$alkyl, —$C_{1-4}$haloalkyl, —$C_{3-6}$cycloalkyl, =$CH_2$, =O, —$(CH_2)_{0-4}CO_2H$, —$(CH_2)_{0-4}CO_2C_{1-4}$alkyl, —$(CH_2)_{0-4}CO_2C_{1-4}$haloalkyl, —$(CH_2)_{0-4}O(CH_2)_{1-5}CO_2H$, —$(CH_2)_{0-4}O(CH_2)_{1-5}CO_2C_{1-4}$alkyl, —$(CH_2)_{1-4}O(CH_2)_{1-4}CHFCO_2H$, —$(CH_2)_{1-4}O(CH_2)_{1-4}CHFCO_2C_{1-4}$alkyl, —$(CH_2)_{1-4}OCH(CH_3)(CH_2)_{1-4}CO_2H$, —$(CH_2)_{1-4}OCH(CH_3)(CH_2)_{1-4}CO_2C_{1-4}$alkyl, —$(CH_2)_{1-4}O(CH_2)_{1-4}CH(CH_3)CO_2H$, —$(CH_2)_{1-4}O(CH_2)_{1-4}CH(CH_3)CO_2C_{1-4}$alkyl, —CHOH$(CH_2)_{1-4}O(CH_2)_{1-5}CO_2H$, —CHOH$(CH_2)_{1-4}O(CH_2)_{1-5}CO_2C_{1-4}$alkyl, —$CHCF_3(CH_2)_{1-4}O(CH_2)_{1-5}CO_2H$, —$CHCF_3(CH_2)_{1-4}O$—$(CH_2)_{1-5}CO_2C_{1-4}$alkyl, —$(CH_2)_{1-4}O(CH_2)_{1-5}CONR^a{}_2$, —$(CH_2)_{1-4}O(CH_2)_{1-5}CONR^aOH$, —$(CH_2)_{1-4}O(CH_2)_{1-5}CONR^aCN$, —$(CH_2)_{1-4}O(CH_2)_{1-5}P(O)OH_2$, —$(CH_2)_{0-4}CONH_2$, —$(CH_2)_{0-4}CONHC_{1-4}$alkyl, —$(CH_2)_{0-4}CON(C_{1-4}$alkyl$)_2$, —$(CH_2)_{0-4}CO(N$-proline$)$, —$(CH_2)_{0-4}CO(N$-pyrrolidine-3-carboxylic acid$)$, —$(CH_2)_{0-4}(N$-pyrazole$)$-$(CH_2)_{0-4}CO_2H$, —$(CH_2)_{0-4}CO(N$-pyrazole$)$-$(CH_2)_{0-4}CO_2C_{1-4}$alkyl, —$(CH_2)_{0-4}(N$-pyrrole$)$-$(CH_2)_{0-4}CO_2H$, —$(CH_2)_{0-4}CO(N$-pyrrole$)$-$(CH_2)_{0-4}CO_2C_{1-4}$alkyl, —$(CH_2)_{0-4}$—O(phenyl)-$(CH_2)_{0-4}CO_2H$, —$(CH_2)_{0-4}$—O(phenyl)-$(CH_2)_{0-4}CO_2C_{1-4}$alkyl, —$(CH_2)_{0-4}$—O(cycloalkane)-$(CH_2)_{0-4}CO_2H$, —$(CH_2)_{0-4}$—O(cycloalkane)-$(CH_2)_{0-4}CO_2C_{1-4}$alkyl, —$(CH_2)_{0-4}C(O)NR^a(CH_2)_{1-4}CO_2H$, —$(CH_2)_{0-4}C(O)NR^a$—$CH(C_{1-4}$alkyl$)$-$CO_2H$, —$(CH_2)_{0-4}C(O)NR^a(CH_2)_{1-4}CONH_2$, —$(CH_2)_{0-4}C(O)NR^a(CH_2)_{1-4}CONHC_{1-4}$alkyl, —$(CH_2)_{0-4}C(O)NR^a(CH_2)_{1-4}CON(C_{1-4}$alkyl$)_2$, —OH, —$(CH_2)_{1-4}OH$, —$(CH_2)_{0-4}OC_{1-4}$alkyl, —$(CH_2)_{0-4}OC(O)C_{1-4}$alkyl, —$NH_2$, —$(CH_2)_{0-4}NR^a(CH_2)_{1-4}CO_2H$, —$(CH_2)_{0-4}NR^a(CH_2)_{1-4}CO_2C_{1-4}$alkyl, —$(CH_2)_{1-4}NH_2$, —$(CH_2)_{0-4}NHC_{1-4}$alkyl, —$(CH_2)_{0-4}NR^aC(O)C_{1-4}$alkyl, —$(CH_2)_{0-4}NR^aC(O)Ph$, —$(CH_2)_{0-4}NR^aCO(CH_2)_{1-4}OH$, —$(CH_2)_{0-4}N(C_{1-4}$alkyl$)_2$, —$(CH_2)_{0-4}SO_3H$, —$(CH_2)_{0-4}SO_2NH_2$, —$(CH_2)_{0-4}SO_2NR^aC_{1-4}$alkyl, —$(CH_2)_{0-4}NR^aSO_2C_{1-4}$alkyl, —$(CH_2)_{0-4}NR^aSO_2Ph$, —$(CH_2)_{0-4}NR^aSO_2(CH_2)_{1-4}CO_2H$, —$(CH_2)_{0-4}OP(OH)_2$, —$(CH_2)_{0-4}OP(OH)(OC_{1-4}$alkyl$)$, or —$(CR_2)_{0-4}OP(O)(H)OH$, wherein $R^a$, independently for each occurrence, is H or $C_{1-4}$alkyl;

m is 1, 2, 3, or 4, particularly 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In particular embodiments, the present disclosure provides a compound of formula I-f-2, wherein:

each $R^6$ is independently halogen, —$C_{1-4}$alkyl, —$C_{1-4}$haloalkyl, —$C_{3-6}$cycloalkyl, =$CH_2$, =O, —$(CH_2)_{0-4}CO_2H$, —$(CH_2)_{0-4}CO_2C_{1-4}$alkyl, —$(CH_2)_{0-4}CO_2C_{1-4}$haloalkyl, —$(CH_2)_{0-4}O(CH_2)_{1-5}CO_2H$, —$(CH_2)_{0-4}O(CH_2)_{1-5}CO_2C_{1-4}$alkyl, —$(CH_2)_{1-4}O(CH_2)_{1-4}CHFCO_2H$, —$(CH_2)_{1-4}O(CH_2)_{1-4}CHFCO_2C_{1-4}$alkyl, —$(CH_2)_{1-4}OCH(CH_3)(CH_2)_{1-4}CO_2H$, —$(CH_2)_{1-4}OCH(CH_3)(CH_2)_{1-4}CO_2C_{1-4}$alkyl, —$(CH_2)_{1-4}O(CH_2)_{1-4}CH(CH_3)CO_2H$, —$(CH_2)_{1-4}O(CH_2)_{1-4}CH(CH_3)CO_2C_{1-4}$alkyl, —$CHOH(CH_2)_{1-4}O(CH_2)_{1-5}CO_2H$, —$CHOH(CH_2)_{1-4}O(CH_2)_{1-5}CO_2C_{1-4}$alkyl, —$CHCF_3(CH_2)_{1-4}O(CH_2)_{1-5}CO_2H$, —$CHCF_3(CH_2)_{1-4}O(CH_2)_{1-5}CO_2C_{1-4}$alkyl, —$(CH_2)_{1-4}O(CH_2)_{1-5}CONR^a_2$, —$(CH_2)_{1-4}O(CH_2)_{1-5}CONR^aOH$, —$(CH_2)_{1-4}O(CH_2)_{1-5}CONR^aCN$, —$(CH_2)_{1-4}O(CH_2)_{1-5}P(O)OH_2$, —$(CH_2)_{0-4}CONH_2$, —$(CH_2)_{0-4}CONHC_{1-4}$alkyl, —$(CH_2)_{0-4}CON(C_{1-4}alkyl)_2$, —$(CH_2)_{0-4}CO$(N-proline), —$(CH_2)_{0-4}CO$(N-pyrrolidine-3-carboxylic acid), —$(CH_2)_{0-4}$(N-pyrazole)-$(CH_2)_{0-4}CO_2H$, —$(CH_2)_{0-4}CO$(N-pyrazole)-$(CH_2)_{0-4}CO_2C_{1-4}$alkyl, —$(CH_2)_{0-4}$(N-pyrrole)-$(CH_2)_{0-4}CO_2H$, —$(CH_2)_{0-4}CO$(N-pyrrole)-$(CH_2)_{0-4}CO_2C_{1-4}$alkyl, —$(CH_2)_{0-4}$—O(phenyl)-$(CH_2)_{0-4}CO_2H$, —$(CH_2)_{0-4}$—O(phenyl)-$(CH_2)_{0-4}CO_2C_{1-4}$alkyl, —$(CH_2)_{0-4}$—O(cycloalkane)-$(CH_2)_{0-4}CO_2H$, —$(CH_2)_{0-4}$—O(cycloalkane)-$(CH_2)_{0-4}CO_2C_{1-4}$alkyl, —$(CH_2)_{0-4}C(O)NR^a(CH_2)_{1-4}CO_2H$, —$(CH_2)_{0-4}C(O)NR^a$—$CH(C_{1-4}$alkyl)-$CO_2H$, —$(CH_2)_{0-4}C(O)NR^a(CH_2)_{1-4}CONH_2$, —$(CH_2)_{0-4}C(O)NR^a(CH_2)_{1-4}CONHC_{1-4}$alkyl, —$(CH_2)_{0-4}C(O)NR^a(CH_2)_{1-4}CON(C_{1-4}alkyl)_2$, —$OH$, —$(CH_2)_{1-4}OH$, —$(CH_2)_{0-4}OC_{1-4}$alkyl, —$(CH_2)_{0-4}OC(O)C_{1-4}$alkyl, —$NH_2$, —$(CH_2)_{0-4}NR^a(CH_2)_{1-4}CO_2H$, —$(CH_2)_{0-4}NR^a(CH_2)_{1-4}CO_2C_{1-4}$alkyl, —$(CH_2)_{1-4}NH_2$, —$(CH_2)_{0-4}NHC_{1-4}$alkyl, —$(CH_2)_{0-4}NR^aC(O)C_{1-4}$alkyl, —$(CH_2)_{0-4}NR^aC(O)Ph$, —$(CH_2)_{0-4}NR^aCO(CH_2)_{1-4}OH$, —$(CH_2)_{0-4}N(C_{1-4}alkyl)_2$, —$(CH_2)_{0-4}SO_3H$, —$(CH_2)_{0-4}SO_2NH_2$, —$(CH_2)_{0-4}SO_2NR^aC_{1-4}$alkyl, —$(CH_2)_{0-4}NR^aSO_2C_{1-4}$alkyl, —$(CH_2)_{0-4}NR^aSO_2Ph$, —$(CH_2)_{0-4}NR^aSO_2(CH_2)_{1-4}CO_2H$, —$(CH_2)_{0-4}OP(OH)_2$, —$(CH_2)_{0-4}OP(OH)(OC_{1-4}alkyl)$, or —$(CR_2)_{0-4}OP(O)(H)OH$, wherein $R^a$, independently for each occurrence, is H or $C_{1-4}$alkyl;

m is 1, 2, 3, or 4, particularly 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In further particular embodiments, the present disclosure provides a compound of formula I-f-2, wherein:
each $R^6$ is independently halogen, —$C_{1-4}$alkyl, —$C_{1-4}$haloalkyl, —$C_{3-6}$cycloalkyl, =$CH_2$, —$(CH_2)_{0-4}CO_2H$, —$(CH_2)_{0-4}O(CH_2)_{1-5}CO_2H$, —$(CH_2)_{0-4}O(CH_2)_{1-5}CO_2C_{1-4}$alkyl, —$(CH_2)_{0-4}CO$(N-proline), —$(CH_2)_{0-4}CO$(N-pyrrolidine-3-carboxylic acid), —$(CH_2)_{0-4}C(O)NR^a(CH_2)_{1-4}CO_2H$, —$(CH_2)_{0-4}C(O)NR^a$—$CH(C_{1-4}$alkyl)-$CO_2H$, —$OH$, —$(CH_2)_{1-4}OH$, —$(CH_2)_{0-4}OC_{1-4}$alkyl, —$(CH_2)_{0-4}OC(O)C_{1-4}$alkyl, —$(CH_2)_{0-4}NR^aC(O)C_{1-4}$alkyl, —$(CH_2)_{0-4}NR^aC(O)Ph$, —$(CH_2)_{0-4}NR^a$CO$(CH_2)_{1-4}OH$, —$(CH_2)_{0-4}SO_3H$, —$(CH_2)_{0-4}SO_2NH_2$, —$(CH_2)_{0-4}NR^aSO_2C_{1-4}$alkyl, —$(CH_2)_{0-4}NR^aSO_2Ph$, —$(CH_2)_{0-4}NR^aSO_2(CH_2)_{1-4}CO_2H$, —$(CH_2)_{0-4}OP(OH)_2$, or —$(CR_2)_{0-4}OP(O)(H)OH$, wherein $R^a$, independently for each occurrence, is H or $C_{1-4}$alkyl;

m is 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In further particular embodiments, the present disclosure provides a compound of formula I-f-2, wherein each $R^6$ is independently fluoro, -methyl, cyclohexyl, -methoxy, —OtBu, —$CF_3$, —$(CH_2)_{1-5}CO_2H$, —$(CH_2)_{1-5}CO_2C_{1-4}$alkyl, —$(CH_2)_{0-4}O(CH_2)_{1-5}CO_2H$, —$(CH_2)_{0-4}O(CH_2)_{1-5}CO_2C_{1-4}$alkyl, or —OH; and m is 1, 2, or 3, particularly 1 or 2.

In particular embodiments, the present disclosure provides a compound of formula I-f-2, wherein:
each $R^6$ is independently halogen, —$C_{1-4}$alkyl, —$C_{1-4}$haloalkyl, —$C_{3-6}$cycloalkyl, =$CH_2$, =O, —$(CH_2)_{0-4}CO_2H$, —$(CH_2)_{0-4}CO_2C_{1-4}$alkyl, —$(CH_2)_{0-4}O(CH_2)_{1-5}CO_2H$, —$(CH_2)_{0-4}O(CH_2)_{1-5}CO_2C_{1-4}$alkyl, —$(CH_2)_{0-4}CONH_2$, —$(CH_2)_{0-4}CONHC_{1-4}$alkyl, —$(CH_2)_{0-4}CON(C_{1-4}alkyl)_2$, —$(CH_2)_{0-4}CO$(N-proline), —$(CH_2)_{0-4}CO$(N-pyrrolidine-3-carboxylic acid), —$(CH_2)_{0-4}C(O)NR^a(CH_2)_{1-4}CO_2H$, —$(CH_2)_{0-4}C(O)NR^a$—$CH(C_{1-4}$alkyl)-$CO_2H$, —$(CH_2)_{0-4}C(O)NR^a(CH_2)_{1-4}CONH_2$, —$(CH_2)_{0-4}C(O)NR^a(CH_2)_{1-4}CONHC_{1-4}$alkyl, —$(CH_2)_{0-4}C(O)NR^a(CH_2)_{1-4}CON(C_{1-4}alkyl)_2$, —$OH$, —$(CH_2)_{1-4}OH$, —$(CH_2)_{0-4}OC_{1-4}$alkyl, —$NH_2$, —$(CH_2)_{1-4}NH_2$, —$(CH_2)_{0-4}NHC_{1-4}$alkyl, —$(CH_2)_{0-4}NR^aC(O)C_{1-4}$alkyl, —$(CH_2)_{0-4}NR^aC(O)Ph$, —$(CH_2)_{0-4}NR^aCO(CH_2)_{1-4}OH$, —$(CH_2)_{0-4}N(C_{1-4}alkyl)_2$, —$(CH_2)_{0-4}SO_3H$, —$(CH_2)_{0-4}SO_2NH_2$, —$(CH_2)_{0-4}SO_2NR^aC_{1-4}$alkyl, —$(CH_2)_{0-4}NR^aSO_2C_{1-4}$alkyl, —$(CH_2)_{0-4}NR^aSO_2Ph$, —$(CH_2)_{0-4}NR^aSO_2(CH_2)_{1-4}CO_2H$, —$(CH_2)_{0-4}OP(OH)_2$, —$(CH_2)_{0-4}OP(OH)(OC_{1-4}alkyl)$, or —$(CR_2)_{0-4}OP(O)(H)OH$, wherein $R^a$, independently for each occurrence, is H or $C_{1-4}$alkyl;

m is 1, 2, 3, or 4, particularly 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In further particular embodiments, the present disclosure provides a compound of formula I-f-2, wherein:
each $R^6$ is independently halogen, —$C_{1-4}$alkyl, q —$C_{1-4}$haloalkyl, —$C_{3-6}$cycloalkyl, =$CH_2$, —$(CH_2)_{0-4}CO_2H$, —$(CH_2)_{1-4}O(CH_2)_{1-5}CO_2H$, —$(CH_2)_{1-4}O(CH_2)_{1-5}CO_2C_{1-4}$alkyl, —$(CH_2)_{0-4}CO$(N-proline), —$(CH_2)_{0-4}CO$(N-pyrrolidine-3-carboxylic acid), —$(CH_2)_{0-4}C(O)NR^a(CH_2)_{1-4}CO_2H$, —$(CH_2)_{0-4}C(O)NR^a$—$CH(C_{1-4}$alkyl)-$CO_2H$, —$OH$, —$(CH_2)_{1-4}OH$, —$(CH_2)_{0-4}OC_{1-4}$alkyl, —$(CH_2)_{0-4}NR^aC(O)C_{1-4}$alkyl, —$(CH_2)_{0-4}NR^aC(O)Ph$, —$(CH_2)_{0-4}NR^aCO(CH_2)_{1-4}OH$, —$(CH_2)_{0-4}SO_3H$, —$(CH_2)_{0-4}SO_2NH_2$, —$(CH_2)_{0-4}NR^aSO_2C_{1-4}$alkyl, —$(CH_2)_{0-4}NR^aSO_2Ph$, —$(CH_2)_{0-4}NR^aSO_2(CH_2)_{1-4}CO_2H$, —$(CH_2)_{0-4}OP(OH)_2$, or —$(CR_2)_{0-4}OP(O)(H)OH$, wherein $R^a$, independently for each occurrence, is H or $C_{1-4}$alkyl;

m is 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In certain embodiments, the present disclosure provides a compound of formula I-f-2, wherein:

- each $R^6$ is independently halogen, =O, —COR, —(CR$_2$)$_{0-6}$CO$_2$R, —(CR$_2$)$_{0-6}$CONR$_2$, —OR, —(CR$_2$)$_{1-4}$OR, —NR$_2$, —(CR$_2$)$_{1-4}$NR$_2$, —NRC(O)OR, —NRC(O)R, —NRC(O)NR$_2$, —SR, —SO$_2$R, —S(O)R, —(CR$_2$)$_{0-6}$SO$_3$R, —(CR$_2$)$_{0-6}$SO$_2$NR$_2$, —(CR$_2$)$_{0-6}$OSO$_2$NR$_2$, —(CR$_2$)$_{0-6}$NRSO$_2$R, —(CR$_2$)$_{0-6}$NRSO$_2$OR, —(CR$_2$)$_{0-6}$OP(OR)$_2$, —(CR$_2$)$_{0-6}$OP(O)(OR)$_2$, —(CR$_2$)$_{0-6}$P(O)(OR)$_2$, —(CR$_2$)$_{0-6}$OP(O)(H)OR, or —B(OR)$_2$;
- m is 1, 2, 3, or 4, particularly 1 or 2; and
- each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In particular embodiments, the present disclosure provides a compound of formula I-f-2, wherein:

- each $R^6$ is independently halogen, =O, —(CH$_2$)$_{0-4}$CO$_2$H, —(CH$_2$)$_{0-4}$CO$_2$C$_{1-4}$alkyl, —(CH$_2$)$_{0-4}$CONH$_2$, —(CH$_2$)$_{0-4}$CONHC$_{1-4}$alkyl, —(CH$_2$)$_{0-4}$CON(C$_{1-4}$alkyl)$_2$, —(CH$_2$)$_{0-4}$CO(N-proline), —(CH$_2$)$_{0-4}$CO(N-pyrrolidine-3-carboxylic acid), —(CH$_2$)$_{0-4}$C(O)NR$^a$(CH$_2$)$_{1-4}$CO$_2$H, —(CH$_2$)$_{0-4}$C(O)NR$^a$—CH(C$_{1-4}$alkyl)-CO$_2$H, —(CH$_2$)$_{0-4}$C(O)NR$^a$(CH$_2$)$_{1-4}$CONH$_2$, —(CH$_2$)$_{0-4}$C(O)NR$^a$(CH$_2$)$_{1-4}$CONHC$_{1-4}$alkyl, —(CH$_2$)$_{0-4}$C(O)NR$^a$(CH$_2$)$_{1-4}$CON(C$_{1-4}$alkyl)$_2$, —OH, —(CH$_2$)$_{1-4}$OH, —(CH$_2$)$_{0-4}$OC$_{1-4}$alkyl, —NH$_2$, —(CH$_2$)$_{1-4}$NH$_2$, —(CH$_2$)$_{0-4}$NHC$_{1-4}$alkyl, —(CH$_2$)$_{0-4}$NR$^a$C(O)C$_{1-4}$alkyl, —(CH$_2$)$_{0-4}$NR$^a$C(O)Ph, —(CH$_2$)$_{0-4}$NR$^a$CO(CH$_2$)$_{1-4}$OH, —(CH$_2$)$_{0-4}$N(C$_{1-4}$alkyl)$_2$, —(CH$_2$)$_{0-4}$SO$_3$H, —(CH$_2$)$_{0-4}$SO$_2$NH$_2$, —(CH$_2$)$_{0-4}$SO$_2$NR$^a$C$_{1-4}$alkyl, —(CH$_2$)$_{0-4}$NR$^a$SO$_2$C$_{1-4}$alkyl, —(CH$_2$)$_{0-4}$NR$^a$SO$_2$Ph, —(CH$_2$)$_{0-4}$NR$^a$SO$_2$(CH$_2$)$_{1-4}$CO$_2$H, —(CH$_2$)$_{0-4}$OP(OH)$_2$, —(CH$_2$)$_{0-4}$OP(OH)(OC$_{1-4}$alkyl), or —(CR$_2$)$_{0-4}$OP(O)(H)OH, wherein $R^a$, independently for each occurrence, is H or $C_{1-4}$alkyl;
- m is 1, 2, 3, or 4, particularly 1 or 2; and
- each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In further particular embodiments, the present disclosure provides a compound of formula I-f-2, wherein:

- each $R^6$ is independently halogen, —(CH$_2$)$_{0-4}$CO$_2$H, —(CH$_2$)$_{0-4}$CO(N-proline), —(CH$_2$)$_{0-4}$CO(N-pyrrolidine-3-carboxylic acid), —(CH$_2$)$_{0-4}$C(O)NR$^a$(CH$_2$)$_{1-4}$CO$_2$H, —(CH$_2$)$_{0-4}$C(O)NR$^a$—CH(C$_{1-4}$alkyl)-CO$_2$H, —OH, —(CH$_2$)$_{1-4}$OH, —(CH$_2$)$_{0-4}$NR$^a$C(O)C$_{1-4}$alkyl, —(CH$_2$)$_{0-4}$NR$^a$C(O)Ph, —(CH$_2$)$_{0-4}$NR$^a$CO(CH$_2$)$_{1-4}$OH, —(CH$_2$)$_{0-4}$SO$_3$H, —(CH$_2$)$_{0-4}$SO$_2$NH$_2$, —(CH$_2$)$_{0-4}$NR$^a$SO$_2$C$_{1-4}$alkyl, —(CH$_2$)$_{0-4}$NR$^a$SO$_2$Ph, —(CH$_2$)$_{0-4}$NR$^a$SO$_2$(CH$_2$)$_{1-4}$CO$_2$H, —(CH$_2$)$_{0-4}$OP(OH)$_2$, or —(CR$_2$)$_{0-4}$OP(O)(H)OH, wherein $R^a$, independently for each occurrence, is H or $C_{1-4}$alkyl;
- m is 1 or 2; and
- each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In particular embodiments, the present disclosure provides a compound of formula I-f-2, wherein,
- m is 1;
- $R^6$ is —(CH$_2$)$_{0-4}$O(CH$_2$)$_{1-5}$CO$_2$H, such as —(CH$_2$)$_{1-2}$O(CH$_2$)$_{2-3}$CO$_2$H, including —CH$_2$O(CH$_2$)$_2$CO$_2$H; and
- each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In certain embodiments, for the above disclosed compounds of formula I-f-2, m is 1 or 2, and at least one $R^6$ includes a terminal —CO$_2$H group. For example, in certain instances, at least one $R^6$ is —(CH$_2$)$_{0-4}$CO$_2$H or —(CH$_2$)$_{0-4}$O(CH$_2$)$_{1-5}$CO$_2$H.

In some embodiments, the present disclosure provides a compound of formula I, wherein Ring A is

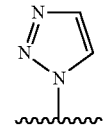

and $R^2$ is

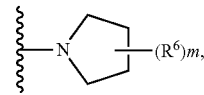

thereby forming a compound of formula I-f-3:

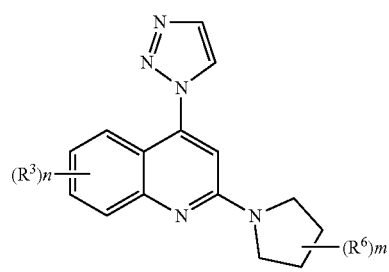

I-f-3 or a pharmaceutically acceptable salt thereof, wherein:
- each $R^6$ is independently halogen, =O, —COR, —(CR$_2$)$_{0-6}$CO$_2$R, —(CR$_2$)$_{0-6}$CONR$_2$, —OR, —(CR$_2$)$_{1-4}$OR, —NR$_2$, —(CR$_2$)$_{1-4}$NR$_2$, —NRC(O)OR, —NRC(O)R, —NRC(O)NR$_2$, —SR, —SO$_2$R, —S(O)R, —(CR$_2$)$_{0-6}$SO$_3$R, —(CR$_2$)$_{0-6}$SO$_2$NR$_2$, —(CR$_2$)$_{0-6}$OSO$_2$NR$_2$, —(CR$_2$)$_{0-6}$NRSO$_2$R, —(CR$_2$)$_{0-6}$NRSO$_2$OR, —(CR$_2$)$_{0-6}$OP(OR)$_2$, —(CR$_2$)$_{0-6}$OP(O)(OR)$_2$, —(CR$_2$)$_{0-6}$P(O)(OR)$_2$, —(CR$_2$)$_{0-6}$OP(O)(H)OR, —B(OR)$_2$, or $R^B$;
- m is 0, 1, 2, 3, or 4, particularly 1, 2, 3, or 4; and
- each of R, $R^3$, $R^B$, and n is as defined above and described in embodiments herein, both singly and in combination.

In some embodiments, the present disclosure provides a compound of formula I-f-3, wherein $R^6$ is not $R^B$.

In certain embodiments, the present disclosure provides a compound of formula I-f-3, wherein $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In certain embodiments, the present disclosure provides a compound of formula I-f-3, wherein:

each $R^6$ is independently halogen, $-C_{1-4}$alkyl, $-C_{1-4}$haloalkyl, $=CR_2$, $=O$, $-COR$, $-(CR_2)_{0-6}CO_2R$, $-(CR_2)_{0-6}CONR_2$, $-OR$, $-(CR_2)_{1-6}OR$, $-NR_2$, $-(CR_2)_{1-4}NR_2$, $-NRC(O)OR$, $-NRC(O)R$, $-NRC(O)NR_2$, $-SR$, $-SO_2R$, $-S(O)R$, $-(CR_2)_{0-6}SO_3R$, $-(CR_2)_{0-6}SO_2NR_2$, $-(CR_2)_{0-6}OSO_2NR_2$, $-(CR_2)_{0-6}NRSO_2R$, $-(CR_2)_{0-6}NRSO_2OR$, $-(CR_2)_{0-6}OP(OR)_2$, $-(CR_2)_{0-6}OP(O)(OR)_2$, $-(CR_2)_{0-6}P(O)(OR)_2$, $-(CR_2)_{0-6}OP(O)(H)OR$, or $-B(OR)_2$;

m is 1, 2, 3, or 4, particularly 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In particular embodiments, the present disclosure provides a compound of formula I-f-3, wherein:

each $R^6$ is independently halogen, $-C_{1-4}$alkyl, $-C_{1-4}$haloalkyl, $=CH_2$, $=O$, $-(CH_2)_{0-4}CO_2H$, $-(CH_2)_{0-4}CO_2C_{1-4}$alkyl, $-(CH_2)_{0-4}CO_2C_{1-4}$haloalkyl, $-(CH_2)_{0-4}CONH_2$, $-(CH_2)_{0-4}CONHC_{1-4}$alkyl, $-(CH_2)_{0-4}CON(C_{1-4}\text{alkyl})_2$, $-(CH_2)_{0-4}CO(\text{N-proline})$, $-(CH_2)_{0-4}CO(\text{N-pyrrolidine-3-carboxylic acid})$, $-(CH_2)_{0-4}(\text{N-pyrazole})-(CH_2)_{0-4}CO_2H$, $-(CH_2)_{0-4}CO(\text{N-pyrazole})-(CH_2)_{0-4}CO_2C_{1-4}$alkyl, $-(CH_2)_{0-4}(\text{N-pyrrole})-(CH_2)_{0-4}CO_2H$, $-(CH_2)_{0-4}CO(\text{N-pyrrole})-(CH_2)_{0-4}CO_2C_{1-4}$alkyl, $-(CH_2)_{0-4}-O(\text{phenyl})-(CH_2)_{0-4}CO_2H$, $-(CH_2)_{0-4}-O(\text{phenyl})-(CH_2)_{0-4}CO_2C_{1-4}$alkyl, $-(CH_2)_{0-4}-O(\text{cycloalkane})-(CH_2)_{0-4}CO_2H$, $-(CH_2)_{0-4}-O(\text{cycloalkane})-(CH_2)_{0-4}CO_2C_{1-4}$alkyl, $-(CH_2)_{0-4}C(O)NR^a(CH_2)_{1-4}CO_2H$, $-(CH_2)_{0-4}C(O)NR^a-CH(C_{1-4}\text{alkyl})-CO_2H$, $-(CH_2)_{0-4}C(O)NR^a(CH_2)_{1-4}CONH_2$, $-(CH_2)_{0-4}C(O)NR^a(CH_2)_{1-4}CONHC_{1-4}$alkyl, $-(CH_2)_{0-4}C(O)NR^a(CH_2)_{1-4}CON(C_{1-4}\text{alkyl})_2$, $-OH$, $-(CH_2)_{1-4}OH$, $-(CH_2)_{0-4}OC_{1-4}$alkyl, $-(CH_2)_{0-4}O(CH_2)_{1-5}CO_2H$, $-(CH_2)_{0-4}O(CH_2)_{1-5}CO_2C_{1-4}$alkyl, $-(CH_2)_{1-4}O(CH_2)_{1-4}CHFCO_2H$, $-(CH_2)_{1-4}O(CH_2)_{1-4}CHFCO_2C_{1-4}$alkyl, $-(CH_2)_{1-4}OCH(CH_3)(CH_2)_{1-4}CO_2H$, $-(CH_2)_{1-4}OCH(CH_3)(CH_2)_{1-4}CO_2C_{1-4}$alkyl, $-(CH_2)_{1-4}O(CH_2)_{1-4}CH(CH_3)CO_2H$, $-(CH_2)_{1-4}O(CH_2)_{1-4}CH(CH_3)CO_2C_{1-4}$alkyl, $-CHOH(CH_2)_{1-4}O(CH_2)_{1-5}CO_2H$, $-CHOH(CH_2)_{1-4}O(CH_2)_{1-5}CO_2C_{1-4}$alkyl, $-CHCF_3(CH_2)_{1-4}O(CH_2)_{1-5}CO_2H$, $-CHCF_3(CH_2)_{1-4}O-(CH_2)_{1-5}CO_2C_{1-4}$alkyl, $-(CH_2)_{1-4}O(CH_2)_{1-5}CONR^a_2$, $-(CH_2)_{1-4}O(CH_2)_{1-5}CONR^aOH$, $-(CH_2)_{1-4}O(CH_2)_{1-5}CONR^aCN$, $-(CH_2)_{1-4}O(CH_2)_{1-5}P(O)OH_2$, $-NH_2$, $-(CH_2)_{0-4}NR^a(CH_2)_{1-4}CO_2H$, $-(CH_2)_{0-4}NR^a(CH_2)_{1-4}CO_2C_{1-4}$alkyl, $-(CH_2)_{1-4}NH_2$, $-(CH_2)_{0-4}NHC_{1-4}$alkyl, $-(CH_2)_{0-4}NR^aC(O)C_{1-4}$alkyl, $-(CH_2)_{0-4}NR^aC(O)Ph$, $-(CH_2)_{0-4}NR^aCO(CH_2)_{1-4}OH$, $-(CH_2)_{0-4}N(C_{1-4}\text{alkyl})_2$, $-(CH_2)_{0-4}SO_3H$, $-(CH_2)_{0-4}SO_2NH_2$, $-(CH_2)_{0-4}SO_2NR^aC_{1-4}$alkyl, $-(CH_2)_{0-4}NR^aSO_2C_{1-4}$alkyl, $-(CH_2)_{0-4}NR^aSO_2Ph$, $-(CH_2)_{0-4}NR^aSO_2(CH_2)_{1-4}CO_2H$, $-(CH_2)_{0-4}OP(OH)_2$, $-(CH_2)_{0-4}OP(OH)(OC_{1-4}\text{alkyl})$, or $-(CR_2)_{0-4}OP(O)(H)OH$, wherein $R^a$, independently for each occurrence, is H or $C_{1-4}$alkyl;

m is 1, 2, 3, or 4, particularly 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In further particular embodiments, the present disclosure provides a compound of formula I-f-3, wherein:

each $R^6$ is independently halogen, $-C_{1-4}$alkyl, $-C_{1-4}$haloalkyl, $=CH_2$, $-(CH_2)_{0-4}CO_2H$, $-(CH_2)_{0-4}CO_2C_{1-4}$alkyl, $-(CH_2)_{0-4}CO_2C_{1-4}$haloalkyl, $-(CH_2)_{0-4}CO(\text{N-proline})$, $-(CH_2)_{0-4}CO(\text{N-pyrrolidine-3-carboxylic acid})$, $-(CH_2)_{0-4}C(O)NR^a(CH_2)_{1-4}CO_2H$, $-(CH_2)_{0-4}C(O)NR^a-CH(C_{1-4}\text{alkyl})-CO_2H$, $-OH$, $-(CH_2)_{1-4}OH$, $-(CH_2)_{0-4}OC_{1-4}$alkyl, $-(CH_2)_{0-4}O(CH_2)_{1-5}CO_2H$, $-(CH_2)_{0-4}O(CH_2)_{1-5}CO_2C_{1-4}$alkyl, $-(CH_2)_{0-4}NR^aC(O)C_{1-4}$alkyl, $-(CH_2)_{0-4}NR^aC(O)Ph$, $-(CH_2)_{0-4}NR^aCO(CH_2)_{1-4}OH$, $-(CH_2)_{0-4}SO_3H$, $-(CH_2)_{0-4}SO_2NH_2$, $-(CH_2)_{0-4}NR^aSO_2C_{1-4}$alkyl, $-(CH_2)_{0-4}NR^aSO_2Ph$, $-(CH_2)_{0-4}NR^aSO_2(CH_2)_{1-4}CO_2H$, $-(CH_2)_{0-4}OP(OH)_2$, or $-(CR_2)_{0-4}OP(O)(H)OH$, wherein $R^a$, independently for each occurrence, is H or $C_{1-4}$alkyl;

m is 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In particular embodiments, the present disclosure provides a compound of formula I-f-3, wherein:

each $R^6$ is independently halogen, $-C_{1-4}$alkyl, $-C_{1-4}$haloalkyl, $-C_{3-6}$cycloalkyl, $=CH_2$, $=O$, $-(CH_2)_{0-4}CO_2H$, $-(CH_2)_{0-4}CO_2C_{1-4}$alkyl, $-(CH_2)_{0-4}CO_2C_{1-4}$haloalkyl, $-(CH_2)_{0-4}O(CH_2)_{1-5}CO_2H$, $-(CH_2)_{0-4}O(CH_2)_{1-5}CO_2C_{1-4}$alkyl, $-(CH_2)_{1-4}O(CH_2)_{1-4}CHFCO_2H$, $-(CH_2)_{1-4}O(CH_2)_{1-4}CHFCO_2C_{1-4}$alkyl, $-(CH_2)_{1-4}OCH(CH_3)(CH_2)_{1-4}CO_2H$, $-(CH_2)_{1-4}OCH(CH_3)(CH_2)_{1-4}CO_2C_{1-4}$alkyl, $-(CH_2)_{1-4}O(CH_2)_{1-4}CH(CH_3)CO_2H$, $-(CH_2)_{1-4}O(CH_2)_{1-4}CH(CH_3)CO_2C_{1-4}$alkyl, $-CHOH(CH_2)_{1-4}O(CH_2)_{1-5}CO_2H$, $-CHOH(CH_2)_{1-4}O(CH_2)_{1-5}CO_2C_{1-4}$alkyl, $-CHCF_3(CH_2)_{1-4}O(CH_2)_{1-5}CO_2H$, $-CHCF_3(CH_2)_{1-4}O-(CH_2)_{1-5}CO_2C_{1-4}$alkyl, $-(CH_2)_{1-4}O(CH_2)_{1-5}CONR^a_2$, $-(CH_2)_{1-4}O(CH_2)_{1-5}CONR^aOH$, $-(CH_2)_{1-4}O(CH_2)_{1-5}CONR^aCN$, $-(CH_2)_{1-4}O(CH_2)_{1-5}P(O)OH_2$, $-(CH_2)_{0-4}CONH_2$, $-(CH_2)_{0-4}CONHC_{1-4}$alkyl, $-(CH_2)_{0-4}CON(C_{1-4}\text{alkyl})_2$, $-(CH_2)_{0-4}CO(\text{N-proline})$, $-(CH_2)_{0-4}CO(\text{N-pyrrolidine-3-carboxylic acid})$, $-(CH_2)_{0-4}(\text{N-pyrazole})-(CH_2)_{0-4}CO_2H$, $-(CH_2)_{0-4}CO(\text{N-pyrazole})-(CH_2)_{0-4}CO_2C_{1-4}$alkyl, $-(CH_2)_{0-4}(\text{N-pyrrole})-(CH_2)_{0-4}CO_2H$, $-(CH_2)_{0-4}CO(\text{N-pyrrole})-(CH_2)_{0-4}CO_2C_{1-4}$alkyl, $-(CH_2)_{0-4}-O(\text{phenyl})-(CH_2)_{0-4}CO_2H$, $-(CH_2)_{0-4}-O(\text{phenyl})-(CH_2)_{0-4}CO_2C_{1-4}$alkyl, $-(CH_2)_{0-4}-O(\text{cycloalkane})-(CH_2)_{0-4}CO_2H$, $-(CH_2)_{0-4}-O(\text{cycloalkane})-(CH_2)_{0-4}CO_2C_{1-4}$alkyl, $-(CH_2)_{0-4}C(O)NR^a(CH_2)_{1-4}CO_2H$, $-(CH_2)_{0-4}C(O)NR^a-CH(C_{1-4}\text{alkyl})-CO_2H$, $-(CH_2)_{0-4}C(O)NR^a(CH_2)_{1-4}CONH_2$, $-(CH_2)_{0-4}C(O)NR^a(CH_2)_{1-4}CONHC_{1-4}$alkyl, $-(CH_2)_{0-4}C(O)NR^a(CH_2)_{1-4}CON(C_{1-4}\text{alkyl})_2$, $-OH$, $-(CH_2)_{1-4}OH$, $-(CH_2)_{0-4}OC_{1-4}$alkyl, $-(CH_2)_{0-4}OC(O)C_{1-4}$alkyl, $-NH_2$, $-(CH_2)_{0-4}NR^a(CH_2)_{1-4}CO_2H$, $-(CH_2)_{0-4}NR^a(CH_2)_{1-4}CO_2C_{1-4}$alkyl, $-(CH_2)_{1-4}$ NH$_2$, —(CH$_2$)$_{0-4}$NHC$_{1-4}$alkyl, —(CH$_2$)$_{0-4}$NR$^a$C(O)C$_{1-4}$alkyl, —(CH$_2$)$_{0-4}$NR$^a$C(O)Ph, —(CH$_2$)$_{0-4}$NR$^a$CO(CH$_2$)$_{1-4}$OH, —(CH$_2$)$_{0-4}$N(C$_{1-4}$alkyl)$_2$, —(CH$_2$)$_{0-4}$SO$_3$H, —(CH$_2$)$_{0-4}$SO$_2$NH$_2$, —(CH$_2$)$_{0-4}$SO$_2$NR$^a$C$_{1-4}$alkyl, —(CH$_2$)$_{0-4}$NR$^a$SO$_2$C$_{1-4}$alkyl, —(CH$_2$)$_{0-4}$NR$^a$SO$_2$Ph, —(CH$_2$)$_{0-4}$NR$^a$SO$_2$(CH$_2$)$_{1-4}$CO$_2$H, —(CH$_2$)$_{0-4}$OP(OH)$_2$, —(CH$_2$)$_{0-4}$OP(OH)(OC$_{1-4}$alkyl), or —(CR$_2$)$_{0-4}$OP(O)(H)OH, wherein R$^a$, independently for each occurrence, is H or C$_{1-4}$alkyl;

m is 1, 2, 3, or 4, particularly 1 or 2; and each R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In further particular embodiments, the present disclosure provides a compound of formula I-f-3, wherein:

each R$^6$ is independently halogen, —C$_{1-4}$alkyl, —C$_{1-4}$haloalkyl, —C$_{3-6}$cycloalkyl, =CH$_2$, —(CH$_2$)$_{0-4}$CO$_2$H, —(CH$_2$)$_{0-4}$O(CH$_2$)$_{1-5}$CO$_2$H, —(CH$_2$)$_{0-4}$O(CH$_2$)$_{1-5}$CO$_2$C$_{1-4}$alkyl, —(CH$_2$)$_{0-4}$CO(N-proline), —(CH$_2$)$_{0-4}$CO(N-pyrrolidine-3-carboxylic acid), —(CH$_2$)$_{0-4}$C(O)NR$^a$(CH$_2$)$_{1-4}$CO$_2$H, —(CH$_2$)$_{0-4}$C(O)NR$^a$—CH(C$_{1-4}$alkyl)-CO$_2$H, —OH, —(CH$_2$)$_{1-4}$OH, —(CH$_2$)$_{0-4}$OC$_{1-4}$alkyl, —(CH$_2$)$_{0-4}$OC(O)C$_{1-4}$alkyl, —(CH$_2$)$_{0-4}$NR$^a$C(O)C$_{1-4}$alkyl, —(CH$_2$)$_{0-4}$NR$^a$C(O)Ph, —(CH$_2$)$_{0-4}$NR$^a$CO(CH$_2$)$_{1-4}$OH, —(CH$_2$)$_{0-4}$SO$_3$H, —(CH$_2$)$_{0-4}$SO$_2$NH$_2$, —(CH$_2$)$_{0-4}$NR$^a$SO$_2$C$_{1-4}$alkyl, —(CH$_2$)$_{0-4}$NR$^a$SO$_2$Ph, —(CH$_2$)$_{0-4}$NR$^a$SO$_2$(CH$_2$)$_{1-4}$CO$_2$H, —(CH$_2$)$_{0-4}$OP(OH)$_2$, or —(CR$_2$)$_{0-4}$OP(O)(H)OH, wherein R$^a$, independently for each occurrence, is H or C$_{1-4}$alkyl;

m is 1 or 2; and each R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In further particular embodiments, the present disclosure provides a compound of formula I-f-3, wherein each R$^6$ is independently fluoro, -methyl, cyclohexyl, -methoxy, —OtBu, —CF$_3$, —(CH$_2$)$_{1-5}$CO$_2$H, —(CH$_2$)$_{1-5}$CO$_2$C$_{1-4}$alkyl, —(CH$_2$)$_{0-4}$O(CH$_2$)$_{1-5}$CO$_2$H, —(CH$_2$)$_{0-4}$O(CH$_2$)$_{1-5}$CO$_2$C$_{1-4}$alkyl, or —OH; and m is 1, 2, or 3, particularly 1 or 2.

In particular embodiments, the present disclosure provides a compound of formula I-f-3, wherein:

each R$^6$ is independently halogen, —C$_{1-4}$alkyl, —C$_{1-4}$haloalkyl, —C$_{3-6}$cycloalkyl, =CH$_2$, =O, —(CH$_2$)$_{0-4}$CO$_2$H, —(CH$_2$)$_{0-4}$CO$_2$C$_{1-4}$alkyl, —(CH$_2$)$_{0-4}$O(CH$_2$)$_{1-5}$CO$_2$H, —(CH$_2$)$_{0-4}$O(CH$_2$)$_{1-5}$CO$_2$C$_{1-4}$alkyl, —(CH$_2$)$_{0-4}$CONH$_2$, —(CH$_2$)$_{0-4}$CONHC$_{1-4}$alkyl, —(CH$_2$)$_{0-4}$CON(C$_{1-4}$alkyl)$_2$, —(CH$_2$)$_{0-4}$CO(N-proline), —(CH$_2$)$_{0-4}$CO(N-pyrrolidine-3-carboxylic acid), —(CH$_2$)$_{0-4}$C(O)NR$^a$(CH$_2$)$_{1-4}$CO$_2$H, —(CH$_2$)$_{0-4}$C(O)NR$^a$—CH(C$_{1-4}$alkyl)-CO$_2$H, —(CH$_2$)$_{0-4}$C(O)NR$^a$(CH$_2$)$_{1-4}$CONH$_2$, —(CH$_2$)$_{0-4}$C(O)NR$^a$(CH$_2$)$_{1-4}$CONHC$_{1-4}$alkyl, —(CH$_2$)$_{0-4}$C(O)NR$^a$(CH$_2$)$_{1-4}$CON(C$_{1-4}$alkyl)$_2$, —OH, —(CH$_2$)$_{1-4}$OH, —(CH$_2$)$_{0-4}$OC$_{1-4}$alkyl, —NH$_2$, —(CH$_2$)$_{1-4}$NH$_2$, —(CH$_2$)$_{0-4}$NHC$_{1-4}$alkyl, —(CH$_2$)$_{0-4}$NR$^a$C(O)C$_{1-4}$alkyl, —(CH$_2$)$_{0-4}$NR$^a$C(O)Ph, —(CH$_2$)$_{0-4}$NR$^a$CO(CH$_2$)$_{1-4}$OH, —(CH$_2$)$_{0-4}$N(C$_{1-4}$alkyl)$_2$, —(CH$_2$)$_{0-4}$SO$_3$H, —(CH$_2$)$_{0-4}$SO$_2$NH$_2$, —(CH$_2$)$_{0-4}$SO$_2$NR$^a$C$_{1-4}$alkyl, —(CH$_2$)$_{0-4}$NR$^a$SO$_2$C$_{1-4}$alkyl, —(CH$_2$)$_{0-4}$NR$^a$SO$_2$Ph, —(CH$_2$)$_{0-4}$NR$^a$SO$_2$(CH$_2$)$_{1-4}$CO$_2$H, —(CH$_2$)$_{0-4}$OP(OH)$_2$, —(CH$_2$)$_{0-4}$OP(OH)(OC$_{1-4}$alkyl), or —(CR$_2$)$_{0-4}$OP(O)(H)OH, wherein R$^a$, independently for each occurrence, is H or C$_{1-4}$alkyl;

m is 1, 2, 3, or 4, particularly 1 or 2; and each R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In further particular embodiments, the present disclosure provides a compound of formula I-f-3, wherein:

each R$^6$ is independently halogen, —C$_{1-4}$alkyl, —C$_{1-4}$haloalkyl, —C$_{3-6}$cycloalkyl, =CH$_2$, —(CH$_2$)$_{0-4}$CO$_2$H, —(CH$_2$)$_{1-4}$O(CH$_2$)$_{1-5}$CO$_2$H, —(CH$_2$)$_{1-4}$O(CH$_2$)$_{1-5}$CO$_2$C$_{1-4}$alkyl, —(CH$_2$)$_{0-4}$CO(N-proline), —(CH$_2$)$_{0-4}$CO(N-pyrrolidine-3-carboxylic acid), —(CH$_2$)$_{0-4}$C(O)NR$^a$(CH$_2$)$_{1-4}$CO$_2$H, —(CH$_2$)$_{0-4}$C(O)NR$^a$—CH(C$_{1-4}$alkyl)-CO$_2$H, —OH, —(CH$_2$)$_{1-4}$OH, —(CH$_2$)$_{0-4}$OC$_{1-4}$alkyl, —(CH$_2$)$_{0-4}$NR$^a$C(O)C$_{1-4}$alkyl, —(CH$_2$)$_{0-4}$NR$^a$C(O)Ph, —(CH$_2$)$_{0-4}$NR$^a$CO(CH$_2$)$_{1-4}$OH, —(CH$_2$)$_{0-4}$SO$_3$H, —(CH$_2$)$_{0-4}$SO$_2$NH$_2$, —(CH$_2$)$_{0-4}$NR$^a$SO$_2$C$_{1-4}$alkyl, —(CH$_2$)$_{0-4}$NR$^a$SO$_2$Ph, —(CH$_2$)$_{0-4}$NR$^a$SO$_2$(CH$_2$)$_{1-4}$CO$_2$H, —(CH$_2$)$_{0-4}$OP(OH)$_2$, or —(CR$_2$)$_{0-4}$OP(O)(H)OH, wherein R$^a$, independently for each occurrence, is H or C$_{1-4}$alkyl;

m is 1 or 2; and each R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In certain embodiments, the present disclosure provides a compound of formula I-f-3, wherein:

each R$^6$ is independently halogen, =O, —COR, —(CR$_2$)$_{0-6}$CO$_2$R, —(CR$_2$)$_{0-6}$CONR$_2$, —OR, —(CR$_2$)$_{1-4}$OR, —NR$_2$, —(CR$_2$)$_{1-4}$NR$_2$, —NRC(O)OR, —NRC(O)R, —NRC(O)NR$_2$, —SR, —SO$_2$R, —S(O)R, —(CR$_2$)$_{0-6}$SO$_3$R, —(CR$_2$)$_{0-6}$SO$_2$NR$_2$, —(CR$_2$)$_{0-6}$OSO$_2$NR$_2$, —(CR$_2$)$_{0-6}$NRSO$_2$R, —(CR$_2$)$_{0-6}$NRSO$_2$OR, —(CR$_2$)$_{0-6}$OP(OR)$_2$, —(CR$_2$)$_{0-6}$OP(O)(OR)$_2$, —(CR$_2$)$_{0-6}$P(O)(OR)$_2$, —(CR$_2$)$_{0-6}$OP(O)(H)OR, or —B(OR)$_2$;

m is 1, 2, 3, or 4, particularly 1 or 2; and each R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In particular embodiments, the present disclosure provides a compound of formula I-f-3, wherein:

each R$^6$ is independently halogen, =O, —(CH$_2$)$_{0-4}$CO$_2$H, —(CH$_2$)$_{0-4}$CO$_2$C$_{1-4}$alkyl, —(CH$_2$)$_{0-4}$CONH$_2$, —(CH$_2$)$_{0-4}$CONHC$_{1-4}$alkyl, —(CH$_2$)$_{0-4}$CON(C$_{1-4}$alkyl)$_2$, —(CH$_2$)$_{0-4}$CO(N-proline), —(CH$_2$)$_{0-4}$CO(N-pyrrolidine-3-carboxylic acid), —(CH$_2$)$_{0-4}$C(O)NR$^a$(CH$_2$)$_{1-4}$CO$_2$H, —(CH$_2$)$_{0-4}$C(O)NR$^a$—CH(C$_{1-4}$alkyl)-CO$_2$H, —(CH$_2$)$_{0-4}$C(O)NR$^a$(CH$_2$)$_{1-4}$CONH$_2$, —(CH$_2$)$_{0-4}$C(O)NR$^a$(CH$_2$)$_{1-4}$CONHC$_{1-4}$alkyl, —(CH$_2$)$_{0-4}$C(O)NR$^a$(CH$_2$)$_{1-4}$CON(C$_{1-4}$alkyl)$_2$, —OH, —(CH$_2$)$_{1-4}$OH, —(CH$_2$)$_{0-4}$OC$_{1-4}$alkyl, —NH$_2$, —(CH$_2$)$_{1-4}$NH$_2$, —(CH$_2$)$_{0-4}$NHC$_{1-4}$alkyl, —(CH$_2$)$_{0-4}$NR$^a$C(O)C$_{1-4}$alkyl, —(CH$_2$)$_{0-4}$NR$^a$C(O)Ph, —(CH$_2$)$_{0-4}$NR$^a$CO(CH$_2$)$_{1-4}$OH, —(CH$_2$)$_{0-4}$N(C$_{1-4}$alkyl)$_2$, —(CH$_2$)$_{0-4}$SO$_3$H, —(CH$_2$)$_{0-4}$SO$_2$NH$_2$, —(CH$_2$)$_{0-4}$SO$_2$NR$^a$C$_{1-4}$alkyl, —(CH$_2$)$_{0-4}$NR$^a$ SO$_2$C$_{1-4}$alkyl, —(CH$_2$)$_{0-4}$NR$^a$SO$_2$Ph, —(CH$_2$)$_{0-4}$NR$^a$SO$_2$(CH$_2$)$_{1-4}$CO$_2$H, —(CH$_2$)$_{0-4}$OP(OH)$_2$, —(CH$_2$)$_{0-4}$OP(OH)(OC$_{1-4}$alkyl), or —(CR$_2$)$_{0-4}$OP(O)(H)OH, wherein R$^a$, independently for each occurrence, is H or C$_{1-4}$alkyl;

m is 1, 2, 3, or 4, particularly 1 or 2; and each R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In further particular embodiments, the present disclosure provides a compound of formula I-f-3, wherein:

each R$^6$ is independently halogen, —(CH$_2$)$_{0-4}$CO$_2$H, —(CH$_2$)$_{0-4}$CO(N-proline), —(CH$_2$)$_{0-4}$CO(N-pyrrolidine-3-carboxylic acid), —(CH$_2$)$_{0-4}$C(O)NR$^a$(CH$_2$)$_{1-4}$CO$_2$H, —(CH$_2$)$_{0-4}$C(O)NR$^a$—CH(C$_{1-4}$alkyl)-CO$_2$H, —OH, —(CH$_2$)$_{1-4}$OH, —(CH$_2$)$_{0-4}$NR$^a$C(O)C$_{1-4}$alkyl, —(CH$_2$)$_{0-4}$NR$^a$C(O)Ph, —(CH$_2$)$_{0-4}$NR$^a$CO(CH$_2$)$_{1-4}$OH, —(CH$_2$)$_{0-4}$SO$_3$H, —(CH$_2$)$_{0-4}$SO$_2$NH$_2$, —(CH$_2$)$_{0-4}$NR$^a$SO$_2$C$_{1-4}$alkyl, —(CH$_2$)$_{0-4}$NR$^a$SO$_2$Ph, —(CH$_2$)$_{0-4}$NR$^a$SO$_2$(CH$_2$)$_{1-4}$CO$_2$H, —(CH$_2$)$_{0-4}$OP(OH)$_2$, or —(CR$_2$)$_{0-4}$OP(O)(H)OH, wherein R$^a$, independently for each occurrence, is H or C$_{1-4}$alkyl;

m is 1 or 2; and each R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In particular embodiments, the present disclosure provides a compound of formula I-f-3, wherein, m is 1;

R$^6$ is —(CH$_2$)$_{0-4}$O(CH$_2$)$_{1-5}$CO$_2$H, such as —(CH$_2$)$_{1-2}$O(CH$_2$)$_{2-3}$CO$_2$H, including —CH$_2$O(CH$_2$)$_2$CO$_2$H; and each R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In certain embodiments, for the above disclosed compounds of formula I-f-3, m is 1 or 2, and at least one R$^6$ includes a terminal —CO$_2$H group. For example, in certain instances, at least one R$^6$ is —(CH$_2$)$_{0-4}$CO$_2$H or —(CH$_2$)$_{0-4}$O(CH$_2$)$_{1-5}$CO$_2$H.

In some embodiments, the present disclosure provides a compound of formula I, wherein Ring A is

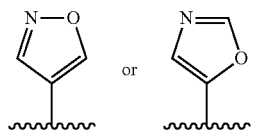

or and R$^2$ is

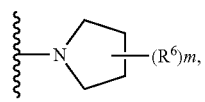

thereby forming a compound of formula I-f-4 or formula I-f-4*, respectively:

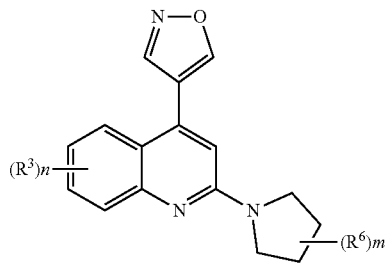

I-f-4

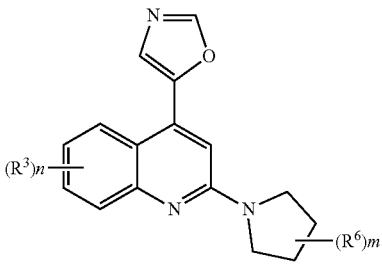

I-f-4* or a pharmaceutically acceptable salt thereof, wherein:

each R$^6$ is independently halogen, =O, —COR, —(CR$_2$)$_{0-6}$CO$_2$R, —(CR$_2$)$_{0-6}$CONR$_2$, —OR, —(CR$_2$)$_{1-4}$OR, —NR$_2$, —(CR$_2$)$_{1-4}$NR$_2$, —NRC(O)OR, —NRC(O)R, —NRC(O)NR$_2$, —SR, —SO$_2$R, —S(O)R, —(CR$_2$)$_{0-6}$SO$_3$R, —(CR$_2$)$_{0-6}$SO$_2$NR$_2$, —(CR$_2$)$_{0-6}$OSO$_2$NR$_2$, —(CR$_2$)$_{0-6}$NRSO$_2$R, —(CR$_2$)$_{0-6}$NRSO$_2$OR, —(CR$_2$)$_{0-6}$OP(OR)$_2$, —(CR$_2$)$_{0-6}$OP(O)(OR)$_2$, —(CR$_2$)$_{0-6}$P(O)(OR)$_2$, —(CR$_2$)$_{0-6}$OP(O)(H)OR, —B(OR)$_2$, or R$^B$;

m is 0, 1, 2, 3, or 4, particularly 1, 2, 3, or 4; and each of R, R$^3$, R$^B$, and n is as defined above and described in embodiments herein, both singly and in combination.

In some embodiments, the present disclosure provides a compound of formula I-f-4 or formula I-f-4*, wherein R$^6$ is not R$^B$.

In certain embodiments, the present disclosure provides a compound of formula I-f-4 or formula I-f-4*, wherein R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In certain embodiments, the present disclosure provides a compound of formula I-f-4 or formula I-f-4*, wherein:

each R$^6$ is independently halogen, —C$_{1-4}$alkyl, —C$_{1-4}$haloalkyl, =CR$_2$, =O, —COR, —(CR$_2$)$_{0-6}$CO$_2$R, —(CR$_2$)$_{0-6}$CONR$_2$, —OR, —(CR$_2$)$_{1-4}$OR, —NR$_2$, —(CR$_2$)$_{1-4}$NR$_2$, —NRC(O)OR, —NRC(O)R, —NRC(O)NR$_2$, —SR, —SO$_2$R, —S(O)R, —(CR$_2$)$_{0-6}$SO$_3$R, —(CR$_2$)$_{0-6}$SO$_2$NR$_2$, —(CR$_2$)$_{0-6}$OSO$_2$NR$_2$, —(CR$_2$)$_{0-6}$NRSO$_2$R, —(CR$_2$)$_{0-6}$NRSO$_2$OR, —(CR$_2$)$_{0-6}$OP(OR)$_2$, —(CR$_2$)$_{0-6}$OP(O)(OR)$_2$, —(CR$_2$)$_{0-6}$P(O)(OR)$_2$, —(CR$_2$)$_{0-6}$OP(O)(H)OR, or —B(OR)$_2$;

m is 1, 2, 3, or 4, particularly 1 or 2; and each R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In particular embodiments, the present disclosure provides a compound of formula I-f-4 or formula I-f-4*, wherein:

each $R^6$ is independently halogen, —$C_{1-4}$alkyl, —$C_{1-4}$haloalkyl, =$CH_2$, =O, —$(CH_2)_{0-4}CO_2H$, —$(CH_2)_{0-4}CO_2C_{1-4}$alkyl, —$(CH_2)_{0-4}CO_2C_{1-4}$haloalkyl, —$(CH_2)_{0-4}CONH_2$, —$(CH_2)_{0-4}CONHC_{1-4}$alkyl, —$(CH_2)_{0-4}CON(C_{1-4}$alkyl$)_2$, —$(CH_2)_{0-4}CO$(N-proline), —$(CH_2)_{0-4}CO$(N-pyrrolidine-3-carboxylic acid), —$(CH_2)_{0-4}$(N-pyrazole)-$(CH_2)_{0-4}CO_2H$, —$(CH_2)_{0-4}CO$(N-pyrazole)-$(CH_2)_{0-4}CO_2C_{1-4}$alkyl, —$(CH_2)_{0-4}$(N-pyrrole)-$(CH_2)_{0-4}CO_2H$, —$(CH_2)_{0-4}CO$(N-pyrrole)-$(CH_2)_{0-4}CO_2C_{1-4}$alkyl, —$(CH_2)_{0-4}$—O(phenyl)-$(CH_2)_{0-4}CO_2H$, —$(CH_2)_{0-4}$—O(phenyl)-$(CH_2)_{0-4}CO_2C_{1-4}$alkyl, —$(CH_2)_{0-4}$—O(cycloalkane)-$(CH_2)_{0-4}CO_2H$, —$(CH_2)_{0-4}$—O(cycloalkane)-$(CH_2)_{0-4}CO_2C_{1-4}$alkyl, —$(CH_2)_{0-4}C(O)NR^a(CH_2)_{1-4}CO_2H$, —$(CH_2)_{0-4}C(O)NR^a$—CH($C_{1-4}$alkyl)-$CO_2H$, —$(CH_2)_{0-4}C(O)NR^a(CH_2)_{1-4}CONH_2$, —$(CH_2)_{0-4}C(O)NR^a(CH_2)_{1-4}CONHC_{1-4}$alkyl, —$(CH_2)_{0-4}C(O)NR^a(CH_2)_{1-4}CON(C_{1-4}$alkyl$)_2$, —OH, —$(CH_2)_{1-4}OH$, —$(CH_2)_{0-4}OC_{1-4}$alkyl, —$(CH_2)_{0-4}O(CH_2)_{1-5}CO_2H$, —$(CH_2)_{0-4}O(CH_2)_{1-5}CO_2C_{1-4}$alkyl, —$(CH_2)_{1-4}O(CH_2)_{1-4}CHFCO_2H$, —$(CH_2)_{1-4}O(CH_2)_{1-4}CHFCO_2C_{1-4}$alkyl, —$(CH_2)_{1-4}OCH(CH_3)(CH_2)_{1-4}CO_2H$, —$(CH_2)_{1-4}OCH(CH_3)(CH_2)_{1-4}CO_2C_{1-4}$alkyl, —$(CH_2)_{1-4}O(CH_2)_{1-4}CH(CH_3)CO_2H$, —$(CH_2)_{1-4}O(CH_2)_{1-4}CH(CH_3)CO_2C_{1-4}$alkyl, —CHOH$(CH_2)_{1-4}O(CH_2)_{1-5}CO_2H$, —CHOH$(CH_2)_{1-4}O(CH_2)_{1-5}CO_2C_{1-4}$alkyl, —$CHCF_3(CH_2)_{1-4}O(CH_2)_{1-5}CO_2H$, —$CHCF_3(CH_2)_{1-4}O$—$(CH_2)_{1-5}CO_2C_{1-4}$alkyl, —$(CH_2)_{1-4}O(CH_2)_{1-5}CONR^a_2$, —$(CH_2)_{1-4}O(CH_2)_{1-5}CONR^aOH$, —$(CH_2)_{1-4}O(CH_2)_{1-5}CONR^aCN$, —$(CH_2)_{1-4}O(CH_2)_{1-5}P(O)OH_2$, —$NH_2$, —$(CH_2)_{0-4}NR^a(CH_2)_{1-4}CO_2H$, —$(CH_2)_{0-4}NR^a(CH_2)_{1-4}CO_2C_{1-4}$alkyl, —$(CH_2)_{1-4}NH_2$, —$(CH_2)_{0-4}NHC_{1-4}$alkyl, —$(CH_2)_{0-4}NR^aC(O)C_{1-4}$alkyl, —$(CH_2)_{0-4}NR^aC(O)Ph$, —$(CH_2)_{0-4}NR^aCO(CH_2)_{1-4}OH$, —$(CH_2)_{0-4}N(C_{1-4}$alkyl$)_2$, —$(CH_2)_{0-4}SO_3H$, —$(CH_2)_{0-4}SO_2NH_2$, —$(CH_2)_{0-4}SO_2NR^aC_{1-4}$alkyl, —$(CH_2)_{0-4}NR^aSO_2C_{1-4}$alkyl, —$(CH_2)_{0-4}NR^aSO_2Ph$, —$(CH_2)_{0-4}NR^aSO_2(CH_2)_{1-4}CO_2H$, —$(CH_2)_{0-4}OP(OH)_2$, —$(CH_2)_{0-4}OP(OH)(OC_{1-4}$alkyl), or —$(CR_2)_{0-4}OP(O)(H)OH$, wherein $R^a$, independently for each occurrence, is H or $C_{1-4}$alkyl;

m is 1, 2, 3, or 4, particularly 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In further particular embodiments, the present disclosure provides a compound of formula I-f-4 or formula I-f-4*, wherein:

each $R^6$ is independently halogen, —$C_{1-4}$alkyl, —$C_{1-4}$haloalkyl, =$CH_2$, —$(CH_2)_{0-4}CO_2H$, —$(CH_2)_{0-4}CO_2C_{1-4}$alkyl, —$(CH_2)_{0-4}CO_2C_{1-4}$haloalkyl, —$(CH_2)_{0-4}CO$(N-proline), —$(CH_2)_{0-4}CO$(N-pyrrolidine-3-carboxylic acid), —$(CH_2)_{0-4}C(O)NR^a(CH_2)_{1-4}CO_2H$, —$(CH_2)_{0-4}C(O)NR^a$—CH($C_{1-4}$alkyl)-$CO_2H$, —OH, —$(CH_2)_{1-4}OH$, —$(CH_2)_{0-4}OC_{1-4}$alkyl, —$(CH_2)_{0-4}O(CH_2)_{1-5}CO_2H$, —$(CH_2)_{0-4}O(CH_2)_{1-5}CO_2C_{1-4}$alkyl, —$(CH_2)_{0-4}NR^aC(O)C_{1-4}$alkyl, —$(CH_2)_{0-4}NR^aC(O)Ph$, —$(CH_2)_{0-4}NR^aCO(CH_2)_{1-4}OH$, —$(CH_2)_{0-4}SO_3H$, —$(CH_2)_{0-4}SO_2NH_2$, —$(CH_2)_{0-4}NR^aSO_2C_{1-4}$alkyl, —$(CH_2)_{0-4}NR^aSO_2Ph$, —$(CH_2)_{0-4}NR^aSO_2(CH_2)_{1-4}CO_2H$, —$(CH_2)_{0-4}OP(OH)_2$, or —$(CR_2)_{0-4}OP(O)(H)OH$, wherein $R^a$, independently for each occurrence, is H or $C_{1-4}$alkyl;

m is 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In particular embodiments, the present disclosure provides a compound of formula I-f-4 or formula I-f-4*, wherein:

each $R^6$ is independently halogen, —$C_{1-4}$alkyl, —$C_{1-4}$haloalkyl, —$C_{3-6}$cycloalkyl, =$CH_2$, =O, —$(CH_2)_{0-4}CO_2H$, —$(CH_2)_{0-4}CO_2C_{1-4}$alkyl, —$(CH_2)_{0-4}CO_2C_{1-4}$haloalkyl, —$(CH_2)_{0-4}O(CH_2)_{1-5}CO_2H$, —$(CH_2)_{0-4}O(CH_2)_{1-5}CO_2C_{1-4}$alkyl, —$(CH_2)_{1-4}O(CH_2)_{1-4}CHFCO_2H$, —$(CH_2)_{1-4}O(CH_2)_{1-4}CHFCO_2C_{1-4}$alkyl, —$(CH_2)_{1-4}OCH(CH_3)(CH_2)_{1-4}CO_2H$, —$(CH_2)_{1-4}OCH(CH_3)(CH_2)_{1-4}CO_2C_{1-4}$alkyl, —$(CH_2)_{1-4}O(CH_2)_{1-4}CH(CH_3)CO_2H$, —$(CH_2)_{1-4}O(CH_2)_{1-4}CH(CH_3)CO_2C_{1-4}$alkyl, —CHOH$(CH_2)_{1-4}O(CH_2)_{1-5}CO_2H$, —CHOH$(CH_2)_{1-4}O(CH_2)_{1-5}CO_2C_{1-4}$alkyl, —$CHCF_3(CH_2)_{1-4}O(CH_2)_{1-5}CO_2H$, —$CHCF_3(CH_2)_{1-4}O$—$(CH_2)_{1-5}CO_2C_{1-4}$alkyl, —$(CH_2)_{1-4}O(CH_2)_{1-5}CONR^a_2$, —$(CH_2)_{1-4}O(CH_2)_{1-5}CONR^aOH$, —$(CH_2)_{1-4}O(CH_2)_{1-5}CONR^aCN$, —$(CH_2)_{1-4}O(CH_2)_{1-5}P(O)OH_2$, —$(CH_2)_{0-4}CONH_2$, —$(CH_2)_{0-4}CONHC_{1-4}$alkyl, —$(CH_2)_{0-4}CON(C_{1-4}$alkyl$)_2$, —$(CH_2)_{0-4}CO$(N-proline), —$(CH_2)_{0-4}CO$(N-pyrrolidine-3-carboxylic acid), —$(CH_2)_{0-4}$(N-pyrazole)-$(CH_2)_{0-4}CO_2H$, —$(CH_2)_{0-4}CO$(N-pyrazole)-$(CH_2)_{0-4}CO_2C_{1-4}$alkyl, —$(CH_2)_{0-4}$(N-pyrrole)-$(CH_2)_{0-4}CO_2H$, —$(CH_2)_{0-4}CO$(N-pyrrole)-$(CH_2)_{0-4}CO_2C_{1-4}$alkyl, —$(CH_2)_{0-4}$—O(phenyl)-$(CH_2)_{0-4}CO_2H$, —$(CH_2)_{0-4}$—O(phenyl)-$(CH_2)_{0-4}CO_2C_{1-4}$alkyl, —$(CH_2)_{0-4}$—O(cycloalkane)-$(CH_2)_{0-4}CO_2H$, —$(CH_2)_{0-4}$—O(cycloalkane)-$(CH_2)_{0-4}CO_2C_{1-4}$alkyl, —$(CH_2)_{0-4}C(O)NR^a(CH_2)_{1-4}CO_2H$, —$(CH_2)_{0-4}C(O)NR^a$—CH($C_{1-4}$alkyl)-$CO_2H$, —$(CH_2)_{0-4}C(O)NR^a(CH_2)_{1-4}CONH_2$, —$(CH_2)_{0-4}C(O)NR^a(CH_2)_{1-4}CONHC_{1-4}$alkyl, —$(CH_2)_{0-4}C(O)NR^a(CH_2)_{1-4}CON(C_{1-4}$alkyl$)_2$, —OH, —$(CH_2)_{1-4}OH$, —$(CH_2)_{0-4}OC_{1-4}$alkyl, —$(CH_2)_{0-4}OC(O)C_{1-4}$alkyl, —$NH_2$, —$(CH_2)_{0-4}NR^a(CH_2)_{1-4}CO_2H$, —$(CH_2)_{0-4}NR^a(CH_2)_{1-4}CO_2C_{1-4}$alkyl, —$(CH_2)_{1-4}NH_2$, —$(CH_2)_{0-4}NHC_{1-4}$alkyl, —$(CH_2)_{0-4}NR^aC(O)C_{1-4}$alkyl, —$(CH_2)_{0-4}NR^aC(O)Ph$, —$(CH_2)_{0-4}NR^aCO(CH_2)_{1-4}OH$, —$(CH_2)_{0-4}N(C_{1-4}$alkyl$)_2$, —$(CH_2)_{0-4}SO_3H$, —$(CH_2)_{0-4}SO_2NH_2$, —$(CH_2)_{0-4}SO_2NR^aC_{1-4}$alkyl, —$(CH_2)_{0-4}NR^aSO_2C_{1-4}$alkyl, —$(CH_2)_{0-4}NR^aSO_2Ph$, —$(CH_2)_{0-4}NR^aSO_2(CH_2)_{1-4}CO_2H$, —$(CH_2)_{0-4}OP(OH)_2$, —$(CH_2)_{0-4}OP(OH)(OC_{1-4}$alkyl), or —$(CR_2)_{0-4}OP(O)(H)OH$, wherein $R^a$, independently for each occurrence, is H or $C_{1-4}$alkyl;

m is 1, 2, 3, or 4, particularly 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In further particular embodiments, the present disclosure provides a compound of formula I-f-4 or formula I-f-4*, wherein:

each $R^6$ is independently halogen, —$C_{1-4}$alkyl, —$C_{1-4}$haloalkyl, —$C_{3-6}$cycloalkyl, =$CH_2$, —$(CH_2)_{0-4}CO_2H$, —$(CH_2)_{0-4}O(CH_2)_{1-5}CO_2H$, —(CH$_2$)$_{0-4}$O(CH$_2$)$_{1-5}$CO$_2$C$_{1-4}$alkyl, —(CH$_2$)$_{0-4}$CO(N-proline), —(CH$_2$)$_{0-4}$CO(N-pyrrolidine-3-carboxylic acid), —(CH$_2$)$_{0-4}$C(O)NR$^a$(CH$_2$)$_{1-4}$CO$_2$H, —(CH$_2$)$_{0-4}$C(O)NR$^a$—CH(C$_{1-4}$alkyl)-CO$_2$H, —OH, —(CH$_2$)$_{1-4}$OH, —(CH$_2$)$_{0-4}$OC$_{1-4}$alkyl, —(CH$_2$)$_{0-4}$OC(O)C$_{1-4}$alkyl, —(CH$_2$)$_{0-4}$NR$^a$C(O)C$_{1-4}$alkyl, —(CH$_2$)$_{0-4}$NR$^a$C(O)Ph, —(CH$_2$)$_{0-4}$NR$^a$CO(CH$_2$)$_{1-4}$OH, —(CH$_2$)$_{0-4}$SO$_3$H, —(CH$_2$)$_{0-4}$SO$_2$NH$_2$, —(CH$_2$)$_{0-4}$NR$^a$SO$_2$C$_{1-4}$alkyl, —(CH$_2$)$_{0-4}$NR$^a$SO$_2$Ph, —(CH$_2$)$_{0-4}$NR$^a$SO$_2$(CH$_2$)$_{1-4}$CO$_2$H, —(CH$_2$)$_{0-4}$OP(OH)$_2$, or —(CR$_2$)$_{0-4}$OP(O)(H)OH, wherein R$^a$, independently for each occurrence, is H or C$_{1-4}$alkyl;

m is 1 or 2; and each R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In further particular embodiments, the present disclosure provides a compound of formula I-f-4 or formula I-f-4*, wherein each R$^6$ is independently fluoro, -methyl, cyclohexyl, -methoxy, —OtBu, —CF$_3$, —(CH$_2$)$_{1-5}$CO$_2$H, —(CH$_2$)$_{1-5}$CO$_2$C$_{1-4}$alkyl, —(CH$_2$)$_{0-4}$O(CH$_2$)$_{1-5}$CO$_2$H, —(CH$_2$)$_{0-4}$O(CH$_2$)$_{1-5}$CO$_2$C$_{1-4}$alkyl, or —OH; and m is 1, 2, or 3, particularly 1 or 2.

In particular embodiments, the present disclosure provides a compound of formula I-f-4 or formula I-f-4*, wherein:

each R$^6$ is independently halogen, —C$_{1-4}$alkyl, —C$_{1-4}$haloalkyl, —C$_{3-6}$cycloalkyl, =CH$_2$, =O, —(CH$_2$)$_{0-4}$CO$_2$H, —(CH$_2$)$_{0-4}$CO$_2$C$_{1-4}$alkyl, —(CH$_2$)$_{0-4}$O(CH$_2$)$_{1-5}$CO$_2$H, —(CH$_2$)$_{0-4}$O(CH$_2$)$_{1-5}$CO$_2$C$_{1-4}$alkyl, —(CH$_2$)$_{0-4}$CONH$_2$, —(CH$_2$)$_{0-4}$CONHC$_{1-4}$alkyl, —(CH$_2$)$_{0-4}$CON(C$_{1-4}$alkyl)$_2$, —(CH$_2$)$_{0-4}$CO(N-proline), —(CH$_2$)$_{0-4}$CO(N-pyrrolidine-3-carboxylic acid), —(CH$_2$)$_{0-4}$C(O)NR$^a$(CH$_2$)$_{1-4}$CO$_2$H, —(CH$_2$)$_{0-4}$C(O)NR$^a$—CH(C$_{1-4}$alkyl)-CO$_2$H, —(CH$_2$)$_{0-4}$C(O)NR$^a$(CH$_2$)$_{1-4}$CONH$_2$, —(CH$_2$)$_{0-4}$C(O)NR$^a$(CH$_2$)$_{1-4}$CONHC$_{1-4}$alkyl, —(CH$_2$)$_{0-4}$C(O)NR$^a$(CH$_2$)$_{1-4}$CON(C$_{1-4}$alkyl)$_2$, —OH, —(CH$_2$)$_{1-4}$OH, —(CH$_2$)$_{0-4}$OC$_{1-4}$alkyl, —NH$_2$, —(CH$_2$)$_{1-4}$NH$_2$, —(CH$_2$)$_{0-4}$NHC$_{1-4}$alkyl, —(CH$_2$)$_{0-4}$NR$^a$C(O)C$_{1-4}$alkyl, —(CH$_2$)$_{0-4}$NR$^a$C(O)Ph, —(CH$_2$)$_{0-4}$NR$^a$CO(CH$_2$)$_{1-4}$OH, —(CH$_2$)$_{0-4}$N(C$_{1-4}$alkyl)$_2$, —(CH$_2$)$_{0-4}$SO$_3$H, —(CH$_2$)$_{0-4}$SO$_2$NH$_2$, —(CH$_2$)$_{0-4}$SO$_2$NR$^a$C$_{1-4}$alkyl, —(CH$_2$)$_{0-4}$NR$^a$SO$_2$C$_{1-4}$alkyl, —(CH$_2$)$_{0-4}$NR$^a$SO$_2$Ph, —(CH$_2$)$_{0-4}$NR$^a$SO$_2$(CH$_2$)$_{1-4}$CO$_2$H, —(CH$_2$)$_{0-4}$OP(OH)$_2$, —(CH$_2$)$_{0-4}$OP(OH)(OC$_{1-4}$alkyl), or —(CR$_2$)$_{0-4}$OP(O)(H)OH, wherein R$^a$, independently for each occurrence, is H or C$_{1-4}$alkyl;

m is 1, 2, 3, or 4, particularly 1 or 2; and each R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In further particular embodiments, the present disclosure provides a compound of formula I-f-4 or formula I-f-4*, wherein:

each R$^6$ is independently halogen, —C$_{1-4}$alkyl, —C$_{1-4}$haloalkyl, —C$_{3-6}$cycloalkyl, =CH$_2$, —(CH$_2$)$_{0-4}$CO$_2$H, —(CH$_2$)$_{1-4}$O(CH$_2$)$_{1-5}$CO$_2$H, —(CH$_2$)$_{1-4}$O(CH$_2$)$_{1-5}$CO$_2$C$_{1-4}$alkyl, —(CH$_2$)$_{0-4}$CO(N-proline), —(CH$_2$)$_{0-4}$CO(N-pyrrolidine-3-carboxylic acid), —(CH$_2$)$_{0-4}$C(O)NR$^a$(CH$_2$)$_{1-4}$CO$_2$H, —(CH$_2$)$_{0-4}$C(O)NR$^a$—CH(C$_{1-4}$alkyl)-CO$_2$H, —OH, —(CH$_2$)$_{1-4}$OH, —(CH$_2$)$_{0-4}$OC$_{1-4}$alkyl, —(CH$_2$)$_{0-4}$NR$^a$C(O)C$_{1-4}$alkyl, —(CH$_2$)$_{0-4}$NR$^a$C(O)Ph, —(CH$_2$)$_{0-4}$NR$^a$CO(CH$_2$)$_{1-4}$OH, —(CH$_2$)$_{0-4}$SO$_3$H, —(CH$_2$)$_{0-4}$SO$_2$NH$_2$, —(CH$_2$)$_{0-4}$NR$^a$SO$_2$C$_{1-4}$alkyl, —(CH$_2$)$_{0-4}$NR$^a$SO$_2$Ph, —(CH$_2$)$_{0-4}$NR$^a$SO$_2$(CH$_2$)$_{1-4}$CO$_2$H, —(CH$_2$)$_{0-4}$OP(OH)$_2$, or —(CR$_2$)$_{0-4}$OP(O)(H)OH, wherein R$^a$, independently for each occurrence, is H or C$_{1-4}$alkyl;

m is 1 or 2; and each R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In certain embodiments, the present disclosure provides a compound of formula I-f-4 or formula I-f-4*, wherein:

each R$^6$ is independently halogen, =O, —COR, —(CR$_2$)$_{0-6}$CO$_2$R, —(CR$_2$)$_{0-6}$CONR$_2$, —OR, —(CR$_2$)$_{1-4}$OR, —NR$_2$, —(CR$_2$)$_{1-4}$NR$_2$, —NRC(O)OR, —NRC(O)R, —NRC(O)NR$_2$, —SR, —SO$_2$R, —S(O)R, —(CR$_2$)$_{0-6}$SO$_3$R, —(CR$_2$)$_{0-6}$SO$_2$NR$_2$, —(CR$_2$)$_{0-6}$OSO$_2$NR$_2$, —(CR$_2$)$_{0-6}$NRSO$_2$R, —(CR$_2$)$_{0-6}$NRSO$_2$OR, —(CR$_2$)$_{0-6}$OP(OR)$_2$, —(CR$_2$)$_{0-6}$OP(O)(OR)$_2$, —(CR$_2$)$_{0-6}$P(O)(OR)$_2$, —(CR$_2$)$_{0-6}$OP(O)(H)OR, or —B(OR)$_2$;

m is 1, 2, 3, or 4, particularly 1 or 2; and each R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In particular embodiments, the present disclosure provides a compound of formula I-f-4 or formula I-f-4*, wherein:

each R$^6$ is independently halogen, =O, —(CH$_2$)$_{0-4}$CO$_2$H, —(CH$_2$)$_{0-4}$CO$_2$C$_{1-4}$alkyl, —(CH$_2$)$_{0-4}$CONH$_2$, —(CH$_2$)$_{0-4}$CONHC$_{1-4}$alkyl, —(CH$_2$)$_{0-4}$CON(C$_{1-4}$alkyl)$_2$, —(CH$_2$)$_{0-4}$CO(N-proline), —(CH$_2$)$_{0-4}$CO(N-pyrrolidine-3-carboxylic acid), —(CH$_2$)$_{0-4}$C(O)NR$^a$(CH$_2$)$_{1-4}$CO$_2$H, —(CH$_2$)$_{0-4}$C(O)NR$^a$—CH(C$_{1-4}$alkyl)-CO$_2$H, —(CH$_2$)$_{0-4}$C(O)NR$^a$(CH$_2$)$_{1-4}$CONH$_2$, —(CH$_2$)$_{0-4}$C(O)NR$^a$(CH$_2$)$_{1-4}$CONHC$_{1-4}$alkyl, —(CH$_2$)$_{0-4}$C(O)NR$^a$(CH$_2$)$_{1-4}$CON(C$_{1-4}$alkyl)$_2$, —OH, —(CH$_2$)$_{1-4}$OH, —(CH$_2$)$_{0-4}$OC$_{1-4}$alkyl, —NH$_2$, —(CH$_2$)$_{1-4}$NH$_2$, —(CH$_2$)$_{0-4}$NHC$_{1-4}$alkyl, —(CH$_2$)$_{0-4}$NR$^a$C(O)C$_{1-4}$alkyl, —(CH$_2$)$_{0-4}$NR$^a$C(O)Ph, —(CH$_2$)$_{0-4}$NR$^a$CO(CH$_2$)$_{1-4}$OH, —(CH$_2$)$_{0-4}$N(C$_{1-4}$alkyl)$_2$, —(CH$_2$)$_{0-4}$SO$_3$H, —(CH$_2$)$_{0-4}$SO$_2$NH$_2$, —(CH$_2$)$_{0-4}$SO$_2$NR$^a$C$_{1-4}$alkyl, —(CH$_2$)$_{0-4}$NR$^a$SO$_2$C$_{1-4}$alkyl, —(CH$_2$)$_{0-4}$NR$^a$SO$_2$Ph, —(CH$_2$)$_{0-4}$NR$^a$SO$_2$(CH$_2$)$_{1-4}$CO$_2$H, —(CH$_2$)$_{0-4}$OP(OH)$_2$, —(CH$_2$)$_{0-4}$OP(OH)(OC$_{1-4}$alkyl), or —(CR$_2$)$_{0-4}$OP(O)(H)OH, wherein R$^a$, independently for each occurrence, is H or C$_{1-4}$alkyl;

m is 1, 2, 3, or 4, particularly 1 or 2; and each R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In further particular embodiments, the present disclosure provides a compound of formula I-f-4 or formula I-f-4*, wherein:

each R$^6$ is independently halogen, —(CH$_2$)$_{0-4}$CO$_2$H, —(CH$_2$)$_{0-4}$CO(N-proline), —(CH$_2$)$_{0-4}$CO(N-pyrrolidine-3-carboxylic acid), —(CH$_2$)$_{0-4}$C(O)NR$^a$(CH$_2$)$_{1-4}$CO$_2$H, —(CH$_2$)$_{0-4}$C(O)NR$^a$—CH(C$_{1-4}$alkyl)-CO$_2$H, —OH, —(CH$_2$)$_{1-4}$OH, —(CH$_2$)$_{0-4}$NR$^a$C(O)C$_{1-4}$alkyl, —(CH$_2$)$_{0-4}$NR$^a$C(O)Ph, —(CH$_2$)$_{0-4}$NR$^a$CO(CH$_2$)$_{1-4}$OH, —(CH$_2$)$_{0-4}$SO$_3$H, —(CH$_2$)$_{0-4}$SO$_2$NH$_2$, —(CH$_2$)$_{0-4}$NR$^a$SO$_2$C$_{1-4}$alkyl, —(CH$_2$)$_{0-4}$NR$^a$SO$_2$Ph, —(CH$_2$)$_{0-4}$NR$^a$SO$_2$(CH$_2$)$_{1-4}$CO$_2$H, —(CH$_2$)$_{0-4}$OP(OH)$_2$, or —(CR$_2$)$_{0-4}$OP(O)(H)OH, wherein R$^a$, independently for each occurrence, is H or C$_{1-4}$alkyl;

m is 1 or 2; and each R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In particular embodiments, the present disclosure provides a compound of formula I-f-4 or formula I-f-4*, wherein, m is 1;

R$^6$ is —(CH$_2$)$_{0-4}$O(CH$_2$)$_{1-5}$CO$_2$H, such as —(CH$_2$)$_{1-2}$O(CH$_2$)$_{2-3}$CO$_2$H, including —CH$_2$O(CH$_2$)$_2$CO$_2$H; and each R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In certain embodiments, for the above disclosed compounds of formula I-f-4 or formula I-f-4*, m is 1 or 2, and at least one R$^6$ includes a terminal —CO$_2$H group. For example, in certain instances, at least one R$^6$ is —(CH$_2$)$_{0-4}$CO$_2$H or —(CH$_2$)$_{0-4}$O(CH$_2$)$_{1-5}$CO$_2$H.

In some embodiments, the present disclosure provides a compound of formula I, wherein Ring A is

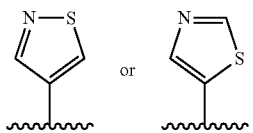

and R$^2$ is

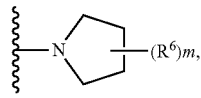

thereby forming a compound of formula I-f-5 or I-f-5*, respectively:

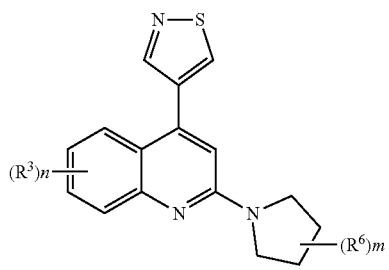

I-f-5

I-f-5*

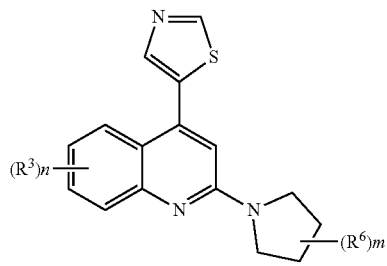

or a pharmaceutically acceptable salt thereof, wherein:

each R$^6$ is independently halogen, =O, —COR, —(CR$_2$)$_{0-6}$CO$_2$R, —(CR$_2$)$_{0-6}$CONR$_2$, —OR, —(CR$_2$)$_{1-4}$OR, —NR$_2$, —(CR$_2$)$_{1-4}$NR$_2$, —NRC(O)OR, —NRC(O)R, —NRC(O)NR$_2$, —SR, —SO$_2$R, —S(O)R, —(CR$_2$)$_{0-6}$SO$_3$R, —(CR$_2$)$_{0-6}$SO$_2$NR$_2$, —(CR$_2$)$_{0-6}$OSO$_2$NR$_2$, —(CR$_2$)$_{0-6}$NRSO$_2$R, —(CR$_2$)$_{0-6}$NRSO$_2$OR, —(CR$_2$)$_{0-6}$OP(OR)$_2$, —(CR$_2$)$_{0-6}$OP(O)(OR)$_2$, —(CR$_2$)$_{0-6}$P(O)(OR)$_2$, —(CR$_2$)$_{0-6}$OP(O)(H)OR, —B(OR)$_2$, or R$^B$;

m is 0, 1, 2, 3, or 4, particularly 1, 2, 3, or 4; and each of R, R$^3$, R$^B$, and n is as defined above and described in embodiments herein, both singly and in combination.

In some embodiments, the present disclosure provides a compound of formula I-f-S or formula I-f-5*, wherein R$^6$ is not R$^B$.

In certain embodiments, the present disclosure provides a compound of formula I-f-S or formula I-f-5*, wherein R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In certain embodiments, the present disclosure provides a compound of formula I-f-S or formula I-f-5*, wherein:

each R$^6$ is independently halogen, —C$_{1-4}$alkyl, —C$_{1-4}$haloalkyl, =CR$_2$, =O, —COR, —(CR$_2$)$_{0-6}$CO$_2$R, —(CR$_2$)$_{0-6}$CONR$_2$, —OR, —(CR$_2$)$_{1-4}$OR, —NR$_2$, —(CR$_2$)$_{1-4}$NR$_2$, —NRC(O)OR, —NRC(O)R, —NRC(O)NR$_2$, —SR, —SO$_2$R, —S(O)R, —(CR$_2$)$_{0-6}$SO$_3$R, —(CR$_2$)$_{0-6}$SO$_2$NR$_2$, —(CR$_2$)$_{0-6}$OSO$_2$NR$_2$, —(CR$_2$)$_{0-6}$NRSO$_2$R, —(CR$_2$)$_{0-6}$NRSO$_2$OR, —(CR$_2$)$_{0-6}$OP(OR)$_2$, —(CR$_2$)$_{0-6}$OP(O)(OR)$_2$, —(CR$_2$)$_{0-6}$P(O)(OR)$_2$, —(CR$_2$)$_{0-6}$OP(O)(H)OR, or —B(OR)$_2$;

m is 1, 2, 3, or 4, particularly 1 or 2; and each R$^3$ is independently optionally substituted C$_{1-6}$ aliphatic, such as methyl, or halogen, such as bromo and/or chloro, including dichloro, including wherein n is 2 and R$^3$ is chloro at the 7- and 8-positions with respect to the quinoline ring.

In particular embodiments, the present disclosure provides a compound of formula I-f-S or formula I-f-5*, wherein:

each R$^6$ is independently halogen, —C$_{1-4}$alkyl, —C$_{1-4}$haloalkyl, =CH$_2$, =O, —(CH$_2$)$_{0-4}$CO$_2$H, —(CH$_2$)$_{0-4}$CO$_2$C$_{1-4}$alkyl, —(CH$_2$)$_{0-4}$CO$_2$C$_{1-4}$haloalkyl, —(CH$_2$)$_{0-4}$CONH$_2$, —(CH$_2$)$_{0-4}$CONHC$_{1-4}$alkyl, —(CH$_2$)$_{0-4}$CON(C$_{1-4}$alkyl)$_2$, —(CH$_2$)$_{0-4}$CO(N-proline), —(CH$_2$)$_{0-4}$CO(N-pyrrolidine-3-carboxylic acid), —(CH$_2$)$_{0-4}$(N-pyrazole)-(CH$_2$)$_{0-4}$CO$_2$H, —(CH$_2$)$_{0-4}$CO(N-pyrazole)-(CH$_2$)$_{0-4}$CO$_2$C$_{1-4}$alkyl, —(CH$_2$)$_{0-4}$(N-pyrrole)-(CH$_2$)$_{0-4}$CO$_2$H, —(CH$_2$)$_{0-4}$CO(N-pyrrole)-$(CH_2)_{0-4}CO_2C_{1-4}$alkyl, —$(CH_2)_{0-4}$—O(phenyl)-$(CH_2)_{0-4}CO_2H$, —$(CH_2)_{0-4}$—O(phenyl)-$(CH_2)_{0-4}CO_2C_{1-4}$alkyl, —$(CH_2)_{0-4}$—O(cycloalkane)-$(CH_2)_{0-4}CO_2H$, —$(CH_2)_{0-4}$—O(cycloalkane)-$(CH_2)_{0-4}CO_2C_{1-4}$alkyl, —$(CH_2)_{0-4}C(O)NR^a(CH_2)_{1-4}$ $CO_2H$, —$(CH_2)_{0-4}C(O)NR^a$—CH$(C_{1-4}$alkyl)-$CO_2H$, —$(CH_2)_{0-4}C(O)NR^a(CH_2)_{1-4}CONH_2$, —$(CH_2)_{0-4}C(O)$ $NR^a(CH_2)_{1-4}CONHC_{1-4}$alkyl, —$(CH_2)_{0-4}C(O)NR^a$ $(CH_2)_{1-4}CON(C_{1-4}$alkyl$)_2$, —OH, —$(CH_2)_{1-4}$OH, —$(CH_2)_{0-4}OC_{1-4}$alkyl, —$(CH_2)_{0-4}O(CH_2)_{1-5}CO_2H$, —$(CH_2)_{0-4}O(CH_2)_{1-5}CO_2C_{1-4}$alkyl, —$(CH_2)_{1-4}O$ $(CH_2)_{1-4}CHFCO_2H$, —$(CH_2)_{1-4}O(CH_2)_{1-4}$ $CHFCO_2C_{1-4}$alkyl, —$(CH_2)_{1-4}OCH(CH_3)(CH_2)_{1-4}$ $CO_2H$, —$(CH_2)_{1-4}OCH(CH_3)(CH_2)_{1-4}CO_2C_{1-4}$alkyl, —$(CH_2)_{1-4}O(CH_2)_{1-4}CH(CH_3)CO_2H$, —$(CH_2)_{1-4}O$ $(CH_2)_{1-4}CH(CH_3)CO_2C_{1-4}$alkyl, —CHOH$(CH_2)_{1-4}O$ $(CH_2)_{1-5}CO_2H$, —CHOH$(CH_2)_{1-4}O(CH_2)_{1-5}$ $CO_2C_{1-4}$alkyl, —CHCF$_3(CH_2)_{1-4}O(CH_2)_{1-5}CO_2H$, —CHCF$_3(CH_2)_{1-4}O$—$(CH_2)_{1-5}CO_2C_{1-4}$alkyl, —$(CH_2)_{1-4}O(CH_2)_{1-5}CONR^a{}_2$, —$(CH_2)_{1-4}$ $O(CH_2)_{1-5}CONR^aOH$, —$(CH_2)_{1-4}O(CH_2)_{1-5}CON$-$R^aCN$, —$(CH_2)_{1-4}O(CH_2)_{1-5}P(O)OH_2$, —$NH_2$, —$(CH_2)_{0-4}NR^a(CH_2)_{1-4}CO_2H$, —$(CH_2)_{0-4}NR^a$ $(CH_2)_{1-4}CO_2C_{1-4}$alkyl, —$(CH_2)_{1-4}NH_2$, —$(CH_2)_{0-4}$ $NHC_{1-4}$alkyl, —$(CH_2)_{0-4}NR^aC(O)C_{1-4}$alkyl, —$(CH_2)_{0-4}NR^aC(O)Ph$, —$(CH_2)_{0-4}NR^aCO(CH_2)_{1-4}$ OH, —$(CH_2)_{0-4}N(C_{1-4}$alkyl$)_2$, —$(CH_2)_{0-4}SO_3H$, —$(CH_2)_{0-4}SO_2NH_2$, —$(CH_2)_{0-4}SO_2NR^aC_{1-4}$alkyl, —$(CH_2)_{0-4}NR^aSO_2C_{1-4}$alkyl, —$(CH_2)_{0-4}NR^aSO_2Ph$, —$(CH_2)_{0-4}NR^aSO_2(CH_2)_{1-4}CO_2H$, —$(CH_2)_{0-4}OP$ $(OH)_2$, —$(CH_2)_{0-4}OP(OH)(OC_{1-4}$alkyl$)$, or —$(CR_2)_{0-4}OP(O)(H)OH$, wherein $R^a$, independently for each occurrence, is H or $C_{1-4}$alkyl;

m is 1, 2, 3, or 4, particularly 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In further particular embodiments, the present disclosure provides a compound of formula I-f-5 or formula I-f-5*, wherein:

each $R^6$ is independently halogen, —$C_{1-4}$alkyl, —$C_{1-4}$haloalkyl, =$CH_2$, —$(CH_2)_{0-4}CO_2H$, —$(CH_2)_{0-4}CO_2C_{1-4}$alkyl, —$(CH_2)_{0-4}CO_2C_{1-4}$haloalkyl, —$(CH_2)_{0-4}CO(N$-proline$)$, —$(CH_2)_{0-4}CO(N$-pyrrolidine-3-carboxylic acid$)$, —$(CH_2)_{0-4}C(O)NR^a$ $(CH_2)_{1-4}CO_2H$, —$(CH_2)_{0-4}C(O)NR^a$—CH$(C_{1-4}$alkyl$)$-$CO_2H$, —OH, —$(CH_2)_{1-4}OH$, —$(CH_2)_{0-4}OC_{1-4}$alkyl, —$(CH_2)_{0-4}O(CH_2)_{1-5}CO_2H$, —$(CH_2)_{0-4}O(CH_2)_{1-5}$ $CO_2C_{1-4}$alkyl, —$(CH_2)_{0-4}NR^aC(O)C_{1-4}$alkyl, —$(CH_2)_{0-4}NR^aC(O)Ph$, —$(CH_2)_{0-4}NR^aCO(CH_2)_{1-4}$ OH, —$(CH_2)_{0-4}SO_3H$, —$(CH_2)_{0-4}SO_2NH_2$, —$(CH_2)_{0-4}NR^aSO_2C_{1-4}$alkyl, —$(CH_2)_{0-4}NR^aSO_2Ph$, —$(CH_2)_{0-4}NR^aSO_2(CH_2)_{1-4}CO_2H$, —$(CH_2)_{0-4}OP$ $(OH)_2$, or —$(CR_2)_{0-4}OP(O)(H)OH$, wherein $R^a$, independently for each occurrence, is H or $C_{1-4}$alkyl;

m is 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In particular embodiments, the present disclosure provides a compound of formula I-f-5 or formula I-f-5*, wherein:

each $R^6$ is independently halogen, —$C_{1-4}$alkyl, —$C_{1-4}$haloalkyl, —$C_{3-6}$cycloalkyl, =$CH_2$, =O, —$(CH_2)_{0-4}CO_2H$, —$(CH_2)_{0-4}CO_2C_{1-4}$alkyl, —$(CH_2)_{0-4}CO_2C_{1-4}$haloalkyl, —$(CH_2)_{0-4}O(CH_2)_{1-5}$ $CO_2H$, —$(CH_2)_{0-4}O(CH_2)_{1-5}CO_2C_{1-4}$alkyl, —$(CH_2)_{1-4}O(CH_2)_{1-4}CHFCO_2H$, —$(CH_2)_{1-4}$ $O(CH_2)_{1-4}CHFCO_2C_{1-4}$alkyl, —$(CH_2)_{1-4}OCH(CH_3)$ $(CH_2)_{1-4}CO_2H$, —$(CH_2)_{1-4}OCH(CH_3)(CH_2)_{1-4}$ $CO_2C_{1-4}$alkyl, —$(CH_2)_{1-4}O(CH_2)_{1-4}CH(CH_3)CO_2H$, —$(CH_2)_{1-4}O(CH_2)_{1-4}CH(CH_3)CO_2C_{1-4}$alkyl, —CHOH$(CH_2)_{1-4}O(CH_2)_{1-5}CO_2H$, —CHOH $(CH_2)_{1-4}O(CH_2)_{1-5}CO_2C_{1-4}$alkyl, —CHCF$_3(CH_2)_{1-4}O$ $(CH_2)_{1-5}CO_2H$, —CHCF$_3(CH_2)_{1-4}O$—$(CH_2)_{1-5}$ $CO_2C_{1-4}$alkyl, —$(CH_2)_{1-4}O(CH_2)_{1-5}CONR^a{}_2$, —$(CH_2)_{1-4}O(CH_2)_{1-5}CONR^aOH$, —$(CH_2)_{1-4}$ $O(CH_2)_{1-5}CONR^aCN$, —$(CH_2)_{1-4}O(CH_2)_{1-5}P(O)OH_2$, —$(CH_2)_{0-4}CONH_2$, —$(CH_2)_{0-4}CONHC_{1-4}$alkyl, —$(CH_2)_{0-4}CON(C_{1-4}$alkyl$)_2$, —$(CH_2)_{0-4}CO(N$-proline$)$, —$(CH_2)_{0-4}CO(N$-pyrrolidine-3-carboxylic acid$)$, —$(CH_2)_{0-4}(N$-pyrazole$)$-$(CH_2)_{0-4}CO_2H$, —$(CH_2)_{0-4}$ $CO(N$-pyrazole$)$-$(CH_2)_{0-4}CO_2C_{1-4}$alkyl, —$(CH_2)_{0-4}$ $(N$-pyrrole$)$-$(CH_2)_{0-4}CO_2H$, —$(CH_2)_{0-4}CO(N$-pyrrole$)$-$(CH_2)_{0-4}CO_2C_{1-4}$alkyl, —$(CH_2)_{0-4}$—O(phenyl)-$(CH_2)_{0-4}CO_2H$, —$(CH_2)_{0-4}$—O(phenyl)-$(CH_2)_{0-4}$ $CO_2C_{1-4}$alkyl, —$(CH_2)_{0-4}$—O(cycloalkane)-$(CH_2)_{0-4}$ $CO_2H$, —$(CH_2)_{0-4}$—O(cycloalkane)-$(CH_2)_{0-4}$ $CO_2C_{1-4}$alkyl, —$(CH_2)_{0-4}C(O)NR^a(CH_2)_{1-4}CO_2H$, —$(CH_2)_{0-4}C(O)NR^a$—CH$(C_{1-4}$alkyl$)$-$CO_2H$, —$(CH_2)_{0-4}C(O)NR^a(CH_2)_{1-4}CONH_2$, —$(CH_2)_{0-4}C(O)$ $NR^a(CH_2)_{1-4}CONHC_{1-4}$alkyl, —$(CH_2)_{0-4}C(O)NR^a$ $(CH_2)_{1-4}CON(C_{1-4}$alkyl$)_2$, —OH, —$(CH_2)_{1-4}OH$, —$(CH_2)_{0-4}OC_{1-4}$alkyl, —$(CH_2)_{0-4}OC(O)C_{1-4}$alkyl, —$NH_2$, —$(CH_2)_{0-4}NR^a(CH_2)_{1-4}CO_2H$, —$(CH_2)_{0-4}NR^a(CH_2)_{1-4}CO_2C_{1-4}$alkyl, —$(CH_2)_{1-4}$ $NH_2$, —$(CH_2)_{0-4}NHC_{1-4}$alkyl, —$(CH_2)_{0-4}NR^a$ $C(O)C_{1-4}$alkyl, —$(CH_2)_{0-4}NR^aC(O)Ph$, —$(CH_2)_{0-4}NR^aCO(CH_2)_{1-4}OH$, —$(CH_2)_{0-4}N(C_{1-4}$alkyl$)_2$, —$(CH_2)_{0-4}SO_3H$, —$(CH_2)_{0-4}SO_2NH_2$, —$(CH_2)_{0-4}SO_2NR^aC_{1-4}$alkyl, —$(CH_2)_{0-4}NR^aS$ $O_2C_{1-4}$alkyl, —$(CH_2)_{0-4}NR^aSO_2Ph$, —$(CH_2)_{0-4}$ $NR^aSO_2(CH_2)_{1-4}CO_2H$, —$(CH_2)_{0-4}OP(OH)_2$, —$(CH_2)_{0-4}OP(OH)(OC_{1-4}$alkyl$)$, or —$(CR_2)_{0-4}OP(O)$ $(H)OH$, wherein $R^a$, independently for each occurrence, is H or $C_{1-4}$alkyl;

m is 1, 2, 3, or 4, particularly 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In further particular embodiments, the present disclosure provides a compound of formula I-f-5 or formula I-f-5*, wherein:

each $R^6$ is independently halogen, —$C_{1-4}$alkyl, —$C_{1-4}$haloalkyl, —$C_{3-6}$cycloalkyl, =$CH_2$, —$(CH_2)_{0-4}CO_2H$, —$(CH_2)_{0-4}O(CH_2)_{1-5}CO_2H$, —$(CH_2)_{0-4}O(CH_2)_{1-5}CO_2C_{1-4}$alkyl, —$(CH_2)_{0-4}CO(N$-proline$)$, —$(CH_2)_{0-4}CO(N$-pyrrolidine-3-carboxylic acid$)$, —$(CH_2)_{0-4}C(O)NR^a(CH_2)_{1-4}CO_2H$, —$(CH_2)_{0-4}C(O)NR^a$—CH$(C_{1-4}$alkyl$)$-$CO_2H$, —OH, —$(CH_2)_{1-4}OH$, —$(CH_2)_{0-4}OC_{1-4}$alkyl, —$(CH_2)_{0-4}OC$ $(O)C_{1-4}$alkyl, —$(CH_2)_{0-4}NR^aC(O)C_{1-4}$alkyl, —$(CH_2)_{0-4}NR^aC(O)Ph$, —$(CH_2)_{0-4}NR^aCO(CH_2)_{1-4}$ OH, —$(CH_2)_{0-4}SO_3H$, —$(CH_2)_{0-4}SO_2NH_2$, —$(CH_2)_{0-4}NR^aSO_2C_{1-4}$alkyl, —$(CH_2)_{0-4}NR^aSO_2Ph$, —$(CH_2)_{0-4}NR^aSO_2(CH_2)_{1-4}CO_2H$, —$(CH_2)_{0-4}OP$ $(OH)_2$, or —$(CR_2)_{0-4}OP(O)(H)OH$, wherein $R^a$, independently for each occurrence, is H or $C_{1-4}$alkyl;

m is 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In further particular embodiments, the present disclosure provides a compound of formula I-f-5 or formula I-f-5*, wherein each $R^6$ is independently fluoro, -methyl, cyclohexyl, -methoxy, —OtBu, —CF$_3$, —(CH$_2$)$_{1-5}$CO$_2$H, —(CH$_2$)$_{1-5}$CO$_2$C$_{1-4}$alkyl, —(CH$_2$)$_{0-4}$O(CH$_2$)$_{1-5}$CO$_2$H, —(CH$_2$)$_{0-4}$O(CH$_2$)$_{1-5}$CO$_2$C$_{1-4}$alkyl, or —OH; and m is 1, 2, or 3, particularly 1 or 2.

In particular embodiments, the present disclosure provides a compound of formula I-f-5 or I-f-5*, wherein:

each $R^6$ is independently halogen, —C$_{1-4}$alkyl, —C$_{1-4}$haloalkyl, —C$_{3-6}$cycloalkyl, =CH$_2$, =O, —(CH$_2$)$_{0-4}$CO$_2$H, —(CH$_2$)$_{0-4}$CO$_2$C$_{1-4}$alkyl, —(CH$_2$)$_{0-4}$O(CH$_2$)$_{1-5}$CO$_2$H, —(CH$_2$)$_{0-4}$O(CH$_2$)$_{1-5}$CO$_2$C$_{1-4}$alkyl, —(CH$_2$)$_{0-4}$CONH$_2$, —(CH$_2$)$_{0-4}$CONHC$_{1-4}$alkyl, —(CH$_2$)$_{0-4}$CON(C$_{1-4}$alkyl)$_2$, —(CH$_2$)$_{0-4}$CO(N-proline), —(CH$_2$)$_{0-4}$CO(N-pyrrolidine-3-carboxylic acid), —(CH$_2$)$_{0-4}$C(O)NR$^a$(CH$_2$)$_{1-4}$CO$_2$H, —(CH$_2$)$_{0-4}$C(O)NR$^a$—CH(C$_{1-4}$alkyl)-CO$_2$H, —(CH$_2$)$_{0-4}$C(O)NR$^a$(CH$_2$)$_{1-4}$CONH$_2$, —(CH$_2$)$_{0-4}$C(O)NR$^a$(CH$_2$)$_{1-4}$CONHC$_{1-4}$alkyl, —(CH$_2$)$_{0-4}$C(O)NR$^a$(CH$_2$)$_{1-4}$CON(C$_{1-4}$alkyl)$_2$, —OH, —(CH$_2$)$_{1-4}$OH, —(CH$_2$)$_{0-4}$OC$_{1-4}$alkyl, —NH$_2$, —(CH$_2$)$_{1-4}$NH$_2$, —(CH$_2$)$_{0-4}$NHC$_{1-4}$alkyl, —(CH$_2$)$_{0-4}$NR$^a$C(O)C$_{1-4}$alkyl, —(CH$_2$)$_{0-4}$NR$^a$C(O)Ph, —(CH$_2$)$_{0-4}$NR$^a$CO(CH$_2$)$_{1-4}$OH, —(CH$_2$)$_{0-4}$N(C$_{1-4}$alkyl)$_2$, —(CH$_2$)$_{0-4}$SO$_3$H, —(CH$_2$)$_{0-4}$SO$_2$NH$_2$, —(CH$_2$)$_{0-4}$SO$_2$NR$^a$C$_{1-4}$alkyl, —(CH$_2$)$_{0-4}$NR$^a$SO$_2$C$_{1-4}$alkyl, —(CH$_2$)$_{0-4}$NR$^a$SO$_2$Ph, —(CH$_2$)$_{0-4}$NR$^a$SO$_2$(CH$_2$)$_{1-4}$CO$_2$H, —(CH$_2$)$_{0-4}$OP(OH)$_2$, —(CH$_2$)$_{0-4}$OP(OH)(OC$_{1-4}$alkyl), or —(CR$_2$)$_{0-4}$OP(O)(H)OH, wherein $R^a$, independently for each occurrence, is H or C$_{1-4}$alkyl;

m is 1, 2, 3, or 4, particularly 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In further particular embodiments, the present disclosure provides a compound of formula I-f-5 or formula I-f-5*, wherein:

each $R^6$ is independently halogen, —C$_{1-4}$alkyl, —C$_{1-4}$haloalkyl, —C$_{3-6}$cycloalkyl, =CH$_2$, —(CH$_2$)$_{0-4}$CO$_2$H, —(CH$_2$)$_{1-4}$O(CH$_2$)$_{1-5}$CO$_2$H, —(CH$_2$)$_{1-4}$O(CH$_2$)$_{1-5}$CO$_2$C$_{1-4}$alkyl, —(CH$_2$)$_{0-4}$CO(N-proline), —(CH$_2$)$_{0-4}$CO(N-pyrrolidine-3-carboxylic acid), —(CH$_2$)$_{0-4}$C(O)NR$^a$(CH$_2$)$_{1-4}$CO$_2$H, —(CH$_2$)$_{0-4}$C(O)NR$^a$—CH(C$_{1-4}$alkyl)-CO$_2$H, —OH, —(CH$_2$)$_{1-4}$OH, —(CH$_2$)$_{0-4}$OC$_{1-4}$alkyl, —(CH$_2$)$_{0-4}$NR$^a$C(O)C$_{1-4}$alkyl, —(CH$_2$)$_{0-4}$NR$^a$C(O)Ph, —(CH$_2$)$_{0-4}$NR$^a$CO(CH$_2$)$_{1-4}$OH, —(CH$_2$)$_{0-4}$SO$_3$H, —(CH$_2$)$_{0-4}$SO$_2$NH$_2$, —(CH$_2$)$_{0-4}$NR$^a$SO$_2$C$_{1-4}$alkyl, —(CH$_2$)$_{0-4}$NR$^a$SO$_2$Ph, —(CH$_2$)$_{0-4}$NR$^a$SO$_2$(CH$_2$)$_{1-4}$CO$_2$H, —(CH$_2$)$_{0-4}$OP(OH)$_2$, or —(CR$_2$)$_{0-4}$OP(O)(H)OH, wherein $R^a$, independently for each occurrence, is H or C$_{1-4}$alkyl;

m is 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In certain embodiments, the present disclosure provides a compound of formula I-f-S or formula I-f-5*, wherein:

each $R^6$ is independently halogen, =O, —COR, —(CR$_2$)$_{0-6}$CO$_2$R, —(CR$_2$)$_{0-6}$CONR$_2$, —OR, —(CR$_2$)$_{1-4}$OR, —NR$_2$, —(CR$_2$)$_{1-4}$NR$_2$, —NRC(O)OR, —NRC(O)R, —NRC(O)NR$_2$, —SR, —SO$_2$R, —S(O)R, —(CR$_2$)$_{0-6}$SO$_3$R, —(CR$_2$)$_{0-6}$SO$_2$NR$_2$, —(CR$_2$)$_{0-6}$OSO$_2$NR$_2$, —(CR$_2$)$_{0-6}$NRSO$_2$R, —(CR$_2$)$_{0-6}$NRSO$_2$OR, —(CR$_2$)$_{0-6}$OP(OR)$_2$, —(CR$_2$)$_{0-6}$OP(O)(OR)$_2$, —(CR$_2$)$_{0-6}$P(O)(OR)$_2$, —(CR$_2$)$_{0-6}$OP(O)(H)OR, or —B(OR)$_2$;

m is 1, 2, 3, or 4, particularly 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In particular embodiments, the present disclosure provides a compound of formula I-f-5 or formula I-f-5*, wherein:

each $R^6$ is independently halogen, =O, —(CH$_2$)$_{0-4}$CO$_2$H, —(CH$_2$)$_{0-4}$CO$_2$C$_{1-4}$alkyl, —(CH$_2$)$_{0-4}$CONH$_2$, —(CH$_2$)$_{0-4}$CONHC$_{1-4}$alkyl, —(CH$_2$)$_{0-4}$CON(C$_{1-4}$alkyl)$_2$, —(CH$_2$)$_{0-4}$CO(N-proline), —(CH$_2$)$_{0-4}$CO(N-pyrrolidine-3-carboxylic acid), —(CH$_2$)$_{0-4}$C(O)NR$^a$(CH$_2$)$_{1-4}$CO$_2$H, —(CH$_2$)$_{0-4}$C(O)NR$^a$—CH(C$_{1-4}$alkyl)-CO$_2$H, —(CH$_2$)$_{0-4}$C(O)NR$^a$(CH$_2$)$_{1-4}$CONH$_2$, —(CH$_2$)$_{0-4}$C(O)NR$^a$(CH$_2$)$_{1-4}$CONHC$_{1-4}$alkyl, —(CH$_2$)$_{0-4}$C(O)NR$^a$(CH$_2$)$_{1-4}$CON(C$_{1-4}$alkyl)$_2$, —OH, —(CH$_2$)$_{1-4}$OH, —(CH$_2$)$_{0-4}$OC$_{1-4}$alkyl, —NH$_2$, —(CH$_2$)$_{1-4}$NH$_2$, —(CH$_2$)$_{0-4}$NHC$_{1-4}$alkyl, —(CH$_2$)$_{0-4}$NR$^a$C(O)C$_{1-4}$alkyl, —(CH$_2$)$_{0-4}$NR$^a$C(O)Ph, —(CH$_2$)$_{0-4}$NR$^a$CO(CH$_2$)$_{1-4}$OH, —(CH$_2$)$_{0-4}$N(C$_{1-4}$alkyl)$_2$, —(CH$_2$)$_{0-4}$SO$_3$H, —(CH$_2$)$_{0-4}$SO$_2$NH$_2$, —(CH$_2$)$_{0-4}$SO$_2$NR$^a$C$_{1-4}$alkyl, —(CH$_2$)$_{0-4}$NR$^a$SO$_2$C$_{1-4}$alkyl, —(CH$_2$)$_{0-4}$NR$^a$SO$_2$Ph, —(CH$_2$)$_{0-4}$NR$^a$SO$_2$(CH$_2$)$_{1-4}$CO$_2$H, —(CH$_2$)$_{0-4}$OP(OH)$_2$, —(CH$_2$)$_{0-4}$OP(OH)(OC$_{1-4}$alkyl), or —(CR$_2$)$_{0-4}$OP(O)(H)OH, wherein $R^a$, independently for each occurrence, is H or C$_{1-4}$alkyl;

m is 1, 2, 3, or 4, particularly 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In further particular embodiments, the present disclosure provides a compound of formula I-f-5 or formula I-f-5*, wherein:

each $R^6$ is independently halogen, —(CH$_2$)$_{0-4}$CO$_2$H, —(CH$_2$)$_{0-4}$CO(N-proline), —(CH$_2$)$_{0-4}$CO(N-pyrrolidine-3-carboxylic acid), —(CH$_2$)$_{0-4}$C(O)NR$^a$(CH$_2$)$_{1-4}$CO$_2$H, —(CH$_2$)$_{0-4}$C(O)NR$^a$—CH(C$_{1-4}$alkyl)-CO$_2$H, —OH, —(CH$_2$)$_{1-4}$OH, —(CH$_2$)$_{0-4}$NR$^a$C(O)C$_{1-4}$alkyl, —(CH$_2$)$_{0-4}$NR$^a$C(O)Ph, —(CH$_2$)$_{0-4}$NR$^a$CO(CH$_2$)$_{1-4}$OH, —(CH$_2$)$_{0-4}$SO$_3$H, —(CH$_2$)$_{0-4}$SO$_2$NH$_2$, —(CH$_2$)$_{0-4}$NR$^a$SO$_2$C$_{1-4}$alkyl, —(CH$_2$)$_{0-4}$NR$^a$SO$_2$Ph, —(CH$_2$)$_{0-4}$NR$^a$SO$_2$(CH$_2$)$_{1-4}$CO$_2$H, —(CH$_2$)$_{0-4}$OP(OH)$_2$, or —(CR$_2$)$_{0-4}$OP(O)(H)OH, wherein $R^a$, independently for each occurrence, is H or C$_{1-4}$alkyl;

m is 1 or 2; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In particular embodiments, the present disclosure provides a compound of formula I-f-5 or formula I-f-5*, wherein, m is 1;

$R^6$ is —$(CH_2)_{0-4}O(CH_2)_{1-5}CO_2H$, such as —$(CH_2)_{1-2}O(CH_2)_{2-3}CO_2H$, including —$CH_2O(CH_2)_2CO_2H$; and each $R^3$ is independently optionally substituted $C_{1-6}$ aliphatic, such as methyl, or halogen, such as bromo and/or chloro, including dichloro, including wherein n is 2 and $R^3$ is chloro at the 7- and 8-positions with respect to the quinoline ring.

In certain embodiments, for the above disclosed compounds of formula I-f-5 or formula I-f-5*, m is 1 or 2, and at least one $R^6$ includes a terminal —$CO_2H$ group. For example, in certain instances, at least one $R^6$ is —$(CH_2)_{0-4}CO_2H$ or —$(CH_2)_{0-4}O(CH_2)_{1-5}CO_2H$.

As defined above and described herein, each R is independently hydrogen or an optionally substituted group selected from $C_{1-6}$ aliphatic; benzyl; phenyl; a 4- to 10-membered saturated or partially unsaturated monocyclic or bicyclic carbocyclic or heterocyclic ring having 1 to 3 heteroatoms independently selected from nitrogen, oxygen, phosphorus, and sulfur; and a 5- to 6-membered heteroaryl ring having 1 to 4 heteroatoms independently selected from nitrogen, oxygen, phosphorus, and sulfur, or two R groups on the same nitrogen are optionally taken together with their intervening atoms to form an optionally substituted 4- to 7-membered saturated, partially unsaturated, or heteroaryl ring having 0 to 3 heteroatoms, in addition to the nitrogen, independently selected from nitrogen, oxygen, phosphorus, and sulfur.

In some embodiments, R is hydrogen. In some embodiments, R is an optionally substituted $C_{1-6}$ aliphatic. In some embodiments, R is an optionally substituted benzyl. In some embodiments, R is an optionally substituted phenyl. In some embodiments, R is an optionally substituted 4- to 10-membered saturated or partially unsaturated monocyclic or bicyclic carbocyclic or heterocyclic ring having 1 to 3 heteroatoms independently selected from nitrogen, oxygen, phosphorus, and sulfur. In some embodiments, R is an optionally substituted 5- to 6-membered heteroaryl ring having 1 to 4 heteroatoms independently selected from nitrogen, oxygen, phosphorus, and sulfur. In some embodiments, two R groups on the same nitrogen are optionally taken together with their intervening atoms to form an optionally substituted 4- to 7-membered saturated, partially unsaturated, or heteroaryl ring having 0 to 3 heteroatoms, in addition to the nitrogen, independently selected from nitrogen, oxygen, phosphorus, and sulfur.

In some embodiments, two R groups on the same carbon atom (e.g., —$(CR_2)$—, etc.) are optionally taken together with their intervening atoms to form an optionally substituted 4- to 7-membered saturated or partially unsaturated ring having 0 to 3 heteroatoms independently selected from nitrogen, oxygen, phosphorus, and sulfur.

In some embodiments, two R groups on different atoms (e.g., —$P(O)(OR)_2$, —$B(OR)_2$, etc.) are optionally taken together with their intervening atoms to form an optionally substituted 4- to 7-membered saturated or partially unsaturated ring having 0 to 3 heteroatoms independently selected from nitrogen, oxygen, phosphorus, and sulfur.

In some embodiments, R is hydrogen. In some embodiments, R is methyl. In some embodiments, R is ethyl. In some embodiments, R is isopropyl. In some embodiments, R is phenyl. In some embodiments, R is benzyl. In some embodiments, R is —$(CH_2)_{1-5}CO_2H$. In some embodiments, R is —$(CH_2)_{1-5}CO_2C_{1-4}alkyl$.

In some embodiments, R is selected from those groups depicted in Table 1.

In some embodiments, R is selected from those groups depicted in Table 2.

In some embodiments, $R^2$ is $R^B$, wherein $R^B$ is an optionally substituted $C_{1-6}$ aliphatic, preferably a substituted $C_{1-6}$ aliphatic, such as —$(CR_2)_{1-4}NR(CR_2)_{0-6}CO_2R$, —$(CR_2)_{1-4}O(CR_2)_{0-6}CO_2R$, —$(CR_2)_{1-4}CO_2R$, —$(CR_2)_{1-4}OH$, —$(CR_2)_{1-4}NH_2$, —$(CR_2)_{1-4}C(O)NH_2$, —$(CR_2)_{1-4}C(O)NHC_{1-4}alkyl$, or —$(CR_2)_{1-4}C(O)N(C_{1-4}alkyl)_2$, particularly —$(CR_2)_{1-4}NR(CR_2)_{0-6}CO_2R$ or —$(CR_2)_{1-4}CO_2R$. In some embodiments, $R^2$ is —$(CH_2)_{1-4}NR^a(CH_2)_{0-4}CO_2R^a$, such as —$(CH_2)_{1-4}NR^a(CH_2)_{0-4}CO_2H$, wherein $R^a$, independently for each occurrence, is H or $C_{1-4}alkyl$. In other embodiments, $R^2$ is —$(CH_2)_{1-4}N(SO_2C_{1-4}alkyl)(CH_2)_{0-4}CO_2R^a$, such as is —$(CH_2)_{1-4}N(SO_2C_{1-4}alkyl)(CH_2)_{0-4}CO_2H$, wherein $R^a$, independently for each occurrence, is H or $C_{1-4}alkyl$. In other embodiments, $R^2$ is —$(CR_2)_{1-4}CO_2R$, such as —$(CR_2)_{1-4}CO_2H$, including —$(CH_2)_{1-4}CO_2H$. In certain embodiments, $R^2$ includes a terminal —$CO_2H$ group. For example, in certain instances, $R^2$ includes a terminal —$(CH_2)_{0-4}CO_2H$ group.

As defined above and described herein, $R^2$ is halogen, —OR, —$NR_2$, —$NRC(O)OR$, —$NRC(O)R$, —$NRC(O)NR_2$, —$NRSO_2R$, —SR, —$SO_2R$, —$SO_2NR_2$, —$S(O)R$, or $R^B$, particularly —$NR_2$ or $R^B$.

In some embodiments, $R^2$ is halogen. In some embodiments, $R^2$ is —OR. In some embodiments, $R^2$ is —$NR_2$. In some embodiments, $R^2$ is —$NRC(O)OR$. In some embodiments, $R^2$ is —$NRC(O)R$. In some embodiments, $R^2$ is —$NRC(O)NR_2$. In some embodiments, $R^2$ is —$NRSO_2R$, —SR. In some embodiments, $R^2$ is —$SO_2R$. In some embodiments, $R^2$ is —$SO_2NR_2$. In some embodiments, $R^2$ is —$S(O)R$. In some embodiments, $R^2$ is $R^B$.

In some embodiments, $R^2$ is hydrogen. In some embodiments, $R^2$ is chloro. In some embodiments, $R^2$ is methyl. In some embodiments, $R^2$ is —$CF_3$. In some embodiments, $R^2$ is phenyl. In some embodiments, $R^2$ is

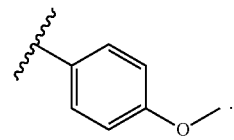 [SMILES: *c1ccc(OC)cc1]

In some embodiments, $R^2$ is

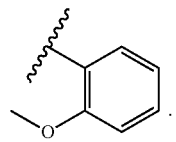 [SMILES: *c1ccccc1OC]

In some embodiments, $R^2$ is

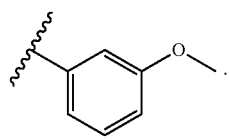 [SMILES: *c1cccc(OC)c1]

101
In some embodiments, R² is
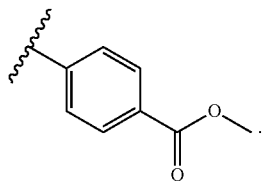 [SMILES: *c1ccc(C(=O)OC)cc1]
In some embodiments, R² is
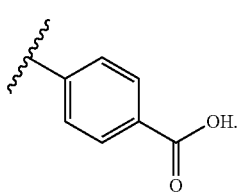 [SMILES: *c1ccc(C(=O)O)cc1]
In some embodiments, R² is
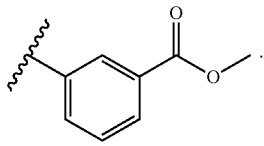 [SMILES: *c1cccc(C(=O)OC)c1]
In some embodiments, R² is
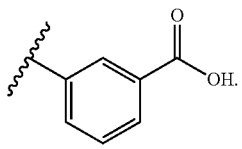 [SMILES: *c1cccc(C(=O)O)c1]
In some embodiments, R² is
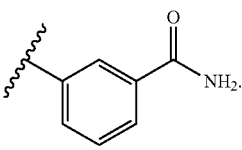 [SMILES: *c1cccc(C(N)=O)c1]
In some embodiments, R² is
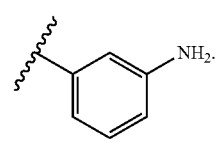 [SMILES: *c1cccc(N)c1]
102
In some embodiments, R² is
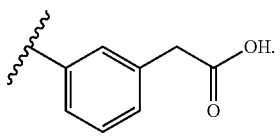 [SMILES: *c1cccc(CC(=O)O)c1]
In some embodiments, R² is
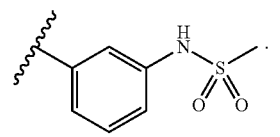 [SMILES: *c1cccc(NS(C)(=O)=O)c1]
In some embodiments, R² is
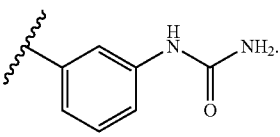 [SMILES: *c1cccc(NC(N)=O)c1]
In some embodiments, R² is
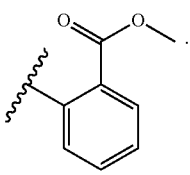 [SMILES: *c1ccccc1C(=O)OC]
In some embodiments, R² is
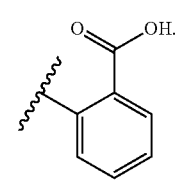 [SMILES: *c1ccccc1C(=O)O]
In some embodiments, R² is
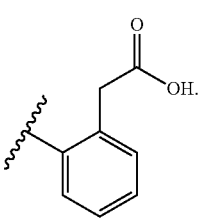 [SMILES: *c1ccccc1CC(=O)O]

In some embodiments, R² is
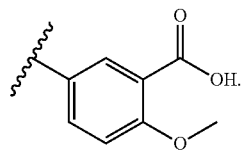 [SMILES: *c1ccc(OC)c(C(=O)O)c1]
In some embodiments, R² is
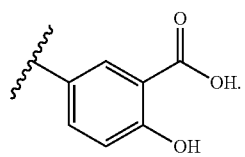 [SMILES: *c1ccc(O)c(C(=O)O)c1]
In some embodiments, R² is
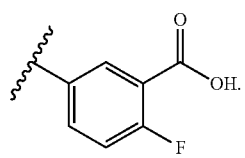 [SMILES: *c1ccc(F)c(C(=O)O)c1]
In some embodiments, R² is
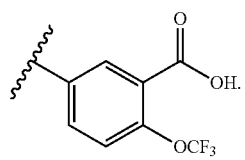 [SMILES: *c1ccc(OC(F)(F)F)c(C(=O)O)c1]
In some embodiments, R² is
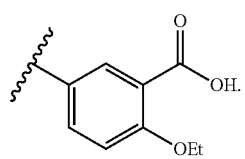 [SMILES: *c1ccc(OCC)c(C(=O)O)c1]
In some embodiments, R² is
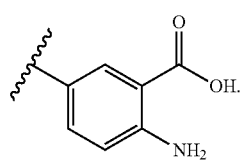
In some embodiments, R² is
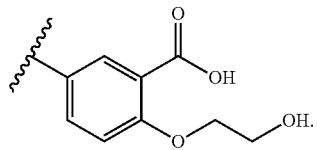 [SMILES: *c1ccc(OCCO)c(C(=O)O)c1]
In some embodiments, R² is
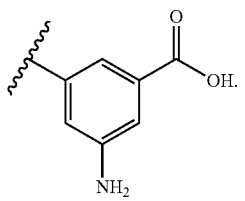 [SMILES: *c1cc(N)cc(C(=O)O)c1]
In some embodiments, R² is
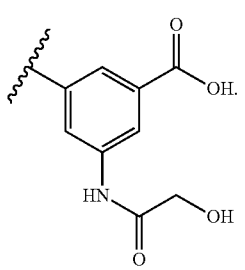 [SMILES: *c1cc(NC(=O)CO)cc(C(=O)O)c1]
In some embodiments, R² is
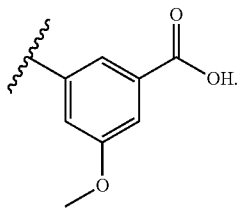 [SMILES: *c1cc(OC)cc(C(=O)O)c1]
In some embodiments, R² is
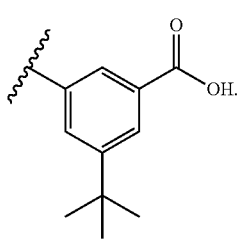 [SMILES: *c1cc(C(=O)O)cc(C(C)(C)C)c1]

In some embodiments, R² is
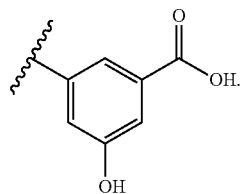 [SMILES: *c1cc(O)cc(C(=O)O)c1]
In some embodiments, R² is
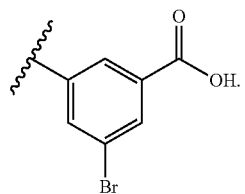 [SMILES: *c1cc(Br)cc(C(=O)O)c1]
In some embodiments, R² is
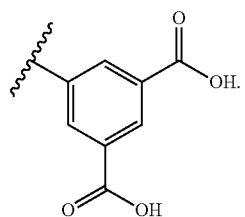 [SMILES: *c1cc(C(=O)O)cc(C(=O)O)c1]
In some embodiments, R² is
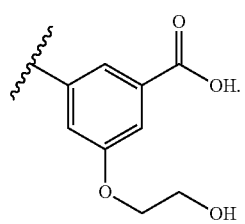 [SMILES: *c1cc(OCCO)cc(C(=O)O)c1]
In some embodiments, R² is
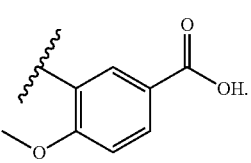 [SMILES: *c1cc(C(=O)O)ccc1OC]
In some embodiments, R² is
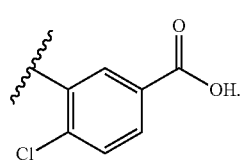 [SMILES: *c1cc(C(=O)O)ccc1Cl]
In some embodiments, R² is
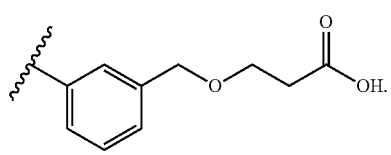 [SMILES: *c1cccc(COCCC(=O)O)c1]
In some embodiments, R² is
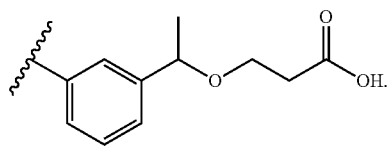 [SMILES: *c1cccc(C(C)OCCC(=O)O)c1]
In some embodiments, R² is
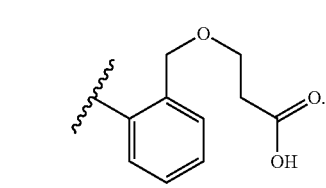 [SMILES: *c1ccccc1COCCC(=O)O]
In some embodiments, R² is
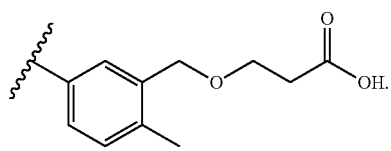 [SMILES: *c1ccc(C)c(COCCC(=O)O)c1]
In some embodiments, R² is
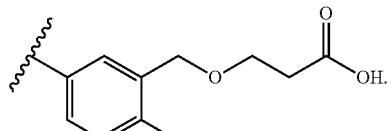
In some embodiments, R² is
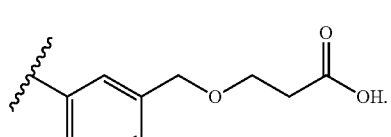

In some embodiments, $R^2$ is
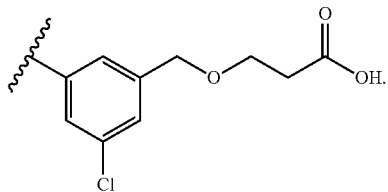 [SMILES: *c1cc(Cl)cc(COCCC(=O)O)c1]
In some embodiments, $R^2$ is
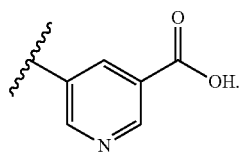 [SMILES: *c1cncc(C(=O)O)c1]
In some embodiments, $R^2$ is
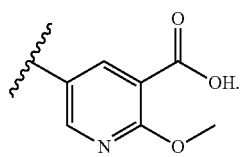 [SMILES: *c1cnc(OC)c(C(=O)O)c1]
In some embodiments, $R^2$ is
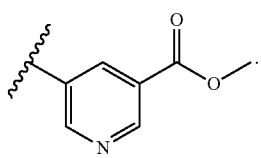 [SMILES: *c1cncc(C(=O)OC)c1]
In some embodiments, $R^2$ is
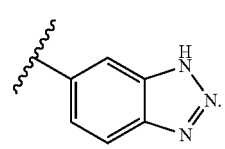 [SMILES: *c1ccc2nn[nH]c2c1]
In some embodiments, $R^2$ is
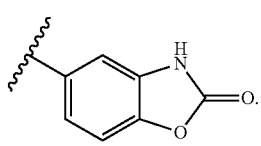 [SMILES: *c1ccc2oc(=O)[nH]c2c1]
In some embodiments, $R^2$ is
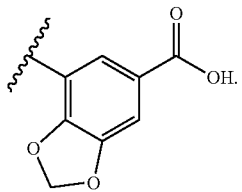 [SMILES: *c1cc(C(=O)O)cc2c1OCO2]
In some embodiments, $R^2$ is
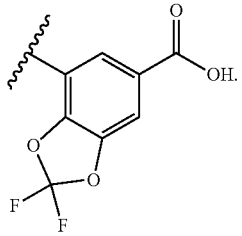 [SMILES: *c1cc(C(=O)O)cc2c1OC(F)(F)O2]
In some embodiments, $R^2$ is
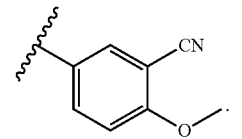 [SMILES: *c1ccc(OC)c(C#N)c1]
In some embodiments, $R^2$ is
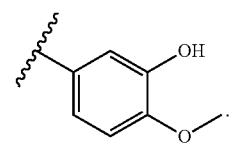
In some embodiments, $R^2$ is
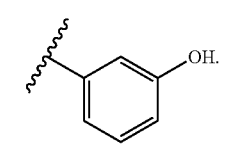 [SMILES: *c1cccc(O)c1]
In some embodiments, $R^2$ is
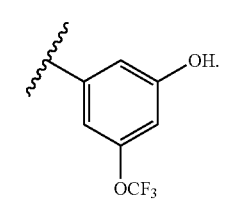 [SMILES: *c1cc(O)cc(OC(F)(F)F)c1]

In some embodiments, R² is
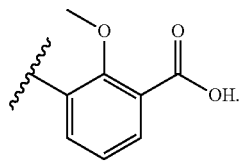 [SMILES: *c1cccc(C(=O)O)c1OC]
In some embodiments, R² is
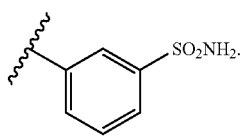 [SMILES: *c1cccc(S(N)(=O)=O)c1]
In some embodiments, R² is
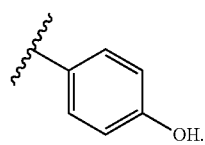 [SMILES: *c1ccc(O)cc1]
In some embodiments, R² is
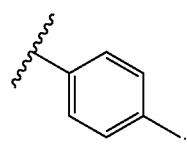 [SMILES: *c1ccc(C)cc1]
In some embodiments, R² is
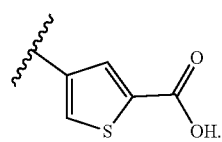 [SMILES: *c1csc(C(=O)O)c1]
In some embodiments, R² is
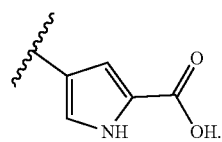 [SMILES: *c1c[nH]c(C(=O)O)c1]
In some embodiments, R² is
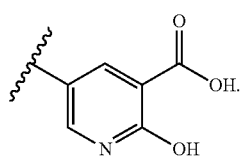 [SMILES: *c1cnc(O)c(C(=O)O)c1]
In some embodiments, R² is
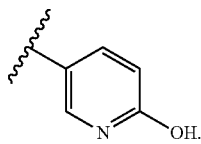 [SMILES: *c1ccc(O)nc1]
In some embodiments, R² is
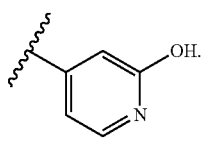 [SMILES: *c1ccnc(O)c1]
In some embodiments, R² is
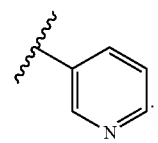 [SMILES: *c1cccnc1]
In some embodiments, R² is
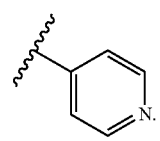 [SMILES: *c1ccncc1]
In some embodiments, R² is
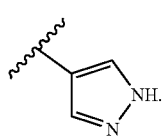
In some embodiments, R² is
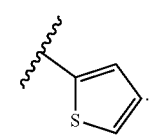 [SMILES: *c1cccs1]
In some embodiments, R² is
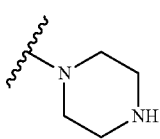

In some embodiments, R² is
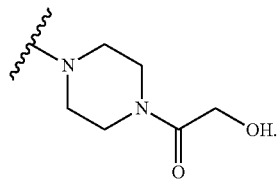 [SMILES: *N1CCN(C(=O)CO)CC1]
In some embodiments, R² is
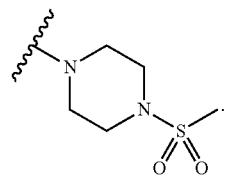 [SMILES: *N1CCN(S(C)(=O)=O)CC1]
In some embodiments, R² is
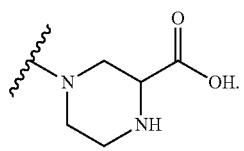 [SMILES: *N1CCNC(C(=O)O)C1]
In some embodiments, R² is
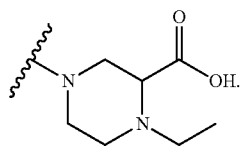 [SMILES: *N1CCN(CC)C(C(=O)O)C1]
In some embodiments, R² is
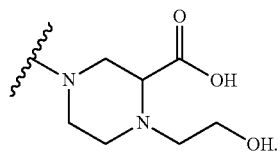 [SMILES: *N1CCN(CCO)C(C(=O)O)C1]
In some embodiments, R² is
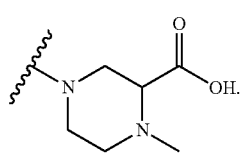 [SMILES: *N1CCN(C)C(C(=O)O)C1]
In some embodiments, R² is
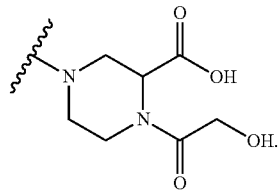 [SMILES: *N1CCN(C(=O)CO)C(C(=O)O)C1]
In some embodiments, R² is
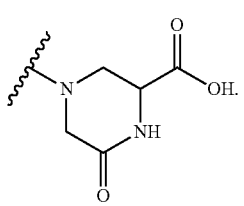 [SMILES: *N1CC(=O)NC(C(=O)O)C1]
In some embodiments, R² is
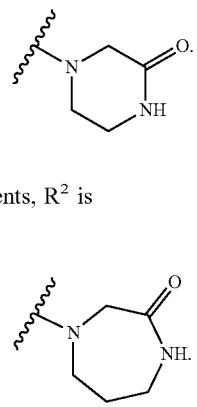
In some embodiments, R² is
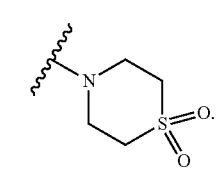 [SMILES: *N1CCS(=O)(=O)CC1]
In some embodiments, R² is
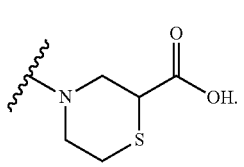 [SMILES: *N1CCSC(C(=O)O)C1]

In some embodiments, R² is
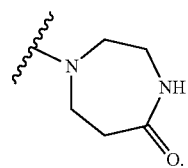 [SMILES: *N1CCNC(=O)CC1]
In some embodiments, R² is
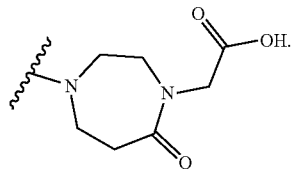 [SMILES: *N1CCC(=O)N(CC(=O)O)CC1]
In some embodiments, R² is
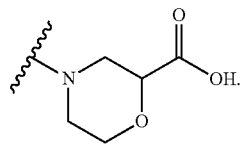 [SMILES: *N1CCOC(C(=O)O)C1]
In some embodiments, R² is
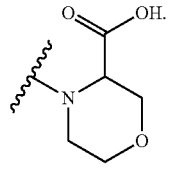
In some embodiments, R² is
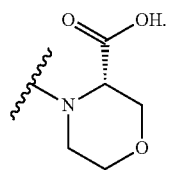 [SMILES: *N1CCOC[C@H]1C(=O)O]
In some embodiments, R² is
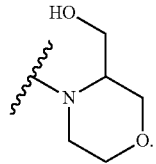 [SMILES: *N1CCOCC1CO]
In some embodiments, R² is
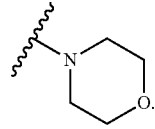 [SMILES: *N1CCOCC1]
In some embodiments, R² is
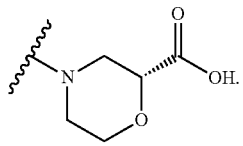 [SMILES: *N1CCO[C@@H](C(=O)O)C1]
In some embodiments, R² is
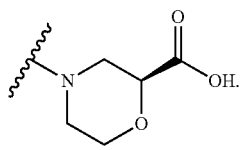 [SMILES: *N1CCO[C@H](C(=O)O)C1]
In some embodiments, R² is
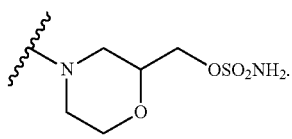
In some embodiments, R² is
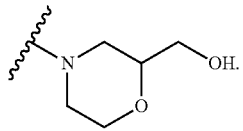 [SMILES: *N1CCOC(CO)C1]
In some embodiments, R² is
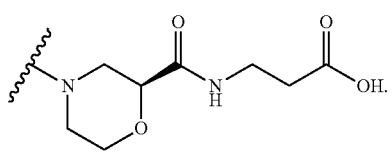 [SMILES: *N1CCO[C@H](C(=O)NCCC(=O)O)C1]
In some embodiments, R² is
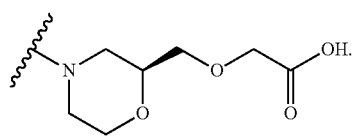 [SMILES: *N1CCO[C@H](COCC(=O)O)C1]

In some embodiments, R² is
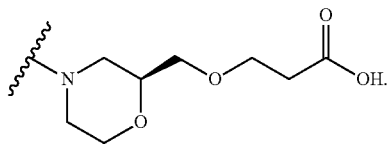 [SMILES: *N1CCO[C@H](COCCC(=O)O)C1]
In some embodiments R² is
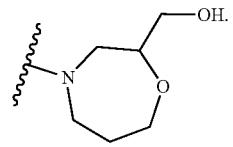 [SMILES: *N1CCCOC(CO)C1]
In some embodiments, R² is
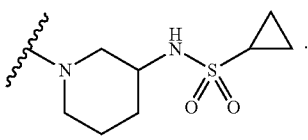 [SMILES: *N1CCCC(NS(=O)(=O)C2CC2)C1]
In some embodiments, R² is
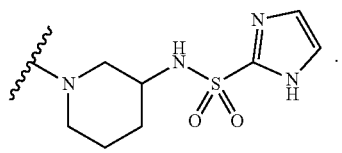 [SMILES: *N1CCCC(NS(=O)(=O)c2ncc[nH]2)C1]
In some embodiments, R² is
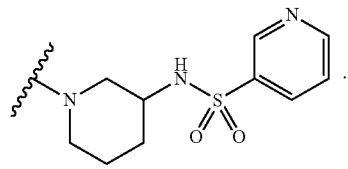 [SMILES: *N1CCCC(NS(=O)(=O)c2cccnc2)C1]
In some embodiments, R² is
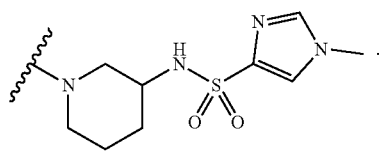 [SMILES: *N1CCCC(NS(=O)(=O)c2cn(C)cn2)C1]
In some embodiments, R² is
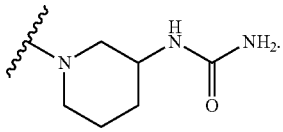 [SMILES: *N1CCCC(NC(N)=O)C1]
In some embodiments, R² is
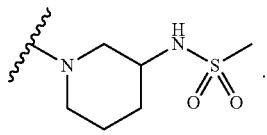 [SMILES: *N1CCCC(NS(C)(=O)=O)C1]
In some embodiments, R² is
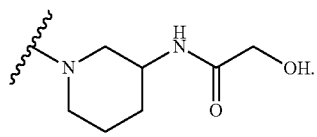 [SMILES: *N1CCCC(NC(=O)CO)C1]
In some embodiments, R² is
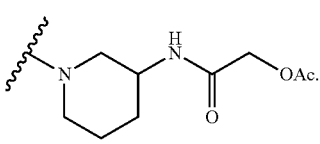 [SMILES: *N1CCCC(NC(=O)COC(C)=O)C1]
In some embodiments, R² is
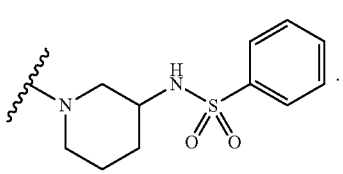 [SMILES: *N1CCCC(NS(=O)(=O)c2ccccc2)C1]
In some embodiments, R² is
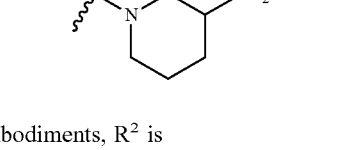
In some embodiments, R² is
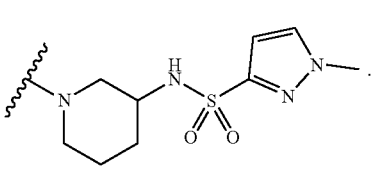 [SMILES: *N1CCCC(NS(=O)(=O)c2ccn(C)n2)C1]

117
In some embodiments, R² is
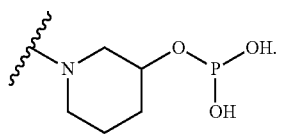 [SMILES: *N1CCCC(OP(O)O)C1]
In some embodiments, R² is
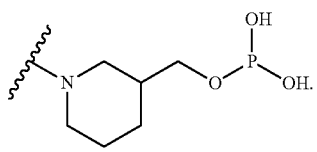 [SMILES: *N1CCCC(COP(O)O)C1]
In some embodiments, R² is
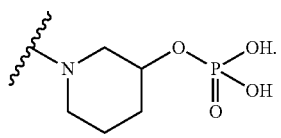 [SMILES: *N1CCCC(OP(=O)(O)O)C1]
In some embodiments, R² is
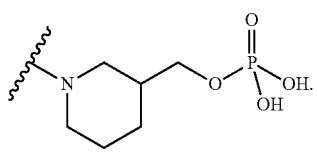 [SMILES: *N1CCCC(COP(=O)(O)O)C1]
In some embodiments, R² is
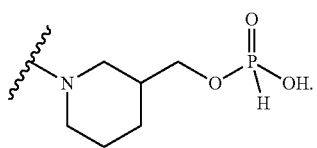 [SMILES: *N1CCCC(CO[PH](=O)O)C1]
In some embodiments, R² is
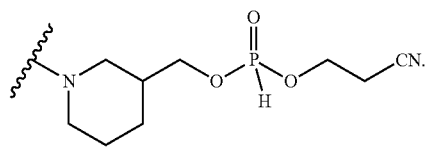 [SMILES: *N1CCCC(CO[PH](=O)OCCC#N)C1]
In some embodiments, R² is
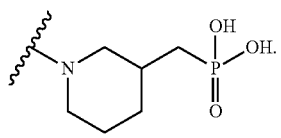
118
In some embodiments, R² is
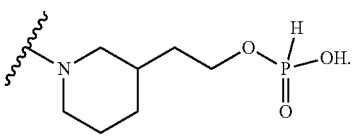 [SMILES: *N1CCCC(CCO[PH](=O)O)C1]
In some embodiments, R² is
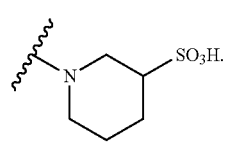
In some embodiments, R² is
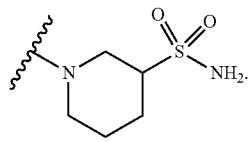 [SMILES: *N1CCCC(S(N)(=O)=O)C1]
In some embodiments, R² is
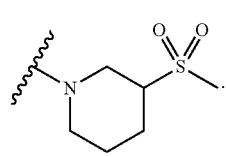 [SMILES: *N1CCCC(S(C)(=O)=O)C1]
In some embodiments, R² is
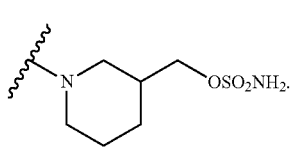
In some embodiments, R² is
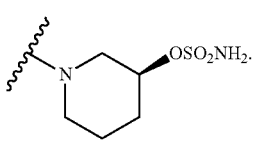
In some embodiments, R² is
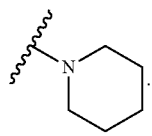

In some embodiments, R² is
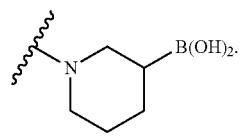 [SMILES: *N1CCCC(B(O)O)C1]
In some embodiments, R² is
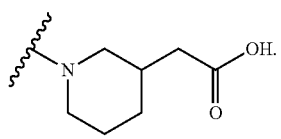 [SMILES: *N1CCCC(CC(=O)O)C1]
In some embodiments, R² is
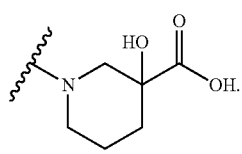 [SMILES: *N1CCCC(O)(C(=O)O)C1]
In some embodiments, R² is
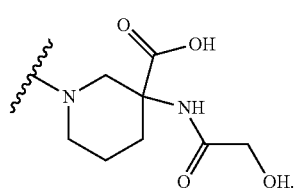 [SMILES: *N1CCCC(NC(=O)CO)(C(=O)O)C1]
In some embodiments, R² is
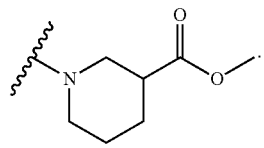 [SMILES: *N1CCCC(C(=O)OC)C1]
In some embodiments, R² is
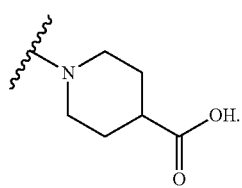 [SMILES: *N1CCC(C(=O)O)CC1]
In some embodiments, R² is
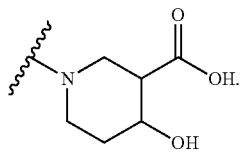 [SMILES: *N1CCC(O)C(C(=O)O)C1]
In some embodiments, R² is
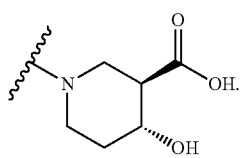 [SMILES: *N1CC[C@@H](O)[C@H](C(=O)O)C1]
In some embodiments, R² is
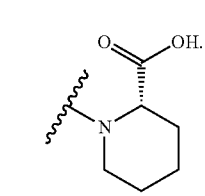 [SMILES: *N1CCCC[C@H]1C(=O)O]
In some embodiments, R² is
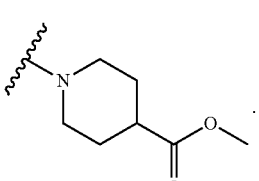
In some embodiments, R² is
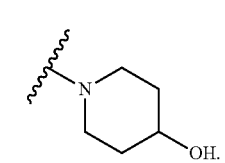 [SMILES: *N1CCC(O)CC1]
In some embodiments, R² is
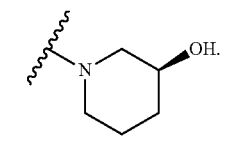 [SMILES: *N1CCC[C@H](O)C1]

In some embodiments, R² is
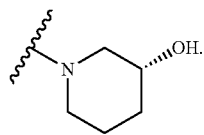 [SMILES: *N1CCC[C@@H](O)C1]
In some embodiments, R² is
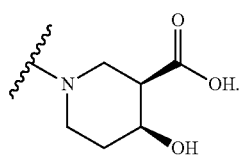 [SMILES: *N1CC[C@H](O)[C@H](C(=O)O)C1]
In some embodiments, R² is
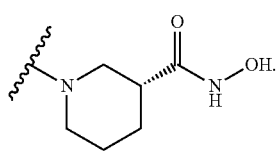 [SMILES: *N1CCC[C@@H](C(=O)NO)C1]
In some embodiments, R² is
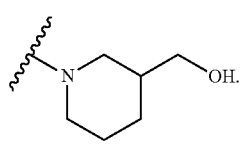 [SMILES: *N1CCCC(CO)C1]
In some embodiments, R² is
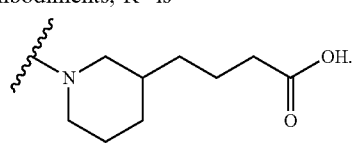
In some embodiments, R² is
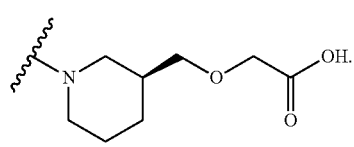 [SMILES: *N1CCC[C@H](COCC(=O)O)C1]
In some embodiments, R² is
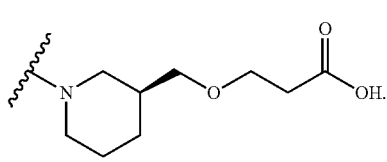 [SMILES: *N1CCC[C@H](COCCC(=O)O)C1]
In some embodiments, R² is
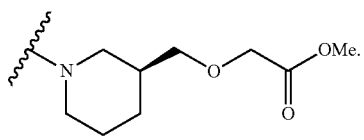 [SMILES: *N1CCC[C@H](COCC(=O)OC)C1]
In some embodiments, R² is
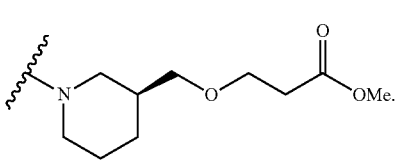 [SMILES: *N1CCC[C@H](COCCC(=O)OC)C1]
In some embodiments, R² is
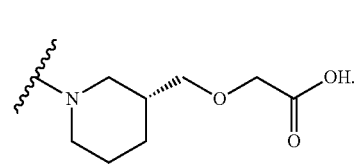 [SMILES: *N1CCC[C@@H](COCC(=O)O)C1]
In some embodiments, R² is
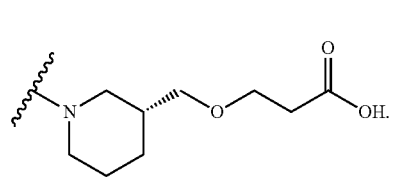 [SMILES: *N1CCC[C@@H](COCCC(=O)O)C1]
In some embodiments, R² is
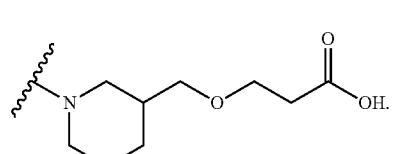
In some embodiments, R² is
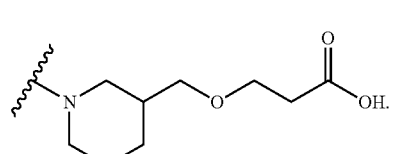

In some embodiments, R² is
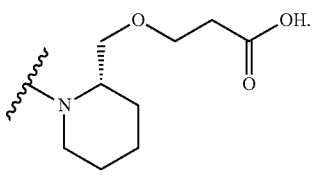 [SMILES: *N1CCCC[C@H]1COCCC(=O)O]
In some embodiments, R² is
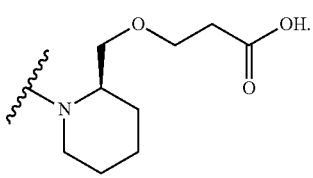 [SMILES: *N1CCCC[C@@H]1COCCC(=O)O]
In some embodiments, R² is
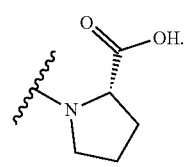 [SMILES: *N1CCC[C@H]1C(=O)O]
In some embodiments, R² is
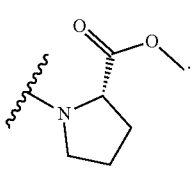 [SMILES: *N1CCC[C@H]1C(=O)OC]
In some embodiments, R² is
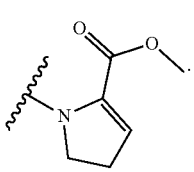 [SMILES: *N1CCC=C1C(=O)OC]
In some embodiments, R² is
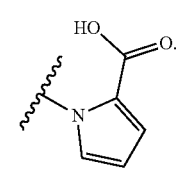 [SMILES: *n1cccc1C(=O)O]
In some embodiments, R² is
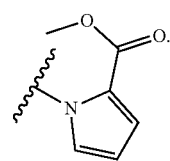 [SMILES: *n1cccc1C(=O)OC]
In some embodiments, R² is
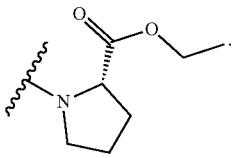 [SMILES: *N1CCC[C@H]1C(=O)OCC]
In some embodiments, R² is
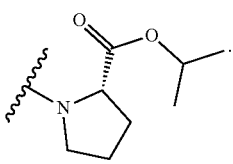 [SMILES: *N1CCC[C@H]1C(=O)OC(C)C]
In some embodiments, R² is
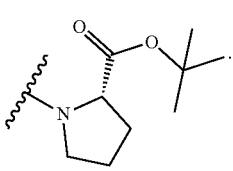 [SMILES: *N1CCC[C@H]1C(=O)OC(C)(C)C]
In some embodiments, R² is
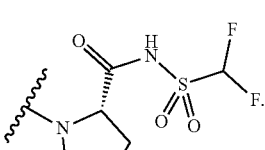
In some embodiments, R² is
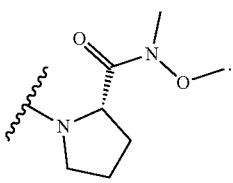 [SMILES: *N1CCC[C@H]1C(=O)N(C)OC]

In some embodiments, R² is
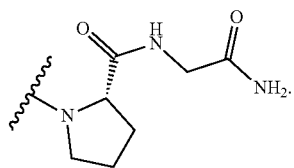 [SMILES: *N1CCC[C@H]1C(=O)NCC(N)=O]
In some embodiments, R² is
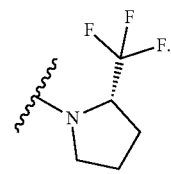
In some embodiments, R² is
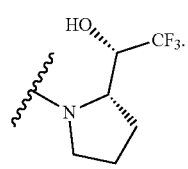 [SMILES: *N1CCC[C@H]1[C@H](O)C(F)(F)F]
In some embodiments, R² is
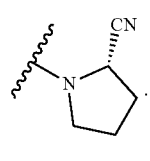
In some embodiments, R² is
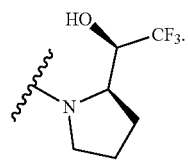 [SMILES: *N1CCC[C@@H]1[C@@H](O)C(F)(F)F]
In some embodiments, R² is
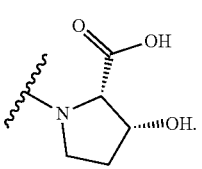
In some embodiments, R² is
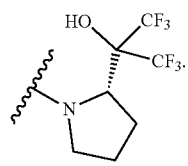 [SMILES: *N1CCC[C@H]1C(O)(C(F)(F)F)C(F)(F)F]
In some embodiments, R² is
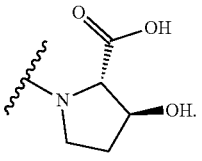
In some embodiments, R² is
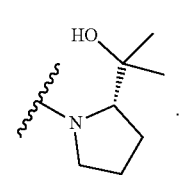 [SMILES: *N1CCC[C@H]1C(C)(C)O]
In some embodiments, R² is
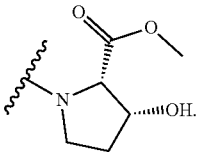
In some embodiments, R² is
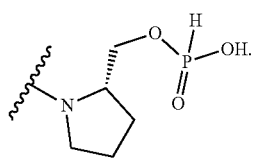 [SMILES: *N1CCC[C@H]1CO[PH](=O)O]
In some embodiments, R² is
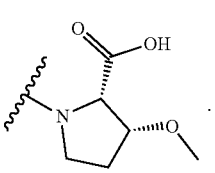 [SMILES: *N1CC[C@@H](OC)[C@H]1C(=O)O]

In some embodiments, R² is
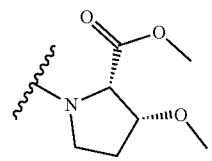
In some embodiments, R² is
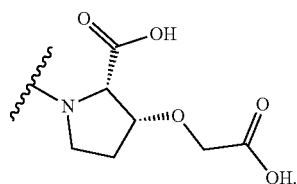 [SMILES: *N1CC[C@@H](OCC(=O)O)[C@H]1C(=O)O]
In some embodiments, R² is
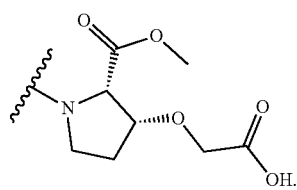 [SMILES: *N1CC[C@@H](OCC(=O)O)[C@H]1C(=O)OC]
In some embodiments, R² is
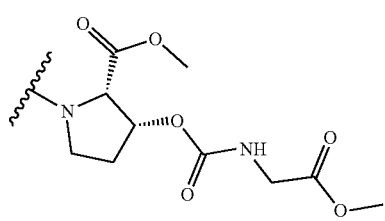
In some embodiments, R² is
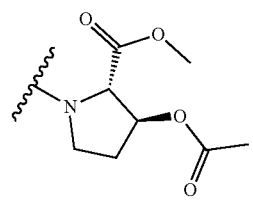
In some embodiments, R² is
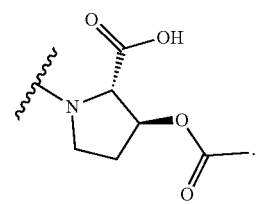 [SMILES: *N1CC[C@H](OC(C)=O)[C@H]1C(=O)O]
In some embodiments, R² is
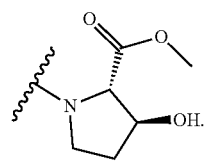 [SMILES: *N1CC[C@H](O)[C@H]1C(=O)OC]
In some embodiments, R² is
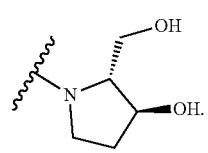 [SMILES: *N1CC[C@H](O)[C@H]1CO]
In some embodiments, R² is
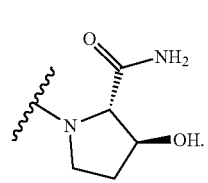 [SMILES: *N1CC[C@H](O)[C@H]1C(N)=O]
In some embodiments, R² is
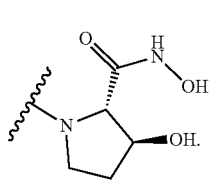 [SMILES: *N1CC[C@H](O)[C@H]1C(=O)NO]
In some embodiments, R² is
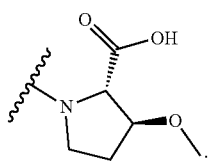 [SMILES: *N1CC[C@H](OC)[C@H]1C(=O)O]
In some embodiments, R² is
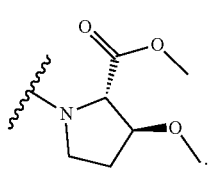 [SMILES: *N1CC[C@H](OC)[C@H]1C(=O)OC]

In some embodiments, R² is
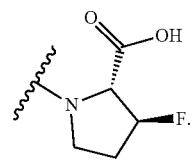 [SMILES: *N1CC[C@H](F)[C@H]1C(=O)O]
In some embodiments, R² is
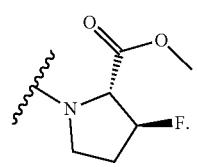 [SMILES: *N1CC[C@H](F)[C@H]1C(=O)OC]
In some embodiments, R² is
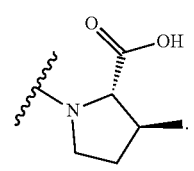 [SMILES: *N1CC[C@H](C)[C@H]1C(=O)O]
In some embodiments, R² is
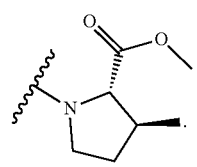 [SMILES: *N1CC[C@H](C)[C@H]1C(=O)OC]
In some embodiments, R² is
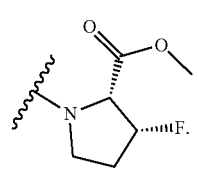 [SMILES: *N1CC[C@@H](F)[C@H]1C(=O)OC]
In some embodiments, R² is
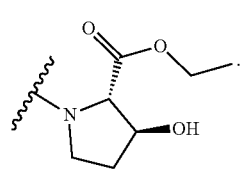 [SMILES: *N1CC[C@H](O)[C@H]1C(=O)OCC]
In some embodiments, R² is
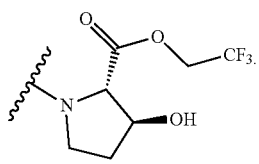 [SMILES: *N1CC[C@H](O)[C@H]1C(=O)OCC(F)(F)F]
In some embodiments, R² is
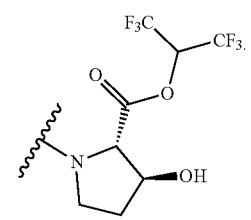 [SMILES: *N1CC[C@H](O)[C@H]1C(=O)OC(C(F)(F)F)C(F)(F)F]
In some embodiments, R² is
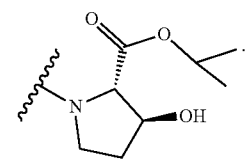 [SMILES: *N1CC[C@H](O)[C@H]1C(=O)OC(C)C]
In some embodiments, R² is
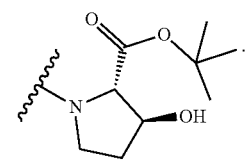 [SMILES: *N1CC[C@H](O)[C@H]1C(=O)OC(C)(C)C]
In some embodiments, R² is
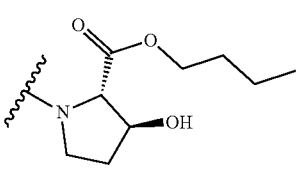
In some embodiments, R² is
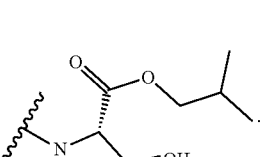

In some embodiments, R² is
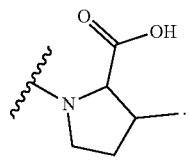 [SMILES: *N1CCC(C)C1C(=O)O]
In some embodiments, R² is
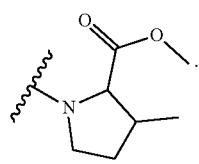 [SMILES: *N1CCC(C)C1C(=O)OC]
In some embodiments, R² is
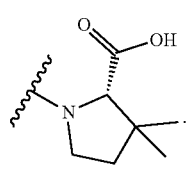 [SMILES: *N1CCC(C)(C)[C@H]1C(=O)O]
In some embodiments, R² is
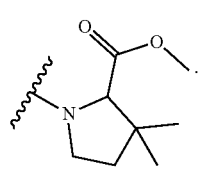 [SMILES: *N1CCC(C)(C)C1C(=O)OC]
In some embodiments, R² is
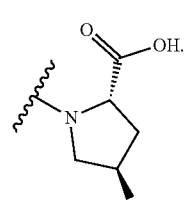
In some embodiments, R² is
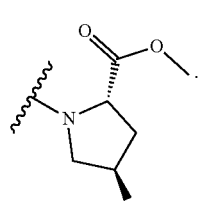
In some embodiments, R² is
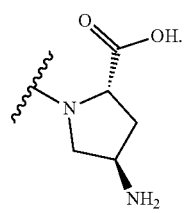 [SMILES: *N1C[C@H](N)C[C@H]1C(=O)O]
In some embodiments, R² is
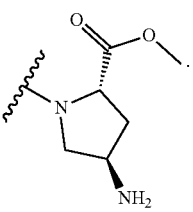 [SMILES: *N1C[C@H](N)C[C@H]1C(=O)OC]
In some embodiments, R² is
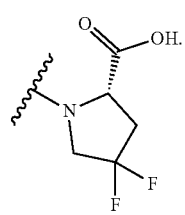 [SMILES: *N1CC(F)(F)C[C@H]1C(=O)O]
In some embodiments, R² is
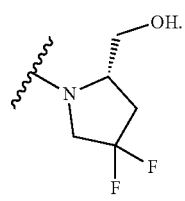 [SMILES: *N1CC(F)(F)C[C@H]1CO]
In some embodiments, R² is
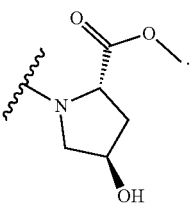 [SMILES: *N1C[C@H](O)C[C@H]1C(=O)OC]

In some embodiments, R² is
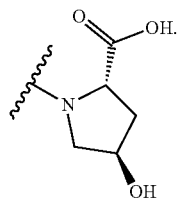 [SMILES: *N1C[C@H](O)C[C@H]1C(=O)O]
In some embodiments, R² is
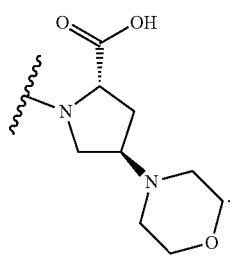 [SMILES: *N1C[C@H](N2CCOCC2)C[C@H]1C(=O)O]
In some embodiments, R² is
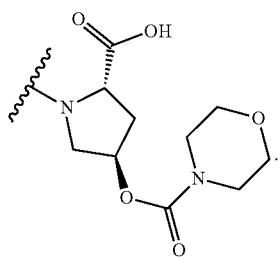 [SMILES: *N1C[C@H](OC(=O)N2CCOCC2)C[C@H]1C(=O)O]
In some embodiments, R² is
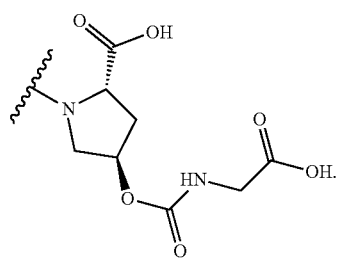 [SMILES: *N1C[C@H](OC(=O)NCC(=O)O)C[C@H]1C(=O)O]
In some embodiments, R² is
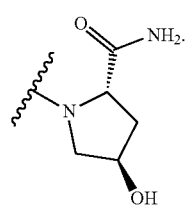 [SMILES: *N1C[C@H](O)C[C@H]1C(N)=O]
In some embodiments, R² is
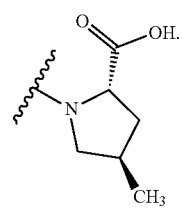 [SMILES: *N1C[C@H](C)C[C@H]1C(=O)O]
In some embodiments, R² is
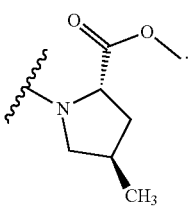 [SMILES: *N1C[C@H](C)C[C@H]1C(=O)OC]
In some embodiments, R² is
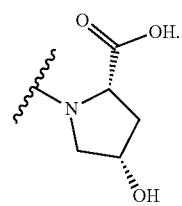 [SMILES: *N1C[C@@H](O)C[C@H]1C(=O)O]
In some embodiments, R² is
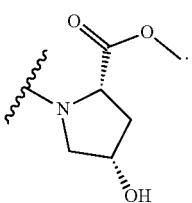 [SMILES: *N1C[C@@H](O)C[C@H]1C(=O)OC]
In some embodiments, R² is
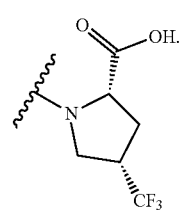

In some embodiments, R² is
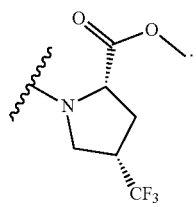 [SMILES: *N1C[C@@H](C(F)(F)F)C[C@H]1C(=O)OC]
In some embodiments, R² is
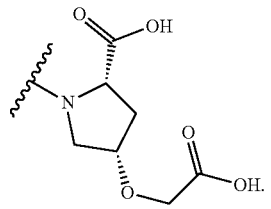 [SMILES: *N1C[C@@H](OCC(=O)O)C[C@H]1C(=O)O]
In some embodiments, R² is
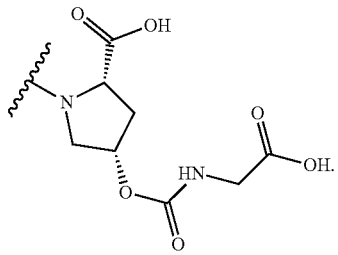 [SMILES: *N1C[C@@H](OC(=O)NCC(=O)O)C[C@H]1C(=O)O]
In some embodiments, R² is
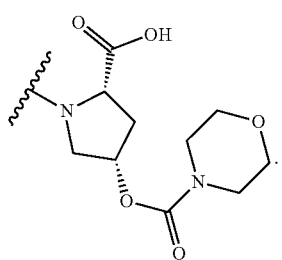 [SMILES: *N1C[C@@H](OC(=O)N2CCOCC2)C[C@H]1C(=O)O]
In some embodiments, R² is
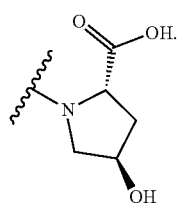 [SMILES: *N1C[C@H](O)C[C@H]1C(=O)O]
In some embodiments, R² is
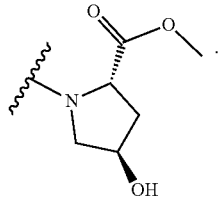 [SMILES: *N1C[C@H](O)C[C@H]1C(=O)OC]
In some embodiments, R² is
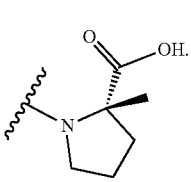 [SMILES: *N1CCC[C@@]1(C)C(=O)O]
In some embodiments, R² is
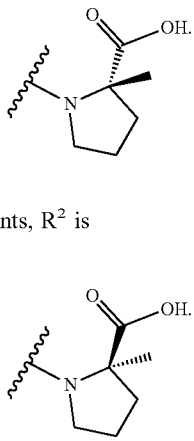
In some embodiments, R² is
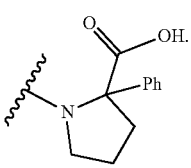 [SMILES: *N1CCCC1(C(=O)O)c1ccccc1]
In some embodiments, R² is
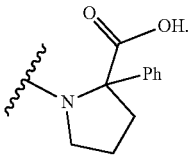
In some embodiments, R² is
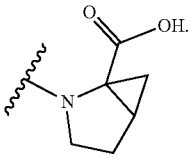 [SMILES: *N1CCC2CC21C(=O)O]
In some embodiments, R² is
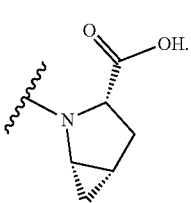 [SMILES: *N1[C@H](C(=O)O)C[C@@H]2C[C@@H]21]

In some embodiments, R² is
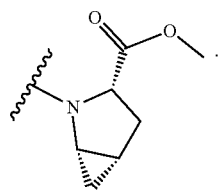 [SMILES: *N1[C@H](C(=O)OC)C[C@@H]2C[C@@H]21]
In some embodiments, R² is
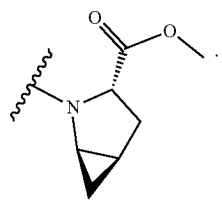 [SMILES: *N1[C@@H]2C[C@@H]2C[C@H]1C(=O)OC]
In some embodiments, R² is
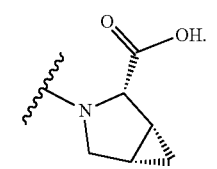 [SMILES: *N1C[C@H]2C[C@H]2[C@H]1C(=O)O]
In some embodiments, R² is
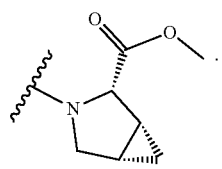 [SMILES: *N1C[C@H]2C[C@H]2[C@H]1C(=O)OC]
In some embodiments, R² is
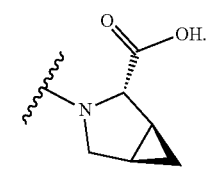 [SMILES: *N1C[C@@H]2C[C@@H]2[C@H]1C(=O)O]
In some embodiments, R² is
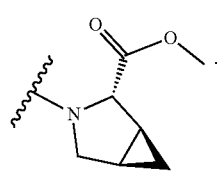 [SMILES: *N1C[C@@H]2C[C@@H]2[C@H]1C(=O)OC]
In some embodiments, R² is
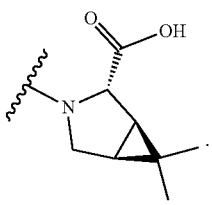 [SMILES: *N1C[C@H]2[C@@H]([C@H]1C(=O)O)C2(C)C]
In some embodiments, R² is
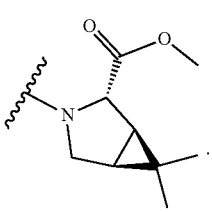 [SMILES: *N1C[C@H]2[C@@H]([C@H]1C(=O)OC)C2(C)C]
In some embodiments, R² is
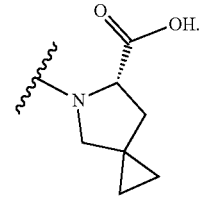 [SMILES: *N1CC2(CC2)C[C@H]1C(=O)O]
In some embodiments, R² is
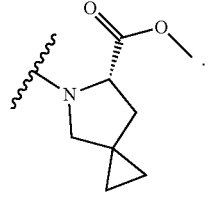 [SMILES: *N1CC2(CC2)C[C@H]1C(=O)OC]
In some embodiments, R² is
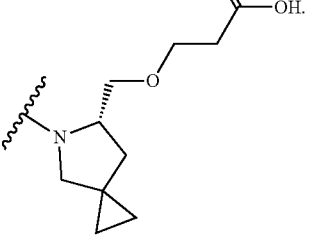

In some embodiments, R² is
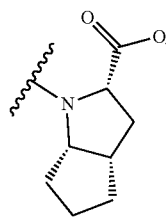
In some embodiments, R² is
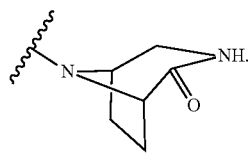 [SMILES: *N1C2CCC1C(=O)NC2]
In some embodiments, R² is
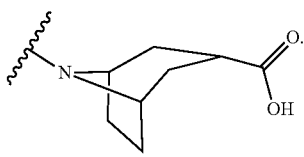 [SMILES: *N1C2CCC1CC(C(=O)O)C2]
In some embodiments, R² is
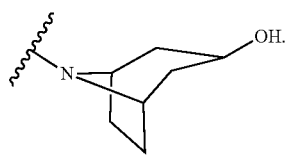 [SMILES: *N1C2CCC1CC(O)C2]
In some embodiments, R² is
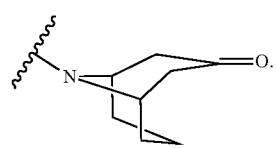 [SMILES: *N1C2CCCC1CC(=O)C2]
In some embodiments, R² is
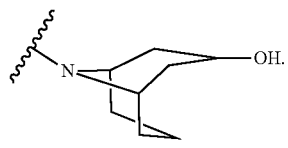 [SMILES: *N1C2CCCC1CC(O)C2]
In some embodiments, R² is
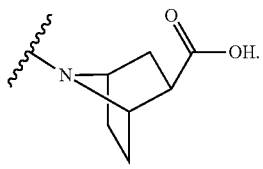 [SMILES: *N1C2CCC1C(C(=O)O)C2]
In some embodiments, R² is
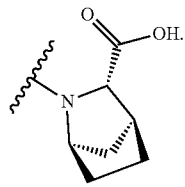 [SMILES: *N1[C@@H]2CC[C@@H](C2)[C@H]1C(=O)O]
In some embodiments, R² is
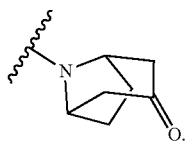 [SMILES: *N1C2CCC1CC(=O)C2]
In some embodiments, R² is
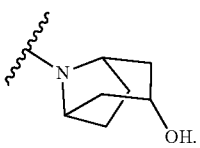 [SMILES: *N1C2CCC1CC(O)C2]
In some embodiments, R² is
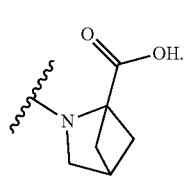
In some embodiments, R² is
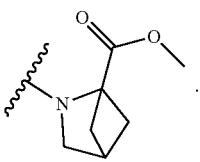 [SMILES: *N1CC2CC1(C(=O)OC)C2]

In some embodiments, R² is
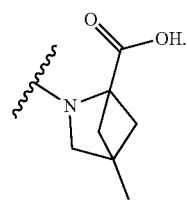 [SMILES: *N1CC2(C)CC1(C(=O)O)C2]
In some embodiments, R² is
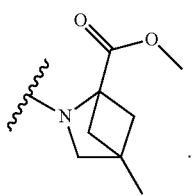 [SMILES: *N1CC2(C)CC1(C(=O)OC)C2]
In some embodiments, R² is
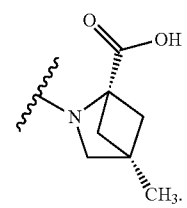
In some embodiments, R² is
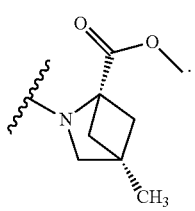 [SMILES: *N1C[C@]2(C)C[C@@]1(C(=O)OC)C2]
In some embodiments, R² is
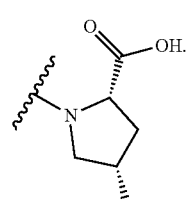
In some embodiments, R² is
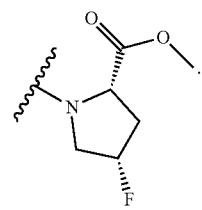 [SMILES: *N1C[C@@H](F)C[C@H]1C(=O)OC]
In some embodiments, R² is
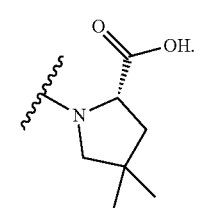 [SMILES: *N1CC(C)(C)C[C@H]1C(=O)O]
In some embodiments, R² is
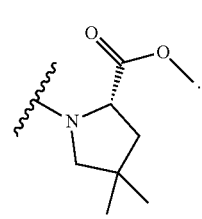 [SMILES: *N1CC(C)(C)C[C@H]1C(=O)OC]
In some embodiments, R² is
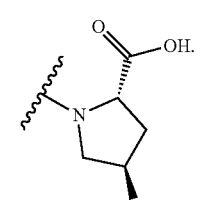
In some embodiments, R² is
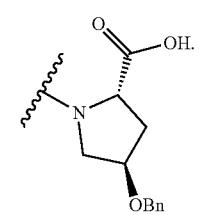 [SMILES: *N1C[C@H](OCc2ccccc2)C[C@H]1C(=O)O]

In some embodiments, R² is
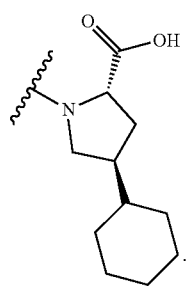 [SMILES: *N1C[C@H](C2CCCCC2)C[C@H]1C(=O)O]
In some embodiments, R² is
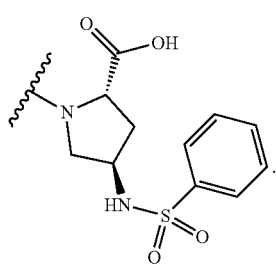 [SMILES: *N1C[C@H](NS(=O)(=O)c2ccccc2)C[C@H]1C(=O)O]
In some embodiments, R² is
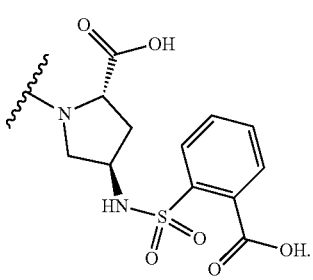 [SMILES: *N1C[C@H](NS(=O)(=O)c2ccccc2C(=O)O)C[C@H]1C(=O)O]
In some embodiments, R² is
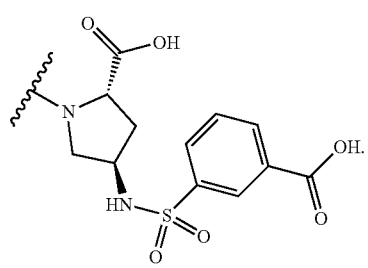 [SMILES: *N1C[C@H](NS(=O)(=O)c2cccc(C(=O)O)c2)C[C@H]1C(=O)O]
In some embodiments, R² is
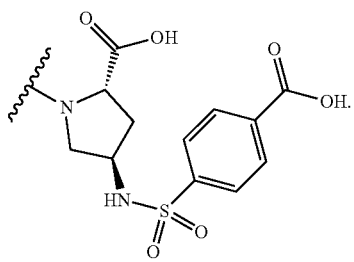 [SMILES: *N1C[C@H](NS(=O)(=O)c2ccc(C(=O)O)cc2)C[C@H]1C(=O)O]
In some embodiments, R² is
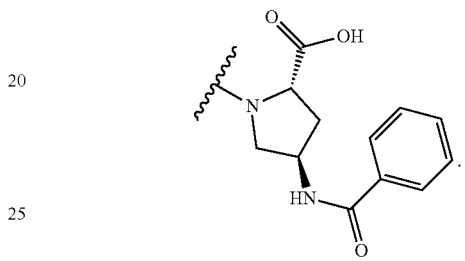
In some embodiments, R² is
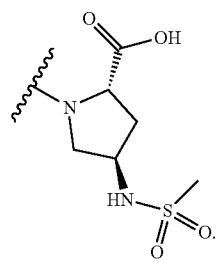 [SMILES: *N1C[C@H](NS(C)(=O)=O)C[C@H]1C(=O)O]
In some embodiments, R² is
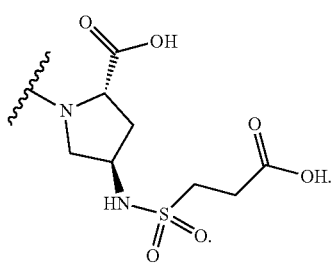 [SMILES: *N1C[C@H](NS(=O)(=O)CCC(=O)O)C[C@H]1C(=O)O]
In some embodiments, R² is
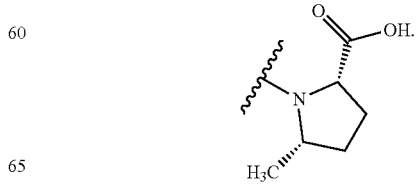

In some embodiments, R² is
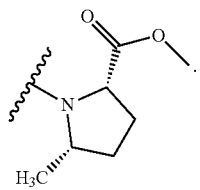 [SMILES: *N1[C@@H](C)CC[C@H]1C(=O)OC]
In some embodiments, R² is
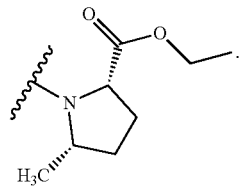
In some embodiments, R² is
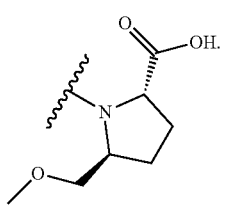 [SMILES: *N1[C@H](COC)CC[C@H]1C(=O)O]
In some embodiments, R² is
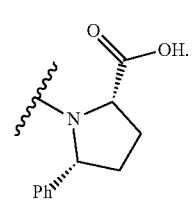 [SMILES: *N1[C@@H](c2ccccc2)CC[C@H]1C(=O)O]
In some embodiments, R² is
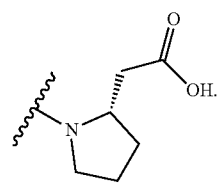 [SMILES: *N1CCC[C@H]1CC(=O)O]
In some embodiments, R² is
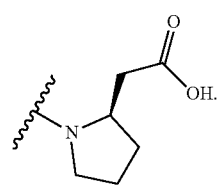 [SMILES: *N1CCC[C@@H]1CC(=O)O]
In some embodiments, R² is
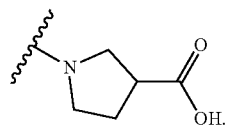 [SMILES: *N1CCC(C(=O)O)C1]
In some embodiments, R² is
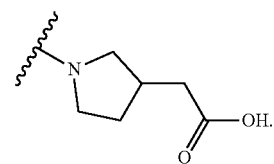 [SMILES: *N1CCC(CC(=O)O)C1]
In some embodiments, R² is
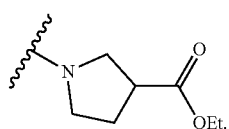 [SMILES: *N1CCC(C(=O)OCC)C1]
In some embodiments, R² is
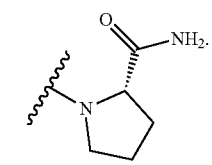 [SMILES: *N1CCC[C@H]1C(N)=O]
In some embodiments, R² is
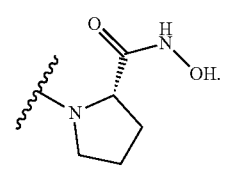 [SMILES: *N1CCC[C@H]1C(=O)NO]
In some embodiments, R² is
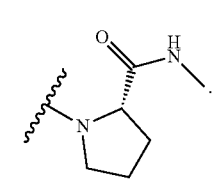 [SMILES: *N1CCC[C@H]1C(=O)NC]

In some embodiments, R² is
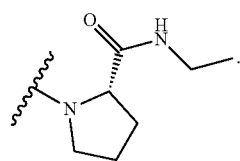 [SMILES: *N1CCC[C@H]1C(=O)NCC]
In some embodiments, R² is
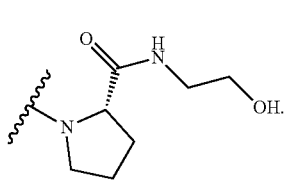 [SMILES: *N1CCC[C@H]1C(=O)NCCO]
In some embodiments, R² is
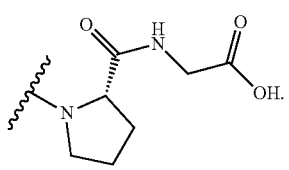 [SMILES: *N1CCC[C@H]1C(=O)NCC(=O)O]
In some embodiments, R² is
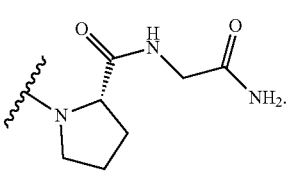 [SMILES: *N1CCC[C@H]1C(=O)NCC(N)=O]
In some embodiments, R² is
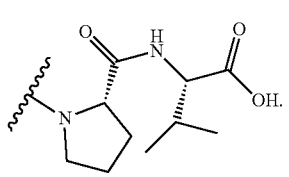 [SMILES: *N1CCC[C@H]1C(=O)N[C@H](C(=O)O)C(C)C]
In some embodiments, R² is
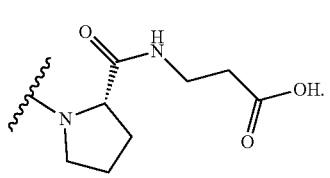 [SMILES: *N1CCC[C@H]1C(=O)NCCC(=O)O]
In some embodiments, R² is
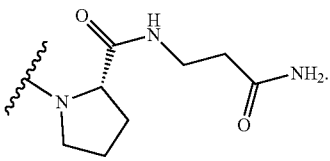 [SMILES: *N1CCC[C@H]1C(=O)NCCC(N)=O]
In some embodiments, R² is
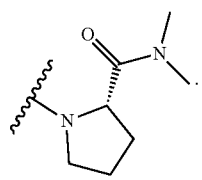 [SMILES: *N1CCC[C@H]1C(=O)N(C)C]
In some embodiments, R² is
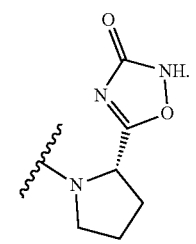 [SMILES: *N1CCC[C@H]1c1nc(=O)[nH]o1]
In some embodiments, R² is
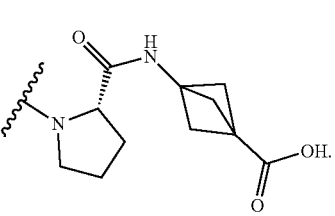 [SMILES: *N1CCC[C@H]1C(=O)NC12CC(C(=O)O)(C1)C2]
In some embodiments, R² is
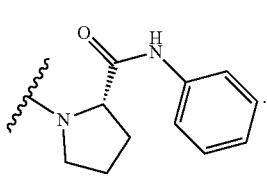 [SMILES: *N1CCC[C@H]1C(=O)Nc1ccccc1]
In some embodiments, R² is
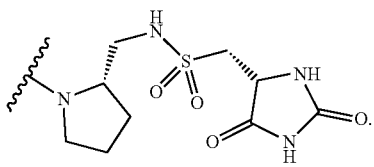

In some embodiments, R² is
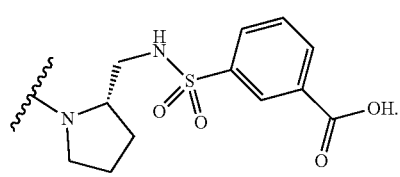 [SMILES: *N1CCC[C@H]1CNS(=O)(=O)c1cccc(C(=O)O)c1]
In some embodiments, R² is
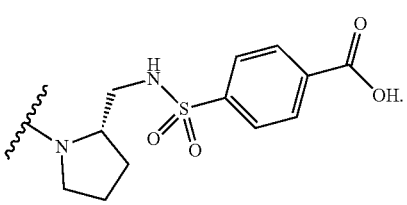 [SMILES: *N1CCC[C@H]1CNS(=O)(=O)c1ccc(C(=O)O)cc1]
In some embodiments, R² is
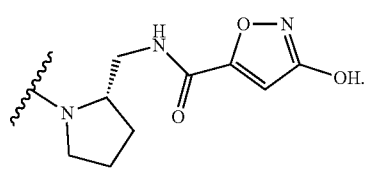 [SMILES: *N1CCC[C@H]1CNC(=O)c1cc(O)no1]
In some embodiments, R² is
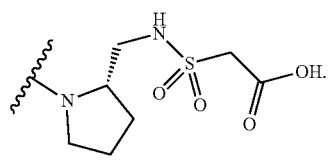 [SMILES: *N1CCC[C@H]1CNS(=O)(=O)CC(=O)O]
In some embodiments, R² is
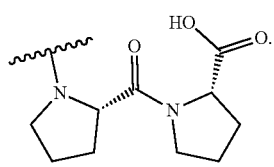 [SMILES: *N1CCC[C@H]1C(=O)N1CCC[C@H]1C(=O)O]
In some embodiments, R² is
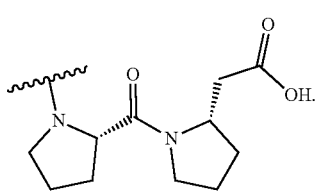 [SMILES: *N1CCC[C@H]1C(=O)N1CCC[C@H]1CC(=O)O]
In some embodiments, R² is
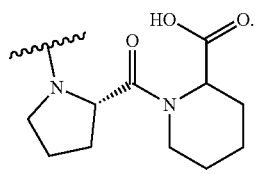 [SMILES: *N1CCC[C@H]1C(=O)N1CCCCC1C(=O)O]
In some embodiments, R² is
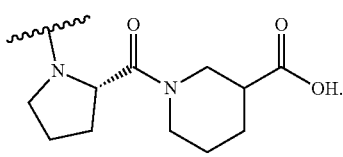 [SMILES: *N1CCC[C@H]1C(=O)N1CCCC(C(=O)O)C1]
In some embodiments, R² is
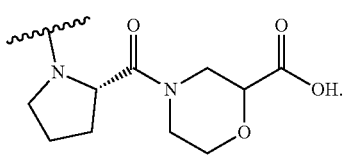
In some embodiments, R² is
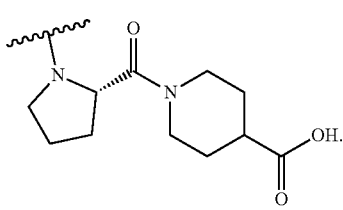 [SMILES: *N1CCC[C@H]1C(=O)N1CCC(C(=O)O)CC1]
In some embodiments, R² is
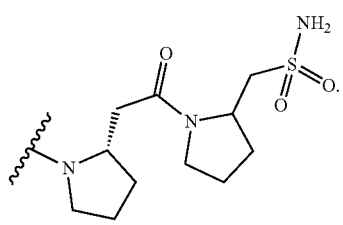 [SMILES: *N1CCC[C@H]1CC(=O)N1CCCC1CS(N)(=O)=O]
In some embodiments, R² is
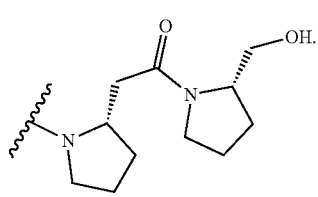 [SMILES: *N1CCC[C@H]1CC(=O)N1CCC[C@H]1CO]

In some embodiments, R² is
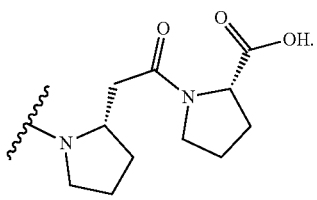 [SMILES: *N1CCC[C@H]1CC(=O)N1CCC[C@H]1C(=O)O]
In some embodiments, R² is
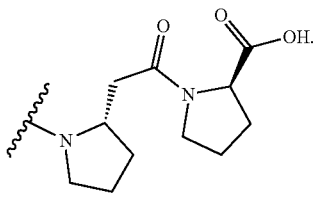 [SMILES: *N1CCC[C@H]1CC(=O)N1CCC[C@@H]1C(=O)O]
In some embodiments, R² is
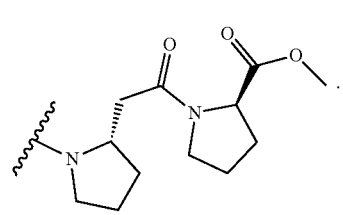 [SMILES: *N1CCC[C@H]1CC(=O)N1CCC[C@@H]1C(=O)OC]
In some embodiments, R² is
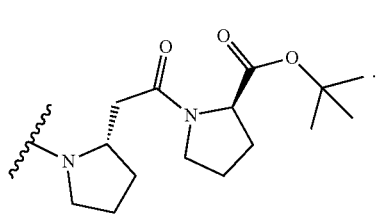 [SMILES: *N1CCC[C@H]1CC(=O)N1CCC[C@@H]1C(=O)OC(C)(C)C]
In some embodiments, R² is
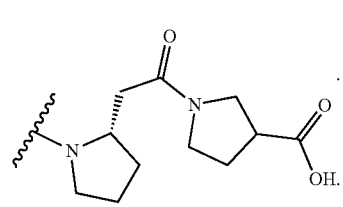 [SMILES: *N1CCC[C@H]1CC(=O)N1CCC(C(=O)O)C1]
In some embodiments, R² is
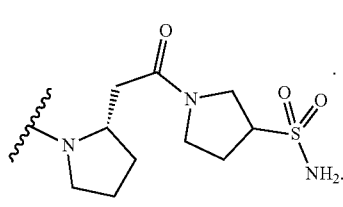 [SMILES: *N1CCC[C@H]1CC(=O)N1CCC(S(N)(=O)=O)C1]
In some embodiments, R² is
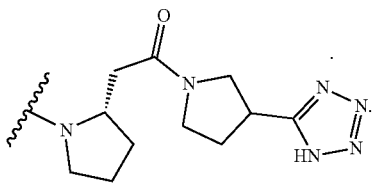 [SMILES: *N1CCC[C@H]1CC(=O)N1CCC(c2nnn[nH]2)C1]
In some embodiments, R² is
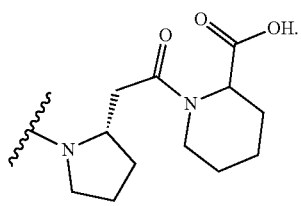 [SMILES: *N1CCC[C@H]1CC(=O)N1CCCCC1C(=O)O]
In some embodiments, R² is
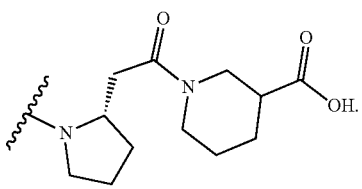 [SMILES: *N1CCC[C@H]1CC(=O)N1CCCC(C(=O)O)C1]
In some embodiments, R² is
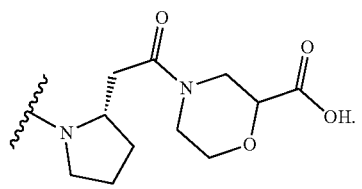 [SMILES: *N1CCC[C@H]1CC(=O)N1CCOC(C(=O)O)C1]
In some embodiments, R² is
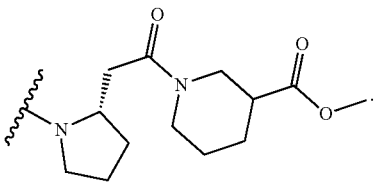 [SMILES: *N1CCC[C@H]1CC(=O)N1CCCC(C(=O)OC)C1]
In some embodiments, R² is
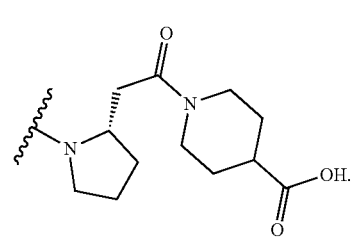 [SMILES: *N1CCC[C@H]1CC(=O)N1CCC(C(=O)O)CC1]

In some embodiments, R² is
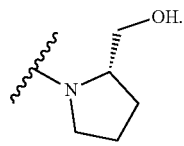 [SMILES: *N1CCC[C@H]1CO]
In some embodiments, R² is embodiments, R² is
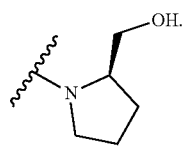 [SMILES: *N1CCC[C@@H]1CO]
In some embodiments, R² is
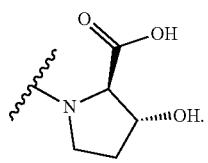 [SMILES: *N1CC[C@@H](O)[C@@H]1C(=O)O]
In some embodiments, R² is
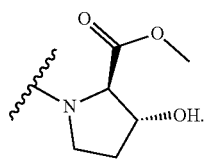 [SMILES: *N1CC[C@@H](O)[C@@H]1C(=O)OC]
In some embodiments, R² is
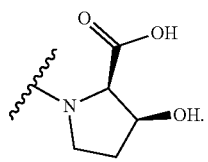 [SMILES: *N1CC[C@H](O)[C@@H]1C(=O)O]
In some embodiments, R² is
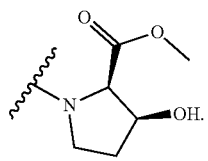 [SMILES: *N1CC[C@H](O)[C@@H]1C(=O)OC]
In some embodiments, R² is
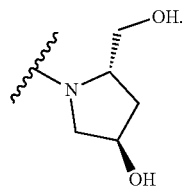 [SMILES: *N1C[C@H](O)C[C@H]1CO]
In some embodiments, R² is
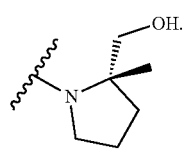 [SMILES: *N1CCC[C@@]1(C)CO]
In some embodiments, R² is
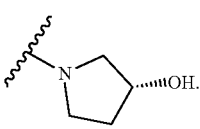 [SMILES: *N1CC[C@@H](O)C1]
In some embodiments, R² is
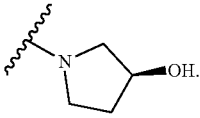 [SMILES: *N1CC[C@H](O)C1]
In some embodiments, R² is
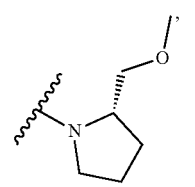 [SMILES: *N1CCC[C@H]1COC]
In some embodiments, R² is
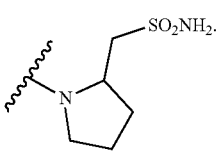 [SMILES: *N1CCCC1CS(N)(=O)=O]

In some embodiments, R² is
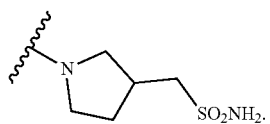 [SMILES: *N1CCC(CS(N)(=O)=O)C1]
In some embodiments, R² is
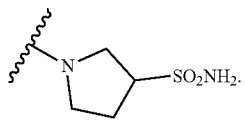
In some embodiments, R² is
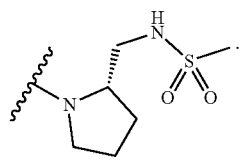 [SMILES: *N1CCC[C@H]1CNS(C)(=O)=O]
In some embodiments, R² is
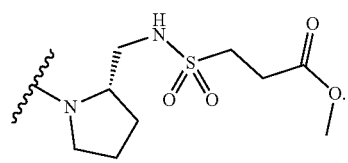 [SMILES: *N1CCC[C@H]1CNS(=O)(=O)CCC(=O)OC]
In some embodiments, R² is
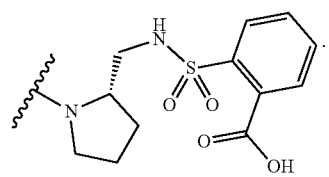 [SMILES: *N1CCC[C@H]1CNS(=O)(=O)c1ccccc1C(=O)O]
In some embodiments, R² is
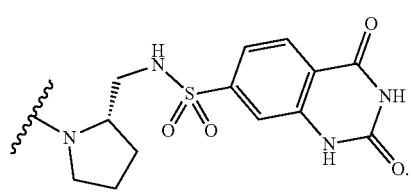 [SMILES: *N1CCC[C@H]1CNS(=O)(=O)c1ccc2c(=O)[nH]c(=O)[nH]c2c1]
In some embodiments, R² is
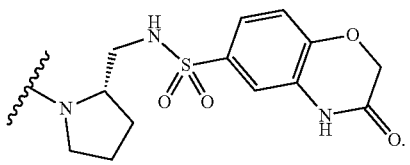 [SMILES: *N1CCC[C@H]1CNS(=O)(=O)c1ccc2c(c1)NC(=O)CO2]
In some embodiments, R² is
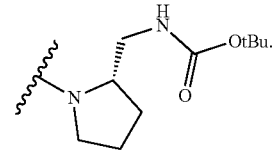 [SMILES: *N1CCC[C@H]1CNC(=O)OC(C)(C)C]
In some embodiments, R² is
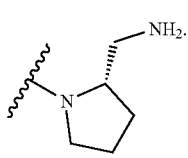
In some embodiments, R² is
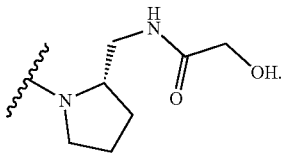 [SMILES: *N1CCC[C@H]1CNC(=O)CO]
In some embodiments, R² is
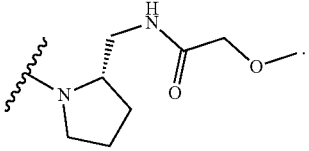 [SMILES: *N1CCC[C@H]1CNC(=O)COC]
In some embodiments, R² is
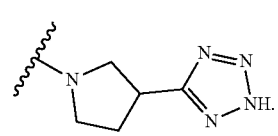

In some embodiments, R² is
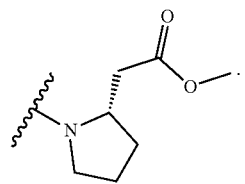 [SMILES: *N1CCC[C@H]1CC(=O)OC]
In some embodiments, R² is
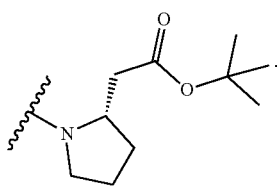 [SMILES: *N1CCC[C@H]1CC(=O)OC(C)(C)C]
In some embodiments, R² is
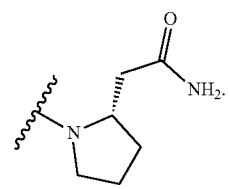 [SMILES: *N1CCC[C@H]1CC(N)=O]
In some embodiments, R² is
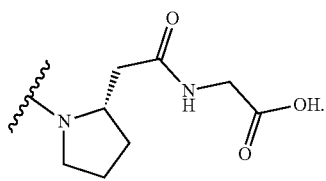 [SMILES: *N1CCC[C@H]1CC(=O)NCC(=O)O]
In some embodiments, R² is
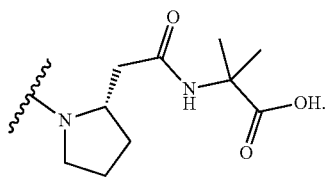 [SMILES: *N1CCC[C@H]1CC(=O)NC(C)(C)C(=O)O]
In some embodiments, R² is
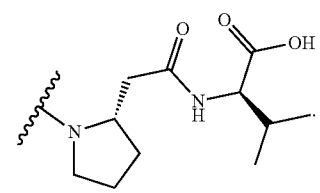 [SMILES: *N1CCC[C@H]1CC(=O)N[C@@H](C(=O)O)C(C)C]
In some embodiments, R² is
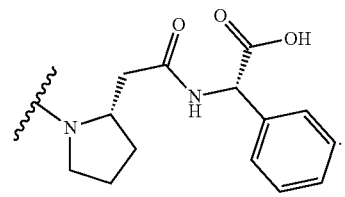 [SMILES: *N1CCC[C@H]1CC(=O)N[C@H](C(=O)O)c1ccccc1]
In some embodiments, R² is
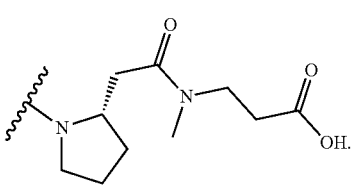 [SMILES: *N1CCC[C@H]1CC(=O)N(C)CCC(=O)O]
In some embodiments, R² is
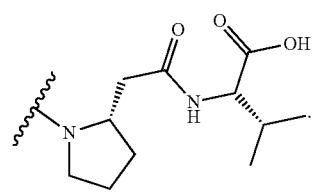
In some embodiments, R² is
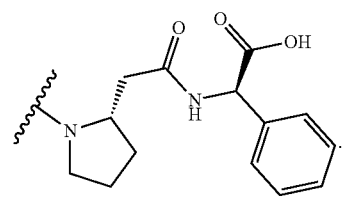 [SMILES: *N1CCC[C@H]1CC(=O)N[C@@H](C(=O)O)c1ccccc1]
In some embodiments, R² is
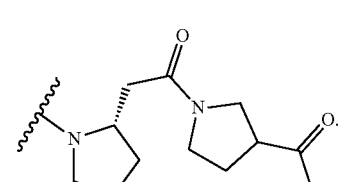
In some embodiments, R² is
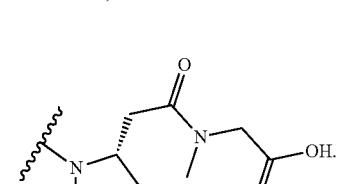

In some embodiments, R² is
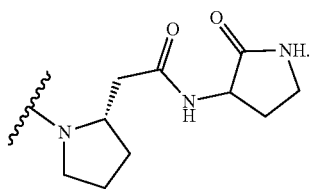 [SMILES: *N1CCC[C@H]1CC(=O)NC1CCNC1=O]
In some embodiments, R² is
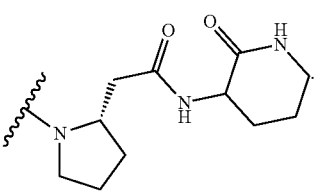 [SMILES: *N1CCC[C@H]1CC(=O)NC1CCCNC1=O]
In some embodiments, R² is
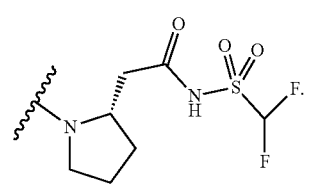 [SMILES: *N1CCC[C@H]1CC(=O)NS(=O)(=O)C(F)F]
In some embodiments, R² is
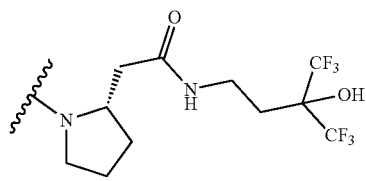 [SMILES: *N1CCC[C@H]1CC(=O)NCCC(O)(C(F)(F)F)C(F)(F)F]
In some embodiments, R² is
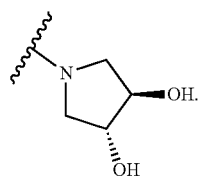 [SMILES: *N1C[C@@H](O)[C@H](O)C1]
In some embodiments, R² is
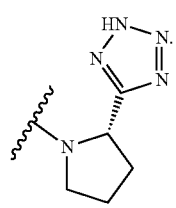 [SMILES: *N1CCC[C@H]1c1nn[nH]n1]
In some embodiments, R² is
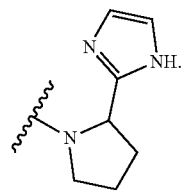 [SMILES: *N1CCCC1c1ncc[nH]1]
In some embodiments, R² is
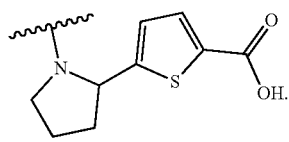 [SMILES: *N1CCCC1c1ccc(C(=O)O)s1]
In some embodiments, R² is
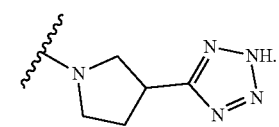 [SMILES: *N1CCC(c2nn[nH]n2)C1]
In some embodiments, R² is
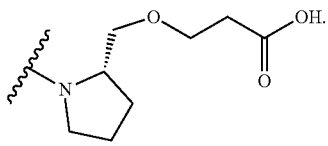 [SMILES: *N1CCC[C@H]1COCCC(=O)O]
In some embodiments, R² is
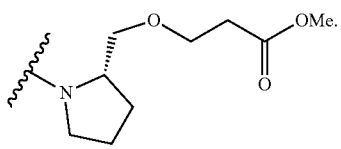 [SMILES: *N1CCC[C@H]1COCCC(=O)OC]
In some embodiments, R² is
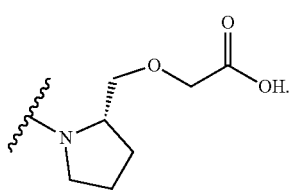 [SMILES: *N1CCC[C@H]1COCC(=O)O]

In some embodiments, R² is
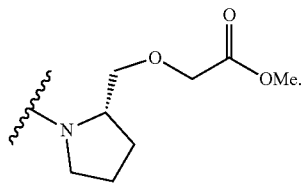 [SMILES: *N1CCC[C@H]1COCC(=O)OC]
In some embodiments, R² is
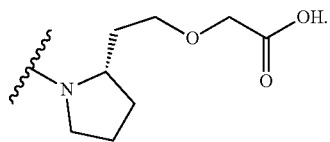 [SMILES: *N1CCC[C@H]1CCOCC(=O)O]
In some embodiments, R² is
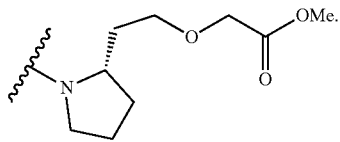 [SMILES: *N1CCC[C@H]1CCOCC(=O)OC]
In some embodiments, R² is
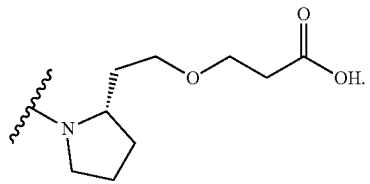 [SMILES: *N1CCC[C@H]1CCOCCC(=O)O]
In some embodiments, R² is
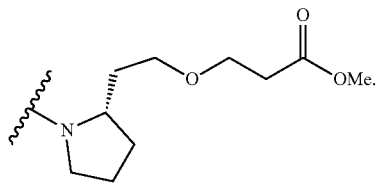 [SMILES: *N1CCC[C@H]1CCOCCC(=O)OC]
In some embodiments, R² is
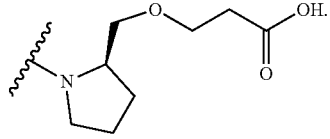 [SMILES: *N1CCC[C@@H]1COCCC(=O)O]
In some embodiments, R² is
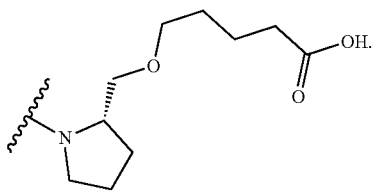 [SMILES: *N1CCC[C@H]1COCCCCC(=O)O]
In some embodiments, R² is
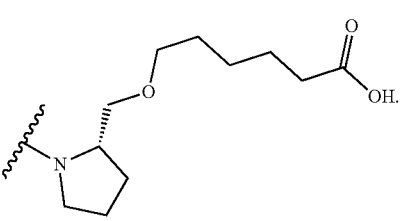 [SMILES: *N1CCC[C@H]1COCCCCCC(=O)O]
In some embodiments, R² is
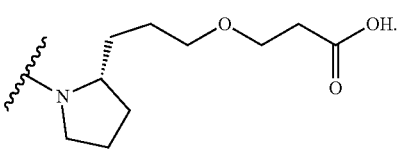 [SMILES: *N1CCC[C@H]1CCCOCCC(=O)O]
In some embodiments, R² is
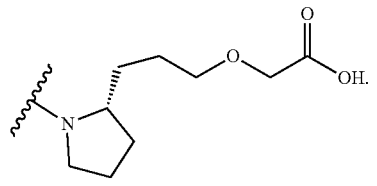 [SMILES: *N1CCC[C@H]1CCCOCC(=O)O]
In some embodiments, R² is
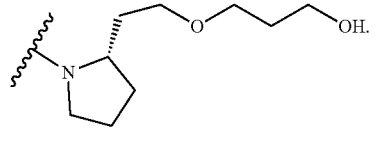 [SMILES: *N1CCC[C@H]1CCOCCCO]
In some embodiments, R² is
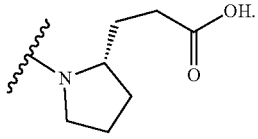 [SMILES: *N1CCC[C@H]1CCC(=O)O]

In some embodiments, R² is
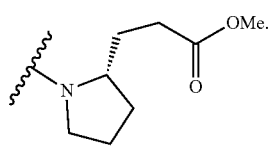 [SMILES: *N1CCC[C@H]1CCC(=O)OC]
In some embodiments, R² is
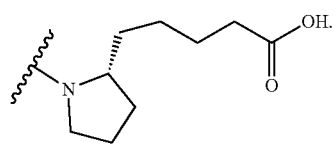 [SMILES: *N1CCC[C@H]1CCCCC(=O)O]
In some embodiments, R² is
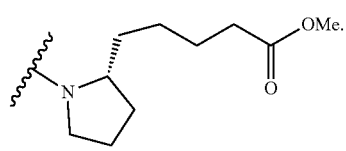 [SMILES: *N1CCC[C@H]1CCCCC(=O)OC]
In some embodiments, R² is
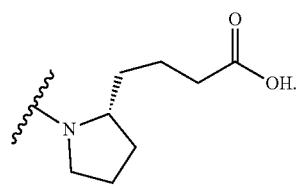 [SMILES: *N1CCC[C@H]1CCCC(=O)O]
In some embodiments, R² is
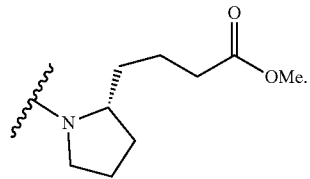 [SMILES: *N1CCC[C@H]1CCCC(=O)OC]
In some embodiments, R² is
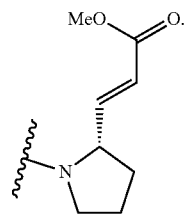 [SMILES: *N1CCC[C@H]1/C=C/C(=O)OC]
In some embodiments, R² is
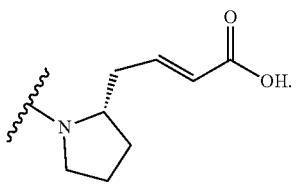 [SMILES: *N1CCC[C@H]1C/C=C/C(=O)O]
In some embodiments, R² is
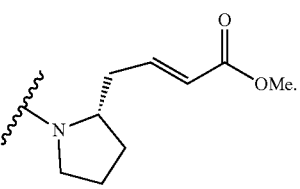 [SMILES: *N1CCC[C@H]1C/C=C/C(=O)OC]
In some embodiments, R² is
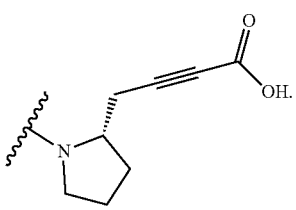 [SMILES: *N1CCC[C@H]1CC#CC(=O)O]
In some embodiments, R² is
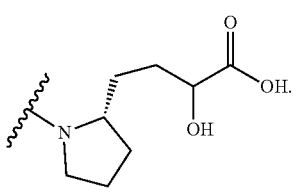 [SMILES: *N1CCC[C@H]1CCC(O)C(=O)O]
In some embodiments, R² is
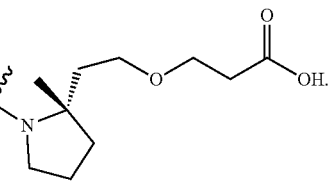
In some embodiments, R² is
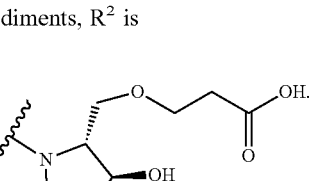

In some embodiments, R² is
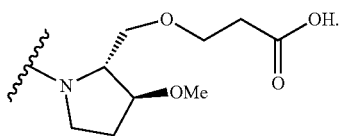 [SMILES: *N1CC[C@H](OC)[C@H]1COCCC(=O)O]
In some embodiments, R² is
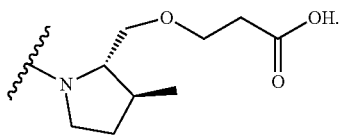 [SMILES: *N1CC[C@H](C)[C@H]1COCCC(=O)O]
In some embodiments, R² is
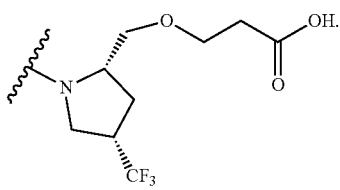 [SMILES: *N1C[C@@H](C(F)(F)F)C[C@H]1COCCC(=O)O]
In some embodiments, R² is
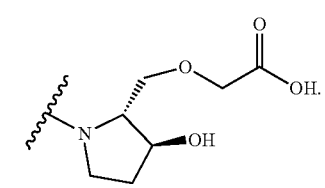 [SMILES: *N1CC[C@H](O)[C@H]1COCC(=O)O]
In some embodiments, R² is
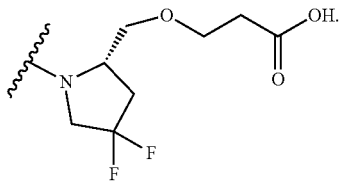 [SMILES: *N1CC(F)(F)C[C@H]1COCCC(=O)O]
In some embodiments, R² is
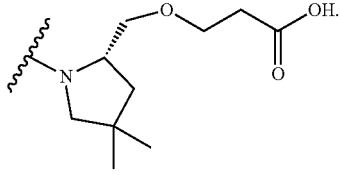 [SMILES: *N1CC(C)(C)C[C@H]1COCCC(=O)O]
In some embodiments, R² is
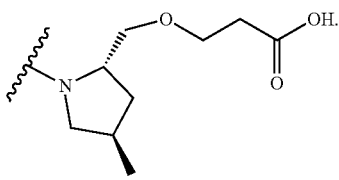 [SMILES: *N1C[C@H](C)C[C@H]1COCCC(=O)O]
In some embodiments, R² is
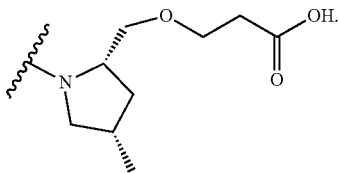 [SMILES: *N1C[C@@H](C)C[C@H]1COCCC(=O)O]
In some embodiments, R² is
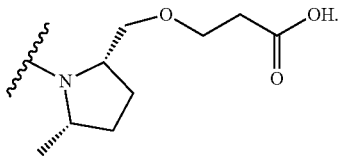 [SMILES: *N1[C@H](COCCC(=O)O)CC[C@@H]1C]
In some embodiments, R² is
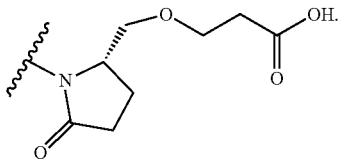 [SMILES: *N1C(=O)CC[C@H]1COCCC(=O)O]
In some embodiments, R² is
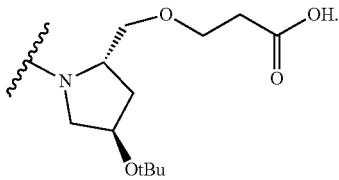 [SMILES: *N1C[C@H](OC(C)(C)C)C[C@H]1COCCC(=O)O]
In some embodiments, R² is
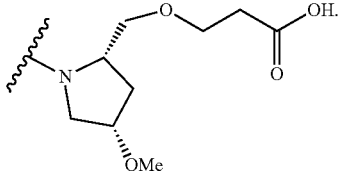 [SMILES: *N1C[C@@H](OC)C[C@H]1COCCC(=O)O]

In some embodiments, R² is
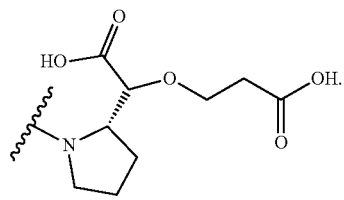 [SMILES: *N1CCC[C@H]1C(OCCC(=O)O)C(=O)O]
In some embodiments, R² is
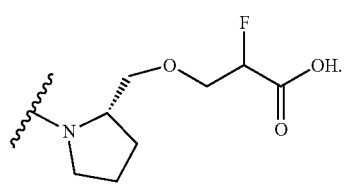 [SMILES: *N1CCC[C@H]1COCC(F)C(=O)O]
In some embodiments, R² is
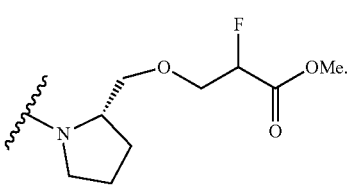 [SMILES: *N1CCC[C@H]1COCC(F)C(=O)OC]
In some embodiments, R² is
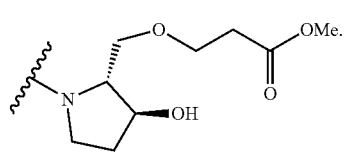 [SMILES: *N1CC[C@H](O)[C@H]1COCCC(=O)OC]
In some embodiments, R² is
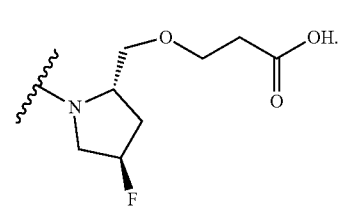 [SMILES: *N1C[C@H](F)C[C@H]1COCCC(=O)O]
In some embodiments, R² is
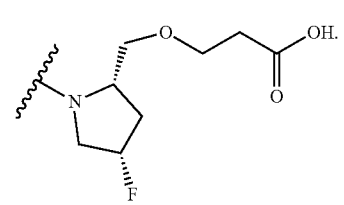 [SMILES: *N1C[C@@H](F)C[C@H]1COCCC(=O)O]
In some embodiments, R² is
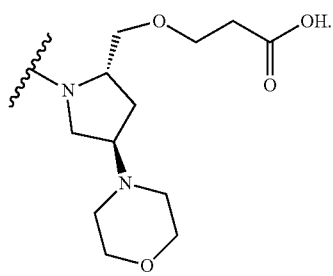 [SMILES: *N1C[C@H](N2CCOCC2)C[C@H]1COCCC(=O)O]
In some embodiments, R² is
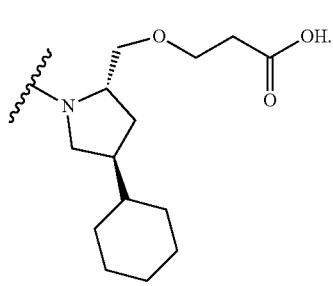 [SMILES: *N1C[C@H](C2CCCCC2)C[C@H]1COCCC(=O)O]
In some embodiments, R² is
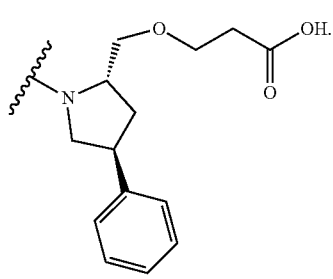 [SMILES: *N1C[C@H](c2ccccc2)C[C@H]1COCCC(=O)O]
In some embodiments, R² is
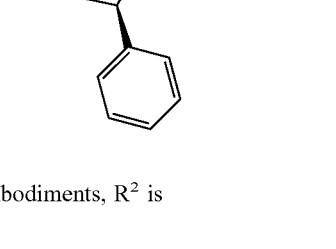
In some embodiments, R² is
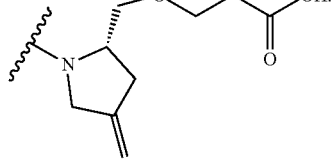
In some embodiments, R² is
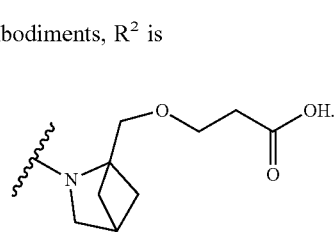

In some embodiments, $R^2$ is
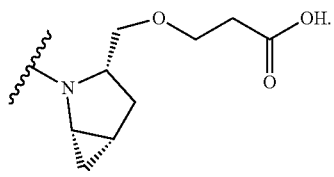 [SMILES: *N1[C@H](COCCC(=O)O)C[C@@H]2C[C@@H]21]
In some embodiments, $R^2$ is
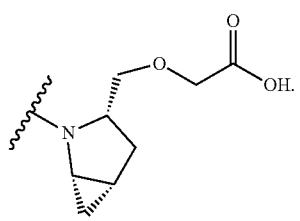 [SMILES: *N1[C@H](COCC(=O)O)C[C@@H]2C[C@@H]21]
In some embodiments, $R^2$ is
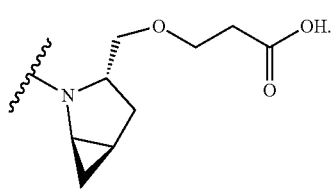 [SMILES: *N1[C@H](COCCC(=O)O)C[C@H]2C[C@H]21]
In some embodiments, $R^2$ is
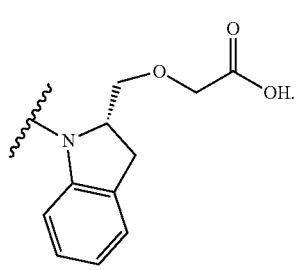 [SMILES: *N1c2ccccc2C[C@H]1COCC(=O)O]
In some embodiments, $R^2$ is
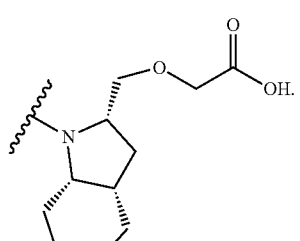
In some embodiments, $R^2$ is
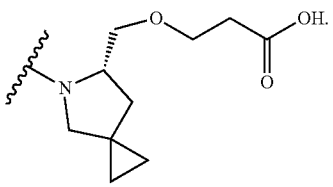 [SMILES: *N1CC2(CC2)C[C@H]1COCCC(=O)O]
In some embodiments, $R^2$ is
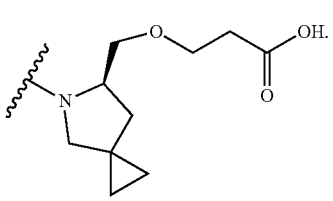 [SMILES: *N1CC2(CC2)C[C@@H]1COCCC(=O)O]
In some embodiments, $R^2$ is
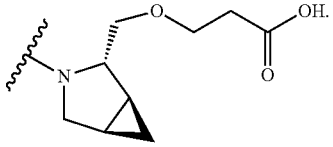 [SMILES: *N1C[C@@H]2C[C@@H]2[C@H]1COCCC(=O)O]
In some embodiments, $R^2$ is
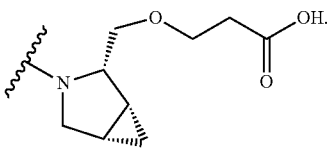 [SMILES: *N1C[C@H]2C[C@H]2[C@H]1COCCC(=O)O]
In some embodiments, $R^2$ is
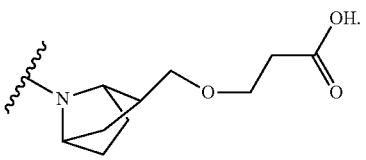 [SMILES: *N1C2CCC1C(COCCC(=O)O)C2]
In some embodiments, $R^2$ is
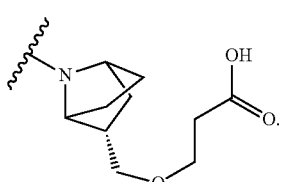

In some embodiments, $R^2$ is
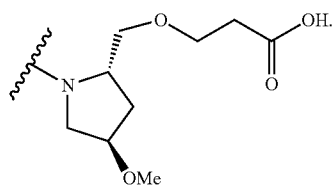 [SMILES: *N1C[C@H](OC)C[C@H]1COCCC(=O)O]
In some embodiments, $R^2$ is
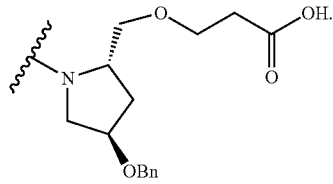 [SMILES: *N1C[C@H](OCc2ccccc2)C[C@H]1COCCC(=O)O]
In some embodiments, $R^2$ is
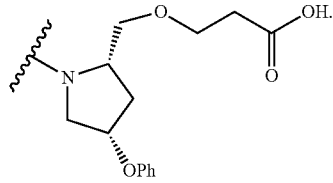 [SMILES: *N1C[C@@H](Oc2ccccc2)C[C@H]1COCCC(=O)O]
In some embodiments, $R^2$ is
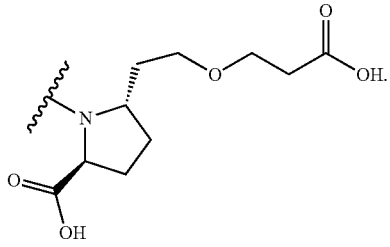 [SMILES: *N1[C@H](CCOCCC(=O)O)CC[C@H]1C(=O)O]
In some embodiments, $R^2$ is
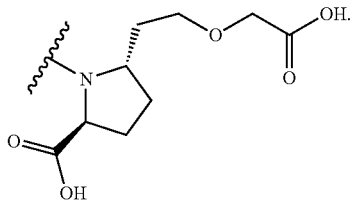 [SMILES: *N1[C@H](CCOCC(=O)O)CC[C@H]1C(=O)O]
In some embodiments, $R^2$ is
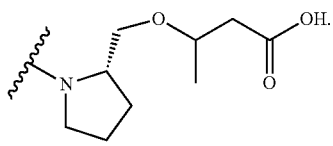 [SMILES: *N1CCC[C@H]1COC(C)CC(=O)O]
In some embodiments, $R^2$ is
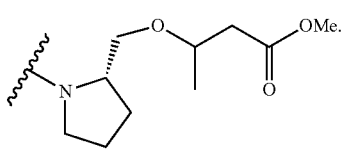 [SMILES: *N1CCC[C@H]1COC(C)CC(=O)OC]
In some embodiments, $R^2$ is
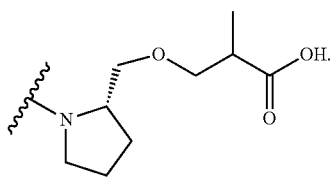 [SMILES: *N1CCC[C@H]1COCC(C)C(=O)O]
In some embodiments, $R^2$ is
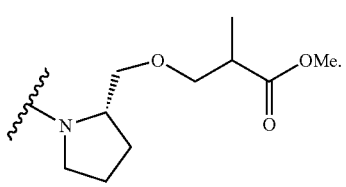 [SMILES: *N1CCC[C@H]1COCC(C)C(=O)OC]
In some embodiments, $R^2$ is
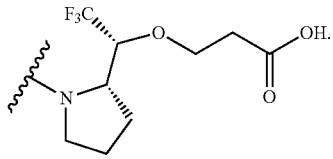 [SMILES: *N1CCC[C@H]1[C@@H](OCCC(=O)O)C(F)(F)F]
In some embodiments, $R^2$ is
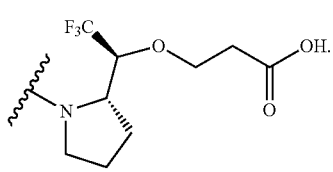 [SMILES: *N1CCC[C@H]1[C@H](OCCC(=O)O)C(F)(F)F]

In some embodiments, R² is
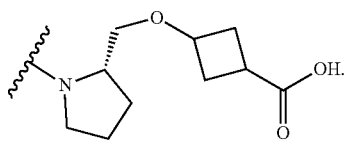 [SMILES: *N1CCC[C@H]1COC1CC(C(=O)O)C1]
In some embodiments, R² is
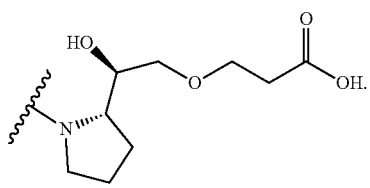 [SMILES: *N1CCC[C@H]1[C@@H](O)COCCC(=O)O]
In some embodiments, R² is
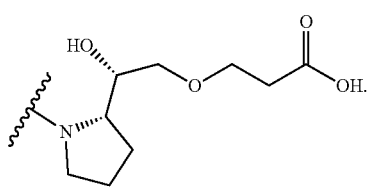 [SMILES: *N1CCC[C@H]1[C@H](O)COCCC(=O)O]
In some embodiments, R² is
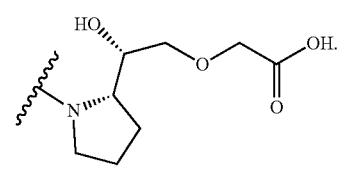 [SMILES: *N1CCC[C@H]1[C@H](O)COCC(=O)O]
In some embodiments, R² is
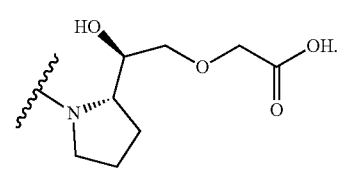 [SMILES: *N1CCC[C@H]1[C@@H](O)COCC(=O)O]
In some embodiments, R² is
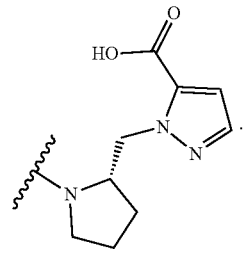 [SMILES: *N1CCC[C@H]1Cn1nccc1C(=O)O]
In some embodiments, R² is
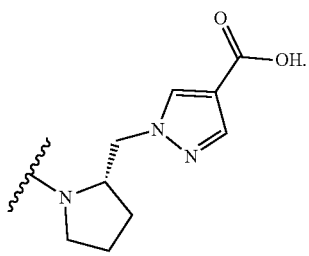 [SMILES: *N1CCC[C@H]1Cn1cc(C(=O)O)cn1]
In some embodiments, R² is
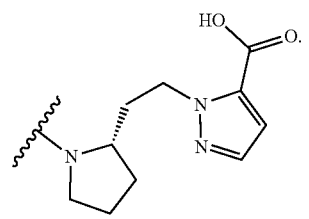 [SMILES: *N1CCC[C@H]1CCn1nccc1C(=O)O]
In some embodiments, R² is
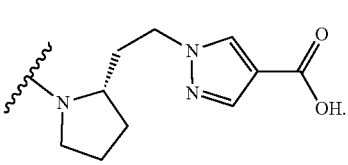 [SMILES: *N1CCC[C@H]1CCn1cc(C(=O)O)cn1]
In some embodiments, R² is
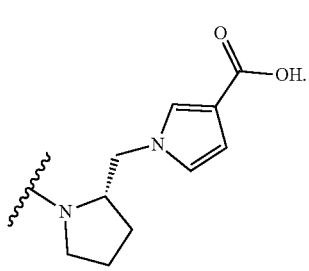 [SMILES: *N1CCC[C@H]1Cn1ccc(C(=O)O)c1]
In some embodiments, R² is
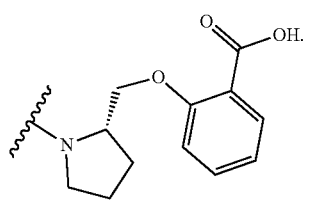 [SMILES: *N1CCC[C@H]1COc1ccccc1C(=O)O]

In some embodiments, R² is
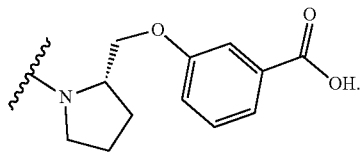 [SMILES: *N1CCC[C@H]1COc1cccc(C(=O)O)c1]
In some embodiments, R² is
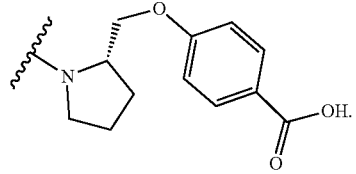 [SMILES: *N1CCC[C@H]1COc1ccc(C(=O)O)cc1]
In some embodiments, R² is
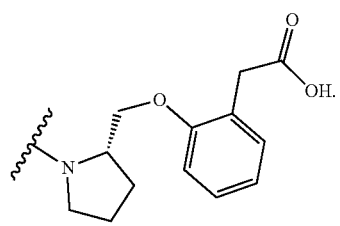 [SMILES: *N1CCC[C@H]1COc1ccccc1CC(=O)O]
In some embodiments, R² is
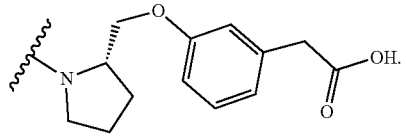 [SMILES: *N1CCC[C@H]1COc1cccc(CC(=O)O)c1]
In some embodiments, R² is
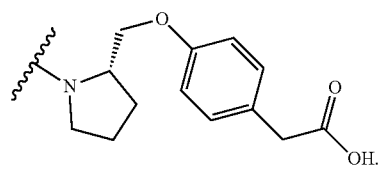 [SMILES: *N1CCC[C@H]1COc1ccc(CC(=O)O)cc1]
In some embodiments, R² is
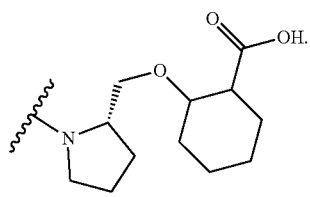 [SMILES: *N1CCC[C@H]1COC1CCCCC1C(=O)O]
In some embodiments, R² is
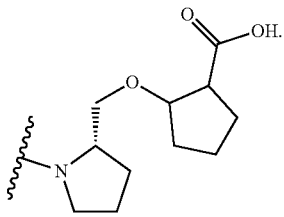 [SMILES: *N1CCC[C@H]1COC1CCCC1C(=O)O]
In some embodiments, R² is
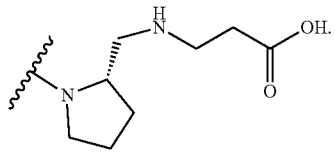 [SMILES: *N1CCC[C@H]1CNCCC(=O)O]
In some embodiments, R² is
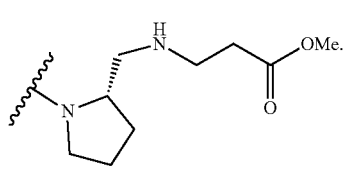 [SMILES: *N1CCC[C@H]1CNCCC(=O)OC]
In some embodiments, R² is
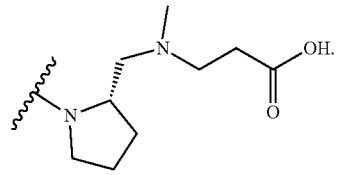 [SMILES: *N1CCC[C@H]1CN(C)CCC(=O)O]
In some embodiments, R² is
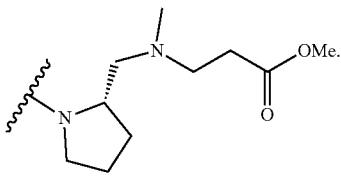 [SMILES: *N1CCC[C@H]1CN(C)CCC(=O)OC]
In some embodiments, R² is
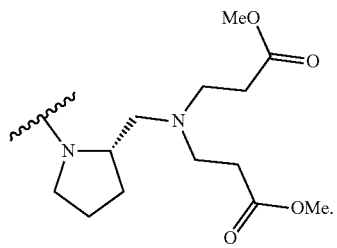 [SMILES: *N1CCC[C@H]1CN(CCC(=O)OC)CCC(=O)OC]

In some embodiments, R² is
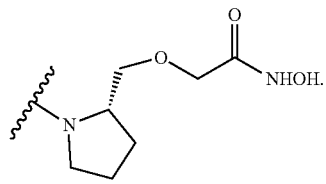
In some embodiments, R² is
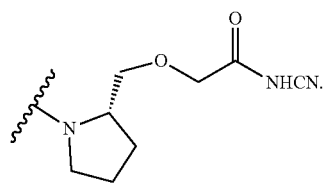
In some embodiments, R² is
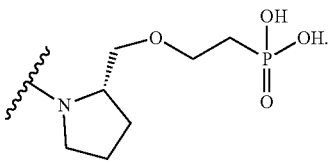 [SMILES: *N1CCC[C@H]1COCCP(=O)(O)O]
In some embodiments, R² is
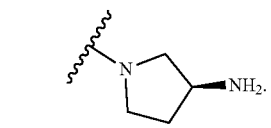 [SMILES: *N1CC[C@H](N)C1]
In some embodiments, R² is
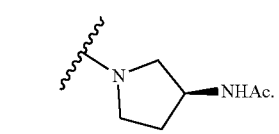 [SMILES: *N1CC[C@H](NC(C)=O)C1]
In some embodiments, R² is
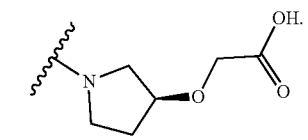 [SMILES: *N1CC[C@H](OCC(=O)O)C1]
In some embodiments, R² is
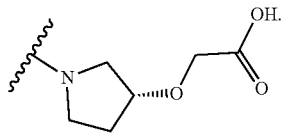 [SMILES: *N1CC[C@@H](OCC(=O)O)C1]
In some embodiments, R² is
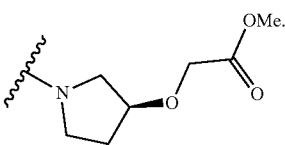 [SMILES: *N1CC[C@H](OCC(=O)OC)C1]
In some embodiments, R² is
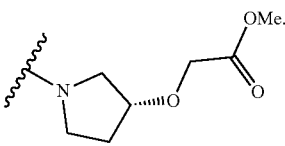 [SMILES: *N1CC[C@@H](OCC(=O)OC)C1]
In some embodiments, R² is
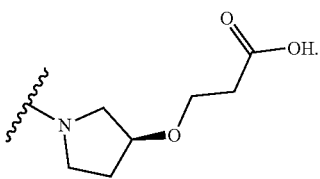 [SMILES: *N1CC[C@H](OCCC(=O)O)C1]
In some embodiments, R² is
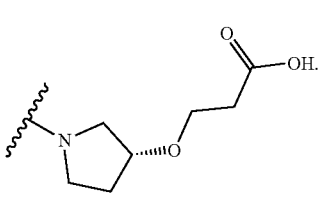 [SMILES: *N1CC[C@@H](OCCC(=O)O)C1]
In some embodiments, R² is
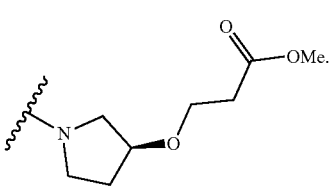 [SMILES: *N1CC[C@H](OCCC(=O)OC)C1]

In some embodiments, R² is
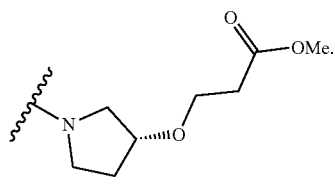 [SMILES: *N1CC[C@@H](OCCC(=O)OC)C1]
In some embodiments, R² is
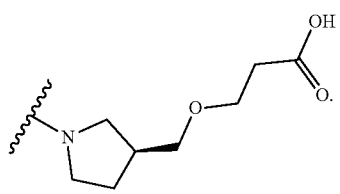 [SMILES: *N1CC[C@H](COCCC(=O)O)C1]
In some embodiments, R² is
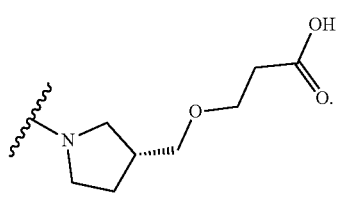 [SMILES: *N1CC[C@@H](COCCC(=O)O)C1]
In some embodiments, R² is
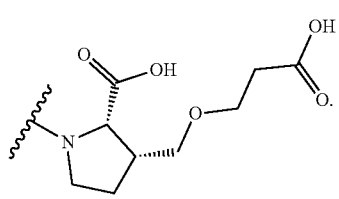 [SMILES: *N1CC[C@@H](COCCC(=O)O)[C@H]1C(=O)O]
In some embodiments, R² is
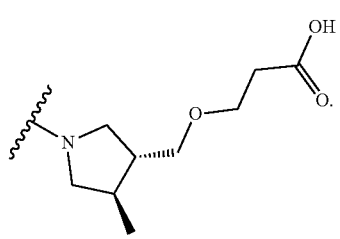 [SMILES: *N1C[C@H](COCCC(=O)O)[C@@H](C)C1]
In some embodiments, R² is
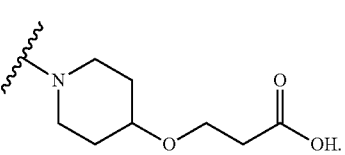 [SMILES: *N1CCC(OCCC(=O)O)CC1]
In some embodiments, R² is
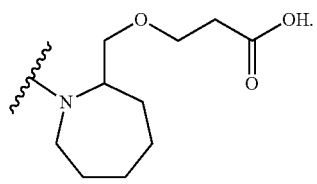 [SMILES: *N1CCCCCC1COCCC(=O)O]
In some embodiments, R² is
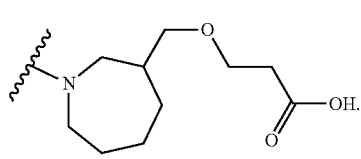
In some embodiments, R² is
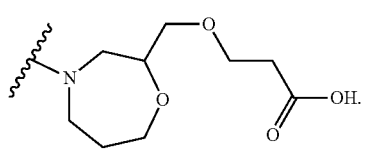
In some embodiments, R² is
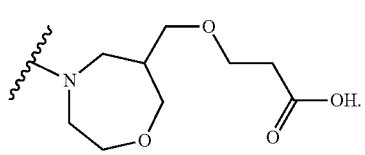 [SMILES: *N1CCCCC(COCCC(=O)O)C1]
In some embodiments, R² is
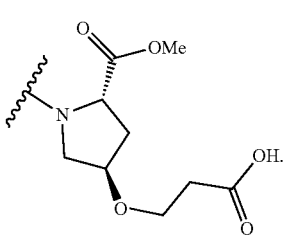 [SMILES: *N1C[C@H](OCCC(=O)O)C[C@H]1C(=O)OC]
In some embodiments, R² is
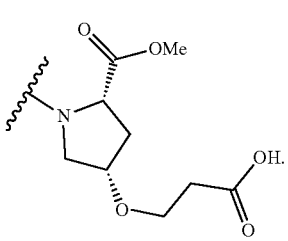 [SMILES: *N1C[C@@H](OCCC(=O)O)C[C@H]1C(=O)OC]

In some embodiments, R² is
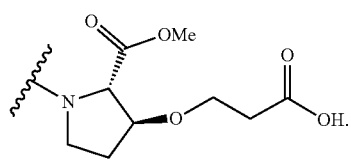 [SMILES: *N1CC[C@H](OCCC(=O)O)[C@H]1C(=O)OC]
In some embodiments, R² is
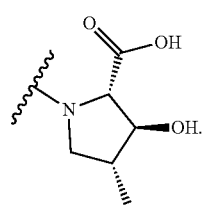 [SMILES: *N1C[C@@H](C)[C@H](O)[C@H]1C(=O)O]
In some embodiments, R² is
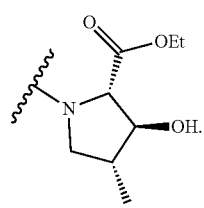 [SMILES: *N1C[C@@H](C)[C@H](O)[C@H]1C(=O)OCC]
In some embodiments, R² is
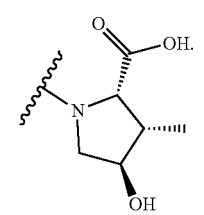 [SMILES: *N1C[C@H](O)[C@@H](C)[C@H]1C(=O)O]
In some embodiments, R² is
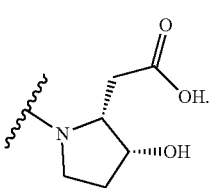 [SMILES: *N1CC[C@@H](O)[C@H]1CC(=O)O]
In some embodiments, R² is
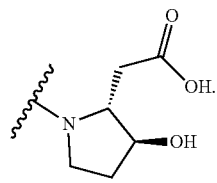 [SMILES: *N1CC[C@H](O)[C@H]1CC(=O)O]
In some embodiments, R² is
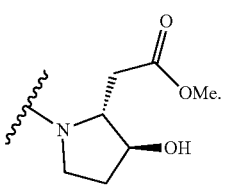 [SMILES: *N1CC[C@H](O)[C@H]1CC(=O)OC]
In some embodiments, R² is
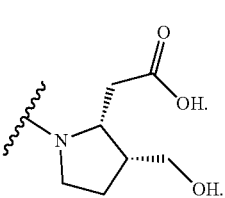 [SMILES: *N1CC[C@@H](CO)[C@H]1CC(=O)O]
In some embodiments, R² is
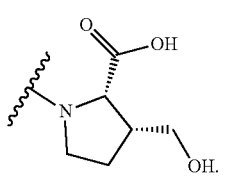 [SMILES: *N1CC[C@@H](CO)[C@H]1C(=O)O]
In some embodiments, R² is
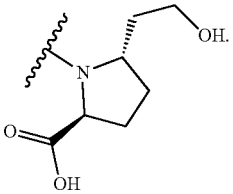 [SMILES: *N1[C@H](CCO)CC[C@H]1C(=O)O]
In some embodiments, R² is
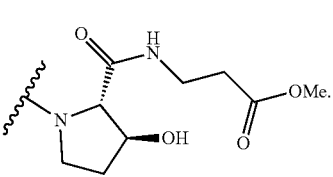 [SMILES: *N1CC[C@H](O)[C@H]1C(=O)NCCC(=O)OC]

In some embodiments, R² is
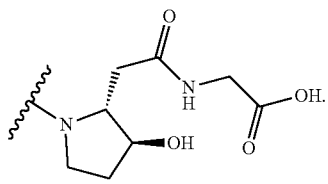 [SMILES: *N1CC[C@H](O)[C@H]1CC(=O)NCC(=O)O]
In some embodiments, R² is
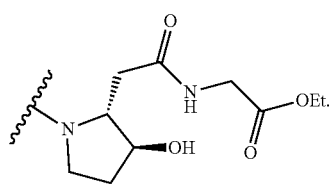 [SMILES: *N1CC[C@H](O)[C@H]1CC(=O)NCC(=O)OCC]
In some embodiments, R² is
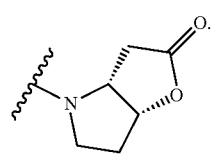 [SMILES: *N1CC[C@H]2OC(=O)C[C@H]21]
In some embodiments, R² is
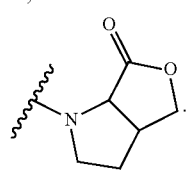
In some embodiments, R² is
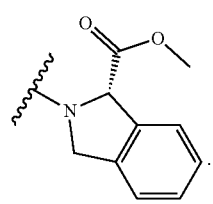 [SMILES: *N1Cc2ccccc2[C@H]1C(=O)OC]
In some embodiments, R² is
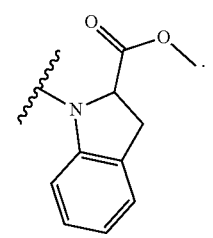 [SMILES: *N1c2ccccc2CC1C(=O)OC]
In some embodiments, R² is
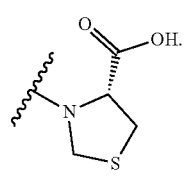 [SMILES: *N1CSC[C@H]1C(=O)O]
In some embodiments, R² is
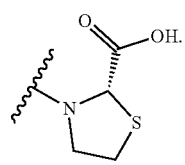 [SMILES: *N1CCS[C@H]1C(=O)O]
In some embodiments, R² is
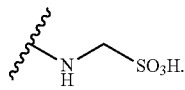 [SMILES: *NCS(=O)(=O)O]
In some embodiments, R² is
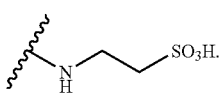
In some embodiments, R² is
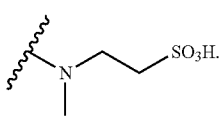 [SMILES: *N(C)CCS(=O)(=O)O]
In some embodiments, R² is
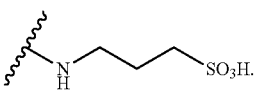 [SMILES: *NCCCS(=O)(=O)O]
In some embodiments, R² is
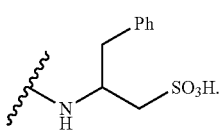

In some embodiments, $R^2$ is
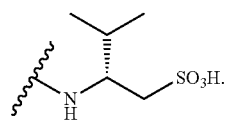
In some embodiments, $R^2$ is
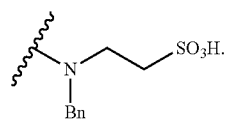
In some embodiments, $R^2$ is
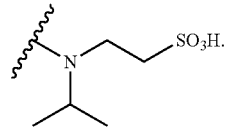 [SMILES: *N(CCS(=O)(=O)O)C(C)C]
In some embodiments, $R^2$ is
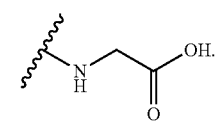
In some embodiments, $R^2$ is
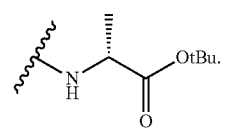 [SMILES: *N[C@H](C)C(=O)OC(C)(C)C]
In some embodiments, $R^2$ is
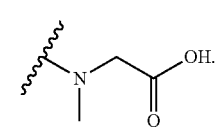 [SMILES: *N(C)CC(=O)O]
In some embodiments, $R^2$ is
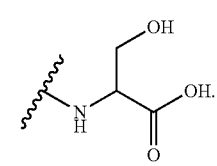 [SMILES: *NC(CO)C(=O)O]
In some embodiments, $R^2$ is
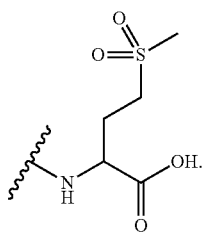 [SMILES: *NC(CCS(C)(=O)=O)C(=O)O]
In some embodiments, $R^2$ is
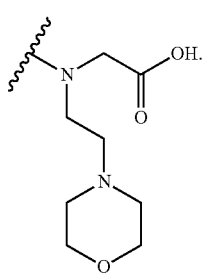 [SMILES: *N(CCN1CCOCC1)CC(=O)O]
In some embodiments, $R^2$ is
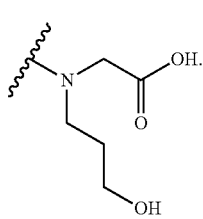 [SMILES: *N(CCCO)CC(=O)O]
In some embodiments, $R^2$ is
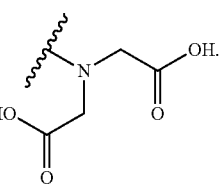
In some embodiments, $R^2$ is
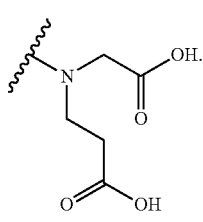 [SMILES: *N(CCC(=O)O)CC(=O)O]

In some embodiments, R² is

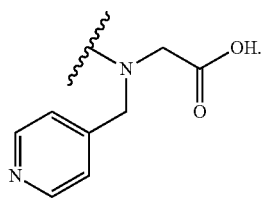 [SMILES: *N(CC(=O)O)Cc1ccncc1]

In some embodiments, R² is

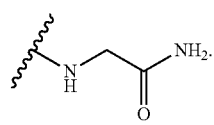

In some embodiments, R² is

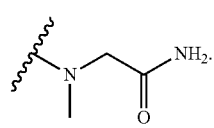 [SMILES: *N(C)CC(N)=O]

In some embodiments, R² is

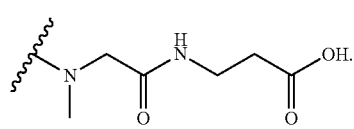 [SMILES: *N(C)CC(=O)NCCC(=O)O]

In some embodiments, R² is

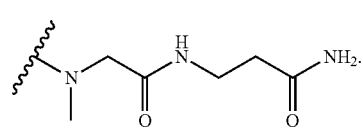 [SMILES: *N(C)CC(=O)NCCC(N)=O]

In some embodiments, R² is

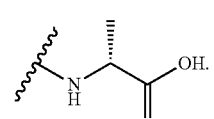

In some embodiments, R² is

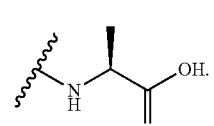

In some embodiments, R² is

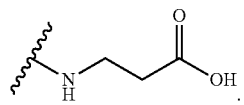

In some embodiments, R² is

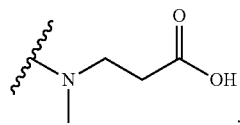 [SMILES: *N(C)CCC(=O)O]

In some embodiments, R² is

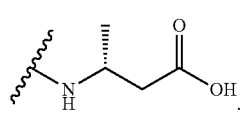 [SMILES: *N[C@H](C)CC(=O)O]

In some embodiments, R² is

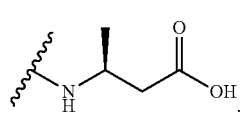 [SMILES: *N[C@@H](C)CC(=O)O]

In some embodiments, R² is

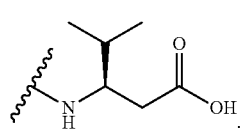 [SMILES: *N[C@H](CC(=O)O)C(C)C]

In some embodiments, R² is

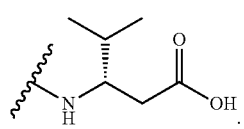 [SMILES: *N[C@@H](CC(=O)O)C(C)C]

In some embodiments, R² is

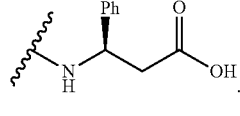 [SMILES: *N[C@H](CC(=O)O)c1ccccc1]

In some embodiments, R² is

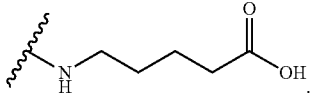 [SMILES: *NCCCCC(=O)O]

In some embodiments, R² is
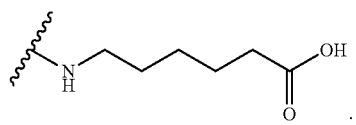 [SMILES: *NCCCCCC(=O)O]
In some embodiments, R² is
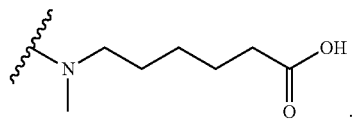 [SMILES: *N(C)CCCCCC(=O)O]
In some embodiments, R² is
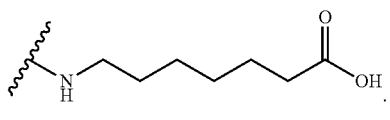 [SMILES: *NCCCCCCC(=O)O]
In some embodiments, R² is
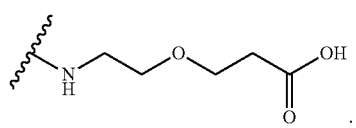 [SMILES: *NCCOCCC(=O)O]
In some embodiments, R² is
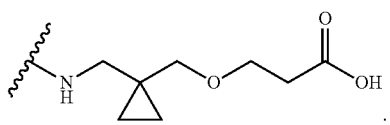 [SMILES: *NCC1(COCCC(=O)O)CC1]
In some embodiments, R² is
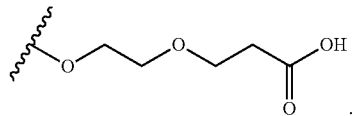 [SMILES: *OCCOCCC(=O)O]
In some embodiments, R² is
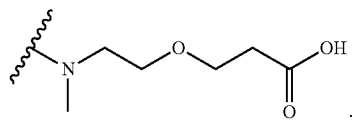 [SMILES: *N(C)CCOCCC(=O)O]
In some embodiments, R² is
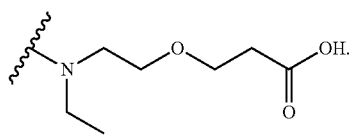 [SMILES: *N(CC)CCOCCC(=O)O]
In some embodiments, R² is
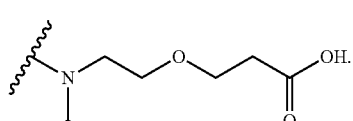
In some embodiments, R² is
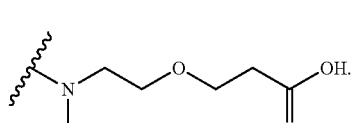
In some embodiments, R² is
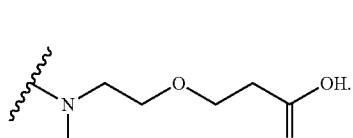
In some embodiments, R² is
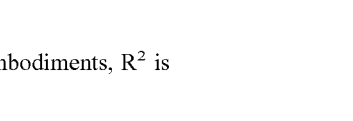
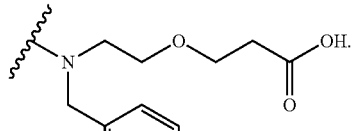
In some embodiments, R² is
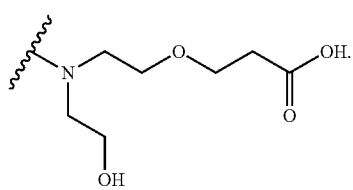 [SMILES: *N(CCO)CCOCCC(=O)O]

In some embodiments, R² is
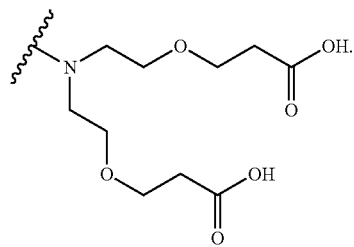 [SMILES: *N(CCOCCC(=O)O)CCOCCC(=O)O]
In some embodiments, R² is
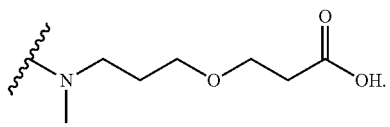 [SMILES: *N(C)CCCOCCC(=O)O]
In some embodiments, R² is
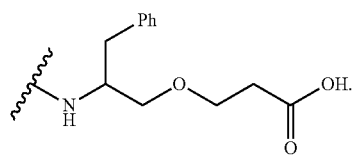 [SMILES: *NC(COCCC(=O)O)Cc1ccccc1]
In some embodiments, R² is
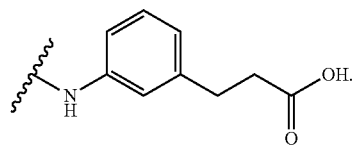 [SMILES: *Nc1cccc(CCC(=O)O)c1]
In some embodiments, R² is
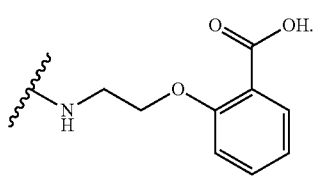 [SMILES: *NCCOc1ccccc1C(=O)O]
In some embodiments, R² is
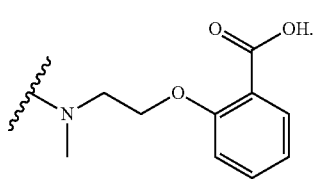 [SMILES: *N(C)CCOc1ccccc1C(=O)O]
In some embodiments, R² is
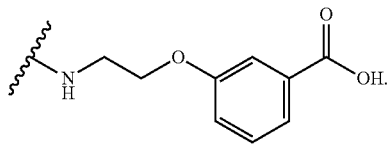 [SMILES: *NCCOc1cccc(C(=O)O)c1]
In some embodiments, R² is
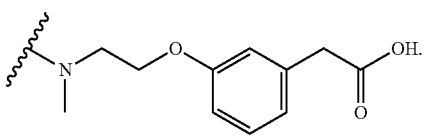 [SMILES: *N(C)CCOc1cccc(CC(=O)O)c1]
In some embodiments, R² is
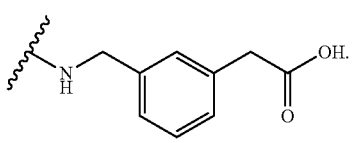
In some embodiments, R² is
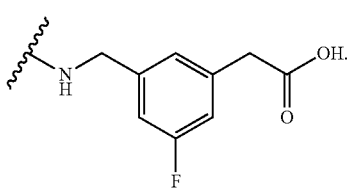 [SMILES: *NCc1cc(F)cc(CC(=O)O)c1]
In some embodiments, R² is
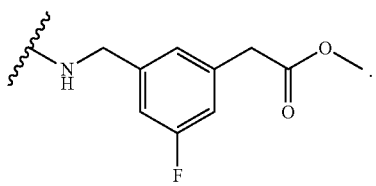 [SMILES: *NCc1cc(F)cc(CC(=O)OC)c1]
In some embodiments, R² is
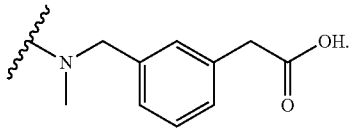 [SMILES: *N(C)Cc1cccc(CC(=O)O)c1]

In some embodiments, R² is
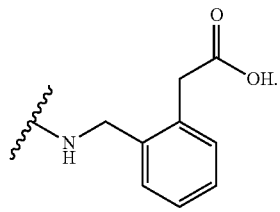 [SMILES: *NCc1ccccc1CC(=O)O]
In some embodiments, R² is
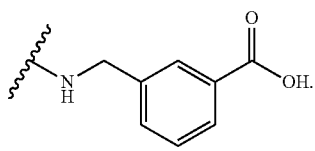 [SMILES: *NCc1cccc(C(=O)O)c1]
In some embodiments, R² is
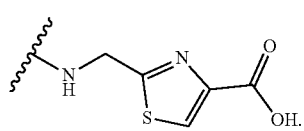 [SMILES: *NCc1nc(C(=O)O)cs1]
In some embodiments, R² is
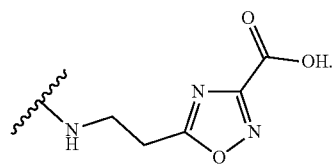 [SMILES: *NCCc1nc(C(=O)O)no1]
In some embodiments, R² is
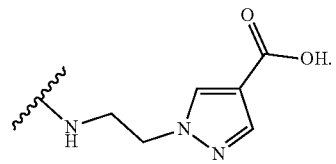 [SMILES: *NCCn1cc(C(=O)O)cn1]
In some embodiments, R² is
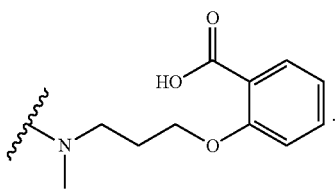 [SMILES: *N(C)CCCOc1ccccc1C(=O)O]
In some embodiments, R² is
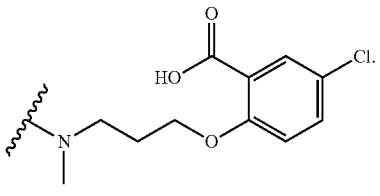 [SMILES: *N(C)CCCOc1ccc(Cl)cc1C(=O)O]
In some embodiments, R² is
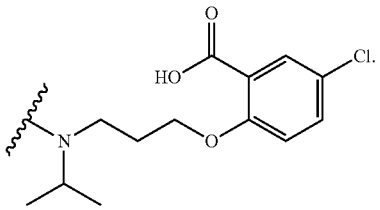 [SMILES: *N(CCCOc1ccc(Cl)cc1C(=O)O)C(C)C]
In some embodiments, R² is
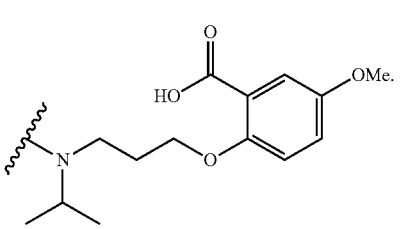 [SMILES: *N(CCCOc1ccc(OC)cc1C(=O)O)C(C)C]
In some embodiments, R² is
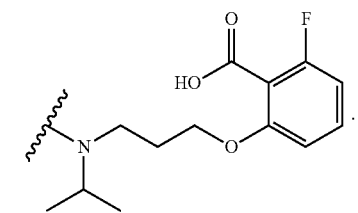 [SMILES: *N(CCCOc1cccc(F)c1C(=O)O)C(C)C]
In some embodiments, R² is
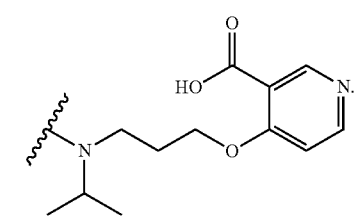 [SMILES: *N(CCCOc1ccncc1C(=O)O)C(C)C]

In some embodiments, R² is
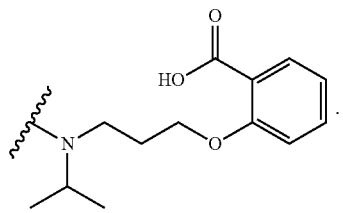 [SMILES: *N(CCCOc1ccccc1C(=O)O)C(C)C]
In some embodiments, R² is
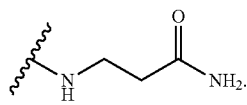 [SMILES: *NCCC(N)=O]
In some embodiments, R² is
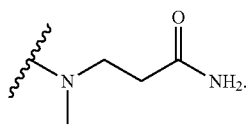 [SMILES: *N(C)CCC(N)=O]
In some embodiments, R² is
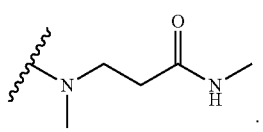 [SMILES: *N(C)CCC(=O)NC]
In some embodiments, R² is
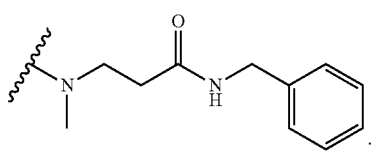 [SMILES: *N(C)CCC(=O)NCc1ccccc1]
In some embodiments, R² is
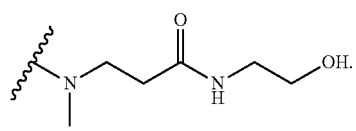 [SMILES: *N(C)CCC(=O)NCCO]
In some embodiments, R² is
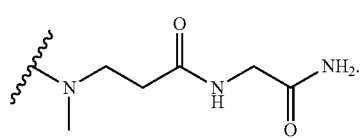 [SMILES: *N(C)CCC(=O)NCC(N)=O]
In some embodiments, R² is
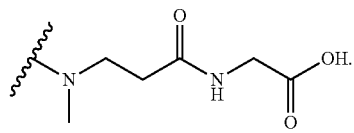 [SMILES: *N(C)CCC(=O)NCC(=O)O]
In some embodiments, R² is
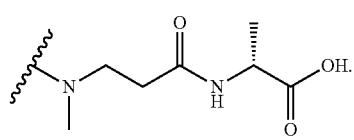 [SMILES: *N(C)CCC(=O)N[C@H](C)C(=O)O]
In some embodiments, R² is
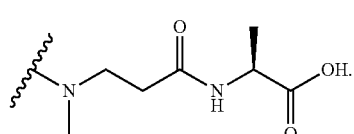
In some embodiments, R² is
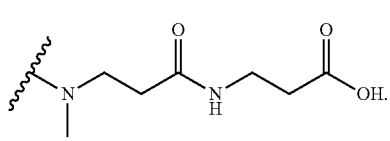 [SMILES: *N(C)CCC(=O)NCCC(=O)O]
In some embodiments, R² is
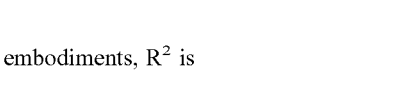
In some embodiments, R² is
In some embodiments, R² is
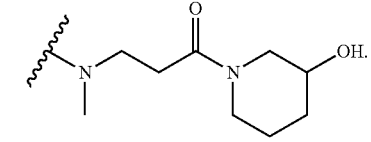 [SMILES: *N(C)CCC(=O)N1CCCC(O)C1]

In some embodiments, R² is

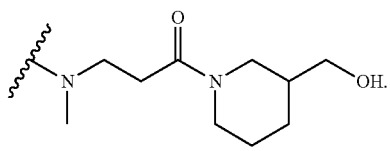 [SMILES: *N(C)CCC(=O)N1CCCC(CO)C1]

In some embodiments, R² is

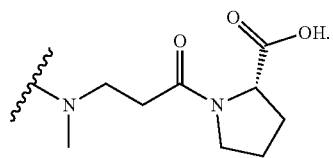 [SMILES: *N(C)CCC(=O)N1CCC[C@H]1C(=O)O]

In some embodiments, R² is

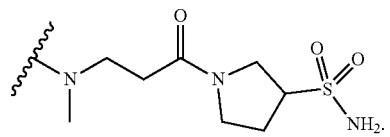

In some embodiments, R² is

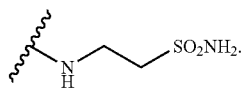

In some embodiments, R² is

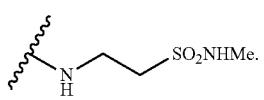

In some embodiments, R² is

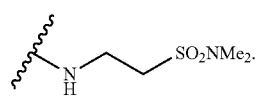

In some embodiments, R² is

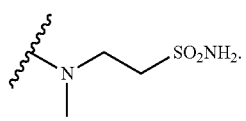 [SMILES: *N(C)CCS(N)(=O)=O]

In some embodiments, R² is

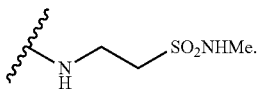

In some embodiments, R² is

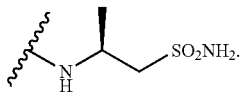 [SMILES: *N[C@@H](C)CS(N)(=O)=O]

In some embodiments, R² is

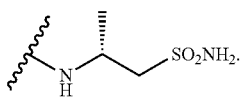

In some embodiments, R² is

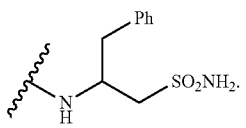 [SMILES: *NC(Cc1ccccc1)CS(N)(=O)=O]

In some embodiments, R² is

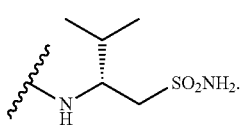 [SMILES: *N[C@@H](CS(N)(=O)=O)C(C)C]

In some embodiments, R² is

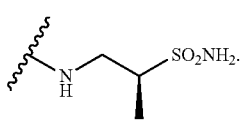

In some embodiments, R² is

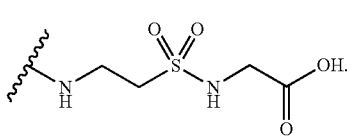 [SMILES: *NCCS(=O)(=O)NCC(=O)O]

In some embodiments, R² is

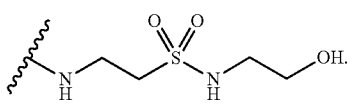 [SMILES: *NCCS(=O)(=O)NCCO]

In some embodiments, R² is
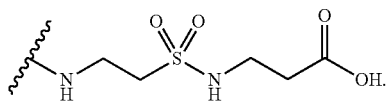 [SMILES: *NCCS(=O)(=O)NCCC(=O)O]
In some embodiments, R² is
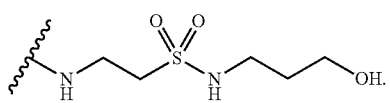 [SMILES: *NCCS(=O)(=O)NCCCO]
In some embodiments, R² is
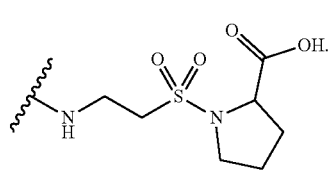 [SMILES: *NCCS(=O)(=O)N1CCCC1C(=O)O]
In some embodiments, R² is
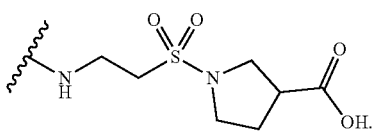 [SMILES: *NCCS(=O)(=O)N1CCC(C(=O)O)C1]
In some embodiments, R² is
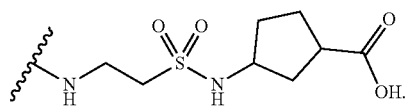 [SMILES: *NCCS(=O)(=O)NC1CCC(C(=O)O)C1]
In some embodiments, R² is
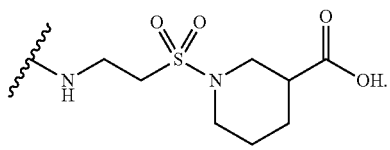 [SMILES: *NCCS(=O)(=O)N1CCCC(C(=O)O)C1]
In some embodiments, R² is
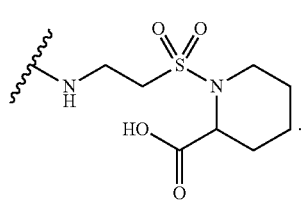 [SMILES: *NCCS(=O)(=O)N1CCCCC1C(=O)O]
In some embodiments, R² is
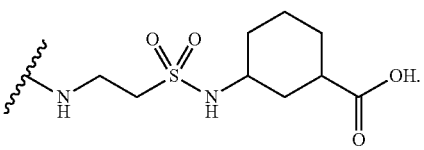 [SMILES: *NCCS(=O)(=O)NC1CCCC(C(=O)O)C1]
In some embodiments, R² is
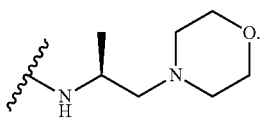 [SMILES: *N[C@@H](C)CN1CCOCC1]
In some embodiments, R² is
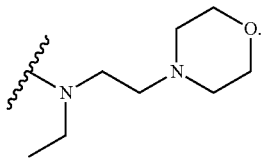 [SMILES: *N(CC)CCN1CCOCC1]
In some embodiments, R² is
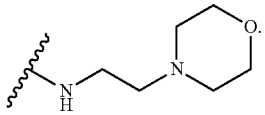 [SMILES: *NCCN1CCOCC1]
In some embodiments, R² is
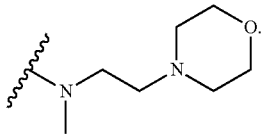 [SMILES: *N(C)CCN1CCOCC1]
In some embodiments, R² is
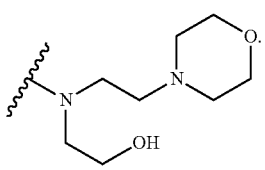 [SMILES: *N(CCO)CCN1CCOCC1]

In some embodiments, R² is
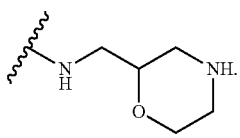 [SMILES: *NCC1CNCCO1]
In some embodiments, R² is
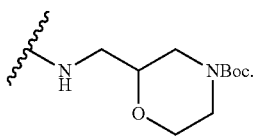 [SMILES: *NCC1CN(C(=O)OC(C)(C)C)CCO1]
In some embodiments, R² is
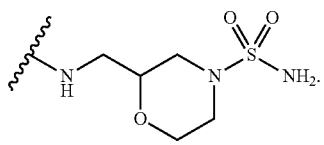 [SMILES: *NCC1CN(S(N)(=O)=O)CCO1]
In some embodiments, R² is
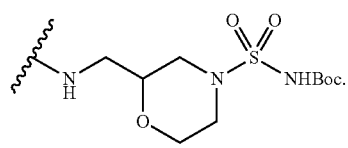 [SMILES: *NCC1CN(S(=O)(=O)NC(=O)OC(C)(C)C)CCO1]
In some embodiments, R² is
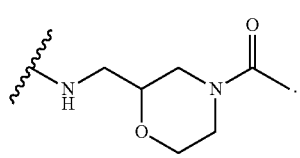 [SMILES: *NCC1CN(C(C)=O)CCO1]
In some embodiments, R² is
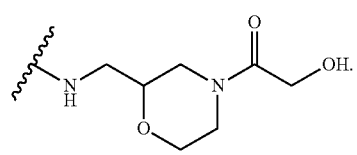 [SMILES: *NCC1CN(C(=O)CO)CCO1]
In some embodiments, R² is
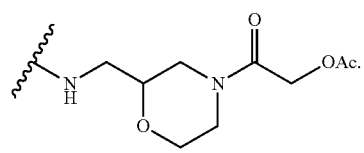 [SMILES: *NCC1CN(C(=O)COC(C)=O)CCO1]
In some embodiments, R² is
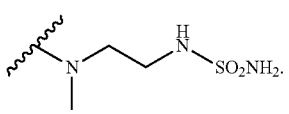 [SMILES: *N(C)CCNS(N)(=O)=O]
In some embodiments, R² is
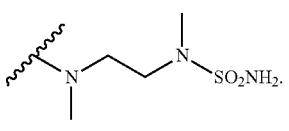 [SMILES: *N(C)CCN(C)S(N)(=O)=O]
In some embodiments, R² is
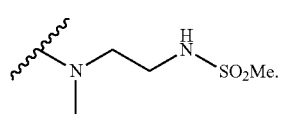 [SMILES: *N(C)CCNS(C)(=O)=O]
In some embodiments, R² is
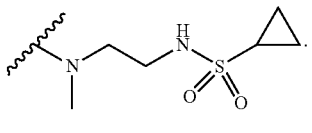 [SMILES: *N(C)CCNS(=O)(=O)C1CC1]
In some embodiments, R² is
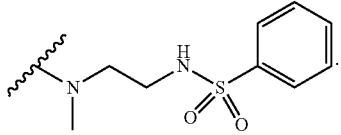 [SMILES: *N(C)CCNS(=O)(=O)c1ccccc1]
In some embodiments, R² is
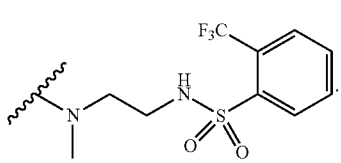 [SMILES: *N(C)CCNS(=O)(=O)c1ccccc1C(F)(F)F]
In some embodiments, R² is
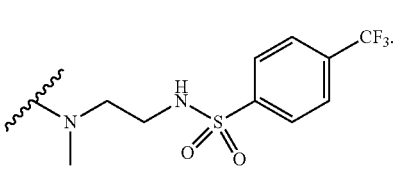 [SMILES: *N(C)CCNS(=O)(=O)c1ccc(C(F)(F)F)cc1]

In some embodiments, R² is
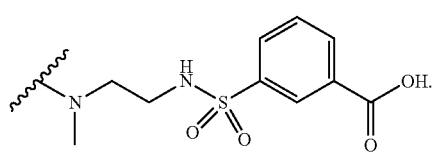 [SMILES: *N(C)CCNS(=O)(=O)c1cccc(C(=O)O)c1]
In some embodiments, R² is
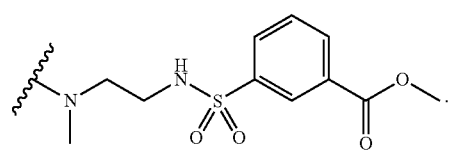 [SMILES: *N(C)CCNS(=O)(=O)c1cccc(C(=O)OC)c1]
In some embodiments, R² is
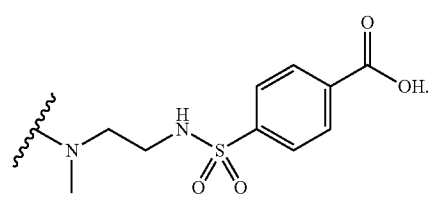 [SMILES: *N(C)CCNS(=O)(=O)c1ccc(C(=O)O)cc1]
In some embodiments, R² is
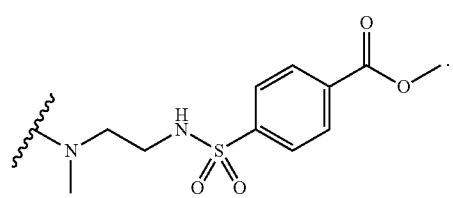 [SMILES: *N(C)CCNS(=O)(=O)c1ccc(C(=O)OC)cc1]
In some embodiments, R² is
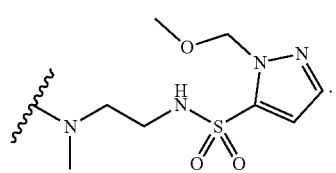 [SMILES: *N(C)CCNS(=O)(=O)c1ccnn1COC]
In some embodiments, R² is
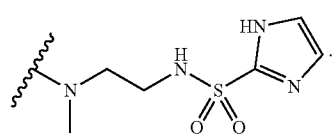 [SMILES: *N(C)CCNS(=O)(=O)c1ncc[nH]1]
In some embodiments, R² is
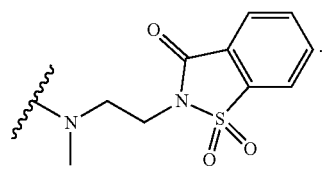 [SMILES: *N(C)CCN1C(=O)c2ccccc2S1(=O)=O]
In some embodiments, R² is
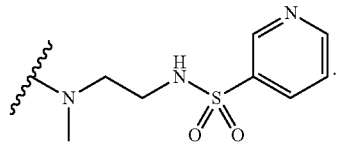 [SMILES: *N(C)CCNS(=O)(=O)c1cccnc1]
In some embodiments, R² is
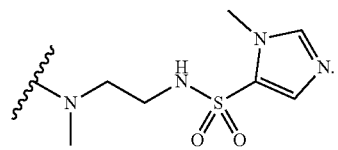 [SMILES: *N(C)CCNS(=O)(=O)c1cncn1C]
In some embodiments, R² is
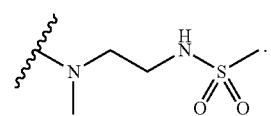 [SMILES: *N(C)CCNS(C)(=O)=O]
In some embodiments, R² is
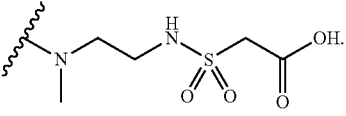 [SMILES: *N(C)CCNS(=O)(=O)CC(=O)O]
In some embodiments, R² is
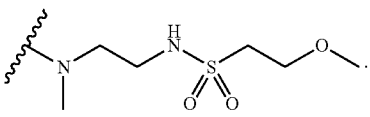 [SMILES: *N(C)CCNS(=O)(=O)CCOC]
In some embodiments, R² is
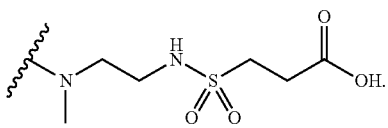 [SMILES: *N(C)CCNS(=O)(=O)CCC(=O)O]

In some embodiments, R² is
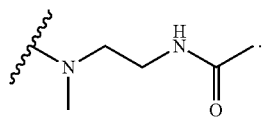 [SMILES: *N(C)CCNC(C)=O]
In some embodiments, R² is
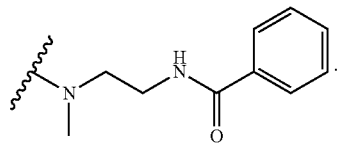 [SMILES: *N(C)CCNC(=O)c1ccccc1]
In some embodiments, R² is
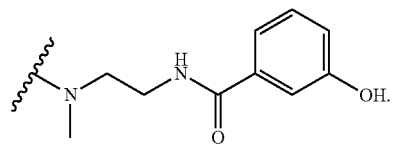 [SMILES: *N(C)CCNC(=O)c1cccc(O)c1]
In some embodiments, R² is
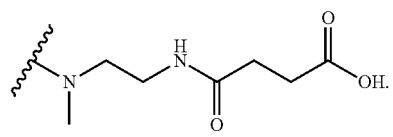 [SMILES: *N(C)CCNC(=O)CCC(=O)O]
In some embodiments, R² is
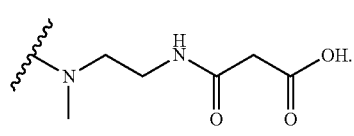 [SMILES: *N(C)CCNC(=O)CC(=O)O]
In some embodiments, R² is
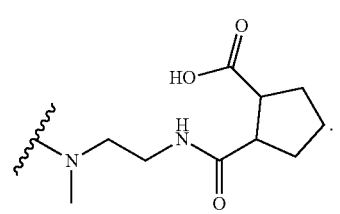 [SMILES: *N(C)CCNC(=O)C1CCCC1C(=O)O]
In some embodiments, R² is
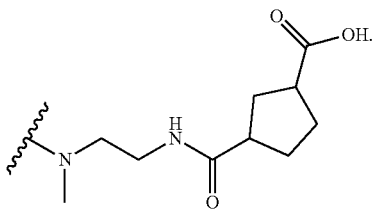 [SMILES: *N(C)CCNC(=O)C1CCC(C(=O)O)C1]
In some embodiments, R² is
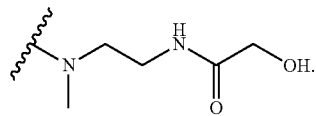 [SMILES: *N(C)CCNC(=O)CO]
In some embodiments, R² is
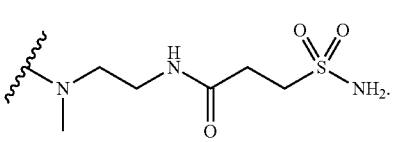 [SMILES: *N(C)CCNC(=O)CCS(N)(=O)=O]
In some embodiments, R² is
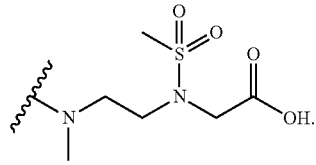 [SMILES: *N(C)CCN(CC(=O)O)S(C)(=O)=O]
In some embodiments, R² is In some embodiments, R² is

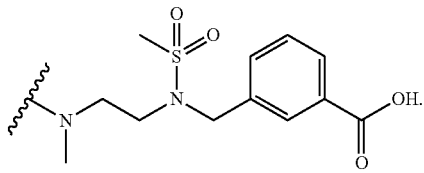 [SMILES: *N(C)CCN(Cc1cccc(C(=O)O)c1)S(C)(=O)=O]

In some embodiments, R² is

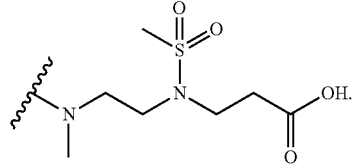 [SMILES: *N(C)CCN(CCC(=O)O)S(C)(=O)=O]

In some embodiments, R² is

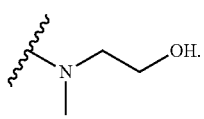 [SMILES: *N(C)CCO]

In some embodiments, R² is

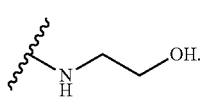 [SMILES: *NCCO]

In some embodiments, R² is

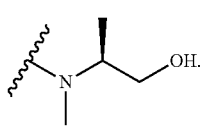 [SMILES: *N(C)[C@@H](C)CO]

In some embodiments, R² is

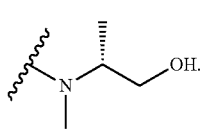 [SMILES: *N(C)[C@H](C)CO]

In some embodiments, R² is

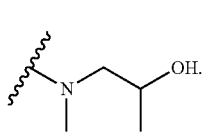 [SMILES: *N(C)CC(C)O]

In some embodiments, R² is

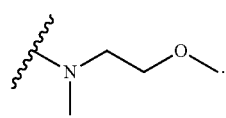 [SMILES: *N(C)CCOC]

In some embodiments, R² is

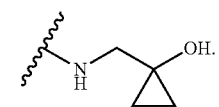

In some embodiments, R² is

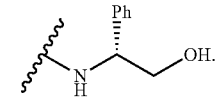

In some embodiments, R² is

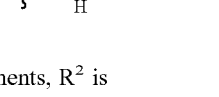

In some embodiments, R² is

In some embodiments, R² is

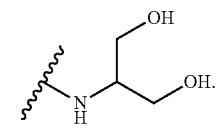 [SMILES: *NC(CO)CO]

In some embodiments, R² is

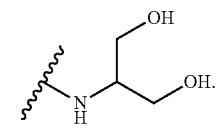 [SMILES: *NC(CO)CO]

In some embodiments, R² is

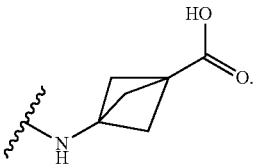 [SMILES: *NC12CC(C(=O)O)(C1)C2]

In some embodiments, $R^2$ is

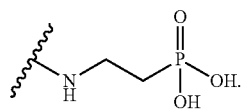 [SMILES: *NCCP(=O)(O)O]

In some embodiments, $R^2$ is

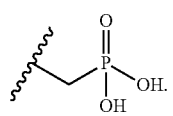 [SMILES: *CP(=O)(O)O]

In some embodiments, $R^2$ is

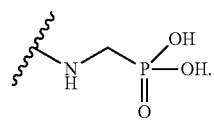 [SMILES: *NCP(=O)(O)O]

In some embodiments, $R^2$ is

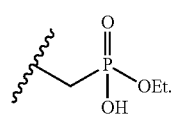 [SMILES: *CP(=O)(O)OCC]

In some embodiments, $R^2$ is

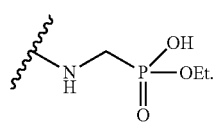

In some embodiments, $R^2$ is

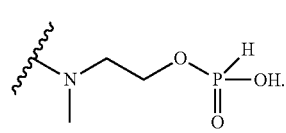 [SMILES: *N(C)CCO[PH](=O)O]

In some embodiments, $R^2$ is

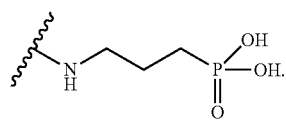 [SMILES: *NCCCP(=O)(O)O]

In some embodiments, $R^2$ is

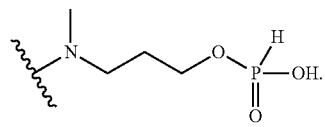 [SMILES: *N(C)CCCO[PH](=O)O]

In some embodiments, $R^2$ is

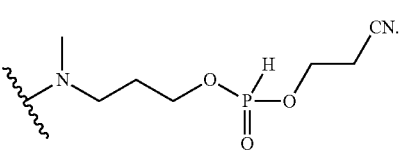 [SMILES: *N(C)CCCO[PH](=O)OCCC#N]

In some embodiments, $R^2$ is

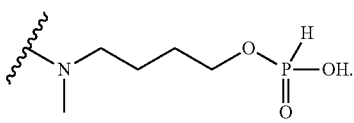 [SMILES: *N(C)CCCCO[PH](=O)O]

In some embodiments, $R^2$ is

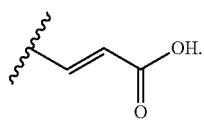 [SMILES: */C=C/C(=O)O]

In some embodiments, $R^2$ is

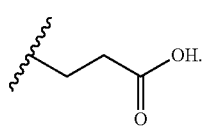 [SMILES: *CCC(=O)O]

In some embodiments, $R^2$ is

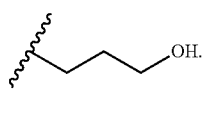 [SMILES: *CCCO]

In some embodiments, $R^2$ is

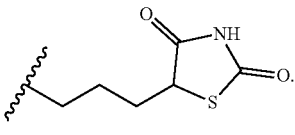 [SMILES: *CCCC1SC(=O)NC1=O]

In some embodiments, R² is
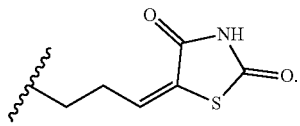 [SMILES: *CC/C=C1/SC(=O)NC1=O]
In some embodiments, R² is
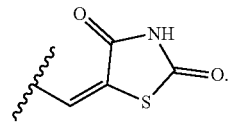 [SMILES: */C=C1/SC(=O)NC1=O]
In some embodiments, R² is
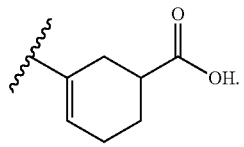 [SMILES: *C1=CCCC(C(=O)O)C1]
In some embodiments, R² is
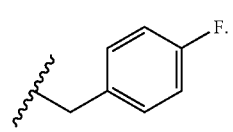 [SMILES: *Cc1ccc(F)cc1]
In some embodiments, R² is
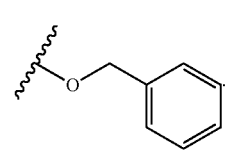 [SMILES: *OCc1ccccc1]
In some embodiments, R² is
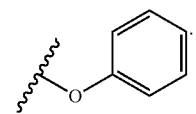
In some embodiments, R² is
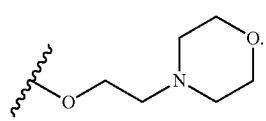 [SMILES: *OCCN1CCOCC1]
In some embodiments, R² is
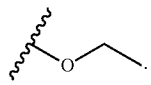 [SMILES: *OCC]
In some embodiments, R² is
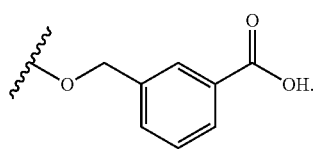 [SMILES: *OCc1cccc(C(=O)O)c1]
In some embodiments, R² is
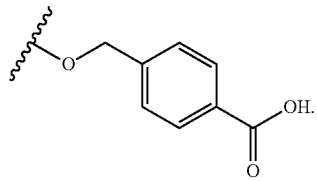 [SMILES: *OCc1ccc(C(=O)O)cc1]
In some embodiments, R² is
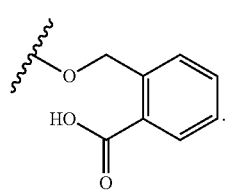 [SMILES: *OCc1ccccc1C(=O)O]
In some embodiments, R² is
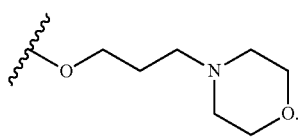 [SMILES: *OCCCN1CCOCC1]
In some embodiments, R² is
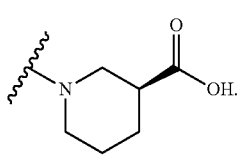

In some embodiments, R² is
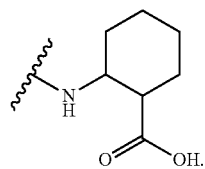 [SMILES: *NC1CCCCC1C(=O)O]
In some embodiments, R² is
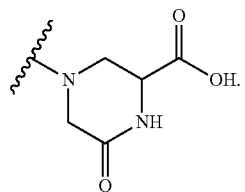 [SMILES: *N1CC(=O)NC(C(=O)O)C1]
In some embodiments, R² is
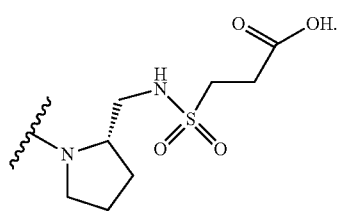 [SMILES: *N1CCC[C@H]1CNS(=O)(=O)CCC(=O)O]
In some embodiments, R² is
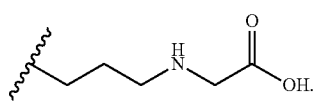 [SMILES: *CCCNCC(=O)O]
In some embodiments, R² is
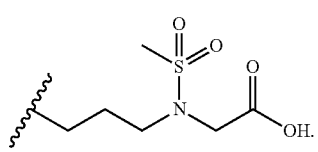 [SMILES: *CCCN(CC(=O)O)S(C)(=O)=O]
In some embodiments, R² is
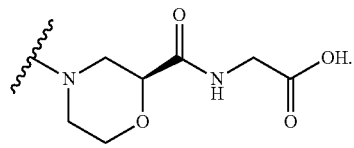 [SMILES: *N1CCO[C@H](C(=O)NCC(=O)O)C1]
In some embodiments, R² is
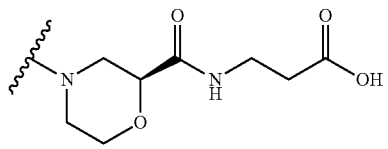 [SMILES: *N1CCO[C@H](C(=O)NCCC(=O)O)C1]
In some embodiments, R² is
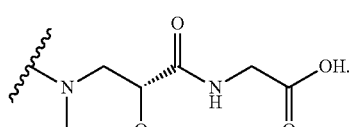
In some embodiments, R² is
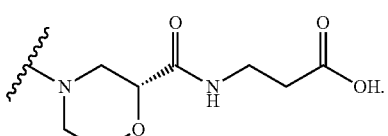
In some embodiments, R² is
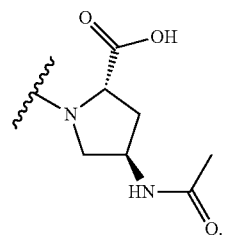 [SMILES: *N1C[C@H](NC(C)=O)C[C@H]1C(=O)O]
In some embodiments, R² is
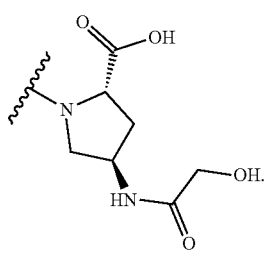 [SMILES: *N1C[C@H](NC(=O)CO)C[C@H]1C(=O)O]

In some embodiments, R² is
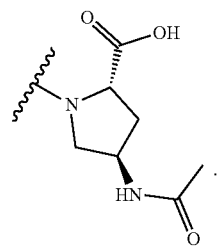 [SMILES: *N1C[C@H](NC(C)=O)C[C@H]1C(=O)O]
In some embodiments, R² is
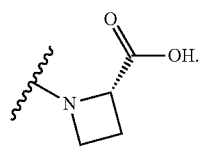 [SMILES: *N1CC[C@H]1C(=O)O]
In some embodiments, R² is
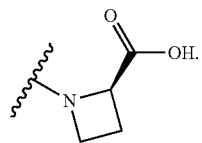 [SMILES: *N1CC[C@@H]1C(=O)O]
In some embodiments, R² is
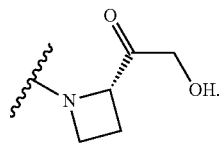 [SMILES: *N1CC[C@H]1C(=O)CO]
In some embodiments, R² is
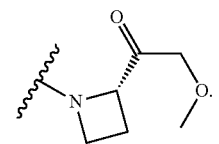 [SMILES: *N1CC[C@H]1C(=O)COC]
In some embodiments, R² is
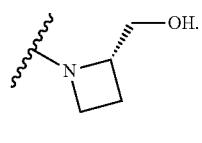 [SMILES: *N1CC[C@H]1CO]
In some embodiments, R² is
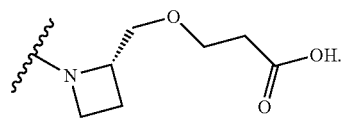 [SMILES: *N1CC[C@H]1COCCC(=O)O]
In some embodiments, R² is
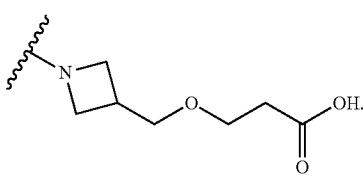 [SMILES: *N1CC(COCCC(=O)O)C1]
In some embodiments, R² is
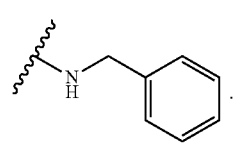
In some embodiments, R² is
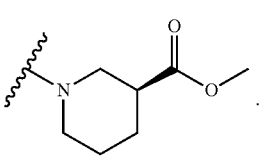 [SMILES: *N1CCC[C@H](C(=O)OC)C1]
In some embodiments, R² is
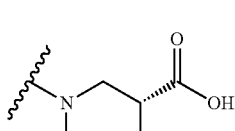
In some embodiments, R² is
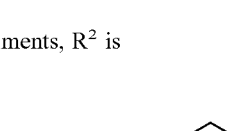

In some embodiments, R² is
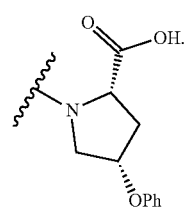 [SMILES: *N1C[C@@H](Oc2ccccc2)C[C@H]1C(=O)O]
In some embodiments, R² is
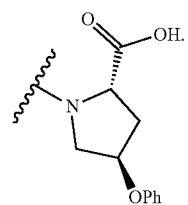 [SMILES: *N1C[C@H](Oc2ccccc2)C[C@H]1C(=O)O]
In some embodiments, R² is
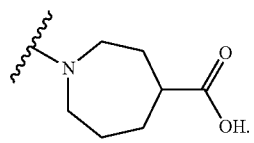 [SMILES: *N1CCCC(C(=O)O)CC1]
In some embodiments, R² is
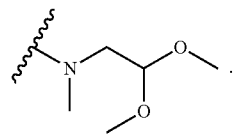 [SMILES: *N(C)CC(OC)OC]
In some embodiments, R² is
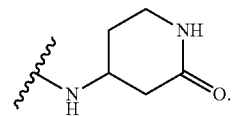 [SMILES: *NC1CCNC(=O)C1]
In some embodiments, R² is
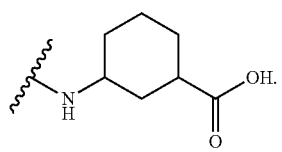 [SMILES: *NC1CCCC(C(=O)O)C1]
In some embodiments, R² is
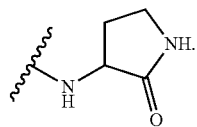 [SMILES: *NC1CCNC1=O]
In some embodiments, R² is
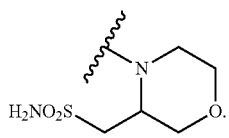
In some embodiments, R² is
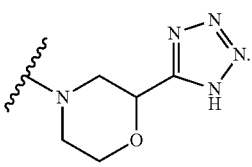 [SMILES: *N1CCOC(c2nnn[nH]2)C1]
In some embodiments, R² is
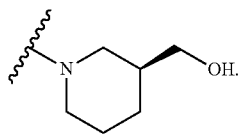 [SMILES: *N1CCC[C@H](CO)C1]
In some embodiments, R² is
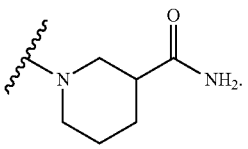 [SMILES: *N1CCCC(C(N)=O)C1]
In some embodiments, R² is
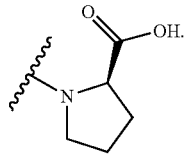 [SMILES: *N1CCC[C@@H]1C(=O)O]
In some embodiments, R² is
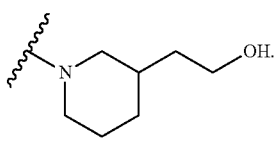 [SMILES: *N1CCCC(CCO)C1]

In some embodiments, R² is
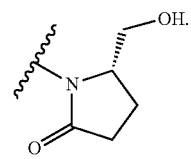 [SMILES: *N1C(=O)CC[C@H]1CO]
In some embodiments, R² is
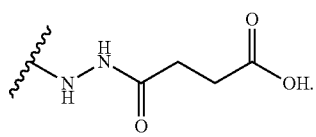 [SMILES: *NNC(=O)CCC(=O)O]
In some embodiments, R² is
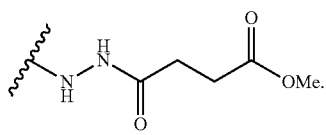 [SMILES: *NNC(=O)CCC(=O)OC]
In some embodiments, R² is
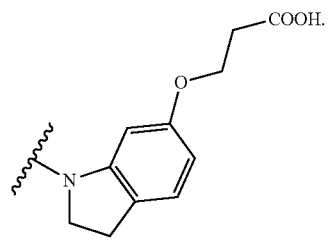 [SMILES: *N1CCc2ccc(OCCC(=O)O)cc21]
In some embodiments, R² is
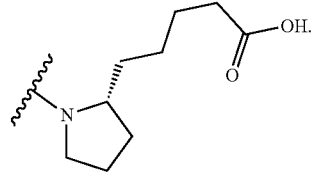 [SMILES: *N1CCC[C@H]1CCCCC(=O)O]
In some embodiments, R² is
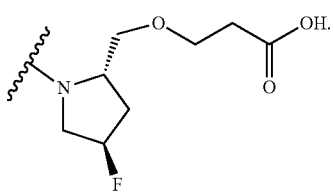 [SMILES: *N1C[C@H](F)C[C@H]1COCCC(=O)O]
In some embodiments, R² is
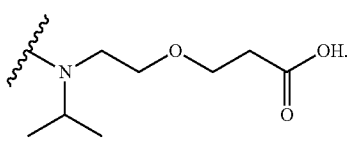 [SMILES: *N(CCOCCC(=O)O)C(C)C]
In some embodiments, R² is
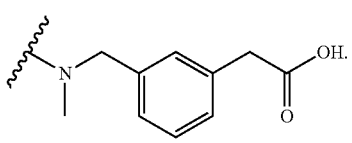 [SMILES: *N(C)Cc1cccc(CC(=O)O)c1]
In some embodiments, R² is
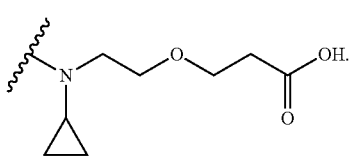 [SMILES: *N(CCOCCC(=O)O)C1CC1]
In some embodiments, R² is
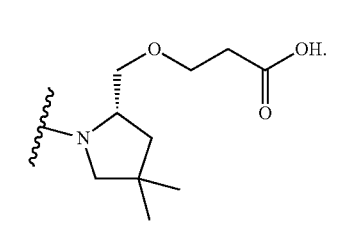 [SMILES: *N1CC(C)(C)C[C@H]1COCCC(=O)O]
In some embodiments, R² is
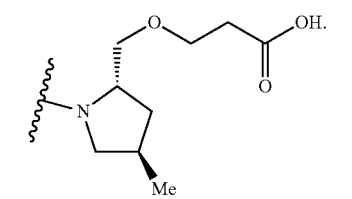 [SMILES: *N1C[C@H](C)C[C@H]1COCCC(=O)O]
In some embodiments, R² is
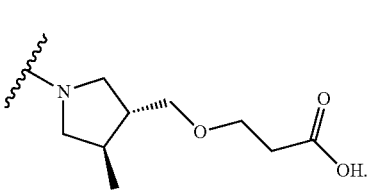 [SMILES: *N1C[C@H](COCCC(=O)O)[C@@H](C)C1]

In some embodiments, $R^2$ is
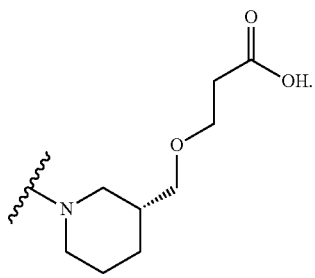 [SMILES: *N1CCC[C@@H](COCCC(=O)O)C1]
In some embodiments, $R^2$ is
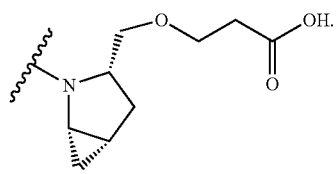 [SMILES: *N1[C@H](COCCC(=O)O)C[C@@H]2C[C@@H]21]
In some embodiments, $R^2$ is
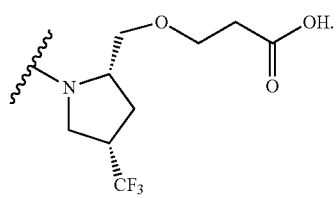 [SMILES: *N1C[C@@H](C(F)(F)F)C[C@H]1COCCC(=O)O]
In some embodiments, $R^2$ is
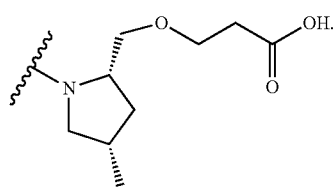 [SMILES: *N1C[C@@H](C)C[C@H]1COCCC(=O)O]
In some embodiments, $R^2$ is
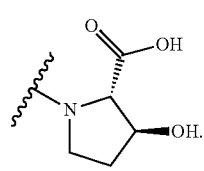 [SMILES: *N1CC[C@H](O)[C@H]1C(=O)O]
In some embodiments, $R^2$ is
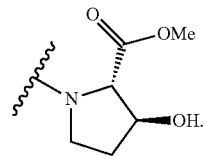 [SMILES: *N1CC[C@H](O)[C@H]1C(=O)OC]
In some embodiments, $R^2$ is
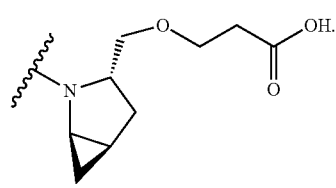 [SMILES: *N1[C@H](COCCC(=O)O)C[C@H]2C[C@H]21]
In some embodiments, $R^2$ is
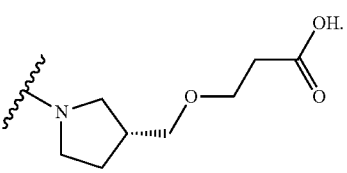 [SMILES: *N1CC[C@@H](COCCC(=O)O)C1]
In some embodiments, $R^2$ is
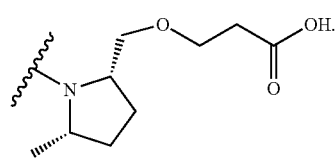 [SMILES: *N1[C@H](COCCC(=O)O)CC[C@@H]1C]
In some embodiments, $R^2$ is
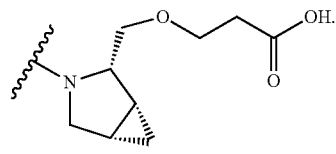 [SMILES: *N1C[C@H]2C[C@H]2[C@H]1COCCC(=O)O]
In some embodiments, $R^2$ is
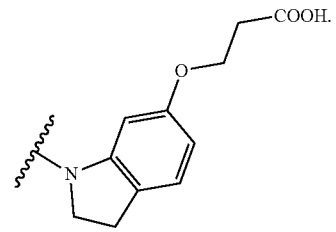 [SMILES: *N1CCc2ccc(OCCC(=O)O)cc21]

223

In some embodiments, $R^2$ is

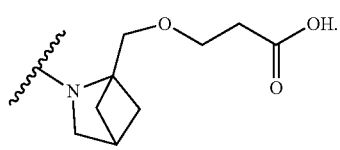 [SMILES: *N1CC2CC1(COCCC(=O)O)C2]

In some embodiments, $R^2$ is

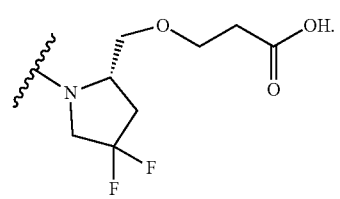 [SMILES: *N1CC(F)(F)C[C@H]1COCCC(=O)O]

In some embodiments, $R^2$ is

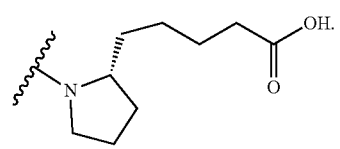 [SMILES: *N1CCC[C@H]1CCCCC(=O)O]

In some embodiments, $R^2$ is

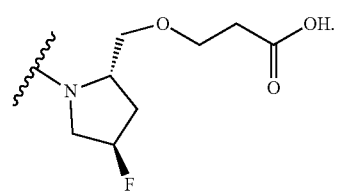 [SMILES: *N1C[C@H](F)C[C@H]1COCCC(=O)O]

In some embodiments, $R^2$ is

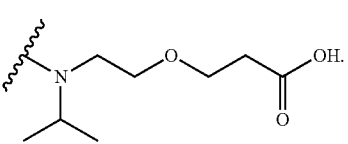 [SMILES: *N(CCOCCC(=O)O)C(C)C]

In some embodiments, $R^2$ is

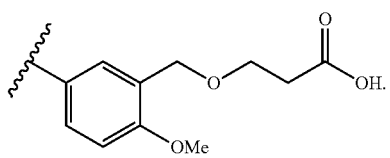 [SMILES: *c1ccc(OC)c(COCCC(=O)O)c1]

224

In some embodiments, $R^2$ is

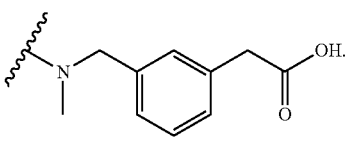 [SMILES: *N(C)Cc1cccc(CC(=O)O)c1]

In some embodiments, $R^2$ is

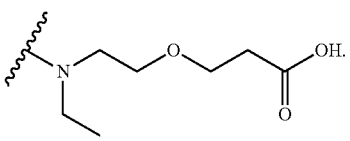 [SMILES: *N(CC)CCOCCC(=O)O]

In some embodiments, $R^2$ is

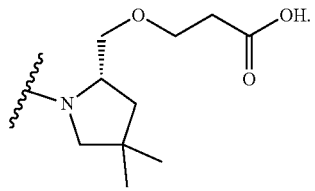 [SMILES: *N1CC(C)(C)C[C@H]1COCCC(=O)O]

In some embodiments, $R^2$ is

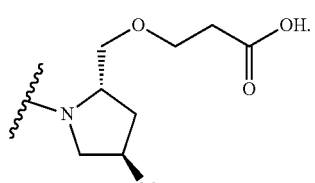

In some embodiments, $R^2$ is

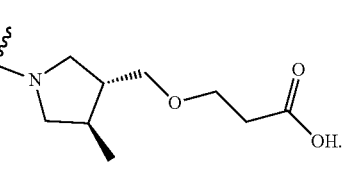

In some embodiments, $R^2$ is

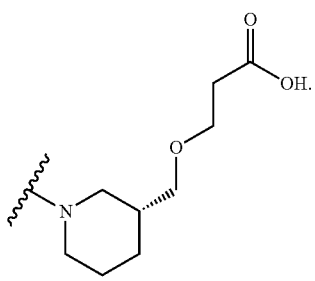 [SMILES: *N1CCC[C@@H](COCCC(=O)O)C1]

In some embodiments, $R^2$ is selected from those groups depicted in Table 1.

In some embodiments, $R^2$ is selected from those groups depicted in Table 2.

As defined above and described herein, each $R^3$ is independently halogen, —OR, —NR$_2$, —SR, or $R^C$, particularly halogen, such as chloro.

In some embodiments, $R^3$ is halogen. In some embodiments, $R^3$ is —OR. In some embodiments, $R^3$ is —NR$_2$. In some embodiments, $R^3$ is —SR. In some embodiments, $R^3$ is $R^C$.

In some embodiments, $R^3$ is fluoro. In some embodiments, $R^3$ is chloro. In some embodiments, $R^3$ is bromo. In some embodiments, $R^3$ is —OH. In some embodiments, $R^3$ is —OMe. In some embodiments, $R^3$ is —OEt. In some embodiments, $R^3$ is methyl. In some embodiments, $R^3$ is isopropyl. In some embodiments, $R^3$ is tert-butyl. In some embodiments, $R^3$ is —CF$_3$. In some embodiments, $R^3$ is phenyl. In some embodiments, $R^3$ is

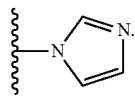

In some embodiments, $R^3$ is selected from those groups depicted in Table 1.

In some embodiments, $R^3$ is selected from those groups depicted in Table 2.

As defined above and described herein, $R^5$ is —(CR$_2$)$_{0-6}$OR, —(CR$_2$)$_{0-6}$CO$_2$R, —(CR$_2$)$_{0-6}$CONR$_2$, —(CR$_2$)$_{0-6}$C(O)NR(CR$_2$)$_{0-6}$CO$_2$R, —(CR$_2$)$_{0-6}$C(O)NR(CR$_2$)$_{0-6}$CONR$_2$, —(CR$_2$)$_{0-6}$SO$_3$R, —(CR$_2$)$_{0-6}$SO$_2$NR$_2$, —(CR$_2$)$_{0-6}$OSO$_2$NR$_2$, —(CR$_2$)$_{0-6}$NRSO$_2$R, —(CR$_2$)$_{0-6}$NRSO$_2$OR, —(CR$_2$)$_{0-6}$OP(OR)$_2$, —(CR$_2$)$_{0-6}$OP(O)(OR)$_2$, —(CR$_2$)$_{0-6}$P(O)(OR)$_2$, —(CR$_2$)$_{0-6}$OP(O)(H)OR, or $R^B$.

In some embodiments, $R^5$ is —(CR$_2$)$_{0-6}$OR. In some embodiments, $R^5$ is —(CR$_2$)$_{0-6}$CO$_2$R. In some embodiments, $R^5$ is —(CR$_2$)$_{0-6}$CONR$_2$. In some embodiments, $R^5$ is —(CR$_2$)$_{0-6}$C(O)NR(CR$_2$)$_{0-6}$CO$_2$R. In some embodiments, $R^5$ is —(CR$_2$)$_{0-6}$C(O)NR(CR$_2$)$_{0-6}$CONR$_2$. In some embodiments, $R^5$ is —(CR$_2$)$_{0-6}$SO$_3$R. In some embodiments, $R^5$ is —(CR$_2$)$_{0-6}$SO$_2$NR$_2$. In some embodiments, $R^5$ is —(CR$_2$)$_{0-6}$OSO$_2$NR$_2$. In some embodiments, $R^5$ is —(CR$_2$)$_{0-6}$NRSO$_2$R. In some embodiments, $R^5$ is —(CR$_2$)$_{0-6}$NRSO$_2$OR. In some embodiments, $R^5$ is —(CR$_2$)$_{0-6}$OP(OR)$_2$. In some embodiments, $R^5$ is —(CR$_2$)$_{0-6}$OP(O)(OR)$_2$. In some embodiments, $R^5$ is —(CR$_2$)$_{0-6}$P(O)(OR)$_2$. In some embodiments, $R$ is —(CR$_2$)$_{0-6}$OP(O)(H)OR. In some embodiments, $R^5$ is $R^B$.

In some embodiments, $R^5$ is

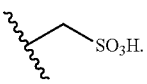

In some embodiments, $R^5$ is

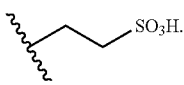 [SMILES: *CCS(=O)(=O)O]

In some embodiments, $R^5$ is

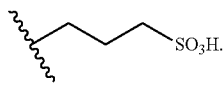 [SMILES: *CCCS(=O)(=O)O]

In some embodiments, $R^5$ is

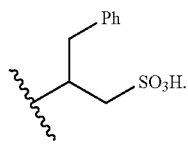 [SMILES: *C(Cc1ccccc1)CS(=O)(=O)O]

In some embodiments, $R^5$ is

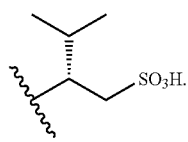 [SMILES: *[C@@H](CS(=O)(=O)O)C(C)C]

In some embodiments, $R^5$ is

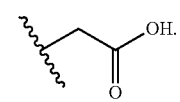

In some embodiments, $R^5$ is

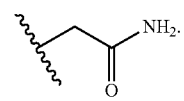

In some embodiments, $R^5$ is

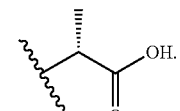

In some embodiments, $R^5$ is

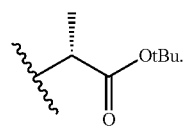 [SMILES: *[C@H](C)C(=O)OC(C)(C)C]

In some embodiments, $R^5$ is
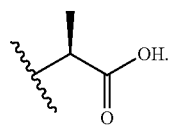 [SMILES: *[C@@H](C)C(=O)O]
In some embodiments, $R^5$ is
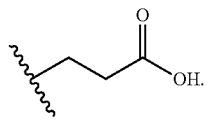 [SMILES: *CCC(=O)O]
In some embodiments, $R^5$ is
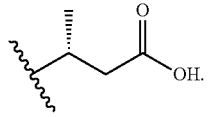
In some embodiments, $R^5$ is
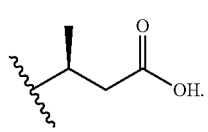 [SMILES: *[C@@H](C)CC(=O)O]
In some embodiments, $R^5$ is
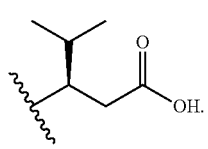 [SMILES: *[C@H](CC(=O)O)C(C)C]
In some embodiments, $R^5$ is
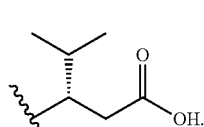
In some embodiments, $R^5$ is
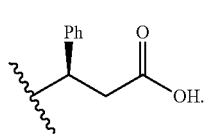 [SMILES: *[C@H](CC(=O)O)c1ccccc1]
In some embodiments, $R^5$ is
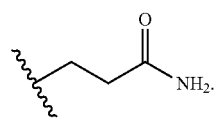 [SMILES: *CCC(N)=O]
In some embodiments, $R^5$ is
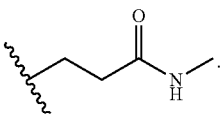 [SMILES: *CCC(=O)NC]
In some embodiments, $R^5$ is
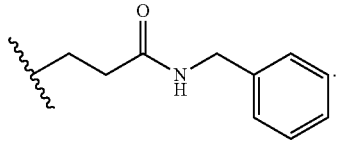 [SMILES: *CCC(=O)NCc1ccccc1]
In some embodiments, $R^5$ is
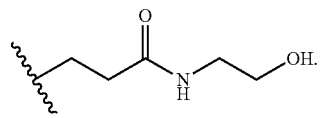 [SMILES: *CCC(=O)NCCO]
In some embodiments, $R^5$ is
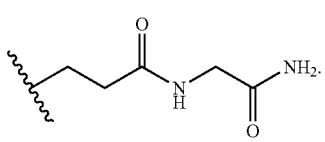 [SMILES: *CCC(=O)NCC(N)=O]
In some embodiments, $R^5$ is
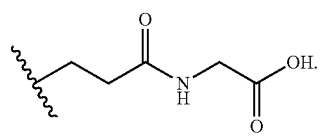 [SMILES: *CCC(=O)NCC(=O)O]
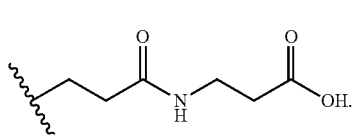 [SMILES: *CCC(=O)NCCC(=O)O]

In some embodiments, $R^5$ is

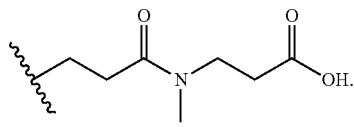 [SMILES: *CCC(=O)N(C)CCC(=O)O]

In some embodiments, $R^5$ is

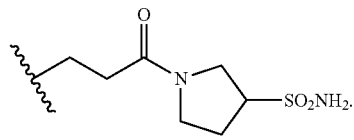 [SMILES: *CCC(=O)N1CCC(S(N)(=O)=O)C1]

In some embodiments, $R^5$ is

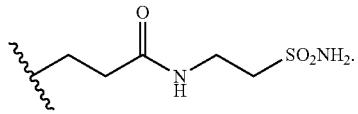 [SMILES: *CCC(=O)NCCS(N)(=O)=O]

In some embodiments, $R^5$ is

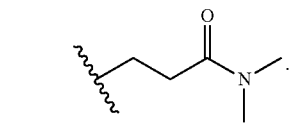 [SMILES: *CCC(=O)N(C)C]

In some embodiments, $R^5$ is

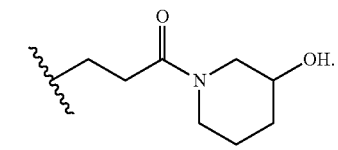 [SMILES: *CCC(=O)N1CCCC(O)C1]

In some embodiments, $R^5$ is

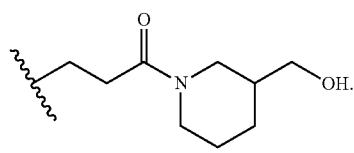 [SMILES: *CCC(=O)N1CCCC(CO)C1]

In some embodiments, $R^5$ is

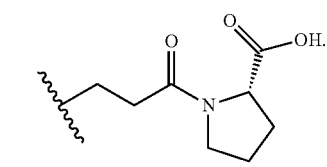 [SMILES: *CCC(=O)N1CCC[C@H]1C(=O)O]

In some embodiments, $R^5$ is

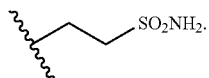

In some embodiments, $R^5$ is

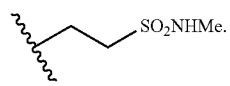

In some embodiments, $R^5$ is

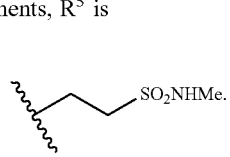

In some embodiments, $R^5$ is

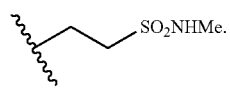

In some embodiments, $R^5$ is

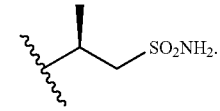 [SMILES: *[C@@H](C)CS(N)(=O)=O]

In some embodiments, $R^5$ is

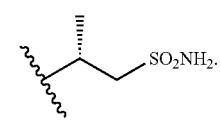

In some embodiments, $R^5$ is

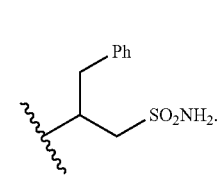 [SMILES: *C(Cc1ccccc1)CS(N)(=O)=O]

In some embodiments, $R^5$ is

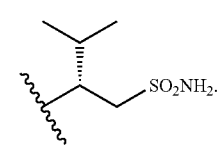 [SMILES: *[C@@H](CS(N)(=O)=O)C(C)C]

In some embodiments, R⁵ is
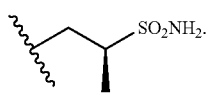 [SMILES: *C[C@H](C)S(N)(=O)=O]
In some embodiments, R⁵ is
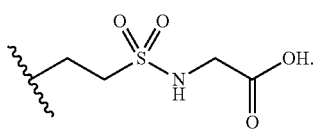 [SMILES: *CCS(=O)(=O)NCC(=O)O]
In some embodiments, R⁵ is
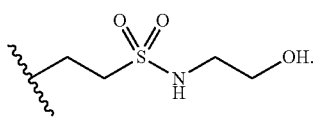 [SMILES: *CCS(=O)(=O)NCCO]
In some embodiments, R⁵ is
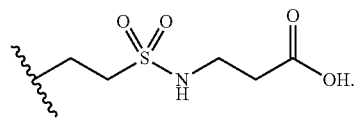 [SMILES: *CCS(=O)(=O)NCCC(=O)O]
In some embodiments, R⁵ is
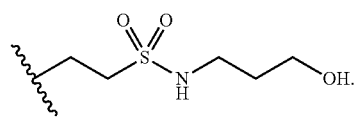 [SMILES: *CCS(=O)(=O)NCCCO]
In some embodiments, R⁵ is
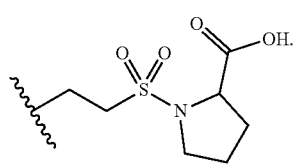 [SMILES: *CCS(=O)(=O)N1CCCC1C(=O)O]
In some embodiments, R⁵ is
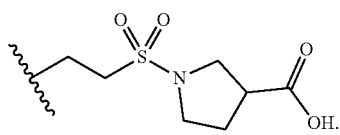 [SMILES: *CCS(=O)(=O)N1CCC(C(=O)O)C1]
In some embodiments, R⁵ is
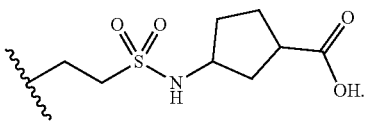 [SMILES: *CCS(=O)(=O)NC1CCC(C(=O)O)C1]
In some embodiments, R⁵ is
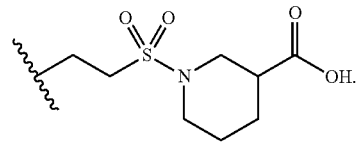 [SMILES: *CCS(=O)(=O)N1CCCC(C(=O)O)C1]
In some embodiments, R⁵ is
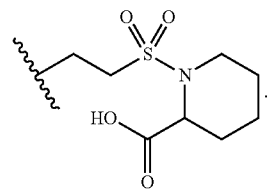 [SMILES: *CCS(=O)(=O)N1CCCCC1C(=O)O]
In some embodiments, R⁵ is
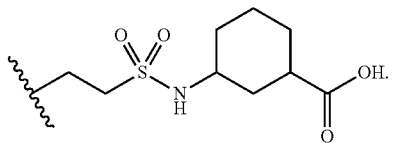 [SMILES: *CCS(=O)(=O)NC1CCCC(C(=O)O)C1]
In some embodiments, R⁵ is
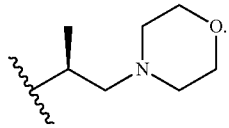 [SMILES: *[C@@H](C)CN1CCOCC1]
In some embodiments, R⁵ is
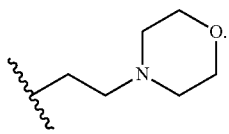 [SMILES: *CCN1CCOCC1]
In some embodiments, R⁵ is
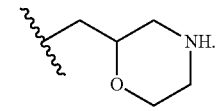

In some embodiments, R⁵ is
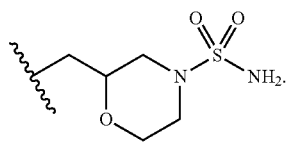 [SMILES: *CC1CN(S(N)(=O)=O)CCO1]
In some embodiments, R⁵ is
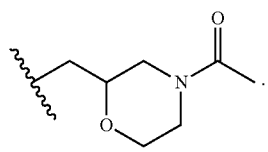 [SMILES: *CC1CN(C(C)=O)CCO1]
In some embodiments, R⁵ is
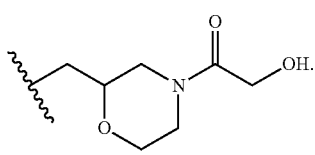 [SMILES: *CC1CN(C(=O)CO)CCO1]
In some embodiments, R⁵ is
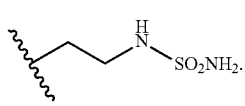 [SMILES: *CCNS(N)(=O)=O]
In some embodiments, R⁵ is
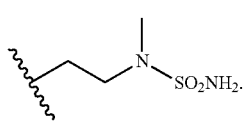 [SMILES: *CCN(C)S(N)(=O)=O]
In some embodiments, R⁵ is
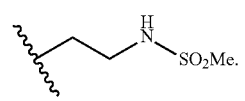
In some embodiments, R⁵ is
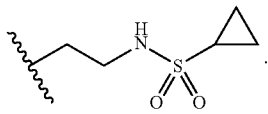 [SMILES: *CCNS(=O)(=O)C1CC1]
In some embodiments, R⁵ is
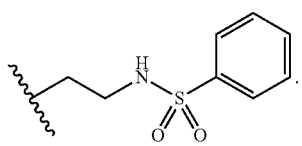 [SMILES: *CCNS(=O)(=O)c1ccccc1]
In some embodiments, R⁵ is
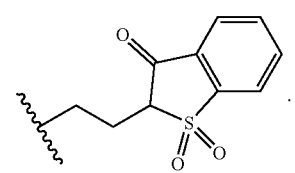 [SMILES: *CCC1C(=O)c2ccccc2S1(=O)=O]
In some embodiments, R⁵ is
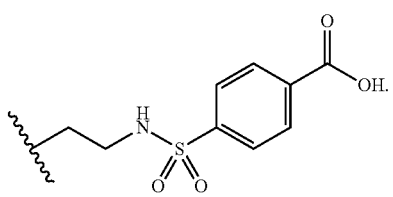 [SMILES: *CCNS(=O)(=O)c1ccc(C(=O)O)cc1]
In some embodiments, R⁵ is
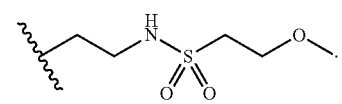
In some embodiments, R⁵ is
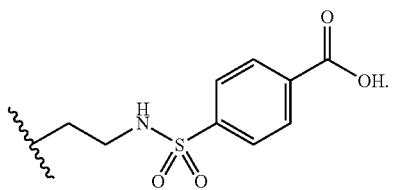 [SMILES: *CCNS(=O)(=O)c1ccc(C(=O)O)cc1]
In some embodiments, R⁵ is
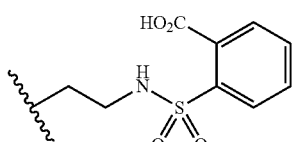

In some embodiments, $R^5$ is
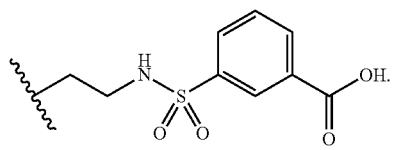 [SMILES: *CCNS(=O)(=O)c1cccc(C(=O)O)c1]
In some embodiments, $R^5$ is
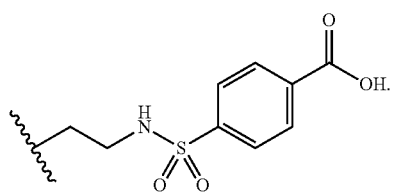 [SMILES: *CCNS(=O)(=O)c1ccc(C(=O)O)cc1]
In some embodiments, $R^5$ is
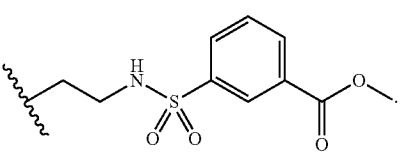
In some embodiments, $R^5$ is
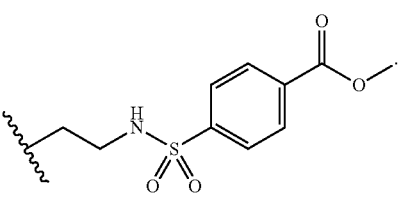
In some embodiments, $R^5$ is
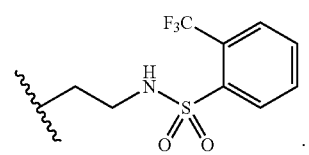 [SMILES: *CCNS(=O)(=O)c1ccccc1C(F)(F)F]
In some embodiments, $R^5$ is
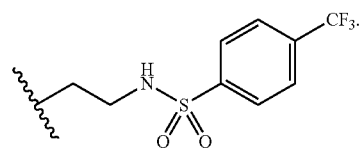 [SMILES: *CCNS(=O)(=O)c1ccc(C(F)(F)F)cc1]
In some embodiments, $R^5$ is
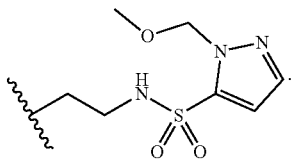 [SMILES: *CCNS(=O)(=O)c1ccnn1COC]
In some embodiments, $R^5$ is
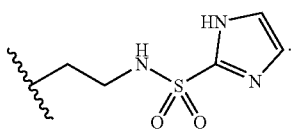 [SMILES: *CCNS(=O)(=O)c1ncc[nH]1]
In some embodiments, $R^5$ is
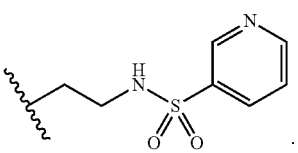 [SMILES: *CCNS(=O)(=O)c1cccnc1]
In some embodiments, $R^5$ is
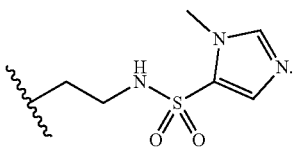 [SMILES: *CCNS(=O)(=O)c1cncn1C]
In some embodiments, $R^5$ is
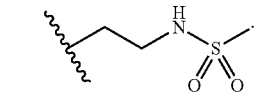
In some embodiments, $R^5$ is
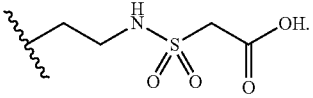 [SMILES: *CCNS(=O)(=O)CC(=O)O]
In some embodiments, $R^5$ is
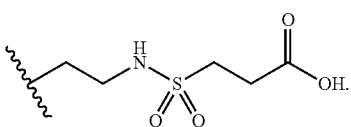 [SMILES: *CCNS(=O)(=O)CCC(=O)O]

In some embodiments, $R^5$ is
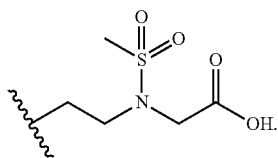 [SMILES: *CCN(CC(=O)O)S(C)(=O)=O]
In some embodiments, $R^5$ is
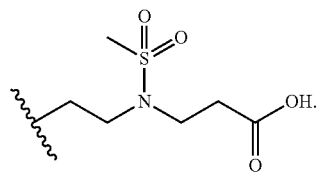 [SMILES: *CCN(CCC(=O)O)S(C)(=O)=O]
In some embodiments, $R^5$ is
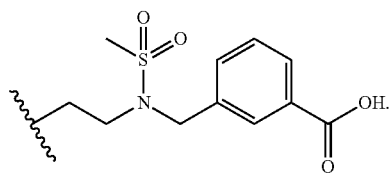 [SMILES: *CCN(Cc1cccc(C(=O)O)c1)S(C)(=O)=O]
In some embodiments, $R^5$ is
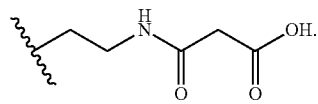 [SMILES: *CCNC(=O)CC(=O)O]
In some embodiments, $R^5$ is
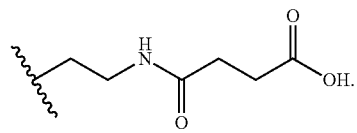 [SMILES: *CCNC(=O)CCC(=O)O]
In some embodiments, $R^5$ is
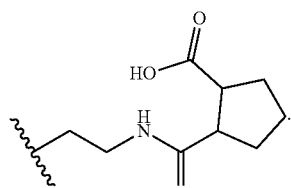
In some embodiments, $R^5$ is
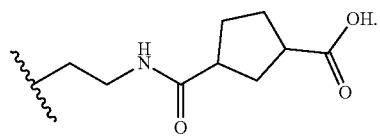 [SMILES: *CCNC(=O)C1CCC(C(=O)O)C1]
In some embodiments, $R^5$ is
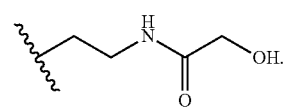 [SMILES: *CCNC(=O)CO]
In some embodiments, $R^5$ is
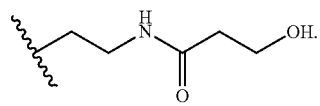 [SMILES: *CCNC(=O)CCO]
In some embodiments, $R^5$ is
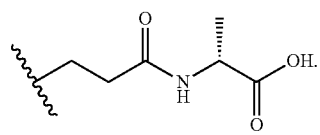 [SMILES: *CCC(=O)N[C@H](C)C(=O)O]
In some embodiments, $R^5$ is
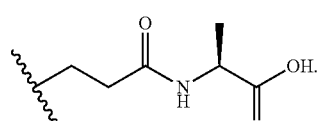
In some embodiments, $R^5$ is
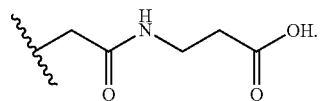 [SMILES: *CC(=O)NCCC(=O)O]
In some embodiments, $R^5$ is
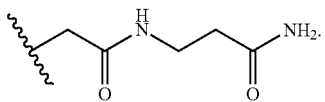 [SMILES: *CC(=O)NCCC(N)=O]

In some embodiments, $R^5$ is

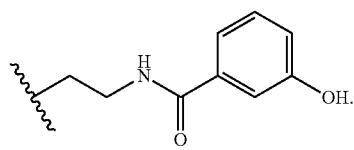 [SMILES: *CCNC(=O)c1cccc(O)c1]

In some embodiments, $R^5$ is

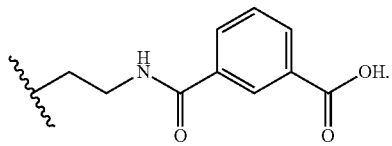 [SMILES: *CCNC(=O)c1cccc(C(=O)O)c1]

In some embodiments, $R^5$ is

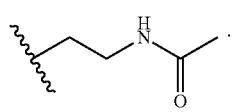 [SMILES: *CCNC(C)=O]

In some embodiments, $R^5$ is

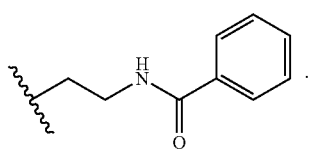 [SMILES: *CCNC(=O)c1ccccc1]

In some embodiments, $R^5$ is

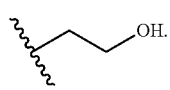 [SMILES: *CCO]

In some embodiments, $R^5$ is

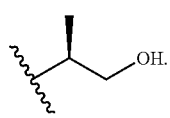 [SMILES: *[C@@H](C)CO]

In some embodiments, $R^5$ is

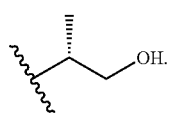 [SMILES: *[C@H](C)CO]

In some embodiments, $R^5$ is

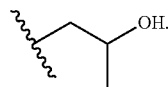

In some embodiments, $R^5$ is

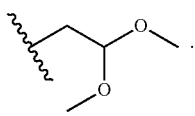 [SMILES: *CC(OC)OC]

In some embodiments, $R^5$ is

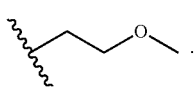 [SMILES: *CCOC]

In some embodiments, $R^5$ is

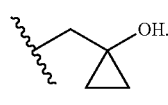

In some embodiments, $R^5$ is

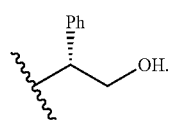

In some embodiments, $R^5$ is

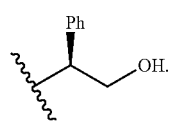

In some embodiments, $R^5$ is

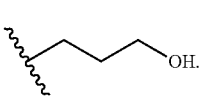

In some embodiments, $R^5$ is

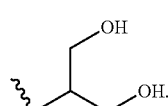

In some embodiments, $R^5$ is

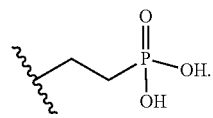 [SMILES: *CCP(=O)(O)O]

In some embodiments, $R^5$ is

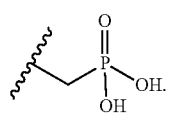 [SMILES: *CP(=O)(O)O]

In some embodiments, $R^5$ is

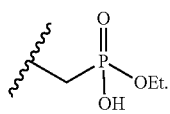 [SMILES: *CP(=O)(O)OCC]

In some embodiments, $R^5$ is

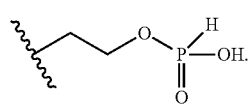 [SMILES: *CCO[PH](=O)O]

In some embodiments, $R^5$ is

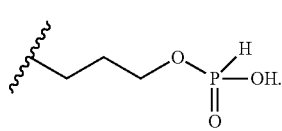 [SMILES: *CCCO[PH](=O)O]

In some embodiments, $R^5$ is

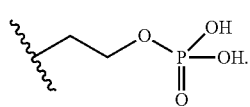

In some embodiments, $R^5$ is

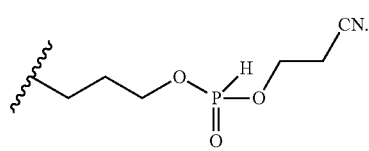 [SMILES: *CCCO[PH](=O)OCCC#N]

In some embodiments, $R^5$ is

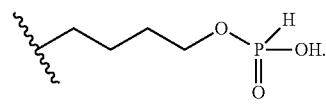 [SMILES: *CCCCO[PH](=O)O]

In some embodiments, $R^5$ is

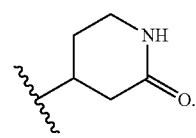 [SMILES: *C1CCNC(=O)C1]

In some embodiments, $R^5$ is

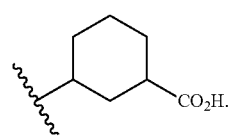

In some embodiments, $R^5$ is

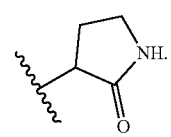 [SMILES: *C1CCNC1=O]

In some embodiments, $R^5$ is

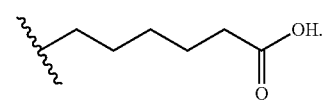 [SMILES: *CCCCCC(=O)O]

In some embodiments, $R^5$ is

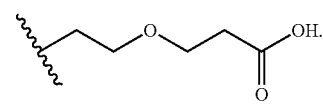 [SMILES: *CCOCCC(=O)O]

In some embodiments, $R^5$ is

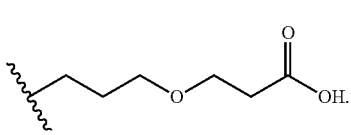 [SMILES: *CCCOCCC(=O)O]

In some embodiments, $R^5$ is
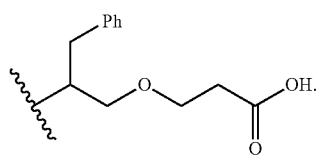 [SMILES: *C(COCCC(=O)O)Cc1ccccc1]
In some embodiments, $R^5$ is
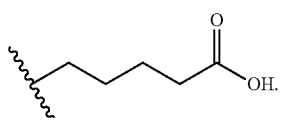 [SMILES: *CCCCC(=O)O]
In some embodiments, $R^5$ is
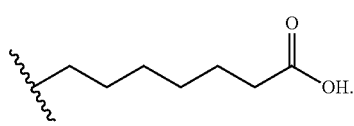 [SMILES: *CCCCCCC(=O)O]
In some embodiments, $R^5$ is
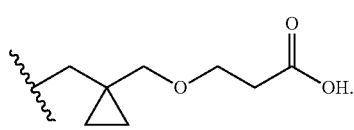 [SMILES: *CC1(COCCC(=O)O)CC1]
In some embodiments, $R^5$ is
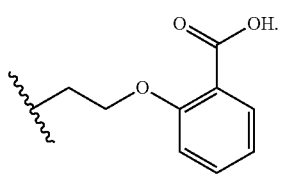 [SMILES: *CCOc1ccccc1C(=O)O]
In some embodiments, $R^5$ is
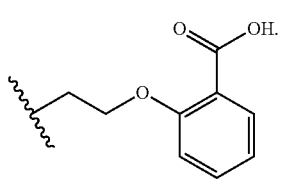 [SMILES: *CCOc1ccccc1C(=O)O]
In some embodiments, $R^5$ is
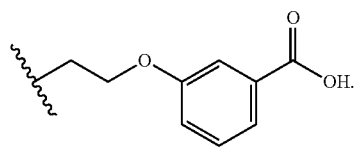 [SMILES: *CCOc1cccc(C(=O)O)c1]
In some embodiments, $R^5$ is
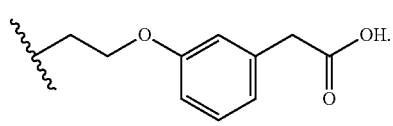 [SMILES: *CCOc1cccc(CC(=O)O)c1]
In some embodiments, $R^5$ is
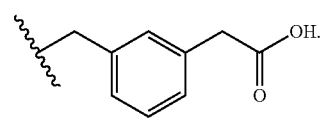 [SMILES: *Cc1cccc(CC(=O)O)c1]
In some embodiments, $R^5$ is
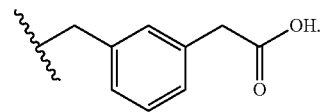 [SMILES: *Cc1cccc(CC(=O)O)c1]
In some embodiments, $R^5$ is
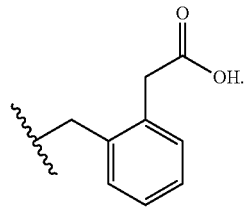 [SMILES: *Cc1ccccc1CC(=O)O]
In some embodiments, $R^5$ is
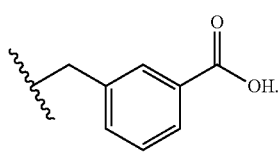 [SMILES: *Cc1cccc(C(=O)O)c1]
In some embodiments, $R^5$ is
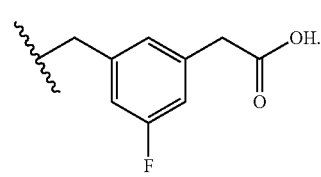 [SMILES: *Cc1cc(F)cc(CC(=O)O)c1]

In some embodiments, R⁵ is

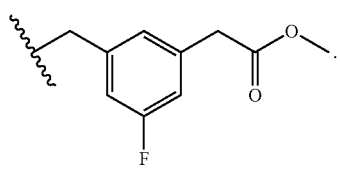 [SMILES: *Cc1cc(F)cc(CC(=O)OC)c1]

In some embodiments, R⁵ is

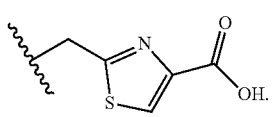 [SMILES: *Cc1nc(C(=O)O)cs1]

In some embodiments, R⁵ is

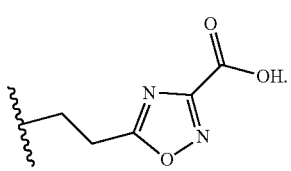 [SMILES: *CCc1nc(C(=O)O)no1]

In some embodiments, R⁵ is

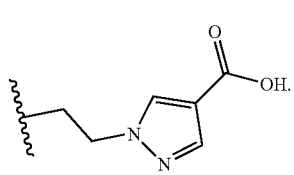 [SMILES: *CCn1cc(C(=O)O)cn1]

In some embodiments, R⁵ is

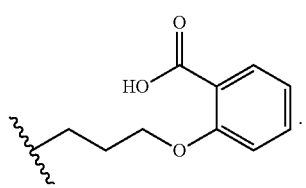 [SMILES: *CCCOc1ccccc1C(=O)O]

In some embodiments, R⁵ is

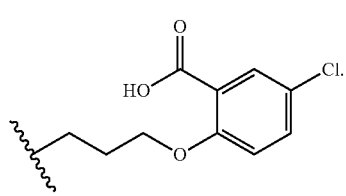 [SMILES: *CCCOc1ccc(Cl)cc1C(=O)O]

In some embodiments, R⁵ is

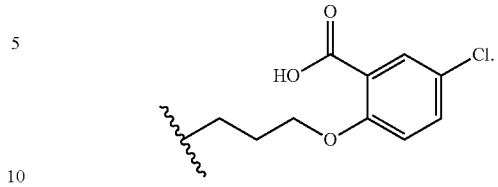

In some embodiments, R⁵ is

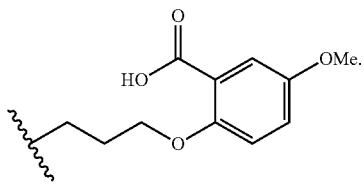 [SMILES: *CCCOc1ccc(OC)cc1C(=O)O]

In some embodiments, R⁵ is

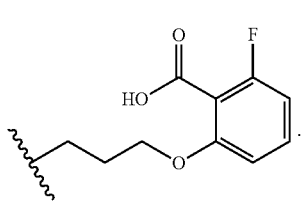 [SMILES: *CCCOc1cccc(F)c1C(=O)O]

In some embodiments, R⁵ is

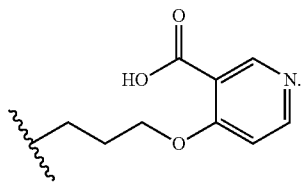 [SMILES: *CCCOc1ccncc1C(=O)O]

In some embodiments, R⁵ is

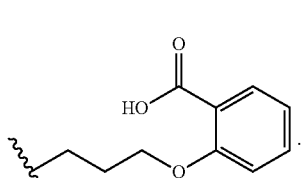

In some embodiments, R⁵ is

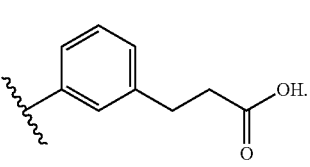 [SMILES: *c1cccc(CCC(=O)O)c1]

In some embodiments, R⁵ is selected from those groups depicted in Table 1.

In some embodiments, $R^5$ is selected from those groups depicted in Table 2.

As defined above and described herein, each $R^6$ is independently halogen, —COR, —$(CR_2)_{0-6}CO_2R$, —$(CR_2)_{0-6}CONR_2$, —OR, —$(CR_2)_{1-4}OR$, —$NR_2$, —$(CR_2)_{1-4}NR_2$, NRC(O)OR, —NRC(O)R, —NRC(O)$NR_2$, —SR, —$SO_2R$, —S(O)R, —$(CR_2)_{0-6}SO_3R$, —$(CR_2)_{0-6}SO_2NR_2$, —$(CR_2)_{0-6}OSO_2NR_2$, —$(CR_2)_{0-6}NRSO_2R$, —$(CR_2)_{0-6}NRSO_2OR$, —$(CR_2)_{0-6}OP(OR)_2$, —$(CR_2)_{0-6}OP(O)(OR)_2$, —$(CR_2)_{0-6}P(O)(OR)_2$, —$(CR_2)_{0-6}OP(O)(H)OR$, —$B(OR)_2$, or $R^B$.

In some embodiments, $R^6$ is halogen. In some embodiments, $R^6$ is —COR. In some embodiments, $R^6$ is —$(CR_2)_{0-6}CO_2R$. In some embodiments, $R^6$ is —$(CR_2)_{0-6}CONR_2$. In some embodiments, $R^6$ is —OR. In some embodiments, $R^6$ is —$(CR_2)_{1-4}OR$. In some embodiments, $R^6$ is —$NR_2$. In some embodiments, $R^6$ is —$(CR_2)_{1-4}NR_2$. In some embodiments, $R^6$ is —NRC(O)OR. In some embodiments, $R^6$ is —NRC(O)R. In some embodiments, $R^6$ is —NRC(O)$NR_2$. In some embodiments, $R^6$ is —SR. In some embodiments, $R^6$ is —$SO_2R$. In some embodiments, $R^6$ is —S(O)R. In some embodiments, $R^6$ is —$(CR_2)_{0-6}SO_3R$. In some embodiments, $R^6$ is —$(CR_2)_{0-6}SO_2NR_2$. In some embodiments, $R^6$ is —$(CR_2)_{0-6}OSO_2NR_2$. In some embodiments, $R^6$ is —$(CR_2)_{0-6}NRSO_2R$. In some embodiments, $R^6$ is —$(CR_2)_{0-6}NRSO_2OR$. In some embodiments, $R^6$ is —$(CR_2)_{0-6}OP(OR)_2$. In some embodiments, $R^6$ is —$(CR_2)_{0-6}OP(O)(OR)_2$. In some embodiments, $R^6$ is —$(CR_2)_{0-6}P(O)(OR)_2$. In some embodiments, $R^6$ is —$(CR_2)_{0-6}OP(O)(H)OR$. In some embodiments, $R^6$ is —$B(OR)_2$. In some embodiments, $R^6$ is $R^B$.

In some embodiments, $R^6$ is fluoro. In some embodiments, $R^6$ is chloro. In some embodiments, $R^6$ is bromo. In some embodiments, $R^6$ is —OH. In some embodiments, $R^6$ is —OMe. In some embodiments, $R^6$ is —OEt. In some embodiments, $R^6$ is —OtBu. In some embodiments, $R^6$ is —OBn. In some embodiments, $R^6$ is —$OCH_2CH_2OH$. In some embodiments, $R^6$ is —$OCH_2CO_2H$. In some embodiments, $R^6$ is —$OCONHCH_2CO_2H$. In some embodiments, $R^6$ is —$CF_3$. In some embodiments, $R^6$ is —$OCF_3$. In some embodiments, $R^6$ is —$CH(OH)CF_3$. In some embodiments, $R^6$ is —$C(OH)(CF_3)_2$. In some embodiments, $R^6$ is cyano. In some embodiments, $R^6$ is methyl. In some embodiments, $R^6$ is =$CH_2$. In some embodiments, $R^6$ is ethyl. In some embodiments, $R^6$ is —$CH_2OH$. In some embodiments, $R^6$ is —$CH_2OMe$. In some embodiments, $R^6$ is acetyl. In some embodiments, $R^6$ is —OAc. In some embodiments, $R^6$ is —$NH_2$. In some embodiments, $R^6$ is —NHBoc. In some embodiments, $R^6$ is —$CH_2NH_2$. In some embodiments, $R^6$ is —$CH_2NHBoc$. In some embodiments, $R^6$ is —$CH_2CH_2OH$. In some embodiments, $R^6$ is tert-butyl. In some embodiments, $R^6$ is —$C_{3-6}$cycloalkyl. In some embodiments, $R^6$ is cyclohexyl. In some embodiments, $R^6$ is phenyl. In some embodiments, $R^6$ is N-morpholinyl. In some embodiments, $R^6$ is —$CO_2H$. In some embodiments, $R^6$ is —$CO_2Me$. In some embodiments, $R^6$ is —$CO_2Et$. In some embodiments, $R^6$ is —$CO_2iPr$. In some embodiments, $R^6$ is —$CO_2nBu$. In some embodiments, $R^6$ is —$CO_2isoBu$. In some embodiments, $R^6$ is —$CO_2tBu$. In some embodiments, $R^6$ is —$CO_2CH_2CF_3$. In some embodiments, $R^6$ is —$CO_2CH(CF_3)_2$. In some embodiments, $R^6$ is —$CONH_2$. In some embodiments, $R^6$ is —CONHOH. In some embodiments, $R^6$ is —CONHOMe. In some embodiments, $R^6$ is —CONHMe. In some embodiments, $R^6$ is —CONHEt. In some embodiments, $R^6$ is —$CONMe_2$. In some embodiments, $R^6$ is —$COCH_2OH$. In some embodiments, $R^6$ is —$COCH_2OAc$. In some embodiments, $R^6$ is —$CONHCH_2CH_2OH$. In some embodiments, $R^6$ is —$CONHCH_2CONH_2$. In some embodiments, $R^6$ is —$CONHCH_2CH_2CONH_2$. In some embodiments, $R^6$ is —$CONHCH_2CO_2Me$. In some embodiments, $R^6$ is —$CONHCH_2CH_2CO_2H$. In some embodiments, $R^6$ is —$NH_2$. In some embodiments, $R^6$ is —NHAc. In some embodiments, $R^6$ is —$CH_2CO_2H$. In some embodiments, $R^6$ is —$CH_2CO_2Me$. In some embodiments, $R^6$ is —$CH_2CO_2tBu$. In some embodiments, $R^6$ is —$CH_2CONH_2$. In some embodiments, $R^6$ is —$CH_2NHSO_2Me$. In some embodiments, $R^6$ is —$NHSO_2Me$. In some embodiments, $R^6$ is —$NHSO_2Ph$. In some embodiments, $R^6$ is —$NHCONH_2$. In some embodiments, $R^6$ is —NHCOPh. In some embodiments, $R^6$ is —$NHCOCH_2OH$. In some embodiments, $R^6$ is —$NHCOCH_2OAc$. In some embodiments, $R^6$ is —$NHSO_2CH_2CH_2CO_2H$. In some embodiments, $R^6$ is —$CH_2NHCOCH_2OH$. In some embodiments, $R^6$ is —$CH_2NHCOCH_2CO_2H$. In some embodiments, $R^6$ is —$SO_3H$. In some embodiments, $R^6$ is —$SO_2Me$. In some embodiments, $R^6$ is —$SO_2NH_2$. In some embodiments, $R^6$ is —$SO_2NHBoc$. In some embodiments, $R^6$ is —$CH_2SO_2NH_2$. In some embodiments, $R^6$ is —$OSO_2NH_2$. In some embodiments, $R^6$ is —$OCONHCH_2CO_2Me$. In some embodiments $R^6$ is —$B(OH)_2$. In some embodiments, $R^6$ is —$CH_2OSO_2NH_2$. In some embodiments, $R^6$ is

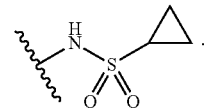 [SMILES: *NS(=O)(=O)C1CC1]

In some embodiments, $R^6$ is

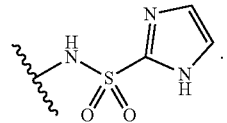 [SMILES: *NS(=O)(=O)c1ncc[nH]1]

In some embodiments, $R^6$ is

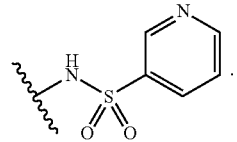 [SMILES: *NS(=O)(=O)c1cccnc1]

In some embodiments, $R^6$ is

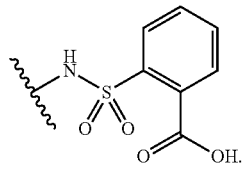 [SMILES: *NS(=O)(=O)c1ccccc1C(=O)O]

In some embodiments, R⁶ is

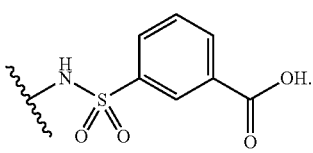 [SMILES: *NS(=O)(=O)c1cccc(C(=O)O)c1]

In some embodiments, R⁶ is

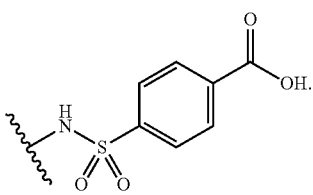 [SMILES: *NS(=O)(=O)c1ccc(C(=O)O)cc1]

In some embodiments, R⁶ is

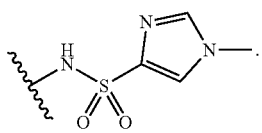 [SMILES: *NS(=O)(=O)c1cn(C)cn1]

In some embodiments, R⁶ is

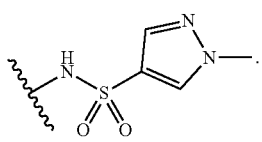 [SMILES: *NS(=O)(=O)c1cnn(C)c1]

In some embodiments, R⁶ is —OP(OH)₂. In some embodiments, R⁶ is —CH₂OP(OH)₂. In some embodiments, R⁶ is —CH₂OP(O)(H)OH. In some embodiments, R⁶ is —OP(O)(OH)₂. In some embodiments, R⁶ is —CH₂OP(O)(OH)₂. In some embodiments, R⁶ is —CH₂P(O)(OH)₂. In some embodiments, R⁶ is

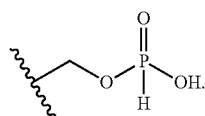 [SMILES: *CO[PH](=O)O]

In some embodiments, R⁶ is

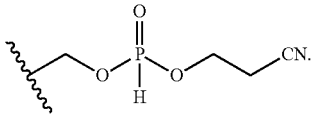 [SMILES: *CO[PH](=O)OCCC#N]

In some embodiments, R⁶ is

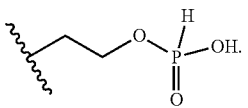

In some embodiments, R⁶ is

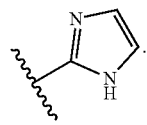

In some embodiments, R⁶ is

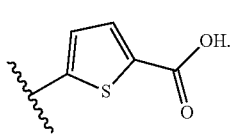 [SMILES: *c1ccc(C(=O)O)s1]

In some embodiments, R⁶ is

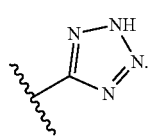 [SMILES: *c1nn[nH]n1]

In some embodiments, R⁶ is

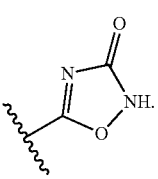 [SMILES: *c1nc(=O)[nH]o1]

In some embodiments, R⁶ is

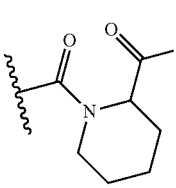

In some embodiments, R⁶ is

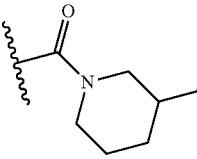

In some embodiments, $R^6$ is
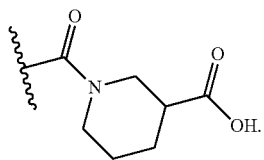 [SMILES: *C(=O)N1CCCC(C(=O)O)C1]
In some embodiments, $R^6$ is
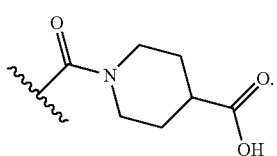 [SMILES: *C(=O)N1CCC(C(=O)O)CC1]
In some embodiments, $R^6$ is
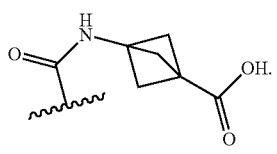 [SMILES: *C(=O)NC12CC(C(=O)O)(C1)C2]
In some embodiments, $R^6$ is
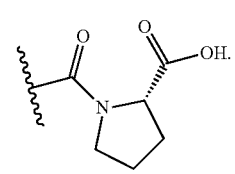 [SMILES: *C(=O)N1CCC[C@H]1C(=O)O]
In some embodiments, $R^6$ is
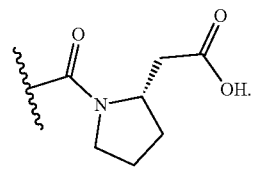 [SMILES: *C(=O)N1CCC[C@H]1CC(=O)O]
In some embodiments, $R^6$ is
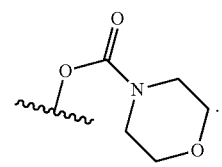 [SMILES: *OC(=O)N1CCOCC1]
In some embodiments, $R^6$ is
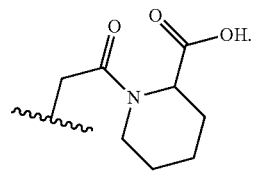 [SMILES: *CC(=O)N1CCCCC1C(=O)O]
In some embodiments, $R^6$ is
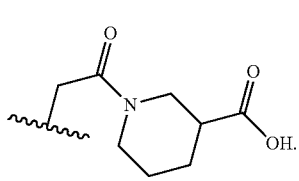 [SMILES: *CC(=O)N1CCCC(C(=O)O)C1]
In some embodiments, $R^6$ is
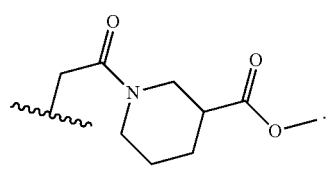 [SMILES: *CC(=O)N1CCCC(C(=O)OC)C1]
In some embodiments, $R^6$ is
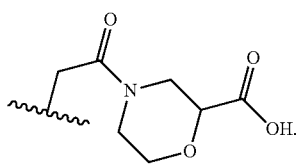 [SMILES: *CC(=O)N1CCOC(C(=O)O)C1]
In some embodiments, $R^6$ is
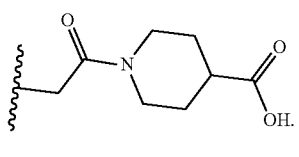 [SMILES: *CC(=O)N1CCC(C(=O)O)CC1]
In some embodiments, $R^6$ is
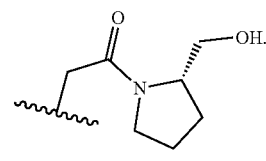 [SMILES: *CC(=O)N1CCC[C@H]1CO]

In some embodiments, $R^6$ is
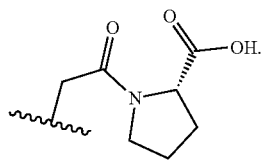 [SMILES: *CC(=O)N1CCC[C@H]1C(=O)O]
In some embodiments, $R^6$ is
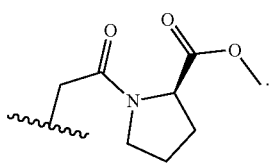 [SMILES: *CC(=O)N1CCC[C@@H]1C(=O)OC]
In some embodiments, $R^6$ is
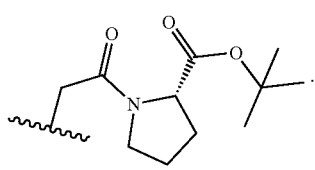 [SMILES: *CC(=O)N1CCC[C@H]1C(=O)OC(C)(C)C]
In some embodiments, $R^6$ is
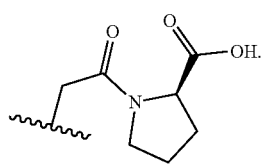 [SMILES: *CC(=O)N1CCC[C@@H]1C(=O)O]
In some embodiments, $R^6$ is
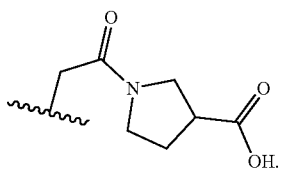 [SMILES: *CC(=O)N1CCC(C(=O)O)C1]
In some embodiments, $R^6$ is
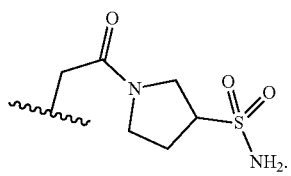 [SMILES: *CC(=O)N1CCC(S(N)(=O)=O)C1]
In some embodiments, $R^6$ is
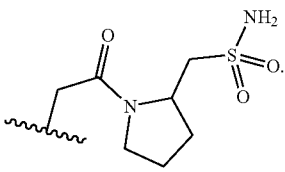 [SMILES: *CC(=O)N1CCCC1CS(N)(=O)=O]
In some embodiments, $R^6$ is
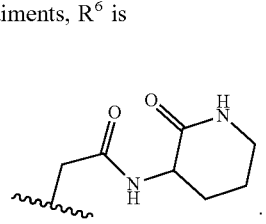
In some embodiments, $R^6$ is
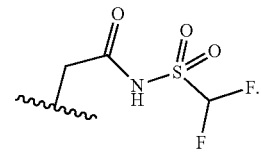 [SMILES: *CC(=O)NS(=O)(=O)C(F)F]
In some embodiments, $R^6$ is
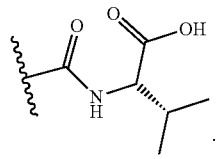
In some embodiments, $R^6$ is
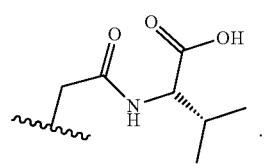

In some embodiments, $R^6$ is
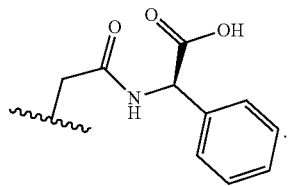 [SMILES: *CC(=O)N[C@@H](C(=O)O)c1ccccc1]
In some embodiments, $R^6$ is
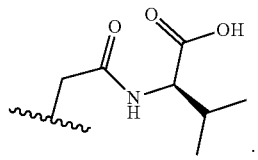 [SMILES: *CC(=O)N[C@@H](C(=O)O)C(C)C]
In some embodiments, $R^6$ is
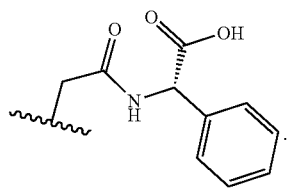 [SMILES: *CC(=O)N[C@H](C(=O)O)c1ccccc1]
In some embodiments, $R^6$ is
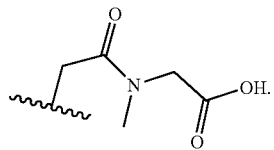 [SMILES: *CC(=O)N(C)CC(=O)O]
In some embodiments, $R^6$ is
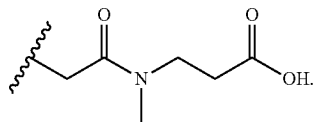 [SMILES: *CC(=O)N(C)CCC(=O)O]
In some embodiments, $R^6$ is
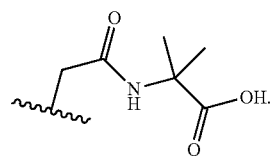 [SMILES: *CC(=O)NC(C)(C)C(=O)O]
In some embodiments, $R^6$ is
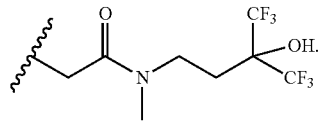 [SMILES: *CC(=O)N(C)CCC(O)(C(F)(F)F)C(F)(F)F]
In some embodiments, $R^6$ is
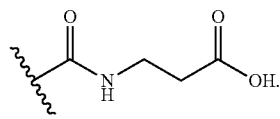 [SMILES: *C(=O)NCCC(=O)O]
In some embodiments, $R^6$ is
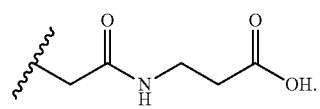 [SMILES: *CC(=O)NCCC(=O)O]
In some embodiments, $R^6$ is
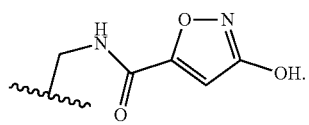 [SMILES: *CNC(=O)c1cc(O)no1]
In some embodiments, $R^6$ is
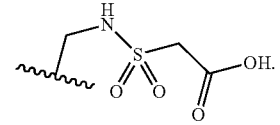 [SMILES: *CNS(=O)(=O)CC(=O)O]
In some embodiments, $R^6$ is
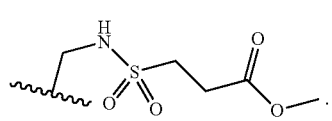 [SMILES: *CNS(=O)(=O)CCC(=O)OC]
In some embodiments, $R^6$ is
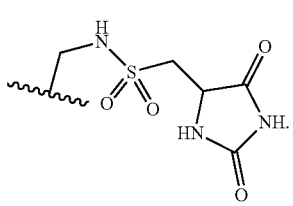 [SMILES: *CNS(=O)(=O)CC1NC(=O)NC1=O]

In some embodiments, R⁶ is
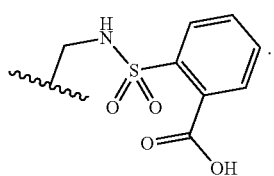 [SMILES: *CNS(=O)(=O)c1ccccc1C(=O)O]
In some embodiments, R⁶ is
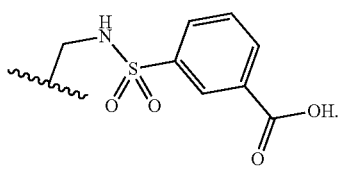 [SMILES: *CNS(=O)(=O)c1cccc(C(=O)O)c1]
In some embodiments, R⁶ is
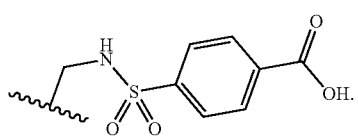 [SMILES: *CNS(=O)(=O)c1ccc(C(=O)O)cc1]
In some embodiments, R⁶ is
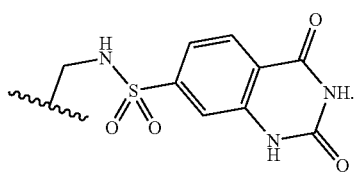 [SMILES: *CNS(=O)(=O)c1ccc2c(=O)[nH]c(=O)[nH]c2c1]
In some embodiments, R⁶ is
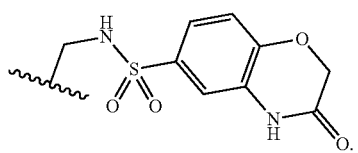 [SMILES: *CNS(=O)(=O)c1ccc2c(c1)NC(=O)CO2]
In some embodiments, R⁶ is
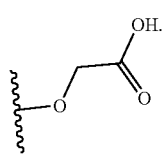
In some embodiments, R⁶ is
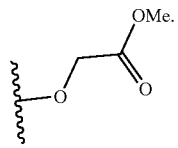 [SMILES: *OCC(=O)OC]
In some embodiments, R⁶ is
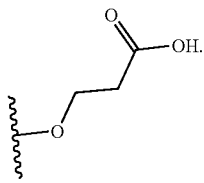 [SMILES: *OCCC(=O)O]
In some embodiments, R⁶ is
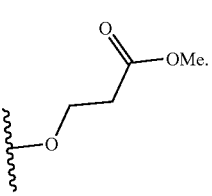 [SMILES: *OCCC(=O)OC]
In some embodiments, R⁶ is
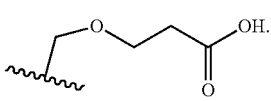 [SMILES: *COCCC(=O)O]
In some embodiments, R⁶ is
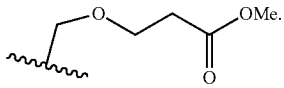 [SMILES: *COCCC(=O)OC]
In some embodiments, R⁶ is
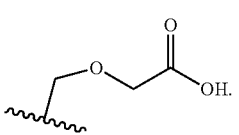 [SMILES: *COCC(=O)O]
In some embodiments, R⁶ is
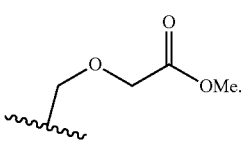 [SMILES: *COCC(=O)OC]

In some embodiments, $R^6$ is

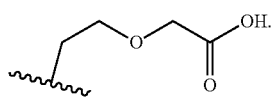 [SMILES: *CCOCC(=O)O]

In some embodiments, $R^6$ is

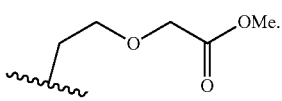 [SMILES: *CCOCC(=O)OC]

In some embodiments, $R^6$ is

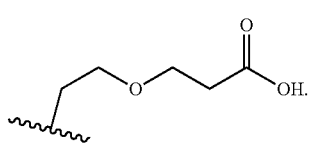 [SMILES: *CCOCCC(=O)O]

In some embodiments, $R^6$ is

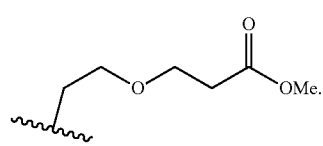 [SMILES: *CCOCCC(=O)OC]

In some embodiments, $R^6$ is

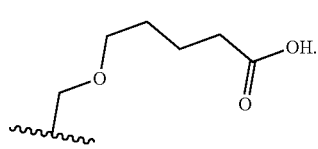 [SMILES: *COCCCCC(=O)O]

In some embodiments, $R^6$ is

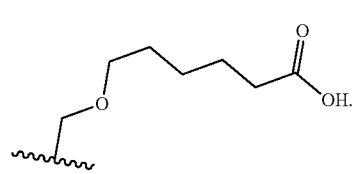 [SMILES: *COCCCCCC(=O)O]

In some embodiments, $R^6$ is

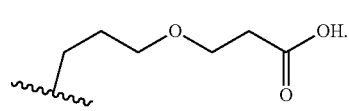 [SMILES: *CCCOCCC(=O)O]

In some embodiments, $R^6$ is

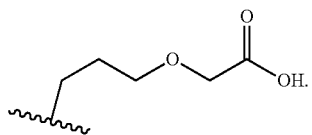 [SMILES: *CCCOCC(=O)O]

In some embodiments, $R^6$ is

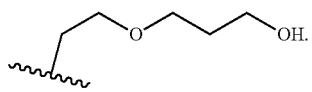 [SMILES: *CCOCCCO]

In some embodiments, $R^6$ is

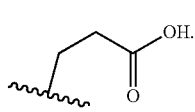 [SMILES: *CCC(=O)O]

In some embodiments, $R^6$ is

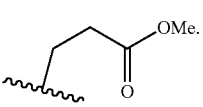 [SMILES: *CCC(=O)OC]

In some embodiments, $R^6$ is

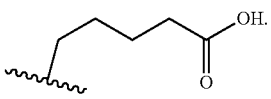 [SMILES: *CCCCC(=O)O]

In some embodiments, $R^6$ is

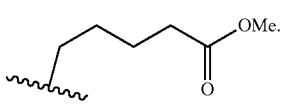 [SMILES: *CCCCC(=O)OC]

In some embodiments, $R^6$ is

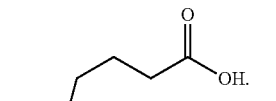

In some embodiments, $R^6$ is

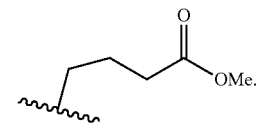 [SMILES: *CCCC(=O)OC]

In some embodiments, $R^6$ is

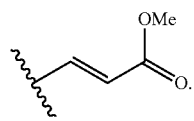 [SMILES: */C=C/C(=O)OC]

In some embodiments, $R^6$ is

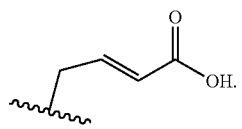

In some embodiments, $R^6$ is

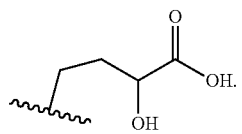 [SMILES: *CCC(O)C(=O)O]

In some embodiments, $R^6$ is

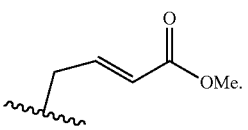 [SMILES: *C/C=C/C(=O)OC]

In some embodiments, $R^6$ is

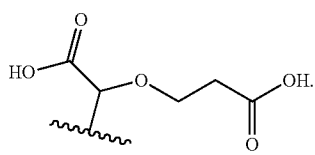 [SMILES: *C(OCCC(=O)O)C(=O)O]

In some embodiments, $R^6$ is

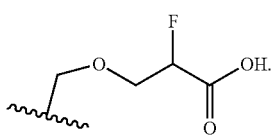

In some embodiments, $R^6$ is

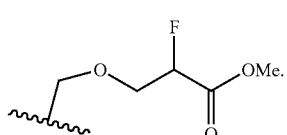

In some embodiments, $R^6$ is

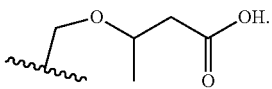 [SMILES: *COC(C)CC(=O)O]

In some embodiments, $R^6$ is

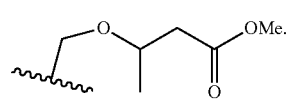 [SMILES: *COC(C)CC(=O)OC]

In some embodiments, $R^6$ is

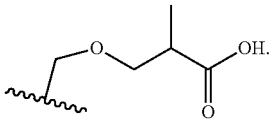 [SMILES: *COCC(C)C(=O)O]

In some embodiments, $R^6$ is

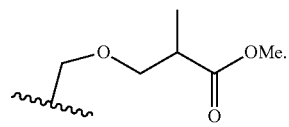 [SMILES: *COCC(C)C(=O)OC]

In some embodiments, $R^6$ is

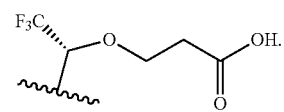 [SMILES: *[C@@H](OCCC(=O)O)C(F)(F)F]

In some embodiments, $R^6$ is

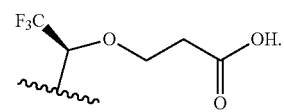

In some embodiments, $R^6$ is

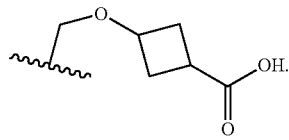 [SMILES: *COC1CC(C(=O)O)C1]

In some embodiments, $R^6$ is

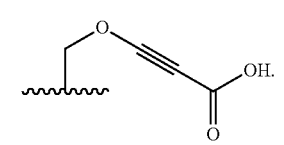 [SMILES: *COC#CC(=O)O]

In some embodiments, $R^6$ is
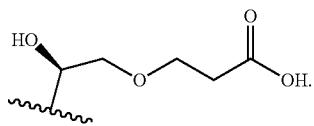 [SMILES: *[C@@H](O)COCCC(=O)O]
In some embodiments, $R^6$ is
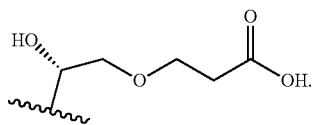 [SMILES: *[C@H](O)COCCC(=O)O]
In some embodiments, $R^6$ is
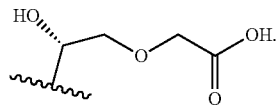 [SMILES: *[C@H](O)COCC(=O)O]
In some embodiments, $R^6$ is
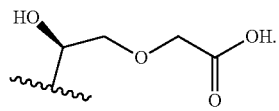 [SMILES: *[C@@H](O)COCC(=O)O]
In some embodiments, $R^6$ is
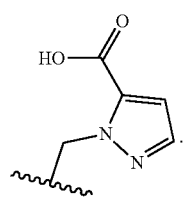 [SMILES: *Cn1nccc1C(=O)O]
In some embodiments, $R^6$ is
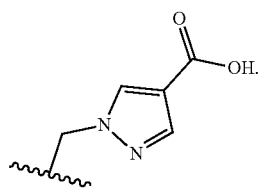 [SMILES: *Cn1cc(C(=O)O)cn1]
In some embodiments, $R^6$ is
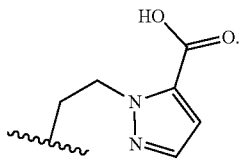 [SMILES: *CCn1nccc1C(=O)O]
In some embodiments, $R^6$ is
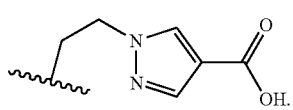 [SMILES: *CCn1cc(C(=O)O)cn1]
In some embodiments, $R^6$ is
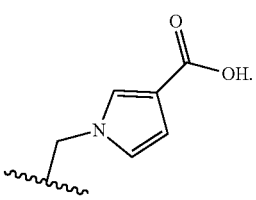 [SMILES: *Cn1ccc(C(=O)O)c1]
In some embodiments, $R^6$ is
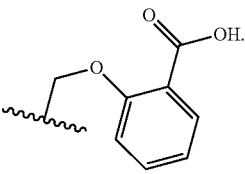 [SMILES: *COc1ccccc1C(=O)O]
In some embodiments, $R^6$ is
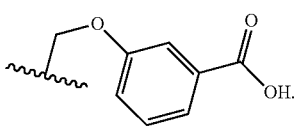 [SMILES: *COc1cccc(C(=O)O)c1]
In some embodiments, $R^6$ is
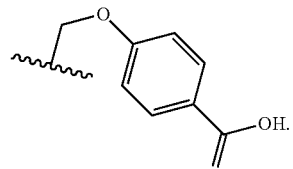

In some embodiments, $R^6$ is
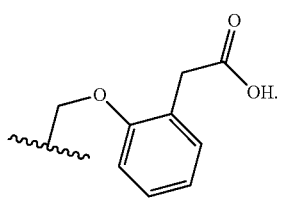 [SMILES: *COc1ccccc1CC(=O)O]
In some embodiments, $R^6$ is
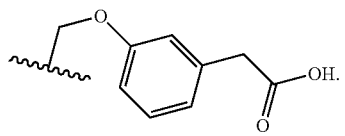 [SMILES: *COc1cccc(CC(=O)O)c1]
In some embodiments, $R^6$ is
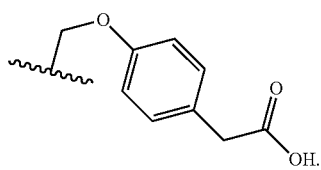 [SMILES: *COc1ccc(CC(=O)O)cc1]
In some embodiments, $R^6$ is
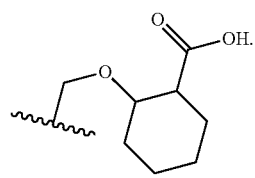 [SMILES: *COC1CCCCC1C(=O)O]
In some embodiments, $R^6$ is
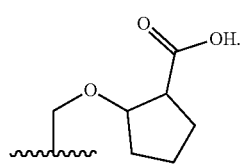 [SMILES: *COC1CCCC1C(=O)O]
In some embodiments, $R^6$ is
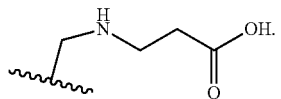 [SMILES: *CNCCC(=O)O]
In some embodiments, $R^6$ is
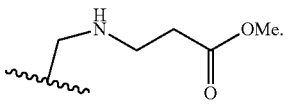 [SMILES: *CNCCC(=O)OC]
In some embodiments, $R^6$ is
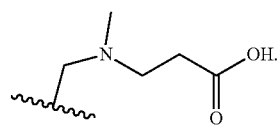 [SMILES: *CN(C)CCC(=O)O]
In some embodiments, $R^6$ is
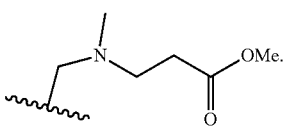 [SMILES: *CN(C)CCC(=O)OC]
In some embodiments, $R^6$ is
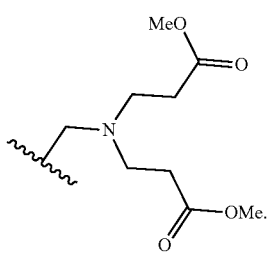 [SMILES: *CN(CCC(=O)OC)CCC(=O)OC]
In some embodiments, $R^6$ is
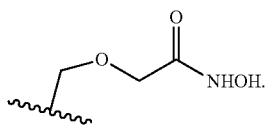
In some embodiments, $R^6$ is
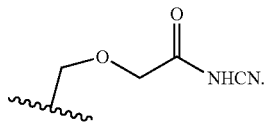
In some embodiments, $R^6$ is
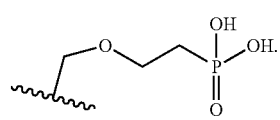 [SMILES: *COCCP(=O)(O)O]

In some embodiments, $R^6$ is

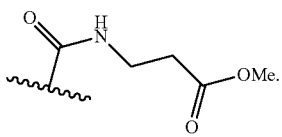 [SMILES: *C(=O)NCCC(=O)OC]

In some embodiments, $R^6$ is

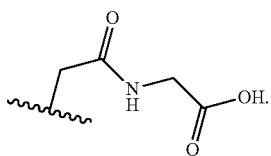 [SMILES: *CC(=O)NCC(=O)O]

In some embodiments, $R^6$ is

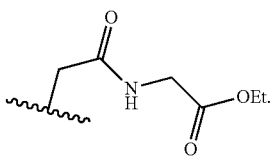 [SMILES: *CC(=O)NCC(=O)OCC]

In some embodiments, $R^6$ is selected from those groups depicted in Table 1.

In some embodiments, $R^6$ is selected from those groups depicted in Table 2.

As defined above and described herein, $R^A$, $R^B$, and $R^C$, independently, are an optionally substituted group selected from $C_{1-6}$ aliphatic; phenyl, including substituted phenyl; a 4- to 10-membered saturated or partially unsaturated monocyclic or bicyclic carbocyclic or heterocyclic ring having 1 to 3 heteroatoms independently selected from nitrogen, oxygen, phosphorus, and sulfur; and a 5- to 6-membered heteroaryl ring having 1 to 4 heteroatoms independently selected from nitrogen, oxygen, phosphorus, and sulfur.

In some embodiments, $R^A$, $R^B$, or $R^C$ is an optionally substituted $C_{1-6}$ aliphatic. In some embodiments, $R^A$, $R^B$, or $R^C$ is an optionally substituted phenyl. In some embodiments, $R^A$, $R^B$, or $R^C$ is an optionally substituted 4- to 10-membered saturated or partially unsaturated monocyclic or bicyclic carbocyclic or heterocyclic ring having 1 to 3 heteroatoms independently selected from nitrogen, oxygen, phosphorus, and sulfur. In some embodiments, $R^A$, $R^B$, or $R^C$ is an optionally substituted 5- to 6-membered heteroaryl ring having 1 to 4 heteroatoms independently selected from nitrogen, oxygen, phosphorus, and sulfur.

In some embodiments, $R^A$, $R^B$, or $R^C$, is selected from those groups depicted in Table 1.

In some embodiments, $R^A$, $R^B$, or $R^C$, is selected from those groups depicted in Table 2.

As defined above and described herein, Ring A is an optionally substituted phenyl, preferably substituted phenyl; optionally substituted HetCy; or optionally substituted HetAr, HetAr is a 5- to 6-membered heteroaryl ring having 1 to 4 heteroatoms independently selected from nitrogen, oxygen, and sulfur; wherein the 5- to 6-membered heteroaryl ring is not imidazole or pyrazole; HetCy is a 4- to 7-membered saturated or partially unsaturated heterocyclic ring having 1 to 3 heteroatoms independently selected from nitrogen, oxygen, and sulfur.

As defined above and described herein, Ring B1 is phenyl, particularly substituted phenyl; a 4- to 10-membered saturated or partially unsaturated monocyclic or bicyclic carbocyclic or heterocyclic ring having 1 to 3 heteroatoms independently selected from nitrogen, oxygen, phosphorus, and sulfur; or a 5- to 6-membered heteroaryl ring having 1 to 4 heteroatoms independently selected from nitrogen, oxygen, phosphorus, and sulfur.

In some embodiments, Ring B1 is phenyl, particularly substituted phenyl. In some embodiments, Ring B1 is a 4- to 10-membered saturated or partially unsaturated monocyclic or bicyclic carbocyclic or heterocyclic ring having 1 to 3 heteroatoms independently selected from nitrogen, oxygen, phosphorus, and sulfur. In some embodiments, Ring B1 is a 5- to 6-membered heteroaryl ring having 1 to 4 heteroatoms independently selected from nitrogen, oxygen, phosphorus, and sulfur.

In some embodiments, Ring B1 is

In some embodiments, Ring B1 is

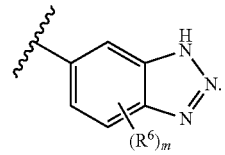

In some embodiments, Ring B1 is

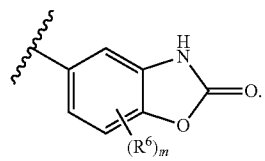

In some embodiments, Ring B1 is

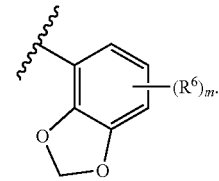

269

In some embodiments, Ring B1 is

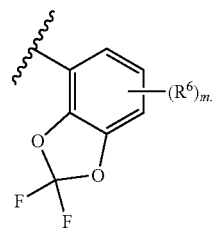

In some embodiments, Ring B1 is

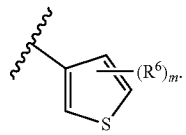

In some embodiments, Ring B1 is

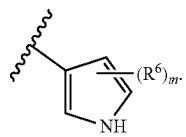

In some embodiments, Ring B1 is

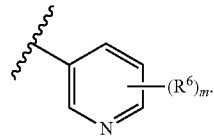

In some embodiments, Ring B1 is

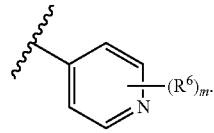

In some embodiments, Ring B1 is

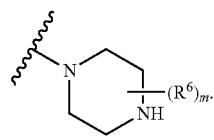

270

In some embodiments, Ring B1 is

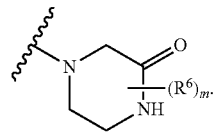

In some embodiments, Ring B1 is

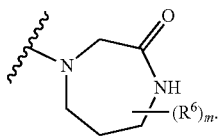

In some embodiments, Ring B1 is

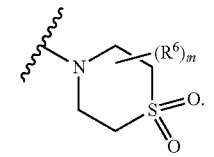

In some embodiments, Ring B1 is

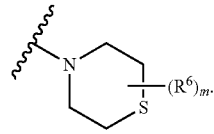

In some embodiments, Ring B1 is

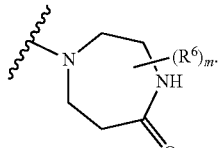

In some embodiments, Ring B1 is

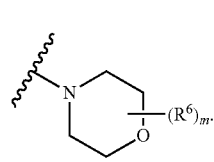

In some embodiments, Ring B1 is

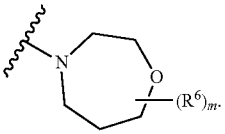

In some embodiments, Ring B1 is

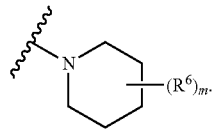

In some embodiments, Ring B1 is

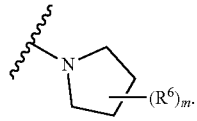

In some embodiments, Ring B1 is

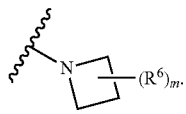

In some embodiments, Ring B1 is

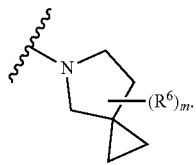

In some embodiments, Ring B1 is selected from those groups depicted in Table 1.

In some embodiments, Ring B1 is selected from those groups depicted in Table 2.

As defined above and described herein, Ring B2 is phenyl, including substituted phenyl; a 4- to 7-membered saturated or partially unsaturated carbocyclic or heterocyclic ring having 1 to 3 heteroatoms independently selected from nitrogen, oxygen, phosphorus, and sulfur; or a 5- to 6-membered heteroaryl ring having 1 to 4 heteroatoms independently selected from nitrogen, oxygen, phosphorus, and sulfur.

In some embodiments, Ring B2 is phenyl. In some embodiments, Ring B2 is a 4- to 7-membered saturated or partially unsaturated carbocyclic or heterocyclic ring having 1 to 3 heteroatoms independently selected from nitrogen, oxygen, phosphorus, and sulfur. In some embodiments, Ring B2 is a 5- to 6-membered heteroaryl ring having 1 to 4 heteroatoms independently selected from nitrogen, oxygen, phosphorus, and sulfur.

In some embodiments, Ring B2 is

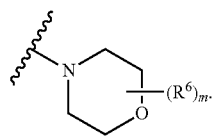

In some embodiments, Ring B2 is

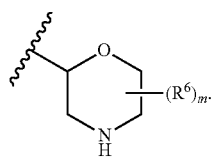

In some embodiments, Ring B2 is

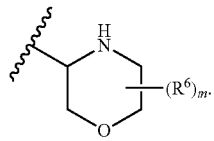

In some embodiments, Ring B2 is selected from those groups depicted in Table 1.

In some embodiments, Ring B2 is selected from those groups depicted in Table 2.

As defined above and described herein, Ring C is pyrrolidinyl or a 4- to 10-membered saturated or partially unsaturated monocyclic, bicyclic, bridged bicyclic, or spirocyclic heterocyclic ring having 0 to 3 heteroatoms (in addition to the nitrogen already depicted in Ring C) independently selected from nitrogen, oxygen, and sulfur.

In some embodiments, Ring C is pyrrolidinyl. In some embodiments, Ring C is a 4- to 10-membered saturated or partially unsaturated monocyclic, bicyclic, bridged bicyclic, or spirocyclic heterocyclic ring having 0 to 3 heteroatoms (in addition to the nitrogen already depicted in Ring C) independently selected from nitrogen, oxygen, and sulfur.

In some embodiments, Ring C is azetidinyl. In some embodiments, Ring C is pyrrolyl. In some embodiments, Ring C is 2,3-dihydro-1H-pyrrolyl. In some embodiments, Ring C is morpholinyl. In some embodiments, Ring C is thiazolidinyl. In some embodiments, Ring C is indolinyl. In some embodiments, Ring C is isoindolinyl. In some embodiments, Ring C is octahydroindolyl. In some embodiments, Ring C is azepanyl. In some embodiments, Ring C is oxazepanyl. In some embodiments, Ring C is an azabicyclohexane. In some embodiments, Ring C is an azabicycloheptane. In some embodiments, Ring C is an azabicyclooctane. In some embodiments, Ring C is an azabicyclononane. In some embodiments, Ring C is an azaspiroheptane. In some embodiments, Ring C is octahydrocyclicpentapyrrole.

In particular embodiments, Ring C is pyrrolidinyl, 2-azabicyclo[3.1.0]hexanyl, 3-azabicyclo[3.1.0]hexane, 5-azaspiro[2.4]heptanyl, or octahydrocyclopenta[b]pyrrolyl.

In some embodiments, Ring C is

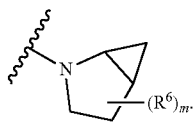

22In some embodiments, Ring C is
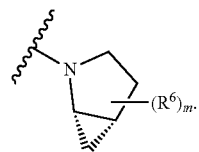
In some embodiments, Ring C is
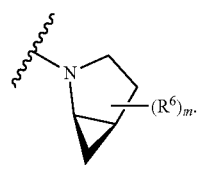
In some embodiments, Ring C is
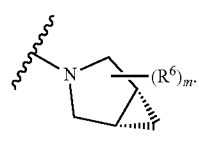
In some embodiments, Ring C is
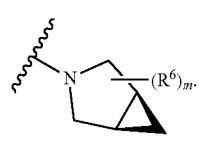
In some embodiments, Ring C is
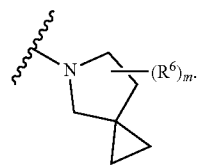
In some embodiments, Ring C is
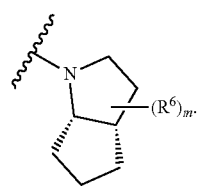
In some embodiments, Ring C is
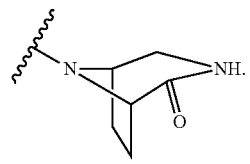 [SMILES: *N1C2CCC1C(=O)NC2]
In some embodiments, Ring C is
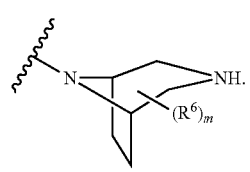
In some embodiments, Ring C is
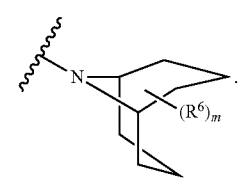
In some embodiments, Ring C is
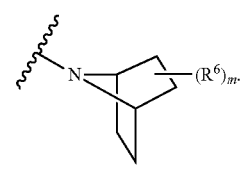
In some embodiments, Ring C is
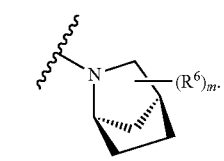
In some embodiments, Ring C is
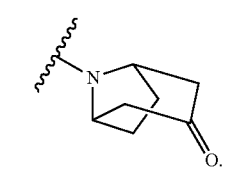 [SMILES: *N1C2CCC1CC(=O)C2]

In some embodiments, Ring C is

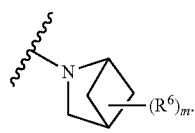

In some embodiments, Ring C is

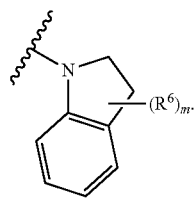

In some embodiments, Ring C is

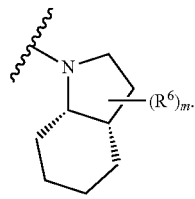

In some embodiments, Ring C is

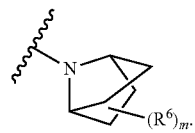

In some embodiments, Ring C is

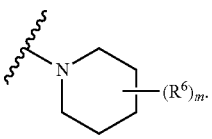

In some embodiments, Ring C is

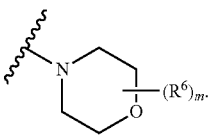

In some embodiments, Ring C is

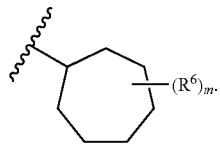

In some embodiments, Ring C is

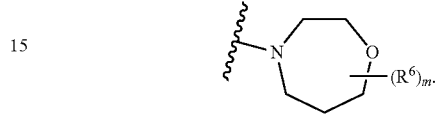

In some embodiments, Ring C is

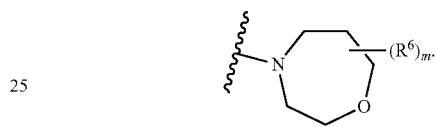

In some embodiments, Ring C is selected from those groups depicted in Table 1.

In some embodiments, Ring C is selected from those groups depicted in Table 2.

As defined above and described herein, n is 1, 2, 3, or 4.

In some embodiments, n is 1. In some embodiments, n is 2. In some embodiments, n is 3. In some embodiments, n is 4.

In some embodiments, n is selected from those groups depicted in Table 1.

In some embodiments, n is selected from those groups depicted in Table 2.

As defined above and described herein, m is 0, 1, 2, 3, or 4.

In some embodiments, m is 0. In some embodiments, m is 1, 2, 3, or 4. In some embodiments, m is 1. In some embodiments, m is 2. In some embodiments, m is 3. In some embodiments, m is 4.

In some embodiments, m is selected from those groups depicted in Table 1.

In some embodiments, m is selected from those groups depicted in Table 2.

As defined above and described herein, p is 0, 1, or 2.

In some embodiments, p is 0. In some embodiments, p is 1. In some embodiments, p is 2.

In some embodiments, p is selected from those groups depicted in Table 1.

In some embodiments, p is selected from those groups depicted in Table 2.

As defined above and described herein, q is 0, 1, or 2.

In some embodiments, q is 0. In some embodiments, q is 1. In some embodiments, q is 2.

In some embodiments, q is selected from those groups depicted in Table 1.

In some embodiments, q is selected from those groups depicted in Table 2.

Exemplary compounds of the present disclosure are set forth in Table 1, below.

TABLE 1
Exemplary Compounds
| I-# | Structure |
|---|---|
| I-892 | 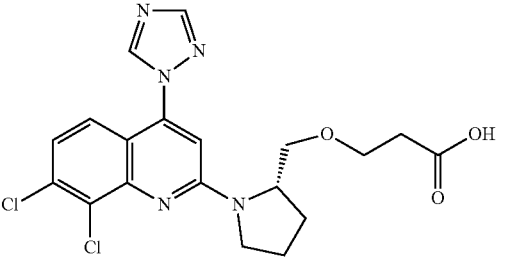 [SMILES: O=C(O)CCOC[C@@H]1CCCN1c1cc(-n2cncn2)c2ccc(Cl)c(Cl)c2n1] |
| I-893 | 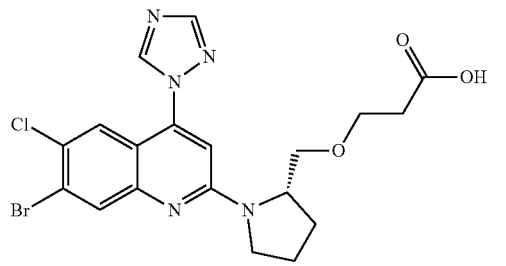 |
| I-894 | 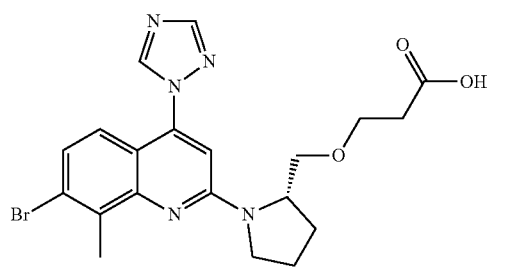 [SMILES: Cc1c(Br)ccc2c(-n3cncn3)cc(N3CCC[C@H]3COCCC(=O)O)nc12] |
| I-895 | 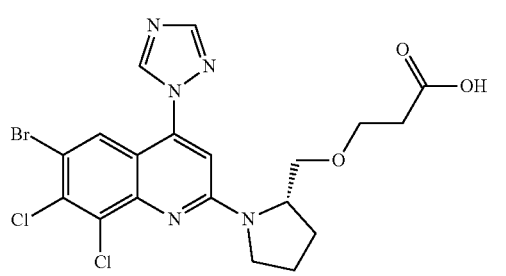 |
| I-896 | 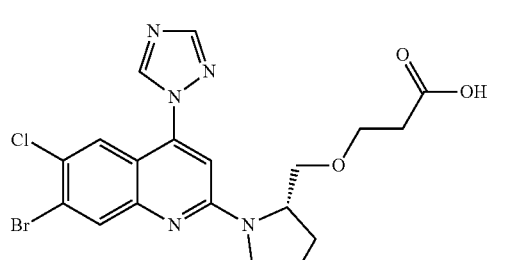 |
TABLE 1-continued
Exemplary Compounds
| I-# | Structure |
|---|---|
| I-897 | 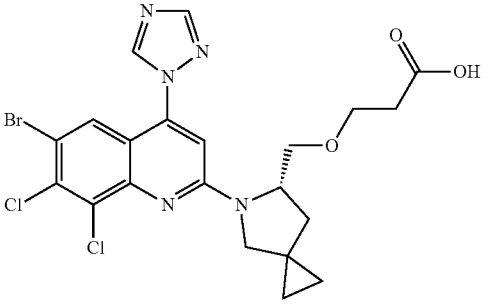 [SMILES: O=C(O)CCOC[C@@H]1CC2(CC2)CN1c1cc(-n2cncn2)c2cc(Br)c(Cl)c(Cl)c2n1] |
| I-898 | 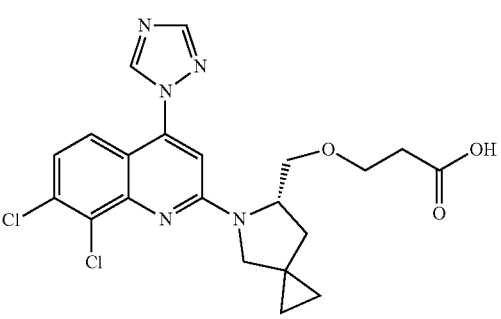 [SMILES: O=C(O)CCOC[C@@H]1CC2(CC2)CN1c1cc(-n2cncn2)c2ccc(Cl)c(Cl)c2n1] |
| I-899 | 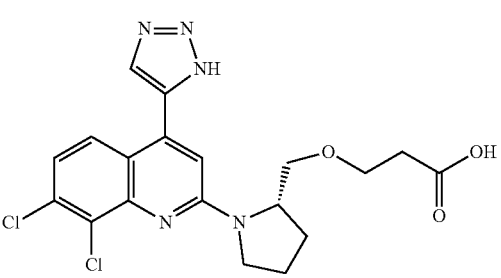 [SMILES: O=C(O)CCOC[C@@H]1CCCN1c1cc(-c2cnn[nH]2)c2ccc(Cl)c(Cl)c2n1] |
| I-900 | 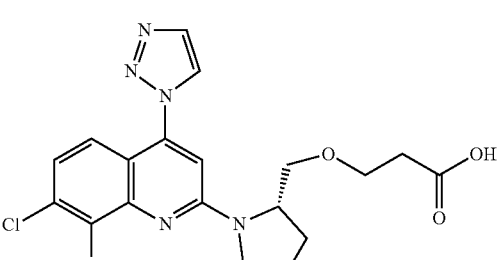 |
| I-901 | 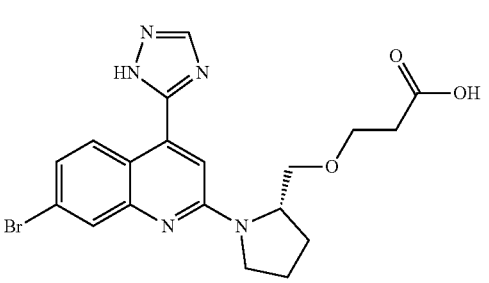 [SMILES: O=C(O)CCOC[C@@H]1CCCN1c1cc(-c2ncn[nH]2)c2ccc(Br)cc2n1] |

TABLE 1-continued
Exemplary Compounds
| I-# | Structure |
|---|---|
| I-902 | 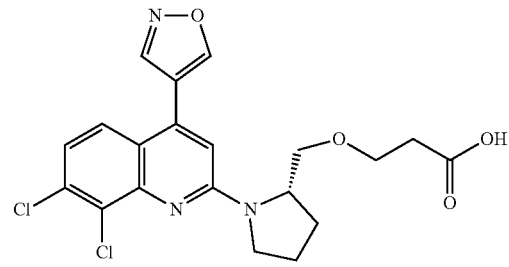 [SMILES: O=C(O)CCOC[C@@H]1CCCN1c1cc(-c2cnoc2)c2ccc(Cl)c(Cl)c2n1] |
| I-903 | 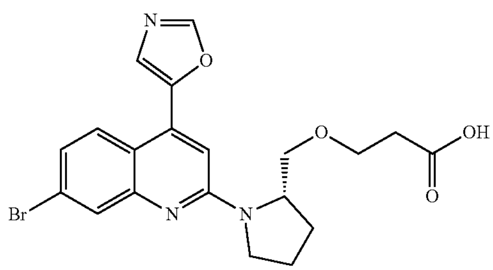 [SMILES: O=C(O)CCOC[C@@H]1CCCN1c1cc(-c2cnco2)c2ccc(Br)cc2n1] |
| I-904 | 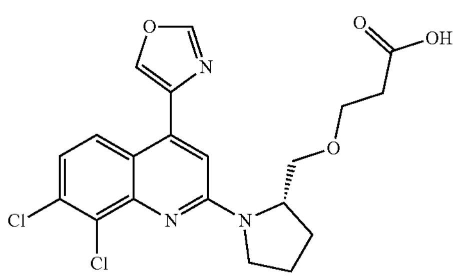 [SMILES: O=C(O)CCOC[C@@H]1CCCN1c1cc(-c2cocn2)c2ccc(Cl)c(Cl)c2n1] |
| I-905 | 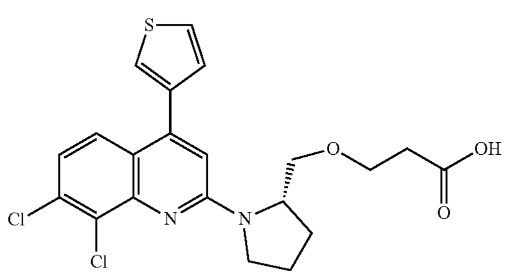 [SMILES: O=C(O)CCOC[C@@H]1CCCN1c1cc(-c2ccsc2)c2ccc(Cl)c(Cl)c2n1] |
| I-906 | 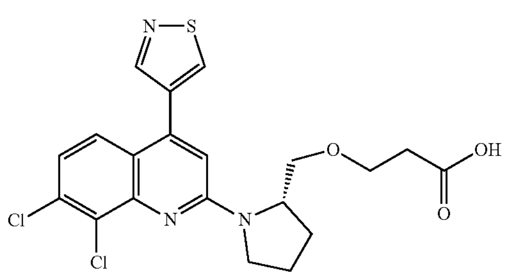 [SMILES: O=C(O)CCOC[C@@H]1CCCN1c1cc(-c2cnsc2)c2ccc(Cl)c(Cl)c2n1] |
| I-907 | |
| I-908 | |
| I-909 | |
| I-910 | |
| I-911 | |

TABLE 1-continued

Exemplary Compounds

| I-# | Structure |
|---|---|
| I-912 | 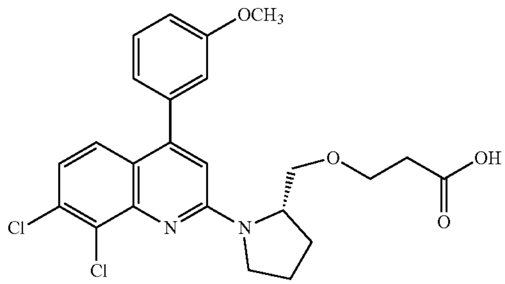 [SMILES: COc1cccc(-c2cc(N3CCC[C@H]3COCCC(=O)O)nc3c(Cl)c(Cl)ccc23)c1] |
| I-913 | 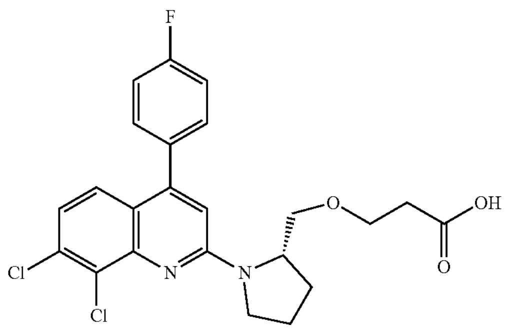 [SMILES: O=C(O)CCOC[C@@H]1CCCN1c1cc(-c2ccc(F)cc2)c2ccc(Cl)c(Cl)c2n1] |
| I-914 | 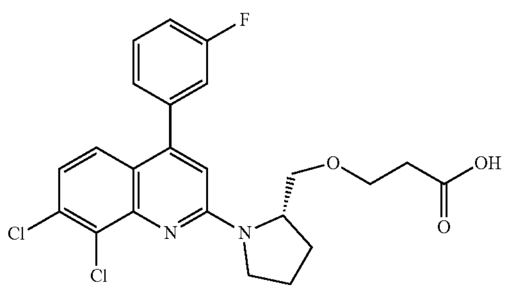 [SMILES: O=C(O)CCOC[C@@H]1CCCN1c1cc(-c2cccc(F)c2)c2ccc(Cl)c(Cl)c2n1] |
| I-915 | 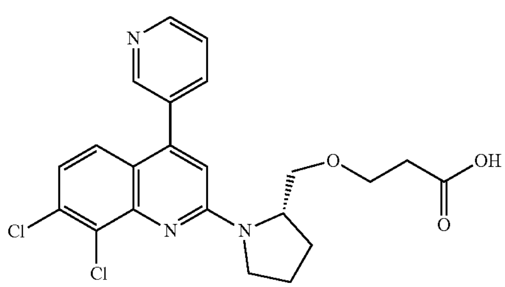 [SMILES: O=C(O)CCOC[C@@H]1CCCN1c1cc(-c2cccnc2)c2ccc(Cl)c(Cl)c2n1] |
| I-916 | 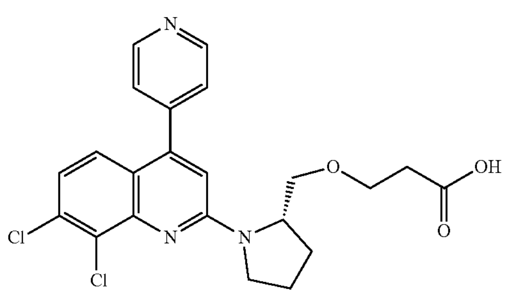 [SMILES: O=C(O)CCOC[C@@H]1CCCN1c1cc(-c2ccncc2)c2ccc(Cl)c(Cl)c2n1] |
| I-917 | |
| I-918 | |
| I-919 | |
| I-920 | |
| I-921 | |

TABLE 1-continued
Exemplary Compounds
| I-# | Structure |
|---|---|
| I-922 | 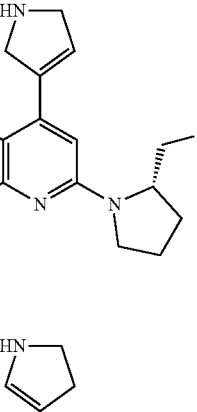 |
| I-923 | 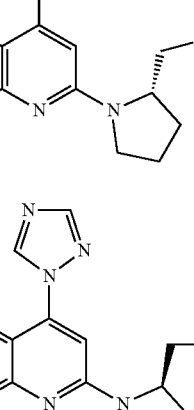 |
| I-924 | 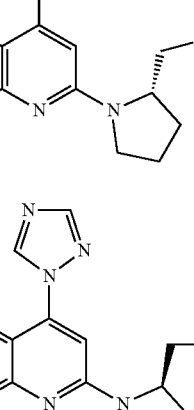 |
| I-925 | 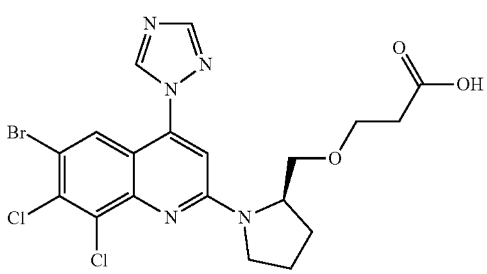 [SMILES: O=C(O)CCOC[C@H]1CCCN1c1cc(-n2cncn2)c2cc(Br)c(Cl)c(Cl)c2n1] |
| I-926 | 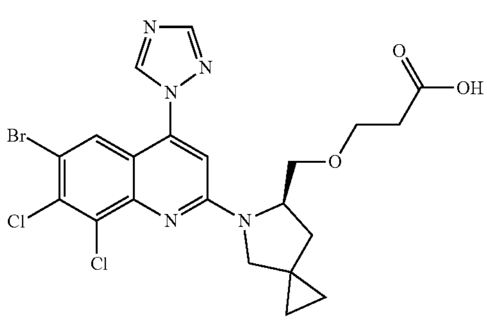 [SMILES: O=C(O)CCOC[C@H]1CC2(CC2)CN1c1cc(-n2cncn2)c2cc(Br)c(Cl)c(Cl)c2n1] |
| I-927 | |
| I-928 | 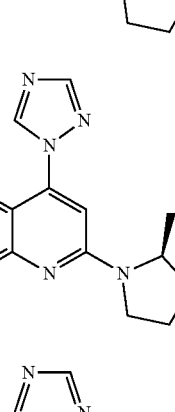 |
| I-929 | |
| I-930 | 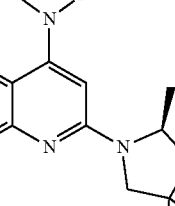 |
| I-931 | |

TABLE 1-continued

Exemplary Compounds

| I-# | Structure |
|---|---|
| I-932 | 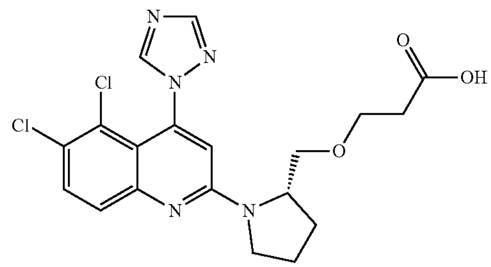 [SMILES: O=C(O)CCOC[C@@H]1CCCN1c1cc(-n2cncn2)c2c(Cl)c(Cl)ccc2n1] |
| I-933 | 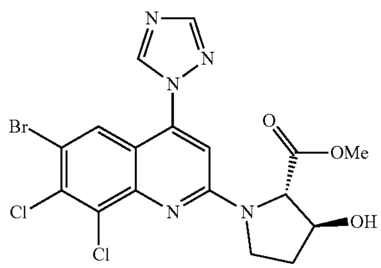 [SMILES: COC(=O)[C@@H]1[C@@H](O)CCN1c1cc(-n2cncn2)c2cc(Br)c(Cl)c(Cl)c2n1] |
| I-934 | 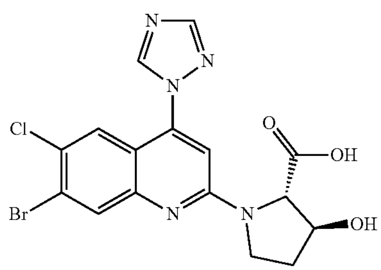 [SMILES: O=C(O)[C@@H]1[C@@H](O)CCN1c1cc(-n2cncn2)c2cc(Cl)c(Br)cc2n1] |
| I-935 | 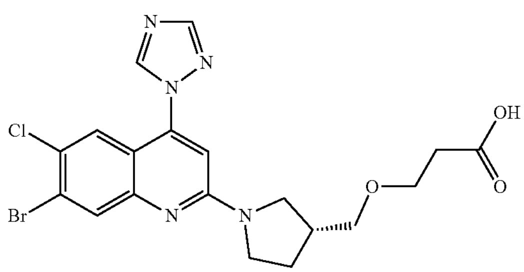 [SMILES: O=C(O)CCOC[C@@H]1CCN(c2cc(-n3cncn3)c3cc(Cl)c(Br)cc3n2)C1] |
| I-936 | 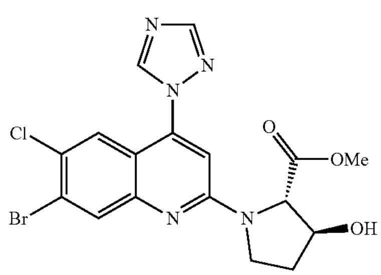 |

TABLE 1-continued

Exemplary Compounds

| I-# | Structure |
|---|---|
| I-937 | |
| I-938 | |

In some embodiments, the present disclosure provides a compound set forth in Table 1, above, or a pharmaceutically acceptable salt thereof or a freebase thereof for compounds reported as salts.

In some embodiments, the present disclosure contemplates additional compounds set forth in Table 2, below, or a pharmaceutically acceptable salt thereof and obtainable by the procedures described herein.

TABLE 2

Exemplary Compounds

| I-# | Structure |
|---|---|
| I-939 | 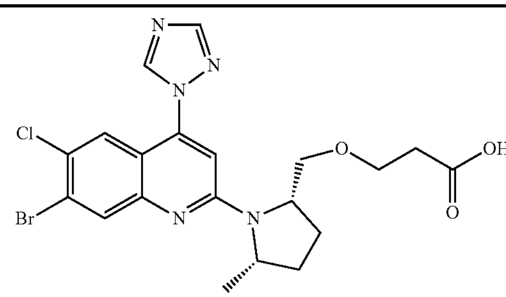 |
| I-940 | 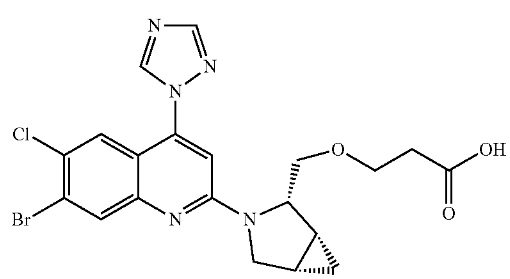 [SMILES: O=C(O)CCOC[C@@H]1[C@@H]2C[C@@H]2CN1c1cc(-n2cncn2)c2cc(Cl)c(Br)cc2n1] |

TABLE 2-continued

Exemplary Compounds

| I-# | Structure |
|---|---|
| I-941 | 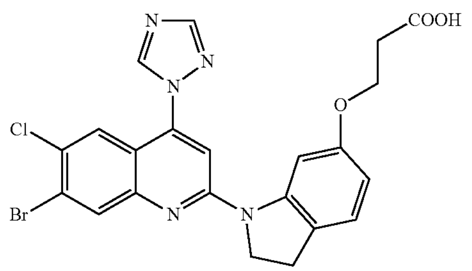 [SMILES: O=C(O)CCOc1ccc2c(c1)N(c1cc(-n3cncn3)c3cc(Cl)c(Br)cc3n1)CC2] |
| I-942 | 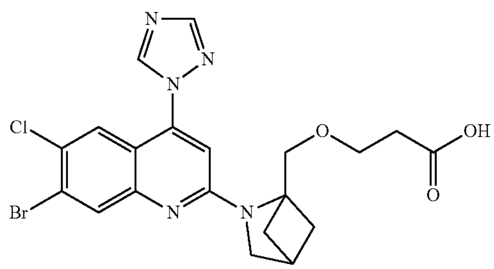 [SMILES: O=C(O)CCOCC12CC(CN1c1cc(-n3cncn3)c3cc(Cl)c(Br)cc3n1)C2] |
| I-943 | 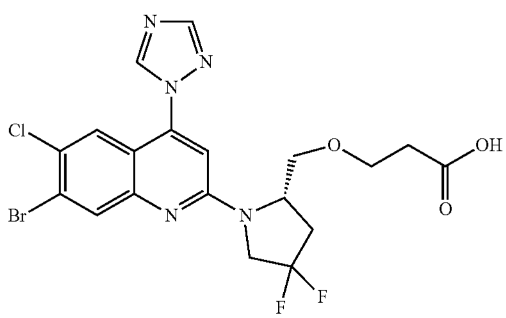 [SMILES: O=C(O)CCOC[C@@H]1CC(F)(F)CN1c1cc(-n2cncn2)c2cc(Cl)c(Br)cc2n1] |
| I-944 | 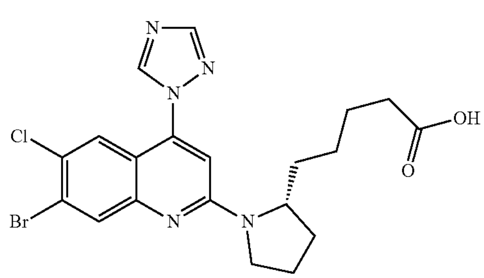 [SMILES: O=C(O)CCCC[C@@H]1CCCN1c1cc(-n2cncn2)c2cc(Cl)c(Br)cc2n1] |
| I-945 | 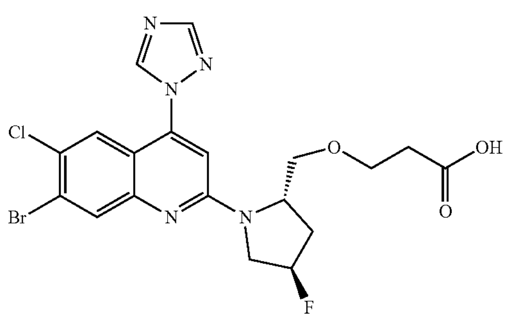 [SMILES: O=C(O)CCOC[C@@H]1C[C@@H](F)CN1c1cc(-n2cncn2)c2cc(Cl)c(Br)cc2n1] |
| I-946 | |
| I-947 | |
| I-948 | |
| I-949 | |
| I-950 | |

TABLE 2-continued
Exemplary Compounds
| I-# | Structure |
|---|---|
| I-951 | 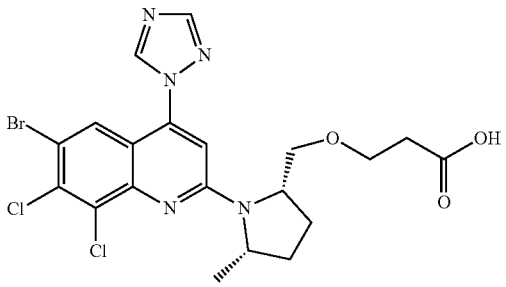 [SMILES: C[C@H]1CC[C@@H](COCCC(=O)O)N1c1cc(-n2cncn2)c2cc(Br)c(Cl)c(Cl)c2n1] |
| I-952 | 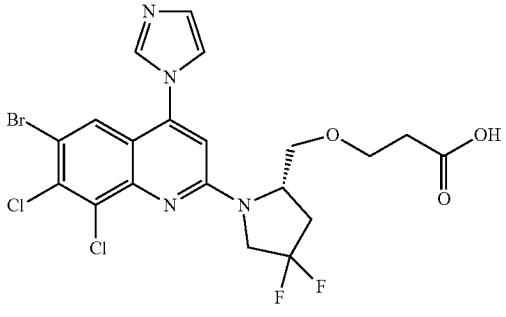 [SMILES: O=C(O)CCOC[C@@H]1CC(F)(F)CN1c1cc(-n2ccnc2)c2cc(Br)c(Cl)c(Cl)c2n1] |
| I-953 | 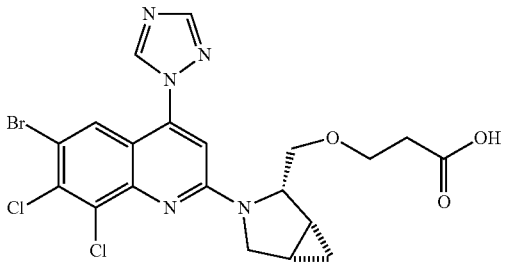 |
| I-954 | 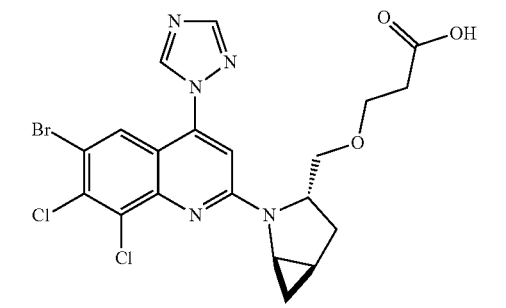 |
| I-955 | 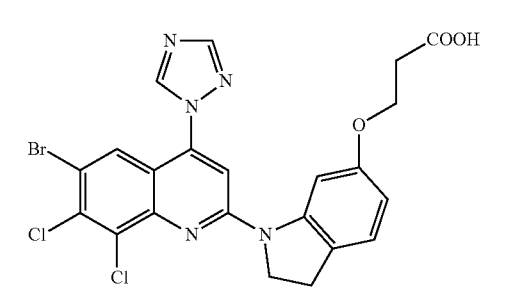 [SMILES: O=C(O)CCOc1ccc2c(c1)N(c1cc(-n3cncn3)c3cc(Br)c(Cl)c(Cl)c3n1)CC2] |
| I-956 | 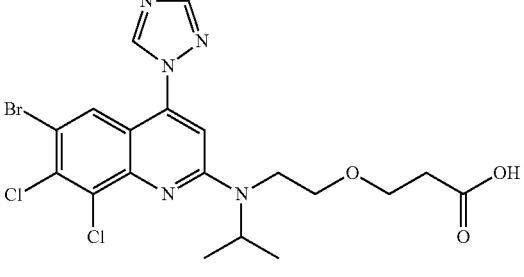 |
| I-957 | 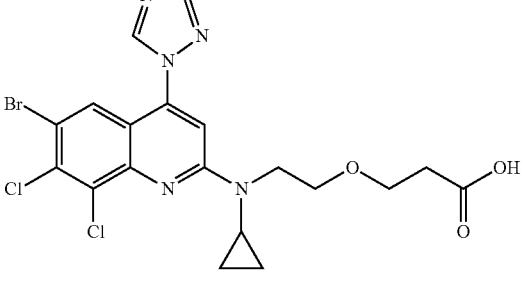 |
| I-958 | 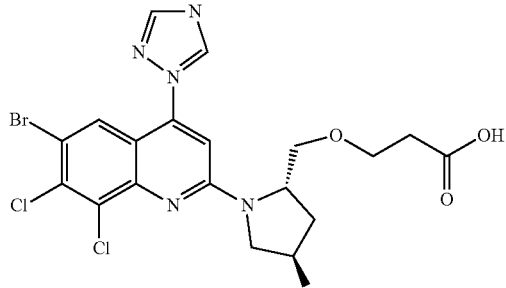 |
| I-959 | 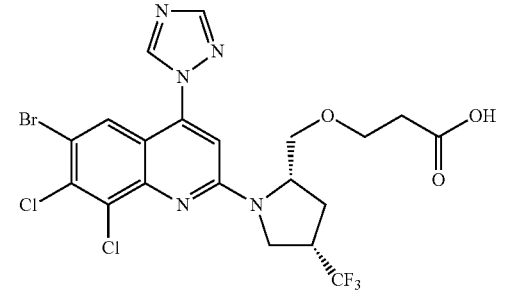 [SMILES: O=C(O)CCOC[C@@H]1C[C@H](C(F)(F)F)CN1c1cc(-n2cncn2)c2cc(Br)c(Cl)c(Cl)c2n1] |
| I-960 | 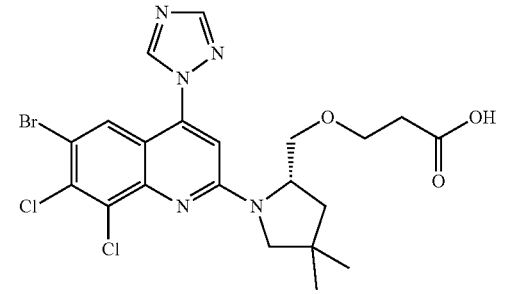 [SMILES: CC1(C)C[C@@H](COCCC(=O)O)N(c2cc(-n3cncn3)c3cc(Br)c(Cl)c(Cl)c3n2)C1] |

TABLE 2-continued

Exemplary Compounds

| I-# | Structure |
|---|---|
| I-961 | [structure] |
| I-962 | [structure] |
| I-963 | [structure] |
| I-964 | [structure] |
| I-965 | [structure] |
| I-966 | [structure] |

3.3. Pharmaceutical Compositions of the Present Compounds

While it is possible that, for use in therapy, a provided compound may be administered as the raw chemical, it is possible to present the provided compound as the active ingredient in a pharmaceutical composition. Such compositions can be prepared in a manner well known in the pharmaceutical art and comprise at least one active compound. Accordingly in one embodiment, the disclosure further provides pharmaceutical compositions comprising a provided compound or a pharmaceutically acceptable salt thereof and one or more pharmaceutically acceptable excipients. The excipient(s) must be acceptable in the sense of being compatible with the other ingredients of the composition and not deleterious to the recipient thereof. In accordance with another aspect of the disclosure there is also provided a process for the preparation of a pharmaceutical composition including a provided compound or pharmaceutically acceptable salt thereof, with one or more pharmaceutically acceptable excipients. The pharmaceutical composition can be for use in the treatment and/or prophylaxis of any of the conditions described herein.

Generally, a provided compound is administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like. Pharmaceutical compositions may be presented in unit dose forms containing a predetermined amount of active ingredient per unit dose. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions.

Preferred unit dosage compositions are those containing a daily dose or sub-dose, or an appropriate fraction thereof, of an active ingredient. Such unit doses may therefore be administered once or more than once a day. Such pharmaceutical compositions may be prepared by any of the methods well known in the pharmacy art.

Pharmaceutical compositions may be adapted for administration by any appropriate route, for example by the oral (including buccal or sublingual), rectal, inhaled, intranasal, topical (including buccal, sublingual or transdermal), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert excipient such as ethanol, glycerol, water and the like. Powders are prepared by reducing the compound to a suitable fine size and mixing with a similarly prepared pharmaceutical excipient such as an edible carbohydrate, as, for example, starch or mannitol. Flavoring, preservative, dispersing and coloring agent can also be present.

Capsules are made by preparing a powder mixture, as described above, and filling formed gelatin sheaths. Excipients including glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, excipients including suitable binders, glidants, lubricants, sweetening agents, flavors, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing a provided compound, suitably comminuted, with a diluent or base as described above, and optionally, with a binder such as carboxymethylcellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. A provided compound can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, suspensions, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The composition can also be prepared to prolong or sustain the release as for example by coating or embedding particulate material in polymers, wax or the like.

The compounds of the disclosure may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. Pharmaceutical compositions adapted for transdermal administration may be presented as discrete patches intended to remain in intimate contact with the epidermis of the recipient for a prolonged period of time.

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or as enemas.

Dosage forms for nasal or inhaled administration may conveniently be formulated as aerosols, solutions, suspension drops, gels or dry powders.

Compositions for intranasal administration include aqueous compositions administered to the nose by drops or by pressurized pump. Suitable compositions contain water as the diluent or carrier for this purpose. Compositions for administration to the lung or nose may contain one or more excipients, for example one or more suspending agents, one or more preservatives, one or more surfactants, one or more tonicity adjusting agents, one or more co-solvents, and may include components to control the pH of the composition, for example a buffer system. Further, the compositions may contain other excipients such as antioxidants, for example sodium metabisulphite, and taste-masking agents. Compositions may also be administered to the nose or other regions of the respiratory tract by nebulization. Intranasal compositions may permit a provided compound or pharmaceutically acceptable salt thereof to be delivered to all areas of the nasal cavities (the target tissue) and further, may permit the provided compound or pharmaceutically acceptable salt thereof to remain in contact with the target tissue for longer periods of time. A suitable dosing regimen for intranasal compositions would be for the patient to inhale slowly through the nose subsequent to the nasal cavity being cleared. During inhalation, the composition would be administered to one nostril while the other is manually compressed. This procedure would then be repeated for the other nostril. Typically, one or two sprays per nostril would be administered by the above procedure one, two, or three times each day, ideally once daily. Of particular interest are intranasal compositions suitable for once-daily administration.

The suspending agent(s), if included, will typically be present in an amount of from 0.1 to 5% (w/w), such as from 1.5% to 2.4% (w/w), based on the total weight of the composition. Examples of pharmaceutically acceptable suspending agents include, but are not limited to, Avicef (microcrystalline cellulose and carboxymethylcellulose sodium), carboxymethylcellulose sodium, veegum, tragacanth, bentonite, methylcellulose, xanthan gum, carbopol and polyethylene glycols.

Compositions for administration to the lung or nose may contain one or more excipients, and may be protected from microbial or fungal contamination and growth by inclusion of one or more preservatives. Examples of pharmaceutically acceptable antimicrobial agents or preservatives include, but are not limited to, quaternary ammonium compounds (for example benzalkonium chloride, benzethonium chloride, cetrimide, cetylpyridinium chloride, lauralkonium chloride and myristyl picolinium chloride), mercurial agents (for example phenylmercuric nitrate, phenylmercuric acetate and thimerosal), alcoholic agents (for example chlorobutanol, phenylethyl alcohol and benzyl alcohol), antibacterial esters (for example esters of p-hydroxybenzoic acid), chelating agents such as disodium edetate (EDTA) and other antimicrobial agents such as chlorhexidine, chlorocresol, sorbic acid and its salts (such as potassium sorbate) and polymyxin. Examples of pharmaceutically acceptable antifungal agents or preservatives include, but are not limited to, sodium benzoate, sorbic acid, sodium propionate, methylparaben, ethylparaben, propylparaben, and butylparaben. The preservative(s), if included, may be present in an amount of from 0.001 to 1% (w/w), such as from 0.015% to 0.5% (w/w) based on the total weight of the composition. Compositions (for example wherein at least one compound is in suspension) may include one or more surfactants which functions to facilitate dissolution of the medicament particles in the aqueous phase of the composition. For example, the amount of surfactant used is an amount which will not cause foaming during mixing. Examples of pharmaceutically acceptable surfactants include fatty alcohols, esters, and ethers, such as polyoxyethylene (20) sorbitan monooleate (Polysorbate 80), macrogol ethers, and poloxamers. The surfactant may be present in an amount of between about 0.01 to 10% (w/w), such as from 0.01 to 0.75% (w/w), for example about 0.5% (w/w), based on the total weight of the composition.

One or more tonicity-adjusting agent(s) may be included to achieve tonicity with body fluids (e.g., fluids of the nasal cavity) resulting in reduced levels of irritancy. Examples of pharmaceutically acceptable tonicity-adjusting agents include, but are not limited to, sodium chloride, dextrose, xylitol, calcium chloride, glucose, glycerine, and sorbitol. A tonicity-adjusting agent, if present, may be included in an amount of from 0.1 to 10% (w/w), such as from 4.5 to 5.5% (w/w), for example about 5.0% (w/w), based on the total weight of the composition.

The compositions of the disclosure may be buffered by the addition of suitable buffering agents such as sodium citrate, citric acid, trometamol, phosphates such as disodium phosphate (e.g., dodecahydrate, heptahydrate, dihydrate and anhydrous forms), or sodium phosphate and mixtures thereof.

A buffering agent, if present, may be included in an amount of from 0.1 to 5% (w/w), for example 1 to 3% (w/w) based on the total weight of the composition.

Examples of taste-masking agents include sucralose, sucrose, saccharin or a salt thereof, fructose, dextrose, glycerol, corn syrup, aspartame, acesulfame-K, xylitol, sorbitol, erythritol, ammonium glycyrrhizinate, thaumatin, neotame, mannitol, menthol, eucalyptus oil, camphor, a natural flavoring agent, an artificial flavoring agent, and combinations thereof.

One or more co-solvent may be included to aid solubility of the medicament compound(s) and/or other excipients. Examples of pharmaceutically acceptable co-solvents include, but are not limited to, propylene glycol, dipropylene glycol, ethylene glycol, glycerol, ethanol, polyethylene glycols (for example PEG300 or PEG400), and methanol. In one embodiment, the co-solvent is propylene glycol.

Co-solvent(s), if present, may be included in an amount of from 0.05 to 30% (w/w), such as from 1 to 25% (w/w), for example from 1 to 10% (w/w) based on the total weight of the composition.

Compositions for inhaled administration include aqueous, organic or aqueous/organic mixtures, dry powder or crystalline compositions administered to the respiratory tract by pressurized pump or inhaler, for example, reservoir dry powder inhalers, unit-dose dry powder inhalers, pre-metered multi-dose dry powder inhalers, nasal inhalers or pressurized aerosol inhalers, nebulizers or insufflators. Suitable compositions contain water as the diluent or carrier for this purpose and may be provided with conventional excipients such as buffering agents, tonicity modifying agents and the like. Aqueous compositions may also be administered to the nose and other regions of the respiratory tract by nebulization. Such compositions may be aqueous solutions or suspensions or aerosols delivered from pressurized packs, such as a metered dose inhaler, with the use of a suitable liquefied propellant.

Compositions for administration topically to the nose (for example, for the treatment of rhinitis) or to the lung, include pressurized aerosol compositions and aqueous compositions delivered to the nasal cavities by pressurized pump. Compositions which are non-pressurized and are suitable for administration topically to the nasal cavity are of particular interest. Suitable compositions contain water as the diluent or carrier for this purpose. Aqueous compositions for administration to the lung or nose may be provided with conventional excipients such as buffering agents, tonicity-modifying agents and the like. Aqueous compositions may also be administered to the nose by nebulization.

A fluid dispenser may typically be used to deliver a fluid composition to the nasal cavities. The fluid composition may be aqueous or non-aqueous, but typically aqueous. Such a fluid dispenser may have a dispensing nozzle or dispensing orifice through which a metered dose of the fluid composition is dispensed upon the application of a user-applied force to a pump mechanism of the fluid dispenser. Such fluid dispensers are generally provided with a reservoir of multiple metered doses of the fluid composition, the doses being dispensable upon sequential pump actuations. The dispensing nozzle or orifice may be configured for insertion into the nostrils of the user for spray dispensing of the fluid composition into the nasal cavity.

Dry powder compositions for topical delivery to the lung by inhalation may, for example, be presented in capsules and cartridges of for example gelatin, or blisters of for example laminated aluminum foil, for use in an inhaler or insufflator. Powder blend compositions generally contain a powder mix for inhalation of a provided compound or pharmaceutically acceptable salt thereof and a suitable powder base (carrier/diluent/excipient substance) such as mono-, di-, or polysaccharides (e.g., lactose or starch). Dry powder compositions may also include, in addition to the drug and carrier, a further excipient (e.g., a ternary agent such as a sugar ester for example cellobiose octaacetate, calcium stearate, or magnesium stearate).

Pharmaceutical compositions adapted for parental administration include aqueous and nonaqueous sterile injection solutions which may contain antioxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (e.g., lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the compositions may include other agents conventional in the art having regard to the type of formulation in question, for example, those suitable for oral administration may include flavoring agents.

3.4. Uses of the Present Pharmaceutical Compositions and Compounds in Therapy A therapeutically effective amount of the agent will depend upon a number of factors including, for example, the age and weight of the subject, the precise condition requiring treatment and its severity, the nature of the formulation, and the route of administration, and will ultimately be at the discretion of the attendant physician or veterinarian. In particular, the subject to be treated is a mammal, particularly a human.

The agent may be administered in a daily dose. This amount may be given in a single dose per day or more usually in a number (e.g., two, three, four, five, or six) of sub-doses per day such that the total daily dose is the same.

Suitably, the amount of the compound of the present disclosure administered may be an amount selected from 0.01 mg to 10 g per day (calculated as the free or unsalted compound).

In some embodiments, a provided compound or a pharmaceutically acceptable salt thereof may be employed alone or in combination with other therapeutic agents. A provided compound or a pharmaceutically acceptable salt thereof and the other pharmaceutically active agent(s) may be administered together or separately and, when administered separately, administration may occur simultaneously or sequentially, in any order, by any convenient route in separate or combined pharmaceutical compositions. The amounts of a provided compound or a pharmaceutically acceptable salt thereof and the other pharmaceutically active agent(s) and the relative timings of administration will be selected in order to achieve the desired combined therapeutic effect. A provided compound or a pharmaceutically acceptable salt thereof and further therapeutic agent(s) may be employed in combination by administration simultaneously in a unitary pharmaceutical composition including both compounds. Alternatively, the combination may be administered separately in separate pharmaceutical compositions, each including one of the compounds in a sequential manner wherein, for example, the compound of the present disclosure is administered first and the other second and vice versa. Such sequential administration may be close in time (e.g. simultaneously) or remote in time. Furthermore, it does not matter if the compounds are administered in the same dosage form, e.g., one compound may be administered topically and the other compound may be administered orally. Suitably, both compounds are administered orally.

The combinations may be presented as a combination kit. By the term "combination kit" "or kit of parts" as used herein is meant the pharmaceutical composition or compositions that are used to administer the combination according to the present disclosure. When both compounds are administered simultaneously, the combination kit can contain both compounds in a single pharmaceutical composition, such as a tablet, or in separate pharmaceutical compositions. When the compounds are not administered simultaneously, the combination kit will contain each compound in separate pharmaceutical compositions either in a single package or in separate pharmaceutical compositions in separate packages. The combination kit can also be provided by instruction, such as dosage and administration instructions. Such dosage and administration instructions can be of the kind that are provided to a doctor, for example by a drug product label, or they can be of the kind that are provided by a doctor, such as instructions to a patient.

When the combination is administered separately in a sequential manner wherein one is administered first and the other second or vice versa, such sequential administration may be close in time or remote in time. For example, administration of the other agent several minutes to several dozen minutes after the administration of the first agent, and administration of the other agent several hours to several days after the administration of the first agent are included, wherein the lapse of time is not limited. For example, one agent may be administered once a day, and the other agent may be administered 2 or 3 times a day, or one agent may be administered once a week, and the other agent may be administered once a day and the like. It will be clear to a person skilled in the art that, where appropriate, the other therapeutic ingredients(s) may be used in the form of salts, for example as alkali metal or amine salts or as acid addition salts, or prodrugs, or as esters, for example lower alkyl esters, or as solvates, for example hydrates, to optimize the activity and/or stability and/or physical characteristics, such as solubility, of the therapeutic ingredient. It will be clear also that, where appropriate, the therapeutic ingredients may be used in optically pure form.

When combined in the same composition it will be appreciated that the two compounds must be stable and compatible with each other and the other components of the composition and may be formulated for administration. When formulated separately they may be provided in any convenient composition, conveniently, in such a manner as known for such compounds in the art.

When a provided compound or a pharmaceutically acceptable salt thereof is used in combination with a second therapeutic agent active against the same disease, condition, or disorder, the dose of each compound may differ from that when the compound is used alone. Appropriate doses will be readily appreciated by those skilled in the art.

In one embodiment, the mammal in the methods and uses of the present disclosure is a human. The provided compounds or pharmaceutically acceptable salts thereof are useful in the treatment of diseases and conditions in which modulation of cGAS is beneficial. As modulators of the immune response, a provided compound or a pharmaceutically acceptable salts thereof may also be useful, as stand-alone, in combination or as adjuvants, in the treatment of diseases and conditions in which modulation of cGAS is beneficial.

In one embodiment, the disease or condition is an inflammatory, allergic, or autoimmune diseases such as systemic lupus erythematosus, psoriasis, insulin-dependent diabetes mellitus (IDDM), scleroderma, Aicardi Goutières syndrome, dermatomyositis, inflammatory bowel diseases, multiple sclerosis, rheumatoid arthritis, and Sjogren's syndrome (SS).

In another embodiment, the disease or condition is an infectious disease such as bacterial, viral or parasitic disease in which modulation of cGAS activity is beneficial.

In another embodiment, the disease or condition is a senescence- or age-related disease, including a neurodegenerative disease such as Alzheimer's or Parkinson disease, cardiovascular diseases such as atherosclerosis or myocardial infarction, liver or renal diseases, cancer, or premature aging.

Inflammation represents a group of vascular, cellular, and neurological responses to trauma. Inflammation can be characterized as the movement of inflammatory cells such as monocytes, neutrophils, and granulocytes into the tissues. This is usually associated with reduced endothelial barrier function and edema into the tissues. Inflammation can be classified as either acute or chronic. Acute inflammation is the initial response of the body to harmful stimuli and is achieved by the increased movement of plasma and leukocytes from the blood into the injured tissues. A cascade of biochemical event propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterized by simultaneous destruction and healing of the tissue from the inflammatory process.

When occurring as part of an immune response to infection or as an acute response to trauma, inflammation can be beneficial and is normally self-limiting. However, inflammation can be detrimental under various conditions. This includes the production of excessive inflammation in response to infectious agents, which can lead to significant organ damage and death (e.g., in the setting of sepsis). Moreover, chronic inflammation is generally deleterious and is at the root of numerous chronic diseases, causing severe and irreversible damage to tissues. In such settings, the immune response is often directed against self-tissues (autoimmunity), although chronic responses to foreign entities can also lead to bystander damage to self-tissues. The aim of anti-inflammatory therapy is therefore to reduce this inflammation, to inhibit autoimmunity when present and to allow for the physiological process or healing and tissue repair to progress.

In some embodiments, a provided compound or a pharmaceutically acceptable salt thereof may be used to treat inflammation of any tissue and organs of the body, including musculoskeletal inflammation, vascular inflammation, neural inflammation, digestive system inflammation, ocular inflammation, inflammation of the reproductive system, and other inflammation, as exemplified below.

Musculoskeletal inflammation refers to any inflammatory condition of the musculoskeletal system, particularly those conditions affecting skeletal joints, including joints of the hand, wrist, elbow, shoulder, jaw, spine, neck, hip, knew, ankle, and foot, and conditions affecting tissues connecting muscles to bones such as tendons. Examples of musculoskeletal inflammation which may be treated with compounds of the present disclosure include arthritis (including, for example, osteoarthritis, rheumatoid arthritis, psoriatic arthritis, ankylosing spondylitis, acute and chronic infectious arthritis, arthritis associated with gout and pseudogout, and juvenile idiopathic arthritis), tendonitis, synovitis, tenosynovitis, bursitis, fibrositis (fibromyalgia), epicondylitis, myositis, and osteitis (including, for example, Paget's disease, osteitis pubis, and osteitis fibrosa cystic). Ocular inflammation refers to inflammation of any structure of the eye, including the eye lids. Examples of ocular inflammation which may be treated with the compounds of the present disclosure include blepharitis, blepharochalasis, conjunctivitis, dacryoadenitis, keratitis, keratoconjunctivitis sicca (dry eye), scleritis, trichiasis, and uveitis. Examples of inflammation of the nervous system which may be treated with the compounds of the present disclosure include encephalitis, Guillain-Barre syndrome, meningitis, neuromyotonia, narcolepsy, multiple sclerosis, myelitis, and schizophrenia.

Examples of inflammation of the vasculature or lymphatic system which may be treated with a provided compound or a pharmaceutically acceptable salt thereof include arthrosclerosis, arthritis, phlebitis, vasculitis, and lymphangitis.

Examples of inflammatory conditions of the digestive system which may be treated with a provided compound or a pharmaceutically acceptable salt thereof include cholangitis, cholecystitis, enteritis, enterocolitis, gastritis, gastroenteritis, inflammatory bowel disease (such as Crohn's disease and ulcerative colitis), ileitis, and proctitis.

Examples of inflammatory conditions of the reproductive system which may be treated with a provided compound or a pharmaceutically acceptable salt thereof include cervicitis, chorioamnionitis, endometritis, epididymitis, omphalitis, oophoritis, orchitis, salpingitis, tubo-ovarian abscess, urethritis, vaginitis, vulvitis, and vulvodynia.

The agents may be used to treat autoimmune conditions having an inflammatory component. Such conditions include systemic lupus erythematosus, acute disseminated alopecia universalise, Behcet's disease, Chagas' disease, chronic fatigue syndrome, dysautonomia, encephalomyelitis, ankylosing spondylitis, aplastic anemia, hidradenitis suppurativa, autoimmune hepatitis, autoimmune oophoritis, celiac disease, Crohn's disease, diabetes mellitus type 1, giant cell arteritis, goodpasture's syndrome. Grave's disease, Guillain-Barre syndrome, Hashimoto's disease, Henoch-Schonlein purpura, Kawasaki's disease, microscopic colitis, microscopic polyarteritis, mixed connective tissue disease, multiple sclerosis, myasthenia gravis, opsoclonus myoclonus syndrome, optic neuritis, ord's thyroiditis, pemphigus, polyarteritis nodosa, polymyalgia, rheumatoid arthritis, Reiter's syndrome, Sjogren's syndrome, Aicardi Goutières syndrome, temporal arteritis, Wegener's granulomatosis, warm autoimmune haemolytic anemia, interstitial cystitis, Lyme disease, morphea, psoriasis, sarcoidosis, scleroderma, ulcerative colitis, and vitiligo.

In some embodiments, a provided compound or a pharmaceutically acceptable salt thereof may be used to treat T-cell mediated hypersensitivity diseases having an inflammatory component. Such conditions include contact hypersensitivity, contact dermatitis (including that due to poison ivy), uticaria, skin allergies, respiratory allergies (hayfever, allergic rhinitis) and gluten-sensitive enteropathy (Celliac disease).

Other inflammatory conditions which may be treated with a provided compound or a pharmaceutically acceptable salt thereof include, for example, appendicitis, dermatitis, dermatomyositis, endocarditis, fibrositis, gingivitis, glossitis, hepatitis, hidradenitis suppurativa, iritis, laryngitis, mastitis, myocarditis, nephritis, otitis, pancreatitis, parotitis, percarditis, peritonoitis, pharyngitis, pleuritis, pneumonitis, prostatistis, pyelonephritis, and stomatisi, transplant rejection (involving organs such as kidney, liver, heart, lung, pancreas (e.g., islet cells), bone marrow, cornea, small bowel, skin allografts, skin homografts, and heart valve xenografts, serum sickness, and graft vs host disease), acute pancreatitis, chronic pancreatitis, acute respiratory distress syndrome. Sexary's syndrome, congenital adrenal hyperplasis, nonsuppurative thyroiditis, hypercalcemia associated with cancer, pemphigus, bullous dermatitis herpetiformis, severe erythema multiforme, exfoliative dermatitis, seborrheic dermatitis, seasonal or perennial allergic rhinitis, bronchial asthma, contact dermatitis, atopic dermatitis, drug hypersensitivity reactions, allergic conjunctivitis, keratitis, herpes zoster ophthalmicus, iritis and oiridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) haemolytic anemia, leukemia and lymphomas in adults, acute leukemia of childhood, regional enteritis, autoimmune vasculitis, multiple sclerosis, chronic obstructive pulmonary disease, solid organ transplant rejection, sepsis. Preferred treatments include treatment of transplant rejection, rheumatoid arthritis, psoriatic arthritis, multiple sclerosis, Type 1 diabetes, asthma, inflammatory bowel disease, systemic lupus erythematosis, psoriasis, chronic pulmonary disease, and inflammation accompanying infectious conditions (e.g., sepsis).

In some embodiments, the disclosure provides a provided compound or a pharmaceutically acceptable salt thereof for use in the treatment of an inflammatory, allergic, or autoimmune disease.

In some embodiments, the disclosure provides a method of treating an inflammatory, allergic, or autoimmune disease comprising: administering to a patient in need thereof a therapeutically effective amount of a provided compound or a pharmaceutically acceptable salt thereof.

In some embodiments, the disclosure provides the use of a provided compound or a pharmaceutically acceptable salt thereof in the manufacture of a medicament for the treatment of an inflammatory, allergic, or autoimmune disease.

In some embodiments, a provided compound or a pharmaceutically acceptable salts thereof may be used in combination with one or more other agents in the prevention or treatment of an allergic, inflammatory, or autoimmune disease, wherein such other agents can include: antigen immunotherapy agents; antihistamines; steroids, NSAIDs; bronchodilators (e.g. beta 2 agonists, adrenergic agonists, anticholinergic agents, theophylline); methotrexate; leukotriene modulators; monoclonal antibody agents such as anti-IgE, anti-TNF, anti-IL-5, anti-IL-6, anti-IL-12, anti-IL-1 and similar agents; receptor therapies agents such as entanercept; and antigen non-specific immunotherapeutic agents such interferon or other cytokines/chemokines, cytokine/chemokine receptor modulators, cytokine agonists or antagonists, and TLR antagonist.

In some embodiments, the present disclosure provides a pharmaceutical composition comprising a provided compound or a pharmaceutically acceptable salt thereof, and at least one further therapeutic agent useful in the treatment of an allergic, inflammatory, or autoimmune disease.

In some embodiments, the present disclosure provides a pharmaceutical composition comprising a provided compound or a pharmaceutically acceptable salt thereof, and at least one further therapeutic agent useful in the treatment of an allergic, inflammatory, or autoimmune disease for use in therapy.

In some embodiments, the present disclosure provides a pharmaceutical composition comprising a provided compound or pharmaceutically acceptable salt thereof, and at least one further therapeutic agent useful in the treatment of an allergic, inflammatory or autoimmune disease, for use in the treatment of allergic, inflammatory, or autoimmune disease.

In some embodiments, the present disclosure provides the use of a pharmaceutical composition comprising a provided compound or a pharmaceutically acceptable salt thereof, and at least one further therapeutic agent useful in the treatment of an allergic, inflammatory, or autoimmune disease in the manufacture of a medicament for the treatment of an allergic, inflammatory or autoimmune disease.

In some embodiments, the present disclosure provides a method of treating an allergic, inflammatory or autoimmune disease comprising: administering to a patient in need thereof a therapeutically effective amount of a pharmaceutical composition comprising a provided compound or a pharmaceutically acceptable salt thereof, and at least one further therapeutic agent useful in the treatment of an allergic, inflammatory, or autoimmune disease.

In some embodiments, the present disclosure provides a pharmaceutical composition comprising a provided compound or a pharmaceutically acceptable salt thereof, at least one further therapeutic agent useful in the treatment of an allergic, inflammatory, or autoimmune disease, and one or more of pharmaceutically acceptable excipients.

In some embodiments, the present disclosure provides a provided compound or a pharmaceutically acceptable salt thereof, for use in the treatment of an infectious disease.

In some embodiments, the present disclosure provides a method of treating an infectious disease comprising administering to a patient in need thereof a therapeutically effective amount of a provided compound or a pharmaceutically acceptable salt thereof.

In some embodiments, the present disclosure provides the use of a provided compound or a pharmaceutically acceptable salt thereof, in the manufacture of a medicament for the treatment of an infectious disease. In one embodiment, a compound of the present disclosure may be employed with other therapeutic methods of treating infectious disease. In particular, bacterial and parasite infections, such as *Mycobacterium tuberculosis* and malaria, respectively, which exploit the type-I interferon pathway for their advantage, may be treated with a cGAS inhibitor.

In some embodiments, a provided compound or a pharmaceutically acceptable salts thereof may be used in combination with one or more agents useful in the prevention or treatment of bacterial and viral infections. Examples of such agents include: polymerase inhibitors; replication inhibitors such as acyclovir, famciclovir, ganciclovir, cidofovir and lamivudine; protease inhibitors such as the HIV protease inhibitors saquinavir, ritonavir, indinavir, nelfinavir, amprenavir, fosamprenavir, brecanavir, atazanavir, tipranavir, palinavir, lasinavir, and the HCV protease inhibitors BILN2061, VX-950, SCH503034; nucleoside and nucleotide reverse transcriptase inhibitors such as zidovudine, didanosine, lamivudine, zalcitabine, abacavir, stavidine, adefovir, adefovir dipivoxil, fozivudine, todoxil, emtricitabine, alovudine, amdoxovir, and elvucitabine; non-nucleoside reverse transcriptase inhibitors (including an agent having antioxidation activity such as immunocal or oltipraz) such as nevirapine, delavirdine, efavirenz, loviride, immunocal, oltipraz, capravirine, TMC-278, TMC-125, and etravirine; entry inhibitors such as enfuvirtide (T-20), T-1249, PRO-542, PRO-140, TNX-355, BMS-806, 5-Helix and similar agents; integrase inhibitors such as L-870 and 180; budding inhibitors such as PA-344 and PA-457; chemokine receptor inhibitors such as vicriviroc (Sch-C), Sch-D, TAK779, maraviroc (UK-427, 857), and TAK449; neuraminidase inhibitors such as CS-8958, zanamivir, oseltamivir, and peramivir; ion channel blockers such as amantadine or rimantadine; interfering RNA and antisense oligonucleotides and such as ISIS-14803; and antiviral agents of undetermined mechanism of action, such as ribavirin.

In some embodiments, a provided compound or a pharmaceutically acceptable salts thereof may also be used in combination with one or more other agents which may be useful in the prevention or treatment of viral infections such as immune therapies (e.g. interferon or other cytokines/chemokines, cytokine/chemokine receptor modulators, cytokine agonists or antagonists and similar agents); therapeutic vaccines; antifibrotic agents; and anti-inflammatory agents such as corticosteroids or NSAIDs (non-steroidal anti-inflammatory agents).

In some embodiments, the present disclosure provides a pharmaceutical composition comprising a provided compound or a pharmaceutically acceptable salt thereof, and at least one further therapeutic agent useful in the treatment of an infectious disease.

In some embodiments, the present disclosure provides a pharmaceutical composition comprising a provided compound or a pharmaceutically acceptable salt thereof, and at least one further therapeutic agent useful in the treatment of an infectious disease for use in therapy.

In some embodiments, the present disclosure provides a pharmaceutical composition comprising a provided compound or a pharmaceutically acceptable salt thereof, and at least one further therapeutic agent useful in the treatment of an infectious disease, for use in the treatment of an infectious disease.

In some embodiments, the present disclosure provides the use of a pharmaceutical composition comprising a provided compound or a pharmaceutically acceptable salt thereof, and at least one further therapeutic agent useful in the treatment of an infectious disease in the manufacture of a medicament for the treatment of an infectious disease.

In some embodiments, the present disclosure provides a method of treating an infectious disease comprising administering to a patient in need thereof, a therapeutically effective amount of a pharmaceutical composition comprising a provided compound or a pharmaceutically acceptable salt thereof, and at least one further therapeutic agent useful in the treatment of an infectious disease.

In some embodiments, the present disclosure provides a pharmaceutical composition comprising a provided compound or a pharmaceutically acceptable salt thereof, at least one further therapeutic agent useful in the treatment of infectious disease, and one or more of pharmaceutically acceptable excipients.

In some embodiments, the disclosure provides a provided compound or a pharmaceutically acceptable salt thereof for use in the treatment of a senescence- or age-related disease.

In some embodiments, the disclosure provides a method of treating a senescence- or age-related disease comprising: administering to a patient in need thereof a therapeutically effective amount of a provided compound or a pharmaceutically acceptable salt thereof.

In some embodiments, the disclosure provides the use of a provided compound or a pharmaceutically acceptable salt thereof in the manufacture of a medicament for the treatment of a senescence- or age-related disease.

In some embodiments, the present disclosure provides a pharmaceutical composition comprising a provided compound or a pharmaceutically acceptable salt thereof, and at least one further therapeutic agent useful in the treatment of a senescence- or age-related disease.

In some embodiments, the present disclosure provides a pharmaceutical composition comprising a provided compound or a pharmaceutically acceptable salt thereof, and at least one further therapeutic agent useful in the treatment of a senescence- or age-related disease for use in therapy.

In some embodiments, the present disclosure provides a pharmaceutical composition comprising a provided compound or pharmaceutically acceptable salt thereof, and at least one further therapeutic agent useful in the treatment of a senescence- or age-related disease, for use in the treatment of a senescence- or age-related disease.

In some embodiments, the present disclosure provides the use of a pharmaceutical composition comprising a provided compound or a pharmaceutically acceptable salt thereof, and at least one further therapeutic agent useful in the treatment of a senescence- or age-related disease in the manufacture of a medicament for the treatment of a senescence- or age-related disease.

In some embodiments, the present disclosure provides a method of treating a senescence- or age-related disease comprising administering to a patient in need thereof, a therapeutically effective amount of a pharmaceutical composition comprising a provided compound or a pharmaceutically acceptable salt thereof, and at least one further therapeutic agent useful in the treatment of a senescence- or age-related disease.

In some embodiments, the present disclosure provides a pharmaceutical composition comprising a provided compound or a pharmaceutically acceptable salt thereof, at least one further therapeutic agent useful in the treatment of a senescence- or age-related disease, and one or more of pharmaceutically acceptable excipients.

The provided compounds may be prepared by methods known in the art of organic synthesis as set forth in the schemes below and/or the specific Examples described below. In all of the methods, it is well understood that protecting groups for sensitive or reactive groups may be employed where necessary in accordance with general principles of chemistry. Protecting groups are manipulated according to standard methods of organic synthesis (T. W. Green and P. G. M. Wuts (1999) Protective Groups in Organic Synthesis, $3^{rd}$ edition, John Wiley & Sons). These groups are removed at a convenient stage of the compound synthesis using methods that are readily apparent to those skilled in the art. The selection of processes as well as the reaction conditions and order of their execution shall be consistent with the preparation of the provided compounds.

The following list provides definitions of certain abbreviations as used herein. It will be appreciated that the list is not exhaustive, but the meaning of those abbreviations not herein below defined will be readily apparent to those skilled in the art: AIBN is 2,2'-azobisisobutyronitrile; ATP is adenosine 5'-triphosphate; BPO is benzoyl peroxide; n-BuLi is n-butyllithium; BzCl is benzoyl chloride; CDI is 1,1'-carbonyldiimidazole; cGAS is cyclic GMP-AMP synthase; CO is carbon monooxide; $Cu(OAc)_2$ is copper(II) acetate; CuCN is copper(I) cynide; CuI is copper(I) iodide; DAST is (diethylamino)sulfur trifluoride; DBU is 1,8-diazabicyclo[5.4.0]undec-7-ene; DCE is dichloroethane; DCM is dichloromethane; DDQ is 2,3-dichloro-5,6-dicyano-p-benzoquinone; DHP is 3,4-dihydro-2H-pyran; DIAD is diisopropyl azodicarboxylate; DIBAL-H is diisobutylaluminum hydride; DIPA is diisopropylamine; DIPEA is N,N-diisopropylethylamine; DMAP is 4-(dimethylamino)pyridine; DMB is 2,4-dimethoxybenzyl; DMF is N,N-dimethylformamide; DMP is Dess-Martin periodinane; DMSO is dimethyl sulfoxide; EA is ethyl acetate; EtMgBr is ethylmagnesium bromide; $Et_2O$ is diethyl ether; EtOH is ethanol; GTP is guanosine triphosphate; HCl is hydrochloric acid; HMTA is hexamethylenetetramine; HOAc is acetic acid; HPLC is high performance liquid chromatography; LAH is lithium aluminum hydride; mCPBA is 3-chloroperbenzoic acid; MeCN is acetonitrile; MeI is iodomethane; MeOH is methanol; MeMgBr is methylmagnesium bromide; MOMCl is chloromethyl methyl ether; MOM is methoxymethoxy; MS is mass spectrometer or mass spectrum; MsCl is methanesulfonyl chloride; MTBE is methyl tert-butyl ether; NaH is sodium hydride; NaOH is sodium hydroxide; NBS is N-bromosuccinimide; NMM is N-methylmorpholine; NMR is nuclear magnetic resonance; $Pd(dba)_2$ is bis(dibenzylideneacetone)palladium(0); $Pd(dppf)Cl_2$ is [1,1'-bis(diphenylphosphino)ferrocene]dichloropalladium(II); $Pd(OAc)_2$ is palladium(II) acetate; $Pd(PPh_3)_2Cl_2$ is bis(triphenylphosphine)palladium(II) dichloride; $Pd(PPh_3)_4$ is tetrakis(triphenylphosphine) palladium(0); Pd/C is palladium on carbon; PDC is pridinium dichromate; PE is petroleum ether; PMB is 4-methoxybenzyl; $PPh_3$ is triphenylphosphine; prep-HPLC is preparative high performance liquid chromatography; prep-TLC is preparative thin-layer chromatography; Py is pyridine; TBAF is tetra-n-butylammonium fluoride; TBSCl is tert-butyldimethylsilyl chloride; TEA is triethylamine; TFA is trifluoroacetic acid; THF is tetrahydrofuran; THP is tetrahydropyranyl; TLC is thin-layer chromatography; TSA is p-toluenesulfonic acid monohydrate, and TsCl is p-toluenesulfonyl chloride.

4. EXAMPLES

The following Examples provide syntheses which can be used to obtain the disclosed compounds and test their in vitro activity. Further examples of preparing structurally related quinoline cGAS antagonist compounds are disclosed in international application no. PCT/US2021/49084, and the skilled artisan would understand that those examples can be relied upon in preparing the compounds disclosed herein.

Intermediates

Preparation of
2,7,8-trichloro-4-(1H-imidazol-1-yl)quinoline
(Intermediate 1)

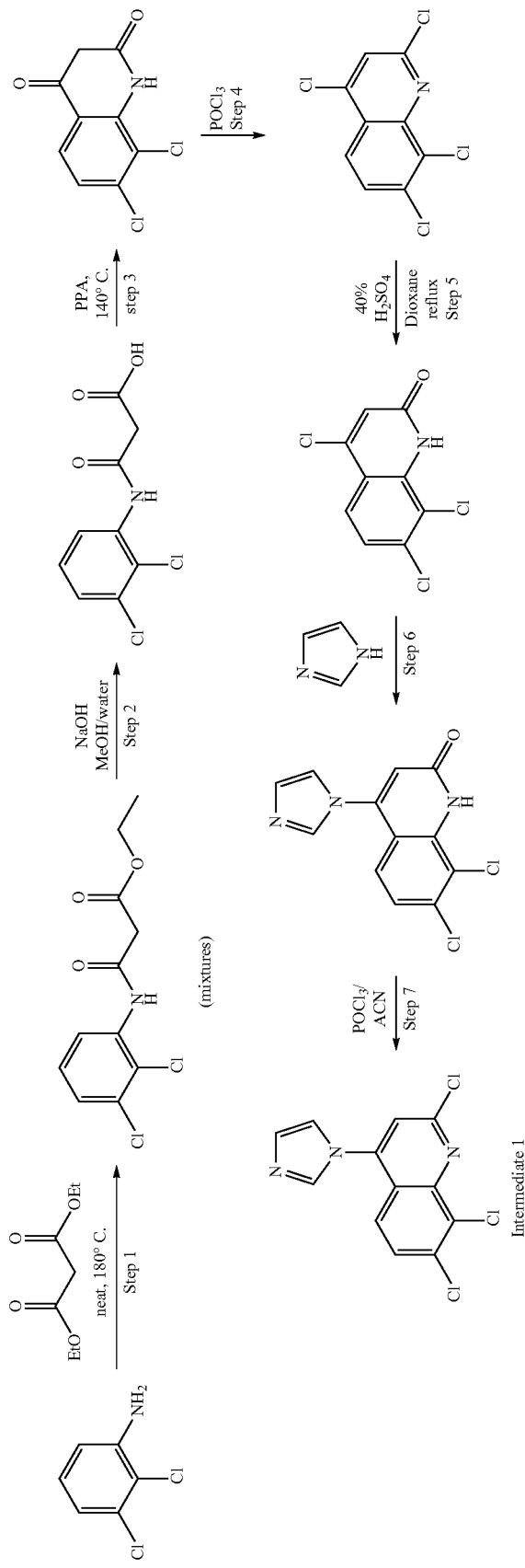

Step 1: Preparation of ethyl 3-((2,3-dichlorophenyl)amino)-3-oxopropanoate. 2,3-dichloroaniline (10.33 g, 64 mmol, 1.0 eq) was mixed with diethyl malonate 1-2 (24 mL, 24.3 g, 158 mmol) and heated at 180° C. for 16 hours until product formation ceased (confirmed by LC-MS). The resulting oil mixture was used in the next step. MS (ES): [M+1]⁺ 276.

Step 2: Preparation of 3-((2,3-dichlorophenyl)amino)-3-oxopropanoic acid. The mixture of the first step was diluted with MeOH (80 mL) and water (80 mL) and chilled with an ice-water bath. To the above solution was added a solution of NaOH (12 g, -2 eq to the amount of diethyl malonate) in 50 mL water slowly. After stirring 30 to 60 min, solids precipitated. Water was added to help stirring. After stirring for 3 to 4 hours at room temperature, starting material was consumed (confirmed by LC-MS), the reaction mixture was acidified with conc. HCl to pH 1 to form a precipitate. After filtration, rinsing with water, and drying under vacuum, the titled compound (10.57 g) was used in the next step without further purification. MS (ES): [M+1]⁺ 248.

Step 3: Preparation of 7,8-dichloroquinoline-2,4(1H,3H)-dione. The product of step 2 (10.57 g) was suspended and stirred with PPA (55 g) at 140° C. for 3 hours until all solids were dissolved. After starting material was consumed (confirmed by LC-MS), the reaction mixture was quenched with ice. The formed solids were collected by filtration and rinsed with water. After drying under vacuum, the titled compound (17 g) was used in the next step without further purification. MS (ES): [M+1]⁺ 230

Step 4: Preparation of 2,4,7,8-tetrachloroquinoline (1.6). The product of step 3 was suspended in POCl₃ (45 g) and heated at 130° C. until all solids were dissolved. After starting material was consumed (confirmed by LC-MS), excess POCl₃ was removed by under vacuum. The residue was treated with ice-water (exothermic) to afford solids and the suspended solids were stirred for 4 hours. Filtration, rinsing with water, and drying under vacuum afforded the crude product as a brown solid (9.25 g) that was suspended in hexane (400 mL) and heated at reflux. After hot filtration to remove residual solids and cooling slowly to room temperature, 5.73 g of the titled compound was obtained as a light brown solid. The solids concentrated from the filtrate and undissolved solids from the above recrystallization were purified by a flash silica column to afford additional product (1.7 g). MS (ES): [M+1]⁺ 266.0. ¹H NMR (400 Hz, CDCl₃): δ 8.074-8.046 (dd, J=9.2 and 2.4 Hz, 1H), 7.705-7.677 (dd, J=9.2 and 2.4 Hz, 1H), 7.571 (s, 1H) ppm.

Step 5: Preparation of 4,7,8-trichloroquinolin-2(1H)-one. The product of step 4 (4.93 g) was suspended in dioxane (80 mL), conc. H₂SO₄ (16 mL), water (24 mL), and heated to reflux for 12 to 16 hours. A clear solution was initially formed followed by the precipitation of solids. After starting material was consumed (confirmed by LC-MS) and the reaction mixture was cooled, 100 mL of ACN was added to form a precipitate. Filtration, rinsing with CAN, and drying under vacuum afforded the titled compound (4.12 g) as colorless powder. MS (ES): [M+1]⁺ 248.0.

Step 6: Preparation of 7,8-dichloro-4-(1H-imidazol-1-yl)quinolin-2(1H)-one (1-8). The product of step 5 (4.12 g) was suspended in DMF (20 mL) with imidazole (4 g) and heated to 130° C. until starting material was consumed (confirmed by LC-MS). Additional imidazole can be added to push the reaction to the completion. After cooling, ACN (150 mL) was added to form a precipitate which was collected by filtration and rinsing with CAN afforded the titled compound (1.8, 3.90 g). MS (ES): [M+1]⁺ 280.0. ¹H NMR (400 Hz, DMSO-d6): δ 8.089 (s, 1H), 7.650 (s, 1H), 7.494-7.516 (d, J=8.8 Hz, 1H), 7.316-7.338 (d, J=8.8 Hz, 1H), 7.225 (s. 1H), 6.795 (s, 1H) ppm.

Step 7: 2,7,8-trichloro-4-(1H-imidazol-1-yl) quinoline (Intermediate 1). The product of step 6 (3.90 g) was suspended in ACN (100 mL) and POCl₃ (8 mL) and heated to reflux until all solids were dissolved and starting material was consumed (confirmed by LC-MS). After concentrating under vacuum, the residue was cooled in an ice bath and carefully neutralized by 5% NaOH to pH 7 to precipitate Intermediate 1. Filtration, rinsing with water, and drying under vacuum afforded Intermediate 1 (3.8 g) as light tan solid. MS (ES): [M+1]⁺ 298. ¹H NMR (400 Hz, DMSO-d6): δ 8.200 (s, 1H), 8.005 (s, 1H), 7.925-7.948 (d, J=9.2 Hz, 1H), 7.785-7.808 (d, J=9.2 Hz, 1H), 7.772 (s. 1H), 7.286 (s, 1H) ppm.

Preparation of
2,7,8-trichloro-4-(1H-pyrazol-4-yl)quinoline
(Intermediate 2)

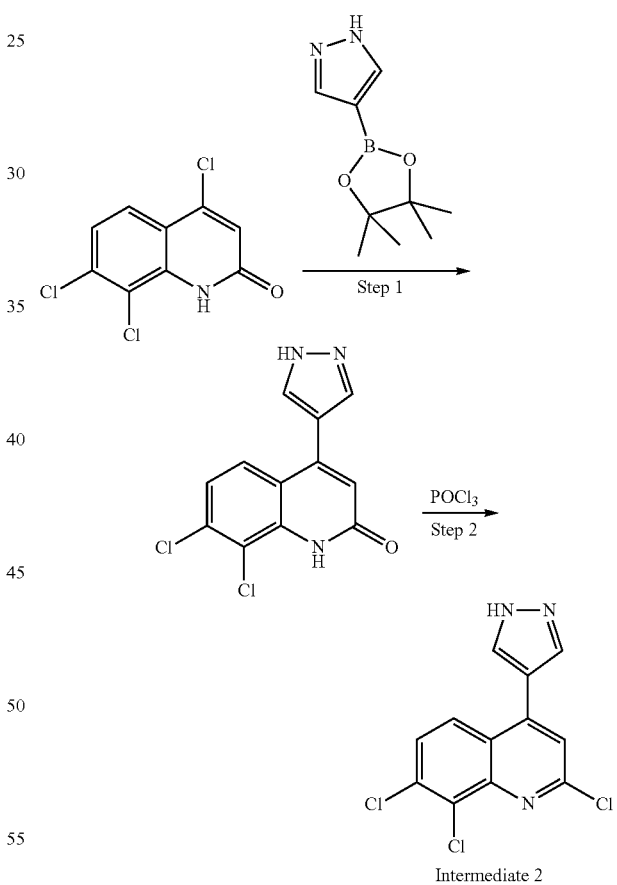

Intermediate 2

Step 1: Preparation of 7,8-dichloro-4-(1H-pyrazol-4-yl)quinolin-2(1H)-one. 4,7,8-trichloroquinolin-2(1H)-one (300 mg, 1.21 mmol), Na₂CO₃ (321 mg, 3.03 mmol), and Pd(PPh₃)₄ (140 mg, 0.121 mmol) were added to a round-bottom flask and diluted with dioxane (10 mL) and water (5 mL). The mixture was cooled in an ice-bath, and vacuumed and purged with N₂ three times. A solution of boron ester 2.1 (703 mg, 3.62 mmol) in dioxane (3 mL) was prepared and degassed. Under N₂, a portion of the boron ester 2.1 (1 mL, 1.0 eq) in dioxane was added to the reaction mixture via a syringe. The reaction mixture was heated at 110° C. for 2 h while LC-MS showed that around 50% of 1.7 was consumed. The rest of the boron ester 2.1 in dioxane was added under N₂. After heating and stirring for an additional 3 h, compound 1.7 was consumed (confirmed by LC-MS). After cooling to room temperature, the reaction mixture was further diluted with water (20 mL). The precipitated solids were collected by centrifuge or filtration and washed with DCM (5 mL×3). After drying under the vacuum, the titled compound was afforded (2.2, 315 mg). MS: [M+1]⁺ 280.

Step 2: Preparation of 2,7,8-trichloro-4-(1H-pyrazol-4-yl) quinoline (Intermediate 2). The product of step 1 (208 mg, 0.743 mmol) was suspended in ACN (2.5 mL) and POCl₃ (0.42 mL). The resultant mixture was heated at 80° C. for 3 h or until less than 10% of compound 2.2 remained (confirmed by LC-MS). After the concentrating under vacuum, the residue was cooled in an ice bath and carefully neutralized by 5% NaOH to pH 7 to precipitate Intermediate 2 as a yellow solid. The solids were collected by centrifuge or filtration and washed with water (15 mL×3). After drying in vacuo, Intermediate 2 was afforded (180 mg). MS: [M+1]⁺ 298. ¹HNMR (400 MHz, DMSO-D6) δ: 8.8.25-8.30 (m, 3H), 7.84 (d, J=9.2 Hz, 1H) and 7.72 (s, 1H) ppm.

Preparation of 2,7-dichloro-4-(1H-imidazol-1-yl) quinoline (Intermediate 3)

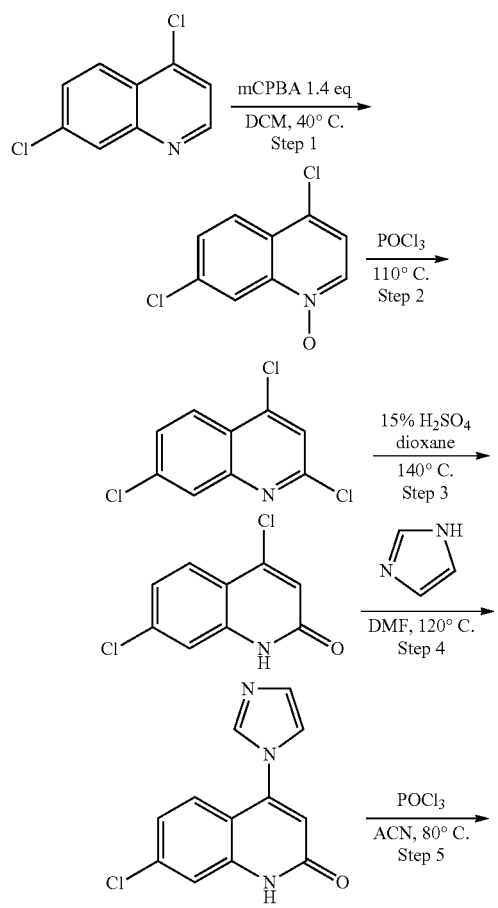

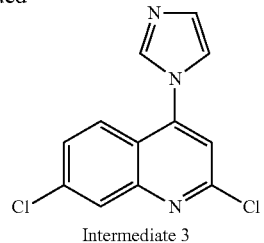

Intermediate 3

Step 1: Preparation of 4,7-dichloroquinoline 1-oxide. To a solution of 4,7-dichloroquinoline (20.0 g, 101.5 mmol) in DCM (400 mL) at room temperature was added 3-chloroperoxybenzoic acid (mCPBA) (28.8 g, 85% purity, 142.1 mmol) in portions and the resulting solution was stirred at 40° C. for 2 hrs. The solution was then washed with aqueous NaHCO₃ (2×50 mL), aqueous Na₂S₂O₃ (100 mL×2), dried over anhydrous Mg₂SO₄, filtered, concentrated under reduced pressure, and dried under high vacuum to yield the titled product (21 g) as a white solid. MS: [M+1]⁺ 214.1.

Step 2: Preparation of 2,4,7-trichloroquinoline. The product of step 1 (20.0 g, 1.0 eq) was dissolved in POCl₃ (74 mL) at rt and the resulting solution was stirred at 110° C. for 2 hrs. The mixture was concentrated under reduced pressure and adjusted to pH 9 with a 10% NaOH solution. The precipitate was collected, washed with water, and dried to afford the titled compound (18 g, yield 83%) as an off-white solid. MS: [M+1]⁺ 234.0. ¹H NMR (400 Hz, CDCl₃): δ 8.148-8.126 (d, J=8.8 Hz, 1H), 8.033 (s, 1H), 7.622-7.596 (dd, J=1.4 Hz, 1H), 7.510 (s, 1H) ppm.

Step 3: Preparation of 4,7-dichloroquinolin-2(1H)-one. To a solution of the product of step 2 (5.0 g, 1.0 eq) in 1,4-diaoxane (125 mL) was added 15% H₂SO₄ (250 mL) at 25° C. The resulting mixture was stirred at 140° C. for 12 hrs. The precipitated solids were collected by filtration, washed with water, and dried to afford the titled compound (3.9 g) as a gray solid. MS: [M+1]⁺ 214.1. ¹H NMR (400 Hz, CDCl₃): δ 12.122 (s, 1H), 7.880-7.859 (d, J=8.4 Hz, 1H), 7.406 (s, 1H), 7.368-7.343 (dd, J=1.4 Hz, 1H), 6.865 (s, 1H) ppm.

Step 4: Preparation of 7-chloro-4-(1H-imidazol-1-yl)quinolin-2(1H)-one. To a solution of 4,7-dichloroquinolin-2(1H)-one (9.0 g, 1.0 eq) in DMF (18 mL) was added imidazole (48.8 g, 17 eq). After stirring at 120° C. for 21 hrs, the reaction mixture was diluted with ACN (100 mL) and stirred for 0.5 hrs. The precipitated solid was collected, washed with ACN, and dried in vacuo to afford the crude titled compound (6.7 g) as a gray solid. MS: [M+1]⁺ 246.1. ¹H NMR (400 MHz, DMSO): δ 12.19 (s, 1H), 8.09 (s, 1H), 7.65 (s, 1H), 7.46 (d, J=2.0 Hz, 1H), 7.39 (d, J=8.8 Hz, 1H), 7.29 (dd, J=8.8, 2.0 Hz, 1H), 7.21 (s, 1H), 6.66 (s, 1H) ppm.

Step 5: Preparation of 2,7-dichloro-4-(1H-imidazol-1-yl) quinolone (Intermediate 3). To a solution of compound 3.5 (5.0 g, 1.0 eq) in ACN (50 mL) was added POCl₃ (10 mL) and the resulting mixture was stirred at 80° C. for 0.5 hrs. The mixture was concentrated in vacuo and the residue was carefully quenched with 5-10% NaOH solution to pH 7 in an ice-bath. The precipitated solid was collected, washed with water, and dried in vacuo to yield Intermediate 3 (4.1 g) as a white solid. MS (ES): [M+1]⁺ 264. ¹H NMR (400 Hz, CDCl₃): δ 8.164 (s, 1H), 7.970 (s, 1H), 7.786-7.763 (d, J=9.2 Hz, 1H), 7.631-7.608 (d, J=9.2 Hz, 1H), 7.422 (s, 1H), 7.357 (s, 1H) ppm.

Preparation of 2,4-dichloro-7-(trifluoromethyl)quinoline (Intermediate 4A) and 2,4-dichloro-5-(trifluoromethyl)quinoline (Intermediate 4B)

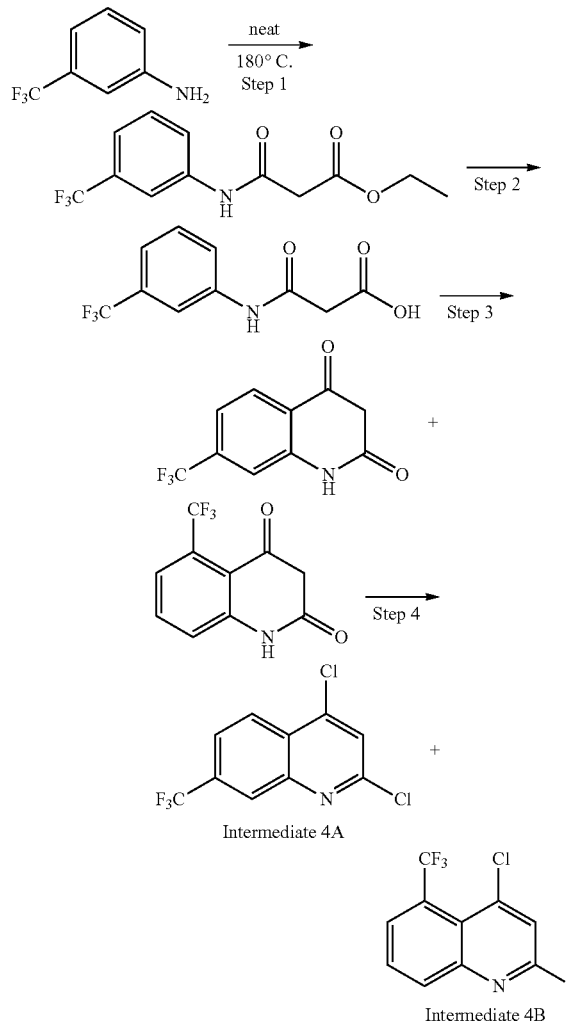

Intermediate 4A

Intermediate 4B

Step 1: 3-Oxo-3-((3-(trifluoromethyl) phenyl) amino) propanoic acid. A mixture of 3-(trifluoromethyl) aniline (5.74 g) and diethyl malonate (14.9 g) was stirred and heated at 180° C. over 4 hours. The resultant mixture was dissolved in MeOH (30 mL) and water (10 mL). Step 2: The solution was cooled in an ice-bath and treated with NaOH (7.1 g). After stirring at room temperature over 2 hours and removal of MeOH under vacuum, the resultant mixture was further diluted with water (60 mL) and acidified to pH 1 to 2 with conc. HCl. After extraction with EtOAc (30 mL×4), the combined organic layers were washed by brine and dried over $Na_2SO_4$. Evaporation of EtOAc under reduced pressure afforded 4.3 (8.76 g) as oil. MS: $[M+1]^+$ 276.

Step 3: 7-(Trifluoromethyl) quinoline-2,4(1H,3H)-dione 4-4 and 5-(trifluoromethyl) quinoline-2,4 (1H,3H)-dione. Neat 4.3 (8.76 g) was suspended in PPA (42 g) and heated at 130° C. over 4 hours. The resultant mixture was further diluted with water (120 mL) and the aqueous layer was extracted with EtOAc (40 mL×3). The combined organic layers were washed with brine and dried over $Na_2SO_4$. Evaporation under reduced pressure afforded a mixture of two titled regioisomers (5.99 g) as sticky solids. MS: $[M+1]^+$ 230.

Step 4: 2,4-Dichloro-7-(trifluoromethyl)quinoline (Intermediate 4A) and 2,4-dichloro-5-(trifluoromethyl)quinoline (Intermediate 4B). The mixture of 4.4 and 4.5 (5.99 g) from the previous step were suspended in $POCl_3$, stirred, and heated at reflux over 3 h. $POCl_3$ was removed under reduced pressure and the resultant mixtures were carefully quenched with ice. The aqueous layer was extracted with EtOAc (30 mL×3) and the combined organic layers were washed with brine and dried over $Na_2SO_4$. Column chromatography, eluting with a gradient of DCM/Hexane from 0 to 50%, afforded Intermediate 4A (3.1 g) and Intermediate 4B (0.59 g). 4A: MS [M+1]: 266.1. $^1$HNMR (400 MHz, CD3Cl) δ: 8.38 (s, 1H), 8.37 (d, J=8 Hz, 1H), 7.86 (dd, J=8 and 4 Hz) and 7.66 (s, 1H) ppm. 4B: MS [M+1]: 266.1. $^1$HNMR (400 MHz, CD3Cl) δ: 8.29 (d, J=8 Hz, 1H), 8.18 (d, J=8 Hz, 1H), 7.85 (t, J=8 Hz) and 7.72 (s, 1H) ppm.

Preparation of 7-bromo-2,6-dichloro-4-(1H-1,2,4-triazol-1-yl)quinoline (Intermediate 5)

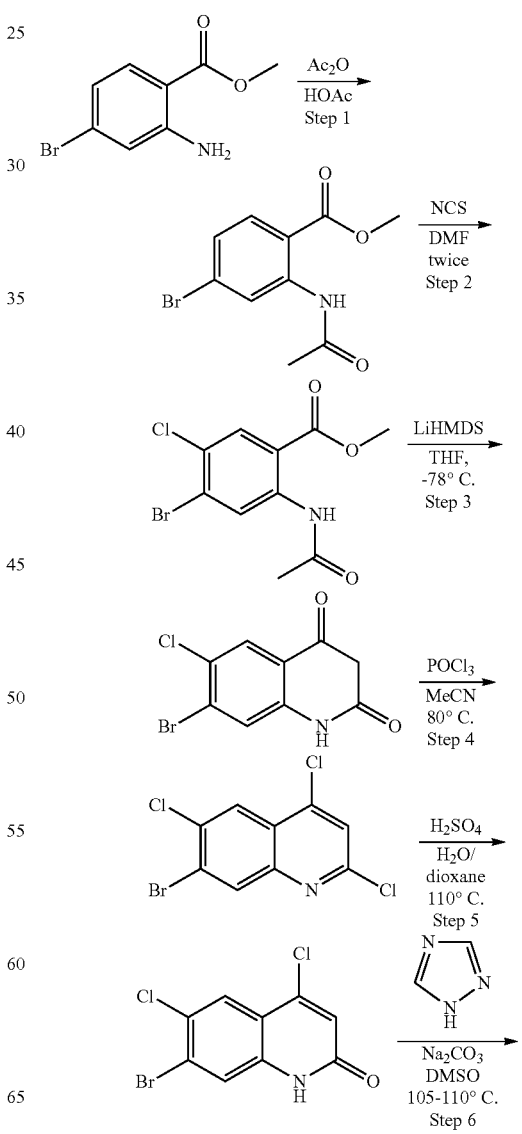

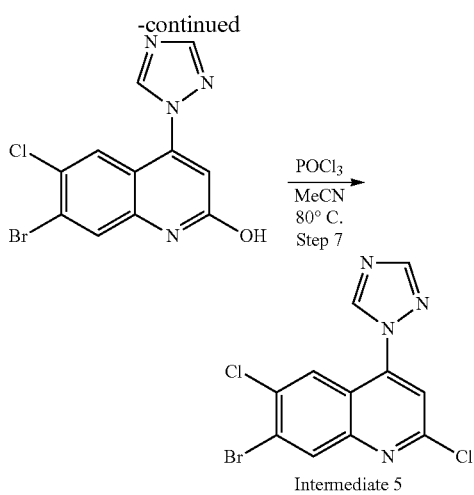

Methyl 2-acetamido-4-bromo-5-chlorobenzoate (product of Step 2 above) was obtained according to the description in PCT Publication WO 2021/127404 (see "Step 12: methyl 2-acetamido-4-bromobenzoate" and "Step 13: methyl 2-acetamido-4-bromo-5-chlorobenzoate" in that PCT Publication).

Step 3: 7-Bromo-6-chloroquinoline-2,4(1H,3H)-dione. To a flask (500 ml) was added anhydrous THF (100 ml) and LiHMDS/THF (1.0 M, 82.2 ml, 3.0 eq.). The mixture was cooled in dry ice/acetone bath. A solution of methyl 2-acetamido-4-bromo-5-chlorobenzoate (8.40 g, 27.4 mmol, 1.0 eq.) in anhydrous THF (83 ml) was added dropwise over 2 hours at −78° C. After the addition, the resulting mixture was allowed to warm to room temperature and was stirred for 1 h. Then the reaction mixture was concentrated under reduced pressure to its half volume and diluted with ice-water (500 g). After filtration to remove the yellow by-product, the filtrate was extracted with ethyl acetate (150 ml×2) to remove the by-product further. The aqueous phase was acidified with HCl/H$_2$O (5 N) in an ice bath to pH 4. The precipitated white solid was collected by filtration, washed with water (140 ml×2), dried under high vacuum. The title compound (4.74 g) was obtained in a 63% yield. MS (ES): [M+1]$^+$ 274.

Step 4: 7-Bromo-2,4,6-trichloroquinoline. To a round bottom flask (250 ml) was added 7-bromo-6-chloroquinoline-2,4(1H,3H)-dione (4.74 g, 17.26 mmol, 1.0 eq.) and anhydrous acetonitrile (60 ml). With stirring, POCl$_3$ (10.04 ml, 107.7 mmol, 6.2 eq.) was added. The reaction mixture was stirred at a temperature between 80° C. to 85° C. for 20 hours. The reaction mixture was checked by HPLC and most of starting material was converted to desired product. The reaction mixture was cooled to room temperature. Most volatiles were removed under reduced pressure. Ice water (100 ml) was added to disperse the precipitated solid. The cloudy mixture was filtered through a fritted funnel and washed with DI water (120 ml×3), dried under high vacuo to afford the title compound (wet). (MS: [M+1]+ 310).

Step 5: 7-Bromo-4,6-dichloroquinolin-2(1H)-one. To a round bottom flask (200 ml) was added 7-bromo-2,4,6-trichloroquinoline (17.26 mmol, wet, containing 11 g of H$_2$O) and 1,4-dioxane (32 ml). In ice bath, H$_2$SO$_4$ (8.27 ml) was added slowly with stirring. The mixture was stirred at 110° C. for 4 hours. The reaction mixture was cooled to room temperature and ice/H$_2$O (70 g) was added. The cloudy mixture was filtered through a fritted funnel, washed with H$_2$O (120 ml×3) and dried under high vacuum to afford the desired product (4.69 g, off-yellow solid, 92.8% yield over two steps). (MS: [M+1]$^+$ 292).

Step 6: 7-Bromo-6-chloro-4-(1H-1,2,4-triazol-1-yl)quinolin-2-ol. To a flask was added 7-bromo-4,6-dichloroquinolin-2(1H)-one (4.69 g, 16.02 mmol, 1.0 eq.), 1,2,4-triazole (3.32 g, 48.07 mmol, 3.0 eq.), Na$_2$CO$_3$ (5.10 g, 48.07 mmol, 3.0 eq.) and DMSO (36 ml). A lot of solid cannot dissolve. The reaction mixture was stirred at 110° C. overnight. After cooling to room temperature, the mixture was mixed with ice-water (200 g), filtered, washed with H$_2$O (140 g×3), and dried under high vacuum to afford the title compound as an off-yellow solid (4.9 g) with 95% yield. (MS: [M+1]$^+$ 325).

Step 7: 7-Bromo-2,6-dichloro-4-(1H-1,2,4-triazol-1-yl)quinoline (Intermediate 5). To a flask (250 ml) was added 7-bromo-6-chloro-4-(1H-1,2,4-triazol-1-yl)quinolin-2-ol (4.9 g, 15.05 mmol, 1.0 eq.) and anhydrous MeCN (80 ml). With stirring, POCl$_3$ (8.4 ml, 90.3 mmol, 6.0 eq.) was added. The reaction mixture was stirred at 80 to 85° C. to reflux for 7 hours. The reaction mixture was checked by HPLC and most of starting material was converted to desired product. The reaction mixture was cooled to room temperature and concentrated under reduced pressure. Ice water (100 g) was added, and the mixture was well mixed via sonication. The mixture was cooled in an ice bath to an inner temperature below 10° C. A precooled aqueous solution of NaOH (10%) was added to neutralize the HCl to pH 7.0 in such a rate that the internal temperature was below 10° C. After stirring in ice bath for 30 min, the cloudy mixture was filtered through a fritted funnel and washed with DI water (140 ml×2), dried under high vacuum to afford desired product compound 8 as an off-yellow solid (5.0 g) with 96% yield. (MS: [M+1]$^+$ 343).

Preparation of 6-bromo-2,7,8-trichloro-4-(1H-1,2,4-triazol-1-yl)quinoline (Intermediate 6)

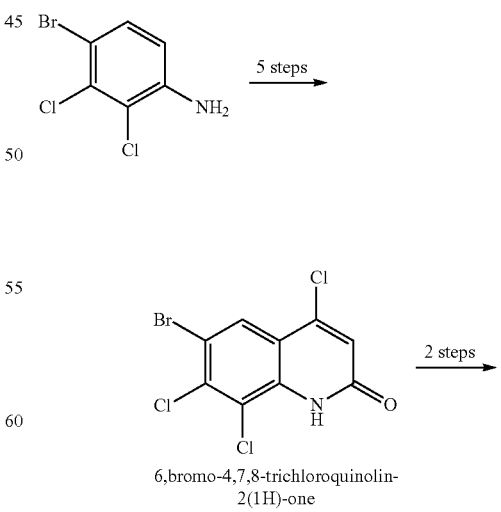

6,bromo-4,7,8-trichloroquinolin-2(1H)-one

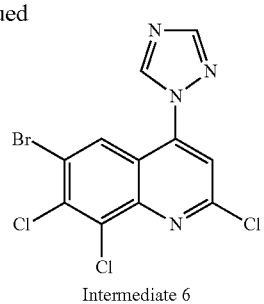

Intermediate 6

6-Bromo-4,7,8-trichloroquinolin-2(1H)-one was prepared from 4-bromo-2,3-dichloroaniline following the procedure according to the first five steps in the synthesis of Intermediate 5. (MS: [M+1]⁺ 326).

6-bromo-2,7,8-trichloro-4-(1H-1,2,4-triazol-1-yl)quinoline (Intermediate 6) was obtained following the procedure according to steps 6 and 7 in the synthesis of Intermediate 5. (MS: [M+1]⁺ 377).

Preparation of 2,7,8-trichloro-4-(1H-1,2,4-triazol-1-yl)quinoline (Intermediate 8)

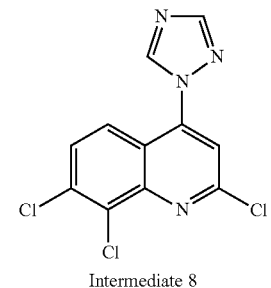

Intermediate 8

The title compound was prepared from 2,3-dichloroaniline following the procedure to prepare Intermediate 6. (MS: [M+1]⁺ 299).

Preparation of 2,6,7-trichloro-4-(1H-1,2,4-triazol-1-yl)quinoline (Intermediate 9A) and 2,5,6-trichloro-4-(1H-1,2,4-triazol-1-yl)quinoline (Intermediate 9B)

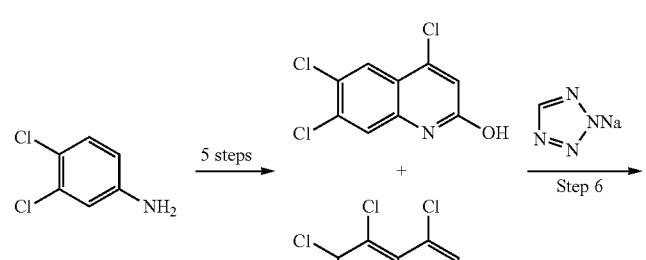

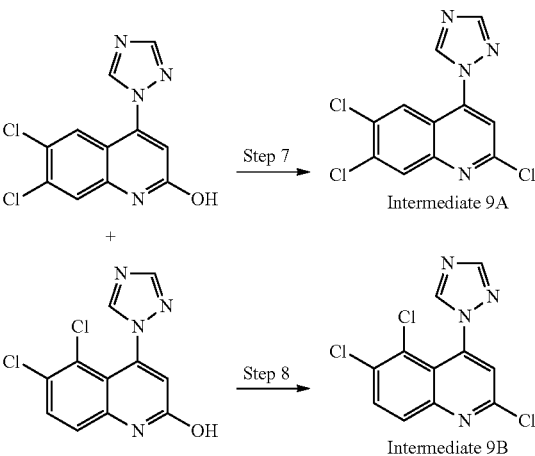

Intermediate 9A

Intermediate 9B

Preparation of 7-bromo-2-chloro-8-methyl-4-(1H-1,2,4-triazol-1-yl)quinoline (Intermediate 7)

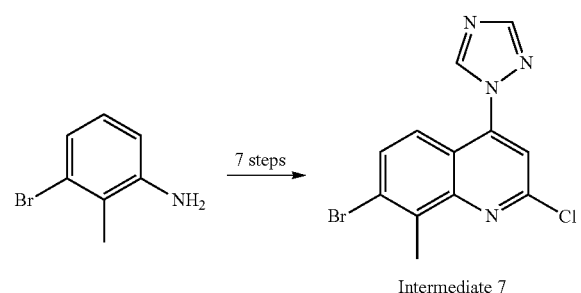 [SMILES: Nc1cccc(Cl)c1Cl ; Clc1cc(-n2cncn2)c2ccc(Cl)c(Cl)c2n1]

Intermediate 7

The title compound was prepared from 3-bromo-2-methylaniline following the procedure to prepare Intermediate 6. (MS: [M+1]+ 323).

Mixture of 4,6,7-trichloroquinolin-2-ol and 4,5,6-trichloroquinolin-2-ol was prepared from 3,4-dichloroaniliane following the procedure according to the first five steps in the synthesis of Intermediate 6. (MS: [M+1]⁺ 248).

Step 6: 6,7-dichloro-4-(1H-1,2,4-triazol-1-yl)quinolin-2-ol and 5,6-dichloro-4-(1H-1,2,4-triazol-1-yl)quinolin-2-ol. A mixture of 4,6,7-trichloroquinolin-2-ol and 4,5,6-trichloroquinolin-2-ol (283 mg) was treated with 1,2,4-triazolylsodium (311 mg) in DMSO (2 mL) at 100° C. overnight. After cooling down to room temperature, the reaction mixtures was quenched with water to afford a suspension. The suspended solid was isolated by filtration and rinsed with water. After drying under vacuum, 6,7-dichloro-4-(1H-1,2,4-triazol-1-yl)quinolin-2-ol (180 mg) was afforded. (MS: [M+1]⁺ 281).

The filtrate from the above filtration was acidified to afford a suspension, the suspended solid was isolated by filtration and rinsed with water to give the desired product (88 mg)-5,6-dichloro-4-(1H-1,2,4-triazol-1-yl)quinolin-2-ol. (MS: [M+1]+ 281).

Step 7: 2,6,7-trichloro-4-(1H-1,2,4-triazol-1-yl)quinoline (Intermediate 9A) was obtained following the procedure for the preparation of intermediate 6, (MS: [M+1]⁺ 299).

Step 8: 2,5,6-trichloro-4-(1H-1,2,4-triazol-1-yl)quinoline (Intermediate 9B) was obtained following the procedure for the preparation of intermediate 6, (MS: [M+1]⁺ 299).

Following the above procedures to prepare Intermediates 1 to 8, the following compounds were prepared.

Example 1: Synthesis of 5-(7,8-dichloro-4-(1H-imidazol-1-yl)quinolin-2-yl)-2-hydroxybenzoic acid (I-42)

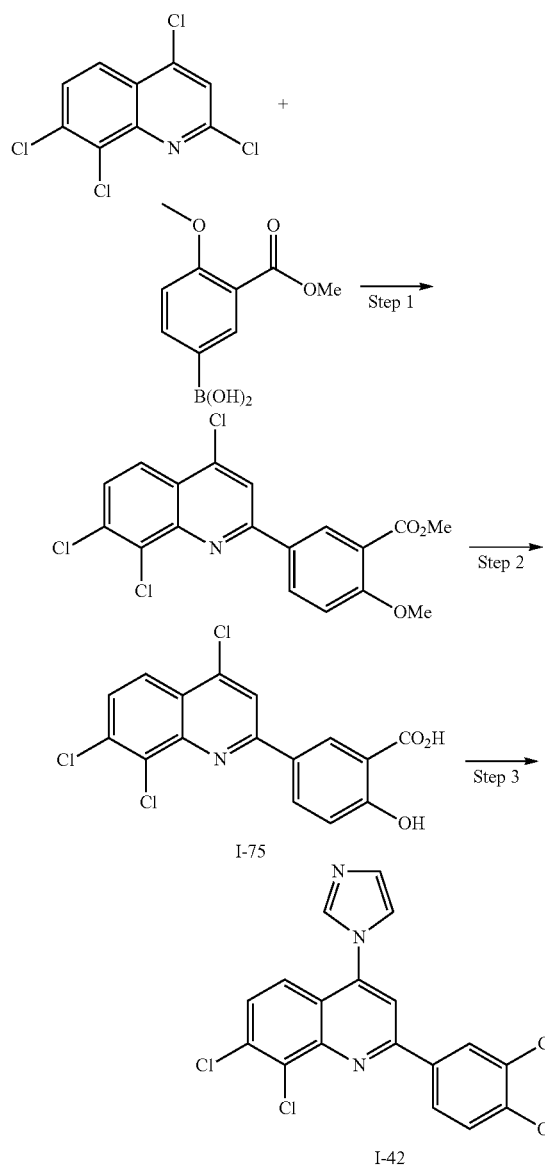

Step 1: Methyl 2-methoxy-5-(4,7,8-trichloroquinolin-2-yl)benzoate. To a suspension of 2,4,7,8-tetrachloroquinoline (200 mg, 0.75 mmol) with (4-methoxy-3-(methoxycarbonyl)phenyl) boronic acid (205.3 mg, 0.98 mmol) and Na$_2$CO$_3$ (178 mg, 1.68 mmol) in dioxane (8.0 mL) and water (2.0 mL) was added Pd(PPh$_3$)$_4$ (79.2 mg). The resultant mixture was vacuumed and purged with N$_2$ for three cycles, then stirred and heated at 80° C. over two hours. After cooling to room temperature, the reaction mixture was dissolved in DCM (50 mL) and washed with water and brine. The resultant organic layer was separated and dried over anhydrous Na$_2$SO$_4$. A silica gel flash column chromatography eluting with DCM/Hexane afforded the desired colorless product (MS: [M+1]⁺ 396).

Step 2: 2-Hydroxy-5-(4,7,8-trichloroquinolin-2-yl)benzoic acid (I-75). Methyl 2-methoxy-5-(4,7,8-trichloroquinolin-2-yl) benzoate (17 mg) in DCM (1.5 mL) was treated with 1M BBr$_3$ in DCM (0.1 mL) at room temperature over 8 hours. The resulting mixture was diluted with EtOAc (25 mL), washed with water (10 mL) and dried over Na$_2$SO$_4$. Concentration under vacuum afforded the desired light brown solid (11 mg), 2-hydroxy-5-(4,7,8-trichloroquinolin-2-yl) benzoic acid (MS: [M+1]⁺ 368).

Step 3: 5-(7,8-dichloro-4-(1H-imidazol-1-yl)quinolin-2-yl)-2-hydroxybenzoic acid. To a solution of 2-hydroxy-5-(4,7,8-trichloroquinolin-2-yl) benzoic acid (11 mg) in DMF (0.5 mL) was added imidazole (55 mg) and K$_2$CO$_3$ (50 mg). The resultant solution was stirred and heated at 120° C. over 5 hours until the starting material was completely consumed. The reaction mixture was diluted with water (3 mL) and treated with Dowex resin until the pH to 3. The resultant colorless solid was isolated by filtration and washed with water (3 mL). After drying under vacuum, the desired product was obtained (MS: [M+1]⁺ 400).

Example 2: Synthesis of (7,8-Dichloro-2-(1H-pyrazol-3-yl)quinolin-4-yl)glycine (I-287)

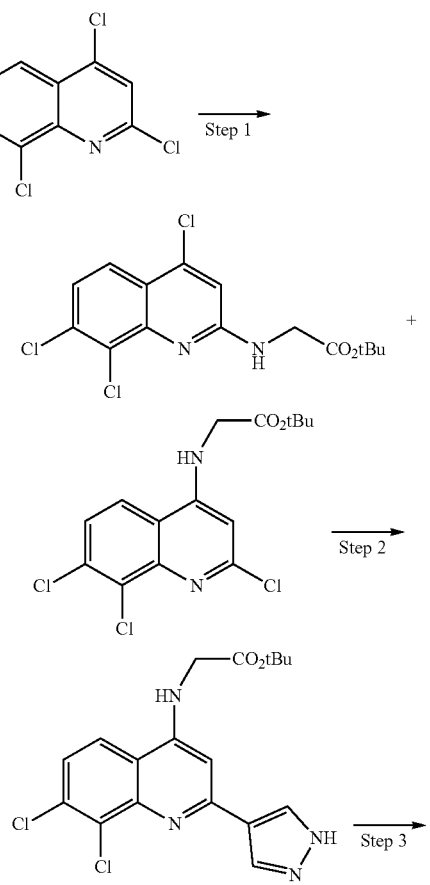

-continued

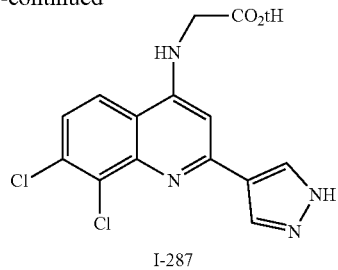

I-287

Step 1: tert-Butyl (4,7,8-trichloroquinolin-2-yl)glycinate and tert-butyl (2,7,8-trichloroquinolin-4-yl)glycinate. To a solution of 2,4,7,8-tetrachloroquinoline (270 mg) and tert-butyl glycinate HCl (270 mg) in DMSO (0.8 mL) was added $K_2CO_3$ (276 mg). The resultant reaction mixture was heated at 85° C. over 4 h. Aqueous work up with EtOAc (30 mL) and a column chromatography eluting with a gradient of DCM/Hexane from 0 to 50% afforded two colorless compounds. The earlier eluted fraction is 4-substituted product (120 mg) (MS: [M+1]+ 361) and the later fraction with 2-substituted product (62 mg) (MS: [M+1]+ 361).

Step 2: tert-Butyl (7,8-dichloro-2-(1H-pyrazol-4-yl)quinolin-4-yl)glycinate. To a mixture of tert-butyl (2,7,8-trichloroquinolin-4-yl)glycinate (52 mg), 4-(4,4,5,5-tetramethyl-1,3,2-dioxaborolan-2-yl)-1H-pyrazole (50 mg), $K_2CO_3$ (48 mg) and Pd(PPh$_3$)$_4$ (16 mg) were added dioxane (2 mL) and water (0.5 mL). The resultant suspended solution was vacuumed and purged with nitrogen repeatedly three time, then stirred and heated at 85° C. under nitrogen over 4 hours. An aqueous work-up with EtOAc and a column chromatography gave the desired colorless product (27 mg) (MS: [M+1]+ 393).

Step 3: (7,8-Dichloro-2-(1H-pyrazol-3-yl)quinolin-4-yl) glycine. To a solution of tert-butyl (7,8-dichloro-2-(1H-pyrazol-3-yl) quinolin-4-yl) glycinate (27 mg) in DCM (0.5 mL) was added TFA (0.2 mL). The resultant solution was stirred overnight. After removal of DCM and TFA under reduced pressure, the resultant was mixed with 0.4 mL water and lyophilized to afford the title product (MS: [M+1]+ 337).

The following compounds are prepared essentially by the same method described above to prepare I-287 and some analogues are prepared from intermediates by additional deprotection.

| I-# | Starting Material | | Structure | MS [M + 1]+ |
|---|---|---|---|---|
| I-307 | (2,4,7,8-tetrachloroquinoline) | (piperazin-2-one) | (7,8-dichloro-2-chloroquinolin-4-yl piperazinone) | 330 |
| I-312 | (2,4,7,8-tetrachloroquinoline) | (N-Boc piperazine) | (7,8-dichloro-2-chloroquinolin-4-yl piperazine) | 316 |

Example 3: Synthesis of 2-(benzyloxy)-7-chloro-4-(1H-imidazol-1-yl)quinoline (I-405)

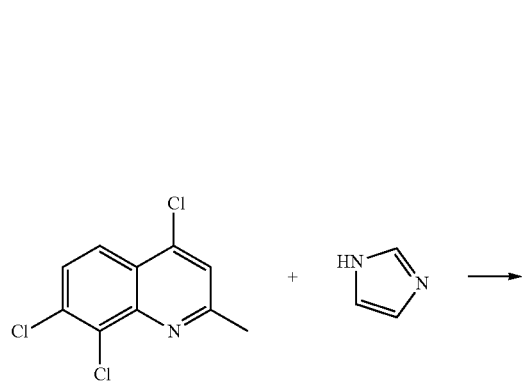

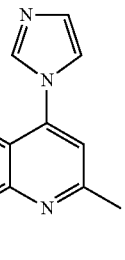

I-405

To a solution of 4,7,8-trichloro-2-methylquinoline (0.5 g) in DMF (4 mL) were added $K_2CO_3$ (0.2 g) and imidizaole (0.54 g). The resultant suspension was heated at 120° C. over 2 h. The reaction mixture was diluted with water (8 mL) to precipitate out the title compound. Filtration and rinsing with water afforded the title compound (0.55 g)-7,8-dichloro-4-(1H-imidazol-1-yl)-2-methylquinoline (MS: $[M+1]^+$ 278).

The following compounds are prepared essentially by the same method described above to prepare I-405. Some analogues were isolated in pure form by precipitation from water and others were purified by column chromatography.

| I-# | Starting Materials | | Structure | MS $[M + 1]^+$ |
|---|---|---|---|---|
| I-305 | (4,7,8-trichloro-2-methylquinoline) | (1,4-diazepan-2-one) | (product structure) | 324 |
| I-310 | (4,7,8-trichloro-2-methylquinoline) | (1,4-diazepan-5-one) | (product structure) | 324 |
| I-302 | (4,7,8-trichloro-2-methylquinoline) | (piperazin-2-one) | (product structure) | 310 |

-continued

| I-# | Starting Materials | Structure | MS [M + 1]⁺ |
|---|---|---|---|
| I-311 | 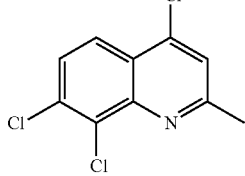 | 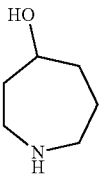 | 325 |
| I-317 | 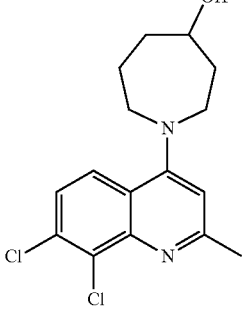 | 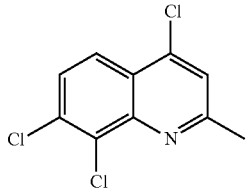 | 374.0 |
| I-303 | 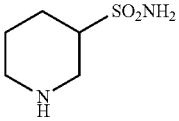 | 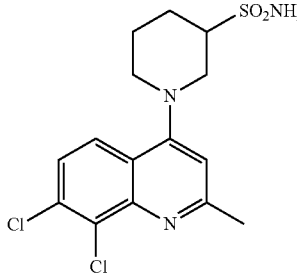 | 345.0 |

Example 4: Synthesis of 7,8-dichloro-2-methyl-4-(1H-pyrazol-4-yl)quinoline (I-406)

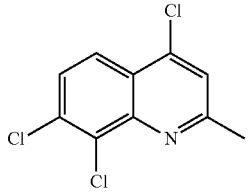
+
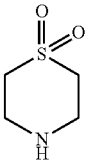
→
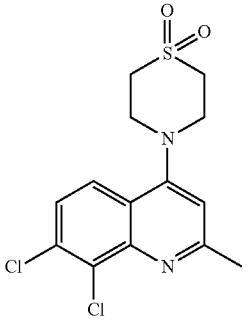 [SMILES: Cc1cc(N2CCS(=O)(=O)CC2)c2ccc(Cl)c(Cl)c2n1]

I-406

To a mixture of 4,7,8-trichloro-2-methylquinoline (0.2 g), 4-(4,4,5,5-tetramethyl-1,3,2-dioxaborolan-2-yl)-1H-pyrazole (281 mg), K₂CO₃ (278 mg) and Pd(PPh₃)₄ (85 mg) were added dioxane (4 mL) and water (2 mL). The resultant mixture was vacuumed and purged with N₂ repeatedly three time, then stirred and heated at 90° C. over 2 hours. A solution of 4-(4,4,5,5-tetramethyl-1,3,2-dioxaborolan-2-yl)-1H-pyrazole (150 mg) in dioxane (2 mL) was degassed and added to the reaction mixture. After 2 hours, the second portion of 4-(4,4,5,5-tetramethyl-1,3,2-dioxaborolan-2-yl)-1H-pyrazole (150 mg) in dioxane (2 mL) was added. After stirring overnight, 2,4,7,8-tetrachloroquinoline was completely consumed. Aqueous work-up and column purification eluting with hexane/EtOAc afforded the title compound (108 mg)-7,8-dichloro-2-methyl-4-(1H-pyrazol-4-yl) quinoline-MS: [M+1]+ 278.

The following compounds are prepared essentially by the same method described above to prepare I-406 and the Suzuki coupling in I-42.

| I-# | Starting Materials | | Structure | MS [M + 1]+ |
|---|---|---|---|---|
| I-407 | 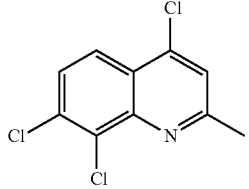 | 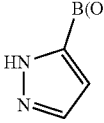 | 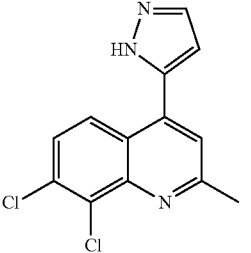 [SMILES: Cc1cc(-c2ccn[nH]2)c2ccc(Cl)c(Cl)c2n1] | 278 |
| I-67 | 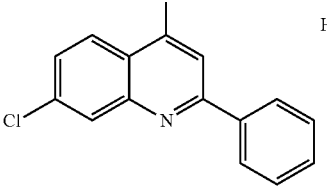 | 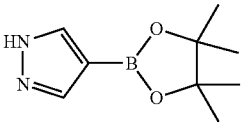 | 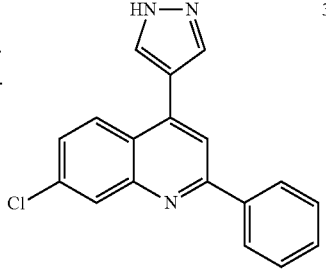 | 306 |
| I-68 | 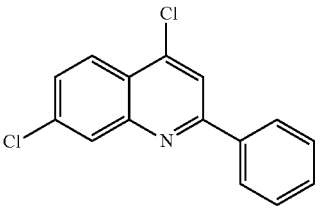 [SMILES: Clc1ccc2c(Cl)cc(-c3ccccc3)nc2c1] | 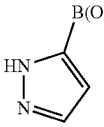 | 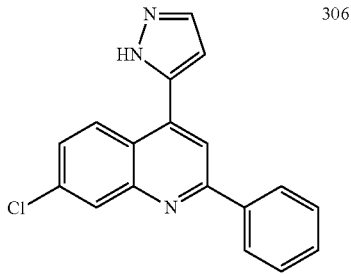 | 306 |
| I-73 | 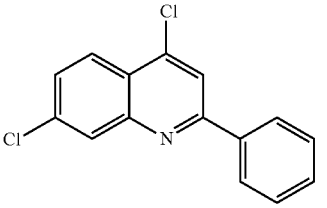 [SMILES: Clc1ccc2c(Cl)cc(-c3ccccc3)nc2c1] | 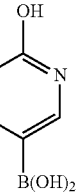 | 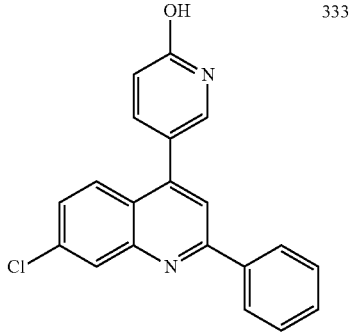 | 333 |

| I-# | Starting Materials | | Structure | MS [M + 1]+ |
|---|---|---|---|---|
| I-72 | | | 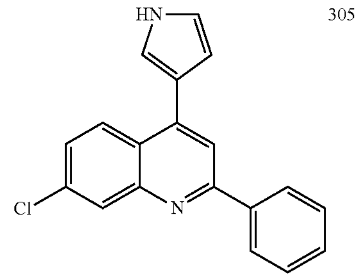 | 305 |
| I-70 | | | 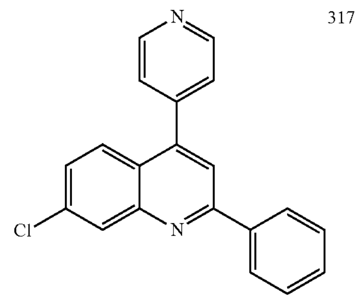 | 317 |
| I-69 | | | 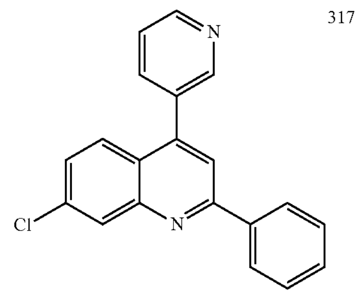 | 317 |
| I-71 | | | 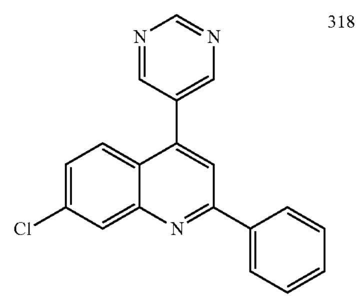 | 318 |
Example 5: Synthesis of 8-chloro-4-(1H-imidazol-1-yl)quinoline (I-408)
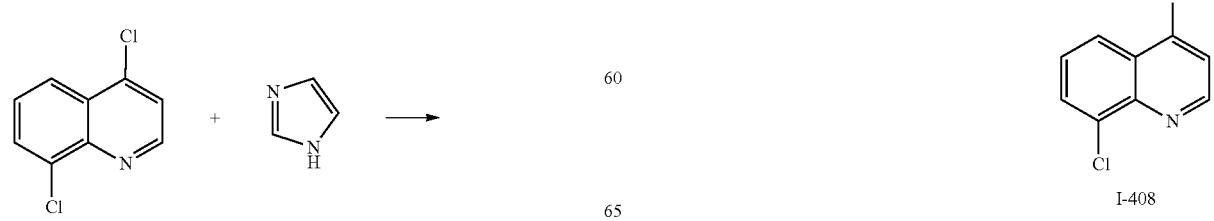

4,8-Dichloroquinoline (50 mg, 0.25 mmol) was placed in a vial with dioxane (2 mL). Imidazole (68 mg, 1.0 mmol) was added and the reaction was heated to 130° C. for 16 h. Water (10 mL) was added to the reaction and then the organics were extracted into ethyl acetate (2×5 mL). The organic phase was dried (Na₂SO₄) and concentrated. The residue was purified by silica chromatography using 30-100% (EtOAc/Hexanes) to afford 8-chloro-4-(1H-imidazol-1-yl)quinoline as a solid (MS: [M+1]⁺ 230).

The following compounds are prepared essentially by the same method described above to prepare I-408.

| I-# | Starting Material | Structure | MS [M + 1]⁺ |
|---|---|---|---|
| I-413 | 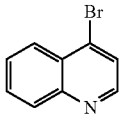 | 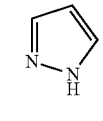 | 196 |
| I-414 | 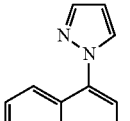 | 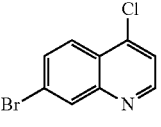 | 274 |
| I-415 | 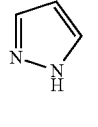 | 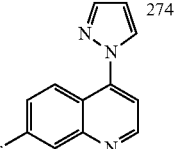 | 274 |
| I-418 | 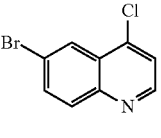 | 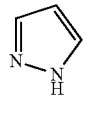 | 275.0 |
| I-419 | 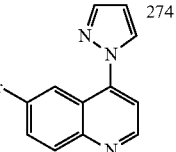 | 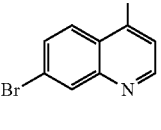 | 275.0 |
| I-420 | 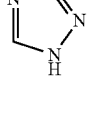 | 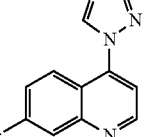 | 274.9 |

Example 6: Synthesis of 3-(((S)-1-(7,8-dichloro-4-((R)-3-hydroxypyrrolidin-1-yl)quinolin-2-yl)pyrrolidin-2-yl)methoxy)propanoic acid (I-821)

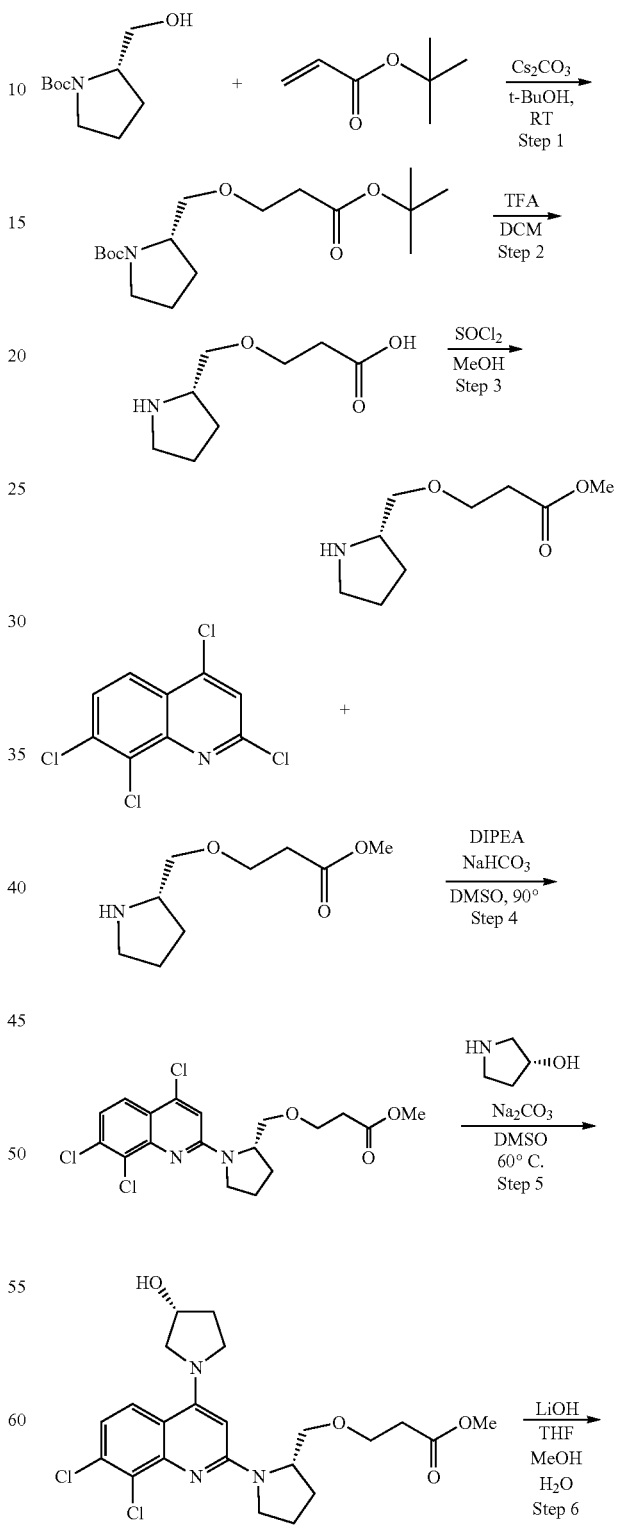

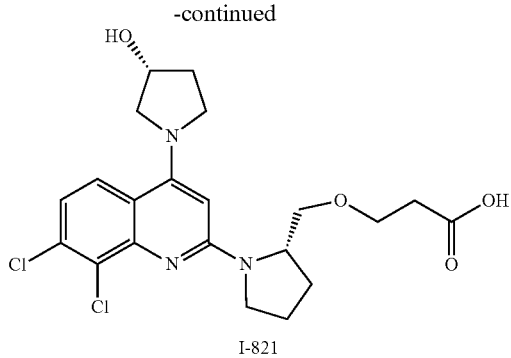

I-821

Step 1: tert-butyl (S)-2-((3-(tert-butoxy)-3-oxopropoxy)methyl)pyrrolidine-1-carboxylate. The procedure was the same as that in the synthesis of I-665.

Step 2: (S)-3-(pyrrolidin-2-ylmethoxy)propanoic acid. The procedure was the same as that in the synthesis of I-665.

Step 3: methyl (S)-3-(pyrrolidin-2-ylmethoxy)propanoate. The procedure was the same as that in the synthesis of I-665.

Step 4: methyl (S)-3-((1-(4,7,8-trichloroquinolin-2-yl)pyrrolidin-2-yl)methoxy)propanoate. The procedure was the same as that in the synthesis of I-665.

Step 5: methyl 3-(((S)-1-(7,8-dichloro-4-((R)-3-hydroxypyrrolidin-1-yl)quinolin-2-yl)pyrrolidin-2-yl)methoxy)propanoate. To a vial were added methyl (S)-3-((1-(4,7,8-trichloroquinolin-2-yl)pyrrolidin-2-yl)methoxy)propanoate (21 mg, 0.050 mmol), (R)-pyrrolidin-3-ol (22 mg, 0.25 mmol), $Na_2CO_3$ (5.3 mg, 0.050 mmol) and DMSO (0.5 ml). The reaction mixture was stirred at 60° C. over-night. After simple work-up, the crude was purified by silica gel chromatography to afford the title product (9.2 mg). (MS: $[M+1]^+$ 454)

Step 6: 3-(((S)-1-(7,8-dichloro-4-((R)-3-hydroxypyrrolidin-1-yl)quinolin-2-yl)pyrrolidin-2-yl)methoxy)propanoic acid. The procedure was the same as that in the synthesis of I-665. (MS: $[M+1]^+$ 454).

The following compounds are prepared essentially by the same methods as for I-821.

| I-# | Starting Material | Structure | MS $[M + 1]^+$ |
|---|---|---|---|
| I-919 | | 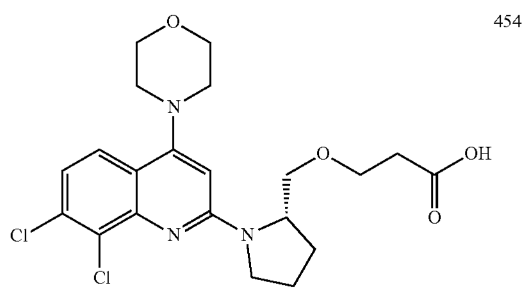 | 454 |
| I-920 | | 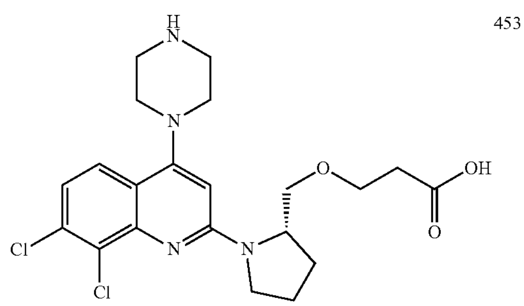 | 453 |
| I-921 | | 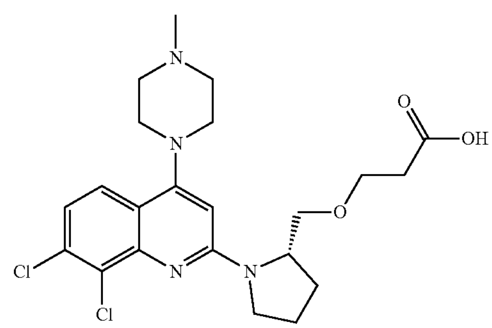 [SMILES: CN1CCN(c2cc(N3CCC[C@H]3COCCC(=O)O)nc3c(Cl)c(Cl)ccc23)CC1] | 467 |

The following additional compounds are prepared using the general nucleophilic substitution in the preparation of I-821.
| I-# | Starting Material | Structure | MS [M + 1]+ |
|---|---|---|---|
| I-892 | 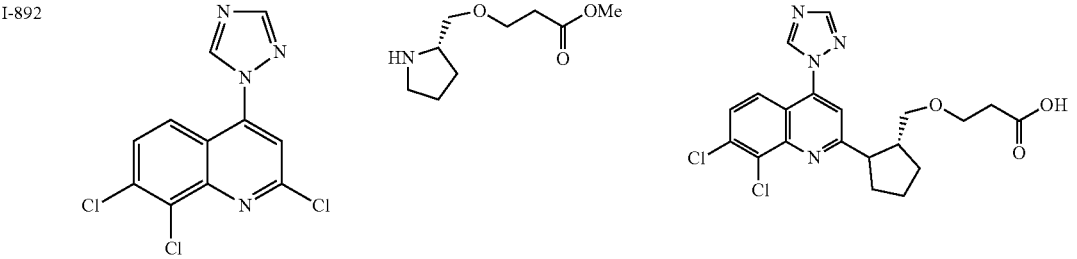 | 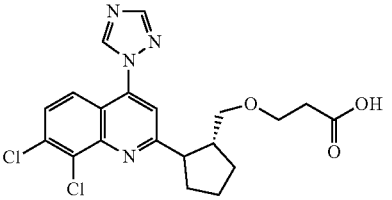 [SMILES: O=C(O)CCOC[C@@H]1CCCC1c1cc(-n2cncn2)c2ccc(Cl)c(Cl)c2n1] | 436 |
| I-893 | 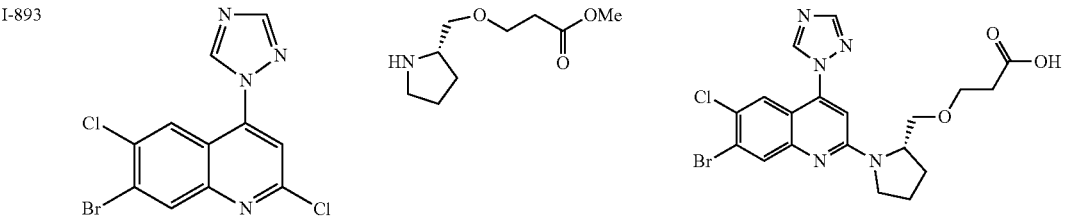 | 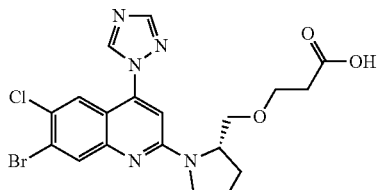 | 480 |
| I-894 | 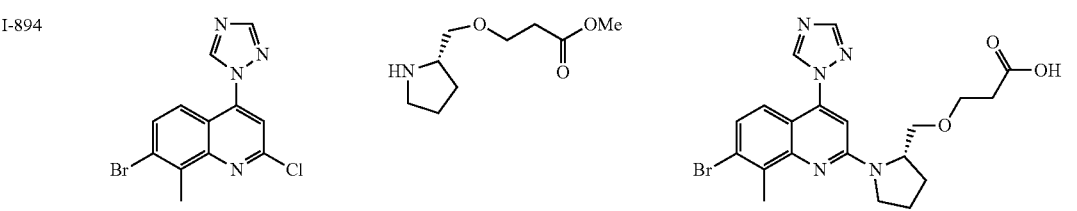 | 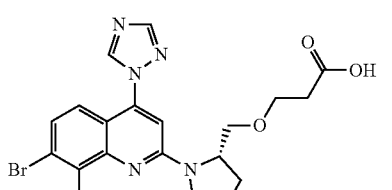 | 460 |
| I-895 | 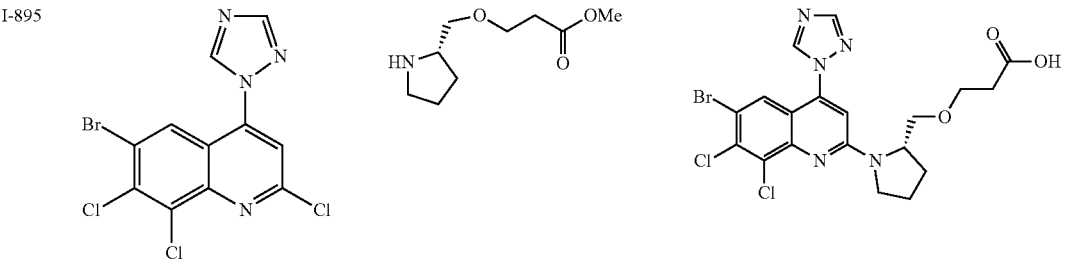 | 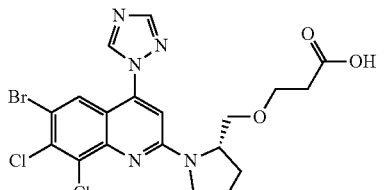 | 514 |
| I-896 | 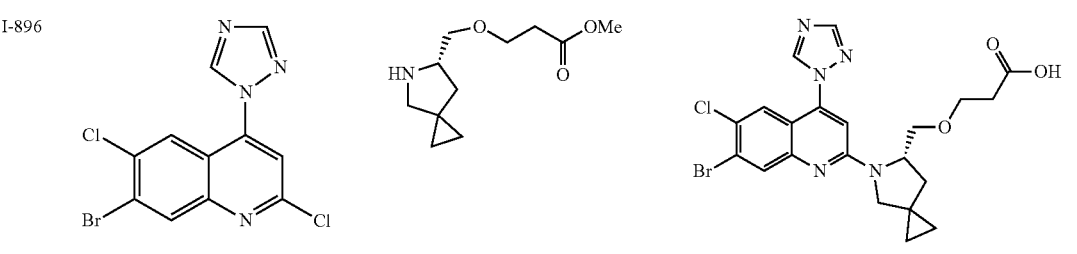 | 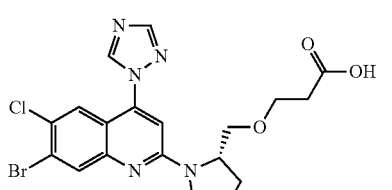 | 506 |
| I-897 | 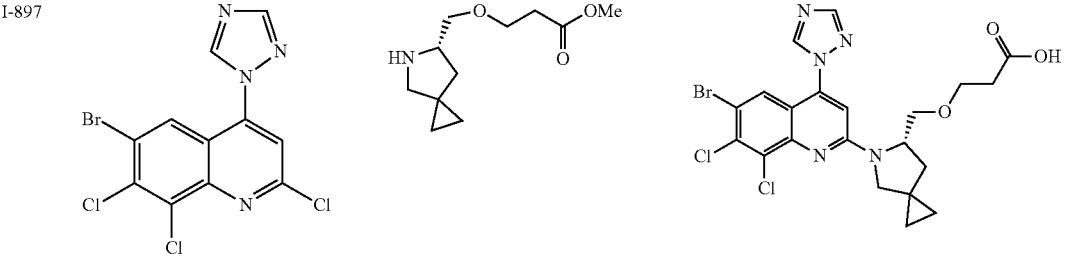 | 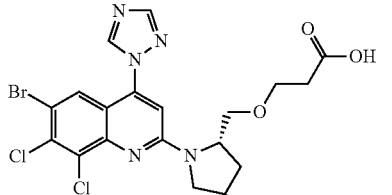 | 540 |

-continued

| I-# | Starting Material | Structure | MS [M + 1]+ |
|---|---|---|---|
| I-898 | | 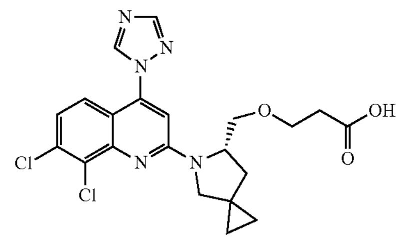 [SMILES: O=C(O)CCOC[C@@H]1CC2(CC2)CN1c1cc(-n2cncn2)c2ccc(Cl)c(Cl)c2n1] | 462 |
| I-924 | | 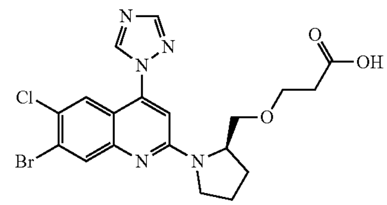 [SMILES: O=C(O)CCOC[C@H]1CCCN1c1cc(-n2cncn2)c2cc(Cl)c(Br)cc2n1] | 480 |
| I-925 | | 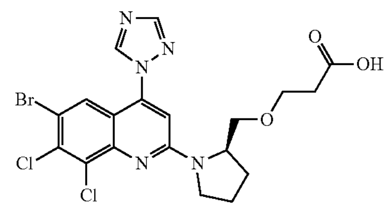 [SMILES: O=C(O)CCOC[C@H]1CCCN1c1cc(-n2cncn2)c2cc(Br)c(Cl)c(Cl)c2n1] | 514 |
| I-926 | | 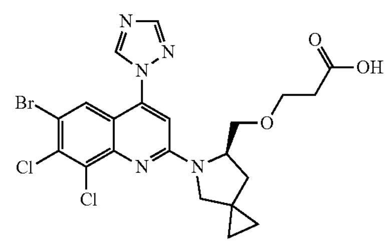 [SMILES: O=C(O)CCOC[C@H]1CC2(CC2)CN1c1cc(-n2cncn2)c2cc(Br)c(Cl)c(Cl)c2n1] | 540 |
| I-927 | | 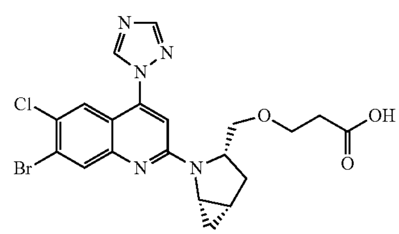 [SMILES: O=C(O)CCOC[C@@H]1C[C@@H]2C[C@@H]2N1c1cc(-n2cncn2)c2cc(Cl)c(Br)cc2n1] | 492 |
| I-928 | | 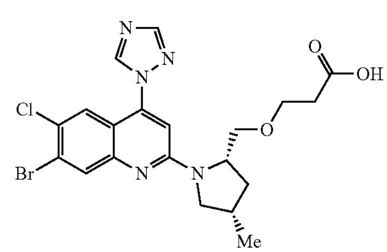 [SMILES: C[C@H]1C[C@@H](COCCC(=O)O)N(c2cc(-n3cncn3)c3cc(Cl)c(Br)cc3n2)C1] | 494 |

-continued

| I-# | Starting Material | | Structure | MS [M + 1]+ |
|---|---|---|---|---|
| I-929 | | | 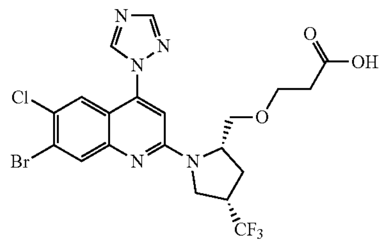 [SMILES: O=C(O)CCOC[C@@H]1C[C@H](C(F)(F)F)CN1c1cc(-n2cncn2)c2cc(Cl)c(Br)cc2n1] | 548 |
| I-930 | | | 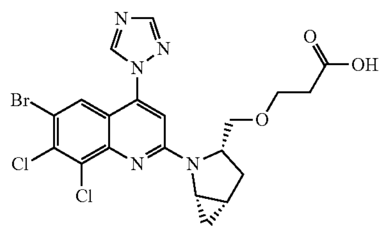 [SMILES: O=C(O)CCOC[C@@H]1C[C@@H]2C[C@@H]2N1c1cc(-n2cncn2)c2cc(Br)c(Cl)c(Cl)c2n1] | 526 |
| I-931 | | | 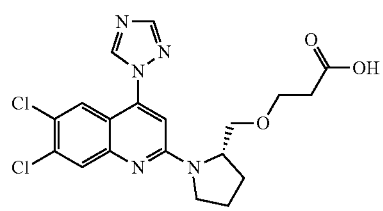 [SMILES: O=C(O)CCOC[C@@H]1CCCN1c1cc(-n2cncn2)c2cc(Cl)c(Cl)cc2n1] | 436 |
| I-932 | | | 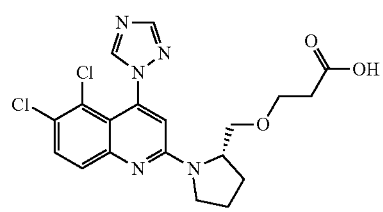 [SMILES: O=C(O)CCOC[C@@H]1CCCN1c1cc(-n2cncn2)c2c(Cl)c(Cl)ccc2n1] | 436 |
| I-933 | | | 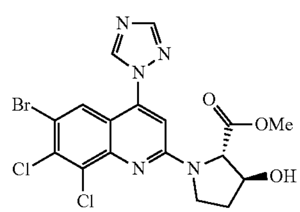 [SMILES: COC(=O)[C@@H]1[C@@H](O)CCN1c1cc(-n2cncn2)c2cc(Br)c(Cl)c(Cl)c2n1] | 486 |
| I-934 | | | 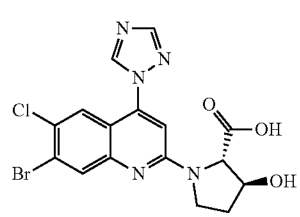 [SMILES: O=C(O)[C@@H]1[C@@H](O)CCN1c1cc(-n2cncn2)c2cc(Cl)c(Br)cc2n1] | 438 |

| I-# | Starting Material | Structure | MS [M + 1]+ |
|---|---|---|---|
| I-935 | | 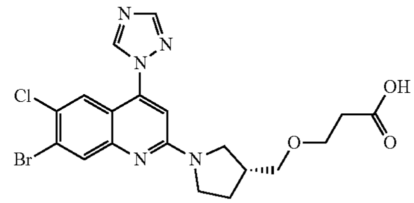 [SMILES: O=C(O)CCOC[C@@H]1CCN(c2cc(-n3cncn3)c3cc(Cl)c(Br)cc3n2)C1] | 480 |
| I-936 | | 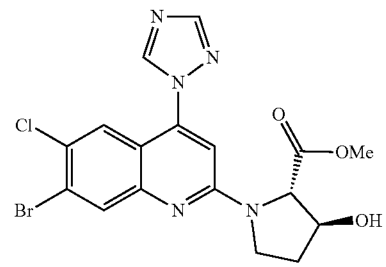 [SMILES: COC(=O)[C@@H]1[C@@H](O)CCN1c1cc(-n2cncn2)c2cc(Cl)c(Br)cc2n1] | 452 |
| I-937 | | 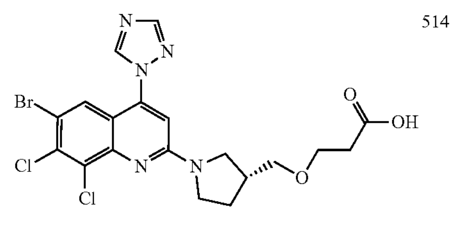 | 514 |
| I-938 | | 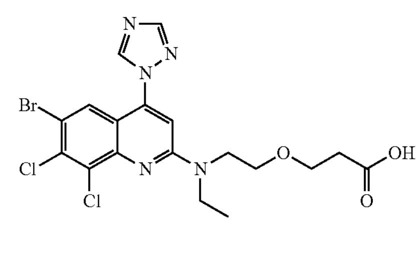 [SMILES: CCN(CCOCCC(=O)O)c1cc(-n2cncn2)c2cc(Br)c(Cl)c(Cl)c2n1] | 502 |
Example 7: Synthesis of (S)-3-((1-(4-(6-aminopyridin-3-yl)-7,8-dichloroquinolin-2-yl)pyrrolidin-2-yl)methoxy)propanoic acid (I-822)
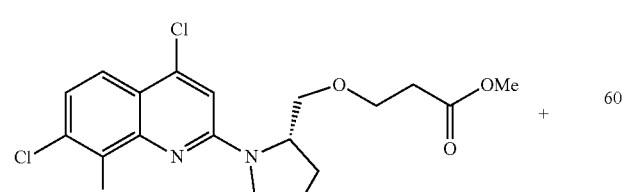
+
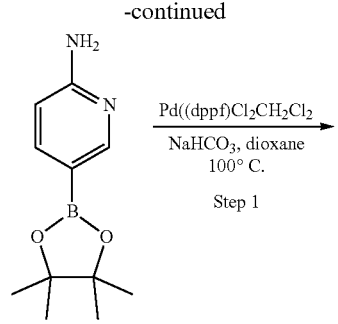
Step 1

-continued

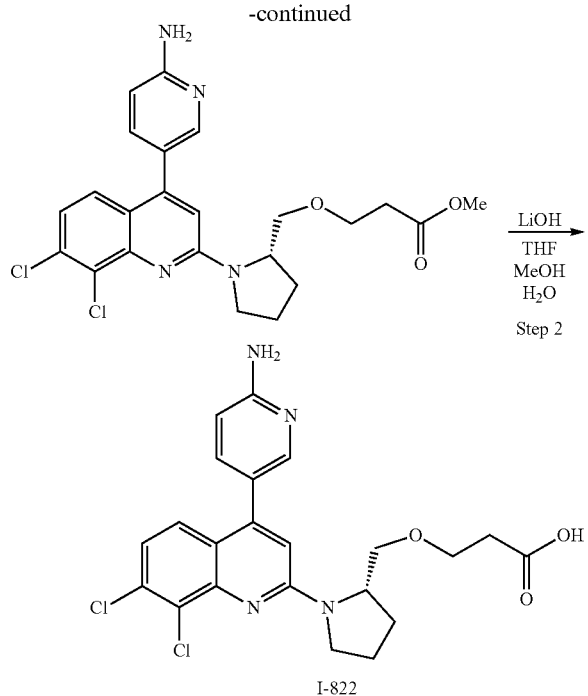

I-822

Step 1: methyl (S)-3-((1-(4-(6-aminopyridin-3-yl)-7,8-dichloroquinolin-2-yl)pyrrolidin-2-yl)methoxy)propanoate.

To a flask were added methyl (S)-3-((1-(4,7,8-trichloroquinolin-2-yl)pyrrolidin-2-yl)methoxy)propanoate (104 mg, 0.25 mmol), 1,4-dioxane (8.0 ml), 5-(4,4,5,5-tetramethyl-1,3,2-dioxaborolan-2-yl)pyridin-2-amine (110 mg, 0.50 mmol), NaHCO$_3$ (62 mg, 0.75 mmol), Pd(dppf)Cl$_2$—CH$_2$Cl$_2$ (41 mg, 0.050 mmol) and H$_2$O (1.0 ml). After degassed with N$_2$ for 4 times, the reaction mixture was stirred at 100° C. for 6 hours. The reaction mixture was diluted with ethyl acetate, washed with H$_2$O, brine and dried over Na$_2$SO$_4$. After concentration the crude was purified by silica gel column to afford the title product (90 mg).

Step 2: (S)-3-((1-(4-(6-aminopyridin-3-yl)-7,8-dichloroquinolin-2-yl)pyrrolidin-2-yl)methoxy)propanoic acid. The procedure was the same as that in the synthesis of I-636. The title compound was obtained as free acid. (MS: [M+1]$^+$ 461)

The following compounds are prepared essentially by the same methods as for I-822.

| Example | Starting Material | | Structure | MS [M + 1]$^+$ |
|---|---|---|---|---|
| I-823 | (structure) | (structure) | (structure) | 435 |
| I-824 | (structure) | (structure) | (structure) | 435 |
| I-902 | (structure) | (structure) | (structure) | 436 |

-continued
| Example | Starting Material | | Structure | MS [M + 1]+ |
|---|---|---|---|---|
| I-904 | 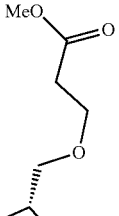 | 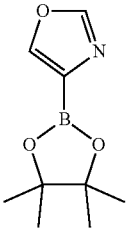 | 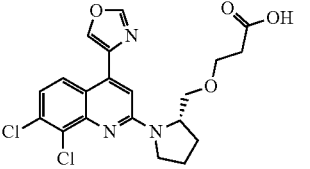 [SMILES: O=C(O)CCOC[C@@H]1CCCN1c1cc(-c2cocn2)c2ccc(Cl)c(Cl)c2n1] | 436 |
| I-905 | 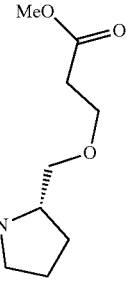 | 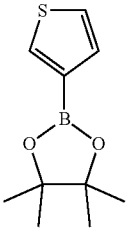 | 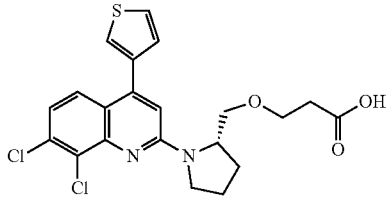 [SMILES: O=C(O)CCOC[C@@H]1CCCN1c1cc(-c2ccsc2)c2ccc(Cl)c(Cl)c2n1] | 451 |
| I-906 | 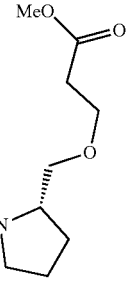 | 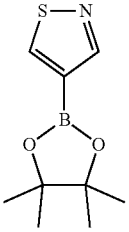 | 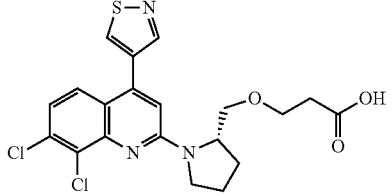 [SMILES: O=C(O)CCOC[C@@H]1CCCN1c1cc(-c2cnsc2)c2ccc(Cl)c(Cl)c2n1] | 452 |
| I-907 | 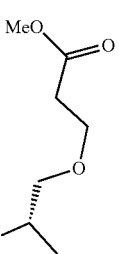 | 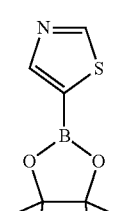 | 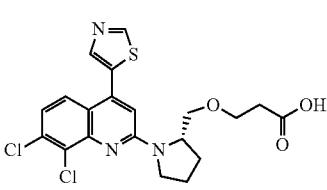 [SMILES: O=C(O)CCOC[C@@H]1CCCN1c1cc(-c2cncs2)c2ccc(Cl)c(Cl)c2n1] | 452 |
| I-908 | 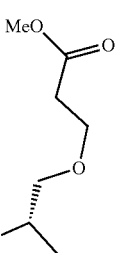 | 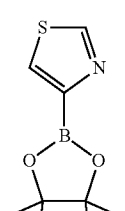 | 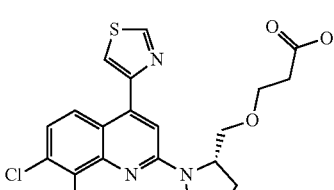 | 452 |

-continued
| Example | Starting Material | | Structure | MS [M + 1]+ |
|---|---|---|---|---|
| I-909 | 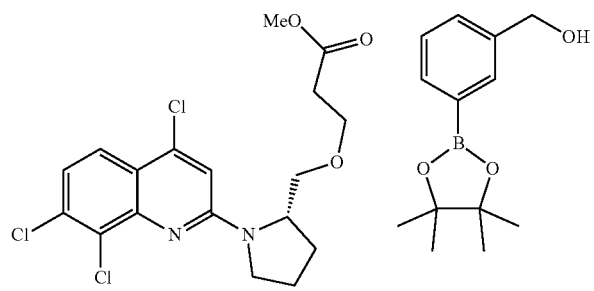 | 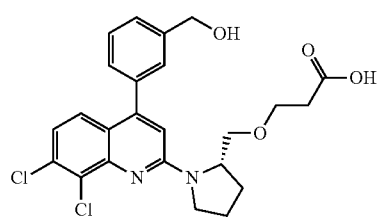 [SMILES: O=C(O)CCOC[C@@H]1CCCN1c1cc(-c2cccc(CO)c2)c2ccc(Cl)c(Cl)c2n1] | 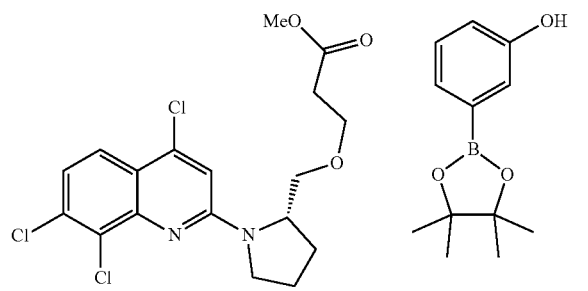 | 475 |
| I-910 | 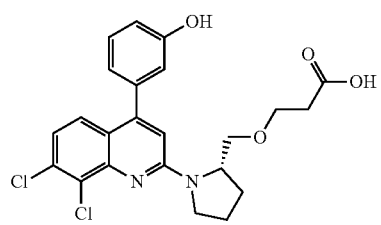 [SMILES: O=C(O)CCOC[C@@H]1CCCN1c1cc(-c2cccc(O)c2)c2ccc(Cl)c(Cl)c2n1] | 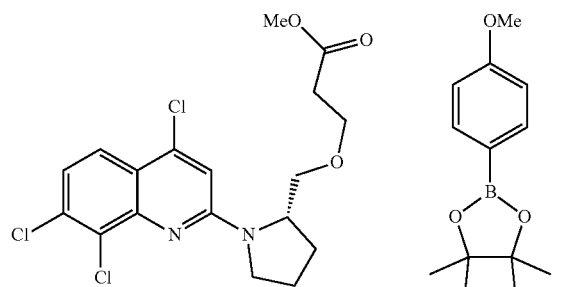 | 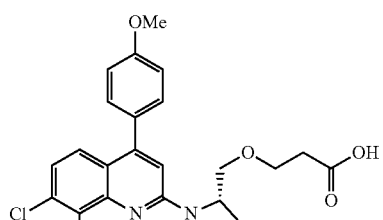 | 461 |
| I-911 | 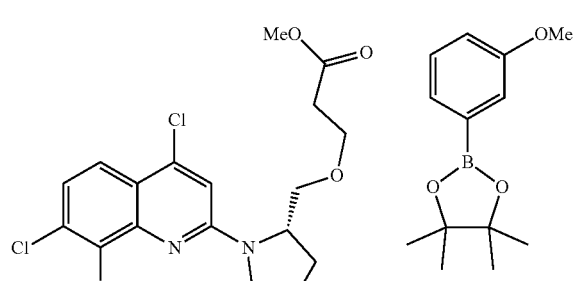 | 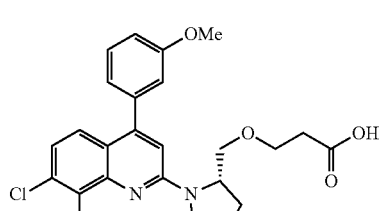 | 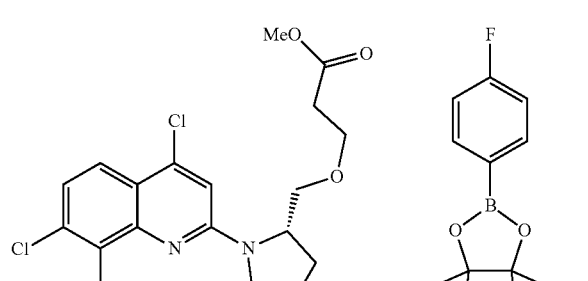 | 475 |
| I-912 | | | 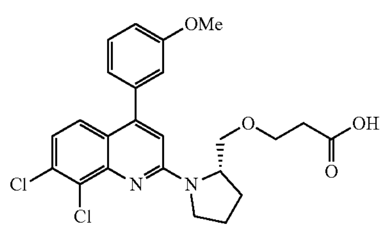 [SMILES: COc1cccc(-c2cc(N3CCC[C@H]3COCCC(=O)O)nc3c(Cl)c(Cl)ccc23)c1] | 475 |
| I-913 | | | 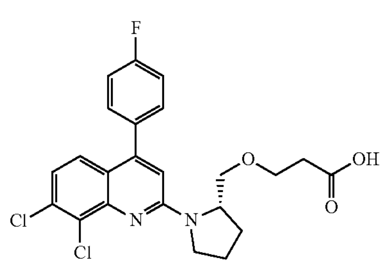 [SMILES: O=C(O)CCOC[C@@H]1CCCN1c1cc(-c2ccc(F)cc2)c2ccc(Cl)c(Cl)c2n1] | 463 |

-continued
| Example | Starting Material | | Structure | MS [M + 1]+ |
|---|---|---|---|---|
| I-914 | 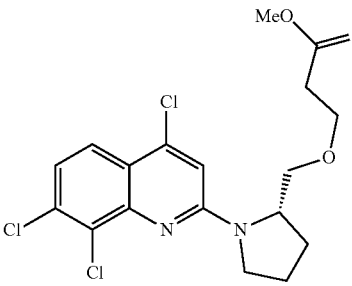 | 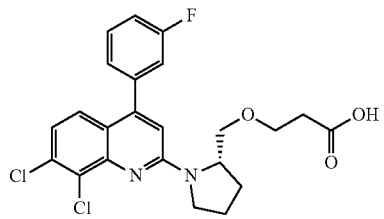 [SMILES: O=C(O)CCOC[C@@H]1CCCN1c1cc(-c2cccc(F)c2)c2ccc(Cl)c(Cl)c2n1] | 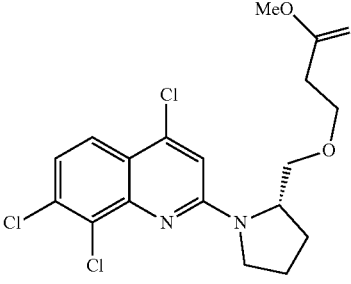 | 463 |
| I-915 | 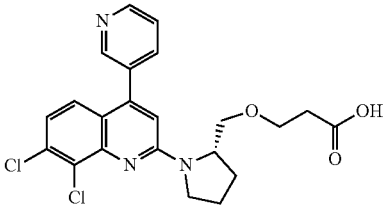 [SMILES: O=C(O)CCOC[C@@H]1CCCN1c1cc(-c2cccnc2)c2ccc(Cl)c(Cl)c2n1] | | 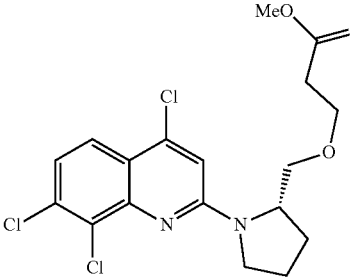 | 446 |
| I-916 | 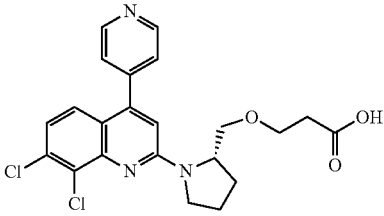 [SMILES: O=C(O)CCOC[C@@H]1CCCN1c1cc(-c2ccncc2)c2ccc(Cl)c(Cl)c2n1] | | 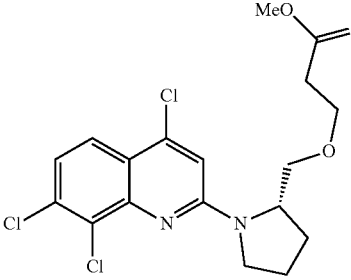 | 446 |
| I-917 | 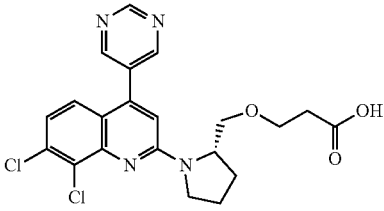 [SMILES: O=C(O)CCOC[C@@H]1CCCN1c1cc(-c2cncnc2)c2ccc(Cl)c(Cl)c2n1] | | 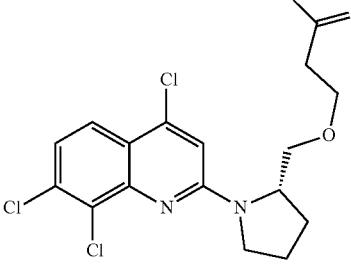 | 447 |
| I-918 | | | 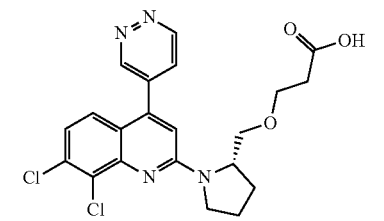 [SMILES: O=C(O)CCOC[C@@H]1CCCN1c1cc(-c2ccnnc2)c2ccc(Cl)c(Cl)c2n1] | 447 |

Example 8: Synthesis of (S)-3-((1-(7-bromo-4-(oxazol-5-yl)quinolin-2-yl)pyrrolidin-2-yl)methoxy)propanoic acid (I-903)

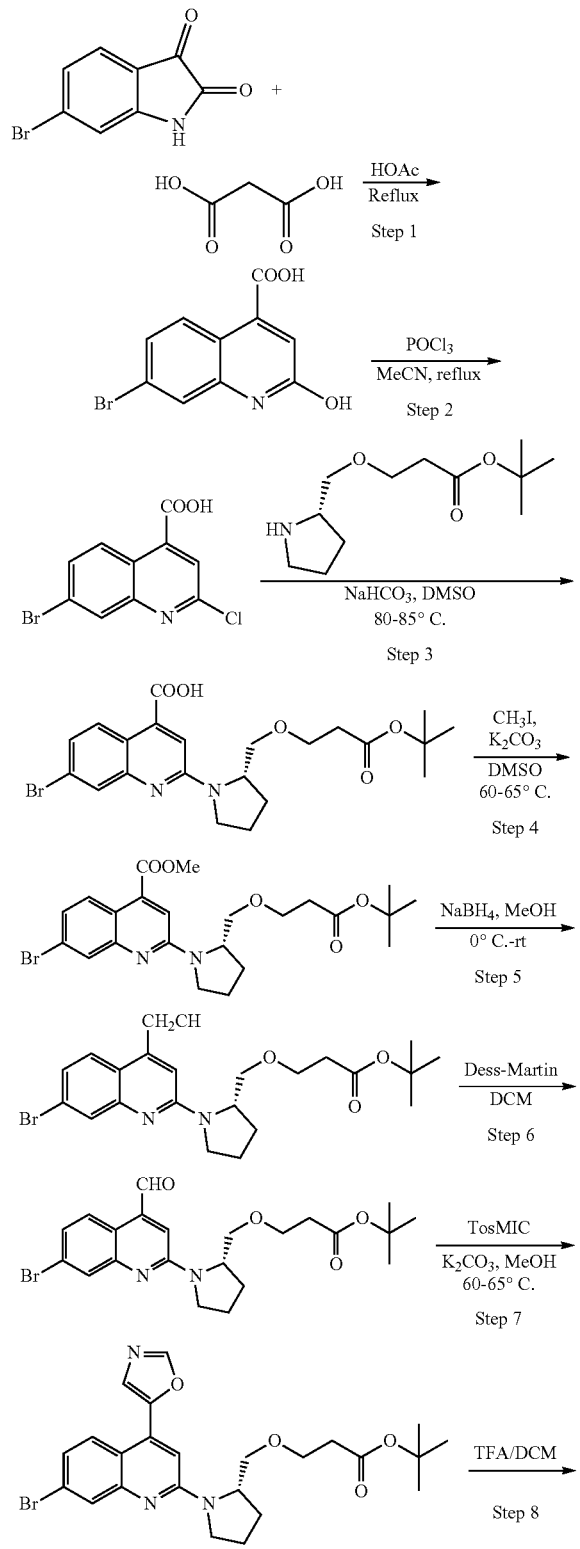

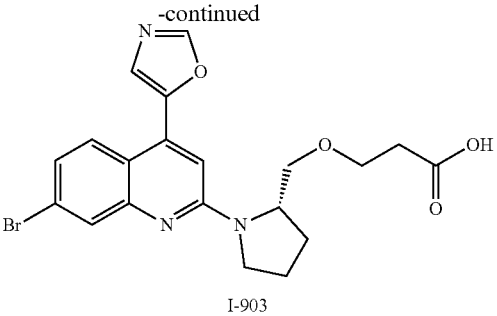

I-903

Step 1: 7-bromo-2-hydroxyquinoline-4-carboxylic acid. To a flask (250 ml) was added 6-bromoindoline-2,3-dione (4.52 g, 20.0 mmol, 1.0 eq.), malonic acid (5.20 g, 50.0 mmol, 2.5 eq.) and acetic acid (60 ml). The reaction mixture was stirred at 120° C. for 26 hours. A lot of dark purple solid precipitated. Most of the acetic acid was removed under reduced pressure. The residue was diluted by ethyl acetate (50 ml), followed by filtration, washing with ethyl acetate (3×15 ml) and drying under high vacuum to afford the title product (5.18 g) as dark purple solid with 96% yield. (MS: [M+1]$^+$ 268)

Step 2: 7-bromo-2-chloroquinoline-4-carboxylic acid. To a flask (50 ml) was added 7-bromo-2-hydroxyquinoline-4-carboxylic acid (1.07 g, 4.0 mmol, 1.0 eq.), anhydrous acetonitrile (10 ml), and phosphoryl trichloride (2.24 ml, 24 mmol, 6.0 eq.). The reaction mixture was stirred at 90° C. for 7 hours. Most of the volatiles were removed under reduced pressure. The residue was diluted by DI water (50 ml), followed by being neutralized with NaHCO$_3$ to pH 3, filtration, washing with DI water (5×10 ml) and drying under high vacuum to afford the title product (992 mg) as solid with 86% yield. (MS: [M+1]+286).

Step 3: (S)-7-bromo-2-(2-((3-(tert-butoxy)-3-oxopropoxy)methyl)pyrrolidin-1-yl)quinoline-4-carboxylic acid. To a vial was added 7-bromo-2-chloroquinoline-4-carboxylic acid (287 mg, 1.0 mmol, 1.0 eq.), anhydrous DMSO (3.0 ml), tert-butyl (S)-3-(pyrrolidin-2-ylmethoxy) propanoate TFA salt (652 mg, 2.0 mmol, 2.0 eq.), NaHCO$_3$ (504 mg, 6.0 mmol, 6.0 eq.). The reaction mixture was stirred at 80° C. to 85° C. for 19 hrs. After cooling to room temperature, the reaction mixture was diluted by ethyl acetate (80 ml), acidified by HOAc/H$_2$O (1 M, 5 ml). The organic phase was washed by H$_2$O (3×15 ml), brine (10 ml) and dried over Na$_2$SO$_4$. After concentration, the crude was used in the next step without any purification. (MS: [M+1]$^+$ 479).

Step 4: methyl (S)-7-bromo-2-(2-((3-(tert-butoxy)-3-oxopropoxy)methyl)pyrrolidin-1-yl)quinoline-4-carboxylate.
To a vial containing (S)-7-bromo-2-(2-((3-(tert-butoxy)-3-oxopropoxy)methyl)pyrrolidin-1-yl)quinoline-4-carboxylic acid (0.8 mmol, 1.0 eq., crude product from step 3) was added anhydrous DMSO (2.0 ml), K$_2$CO$_3$ (288 mg, 2.1 mmol, 2.6 eq) and iodomethane (750 l, 12.0 mmol, 15.0 eq.). The reaction mixture was stirred at 60° C. to 65° C. for 24 hrs. After cooling to room temperature, the reaction mixture was diluted by ethyl acetate (80 ml), washed by H$_2$O (3×15 ml), brine (10 ml) and dried over Na$_2$SO$_4$. After concentration, the crude product was purified by silica gel chromatography, eluted with ethyl acetate in hexanes (5% to 15%) to afford the title product (141 mg) as a solid with 36% yield. (MS: [M+1]$^+$ 493).

Step 5: tert-butyl (S)-3-((1-(7-bromo-4-(hydroxymethyl)quinolin-2-yl)pyrrolidin-2-yl)methoxy)propanoate. To a vial was added methyl (S)-7-bromo-2-(2-((3-(tert-butoxy)-3-oxopropoxy)methyl)pyrrolidin-1-yl)quinoline-4-carboxylate (70 mg, 0.142 mmol, 1.0 eq.), MeOH (2.0 ml). After the solution was cooled in ice bath, NaBH₄ (216 mg, 5.7 mmol, 40 eq.) was added. The reaction mixture was stirred at room temperature overnight, diluted with ethyl acetate (40 ml), washed with H₂O (2×15 ml), brine (15 ml), and dried over Na₂SO₄. After concentration, the crude product was used in the next step without any purification. (MS: [M+1]⁺ 465).

Step 6: tert-butyl (S)-3-((1-(7-bromo-4-formylquinolin-2-yl)pyrrolidin-2-yl)methoxy)propanoate. To a vial was added tert-butyl (S)-3-((1-(7-bromo-4-(hydroxymethyl)quinolin-2-yl)pyrrolidin-2-yl)methoxy)propanoate (0.142 mmol, 1.0 eq., crude product from step 5), DCM (1.0 ml). When the solution was cooled in ice bath, Dess-Martin reagent (72 mg, 0.170 mmol, 1.2 eq.) was added. The reaction mixture was stirred at room temperature for 30 min and diluted with ethyl acetate/hexanes (20 ml/20 ml). After filtration, the filtrate was washed with aqueous NaHCO₃ (5%, 10 ml), brine (10 ml), and dried over Na₂SO₄. After concentration, the crude product was used in the next step without any purification. (MS: [M+1]⁺ 463).

Step 7: tert-butyl (S)-3-((1-(7-bromo-4-(oxazol-5-yl)quinolin-2-yl)pyrrolidin-2-yl)methoxy)propanoate. To a vial was added TosMIC (16.7, 0.086 mmol, 1.2 eq.), K₂CO₃ (19.6 mg, 0.142 mmol, 2.0 eq), tert-butyl (S)-3-((1-(7-bromo-4-formylquinolin-2-yl)pyrrolidin-2-yl)methoxy)propanoate (0.071 mmol, 1.0 eq., crude product from step 6) and MeOH (0.5 ml). The reaction mixture was stirred at a temperature between 60° C. to 65° C. for 4 hours, diluted with ethyl acetate (40 ml), washed with H₂O (2×15 ml), brine (15 ml), and dried over Na₂SO₄. After concentration, the crude product was purified by silica gel chromatography, eluted with ethyl acetate in hexanes (20% to 40%) to afford the title product (10 mg) as solid with 28% yield. (MS: [M+1]⁺ 502).

Step 8: (S)-3-((1-(7-bromo-4-(oxazol-5-yl)quinolin-2-yl)pyrrolidin-2-yl)methoxy)propanoic acid (I-903). To a vial containing tert-butyl (S)-3-((1-(7-bromo-4-(oxazol-5-yl)quinolin-2-yl)pyrrolidin-2-yl)methoxy)propanoate (10 mg, 0.020 mmol) was added DCM (0.5 ml) and TFA (0.5 ml). The reaction mixture was stirred at room temperature for 2 hrs. After concentrations via co-evaporation with MeCN/toluene (2/1, 2 ml×2), the residue was mixed with DI H₂O (1 ml) and lyophilized to afford the title product (9.0 mg) as a solid with 100% yield. (MS: [M+1]⁺ 446).

Example 9: Synthesis of (S)-3-((1-(7,8-dichloro-4-(1H-1,2,3-triazol-4-yl)quinolin-2-yl)pyrrolidin-2-yl)methoxy)propanoic acid (I-899)

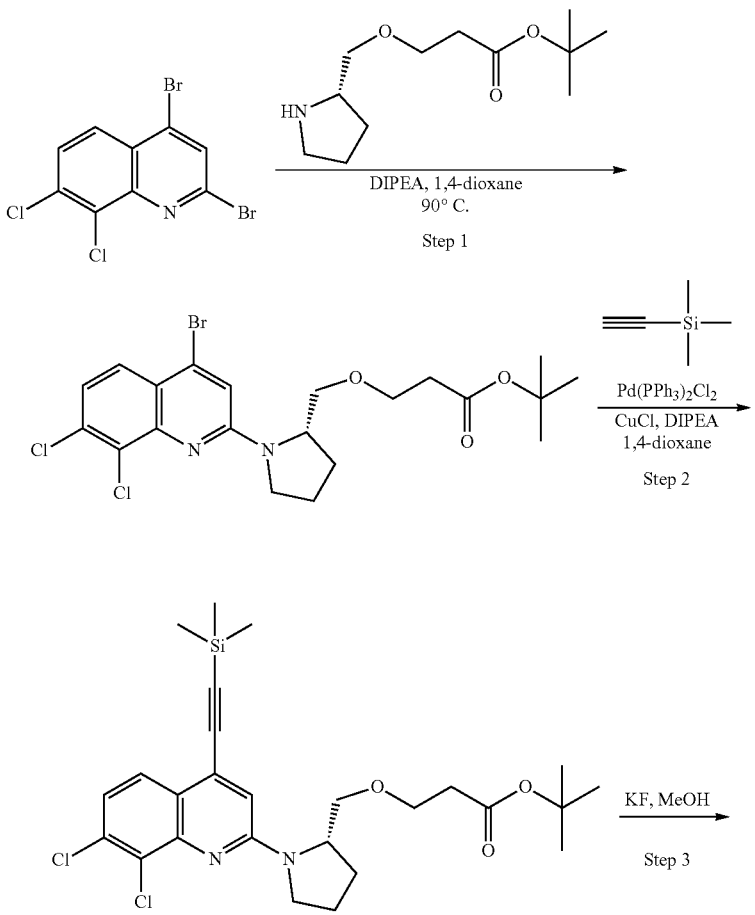

-continued

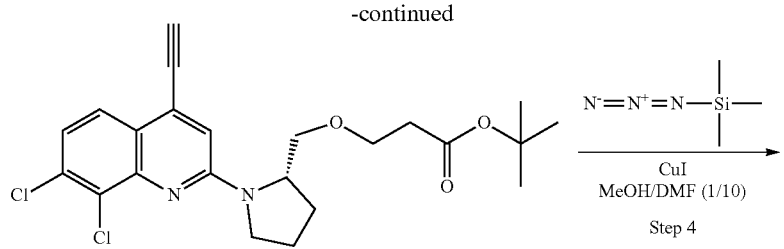

Step 4

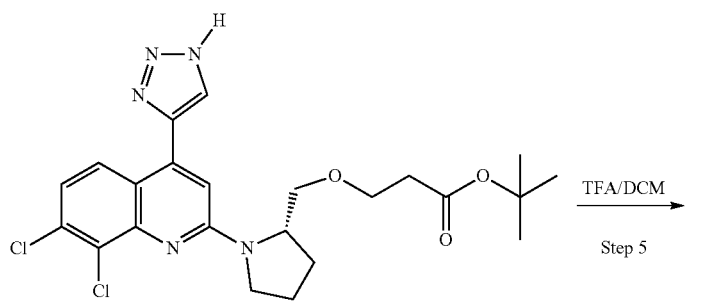

TFA/DCM

Step 5

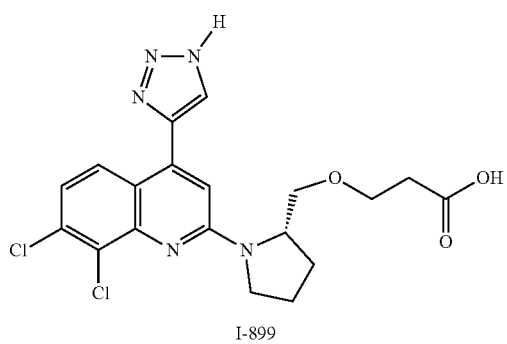 [SMILES: O=C(O)CCOC[C@@H]1CCCN1c1cc(-c2c[nH]nn2)c2ccc(Cl)c(Cl)c2n1]

I-899

Step 1: tert-butyl (S)-3-((1-(4-bromo-7,8-dichloroquinolin-2-yl)pyrrolidin-2-yl)methoxy)propanoate. To a flask (100 ml) was added 2,4-dibromo-7,8-dichloroquinoline (5.95 g, 16.7 mmol, 1.0 eq.), tert-butyl (S)-3-(pyrrolidin-2-ylmethoxy)propanoate TFA salt (5.45 g, 16.7 mmol, 1.0 eq.), DIPEA (8.7 ml, 50.1 mmol, 3.0 eq.) and 1,4-dioxane (30 ml). The reaction mixture was stirred at 90° C. for 5 hrs. After concentration, the crude product was purified by silica gel chromatography, eluted with ethyl acetate in hexanes (0% to 10%) to afford the title product (4.21 g) as an oil with 50% yield. (MS: [M+1]$^+$ 503).

Step 2: tert-butyl (S)-3-((1-(7,8-dichloro-4-((trimethylsilyl)ethynyl)quinolin-2-yl)pyrrolidin-2-yl)methoxy)propanoate. To a vial was added tert-butyl (S)-3-((1-(4-bromo-7,8-dichloroquinolin-2-yl)pyrrolidin-2-yl)methoxy)propanoate (252 mg, 0.50 mmol, 1.0 eq.), CuI (9.5 mg, 0.05 mmol, 0.1 eq.), Pd(PPh$_3$)$_2$Cl$_2$ (35 mg, 0.05 mmol, 0.1 eq.), 1,4-dioxane (5.0 ml). The reaction mixture was degassed four times under N$_2$. DIPEA (131 μl, 0.75 mmol, 1.5 eq.) and ethynyltrimethylsilane (76 μl, 0.55 mmol, 1.1 eq.) were added via syringe under N$_2$. The reaction mixture was stirred at room temperature for 3 hrs. After concentration, the residue was diluted with ethyl acetate (40 ml), washed with H$_2$O (2×15 ml), brine (15 ml), and dried over Na$_2$SO$_4$. After concentration, the crude product was purified by silica gel chromatography, eluted with ethyl acetate in hexanes (0% to 5%) to afford the title product (250 mg) as a solid with 95% yield. (MS: [M+1]$^+$ 521).

Step 3: tert-butyl (S)-3-((1-(7,8-dichloro-4-ethynylquinolin-2-yl)pyrrolidin-2-yl)methoxy)propanoate. To a vial was added tert-butyl (S)-3-((1-(7,8-dichloro-4-((trimethylsilyl)ethynyl)quinolin-2-yl)pyrrolidin-2-yl)methoxy)propanoate (129 mg, 0.25 mmol, 1.0 eq.), MeOH (2.0 ml) and KF (29 mg, 0.50 mmol, 2.0 eq.). The reaction mixture was stirred at room temperature for 1 hour and was diluted with ethyl acetate (40 ml), washed with H$_2$O (2×15 ml), brine (15 ml), and dried over Na$_2$SO$_4$. After concentration, the crude was used in the next step without any purification. (MS: [M+1]$^+$ 449).

Step 4: tert-butyl (S)-3-((1-(7,8-dichloro-4-(1H-1,2,3-triazol-4-yl)quinolin-2-yl)pyrrolidin-2-yl)methoxy)propanoate. To a vial was added tert-butyl (S)-3-((1-(7,8-dichloro-4-ethynylquinolin-2-yl)pyrrolidin-2-yl)methoxy)propanoate (33 mg, 0.0734 mmol, 1.0 eq., crude product from step 3), DMF (0.5 ml), MeOH (0.05 ml), azidotrimethylsilane (13 mg, 0.11 mmol, 1.5 eq.), CuI (0.7 mg, 0.00367 mmol, 0.05 eq.). After bubbling with N$_2$ for 10 min, the reaction mixture was stirred at 100° C. for 2 hours and was diluted with ethyl acetate (20 ml), washed by H$_2$O (2×5 ml), brine (5 ml), and dried over Na$_2$SO$_4$. After concentration, the crude product was purified by silica gel chromatography, eluted with ethyl acetate in hexanes (20% to 40%) to afford the title product (20 mg) as a solid with 55% yield. (MS: [M+1]$^+$ 492).

Step 5: (S)-3-((1-(7,8-dichloro-4-(1H-1,2,3-triazol-4-yl)quinolin-2-yl)pyrrolidin-2-yl)methoxy)propanoic acid (I-899). To a vial containing tert-butyl (S)-3-((1-(7,8-dichloro-4-(1H-1,2,3-triazol-4-yl)quinolin-2-yl)pyrrolidin-2-yl)methoxy)propanoate (20 mg, 0.0406 mmol) was added DCM (0.3 ml) and TFA (0.15 ml). The reaction mixture was stirred at room temperature for 2 hrs. After concentrations via co-evaporation with MeCN/toluene (2/1, 2 ml×2), the residue was carefully neutralized to pH 4 to 5 with sat. NaHCO₃ solution, the resulted solid was collected via centrifuge, rinsed with DI water and lyophilized to afford the title product (18 mg) as a solid with 100% yield. (MS: [M+1]⁺ 436).

The following compounds are prepared following the similar preparation method of I-822 and I-899 and its final TFA salts were simply collected by lyophilization without neutralization.

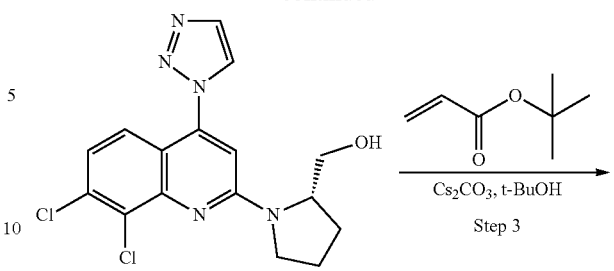

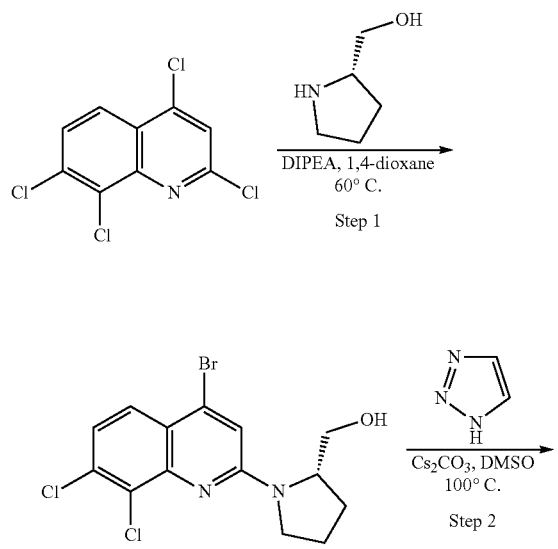

| Example | Starting Material | Structure | MS [M + 1]⁺ |
|---|---|---|---|
| I-922 | (structure) | (structure) | 436 |
| I-923 | (structure) | (structure) | 436 |

Example 10: Synthesis of (S)-3-((1-(7,8-dichloro-4-(1H-1,2,3-triazol-1-yl)quinolin-2-yl)pyrrolidin-2-yl)methoxy)propanoic acid (I-900)

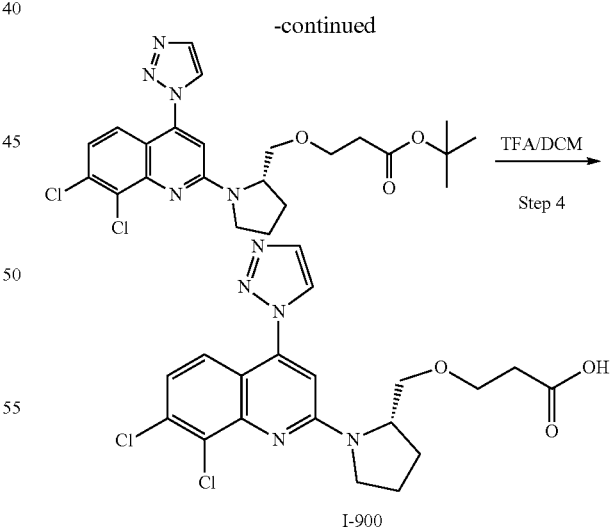

Step 1: (S)-(1-(4,7,8-trichloroquinolin-2-yl)pyrrolidin-2-yl)methanol. See step 1 in the preparation of I-899. (MS: [M+1]⁺ 331).

Step 2: (S)-(1-(7,8-dichloro-4-(1H-1,2,3-triazol-1-yl)quinolin-2-yl)pyrrolidin-2-yl)methanol. To a vial was added (S)-(1-(4,7,8-trichloroquinolin-2-yl)pyrrolidin-2-yl)methanol (33 mg, 0.10 mmol, 1.0 eq.), DMSO (0.5 ml), Cs$_2$CO$_3$ (49 mg, 0.15 mmol, 1.5 eq.) and 1H-1,2,3-triazole (35 mg, 0.5 mmol, 5.0 eq.). The reaction mixture was stirred at 100° C. overnight and was diluted with ethyl acetate (20 ml), washed with H$_2$O (2×5 ml), brine (5 ml), and dried over Na$_2$SO$_4$. After concentration, the crude product was purified by silica gel chromatography, eluted with a mixture solution (5% MeOH in DCM-ethyl acetate 1:1) in hexanes (0% to 75%) to afford the title product (15 mg) as a solid with 41% yield. (MS: [M+1]+364).

Step 3: tert-butyl (S)-3-((1-(7,8-dichloro-4-(1H-1,2,3-triazol-1-yl)quinolin-2-yl)pyrrolidin-2-yl)methoxy)propanoate. The procedure was the same as that in step 1 in the synthesis of I-821, the Michael addition reaction afforded the title compound. (MS: [M+1]$^+$ 492).

Step 4: (S)-3-((1-(7,8-dichloro-4-(1H-1,2,3-triazol-1-yl)quinolin-2-yl)pyrrolidin-2-yl)methoxy)propanoic acid. See step 8 in the preparation of I-903. (MS: [M+1]$^+$ 436).

Example 11: Synthesis of (S)-3-((1-(7-bromo-4-(4H-1,2,4-triazol-3-yl)quinolin-2-yl)pyrrolidin-2-yl)methoxy)propanoic acid (I-901)

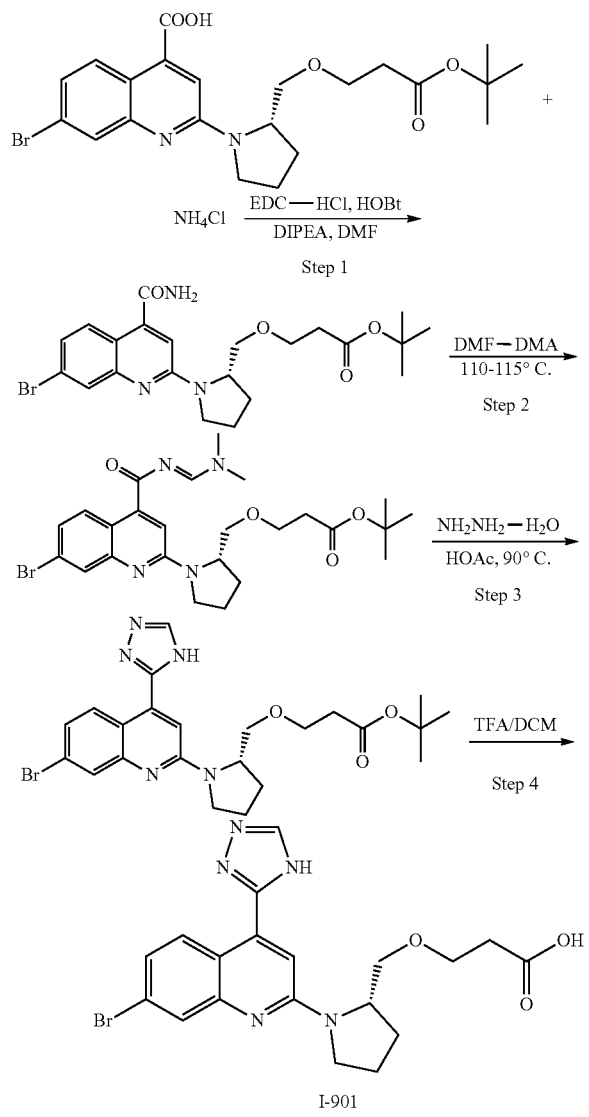

I-901

Step 1: tert-butyl (S)-3-((1-(7-bromo-4-carbamoylquinolin-2-yl)pyrrolidin-2-yl)methoxy)propanoate. To a vial was added (S)-7-bromo-2-(2-((3-(tert-butoxy)-3-oxopropoxy)methyl)pyrrolidin-1-yl)quinoline-4-carboxylic acid (96 mg, 0.20 mmol, 1.0 eq.), NH$_4$Cl (54 mg, 1.0 mmol, 5.0 eq.), EDC-HCl (58 mg, 0.30 mmol, 1.5 eq.), HOBt (41 mg, 0.30 mmol, 1.5 eq.), DMF (2.0 ml). With stirring, DIPEA (174 µl, 1.0 mmol, 5.0 eq.) was added. The reaction mixture was stirred at room temperature for 3 hrs and was diluted with ethyl acetate (20 ml), washed with H$_2$O (2×5 ml), brine (5 ml), and dried over Na$_2$SO$_4$. After concentration, the crude product was used in next step without any purification. (MS: [M+1]$^+$ 478).

Step 2: tert-butyl (S,E)-3-((1-(7-bromo-4-(((dimethylamino)methylene)carbamoyl)quinolin-2-yl)pyrrolidin-2-yl)methoxy)propanoate. To a vial containing tert-butyl (S)-3-((1-(7-bromo-4-carbamoylquinolin-2-yl)pyrrolidin-2-yl)methoxy)propanoate (0.10 mmol, 1.0 eq., crude product from step 1) was added N,N-Dimethylformamide dimethyl acetal (1.0 ml, 7.5 mmol, 75 eq.). The reaction mixture was stirred at 110° C. to 115° C. for 3 hours followed by concentration under reduced pressure. The crude was used in next step without any purification. (MS: [M+1]$^+$ 533).

Step 3: tert-butyl (S)-3-((1-(7-bromo-4-(4H-1,2,4-triazol-3-yl)quinolin-2-yl)pyrrolidin-2-yl)methoxy)propanoate. To a vial containing tert-butyl (S,E)-3-((1-(7-bromo-4-(((dimethylamino)methylene)carbamoyl)quinolin-2-yl)pyrrolidin-2-yl)methoxy)propanoate (0.1 mmol, 1.0 eq., crude product from step 2) was added hydrazine monohydrate (6.0 mg, 0.12 mmol, 1.2 eq.) and acetic acid (1.0 ml). The reaction mixture was stirred at 90° C. to 95° C. for 1 hour and was diluted with ethyl acetate (40 ml), washed with H$_2$O (2×15 ml), brine (15 ml), and dried over Na$_2$SO$_4$. After concentration, the crude was purified by silica gel chromatography, eluted with ethyl acetate in hexanes (30% to 60%) to afford the title product (20 mg) as a solid with 40% yield over 3 step reactions. (MS: [M+1]$^+$ 502).

Step 4: (S)-3-((1-(7-bromo-4-(4H-1,2,4-triazol-3-yl)quinolin-2-yl)pyrrolidin-2-yl)methoxy)propanoic acid (I-901). See step 8 in the preparation of I-903. (MS: [M+1]$^+$ 446).

Example 12: Biology

Expression and Purification of Recombinant cGAS Protein: cDNA encoding full-length or amino acids 147-520 of human cGAS was inserted into a modified pET28a vector containing an in-frame His6-SUMO tag. The *E. coli* strain BL21/pLys harboring the plasmid was induced with 0.5 mM IPTG at 18° C. overnight. His6-SUMO tag was removed by a SUMO protease digestion following purification of the His6-SUMO-cGAS as described previously (Sun et al, 2013, *Science* 339, 786).

In vitro inhibition assay of cGAS activity: A 60 µL mixture containing 20 mM Tris-Cl, pH 7.5, 5 mM MgCl$_2$, 0.2 mg/mL BSA, 0.01 mg/mL Herring testis DNA, 6.6 µM ATP, 0.1 mM GTP, 1.5 µg/mL of recombinant human cGAS (aa147-522) and serial dilutions of a test compound in DMSO is added to a 96-well plate and incubated at 37° C. for 20 minutes. At the end of reaction, 40 µL of KinaseGlo Max (Promega) is added and chemiluminescence was measured with a luminometer. Inhibitory effect of a compound is evaluated by plotting percentage of ATP consumption against logarithm of compound concentrations. IC$_{50}$ value is calculated using GraphPad Prism 8 (GraphPad Software, Inc.).

The results of the cGAS inhibition assay for compounds of the disclosure are presented in Table 3. The letter codes for cGAS IC$_{50}$ include: A (<2 μM); B (2-30 μM); C (>30 μM).

TABLE 3 cGAS Inhibition Results

| I-# | IC$_{50}$ | I-# | IC$_{50}$ | I-# | IC$_{50}$ |
|---|---|---|---|---|---|
| I-892 | A | I-893 | A | I-894 | A |
| I-895 | A | I-896 | A | I-897 | A |
| I-898 | A | I-899 | A | I-900 | A |
| I-901 | B | I-902 | A | I-903 | A |
| I-904 | C | I-905 | C | I-906 | A |
| I-907 | A | I-908 | C | I-909 | C |
| I-910 | C | I-911 | C | I-912 | C |
| I-913 | C | I-914 | B | I-915 | C |
| I-916 | C | I-917 | A | I-918 | C |
| I-919 | C | I-920 | C | I-921 | C |
| I-922 | C | I-923 | B | I-924 | B |
| I-925 | A | I-926 | A | I-927 | A |
| I-928 | A | I-929 | A | I-930 | A |
| I-931 | A | I-932 | A | I-933 | A |
| I-934 | A | I-935 | A | I-936 | A |
| I-937 | A | I-938 | A | | |

Cellular assay to measure cGAS activity: Reporter THP1 cell line harboring a gene encoding Gaussia Luciferase under the control of 5 tandem repeats of interferon-stimulated response elements (ISRE) fused to an ISG54 minimal promoter was used to test inhibition of cGAS activity by synthetic compounds in human cells. These cells were plated on 96-well plates at 0.3×10$^6$/well and incubated with serial dilutions of compounds or DMSO for 5 min, followed by transfection of 2 μg/mL of ISD (Interferon Stimulatory DNA, a 45 bp DNA oligo) or mock transfected using lipofectamine 2000 (Life Technology) method, according to manufacturer's instructions. 16 hours later, 15 μL of the media from each well was transferred to a new plate, 50 μL of solution containing 50 mM Hepes-NaOH, pH 6.5, 50 mM NaCl, 10 mM EDTA, 1 μM of coeleanterazine is added to each well and luminescence is measured immediately. Fold increase in luminescence compared to mock transfection was plotted against concentrations of each compound, and IC$_{50}$ is calculated using Graphpad. To evaluate the specificity of a compound, the same procedure is performed except that cells are transfected with 2 μg/mL poly(L:C) or infected with Sendai Virus (SeV) at 50 Unit/mL, which are known to activate the RIG-I-MAVS pathway. A specific inhibitory compound should inhibit interferon induction by DNA but have minimal effect on poly(I:C) or Sendai virus induced interferon reporter gene expression.

The results of the cellular assay for compounds of the disclosure are presented in Table 4. The letter codes for cGAS IC$_{50}$ include: A (<2 μM); B (2-10 μM); C (>10 μM).

TABLE 4

Cellular Assay Results

| I-# | IC$_{50}$ | I-# | IC$_{50}$ | I-# | IC$_{50}$ |
|---|---|---|---|---|---|
| I-892 | A | I-893 | A | I-894 | A |
| I-895 | A | I-896 | A | I-897 | A |
| I-898 | A | I-899 | A | I-900 | A |
| I-901 | C | I-902 | B | I-903 | B |
| I-904 | C | I-905 | C | I-906 | A |
| I-907 | A | I-908 | C | I-909 | C |
| I-910 | C | I-911 | C | I-912 | C |
| I-913 | C | I-914 | C | I-915 | C |
| I-916 | C | I-917 | C | I-918 | C |
| I-919 | C | I-920 | C | I-921 | C |
| I-922 | C | I-923 | C | I-924 | C |
| I-925 | A | I-926 | A | I-927 | A |
| I-928 | A | I-929 | A | I-930 | A |
| I-931 | A | I-932 | A | I-933 | A |
| I-934 | C | I-935 | A | I-936 | A |
| I-937 | A | I-938 | A | | |

All publications, patents, patent applications and other documents cited in this application, including international application no. PCT/US2021/49084, are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the claimed invention(s).

What is claimed is:

1. A compound, wherein the compound is of Formula I:

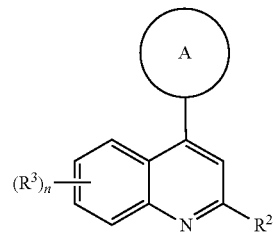

or is a pharmaceutically acceptable salt thereof, wherein:
Ring A is an optionally substituted triazole, wherein substitution
(a) when on a substitutable carbon atom, is with one or more groups selected from halogen; —(CH$_2$)$_{0-6}$R°; —(CH$_2$)$_{0-6}$OR°; —O(CH$_2$)$_{0-6}$R°; —O—(CH$_2$)$_{0-6}$C(O)OR°; —(CH$_2$)$_{0-6}$CH(OR°)$_2$; —(CH$_2$)$_{0-6}$SR°; —(CH$_2$)$_{0-6}$Ph, which Ph may be substituted with R°; —(CH$_2$)$_{0-6}$O(CH$_2$)$_{0-1}$Ph which Ph may be substituted with R°; —CH═CHPh, which Ph may be substituted with R°; —(CH$_2$)$_{0-6}$O(CH$_2$)$_{0-1}$-pyridyl which pyridyl may be substituted with R°; —NO$_2$; —CN; —N$_3$; —(CH$_2$)$_{0-6}$N(R°)$_2$; —(CH$_2$)$_{0-6}$N(R°)C(O)R°; —N(R°)C(S)R°; —(CH$_2$)$_{0-6}$N(R°)C(O)NR°$_2$; —N(R°)C(S)NR°$_2$; —(CH$_2$)$_{0-6}$N(R°)C(O)OR°; —N(R°)N(R°)C(O)R°; —N(R°)N(R°)C(O)NR°$_2$; —N(R°)N(R°)C(O)OR°; —(CH$_2$)$_{0-6}$C(O)R°; —C(S)R°; —(CH$_2$)$_{0-6}$C(O)OR°; —(CH$_2$)$_{0-6}$C(O)SR°; —(CH$_2$)$_{0-6}$C(O)OSiR°$_3$; —(CH$_2$)$_{0-6}$OC(O)R°; —OC(O)(CH$_2$)$_{0-6}$SR°, —(CH$_2$)$_{0-6}$SC(O)R°; —(CH$_2$)$_{0-6}$C(O)NR°$_2$; —C(S)NR°$_2$; —C(S)SR°; —SC(S)SR°, —(CH$_2$)$_{0-6}$OC(O)NR°$_2$; —C(O)N(OR°)R°; —C(O)C(O)R°; —C(O)CH$_2$C(O)R°; —C(NOR°)R°; —(CH$_2$)$_{0-6}$SSR°; —(CH$_2$)$_{0-6}$S(O)$_2$R°; —(CH$_2$)$_{0-6}$S(O)$_2$OR°; —(CH$_2$)$_{0-6}$OS(O)$_2$R°; —S(O)$_2$NR°$_2$; —(CH$_2$)$_{0-6}$S(O)R°; —N(R°)S(O)$_2$NR°$_2$; —N(R°)S(O)$_2$R°; —N(OR°)R°; —C(NH)NR°$_2$; —P(O)$_2$R°; —P(O)

$R^\circ{}_2$; —P(O)(OR$^\circ$)$_2$; —OP(O)(R$^\circ$)OR$^\circ$; —OP(O)R$^\circ{}_2$; —OP(O)(OR$^\circ$)$_2$; SiR$^\circ{}_3$; —(C$_{1-4}$ straight or branched alkylene)O—N(R$^\circ$)$_2$; or —(C$_{1-4}$ straight or branched alkylene)C(O)O—N(R$^\circ$)$_2$, wherein each R$^\circ$ is independently hydrogen, C$_{1-6}$ aliphatic, —CH$_2$Ph, —O(CH$_2$)$_{0-1}$Ph, or a 5- to 6-membered saturated, partially unsaturated, or aryl ring having 0 to 4 heteroatoms independently selected from nitrogen, oxygen, or sulfur; or (b) when on a substitutable nitrogen atom, is with one or more groups selected from —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†, wherein each R† is independently hydrogen, C$_{1-6}$ aliphatic, —OPh, or an unsubstituted 5- to 6-membered saturated, partially unsaturated, or aryl ring having 0 to 4 heteroatoms independently selected from nitrogen, oxygen, or sulfur;

R$^2$ is —NR$^a$R$^5$,

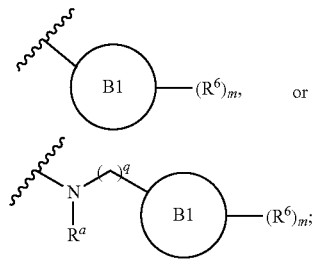

or each R$^3$ is independently halogen, —OR, —NR$_2$, or —SR;

Ring B1 is a 4- to 10-membered saturated or partially unsaturated monocyclic or bicyclic carbocyclic or heterocyclic ring having 1 to 3 heteroatoms independently selected from A nitrogen, oxygen, and sulfur; or a thienyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, or pyrido[2,3-b]-1,4-oxazin-3(4H)-one ring;

Ring B2 is phenyl; a 4- to 7-membered saturated or partially unsaturated carbocyclic or heterocyclic ring having 1 to 3 heteroatoms independently selected from nitrogen, oxygen, and sulfur; or a 5- to 6-membered heteroaryl ring having 1 to 4 heteroatoms independently selected from nitrogen, oxygen, and sulfur;

each R is independently hydrogen or an optionally substituted group selected from C$_{1-6}$ aliphatic; benzyl; phenyl; a 4- to 10-membered saturated or partially unsaturated monocyclic or bicyclic carbocyclic or heterocyclic ring having 1 to 3 heteroatoms independently selected from nitrogen, oxygen, phosphorus, and sulfur; and a 5- to 6-membered heteroaryl ring having 1 to 4 heteroatoms independently selected from nitrogen, oxygen, phosphorus, and sulfur, or:

two R groups on the same nitrogen are optionally taken together with their intervening atoms to form an optionally substituted 4- to 7-membered saturated, partially unsaturated, or heteroaryl ring having 0 to 3 heteroatoms, in addition to the nitrogen, independently selected from nitrogen, oxygen, phosphorus, and sulfur;

R$^5$ is —(CR$_2$)$_{0-4}$OR, —(CR$_2$)$_{0-5}$CO$_2$R, —(CR$_2$)$_{0-5}$CONR$_2$, —(CR$_2$)$_{0-4}$C(O)NR(CR$_2$)$_{0-4}$CO$_2$R, —(CR$_2$)$_{0-4}$C(O)NR(CR$_2$)$_{0-4}$CONR$_2$, —(CR$_2$)$_{0-4}$NRC(O)R, —(CR$_2$)$_{0-4}$SO$_3$R, —(CR$_2$)$_{0-4}$SO$_2$NR$_2$, —(CR$_2$)$_{0-4}$OSO$_2$NR$_2$, —(CR$_2$)$_{0-4}$NRSO$_2$R, —(CR$_2$)$_{0-4}$NRSO$_2$OR, —(CR$_2$)$_{0-4}$OP(OR)$_2$, —(CR$_2$)$_{0-4}$OP(O)(OR)$_2$, —(CR$_2$)$_{0-4}$P(O)(OR)$_2$—(CR$_2$)$_{0-4}$OP(O)(H)OR, or R$^B$;

each R$^6$ is independently halogen, —COR, —(CR$_2$)$_{0-4}$CO$_2$R, —(CR$_2$)$_{0-4}$CONR$_2$, —OR, —(CR$_2$)$_{1-4}$OR, —NR$_2$, —(CR$_2$)$_{1-4}$NR$_2$, —NRC(O)OR, —NRC(O)R, —NRC(O)NR$_2$, —SR, —SO$_2$R, —S(O)R, —(CR$_2$)$_{0-4}$SO$_3$R, —(CR$_2$)$_{0-4}$SO$_2$NR$_2$, —(CR$_2$)$_{0-4}$OSO$_2$NR$_2$, —(CR$_2$)$_{0-4}$NRSO$_2$R, —(CR$_2$)$_{0-4}$NRSO$_2$OR, —(CR$_2$)$_{0-4}$OP(OR)$_2$, —(CR$_2$)$_{0-4}$OP(O)(OR)$_2$, —(CR$_2$)$_{0-4}$P(O)(OR)$_2$, —(CR$_2$)$_{0-4}$OP(O)(H)OR, —B(OR)$_2$ or R$^B$;

R$^B$ is an optionally substituted group selected from C$_{1-6}$ aliphatic; phenyl; a 4- to 10-membered saturated or partially unsaturated monocyclic or bicyclic carbocyclic or heterocyclic ring having 1 to 3 heteroatoms independently selected from nitrogen, oxygen, and sulfur; and a 5- to 6-membered heteroaryl ring having 1 to 4 heteroatoms independently selected from nitrogen, oxygen, and sulfur;

each R$^a$ is independently H or C$_{1-6}$alkyl;

each m is 0, 1, 2, 3, or 4;

n is 1, 2, 3, or 4;

q is 0, 1, or 2.

2. The compound of claim 1, wherein Ring A is selected from

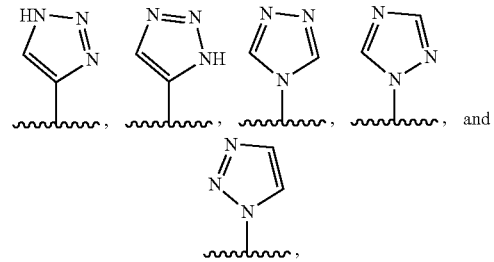

3. The compound of claim 1, wherein at least one occurrence of R$^3$ is halogen.

4. The compound of claim 3, wherein at least one occurrence of R$^3$ is chloro.

5. The compound of claim 3, wherein at least one occurrence of R$^3$ is bromo.

6. The compound of claim 3, wherein n is 2 or 3 and all occurrences of R$^3$ are halogen.

7. The compound of claim 1, wherein R$^2$ is —NR$^a$R$^5$.

8. The compound of claim 1, wherein R$^2$ is

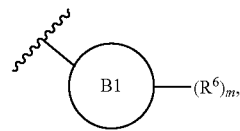

wherein Ring B1 is a 4- to 10-membered saturated or partially unsaturated monocyclic or bicyclic carbocyclic or heterocyclic ring having 1 to 3 heteroatoms independently selected from nitrogen, oxygen, and sulfur.

9. The compound of claim 8, wherein $R^2$ is

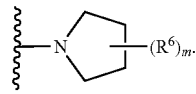

10. The compound of claim 8, wherein $R^2$ is

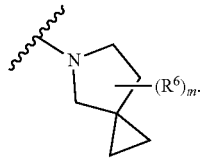

11. The compound of claim 8, wherein each $R^6$ is independently halogen, =$CH_2$, =O, —$C_{1-4}$alkyl, —$C_{1-4}$haloalkyl, —$(CH_2)_{0-4}CO_2H$, —$(CH_2)_{0-4}CO_2C_{1-4}$alkyl, —$(CH_2)_{0-4}CO_2C_{1-4}$haloalkyl, —$(CH_2)_{0-4}CONH_2$, —$(CH_2)_{0-4}CONHC_{1-4}$alkyl, —$(CH_2)_{0-4}CON(C_{1-4}$alkyl$)_2$, —$(CH_2)_{0-4}CO(N\text{-proline})$, —$(CH_2)_{0-4}C(O)NR^a(CH_2)_{1-4}CO_2H$, —$(CH_2)_{0-4}C(O)NR^a(CH_2)_{1-4}CONH_2$, —$(CH_2)_{0-4}C(O)NR^a(CH_2)_{1-4}CONHC_{1-4}$alkyl, —$(CH_2)_{0-4}C(O)NR^a(CH_2)_{1-4}CON(C_{1-4}$alkyl$)_2$, —OH, —$(CH_2)_{1-4}OH$, —$(CH_2)_{0-4}OC_{1-4}$alkyl, —$(CH_2)_{0-4}O(CH_2)_{1-5}CO_2H$, —$(CH_2)_{0-4}O(CH_2)_{1-5}CO_2C_{1-4}$alkyl, —$(CH_2)_{0-4}OC(O)C_{1-4}$alkyl, —$NH_2$, —$(CH_2)_{1-4}NH_2$, —$(CH_2)_{0-4}NHC_{1-4}$alkyl, —$(CH_2)_{0-4}N(C_{1-4}$alkyl$)_2$, —$(CH_2)_{0-4}SO_3H$, —$(CH_2)_{0-4}SO_2NH_2$, —$(CH_2)_{0-4}SO_2NHC_{1-4}$alkyl, —$(CH_2)_{0-4}NR^aSO_2C_{1-4}$alkyl, —$(CH_2)_{0-4}OP(OH)_2$, —$(CH_2)_{0-4}OP(OH)(OC_{1-4}$alkyl$)$, or —$(CR_2)_{0-4}OP(O)(H)OH$, wherein $R^a$, independently for each occurrence, is H or $C_{1-4}$alkyl.

12. The compound of claim 11, wherein each $R^6$ is independently halogen, =$CH_2$, =O, —$C_{1-4}$alkyl, —$C_{1-4}$haloalkyl, —$CO_2H$, —$CO_2C_{1-4}$alkyl, —$CO(N\text{-proline})$, —$CH_2CO_2H$, —OH, —$OC_{1-4}$alkyl, —$(CH_2)_{0-4}O(CH_2)_{1-5}CO_2H$, —$(CH_2)_{0-4}O(CH_2)_{1-5}CO_2C_{1-4}$alkyl, —$OC(O)C_{1-4}$alkyl, —$SO_3H$, —$SO_2NH_2$, —$NR^aSO_2C_{1-4}$alkyl, —$OP(OH)_2$ or —$OP(O)(H)OH$.

13. The compound of claim 1, wherein:
$R^2$ is

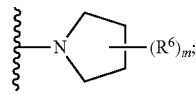

at least one occurrence of $R^3$ is halogen;
m is 1, 2, 3, or 4; and
at least one $R^6$ includes a terminal —$CO_2H$ or —$CO_2C_{1-4}$alkyl group.

14. The compound of claim 13, wherein at least one occurrence of $R^3$ is chloro or bromo.

15. The compound of claim 1, wherein:
$R^2$ is

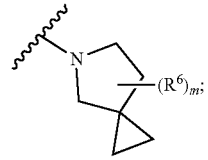

at least one occurrence of $R^3$ is halogen;
m is 1, 2, 3, or 4; and
at least one $R^6$ includes a terminal —$CO_2H$ or —$CO_2C_{1-4}$alkyl group.

16. The compound of claim 15, wherein at least one occurrence of $R^3$ is chloro or bromo.

17. The compound of claim 13, wherein:
at least one occurrence of $R^3$ is chloro;
at least one occurrence of $R^3$ is bromo;
m is 1 or 2; and
at least one $R^6$ is —$(CH_2)_{0-4}O(CH_2)_{1-5}CO_2H$, —$(CH_2)_{0-4}O(CH_2)_{1-5}CO_2C_{1-4}$alkyl, —$(CH_2)_{0-4}CO_2H$ or —$(CH_2)_{0-4}CO_2C_{1-4}$alkyl.

18. The compound of claim 17, wherein:
Ring A is unsubstituted triazole; and
at least one $R^6$ is

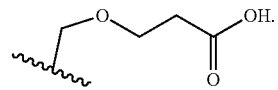 [SMILES: *COCCC(=O)O]

19. The compound of claim 15, wherein:
at least one occurrence of $R^3$ is chloro;
at least one occurrence of $R^3$ is bromo;
m is 1 or 2; and
at least one $R^6$ is —$(CH_2)_{0-4}O(CH_2)_{1-5}CO_2H$, —$(CH_2)_{0-4}O(CH_2)_{1-5}CO_2C_{1-4}$alkyl, —$(CH_2)_{0-4}CO_2H$ or —$(CH_2)_{0-4}CO_2C_{1-4}$alkyl.

20. The compound of claim 19, wherein:
Ring A is unsubstituted triazole; and
at least one $R^6$ is

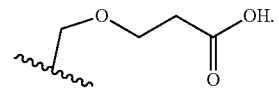 [SMILES: *COCCC(=O)O]

21. A compound, wherein the compound is selected from:

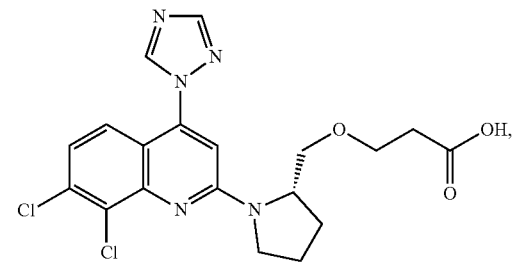

I-892

I-893
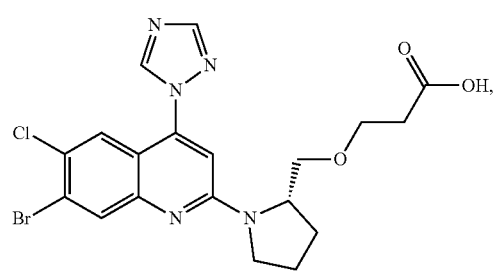
I-895
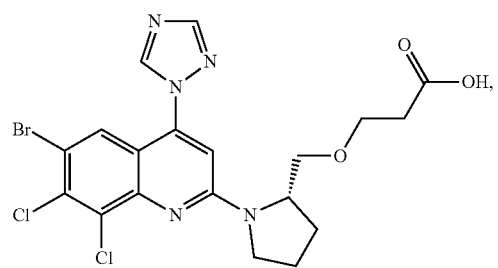
I-896
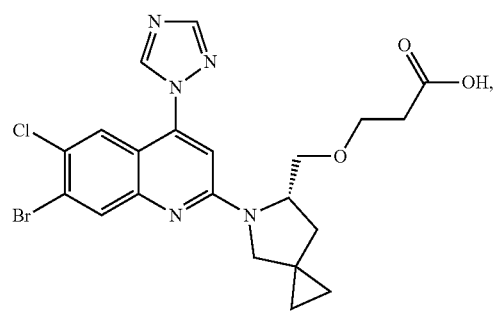
I-897
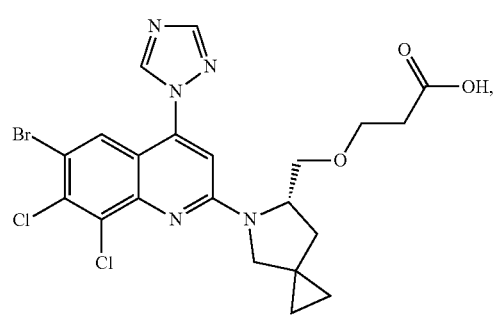
I-898
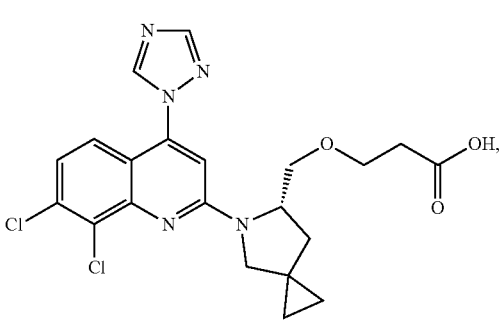
I-899
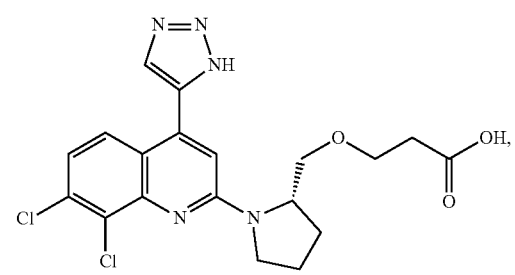
I-900
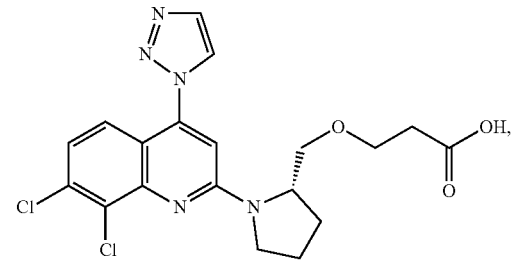
I-901
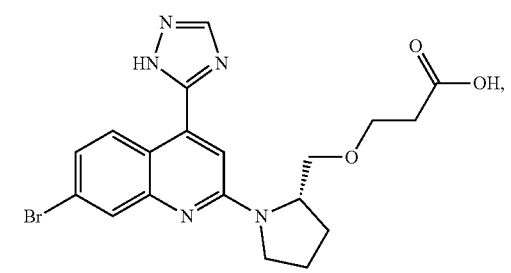
I-924
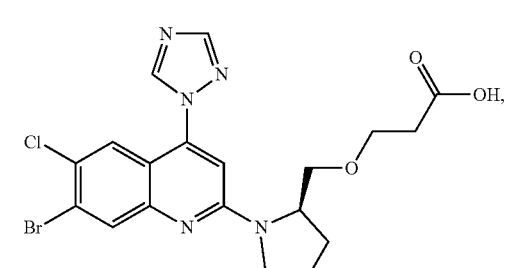
I-925
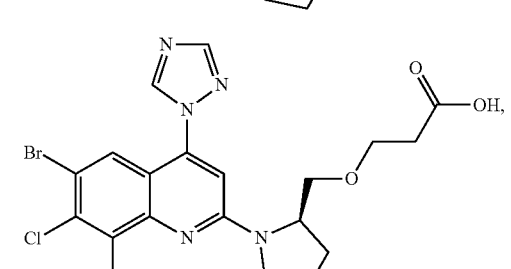
I-926
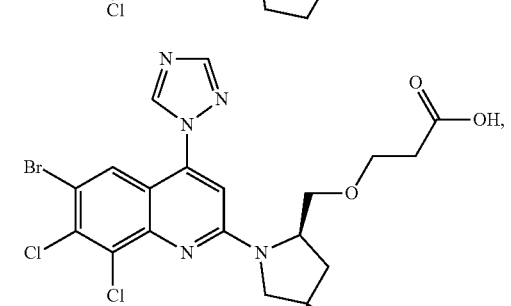

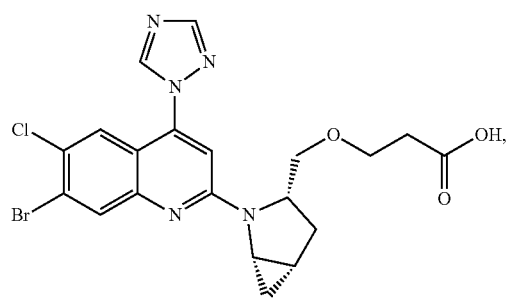
I-927
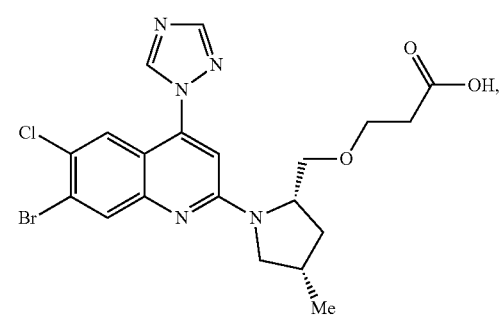
I-928
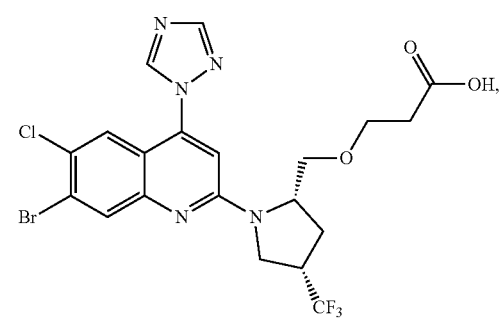
I-929
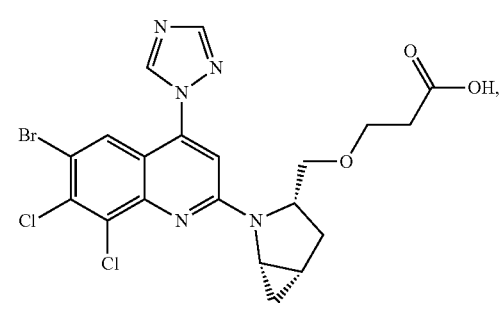
I-930
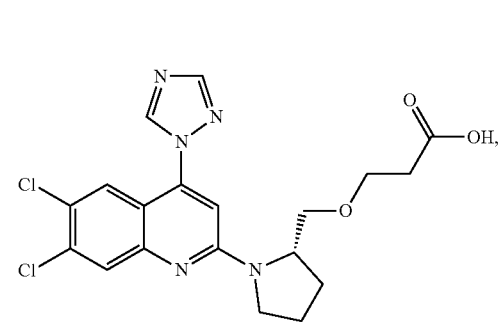
I-931
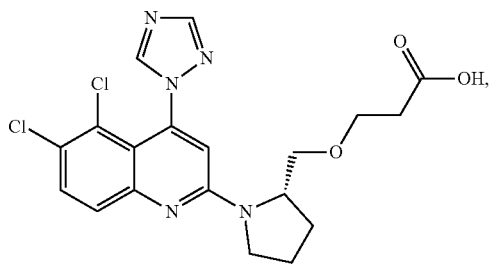
I-932
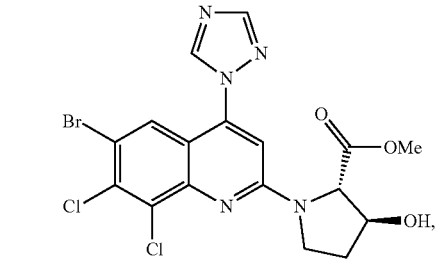
I-933
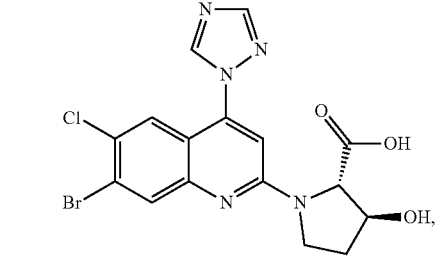
I-934
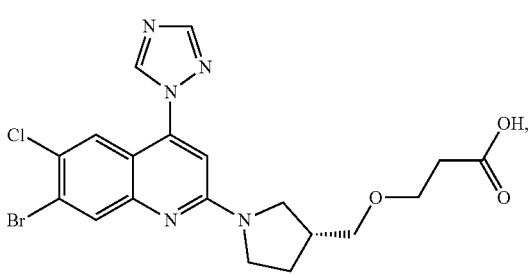
I-935
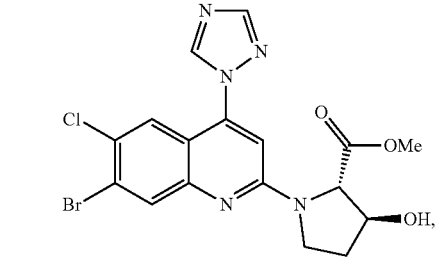
I-936
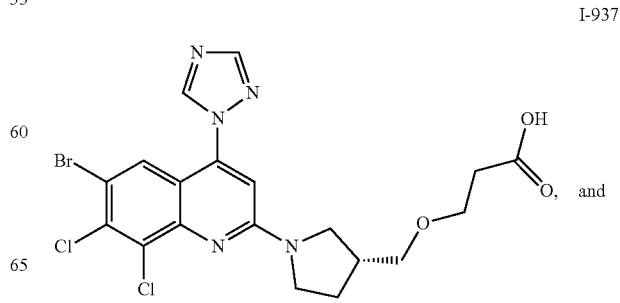
I-937

-continued
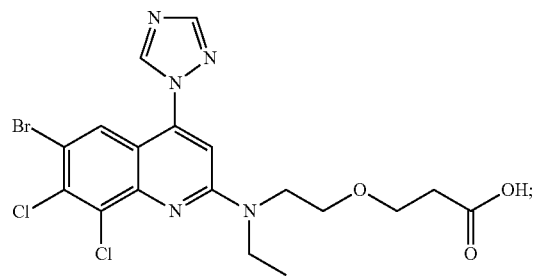
I-938
or is a pharmaceutically acceptable salt thereof.
22. A compound, wherein the compound is selected from:
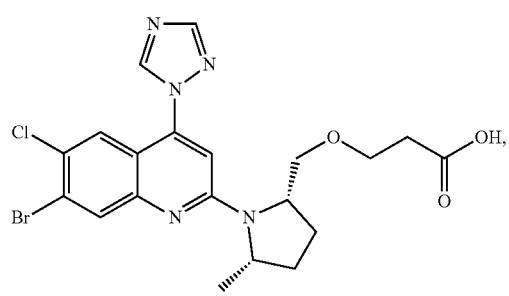
I-939
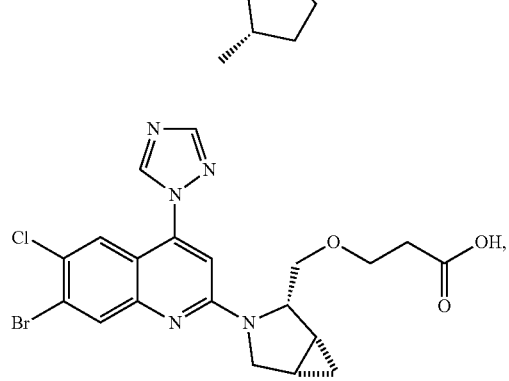
I-940
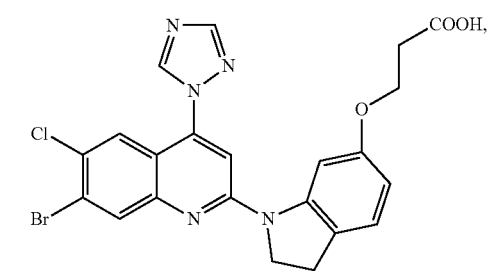
I-941
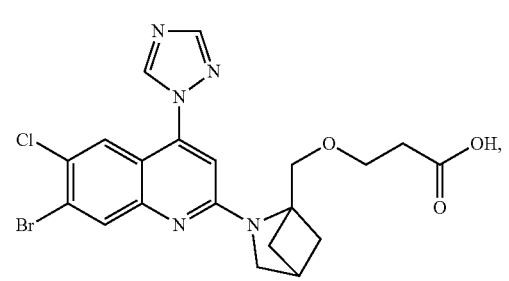
I-942
-continued
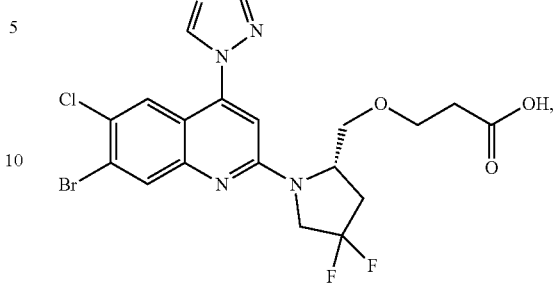
I-943
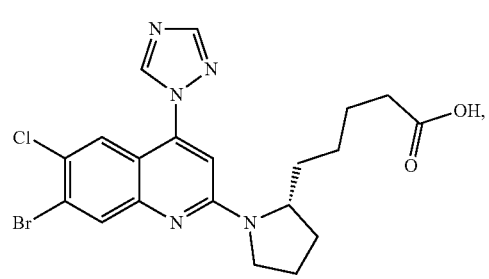
I-944
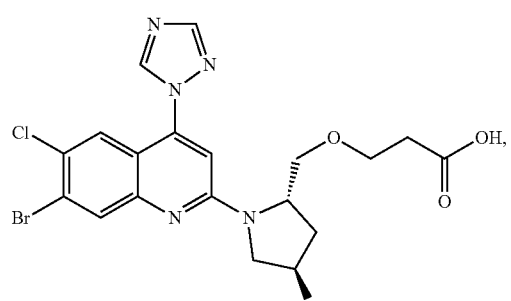
I-945
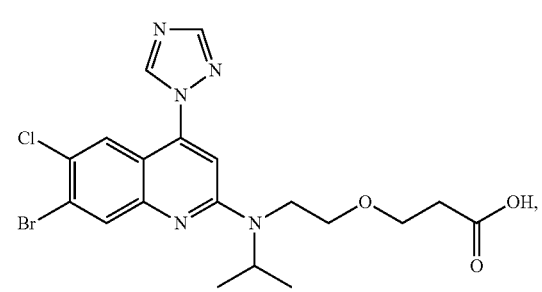
I-946
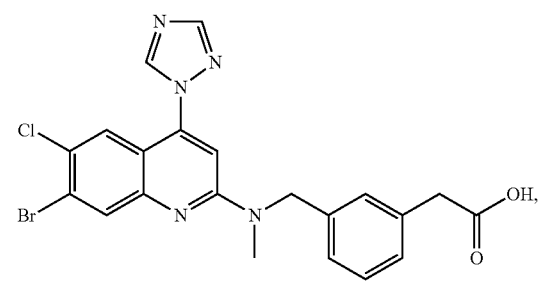
I-948

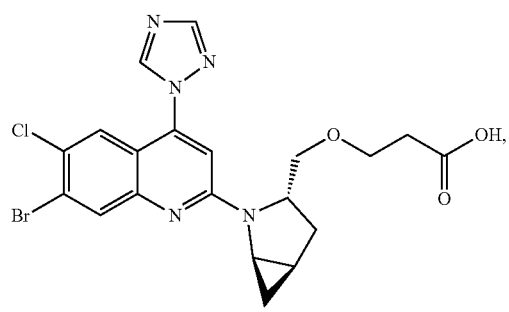
I-949
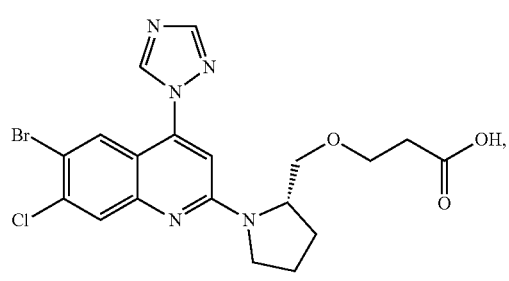
I-950
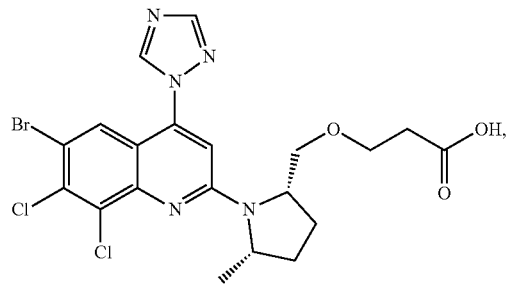
I-951
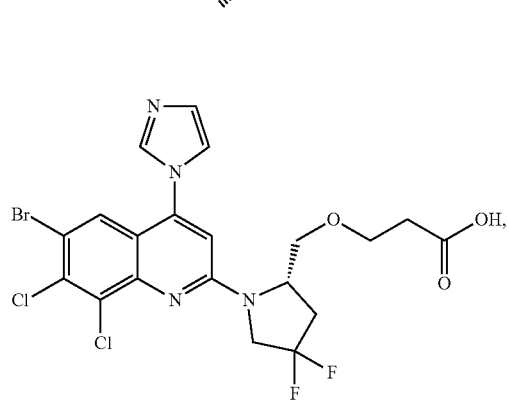
I-952
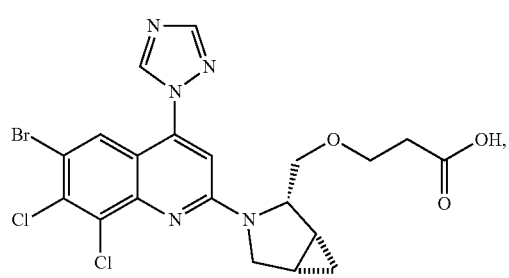
I-953
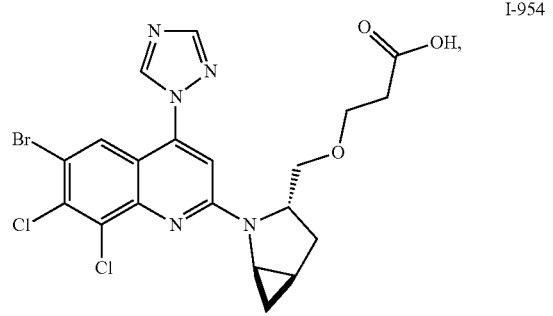
I-954
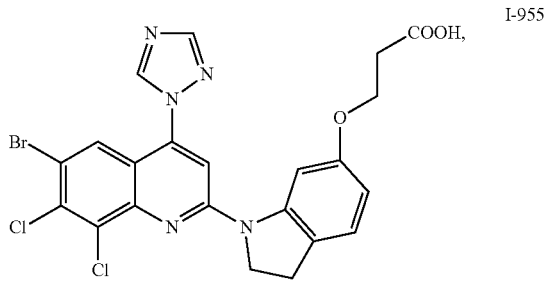
I-955
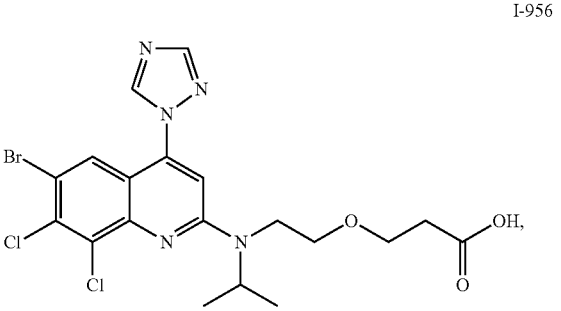
I-956
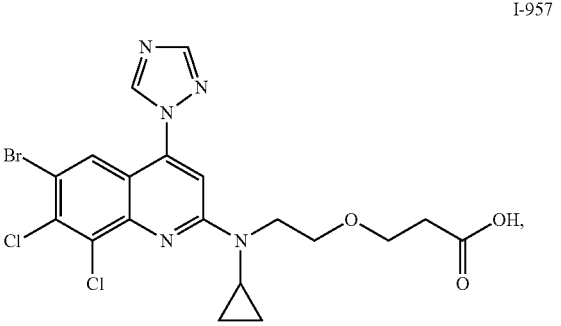
I-957
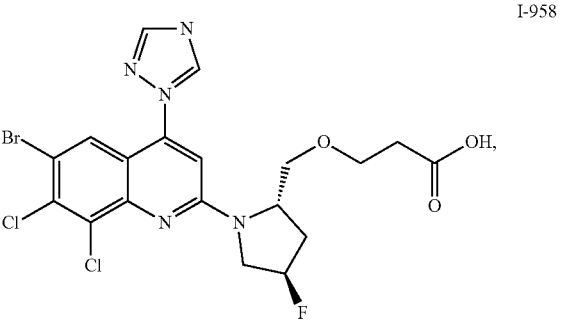
I-958

-continued

I-959
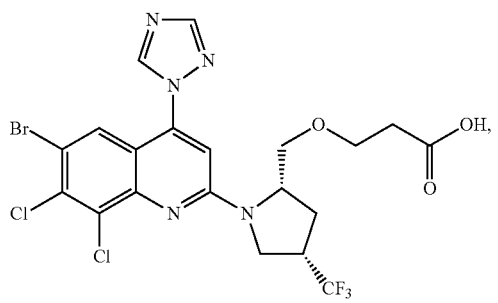

I-960
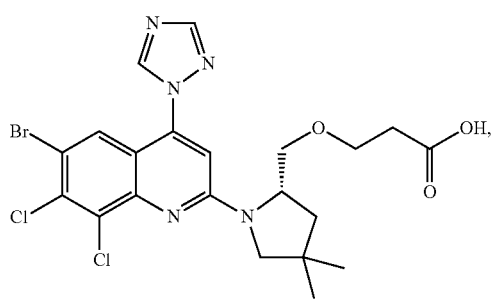

I-961
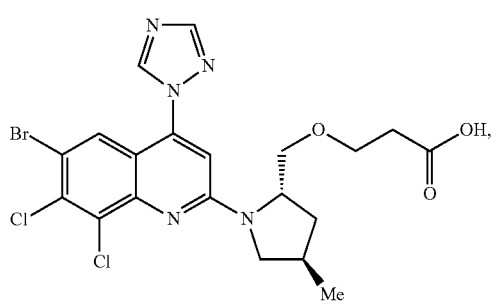

I-962
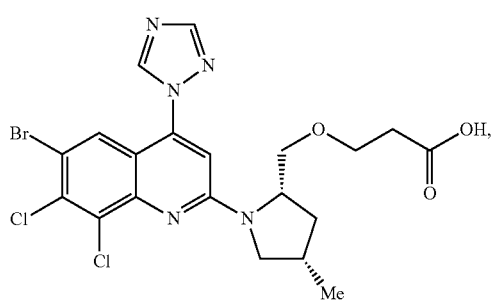

I-963
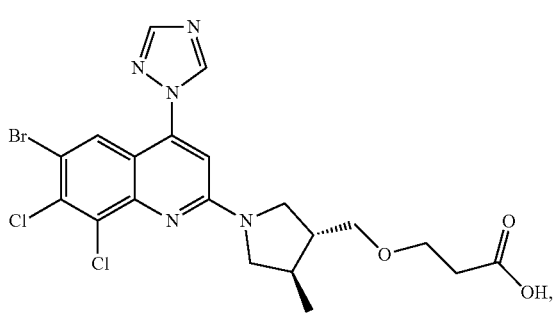

-continued

I-964
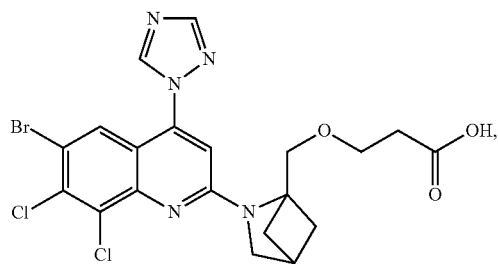

I-965
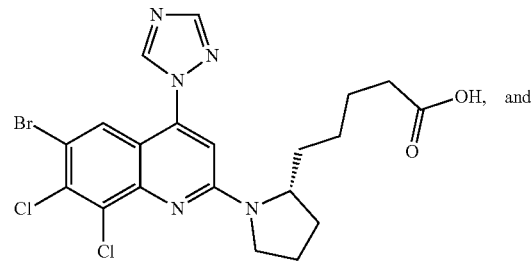

and

I-966
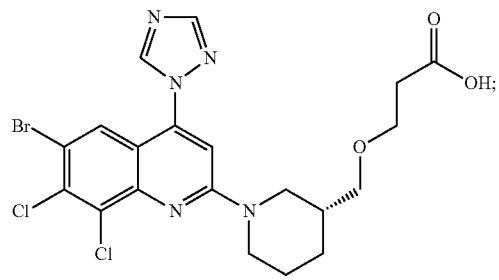

or is a pharmaceutically acceptable salt thereof.

23. A pharmaceutical composition comprising a compound of claim 1 and one or more pharmaceutically acceptable excipients.

24. A method of antagonizing cyclic GMP-AMP synthase (cGAS) in a patient in need thereof, comprising administering an effective amount of a compound of claim 1.

25. A method of treating an inflammatory, allergic, autoimmune, cardiovascular, ocular inflammation, or neurodegenerative disease in a patient in need thereof, comprising administering an effective amount of a compound of claim 1; wherein the inflammatory disease is selected from arthritis, dermatomyositis, tendonitis, synovitis, tenosynovitis, bursitis, fibrositis (fibromyalgia), epicondylitis, myositis, osteitis, blepharitis, blepharochalasis, conjunctivitis, dacryoadenitis, keratitis, keratoconjunctivitis sicca (dry eye), scleritis, trichiasis, uveitis, encephalitis, Guillain-Barre syndrome, meningitis, neuromyotonia, narcolepsy, multiple sclerosis, myelitis, schizophrenia, arthrosclerosis, arthritis, phlebitis, vasculitis, lymphangitis, cholangitis, cholecystitis, enteritis, enterocolitis, gastritis, gastroenteritis, inflammatory bowel disease, ileitis, proctitis, cervicitis, chorioamnionitis, endometritis, epididymitis, omphalitis, oophoritis, orchitis, salpingitis, tubo-ovarian abscess, urethritis, vaginitis, vulvitis, and vulvodynia;

the autoimmune disease is selected from systemic lupus erythematosus (SLE), insulin-dependent diabetes mellitus (IDDM), acute disseminated alopecia universalise, Behcet's disease, Chagas' disease, chronic fatigue syndrome, dysautonomia, encephalomyelitis, ankylosing spondylitis, aplastic anemia, hidradenitis suppurativa, autoimmune hepatitis, autoimmune oophoritis, celiac disease, Crohn's disease, diabetes mellitus type 1, giant cell arteritis, goodpasture's syndrome, Grave's disease, Guillain-Barre syndrome, Hashimoto's disease, Henoch-Schonlein purpura, Kawasaki's disease, microscopic colitis, microscopic polyarteritis, mixed connective tissue disease, multiple sclerosis, myasthenia gravis, opsoclonus myoclonus syndrome, optic neuritis, ord's thyroiditis, pemphigus, polyarteritis nodosa, polymyalgia, rheumatoid arthritis, Reiter's syndrome, Sjogren's syndrome, Aicardi Goutières syndrome, temporal arteritis, Wegener's granulomatosis, warm autoimmune haemolytic anemia, interstitial cystitis, Lyme disease, morphea, psoriasis, sarcoidosis, scleroderma, ulcerative colitis, and vitiligo; and the neurodegenerative disease is selected from Alzheimer's and Parkinson's disease.

26. The compound of claim 21, wherein the compound is:

I-893 or is a pharmaceutically acceptable salt thereof.

27. The compound of claim 21, wherein the compound is:

I-896 or is a pharmaceutically acceptable salt thereof.

28. The compound of claim 21, wherein the compound is:

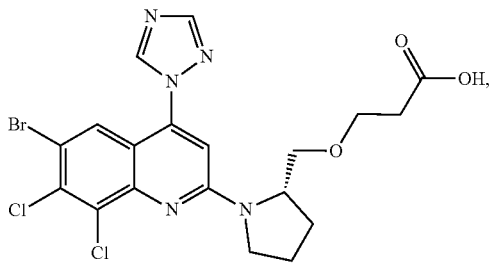

I-895 or is a pharmaceutically acceptable salt thereof.

29. The compound of claim 21, wherein the compound is:

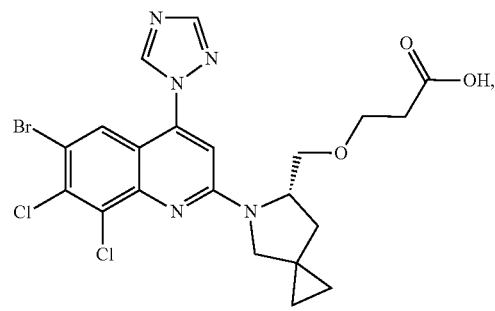

I-897 or is a pharmaceutically acceptable salt thereof.

* * * * *